(12) United States Patent
Burk et al.

(10) Patent No.: US 9,133,487 B2
(45) Date of Patent: Sep. 15, 2015

(54) MICROORGANISMS FOR PRODUCING METHACRYLIC ACID AND METHACRYLATE ESTERS AND METHODS RELATED THERETO

(75) Inventors: Mark J. Burk, San Diego, CA (US); Anthony P. Burgard, Bellefonte, PA (US); Robin E. Osterhout, San Diego, CA (US); Jun Sun, San Diego, CA (US); Priti Pharkya, San Diego, CA (US)

(73) Assignee: GENOMATICA, INC., San Diego, CA (US)

( * ) Notice: Subject to any disclaimer, the term of this patent is extended or adjusted under 35 U.S.C. 154(b) by 0 days.

(21) Appl. No.: 13/436,811

(22) Filed: Mar. 30, 2012

(65) Prior Publication Data

US 2013/0065279 A1  Mar. 14, 2013

Related U.S. Application Data

(60) Provisional application No. 61/471,078, filed on Apr. 1, 2011, provisional application No. 61/571,232, filed on Jun. 22, 2011, provisional application No. 61/509,560, filed on Jul. 19, 2011, provisional application No. 61/510,054, filed on Jul. 20, 2011, provisional application No. 61/512,348, filed on Jul. 27, 2011.

(51) Int. Cl.

| | |
|---|---|
| C12N 1/12 | (2006.01) |
| C12N 1/20 | (2006.01) |
| C12P 7/40 | (2006.01) |
| C12P 19/32 | (2006.01) |
| C12P 7/42 | (2006.01) |
| C12P 7/62 | (2006.01) |

(52) U.S. Cl.
CPC ... *C12P 7/40* (2013.01); *C12P 7/42* (2013.01); *C12P 7/62* (2013.01); *C12P 19/32* (2013.01)

(58) Field of Classification Search
None
See application file for complete search history.

(56) References Cited

U.S. PATENT DOCUMENTS

| | | | |
|---|---|---|---|
| 6,582,943 | B1 | 6/2003 | Chauhan et al. |
| 7,901,915 | B2 * | 3/2011 | Symes et al. ............... 435/135 |
| 8,241,877 | B2 | 8/2012 | Burgard et al. |
| 2009/0130729 | A1 | 5/2009 | Symes et al. |
| 2009/0275096 | A1 | 11/2009 | Burgard et al. |
| 2010/0291644 | A1 | 11/2010 | Marx et al. |
| 2012/0276604 | A1 | 11/2012 | Burgard et al. |
| 2012/0276605 | A1 | 11/2012 | Burgard et al. |

OTHER PUBLICATIONS

Branden et al., "Introduction to Protein Structure Second Edition", Garland Publishing Inc., New York, 1999, p. 247.*
Seffernick et al. (J. Bacteriol. 183(8):2405-2410, 2001).*
Witkowski et al., Biochemistry, 38, 11643-11650, 1999.*
Carrie C., et al., (2007) *Nine 3-ketoacyl-CoA thiolases (KATS) and acetoacetyl-CoA thiolases (ACATs) encoded by five genes in Arabidopsis thaliana are targeted either to peroxisomes or cytosol but not to mitochondria*, Plant Mol Biol 63:97-108.
Krug, A., et al., (2005) *Identification of AcnR, a TetR-type Repressor of the Aconitase Gene acn in Corynebacterium glutamicum*, J. Biol. Chem. 280:585-595.
Loh, K.D., et al., (2006) *A previously undescribed pathway for pyrimidine catabolism*, PNAS 103:5114-5119.
Liu, Q., et al., (2007) *The impact of PHB accumulation on $_L$-glutamate production by recombinant Corynebacterium glutamicum*, Journal of Biotechnology 132:273-279.
Musfeldt M. and Schönheit, P., (2002) *Novel Type of ADP-Forming Acetyl Coenzyme A Synthetase in Hyperthermophilic Archaea: Heterologous Expression and Characterization of Isoenzymes from the Sulfate Reducer Archaeoglobus fulgidus and the Methanogen Methanococcis jannaschii*, Journal of Bacteriology 184: 636-644.
Ratnatilleke A., et al., (1999) *Cloning and Sequencing of the Coenzyme $B_{12}$-binding Domain of Isobutyryl-CoA Mutase from Streptomyces cinnamonensis, Reconstitution of Mutase Activity, and Characterization of the Recombinant Enzyme Produced in Escherichia coli*, J. Biol. Chem. 274:31679-31685.
Rohwerder T. and Müller, R.H., (2010) *Synthesis of 2-hydroxyisobutyric acid (2-HIBA) from renewable carbon*, Microbial Cell Factories 9: 1-10.
Barton, N. R., et al., (2015) *An integrated biotechnology platform for developing sustainable chemical processes*, J Ind Microbiol Biotechnol 42: 349-360.
Bonnarme, P., et al., (1995) *Itaconate Biosynthesis in Aspergillus terreus*, Journal of Bacteriology 177: 3573-3578.
Korotkova, N., et al., (2002) *Glyoxylate Regeneration Pathway in the Methylotroph Methylobacterium extorquens AM1*, Journal of Bacteriology 184: 1750-1758.
Nagasawa, T., et al., (1990) *Production of acrylic acid and methacrylic acid using Rhodococcus rhodochrous J1 nitrilase*, Appl Microbiol Biotechnol 34: 322-324.
Smith, M.R., et al., (1994) *The Utilization of 3-Mercapto-2-Methylpropionate as Sulphur Source by a Phototrophic Bacterium*, Bioorganic & Medicinal Chemistry 2: 589-593.
Yim, H., et al., (2011) *Metabolic engineering of Escherichia coli for direct production of 1,4-butanediol*, Nature Chemical Biology 7: 445-452.

* cited by examiner

*Primary Examiner* — Suzanne M Noakes
*Assistant Examiner* — Jae W Lee
(74) *Attorney, Agent, or Firm* — Kagan Binder, PLLC

(57) ABSTRACT

The invention provides a non-naturally occurring microbial organism having a methacrylic acid, methacrylate ester, 3-hydroxyisobutyrate and/or 2-hydroxyisobutyrate pathway. The microbial organism contains at least one exogenous nucleic acid encoding an enzyme in a methacrylic acid pathway. The invention additionally provides a method for producing methacrylic acid, methacrylate ester, 3-hydroxyisobutyrate and/or 2-hydroxyisobutyrate. The method can include culturing methacrylic acid, methacrylate ester, 3-hydroxyisobutyrate and/or 2-hydroxyisobutyrate producing microbial organism, where the microbial organism expresses at least one exogenous nucleic acid encoding a methacrylic acid pathway enzyme in a sufficient amount to produce methacrylic acid, methacrylate ester, 3-hydroxyisobutyrate and/or 2-hydroxyisobutyrate, under conditions and for a sufficient period of time to produce methacrylic acid, methacrylate ester, 3-hydroxyisobutyrate and/or 2-hydroxyisobutyrate.

7 Claims, 39 Drawing Sheets

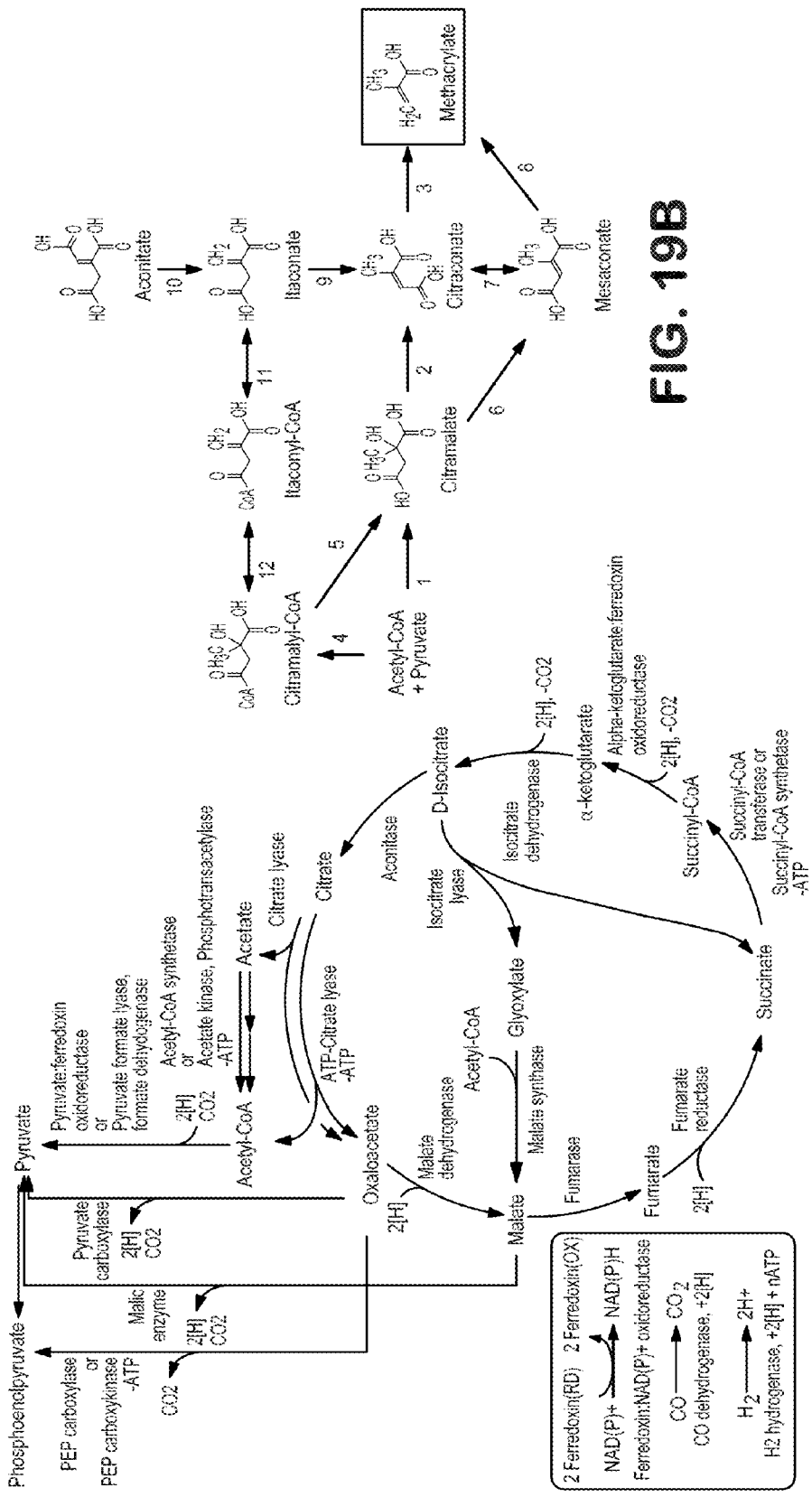

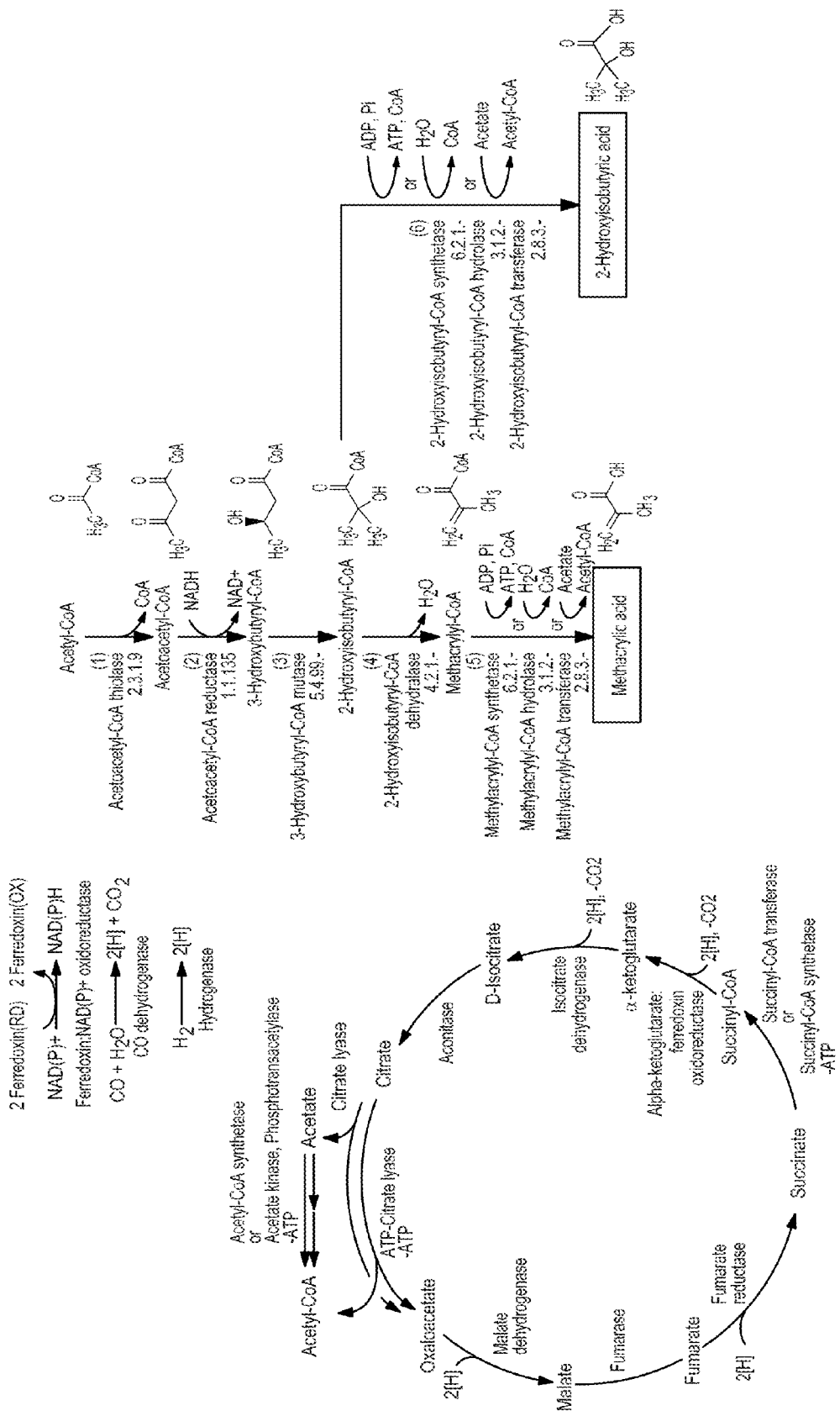

```
ATGGCAGTGGATTCACCGGATGAGCGGCTACAGCGCCGCATTGCACAGTTGTTTGCAGAAGATG
AGCAGGTCAAGGCCGCACGTCCGCTCGAAGCGGTGAGCGCGGCGGTGAGCGCGCCCGGTATGCG
GCTGGCGCAGATCGCCGCCACTGTTATGGCGGGTTACGCCGACCGCCCGGCCGCCGGGCAGCGT
GCGTTCGAACTGAACACCGACGACGCGACGGGCCGCACCTCGCTGCGGTTACTTCCCCGATTCG
AGACCATCACCTATCGCGAACTGTGGCAGCGAGTCGGCGAGGTTGCCGCGGCCTGGCATCATGA
TCCCGAGAACCCCTTGCGCGCAGGTGATTTCGTCGCCCTGCTCGGCTTCACCAGCATCGACTAC
GCCACCCTCGACCTGGCCGATATCCACCTCGGCGCGGTTACCGTGCCGTTGCAGGCCAGCGCGG
CGGTGTCCCAGCTGATCGCTATCCTCACCGAGACTTCGCCGCGGCTGCTCGCCTCGACCCCGGA
GCACCTCGATGCGGCGGTCGAGTGCCTACTCGCGGGCACCACACCGGAACGACTGGTGGTCTTC
GACTACCACCCCGAGGACGACGACCAGCGTGCGGCCTTCGAATCCGCCCGCCGCCGCCTTGCCG
ACGCGGGCAGCTTGGTGATCGTCGAAACGCTCGATGCCGTGCGTGCCCGGGGCCGCGACTTACC
GGCCGCGCCACTGTTCGTTCCCGACACCGACGACGACCCGCTGGCCCTGCTGATCTACACCTCC
GGCAGCACCGGAACGCCGAAGGGCGCGATGTACACCAATCGGTTGGCCGCCACGATGTGGCAGG
GGAACTCGATGCTGCAGGGGAACTCGCAACGGGTCGGGATCAATCTCAACTACATGCCGATGAG
CCACATCGCCGGTCGCATATCGCTGTTCGGCGTGCTCGCTCGCGGTGGCACCGCATACTTCGCG
GCCAAGAGCGACATGTCGACACTGTTCGAAGACATCGGCTTGGTACGTCCCACCGAGATCTTCT
TCGTCCCGCGCGTGTGCGACATGGTCTTCCAGCGCTATCAGAGCGAGCTGGACCGGCGCTCGGT
GGCGGGCGCCGACCTGGACACGCTCGATCGGGAAGTGAAAGCCGACCTCCGGCAGAACTACCTC
GGTGGGCGCTTCCTGGTGGCGGTCGTCGGCAGCGCGCCGCTGGCCGCGGAGATGAAGACGTTCA
TGGAGTCCGTCCTCGATCTGCCACTGCACGACGGGTACGGGTCGACCGAGGCGGGCGCAAGCGT
GCTGCTCGACAACCAGATCCAGCGGCCGCCGGTGCTCGATTACAAGCTCGTCGACGTGCCCGAA
CTGGGTTACTTCCGCACCGACCGGCCGCATCCGCGCGGTGAGCTGTTGTTGAAGGCGGAGACCA
CGATTCCGGGCTACTACAAGCGGCCCGAGGTCACCGCGGAGATCTTCGACGAGGACGGCTTCTA
CAAGACCGGCGATATCGTGGCCGAGCTCGAGCACGATCGGCTGGTCTATGTCGACCGTCGCAAC
AATGTGCTCAAACTGTCGCAGGGCGAGTTCGTGACCGTCGCCCATCTCGAGGCCGTGTTCGCCA
GCAGCCCGCTGATCCGGCAGATCTTCATCTACGGCAGCAGCGAACGTTCCTATCTGCTCGCGGT
GATCGTCCCCACCGACGACGCGCTGCGCGGCCGCGACACCGCCACCTTGAAATCGGCACTGGCC
GAATCGATTCAGCGCATCGCCAAGGACGCGAACCTGCAGCCCTACGAGATTCCGCGCGATTTCC
TGATCGAGACCGAGCCGTTCACCATCGCCAACGGACTGCTCTCCGGCATCGCGAAGCTGCTGCG
CCCCAATCTGAAGGAACGCTACGGCGCTCAGCTGGAGCAGATGTACACCGATCTCGCGACAGGC
CAGGCCGATGAGCTGCTCGCCCTGCGCCGCGAAGCCGCCGACCTGCCGGTGCTCGAAACCGTCA
GCCGGGCAGCGAAAGCGATGCTCGGCGTCGCCTCCGCCGATATGCGTCCCGACGCGCACTTCAC
CGACCTGGGCGGCGATTCCCTTTCCGCGCTGTCGTTCTCGAACCTGCTGCACGAGATCTTCGGG
GTCGAGGTGCCGGTGGGTGTCGTCGTCAGCCCGGCGAACGAGCTGCGCGATCTGGCGAATTACA
TTGAGGCGGAACGCAACTCGGGCGCGAAGCGTCCCACCTTCACCTCGGTGCACGGCGGCGGTTC
CGAGATCCGCGCCGCCGATCTGACCCTCGACAAGTTCATCGATGCCCGCACCCTGGCCGCCGCC
GACAGCATTCCGCACGCGCCGGTGCCAGCGCAGACGGTGCTGCTGACCGGCGCGAACGGCTACC
TCGGCCGGTTCCTGTGCCTGGAATGGCTGGAGCGGCTGGACAAGACGGGTGGCACGCTGATCTG
CGTCGTGCGCGGTAGTGACGCGGCCGCGGCCCGTAAACGGCTGGACTCGGCGTTCGACAGCGGC
GATCCCGGCCTGCTCGAGCACTACCAGCAACTGGCCGCACGGACCCTGGAAGTCCTCGCCGGTG
ATATCGGCGACCCGAATCTCGGTCTGGACGACGCGACTTGGCAGCGGTTGGCCGAAACCGTCGA
CCTGATCGTCCATCCCGCCGCGTTGGTCAACCACGTCCTTCCCTACACCCAGCTGTTCGGCCCC
```

FIG. 22A

```
AATGTCGTCGGCACCGCCGAAATCGTCCGGTTGGCGATCACGGCGCGGCGCAAGCCGGTCACCT
ACCTGTCGACCGTCGGAGTGGCCGACCAGGTCGACCCGGCGGAGTATCAGGAGGACAGCGACGT
CCGCGAGATGAGCGCGGTGCGCGTCGTGCGCGAGAGTTACGCCAACGGCTACGGCAACAGCAAG
TGGGCGGGGGAGGTCCTGCTGCGCAAGCACACGATCTGTGTGGCTTGCCGGTCGCGGTGTTCC
GTTCGGACATGATCCTGGCGCACAGCCGGTACGCGGGTCAGCTCAACGTCCAGGACGTGTTCAC
CCGGCTGATCCTCAGCCTGGTCGCCACCGGCATCGCGCCGTACTCGTTCTACCGAACCGACGCG
GACGGCAACCGGCAGCGGGCCCACTATGACGGCTTGCCGGCGGACTTCACGGCGGCGGCGATCA
CCGCGCTCGGCATCCAAGCCACCGAAGGCTTCCGGACCTACGACGTGCTCAATCCGTACGACGA
TGGCATCTCCCTCGATGAATTCGTCGACTGGCTCGTCGAATCCGGCCACCCGATCCAGCGCATC
ACCGACTACAGCGACTGGTTCCACCGTTTCGAGACGGCGATCCGCGCGCTGCCGGAAAAGCAAC
GCCAGGCCTCGGTGCTGCCGTTGCTGGACGCCTACCGCAACCCCTGCCCGGCGGTCCGCGGCGC
GATACTCCCGGCCAAGGAGTTCCAAGCGGCGGTGCAAACAGCCAAAATCGGTCCGGAACAGGAC
ATCCCGCATTTGTCCGCGCCACTGATCGATAAGTACGTCAGCGATCTGGAACTGCTTCAGCTGC
TCTAA
```

FIG. 22A (Cont)

```
mavdspderlqrriaqlfaedeqvkaarpleavsaavsapgmrlaqiaatvmagyadrpaagqr
afelntddatgrtslrllprfetityrelwqrvgevaaawhhdpenplragdfvallgftsidy
atldladihlgavtvplqasaavsqliailtetsprllastpehldaaveclagttperlvvf
dyhpedddqraafesarrrladagslvivetldavrargrdlpaaplfvpdtdddplalliyts
gstgtpkgamytnrlaatmwqgnsmlqgnsqrvginlnympmshiagrislfgvlarggtayfa
aksdmstlfediglvrpteiffvprvcdmvfqryqseldrrsvagadldtldrevkadlrqnyl
ggrflvavvgsaplaaemktfmesvldlplhdgygsteagasvlldnqiqrppvldyklvdvpe
lgyfrtdrphprgelllkaettipgyykrpevtaeifdedgfyktgdivaelehdrlvyvdrrn
nvlklsqgefvtvahleavfassplirqifiygssersyllavivptddalrgrdtatlksala
esiqriakdanlqpyeiprdflietepftiangllsgiakllrpnlkerygaqleqmytdlatg
qadellalrreaadlpvletvsraakamlgvasadmrpdahftdlggdslsalsfsnllheifg
vevpvgvvvspanelrdlanyieaernsgakrptftsvhgggseiraadltldkfidartlaaa
dsiphapvpaqtvlltgangylgrflclewlerldktggtlicvvrgsdaaaarkrldsafdsg
dpgllehyqqlaartlevlagdigdpnlgddatwqrlaetvdlivhpaalvnhvlpytqlfgp
nvvgtaeivrlaitarrkpvtylstvgvadqvdpaeyqedsdvremsavrvvresyangygnsk
wagevllreahdlcglpvavfrsdmilahsryagqlnvqdvftrlilslvatgiapysfyrtda
dgnrqrahydglpadftaaaitalgiqategfrtydvlnpyddgisldefvdwlvesghpiqri
tdysdwfhrfetairalpekqrqasvlplldayrnpcpavrgailpakefqaavqtakigpeqd
iphlsaplidkyvsdlellqll*
```

FIG. 22B

```
ATGATTGAAACCATTCTGCCTGCAGGCGTTGAAAGCGCAGAACTGCTGGAATATCCGGAAGATC
TGAAAGCACATCCGGCAGAAGAACATCTGATTGCCAAAAGCGTTGAAAAACGTCGTCGTGATTT
TATTGGTGCACGTCATTGTGCACGTCTGGCACTGGCAGAACTGGGTGAACCTCCGGTTGCAATT
GGTAAAGGTGAACGTGGTGCACCGATTTGGCCTCGTGGTGTTGTTGGTAGCCTGACCCATTGTG
ATGGTTATCGTGCAGCAGCAGTTGCACATAAAATGCGCTTTCGCAGCATTGGTATTGATGCAGA
ACCGCATGCAACCCTGCCGGAAGGTGTTCTGGATAGCGTTAGCCTGCCGCCGGAACGTGAATGG
CTGAAAACCACCGATAGCGCACTGCATCTGGATCGTCTGCTGTTTTGTGCAAAAGAAGCCACCT
ATAAAGCCTGGTGGCCGCTGACAGCACGTTGGCTGGGTTTTGAAGAAGCCCATATTACCTTTGA
AATTGAAGATGGTAGCGCAGATAGCGGTAATGGCACCTTTCATAGCGAACTGCTGGTTCCGGGT
CAGACCAATGATGGTGGTACACCGCTGCTGAGCTTTGATGGTCGTTGGCTGATTGCAGATGGTT
TTATTCTGACCGCAATTGCCTATGCCTAA
```

FIG. 23A

```
mietilpagvesaelleypedlkahpaeehliaksvekrrrdfigarhcarlalaelgeppvai
gkgergapiwprgvvgslthcdgyraaavahkmrfrsigidaephatlpegvldsvslpperew
lkttdsalhldrllfcakeatykawwpltarwlgfeeahitfeiedgsadsgngtfhsellvpg
qtndggtpllsfdgrwliadgfiltaiaya*
```

FIG. 23B atgaccagcgatgttcacgacgccacagacggcgtcaccgaaaccgcactcgacgacgagcagtcgacccgccgcat
cgccgagctgtacgccaccgatcccgagttcgccgccgccgcaccgttgcccgccgtggtcgacgcggcgcacaaac
ccgggctgcggctggcagagatcctgcagaccctgttcaccggctacggtgaccgcccggcgctgggataccgcgcc
cgtgaactggccaccgacgagggcgggcgcaccgtgacgcgtctgctgccgcggttcgacacccctcacctacgccca
ggtgtggtcgcgcgtgcaagcggtcgccgcggccctgcgccacaacttcgcgcagccgatctaccccggcgacgccg
tcgcgacgatcggtttcgcgagtcccgattacctgacgctggatctcgtatgcgcctacctgggcctcgtgagtgtt
ccgctgcagcacaacgcaccggtcagccggctcgccccgatcctggccgaggtcgaaccgcggatcctcaccgtgag
cgccgaatacctcgacctcgcagtcgaatccgtgcgggacgtcaactcggtgtcgcagctcgtggtgttcgaccatc
accccgaggtcgacgaccaccgcgacgcactggcccgcgcgcgtgaacaactcgccggcaagggcatcgccgtcacc
accctggacgcgatcgccgacgagggcgccgggctgccggccgaaccgatctacaccgccgaccatgatcagcgcct
cgcgatgatcctgtacacctcgggttccaccggcgcacccaagggtgcgatgtacaccgaggcgatggtggcgcggc
tgtggaccatgtcgttcatcacgggtgaccccacgccggtcatcaacgtcaacttcatgccgctcaaccacctgggc
gggcgcatccccatttccaccgccgtgcagaacggtggaaccagttacttcgtaccggaatccgacatgtccacgct
gttcgaggatctcgcgctggtgcgcccgaccgaactcggcctggttccgcgcgtcgccgacatgctctaccagcacc
acctcgccaccgtcgaccgcctggtcacgcagggcgccgacgaactgaccgccgagaagcaggccggtgccgaactg
cgtgagcaggtgctcggcggacgcgtgatcaccggattcgtcagcaccgcaccgctggccgcggagatgagggcgtt
cctcgacatcaccctgggcgcacacatcgtcgacgctacgggctcaccgagaccggcgccgtgacacgcgacggtg
tgatcgtgcggccaccggtgatcgactacaagctgatcgacgttcccgaactcggctacttcagcaccgacaagcc
taccccgcgtggcgaactgctggtcaggtcgcaaacgctgactcccggggtactacaagcgccccgaggtcaccgcgag
cgtcttcgaccgggacggctactaccacaccggcgacgtcatggccgagaccgcacccgaccacctggtgtacgtgg
accgtcgcaacaacgtcctcaaactcgcgcagggcgagttcgtggcggtcgccaacctggaggcggtgttctccggc
gcggcgctggtgcgccagatcttcgtgtacggcaacagcgagcgcagtttccttctggccgtggtggtcccgacgcc
ggaggcgctcgagcagtacgatccggccgcgctcaaggccgcgctggccgactcgctgcagcgcaccgcacgcgacg
ccgaactgcaatcctacgaggtgccggccgatttcatcgtcgagaccgagccgttcagcgccgccaacgggctgctg
tcgggtgtcggaaaactgctgcgggcccaacctcaaagaccgctacgggcagcgcctggagcagatgtacgccgatat
cgcggccacgcaggccaaccagttgcgcgaactgcggcgcgcggccgccacacaaccggtgatcgacaccctcaccc
aggccgctgccacgatcctcggcaccgggagcgaggtggcatccgacgccacttcaccgacctgggcggggattcc
ctgtcggcgctgacactttcgaacctgctgagcgatttcttcggtttcgaagttcccgtcggcaccatcgtgaaccc
ggccaccaacctcgcccaactcgcccagcacatcgaggcgcagcgcaccgcgggtgaccgcaggccgagtttcacca
ccgtgcacggcgcggacgccaccgagatccgggcgagtgagctgaccctggacaagttcatcgacgccgaaacgctc
cgggccgcaccgggtctgcccaaggtcaccaccgagccacggacggtgttgctctcgggcgccaacggctggctggg
ccggttcctcacgttgcagtggctggaacgcctggcacctgtcggcggcaccctcatcacgatcgtgcggggccgcg
acgacgccgcggcccgcgcacggctgacccaggcctacgacaccgatcccgagttgtcccgccgcttcgccgagctg
gccgaccgccacctgcgggtggtcgcggtgacatcggcgacccgaatctgggcctcacacccgagatctggcaccg
gctcgccgccgaggtcgacctggtggtgcatccggcagcgctggtcaaccacgtgctcccctaccggcagctgttcg
gccccaacgtcgtgggcacggccgaggtgatcaagctggccctcaccgaacggatcaagcccgtcacgtacctgtcc
accgtgtcggtggccatggggatccccgacttcgaggaggacggcgacatccggaccgtgagcccggtgcgcccgct
cgacggcggatacgccaacggctacggcaacagcaagtgggccggcgaggtgctgctgcgggaggccacgatctgt
gcgggctgccgtggcgacgttccgctcggacatgatcctggcgcatccgcgctaccgcggtcaggtcaacgtgcca
gacatgttcacgcgactcctgttgagcctcttgatcaccggcgtcgcgccgcggtcgttctactcggagacggtga
gcgcccgcgggcgcactaccccggcctgacggtcgatttcgtggccgaggcggtcacgacgctcggcgcgcagcagc
gcgagggatacgtgtcctacgacgtgatgaacccgcacgacgacgggatctccctggatgtgttcgtggactggctg
atccgggcgggccatccgatcgaccgggtcgacgactacgacgactgggtgcgtcggttcgagaccgcgttgaccgc
gcttcccgagaagcgccgcacagaccgtactgccgctgctgcacgcgttccgcgctccgcaggcaccgttgcgcg
gcgcacccgaacccacggaggtgttccacgccgcggtgcgcaccgcgaaggtgggcccgggagacatcccgcacctc
gacgaggcgctgatcgacaagtacatacgcgatctgcgtgagttcggtctgatctaa

```
MTSDVHDATDGVTETALDDEQSTRRIAELYATDPEFAAAAPLPAVVDAAHKPGLRLAEILQTLFTGYGDRPALGYRA
RELATDEGGRTVTRLLPRFDTLTYAQVWSRVQAVAAALRHNFAQPIYPGDAVATIGFASPDYLTLDLVCAYLGLVSV
PLQHNAPVSRLAPILAEVEPRILTVSAEYLDLAVESVRDVNSVSQLVVFDHHPEVDDHRDALARAREQLAGKGIAVT
TLDAIADEGAGLPAEPIYTADHDQRLAMILYTSGSTGAPKGAMYTEAMVARLWTMSFITGDPTPVINVNFMPLNHLG
GRIPISTAVQNGGTSYFVPESDMSTLFEDLALVRPTELGLVPRVADMLYQHHLATVDRLVTQGADELTAEKQAGAEL
REQVLGGRVITGFVSTAPLAAEMRAFLDITLGAHIVDGYGLTETGAVTRDGVIVRPPVIDYKLIDVPELGYFSTDKP
YPRGELLVRSQTLTPGYYKRPEVTASVFDRDGYYHTGDVMAETAPDHLVYVDRRNNVLKLAQGEFVAVANLEAVFSG
AALVRQIFVYGNSERSFLLAVVVPTPEALEQYDPAALKAALADSLQRTARDAELQSYEVPADFIVETEPFSAANGLL
SGVGKLLRPNLKDRYGQRLEQMYADIAATQANQLRELRRAAATQPVIDTLTQAAATILGTGSEVASDAHFTDLGGDS
LSALTLSNLLSDFFGFEVPVGTIVNPATNLAQLAQHIEAQRTAGDRRPSFTTVHGADATEIRASELTLDKFIDAETL
RAAPGLPKVTTEPRTVLLSGANGWLGRFLTLQWLERLAPVGGTLITIVRGRDDAAARARLTQAYDTDPELSRRFAEL
ADRHLRVVAGDIGDPNLGLTPEIWHRLAAEVDLVVHPAALVNHVLPYRQLFGPNVVGTAEVIKLALTERIKPVTYLS
TVSVAMGIPDFEEDGDIRTVSPVRPLDGGYANGYGNSKWAGEVLLREAHDLCGLPVATFRSDMILAHPRYRGQVNVP
DMFTRLLLSLLITGVAPRSFYIGDGERPRAHYPGLTVDFVAEAVTTLGAQQREGYVSYDVMNPHDDGISLDVFVDWL
IRAGHPIDRVDDYDDWVRRFETALTALPEKRRAQTVLPLLHAFRAPQAPLRGAPEPTEVFHAAVRTAKVGPGDIPHL
DEALIDKYIRDLREFGLI
```

FIG. 24B

```
atgtcgactgccacccatgacgaacgactcgaccgtcgcgtccacgaactcatcgccaccgacccgcaattcgccgc
cgcccaacccgaccggcgatcaccgccgccctcgaacagcccgggctgcggctgccgcagatcatccgcaccgtgc
tcgacggctacgccgaccggccggcgctgggacagcgcgtggtggagttcgtcacggacgccaagaccgggcgcacg
tggcgcagctgctcccccgcttcgagaccatcacgtacagcgaagtagcgcagcgtgtttcggcgctgggccgcgc
cctgtccgacgacgcggtgcacccggcgacggggtgtgcgtgctgggcttcaacagcgtcgactacgccaccatcg
acatggcgctgggcgccatcggcgccgtctcggtgccgctgcagaccagcgcggcaatcagctcgctgcagccgatc
gtggccgagaccgagcccaccctgatcgcgtccagcgtgaaccagctgtccgacgcggtgcagctgatcaccggcgc
cgagcaggcgccacccggctggtggtgttcgactaccacccgcaggtcgacgaccagcgcgaggccgtccaggacg
ccgcggcgcggctgtccagcaccggcgtggccgtccagacgctggccgagctgctggagcgcggcaaggacctgccc
gccgtcgcggagccgccccgccgacgaggactcgctggccctgctgatctacacctccgggtccaccggcgccccaa
gggcgcgatgtacccacagagcaacgtcggcaagatgtggccgccgcggcagcaagaactggttcggcgagagcgccg
cgtcgatcaccctgaacttcatgccgatgagccacgtgatgggccgaagcatcctctacggcacgctgggcaacgc
ggcaccgcctacttcgccgcccgcagcgacctgtccaccctgcttgaggacctcgagctggtgcggcccaccgagct
caacttcgtcccgcggatctgggagacgctgtacggcgaattccagcgtcaggtcgagcggcggctctccgaggccg
gggacgccggcgaacgtcgcgccgtcgaggccgaggtgctggccgagcagcgccagtacctgctgggcgggcggttc
accttcgcgatgacgggctcggcgcccatctcgccggagctgcgcaactgggtcgagtcgctgctcgaaatgcacct
gatggacggctacggctccaccgaggccggaatggtgttgttcgacggggagattcagcgcccgccggtgatcgact
acaagctggtcgacgtgccggacctgggctacttcagcaccgaccggccgcatccgcgcggcgagctgctgctgcgc
accgagaacatgttcccgggctactacaagcgggccgaaaccaccgcgggcgtcttcgacgaggacggctactaccg
caccggcgacgtgttcgccgagatcgccccggaccggctggtctacgtcgaccgccgcaacaacgtgctcaagctgg
cgcagggcgaattcgtcacgctggccaagctggaggcggtgttcggcaacagcccgctgatccgccagatctacgtc
tacggcaacagcgcccagccctacctgctggcggtcgtggtgcccaccgaggaggcgctggcctcgggtgaccccga
gacgctcaagcccaagatcgccgactcgctgcagcaggtcgccaaggaggccggcctgcagtcctacgaggtgccgc
gcgacttcatcatcgagaccaccccgttcagcctggaaaacggtctgctgaccgggatccggaagctggcgtggccg
aaactgaagcagcactacggggaacggctggagcagatgtacgccgacctggccgccggacaggccaacgagctggc
cgagctgcgccgcaacggtgccaggcgccggtgttgcagaccgtgagccgcgccgcgggcgccatgctgggttcgg
ccgcctcgacctgtcccccgacgccccacttcaccgatctgggcggagactcgttgtcggcgttgacattcggcaac
ctgctgcgcgagatcttcgacgtcgacgtgccggtaggcgtgatcgtcagcccggccaacgacctggcggccatcgc
gagctacatcgaggccgagcggcagggcagcaagcgcccgacgttcgcctcggtgcacgccgggacgcgaccgtgg
tgcgcgccgcgacctgacgctggacaagttcctcgacgccgagacgctggccgccgcgccgaacctgcccaagccg
gccaccgaggtgcgcaccgtgctgctgaccggcgccaccggcttcctgggccgctacctggccctggaatggctgga
gcggatggacatggtggacggcaaggtcatcgccctggtccgggcccgctccgacgaggaggcacgcgcccggctgg
acaagaccttcgacagcggcgacccgaaactgctcgcgcactaccagcagctggccgccgatcacctggaggtcatc
gccggcgacaagggcgaggccaatctgggcctgggccaagacgtttggcaacgactggccgacacggtcgacgtgat
cgtcgaccccgccgcgctggtcaaccacgtgttgccgtacagcgagctgttcgggccaacgccctgggcaccgcgg
agctgatccggctggcgctgacgtccaagcagaagccgtacacctacgtgtccaccatcggcgtgggcgaccagatc
gagccgggcaagttcgtcgagaacgccgacatccggcagatgagcgccaccgggcgatcaacgacagctacgccaa
cggctatggcaacagcaagtgggccggcgaggtgctgctgcgcgaggcgcacgacctgtgcgggctgcccgtcgcgg
tgttccgctgcgacatgatcctggccgacaccacgtatgccgggcagctcaacctgccggacatgttcaccggctg
atgctgagcctggtggccaccgggatcgcgccggctcgttctacgagctcgacgccgacggcaaccggcagcgggc
gcactacgacggcctgccggtcgagttcatcgccgcggcgatctcgacgctgggttcgcagatcaccgacagcgaca
ccggcttccagacctaccacgtgatgaaccctacgatgacgcgtcggtctggacgagtacgtcgattggctggtg
gacgccggctattcgatcgagcggatcgccgactactccgaatggctgcggcggttcgagacctcgctgcgggccct
gccggaccggcagcgccagtactcgctgctgccgctgctgcacaactaccgcacgccggagaagccgatcaacgggt
cgatagctcccaccgacgtgttccgggcagcggtgcaggaggcgaaaatcggccccgacaaagacattccgcacgtg
tcgccgccggtcatcgtcaagtacatcaccgacctgcagctgctcggcctgctctaa
```

FIG. 25A

```
MSTATHDERLDRRVHELIATDPQFAAAQPDPAITAALEQPGLRLPQIIRTVLDGYADRPALGQRVVEFVTDAKTGRT
SAQLLPRFETITYSEVAQRVSALGRALSDDAVHPGDRVCVLGFNSVDYATIDMALGAIGAVSVPLQTSAAISSLQPI
VAETEPTLIASSVNQLSDAVQLITGAEQAPTRLVVFDYHPQVDDQREAVQDAAARLSSTGVAVQTLAELLERGKDLP
AVAEPPADEDSLALLIYTSGSTGAPKGAMYPQSNVGKMWRRGSKNWFGESAASITLNFMPMSHVMGRSILYGTLGNG
GTAYFAARSDLSTLLEDLELVRPTELNFVPRIWETLYGEFQRQVERRLSEAGDAGERRAVEAEVLAEQRQYLLGGRF
TFAMTGSAPISPELRNWVESLLEMHLMDGYGSTEAGMVLFDGEIQRPPVIDYKLVDVPDLGYFSTDRPHPRGELLLR
TENMFPGYYKRAETTAGVFDEDGYYRTGDVFAEIAPDRLVYVDRRNNVLKLAQGEFVTLAKLEAVFGNSPLIRQIYV
YGNSAQPYLLAVVVPTEEALASGDPETLKPKIADSLQQVAKEAGLQSYEVPRDFIIETTPFSLENGLLTGIRKLAWP
KLKQHYGERLEQMYADLAAGQANELAELRRNGAQAPVLQTVSRAAGAMLGSAASDLSPDAHFTDLGGDSLSALTFGN
LLREIFDVDVPVGVIVSPANDLAAIASYIEAERQGSKRPTFASVHGRDATVVRAADLTLDKFLDAETLAAAPNLPKP
ATEVRTVLLTGATGFLGRYLALEWLERMDMVDGKVIALVRARSDEEARARLDKTFDSGDPKLLAHYQQLAADHLEVI
AGDKGEANLGLGQDVWQRLADTVDVIVDPAALVNHVLPYSELFGPNALGTAELIRLALTSKQKPYTYVSTIGVGDQI
EPGKFVENADIRQMSATRAINDSYANGYGNSKWAGEVLLREAHDLCGLPVAVFRCDMILADTTYAGQLNLPDMFTRL
MLSLVATGIAPGSFYELDADGNRQRAHYDGLPVEFIAAAISTLGSQITDSDTGFQTYHVMNPYDDGVGLDEYVDWLV
DAGYSIERIADYSEWLRRFETSLRALPDRQRQYSLLPLLHNYRTPEKPINGSIAPTDVFRAAVQEAKIGPDKDIPHV
SPPVIVKYITDLQLLGLL
```

FIG. 25B

```
atgtcgccaatcacgcgtgaagagcggctcgagcgccgcatccaggacctctacgccaacgacccgcagttcgccgc
cgccaaacccgccacggcgatcaccgcagcaatcgagcggccgggtctaccgctaccccagatcatcgagaccgtca
tgaccggatacgccgatcggccggctctcgctcagcgctcggtcgaattcgtgaccgacgccggcaccggccacacc
acgctgcgactgctcccccacttcgaaaccatcagctacggcgagctttgggaccgcatcagcgcactggccgacgt
gctcagcaccgaacagacggtgaaaccgggcgacgggtctgcttgttgggcttcaacagcgtcgactacgccacga
tcgacatgactttggcgcggctgggcgcggtggccgtaccactgcagaccagcgcggcgataacccagctgcagccg
atcgtcgccgagacccagcccaccatgatcgcggccagcgtcgacgcactcgctgacgccaccgaattggctctgtc
cggtcagaccgctaccgagtcctggtgttcgaccaccaccggcaggttgacgcacaccgcgcagcggtcgaatccg
cccgggagcgcctggccggctcggcggtcgtcgaaaccctggccgaggccatcgcgcgcggcgacgtgccccgcggt
gcgtccgccggctcggcgcccggcaccgatgtgtccgacgactcgctcgcgctactgatctacacctcgggcagcac
gggtgcgcccaagggcgcgatgtaccccgacgcaacgttgcgaccttctggcgcaagcgcacctggttcgaaggcg
gctacgagccgtcgatcacgctgaacttcatgccaatgagccacgtcatgggccgccaaatcctgtacggcacgctg
tgcaatggcggcaccgcctacttcgtggcgaaaagcgatctctccaccttgttcgaagacctggcgctggtgcgcc
accgagctgaccttcgtgccgcgcgtgtgggacatggtgttcgacgagtttcagagtgaggtcgaccgccgcctgg
tcgacggcgccgaccgggtcgcgctcgaagcccaggtcaaggccgagatacgcaacgacgtgctcggtggacggtat
accagcgcactgaccggctccgcccctatctccgacgagatgaaggcgtgggtcgaggagctgctcgacatgcatct
ggtcgagggctacggctccaccgaggccgggatgatcctgatcgacggagccattcggcgcccggcggtactcgact
acaagctggtcgatgttcccgacctgggttacttcctgaccgaccggccacatccgcggggcgagttgctggtcaag
accgatagtttgttcccgggctactaccagcgagccgaagtcaccgccgacgtgttcgatgctgacggcttctaccg
gaccggcgacatcatggccgaggtcggccccgaacagttcgtgtacctcgaccgccgcaacaacgtgttgaagctgt
cgcagggcgagttcgtcaccgtctccaaactcgaagcggtgtttggcgacagcccactggtacggcagatctacatc
tacggcaacagcgccgtgcctacctgttggcggtgatcgtcccacccaggaggcgctggacgccgtgcctgtcga
ggagctcaaggcgcggctgggcgactcgctgcaagaggtcgcaaaggccgccggcctgcagtcctacgagatcccgc
gcgacttcatcatcgaaacaacaccatggacgctggagaacggcctgctcaccggcatccgcaagttggccaggccg
cagctgaaaaagcattacggcgagcttctcgagcagatctacacggacctggcacacggccaggccgacgaactgcg
ctcgctgcgccaaagcggtgccgatgcgccggtgctggtgacggtgtgccgtgcggcggccgcgctgtttgggcggca
gcgcctctgacgtccagcccgatgcgcacttcaccgatttgggcggcgactcgctgtcggcgctgtcgttcaccaac
ctgctgcacgagatcttcgacatcgaagtgccggtgggcgtcatcgtcagcccgccaacgacttgcaggccctggc
cgactacgtcgaggcggctcgcaaacccggctcgtcacggccgaccttcgcctcggtccacggcgcctcgaatgggc
aggtcaccgaggtgcatgccggtgacctgtcccggacaaattcatcgatgccgcaaccctggccgaagctccccgg
ctgccgccgcaaacacccaagtgcgcaccgtgctgctgaccggcgccaccggcttcctcgggcgctacctggcct
ggaatggctggagcggatggacctggtcgacggcaaactgatctgcctggtccgggccaagtccgacaccgaagcac
gggcgcggctggacaagacgttcgacagcggcgaccccgaactgctggcccactaccgcgcactggccggcgaccac
ctcgaggtgctcgccggtgacaagggcgaagccgacctcggactggaccggcagacctggcaacgcctggccgacac
ggtcgacctgatcgtcgaccccgcggccctggtcaaccacgtactgccatacagccagctgttcgggcccaacgcgc
tgggcaccgccgagctgctgcggctggcgctcacctccaagatcaagccctacagctacacctcgacaatcggtgtc
gccgaccagatcccgcgtcggcgttcaccgaggacgccgacatccgggtcatcagcgccacccgcgcggtcgacga
cagctacgccaatggctactcgaacagcaagtgggccggcgaggtgctgttgcgcgaggcgcatgacctgtgtggcc
tgccggttgcggtgttccgctgcgacatgatcctggccgacaccacatgggcgggacagctcaatgtgccggacatg
ttcacccggatgatcctgagcctggcggccaccggtatcgcgccgggttcgttctatgagcttgcggccgacggcgc
ccggcaacgcgccactatgacggtctgcccgtcgagttcatcgccgaggcgatttcgactttgggtgcgcagagcc
aggatggtttccacacgtatcacgtgatgaaccctacgacgacggcatcggactcgacgagttcgtcgactggctc
aacgagtccggttgccccatccagcgcatcgctgactatggcgactggctgcagcgcttcgaaaccgcactgcgcg
actgcccgatcggcagcggcacagctcactgctgccgctgttgcacaactatcggcagccggagcggcccgtccgcg
ggtcgatcgccctaccgatcgcttccgggcagcggtgcaagaggccaagatcggccccgacaaagacattccgcac
gtcggcgcgccgatcatcgtgaagtacgtcagcgacctgcgcctactcggcctgctctaa
```

FIG. 26A

```
MSPITREERLERRIQDLYANDPQFAAAKPATAITAAIERPGLPLPQIIETVMTGYADRPALAQRSVEFVTDAGTGHT
TLRLLPHFETISYGELWDRISALADVLSTEQTVKPGDRVCLLGFNSVDYATIDMTLARLGAVAVPLQTSAAITQLQP
IVAETQPTMIAASVDALADATELALSGQTATRVLVFDHHRQVDAHRAAVESARERLAGSAVVETLAEAIARGDVPRG
ASAGSAPGTDVSDDSLALLIYTSGSTGAPKGAMYPRRNVATFWRKRTWFEGGYEPSITLNFMPMSHVMGRQILYGTL
CNGGTAYFVAKSDLSTLFEDLALVRPTELTFVPRVWDMVFDEFQSEVDRRLVDGADRVALEAQVKAEIRNDVLGGRY
TSALTGSAPISDEMKAWVEELLDMHLVEGYGSTEAGMILIDGAIRRPAVLDYKLVDVPDLGYFLTDRPHPRGELLVK
TDSLFPGYYQRAEVTADVFDADGFYRTGDIMAEVGPEQFVYLDRRNNVLKLSQGEFVTVSKLEAVFGDSPLVRQIYI
YGNSARAYLLAVIVPTQEALDAVPVEELKARLGDSLQEVAKAAGLQSYEIPRDFIIETTPWTLENGLLTGIRKLARP
QLKKHYGELLEQIYTDLAHGQADELRSLRQSGADAPVLVTVCRAAAALLGGSASDVQPDAHFTDLGGDSLSALSFTN
LLHEIFDIEVPVGVIVSPANDLQALADYVEAARKPGSSRPTFASVHGASNGQVTEVHAGDLSLDKFIDAATLAEAPR
LPAANTQVRTVLLTGATGFLGRYLALEWLERMDLVDGKLICLVRAKSDTEARARLDKTFDSGDPELLAHYRALAGDH
LEVLAGDKGEADLGLDRQTWQRLADTVDLIVDPAALVNHVLPYSQLFGPNALGTAELLRLALTSKIKPYSYTSTIGV
ADQIPPSAFTEDADIRVISATRAVDDSYANGYSNSKWAGEVLLREAHDLCGLPVAVFRCDMILADTTWAGQLNVPDM
FTRMILSLAATGIAPGSFYELAADGARQRAHYDGLPVEFIAEAISTLGAQSQDGFHTYHVMNPYDDGIGLDEFVDWL
NESGCPIQRIADYGDWLQRFETALRALPDRQRHSSLLPLLHNYRQPERPVRGSIAPTDRFRAAVQEAKIGPDKDIPH
VGAPIIVKYVSDLRLLGLL
```

FIG. 26B

```
atgagcaccgcaacccatgatgaacgtctggatcgtcgtgttcatgaactgattgcaaccgatc
cgcagtttgcagcagcacagccggatcctgcaattaccgcagcactggaacagcctggtctgcg
tctgccgcagattattcgtaccgttctggatggttatgcagatcgtccggcactgggtcagcgt
gttgttgaatttgttaccgatgcaaaaaccggtcgtaccagcgcacagctgctgcctcgttttg
aaaccattacctatagcgaagttgcacagcgtgttagcgcactgggtcgtgcactgagtgatga
tgcagttcatccgggtgatcgtgtttgtgttctgggttttaatagcgttgattatgccaccatt
gatatggcactgggtgcaattggtgcagttagcgttccgctgcagaccagcgcagcaattagca
gcctgcagccgattgttgcagaaaccgaaccgaccctgattgcaagcagcgttaatcagctgtc
agatgcagttcagctgattaccggtgcagaacaggcaccgacccgtctggttgtttttgattat
catccgcaggttgatgatcagcgtgaagcagttcaggatgcagcagcacgtctgagcagcaccg
gtgttgcagttcagaccctggcagaactgctggaacgtggtaaagatctgcctgcagttgcaga
accgcctgcagatgaagatagcctggcactgctgatttataccagcggtagcacaggtgcaccg
aaaggtgcaatgtatccgcagagcaatgttggtaaaatgtggcgtcgtggtagcaaaaattggt
ttggtgaaagcgcagcaagcattaccctgaatttcatgccgatgagccatgttatgggtcgtag
cattctgtatggcaccctgggtaatggtggcaccgcatattttgcagcacgtagcgatctgagc
accctgctggaagatctggaactggttcgtccgaccgaactgaattttgttccgcgtatttggg
aaaccctgtatggtgaatttcagcgtcaggttgaacgtcgtctgagcgaagctggcgatgccgg
tgaacgtcgtgcagttgaagcagaagttctggcagaacagcgtcagtatctgctgggtggtcgt
tttacctttgcaatgaccggtagcgcaccgattagtccggaactgcgtaattgggttgaaagcc
tgctggaaatgcatctgatggatggctatggtagcaccgaagcaggtatggttctgtttgatgg
cgaaattcagcgtccgcctgtgattgattataaactggttgatgttccggatctgggttatttt
agcaccgatcgtccgcatccgcgtggtgaactgctgctgcgtaccgaaaatatgtttccgggtt
attataaacgtgcagaaaccaccgcaggcgttttgatgaagatggttattatcgtaccggtga
tgtgtttgcagaaattgcaccggatcgtctggtttatgttgatcgtcgtaataatgttctgaaa
ctggcacagggtgaatttgtgaccctggccaaactggaagcagttttggtaatagtccgctga
ttcgtcagatttatgtgtatggtaatagcgcacagccgtatctgctggcagttgttgttccgac
cgaagaggcactggcaagcggtgatccggaaaccctgaaaccgaaaattgcagatagcctgcag
caggttgcaaaagaagcaggtctgcagagctatgaagttccgcgtgattttattattgaaacca
ccccgtttagcctggaaaatggtctgctgaccggtattcgtaaactggcatggccgaaactgaa
acagcattatggtgaacgcctggaacaaatgtatgcagatctggcagcaggtcaggcaaatgaa
ctggccgaactgcgtcgtaatggtgcacaggcaccggttctgcagaccgttagccgtgcagccg
gtgcaatgctgggtagcgcagccagcgatctgagtccggatgcacattttaccgatctgggtgg
tgatagcctgagcgcactgaccctttggtaatctgctgcgtgaaattttgatgttgatgtgccg
gttggtgttattgttagtccggctaatgatctggcagccattgcaagctatattgaagcagaac
gtcagggtagcaaacgtccgacctttgcaagcgttcatggtcgtgatgcaaccgttgttcgtgc
agcagatctgaccctggataaatttctggatgcagaaaccctggcagcagcaccgaatctgccg
aaaccggcaaccgaagttcgtaccgtgctgctgacaggtgcaaccggttttctgggtcgttatc
tggcactggaatggctggaacgtatggatatggttgatggtaaagttattgcactggttcgtgc
ccgtagtgatgaagaagcacgcgcacgtctggataaaacctttgatagtggtgatccgaaactg
ctggcacattatcagcagctggctgcagatcatctggaagttattgccggtgataaaggtgaag
caaatctgggtctgggtcaggatgtttggcagcgtctggcagataccgttgatgttattgtgga
tccggcagcactggttaatcatgttctgccgtatagcgaactgtttggtccgaatgcactgggc
```

FIG. 27A

```
accgcagaactgattcgtctggcactgaccagcaaacagaaaccgtatacctatgttagcacca
ttggtgttggcgatcagattgaacccgggtaaatttgttgaaaatgccgatattcgtcagatgag
cgcaacccgtgcaattaatgatagctatgcaaatggctacggcaatagcaaatgggcaggcgaa
gttctgctgcgcgaagcacatgatctgtgtggtctgccggttgcagttttcgttgtgatatga
ttctggccgataccacctatgcaggtcagctgaatctgccggatatgtttacccgtctgatgct
gagcctggttgcaaccggtattgcaccgggtagcttttatgaactggatgcagatggtaatcgt
cagcgtgcacattatgatggcctgccggttgaatttattgcagcagccattagcaccctgggtt
cacagattaccgatagcgataccggttttcagacctatcatgttatgaacccgtatgatgatgg
tgttggtctggatgaatatgttgattggctggttgatgccggttatagcattgaacgtattgca
gattatagcgaatggctgcgtcgctttgaaacctcactgcgtgcactgccggatcgtcagcgcc
agtatagcctgctgccgctgctgcacaattatcgtacaccggaaaaaccgattaatggtagcat
tgcaccgaccgatgttttcgtgcagccgttcaagaagccaaaattggtccggataaagatatt
ccgcatgttagccctccggtgattgttaaatatattaccgatctgcagctgctgggtctgctgt
aa
```

FIG. 27A(Cont)

```
MSTATHDERLDRRVHELIATDPQFAAAQPDPAITAALEQPGLRLPQIIRTVLDGYADRPALGQR
VVEFVTDAKTGRTSAQLLPRFETITYSEVAQRVSALGRALSDDAVHPGDRVCVLGFNSVDYATI
DMALGAIGAVSVPLQTSAAISSLQPIVAETEPTLIASSVNQLSDAVQLITGAEQAPTRLVVFDY
HPQVDDQREAVQDAAARLSSTGVAVQTLAELLERGKDLPAVAEPPADEDSLALLIYTSGSTGAP
KGAMYPQSNVGKMWRRGSKNWFGESAASITLNFMPMSHVMGRSILYGTLGNGGTAYFAARSDLS
TLLEDLELVRPTELNFVPRIWETLYGEFQRQVERRLSEAGDAGERRAVEAEVLAEQRQYLLGGR
FTFAMTGSAPISPELRNWVESLLEMHLMDGYGSTEAGMVLFDGEIQRPPVIDYKLVDVPDLGYF
STDRPHPRGELLLRTENMFPGYYKRAETTAGVFDEDGYYRTGDVFAEIAPDRLVYVDRRNNVLK
LAQGEFVTLAKLEAVFGNSPLIRQIYVYGNSAQPYLLAVVVPTEEALASGDPETLKPKIADSLQ
QVAKEAGLQSYEVPRDFIIETTPFSLENGLLTGIRKLAWPKLKQHYGERLEQMYADLAAGQANE
LAELRRNGAQAPVLQTVSRAAGAMLGSAASDLSPDAHFTDLGGDSLSALTFGNLLREIFDVDVP
VGVIVSPANDLAAIASYIEAERQGSKRPTFASVHGRDATVVRAADLTLDKFLDAETLAAAPNLP
KPATEVRTVLLTGATGFLGRYLALEWLERMDMVDGKVIALVRARSDEEARARLDKTFDSGDPKL
LAHYQQLAADHLEVIAGDKGEANLGLGQDVWQRLADTVDVIVDPAALVNHVLPYSELFGPNALG
TAELIRLALTSKQKPYTYVSTIGVGDQIEPGKFVENADIRQMSATRAINDSYANGYGNSKWAGE
VLLREAHDLCGLPVAVFRCDMILADTTYAGQLNLPDMFTRLMLSLVATGIAPGSFYELDADGNR
QRAHYDGLPVEFIAAAISTLGSQITDSDTGFQTYHVMNPYDDGVGLDEYVDWLVDAGYSIERIA
DYSEWLRRFETSLRALPDRQRQYSLLPLLHNYRTPEKPINGSIAPTDVFRAAVQEAKIGPDKDI
PHVSPPVIVKYITDLQLLGLL
```

FIG. 27B

MICROORGANISMS FOR PRODUCING METHACRYLIC ACID AND METHACRYLATE ESTERS AND METHODS RELATED THERETO

This application claims the benefit of priority of U.S. Provisional application Ser. No. 61/471,078, filed Apr. 1, 2011, and U.S. Provisional application Ser. No. 61/571,232, filed Jun. 22, 2011, and U.S. Provisional application Ser. No. 61/509,560, filed Jul. 19, 2011, and U.S. Provisional application Ser. No. 61/510,054, filed Jul. 20, 2011, and U.S. Provisional application Ser. No. 61/512,348, filed Jul. 27, 2011, each of which the entire contents are incorporated herein by reference.

Incorporated herein by reference is the Sequence Listing being submitted via EFS-Web as an ASCII text file named 12956-122-999_SequenceListing.TXT, created Nov. 9, 2012, and being 78,078 bytes in size.

BACKGROUND OF THE INVENTION

The present invention relates generally to biosynthetic processes, and more specifically to organisms having methacrylic acid biosynthetic capabilities.

Methyl methacrylate (MMA) is an organic compound with the formula $CH_2=C(CH_3)CO_2CH_3$. This colourless liquid is the methyl ester of methacrylic acid (MMA) and is the monomer for the production of the transparent plastic polymethyl methacrylate (PMMA).

The principal application of methyl methacrylate is the production of polymethyl methacrylate acrylic plastics. Also, methyl methacrylate is used for the production of the co-polymer methyl methacrylate-butadiene-styrene (MBS), used as a modifier for PVC. Methyl methacrylate polymers and co-polymers are used for waterborne coatings, such as latex paint. Uses are also found in adhesive formulations. Contemporary applications include the use in plates that keep light spread evenly across liquid crystal display (LCD) computer and TV screens. Methyl methacrylate is also used to prepare corrosion casts of anatomical organs, such as coronary arteries of the heart.

Methacrylic acid, or 2-methyl-2-propenoic acid, is a low molecular weight carboxylic acid that occurs naturally in small amounts in the oil of Roman chamomile. It is a corrosive liquid with an acrid unpleasant odor. It is soluble in warm water and miscible with most organic solvents. Methacrylic acid polymerizes readily upon heating or treatment with a catalytic amount of strong acid, such as HCl. The resulting polymer is a ceramic-looking plastic. Methacrylic acid is used industrially in the preparation of its esters, known collectively as methacrylates, such as methyl methacrylate. The methacrylates have numerous uses, most notably in the manufacture of polymers.

Most commercial producers apply an acetone cyanohydrin (ACH) route to produce methacrylic acid (MAA), with acetone and hydrogen cyanide as raw materials. The intermediate cyanohydrin is converted with sulfuric acid to a sulfate ester of the methacrylamide, hydrolysis of which gives ammonium bisulfate and MAA. Some producers start with an isobutylene or, equivalently, tert-butanol, which is oxidized to methacrolein, and again oxidized to methacrylic acid. MAA is then esterified with methanol to MMA.

The conventional production process, using the acetone cyanohydrin route, involves the conversion of hydrogen cyanide (HCN) and acetone to acetone cyanohydrin, which then undergoes acid assisted hydrolysis and esterification with methanol to give MMA. Difficulties in handling potentially deadly HCN along with the high costs of byproduct disposal (1.2 tons of ammonium bisulfate are formed per ton of MMA) have sparked a great deal of research aimed at cleaner and more economical processes. A number of new processes have been commercialized over the last two decades and many more are close to commercialization. The Asahi "Direct Metha" route, which involves the oxidation of isobutylene to methacrolein, which is then mixed with methanol, oxidized with air, and esterified to MMA, has been described as an economical process.

Other than MMA polymers, the other major product of this industry is crude methacrylic acid, which accounts for about 20 percent of the total production of MMA. Crude MAA is processed into butyl methacrylates and/or "glacial" MAA, which is highly purified crude MAA. Glacial MAA can be used directly as a comonomer in various polymers and is also used to make a variety of small volume methacrylates. On the other hand, MAA can also be converted into MMA via esterification with methanol.

Thus, there exists a need for alternative methods for effectively producing compounds such as methacrylic acid. The present invention satisfies this need and provides related advantages as well.

SUMMARY OF INVENTION

The invention provides a non-naturally occurring microbial organism having a methacrylic acid, methacrylate ester such as methyl methacrylate, 3-hydroxyisobutyrate and/or 2-hydroxyisobutyrate pathway. The microbial organism contains at least one exogenous nucleic acid encoding an enzyme in a methacrylic acid pathway. The invention additionally provides a method for producing methacrylic acid, methacrylate ester such as methyl methacrylate, 3-hydroxyisobutyrate and/or 2-hydroxyisobutyrate. The method can include culturing methacrylic acid, methacrylate ester, 3-hydroxyisobutyrate and/or 2-hydroxyisobutyrate producing microbial organism, where the microbial organism expresses at least one exogenous nucleic acid encoding a methacrylic acid pathway enzyme in a sufficient amount to produce methacrylic acid, methacrylate ester, 3-hydroxyisobutyrate and/or 2-hydroxyisobutyrate, under conditions and for a sufficient period of time to produce methacrylic acid, methacrylate ester, 3-hydroxyisobutyrate and/or 2-hydroxyisobutyrate.

The invention also provides non-naturally occurring microbial organisms containing methacrylate ester or methyl methacrylate pathways comprising at least one exogenous nucleic acid encoding a methacrylate ester or a methyl methacrylate enzyme expressed in a sufficient amount to produce methacrylate ester or methyl methacrylate. The microbial organism contains at least one exogenous nucleic acid encoding an enzyme in the methacrylate ester or methyl methacrylate pathway and at least one exogenous nucleic acid that encodes an enzyme that increases the yields of methacrylate ester or methyl methacrylate by (i) enhancing carbon fixation via the reductive TCA cycle, and/or (ii) accessing additional reducing equivalents from gaseous carbon sources and/or syngas components such as CO, $CO_2$, and/or $H_2$. In some aspects, the non-naturally occurring microbial organisms comprise (i) a reductive TCA pathway comprising at least one exogenous nucleic acid encoding a reductive TCA pathway enzyme, wherein the at least one exogenous nucleic acid is selected from an ATP-citrate lyase, a citrate lyase, a fumarate reductase, and an alpha-ketoglutarate:ferredoxin oxidoreductase; (ii) a reductive TCA pathway comprising at least one exogenous nucleic acid encoding a reductive TCA pathway enzyme, wherein the at least one exogenous nucleic acid is selected from a pyruvate:ferredoxin oxidoreductase, a phosphoenolpyruvate carboxylase, a phosphoenolpyruvate carboxykinase, a CO dehydrogenase, and an $H_2$ hydrogenase; or (iii) at least one exogenous nucleic acid encodes an enzyme selected from a CO dehydrogenase, an $H_2$ hydrogenase, and combinations thereof. The invention additionally provides methods of using such microbial organisms to produce methacrylate ester or methyl methacrylate, by culturing a non-naturally occurring microbial organism containing methacrylate ester or methyl methacrylate pathways under conditions and for a sufficient period of time to produce methacrylate ester or methyl methacrylate.

BRIEF DESCRIPTION OF THE DRAWINGS

FIG. 17A shows the pathways for fixation of $CO_2$ to succinyl-CoA using the reductive TCA cycle. FIG. 17B shows exemplary pathways for the biosynthesis of 3-hydroxyisobutric acid and methacrylic acid from succinyl-CoA; the enzymatic transformations shown are carried out by the following enzymes: A. Methylmalonyl-CoA mutase, B. Methylmalonyl-CoA epimerase, C. Methylmalonyl-CoA reductase, D. Methylmalonate semialdehyde reductase, E. 3-Hydroxyisobutyrate dehydratase.

FIG. 18A shows the pathways for fixation of $CO_2$ to succinate using the reductive TCA cycle. FIG. 18B shows exemplary pathways for the biosynthesis of 3-hydroxyisobutyric acid and methacrylic acid from succinate; the enzymatic transformations shown are carried out by the following enzymes: A. 3-Hydroxyisobutyryl-CoA dehydratase, B. Methacrylyl-CoA synthetase, transferase or hydrolase, C. Succinyl-CoA transferase or synthetase, D. Succinyl-CoA reductase (aldehyde forming), E. 4-Hydroxybutyrate dehydrogenase, F. 4-Hydroxybutyrate kinase, G. Phosphotrans-4-hydroxybutyrylase, H. Succinate reductase, I. Succinyl-CoA reductase (alcohol forming), J. 4-Hydroxybutyryl-CoA synthetase or transferase, K. 4-Hydroxybutyryl-CoA mutase, L. 3-Hydroxyisobutyryl-CoA synthetase, transferase or hydrolase, M. 3-Hydroxyisobutyrate dehydratase.

FIGS. 19A and 19B show exemplary pathways. FIG. 19A shows the pathways for fixation of $CO_2$ to acetyl-CoA and pyruvate using the reductive TCA cycle. FIG. 19B shows exemplary pathways for the biosynthesis of methacrylate from acetyl-CoA and pyruvate; the enzymatic transformations shown are carried out by the following enzymes: 1. Citramalate synthase, 2. Citramalate dehydratase (citraconate forming), 3. Citraconate decarboxylase, 4. Citramalyl-CoA lyase, 5. Citramalyl-CoA transferase, synthetase or hydrolase, 6. Citramalate dehydratase (mesaconate forming), 7. Citraconate isomerase, 8. Mesaconate decarboxylase, 9. Aconitate decarboxylase, 10. Itaconate isomerase, 11. Itaconyl-CoA transferase or synthetase, 12. Itaconyl-CoA hydratase.

FIGS. 20A and 20B show exemplary pathways. FIG. 20A shows the pathways for fixation of $CO_2$ to acetyl-CoA using the reductive TCA cycle. FIG. 20B shows exemplary pathways for the biosynthesis of methacrylic acid and 2-hydroxyisobutyric acid from acetyl-CoA.

FIG. 21A shows the pathways for fixation of CO2 to acetyl-CoA using the reductive TCA cycle. FIG. 21B shows exemplary pathways for the biosynthesis of methacrylic acid and 3-hydroxyisobutyric acid from acetyl-CoA; the enzymatic transformations shown are carried out by the following enzymes: 1) Acetoacetyl-CoA thiolase (AtoB), 2) 3-Hydroxybutyryl-CoA dehydrogenase (Hbd), 3) Crotonase (Crt), 4) Crotonyl-CoA hydratase (4-Budh), 5) 4-hydroxybutyryl-CoA mutase, 6) 3-hydroxyisobutyryl-CoA hydrolase, synthetase, or transferase, 7) 3-hydroxyisobutyric acid dehydratase, 8) 3-hydroxyisobutyryl-CoA dehydratase, 9) methacrylyl-CoA hydrolase, synthetase, or transferase.

FIG. 22A shows the nucleotide sequence (SEQ ID NO:1) of carboxylic acid reductase from *Nocardia iowensis* (GNM 720), and FIG. 22B shows the encoded amino acid sequence (SEQ ID NO:2).

FIG. 23A shows the nucleotide sequence (SEQ ID NO:3) of phosphpantetheine transferase, which was codon optimized, and FIG. 23B shows the encoded amino acid sequence (SEQ ID NO:4).

FIG. 24A shows the nucleotide sequence (SEQ ID NO:5) of carboxylic acid reductase from *Mycobacterium smegmatis* mc(2)155 (designated 890), and FIG. 24B shows the encoded amino acid sequence (SEQ ID NO:6).

FIG. 25A shows the nucleotide sequence (SEQ ID NO:7) of carboxylic acid reductase from *Mycobacterium avium* subspecies paratuberculosis K-10 (designated 891), and FIG. 25B shows the encoded amino acid sequence (SEQ ID NO:8).

FIG. 26A shows the nucleotide sequence (SEQ ID NO:9) of carboxylic acid reductase from *Mycobacterium marinum* M (designated 892), and FIG. 26B shows the encoded amino acid sequence (SEQ ID NO:10).

FIG. 27A shows the nucleotide sequence (SEQ ID NO:11) of carboxylic acid reductase designated 891GA, and FIG. 27B shows the encoded amino acid sequence (SEQ ID NO:12).

DETAILED DESCRIPTION OF THE INVENTION

The present invention is directed to the design and production of cells and organisms having biosynthetic production capabilities for methacrylic acid, methacrylate ester, 3-hydroxyisobutyrate and/or 2-hydroxyisobutyrate. As disclosed herein, metabolic pathways can be designed and recombinantly engineered to achieve the biosynthesis of methacrylic acid, methacrylate ester, 3-hydroxyisobutyrate and/or 2-hydroxyisobutyrate in microbial organisms such as *Escherichia coli* and other cells or organisms. Biosynthetic production of methacrylic acid, methacrylate ester, 3-hydroxyisobutyrate and/or 2-hydroxyisobutyrate is confirmed by construction of strains having the designed metabolic genotype. These metabolically engineered cells or organisms also can be subjected to adaptive evolution to further augment methacrylic acid, methacrylate ester, 3-hydroxyisobutyrate and/or 2-hydroxyisobutyrate biosynthesis, including under conditions approaching theoretical maximum growth.

Figure 1:
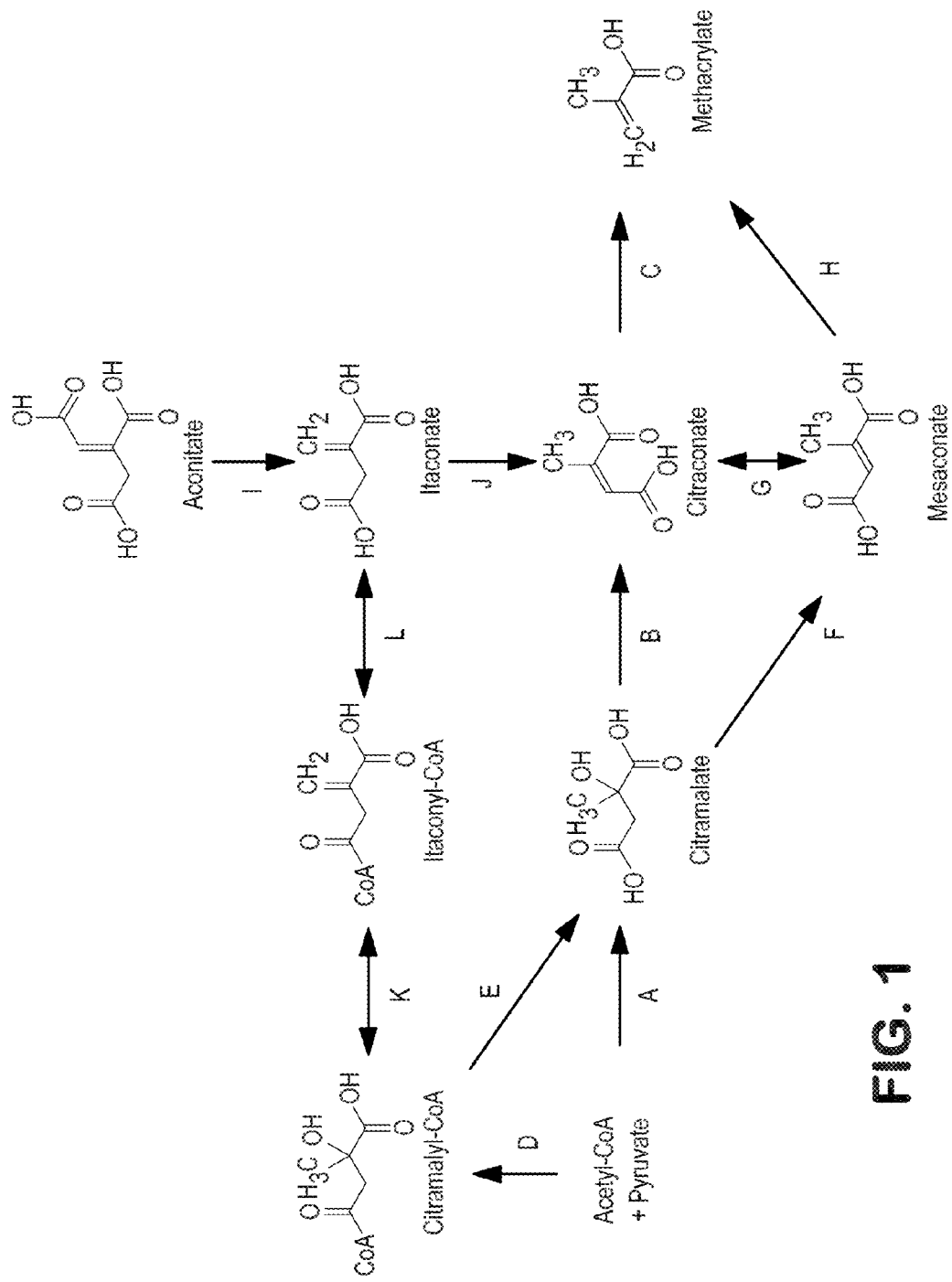
FIG. 1 shows exemplary pathways to methacrylic acid from pyruvate and acetyl-CoA, and aconitate. The enzymes are A. citramalate synthase, B. citramalate dehydratase (citraconate forming), C. citraconate decarboxylase, D. citramalyl-CoA lyase, E. citramalyl-CoA transferase, synthetase or hydrolase, F. citramalate dehydratase (mesaconate forming), G. citraconate isomerase, H. mesaconate decarboxylase, I. aconitate decarboxylase, J. itaconate isomerase, K. citramalyl-CoA dehydratase and L. itaconyl-CoA transferase, synthetase or hydrolase.

Microorganisms for the production of methacrylic acid (MAA) have been previously described (see, for example, WO 2009/135074 and U.S. publication 2009/0275096, which is incorporated herein by reference). The present invention provides additional pathways for engineering microbial organisms for the production of methacrylic acid (MAA). FIG. 1 provides exemplary pathways to MAA from acetyl-CoA and pyruvate via intermediate citramalate. Also shown are pathways to MAA from aconitate. In one pathway, acetyl-CoA and pyruvate are first converted to citramalate by citramalate synthase. Dehydration of citramalate can yield either citraconate (Step B) or mesaconate (Step C). Mesaconate and citraconate are interconverted by a cis/trans isomerase in Step G. Decarboxylation of mesaconate (Step H) or citraconate (Step C) yields MAA. In an alternate pathway, citramalate is formed from acetyl-CoA and pyruvate via a citramalyl-CoA intermediate in Steps D and E, catalyzed by citramalyl-CoA lyase and citramalyl-coA hydrolase, transferase or synthetase.

The invention also encompasses pathways from aconitate to MAA. In one pathway, aconitate is first decarboxylated to itaconate by aconitate decarboxylase (Step I). Itaconate is then isomerized to citraconate by itaconate delta-isomerase (Step J). Conversion of citraconate to MAA proceeds either directly by decarboxylation or indirectly via mesaconate. In an alternate pathway, the itaconate intermediate is first converted to itaconyl-CoA by a CoA transferase or synthetase (Step L). Hydration of itaconyl-CoA yields citramalyl-CoA, which can then be converted to MAA as described previously. Additionally details and embodiments of the exemplary MAA pathways are described herein below.

As used herein, the term "non-naturally occurring" when used in reference to a microbial organism or microorganism of the invention is intended to mean that the microbial organism has at least one genetic alteration not normally found in a naturally occurring strain of the referenced species, including wild-type strains of the referenced species. Genetic alterations include, for example, modifications introducing expressible nucleic acids encoding metabolic polypeptides, other nucleic acid additions, nucleic acid deletions and/or other functional disruption of the microbial organism's genetic material. Such modifications include, for example, coding regions and functional fragments thereof, for heterologous, homologous or both heterologous and homologous polypeptides for the referenced species. Additional modifications include, for example, non-coding regulatory regions in which the modifications alter expression of a gene or operon. Exemplary metabolic polypeptides include enzymes or proteins within a methacrylic acid, methacrylate ester, 3-hydroxyisobutyrate and/or 2-hydroxyisobutyrate biosynthetic pathway.

A metabolic modification refers to a biochemical reaction that is altered from its naturally occurring state. Therefore, non-naturally occurring microorganisms can have genetic modifications to nucleic acids encoding metabolic polypeptides, or functional fragments thereof. Exemplary metabolic modifications are disclosed herein.

As used herein, the term "isolated" when used in reference to a microbial organism is intended to mean an organism that is substantially free of at least one component as the referenced microbial organism is found in nature. The term includes a microbial organism that is removed from some or all components as it is found in its natural environment. The term also includes a microbial organism that is removed from some or all components as the microbial organism is found in non-naturally occurring environments. Therefore, an isolated microbial organism is partly or completely separated from other substances as it is found in nature or as it is grown, stored or subsisted in non-naturally occurring environments. Specific examples of isolated microbial organisms include partially pure microbes, substantially pure microbes and microbes cultured in a medium that is non-naturally occurring.

As used herein, the terms "microbial," "microbial organism" or "microorganism" are intended to mean any organism that exists as a microscopic cell that is included within the domains of archaea, bacteria or eukarya. Therefore, the term is intended to encompass prokaryotic or eukaryotic cells or organisms having a microscopic size and includes bacteria, archaea and eubacteria of all species as well as eukaryotic microorganisms such as yeast and fungi. The term also includes cell cultures of any species that can be cultured for the production of a biochemical.

As used herein, "methacrylic acid," having the chemical formula $CH_2=C(CH_3)CO_2$ (see FIG. 1) (IUPAC name 2-methyl-2-propenoic acid), is the acid form of methacrylate, and it is understood that methacrylic acid and methacrylate can be used interchangeably throughout to refer to the compound in any of its neutral or ionized forms, including any salt forms thereof. It is understood by those skilled understand that the specific form will depend on the pH.

As used herein, "methacrylate ester," refers to a compound having the chemical formula $CH_2=C(CH_3)COOR$ (see FIGS. 28 and 29), wherein R is a lower alkyl, that is C1 to C6, branched or straight chain, including, without limitation, methyl, ethyl, n-propyl, n-butyl, i-propyl, sec-butyl, and tert-butyl, pentyl, or hexyl, any of which can be unsaturation thereby being, for example, propenyl, butenyl, pentyl, and hexenyl. Exemplary methacrylate esters include, without limitation, methyl methacrylate, ethyl methacrylate, and n-propyl methacrylate. Methacrylate esters as used herein also include other R groups that are medium to long chain groups, that is C7-C22, wherein the methacrylate esters are derived from fatty alcohols, such as heptyl, octyl, nonyl, decyl, undecyl, lauryl, tridecyl, myristyl, pentadecyl, cetyl, palmitolyl, heptadecyl, stearyl, nonadecyl, arachidyl, heneicosyl, and behenyl alcohols, any one of which can be optionally branched and/or contain unsaturations.

As used herein, the term "CoA" or "coenzyme A" is intended to mean an organic cofactor or prosthetic group (nonprotein portion of an enzyme) whose presence is required for the activity of many enzymes (the apoenzyme) to form an active enzyme system. Coenzyme A functions in certain condensing enzymes, acts in acetyl or other acyl group transfer and in fatty acid synthesis and oxidation, pyruvate oxidation and in other acetylation.

As used herein, the term "substantially anaerobic" when used in reference to a culture or growth condition is intended to mean that the amount of oxygen is less than about 10% of saturation for dissolved oxygen in liquid media. The term also is intended to include sealed chambers of liquid or solid medium maintained with an atmosphere of less than about 1% oxygen.

"Exogenous" as it is used herein is intended to mean that the referenced molecule or the referenced activity is introduced into the host microbial organism. The molecule can be introduced, for example, by introduction of an encoding nucleic acid into the host genetic material such as by integration into a host chromosome or as non-chromosomal genetic material such as a plasmid. Therefore, the term as it is used in reference to expression of an encoding nucleic acid refers to introduction of the encoding nucleic acid in an expressible form into the microbial organism. When used in reference to a biosynthetic activity, the term refers to an activity that is introduced into the host reference organism. The source can be, for example, a homologous or heterologous encoding nucleic acid that expresses the referenced activity following introduction into the host microbial organism. Therefore, the term "endogenous" refers to a referenced molecule or activity that is present in the host. Similarly, the term when used in reference to expression of an encoding nucleic acid refers to expression of an encoding nucleic acid contained within the microbial organism. The term "heterologous" refers to a molecule or activity derived from a source other than the referenced species whereas "homologous" refers to a molecule or activity derived from the host microbial organism. Accordingly, exogenous expression of an encoding nucleic acid of the invention can utilize either or both a heterologous or homologous encoding nucleic acid.

It is understood that when more than one exogenous nucleic acid is included in a microbial organism that the more than one exogenous nucleic acids refers to the referenced encoding nucleic acid or biosynthetic activity, as discussed above. It is further understood, as disclosed herein, that such more than one exogenous nucleic acids can be introduced into the host microbial organism on separate nucleic acid molecules, on polycistronic nucleic acid molecules, or a combination thereof, and still be considered as more than one exogenous nucleic acid. For example, as disclosed herein a microbial organism can be engineered to express two or more exogenous nucleic acids encoding a desired pathway enzyme or protein. In the case where two exogenous nucleic acids encoding a desired activity are introduced into a host microbial organism, it is understood that the two exogenous nucleic acids can be introduced as a single nucleic acid, for example, on a single plasmid, on separate plasmids, can be integrated into the host chromosome at a single site or multiple sites, and still be considered as two exogenous nucleic acids. Similarly, it is understood that more than two exogenous nucleic acids can be introduced into a host organism in any desired combination, for example, on a single plasmid, on separate plasmids, can be integrated into the host chromosome at a single site or multiple sites, and still be considered as two or more exogenous nucleic acids, for example three exogenous nucleic acids. Thus, the number of referenced exogenous nucleic acids or biosynthetic activities refers to the number of encoding nucleic acids or the number of biosynthetic activities, not the number of separate nucleic acids introduced into the host organism.

The non-naturally occurring microbial organisms of the invention can contain stable genetic alterations, which refers to microorganisms that can be cultured for greater than five generations without loss of the alteration. Generally, stable genetic alterations include modifications that persist greater than 10 generations, particularly stable modifications will persist more than about 25 generations, and more particularly, stable genetic modifications will be greater than 50 generations, including indefinitely.

Those skilled in the art will understand that the genetic alterations, including metabolic modifications exemplified herein, are described with reference to a suitable host organism such as E. coli and their corresponding metabolic reactions or a suitable source organism for desired genetic material such as genes for a desired metabolic pathway. However, given the complete genome sequencing of a wide variety of organisms and the high level of skill in the area of genomics, those skilled in the art will readily be able to apply the teachings and guidance provided herein to essentially all other organisms. For example, the E. coli metabolic alterations exemplified herein can readily be applied to other species by incorporating the same or analogous encoding nucleic acid from species other than the referenced species. Such genetic alterations include, for example, genetic alterations of species homologs, in general, and in particular, orthologs, paralogs or nonorthologous gene displacements.

An ortholog is a gene or genes that are related by vertical descent and are responsible for substantially the same or identical functions in different organisms. For example, mouse epoxide hydrolase and human epoxide hydrolase can be considered orthologs for the biological function of hydrolysis of epoxides. Genes are related by vertical descent when, for example, they share sequence similarity of sufficient amount to indicate they are homologous, or related by evolution from a common ancestor. Genes can also be considered orthologs if they share three-dimensional structure but not necessarily sequence similarity, of a sufficient amount to indicate that they have evolved from a common ancestor to the extent that the primary sequence similarity is not identifiable. Genes that are orthologous can encode proteins with sequence similarity of about 25% to 100% amino acid sequence identity. Genes encoding proteins sharing an amino acid similarity less that 25% can also be considered to have arisen by vertical descent if their three-dimensional structure also shows similarities. Members of the serine protease family of enzymes, including tissue plasminogen activator and elastase, are considered to have arisen by vertical descent from a common ancestor.

Orthologs include genes or their encoded gene products that through, for example, evolution, have diverged in structure or overall activity. For example, where one species encodes a gene product exhibiting two functions and where such functions have been separated into distinct genes in a second species, the three genes and their corresponding products are considered to be orthologs. For the production of a biochemical product, those skilled in the art will understand that the orthologous gene harboring the metabolic activity to be introduced or disrupted is to be chosen for construction of the non-naturally occurring microorganism. An example of orthologs exhibiting separable activities is where distinct activities have been separated into distinct gene products between two or more species or within a single species. A specific example is the separation of elastase proteolysis and plasminogen proteolysis, two types of serine protease activity, into distinct molecules as plasminogen activator and elastase. A second example is the separation of mycoplasma 5'-3' exonuclease and Drosophila DNA polymerase III activity. The DNA polymerase from the first species can be considered an ortholog to either or both of the exonuclease or the polymerase from the second species and vice versa.

In contrast, paralogs are homologs related by, for example, duplication followed by evolutionary divergence and have similar or common, but not identical functions. Paralogs can originate or derive from, for example, the same species or from a different species. For example, microsomal epoxide hydrolase (epoxide hydrolase I) and soluble epoxide hydrolase (epoxide hydrolase II) can be considered paralogs because they represent two distinct enzymes, co-evolved from a common ancestor, that catalyze distinct reactions and have distinct functions in the same species. Paralogs are proteins from the same species with significant sequence similarity to each other suggesting that they are homologous, or related through co-evolution from a common ancestor. Groups of paralogous protein families include HipA homologs, luciferase genes, peptidases, and others.

A nonorthologous gene displacement is a nonorthologous gene from one species that can substitute for a referenced gene function in a different species. Substitution includes, for example, being able to perform substantially the same or a similar function in the species of origin compared to the referenced function in the different species. Although generally, a nonorthologous gene displacement will be identifiable as structurally related to a known gene encoding the referenced function, less structurally related but functionally similar genes and their corresponding gene products nevertheless will still fall within the meaning of the term as it is used herein. Functional similarity requires, for example, at least some structural similarity in the active site or binding region of a nonorthologous gene product compared to a gene encoding the function sought to be substituted. Therefore, a nonorthologous gene includes, for example, a paralog or an unrelated gene.

Therefore, in identifying and constructing the non-naturally occurring microbial organisms of the invention having methacrylic acid biosynthetic capability, those skilled in the art will understand with applying the teaching and guidance provided herein to a particular species that the identification of metabolic modifications can include identification and inclusion or inactivation of orthologs. To the extent that paralogs and/or nonorthologous gene displacements are present in the referenced microorganism that encode an enzyme catalyzing a similar or substantially similar metabolic reaction, those skilled in the art also can utilize these evolutionarily related genes.

Orthologs, paralogs and nonorthologous gene displacements can be determined by methods well known to those skilled in the art. For example, inspection of nucleic acid or amino acid sequences for two polypeptides will reveal sequence identity and similarities between the compared sequences. Based on such similarities, one skilled in the art can determine if the similarity is sufficiently high to indicate the proteins are related through evolution from a common ancestor. Algorithms well known to those skilled in the art, such as Align, BLAST, Clustal W and others compare and determine a raw sequence similarity or identity, and also determine the presence or significance of gaps in the sequence which can be assigned a weight or score. Such algorithms also are known in the art and are similarly applicable for determining nucleotide sequence similarity or identity. Parameters for sufficient similarity to determine relatedness are computed based on well known methods for calculating statistical similarity, or the chance of finding a similar match in a random polypeptide, and the significance of the match determined. A computer comparison of two or more sequences can, if desired, also be optimized visually by those skilled in the art. Related gene products or proteins can be expected to have a high similarity, for example, 25% to 100% sequence identity. Proteins that are unrelated can have an identity which is essentially the same as would be expected to occur by chance, if a database of sufficient size is scanned (about 5%). Sequences between 5% and 24% may or may not represent sufficient homology to conclude that the compared sequences are related. Additional statistical analysis to determine the significance of such matches given the size of the data set can be carried out to determine the relevance of these sequences.

Exemplary parameters for determining relatedness of two or more sequences using the BLAST algorithm, for example, can be as set forth below. Briefly, amino acid sequence alignments can be performed using BLASTP version 2.0.8 (Jan. 5.1999) and the following parameters: Matrix: 0 BLOSUM62; gap open: 11; gap extension: 1; x_dropoff: 50; expect: 10.0; wordsize: 3; filter: on. Nucleic acid sequence alignments can be performed using BLASTN version 2.0.6 (Sep. 16.1998) and the following parameters: Match: 1; mismatch: −2; gap open: 5; gap extension: 2; x_dropoff: 50; expect: 10.0; wordsize: 11; filter: off. Those skilled in the art will know what modifications can be made to the above parameters to either increase or decrease the stringency of the comparison, for example, and determine the relatedness of two or more sequences.

In one embodiment, the invention provides a non-naturally occurring microbial organism having a methacrylate ester pathway comprising at least one exogenous nucleic acid encoding a methacrylate ester pathway enzyme expressed in a sufficient amount to produce a methacrylate ester, where the methacrylate ester pathway comprises an alcohol transferase or an ester-forming enzyme, and a dehydratase. In a particular embodiment, the microbial organism comprises two exogenous nucleic acids each encoding a methacrylate ester pathway enzyme. For example, the two exogenous nucleic acids can encode an alcohol transferase and a dehydratase or alternatively an ester-forming enzyme and a dehydratase. In a particular embodiment, the at least one exogenous nucleic acid can be a heterologous nucleic acid. In another embodiment, the non-naturally occurring microbial organism can be in a substantially anaerobic culture medium. The invention additionally provides a method for producing methacrylate ester, comprising culturing the non-naturally occurring microbial organism disclosed herein having a methacrylate ester pathway under conditions and for a sufficient period of time to produce methacrylate ester.

The invention additionally provides a non-naturally occurring microbial organism having a methyl methacrylate pathway comprising at least one exogenous nucleic acid encoding a methyl methacrylate pathway enzyme expressed in a sufficient amount to produce a methyl methacrylate, the methyl methacrylate pathway comprising an alcohol transferase or an ester-forming enzyme, and a dehydratase. In a further embodiment, the microbial organism can comprise two exogenous nucleic acids each encoding a methyl methacrylate pathway enzyme. In a particular embodiment, the two exogenous nucleic acids can encode an alcohol transferase and a dehydratase or alternatively an ester-forming enzyme and a dehydratase. In another embodiment, the at least one exogenous nucleic acid can a heterologous nucleic acid. In another embodiment, the non-naturally occurring microbial organism can be in a substantially anaerobic culture medium. The invention also provides a method for producing methyl methacrylate by culturing a non-naturally occurring microbial organism having a methyl methacrylate pathway under conditions and for a sufficient period of time to produce methyl methacrylate.

In one embodiment, the invention provides a non-naturally occurring microbial organism, comprising a microbial organism having a methacrylate ester pathway comprising at least one exogenous nucleic acid encoding a methacrylate ester pathway enzyme expressed in a sufficient amount to produce a methacrylate ester, said methacrylate ester pathway comprising an alcohol transferase or an ester-forming enzyme, and a dehydratase. In one aspect, the non-naturally occurring microbial organism comprises two exogenous nucleic acids each encoding a methacrylate ester pathway enzyme. In one aspect, the two exogenous nucleic acids encode an alcohol transferase and a dehydratase or alternatively an ester-forming enzyme and a dehydratase. In another aspect, the at least one exogenous nucleic acid is a heterologous nucleic acid. In another aspect, the non-naturally occurring microbial organism is in a substantially anaerobic culture medium.

In one embodiment, the invention provides a non-naturally occurring microbial organism, wherein said dehydratase converts a 3-hydroxyisobutyrate ester or a 2-hydroxyisobutyrate ester to said methacrylate ester. In one embodiment, the invention provides a non-naturally occurring microbial organism, wherein said alcohol transferase coverts 3-hydroxyisobutyryl-CoA to a 3-hydroxyisobutyrate ester or 2-hydroxyisobutyryl-CoA to 2-hydroxyisobutyrate ester.

In one embodiment, the invention provides a non-naturally occurring microbial organism, wherein said microbial organism further comprises a methacyrlate ester pathway comprising at least one exogenous nucleic acid encoding a methacrylate ester pathway enzyme expressed in a sufficient amount to produce a methacrylate ester, said methacrylate ester pathway comprising a pathway selected from: (a) a 3-hydroxyisobutyrate-CoA transferase or a 3-hydroxyisobutyrate-CoA synthetase; an alcohol transferase; and a dehydratase; (b) a 3-hydroxyisobutyrate ester-forming enzyme and a dehydratasedehydratase; (c) a 2-hydroxyisobutyrate-CoA transferase or a 2-hydroxyisobutyrate-CoA synthetase; an alcohol transferase; and a dehydratase; or (d) a 2-hydroxyisobutyrate ester-forming enzyme and a dehydratase. In one aspect, the invention provides a method for producing methacrylate ester by culturing the non-naturally occurring microbial organism as disclosed herein under conditions and for a sufficient period of time to produce methacrylate ester.

In one embodiment, the invention provides a non-naturally occurring microbial organism, comprising a microbial organism having a methyl methacrylate pathway comprising at least one exogenous nucleic acid encoding a methyl methacrylate pathway enzyme expressed in a sufficient amount to produce a methyl methacrylate, said methyl methacrylate pathway comprising an alcohol transferase or an ester-forming enzyme, and a dehydratase. In one aspect, the microbial organism comprises two exogenous nucleic acids each encoding a methyl methacrylate pathway enzyme. In another aspect, the two exogenous nucleic acids encode an alcohol transferase and a dehydratase or alternatively an ester-forming enzyme and a dehydratase. In another aspect, the at least one exogenous nucleic acid is a heterologous nucleic acid. In another aspect, the non-naturally occurring microbial organism is in a substantially anaerobic culture medium.

In one embodiment, the invention provides a method for producing methyl methacrylate, comprising culturing the non-naturally occurring microbial organism as described herein under conditions and for a sufficient period of time to produce methyl methacrylate.

In one embodiment, the invention provides a method for producing a methacrylate ester comprising, culturing a non-naturally occurring microbial organism under conditions and for a sufficient period of time to produce a 3-hydroxyisobutyrate ester, wherein said non-naturally occurring microbial organism comprises an exogenous nucleic acid encoding an alcohol transferase or a 3-hydroxyisobutyrate ester-forming enzyme expressed in a sufficient amount to produce a 3-hydroxyisobutyrate ester, and chemically dehydrating said 3-hydroxyisobutyrate ester to produce a methacrylate ester.

In one embodiment, the invention provides a method for producing a methacrylate ester comprising, culturing a non-naturally occurring microbial organism under conditions and for a sufficient period of time to produce a 2-hydroxyisobutyrate ester, wherein said non-naturally occurring microbial organism comprises an exogenous nucleic acid encoding an alcohol transferase or a 2-hydroxyisobutyrate ester-forming enzyme expressed in a sufficient amount to produce a 2-hydroxyisobutyrate ester, and chemically dehydrating said 2-hydroxyisobutyrate ester to produce a methacrylate ester.

In one embodiment, the invention provides a method for producing methyl methacrylate comprising, culturing a non-naturally occurring microbial organism under conditions and for a sufficient period of time to produce methyl-3-hydroxyisobutyrate, wherein said non-naturally occurring microbial organism comprises an exogenous nucleic acid encoding an alcohol transferase or an ester-forming enzyme expressed in a sufficient amount to produce methyl-3-hydroxyisobutyrate, and chemically dehydrating said methyl-3-hydroxyisobutyrate to produce methyl methacrylate.

In one aspect of the above methods, the exogenous nucleic acid is a heterologous nucleic acid. In another aspect of the above methods, the non-naturally occurring microbial organism is in a substantially anaerobic culture medium.

In one embodiment, the invention provides a method wherein said microbial organism further comprises a 3-hydroxyisobutyrate ester pathway comprising at least one exogenous nucleic acid encoding a 3-hydroxyisobutyrate ester pathway enzyme expressed in a sufficient amount to produce a 3-hydroxyisobutyrate ester, said 3-hydroxyisobutyrate ester pathway comprising a pathway selected from: (a) a 3-hydroxyisobutyrate-CoA transferase or a 3-hydroxyisobutyrate-CoA synthetase; and an alcohol transferase; or (b) a 3-hydroxyisobutyrate ester-forming enzyme. In another embodiment, the invention provides a method wherein said microbial organism further comprises a 2-hydroxyisobutyrate ester pathway comprising at least one exogenous nucleic acid encoding a 2-hydroxyisobutyrate ester pathway enzyme expressed in a sufficient amount to produce a 2-hydroxyisobutyrate ester, said 2-hydroxyisobutyrate ester pathway comprising a pathway selected from: (a) a 2-hydroxyisobutyrate-CoA transferase or a 2-hydroxyisobutyrate-CoA synthetase; and an alcohol transferase; or (b) a 2-hydroxyisobutyrate ester-forming enzyme.

As disclosed herein, the invention provides non-naturally occurring microbial organisms having a methacrylic acid pathway comprising at least one exogenous nucleic acid encoding a methacrylic acid pathway enzyme expressed in a sufficient amount to produce methacrylic acid. Exemplary pathways include, but are not limited to, the pathways disclosed in FIG. 1. Exemplary methacrylic acid pathways include, for example, the pathways corresponding to the enzymes shown in FIG. 1 as follows and as discussed below in more detail: pathway (1) A/B/C; pathway (2) A/B/G/H; pathway (3) A/F/G/C; pathway (4) A/F/H; pathway (5) D/E/B/C; pathway (6) D/E/B/G/H; pathway (7) D/E/F/H; pathway (8) D/E/F/G/C; pathway (9) I/J/C; pathway (10) I/J/G/H; pathway (11) I/L/K/E/B/C; pathway (12) I/L/K/E/B/G/H; pathway (13) I/L/K/E/F/H; and pathway (14) I/L/K/E/F/G/C.

In a particular embodiment, the invention provides a non-naturally occurring microbial organism, comprising a microbial organism having a methacrylic acid pathway comprising at least one exogenous nucleic acid encoding a methacrylic acid pathway enzyme expressed in a sufficient amount to produce methacrylic acid, the methacrylic acid pathway comprising citramalate synthase (A), citramalate dehydratase (citraconate forming) (B), and citraconate decarboxylase (C) (FIG. 1, pathway (1) A/B/C). As disclosed herein, the microbial organism can comprise more than one exogenous nucleic acid encoding a methacrylic acid pathway enzyme, including up to all enzymes in a pathway, for example, three exogenous nucleic acids encode citramalate synthase, citramalate dehydratase (citraconate forming), and citraconate decarboxylase.

In a particular embodiment, MAA producing non-naturally occurring microbial organism of the invention can have at least one exogenous nucleic acid that is a heterologous nucleic acid. In another embodiment the non-naturally occurring microbial organism producing MAA can be in a substantially anaerobic culture medium.

In another embodiment, the invention provides a non-naturally occurring microbial organism comprising a methacrylic acid pathway comprising at least one exogenous nucleic acid encoding a methacrylic acid pathway enzyme expressed in a sufficient amount to produce methacrylic acid, the methacrylic acid pathway comprising citramalate synthase (A), citramalate dehydratase (citraconate forming) (B), citraconate isomerase (G), and mesaconate decarboxylase (H) (FIG. 1, pathway (2) A/B/G/H). In still another embodiment, the invention provides a non-naturally occurring microbial organism, comprising a methacrylic acid pathway comprising at least one exogenous nucleic acid encoding a methacrylic acid pathway enzyme expressed in a sufficient amount to produce methacrylic acid, the methacrylic acid pathway comprising citramalate synthase (A), citramalate dehydratase (mesaconate forming) (F) citraconate isomerase (G), and citraconate decarboxylase (C) (FIG. 1, pathway (3) A/F/G/C).

In a further embodiment, the invention provides a non-naturally occurring microbial organism, comprising a methacrylic acid pathway comprising at least one exogenous nucleic acid encoding a methacrylic acid pathway enzyme expressed in a sufficient amount to produce methacrylic acid, the methacrylic acid pathway comprising citramalate synthase (A), citramalate dehydratase (mesaconate forming) (F), and mesaconate decarboxylase (H) (FIG. 1, pathway (4) A/F/H). In yet a further embodiment, the invention provides a non-naturally occurring microbial organism, comprising a methacrylic acid pathway comprising at least one exogenous nucleic acid encoding a methacrylic acid pathway enzyme expressed in a sufficient amount to produce methacrylic acid, the methacrylic acid pathway comprising citramalyl-CoA lyase (D), citramalyl-CoA transferase, synthetase or hydrolase (E), citramalate dehydratase (citraconate forming) (B), and citraconate decarboxylase (C) (FIG. 1, pathway (5) D/E/B/C).

In an additional embodiment, the invention provides a non-naturally occurring microbial organism, comprising a methacrylic acid pathway comprising at least one exogenous nucleic acid encoding a methacrylic acid pathway enzyme expressed in a sufficient amount to produce methacrylic acid, the methacrylic acid pathway comprising citramalyl-CoA lyase (D), citramalyl-CoA transferase, synthetase or hydrolase (E), citramalate dehydratase (citraconate forming) (B), citraconate isomerase (G), and mesaconate decarboxylase (H) (FIG. 1, pathway (6) D/E/B/G/H). In still another embodiment, the invention provides a non-naturally occurring microbial organism, comprising a methacrylic acid pathway comprising at least one exogenous nucleic acid encoding a methacrylic acid pathway enzyme expressed in a sufficient amount to produce methacrylic acid, the methacrylic acid pathway comprising citramalyl-CoA lyase (D), citramalyl-CoA transferase, synthetase or hydrolase (E), citramalate dehydratase (mesaconate forming) (F), and mesaconate decarboxylase (H) (FIG. 1, pathway (7) D/E/F/H).

In another embodiment, the invention provides a non-naturally occurring microbial organism, comprising a methacrylic acid pathway comprising at least one exogenous nucleic acid encoding a methacrylic acid pathway enzyme expressed in a sufficient amount to produce methacrylic acid, the methacrylic acid pathway comprising citramalyl-CoA lyase (D), citramalyl-CoA transferase, synthetase or hydrolase (E), citramalate dehydratase (mesaconate forming) (F), citraconate isomerase (G), and citraconate decarboxylase (C) (FIG. 1, pathway (8) D/E/F/G/C). Additionally, the invention provides a non-naturally occurring microbial organism, comprising a methacrylic acid pathway comprising at least one exogenous nucleic acid encoding a methacrylic acid pathway enzyme expressed in a sufficient amount to produce methacrylic acid, the methacrylic acid pathway comprising aconitate decarboxylase (I), itaconate isomerase (J), and citraconate decarboxylase (C) (FIG. 1, pathway (9) I/J/C).

In yet a further embodiment, the invention provides a non-naturally occurring microbial organism, comprising a methacrylic acid pathway comprising at least one exogenous nucleic acid encoding a methacrylic acid pathway enzyme expressed in a sufficient amount to produce methacrylic acid, the methacrylic acid pathway comprising aconitate decarboxylase (I), itaconate isomerase (J), citraconate isomerase (G), and mesaconate decarboxylase (H) (FIG. 1, pathway (10) I/J/G/H). In an additional embodiment, the invention provides a non-naturally occurring microbial organism, comprising a methacrylic acid pathway comprising at least one exogenous nucleic acid encoding a methacrylic acid pathway enzyme expressed in a sufficient amount to produce methacrylic acid, the methacrylic acid pathway comprising aconitate decarboxylase (I), itaconyl-CoA transferase, synthetase or hydrolase (L), citramalyl-CoA dehydratase (K), citramalyl-CoA transferase, synthetase or hydrolase (E), citramalate dehydratase (citraconate forming) (B), and citraconate decarboxylase (C) (FIG. 1, pathway (11) I/L/K/E/B/C).

The invention also provides a non-naturally occurring microbial organism, comprising a methacrylic acid pathway comprising at least one exogenous nucleic acid encoding a methacrylic acid pathway enzyme expressed in a sufficient amount to produce methacrylic acid, the methacrylic acid pathway comprising aconitate decarboxylase (I), itaconyl-CoA transferase, synthetase or hydrolase (L), citramalyl-CoA dehydratase (K), citramalyl-CoA transferase, synthetase or hydrolase (E), citramalate dehydratase (citraconate forming) (B), citraconate isomerase (G), and mesaconate decarboxylase (H) (FIG. 1, pathway (12) I/L/K/E/B/G/H). In still a further embodiment, the invention provides a non-naturally occurring microbial organism, comprising a microbial organism having a methacrylic acid pathway comprising at least one exogenous nucleic acid encoding a methacrylic acid pathway enzyme expressed in a sufficient amount to produce methacrylic acid, the methacrylic acid pathway comprising aconitate decarboxylase (I), itaconyl-CoA transferase, synthetase or hydrolase (L), citramalyl-CoA dehydratase (K), citramalyl-CoA transferase, synthetase or hydrolase (E), citramalate dehydratase (mesaconate forming) (F), and mesaconate decarboxylase (H) (FIG. 1, pathway (13) I/L/K/E/F/H). In an additional embodiment, the invention provides a non-naturally occurring microbial organism, comprising a methacrylic acid pathway comprising at least one exogenous nucleic acid encoding a methacrylic acid pathway enzyme expressed in a sufficient amount to produce methacrylic acid, the methacrylic acid pathway comprising aconitate decarboxylase (I), itaconyl-CoA transferase, synthetase or hydrolase (L), citramalyl-CoA dehydratase (K), citramalyl-CoA transferase, synthetase or hydrolase (E), citramalate dehydratase (mesaconate forming) (F), citraconate isomerase (G), and citraconate decarboxylase (C) (FIG. 1, pathway (14) I/L/K/E/F/G/C).

In an additional embodiment, the invention provides a non-naturally occurring microbial organism having a methacrylic acid pathway, wherein the non-naturally occurring microbial organism comprises at least one exogenous nucleic acid encoding an enzyme or protein that converts a substrate to a product selected from the group consisting of acetyl-CoA and pyruvate to citramalate, citramalate to citraconate, and citraconate to methacrylate; acetyl-CoA and pyruvate to citramalyl-CoA, citramalyl-CoA to citramalate, citramalate to citraconate, and citraconate to methyacrylate; aconitate to itaconate, itaconate to itaconyl-CoA, itaconyl-CoA to citramalyl-CoA, citramalyl-CoA to citramalate, citramalate to mesaconate, mesaconate to methacrylate, and so forth such as the reactions described herein and those substrates and products shown in the exemplary methacrylic acid pathways shown in FIG. 1. One skilled in the art will understand that these are merely exemplary and that any of the substrate-product pairs disclosed herein suitable to produce a desired product and for which an appropriate activity is available for the conversion of the substrate to the product can be readily determined by one skilled in the art based on the teachings herein. Thus, the invention provides a non-naturally occurring microbial organism containing at least one exogenous nucleic acid encoding an enzyme or protein, where the enzyme or protein converts the substrates and products of a methacrylic acid pathway, such as that shown in FIG. 1. Additionally provided is a methacrylic acid pathway comprising acetoacetyl-CoA thiolase, acetoacetyl-CoA reductase, crotonase, 4-hydroxybutyryl-CoA dehydratase (or crotonyl-CoA hydratase, 4-hydroxy), 4-hydroxybutyryl-CoA mutase, 3-hydroxyisobutyryl-CoA synthetase or 3-hydroxyisobutyryl-CoA hydrolase or 3-hydroxyisobutyryl-CoA transferase, and 3-hydroxyisobutyrate dehydratase (see Example XXII and FIG. 21). Also provided is a methacrylic acid pathway comprising acetoacetyl-CoA thiolase, acetoacetyl-CoA reductase, crotonase, 4-hydroxybutyryl-CoA dehydratase, 4-hydroxybutyryl-CoA mutase, 3-hydroxyisobutyryl-CoA dehydratase, and methacrylyl-CoA synthetase or methacrylyl-CoA hydrolase or methacrylyl-CoA transferase (see Example XXII and FIG. 21).

While generally described herein as a microbial organism that contains a methacrylic acid pathway, it is understood that the invention additionally provides a non-naturally occurring microbial organism comprising at least one exogenous nucleic acid encoding a methacrylic acid pathway enzyme expressed in a sufficient amount to produce an intermediate of a methacrylic acid pathway. For example, as disclosed herein, a methacrylic acid pathway is exemplified in FIG. 1. Therefore, in addition to a microbial organism containing a methacrylic acid pathway that produces methacrylic acid, the invention additionally provides a non-naturally occurring microbial organism comprising at least one exogenous nucleic acid encoding a methacrylic acid pathway enzyme, where the microbial organism produces a methacrylic acid pathway intermediate, for example, citramalyl-CoA, itaconyl-CoA, itaconate, citraconate, citramalate and mesaconate.

It is understood that any of the pathways disclosed herein, as described in the Examples and exemplified in the pathways of FIGS. 1-30, can be utilized to generate a non-naturally occurring microbial organism that produces any pathway intermediate or product, as desired. As disclosed herein, such a microbial organism that produces an intermediate can be used in combination with another microbial organism expressing downstream pathway enzymes to produce a desired product. However, it is understood that a non-naturally occurring microbial organism that produces a methacrylic acid pathway intermediate can be utilized to produce the intermediate as a desired product.

This invention is also directed, in part to engineered biosynthetic pathways to improve carbon flux through a central metabolism intermediate en route to methacrylic acid, methacrylate ester, 3-hydroxyisobutyrate and/or 2-hydroxyisobutyrate. The present invention provides non-naturally occurring microbial organisms having one or more exogenous genes encoding enzymes that can catalyze various enzymatic transformations en route to methacrylic acid, methacrylate ester, 3-hydroxyisobutyrate and/or 2-hydroxyisobutyrate. In some embodiments, these enzymatic transformations are part of the reductive tricarboxylic acid (RTCA) cycle and are used to improve product yields, including but not limited to, from carbohydrate-based carbon feedstock.

In numerous engineered pathways, realization of maximum product yields based on carbohydrate feedstock is hampered by insufficient reducing equivalents or by loss of reducing equivalents and/or carbon to byproducts. In accordance with some embodiments, the present invention increases the yields of methacrylic acid, methacrylate ester, 3-hydroxyisobutyrate and/or 2-hydroxyisobutyrate by (i) enhancing carbon fixation via the reductive TCA cycle, and/or (ii) accessing additional reducing equivalents from gaseous carbon sources and/or syngas components such as CO, $CO_2$, and/or $H_2$. In addition to syngas, other sources of such gases include, but are not limited to, the atmosphere, either as found in nature or generated.

Figure 12:
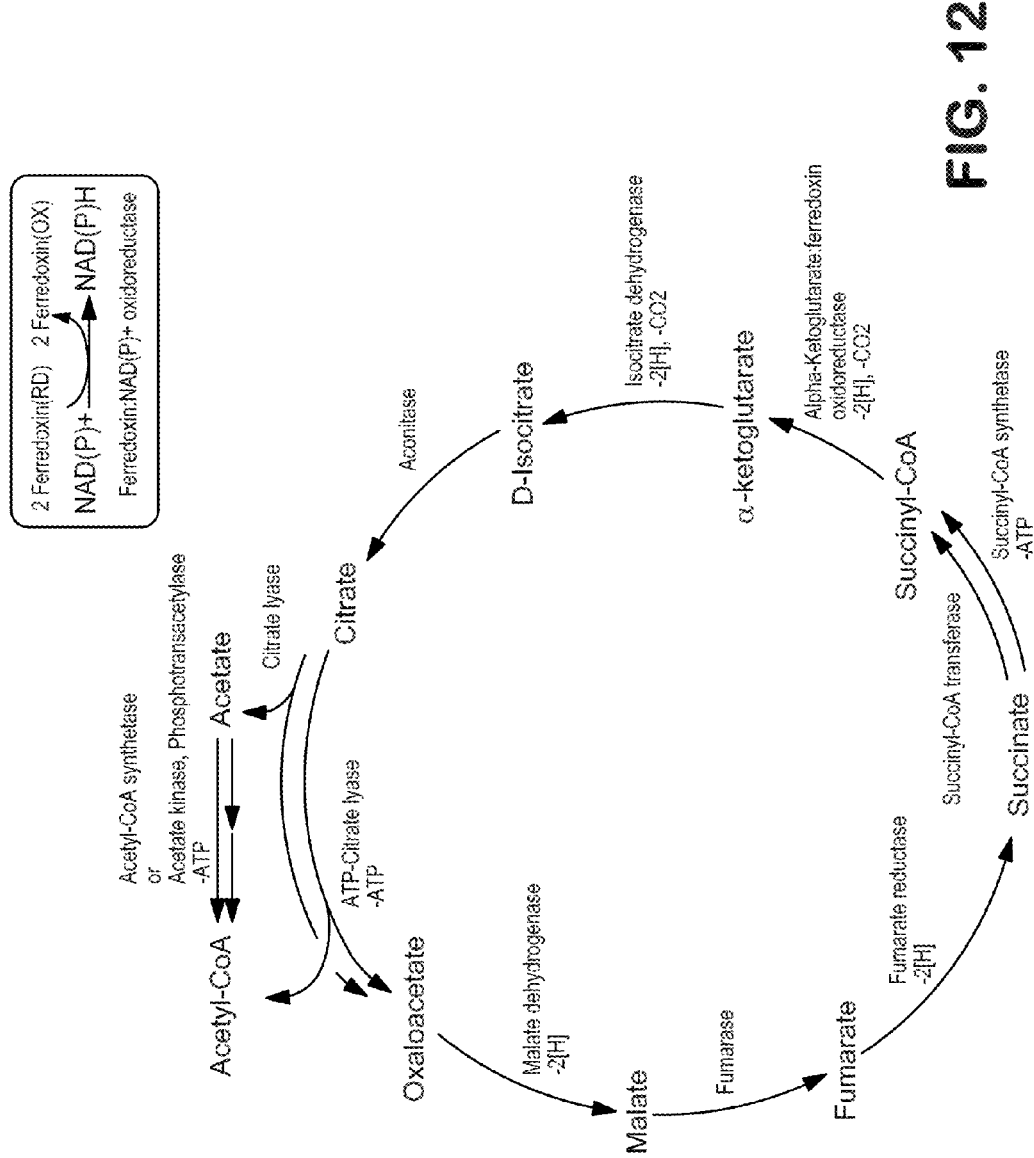
FIG. 12 shows the reverse TCA cycle for fixation of $CO_2$ on carbohydrates as substrates. The enzymatic transformations are carried out by the enzymes as shown.
Figure 13:
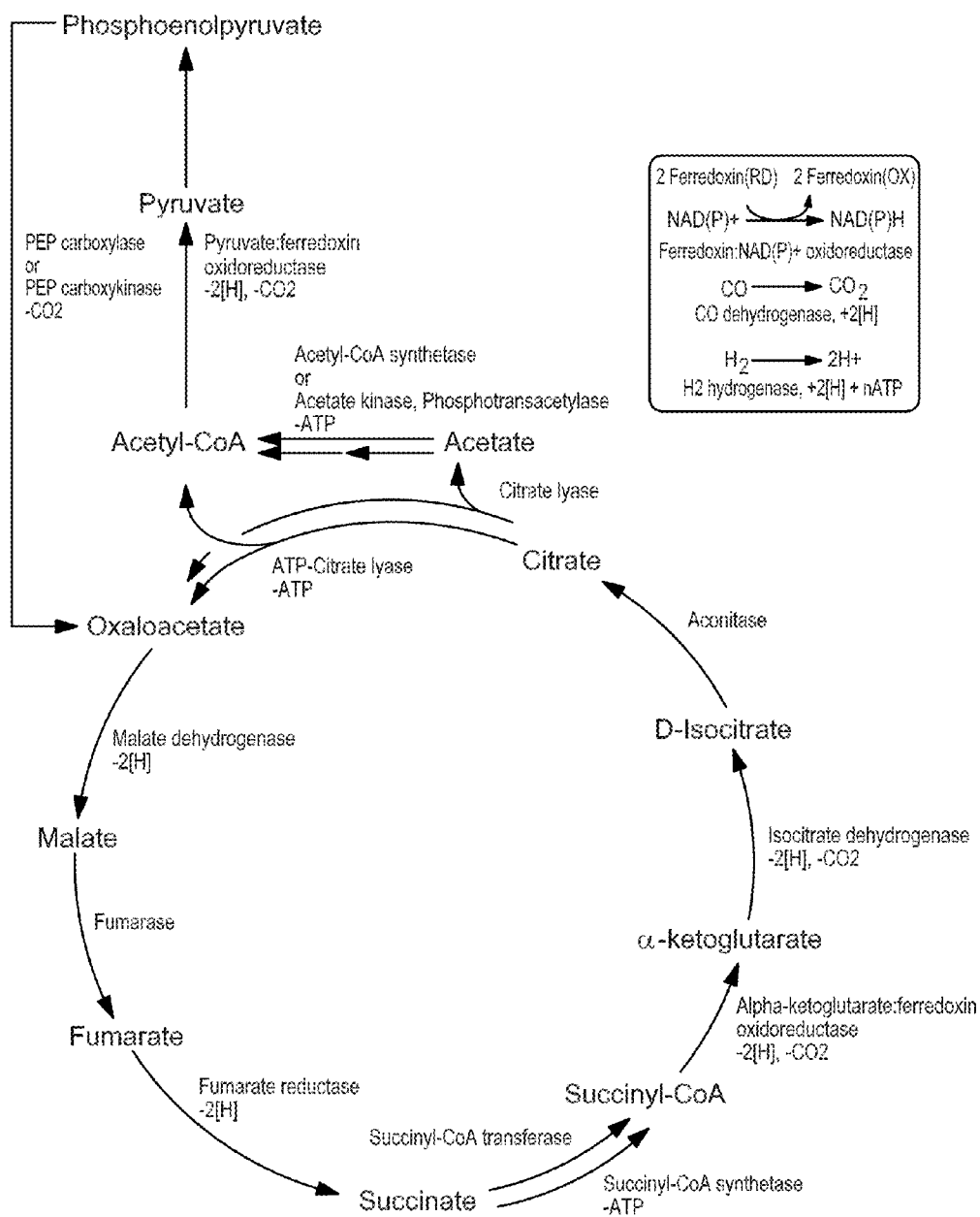
FIG. 13 shows the pathway for the reverse TCA cycle coupled with carbon monoxide dehydrogenase and hydrogenase for the conversion of syngas to acetyl-CoA.

The $CO_2$-fixing reductive tricarboxylic acid (RTCA) cycle is an endergenic anabolic pathway of $CO_2$ assimilation which uses reducing equivalents and ATP (FIG. 12). One turn of the RTCA cycle assimilates two moles of $CO_2$ into one mole of acetyl-CoA, or four moles of $CO_2$ into one mole of oxaloacetate. This additional availability of acetyl-CoA improves the maximum theoretical yield of product molecules derived from carbohydrate-based carbon feedstock. Exemplary carbohydrates include but are not limited to glucose, sucrose, xylose, arabinose and glycerol.

In some embodiments, the reductive TCA cycle, coupled with carbon monoxide dehydrogenase and/or hydrogenase enzymes, can be employed to allow syngas, $CO_2$, CO, $H_2$, and/or other gaseous carbon source utilization by microorganisms. Synthesis gas (syngas), in particular is a mixture of primarily $H_2$ and CO, sometimes including some amounts of $CO_2$, that can be obtained via gasification of any organic feedstock, such as coal, coal oil, natural gas, biomass, or waste organic matter. Numerous gasification processes have been developed, and most designs are based on partial oxidation, where limiting oxygen avoids full combustion, of organic materials at high temperatures (500-1500° C.) to provide syngas as a 0.5:1-3:1 $H_2$/CO mixture. In addition to coal, biomass of many types has been used for syngas production and represents an inexpensive and flexible feedstock for the biological production of renewable chemicals and fuels. Carbon dioxide can be provided from the atmosphere or in condensed from, for example, from a tank cylinder, or via sublimation of solid $CO_2$. Similarly, CO and hydrogen gas can be provided in reagent form and/or mixed in any desired ratio. Other gaseous carbon forms can include, for example, methanol or similar volatile organic solvents.

The components of synthesis gas and/or other carbon sources can provide sufficient $CO_2$, reducing equivalents, and ATP for the reductive TCA cycle to operate. One turn of the RTCA cycle assimilates two moles of $CO_2$ into one mole of acetyl-CoA and requires 2 ATP and 4 reducing equivalents. CO and/or $H_2$ can provide reducing equivalents by means of carbon monoxide dehydrogenase and hydrogenase enzymes, respectively. Reducing equivalents can come in the form of NADH, NADPH, FADH, reduced quinones, reduced ferredoxins, reduced flavodoxins and thioredoxins. The reducing equivalents, particularly NADH, NADPH, and reduced ferredoxin, can serve as cofactors for the RTCA cycle enzymes, for example, malate dehydrogenase, fumarate reductase, alpha-ketoglutarate:ferredoxin oxidoreductase (alternatively known as 2-oxoglutarate:ferredoxin oxidoreductase, alpha-ketoglutarate synthase, or 2-oxoglutarate synthase), pyruvate:ferredoxin oxidoreductase and isocitrate dehydrogenase. The electrons from these reducing equivalents can alternatively pass through an ion-gradient producing electron transport chain where they are passed to an acceptor such as oxygen, nitrate, oxidized metal ions, protons, or an electrode. The ion-gradient can then be used for ATP generation via an ATP synthase or similar enzyme.

The reductive TCA cycle was first reported in the green sulfur photosynthetic bacterium *Chlorobium limicola* (Evans et al., *Proc. Natl. Acad. Sci. U.S.A.* 55:928-934 (1966)). Similar pathways have been characterized in some prokaryotes (proteobacteria, green sulfur bacteria and thermophilic Knallgas bacteria) and sulfur-dependent archaea (Hugler et al., *J. Bacteriol.* 187:3020-3027 (2005; Hugler et al., *Environ. Microbiol.* 9:81-92 (2007). In some cases, reductive and oxidative (Krebs) TCA cycles are present in the same organism (Hugler et al., supra (2007); Siebers et al., *J. Bacteriol.* 186:2179-2194 (2004)). Some methanogens and obligate anaerobes possess incomplete oxidative or reductive TCA cycles that may function to synthesize biosynthetic intermediates (Ekiel et al., *J. Bacteriol.* 162:905-908 (1985); Wood et al., *FEMS Microbiol. Rev.* 28:335-352 (2004)).

The key carbon-fixing enzymes of the reductive TCA cycle are alpha-ketoglutarate:ferredoxin oxidoreductase, pyruvate: ferredoxin oxidoreductase and isocitrate dehydrogenase. Additional carbon may be fixed during the conversion of phosphoenolpyruvate to oxaloacetate by phosphoenolpyruvate carboxylase or phosphoenolpyruvate carboxykinase or by conversion of pyruvate to malate by malic enzyme.

Many of the enzymes in the TCA cycle are reversible and can catalyze reactions in the reductive and oxidative directions. However, some TCA cycle reactions are irreversible in vivo and thus different enzymes are used to catalyze these reactions in the directions required for the reverse TCA cycle. These reactions are: (1) conversion of citrate to oxaloacetate and acetyl-CoA, (2) conversion of fumarate to succinate, and (3) conversion of succinyl-CoA to alpha-ketoglutarate. In the TCA cycle, citrate is formed from the condensation of oxaloacetate and acetyl-CoA. The reverse reaction, cleavage of citrate to oxaloacetate and acetyl-CoA, is ATP-dependent and catalyzed by ATP-citrate lyase, or citryl-CoA synthetase and citryl-CoA lyase. Alternatively, citrate lyase can be coupled to acetyl-CoA synthetase, an acetyl-CoA transferase, or phosphotransacetylase and acetate kinase to form acetyl-CoA and oxaloacetate from citrate. The conversion of succinate to fumarate is catalyzed by succinate dehydrogenase while the reverse reaction is catalyzed by fumarate reductase. In the TCA cycle succinyl-CoA is formed from the $NAD(P)^+$ dependent decarboxylation of alpha-ketoglutarate by the alpha-ketoglutarate dehydrogenase complex. The reverse reaction is catalyzed by alpha-ketoglutarate:ferredoxin oxidoreductase.

An organism capable of utilizing the reverse tricarboxylic acid cycle to enable production of acetyl-CoA-derived products on 1) CO, 2) $CO_2$ and $H_2$, 3) CO and $CO_2$, 4) synthesis gas comprising CO and $H_2$, and 5) synthesis gas or other gaseous carbon sources comprising CO, $CO_2$, and $H_2$ can include any of the following enzyme activities: ATP-citrate lyase, citrate lyase, aconitase, isocitrate dehydrogenase, alpha-ketoglutarate:ferredoxin oxidoreductase, succinyl-CoA synthetase, succinyl-CoA transferase, fumarate reductase, fumarase, malate dehydrogenase, acetate kinase, phosphotransacetylase, acetyl-CoA synthetase, acetyl-CoA transferase, pyruvate:ferredoxin oxidoreductase, NAD(P)H: ferredoxin oxidoreductase, carbon monoxide dehydrogenase, hydrogenase, and ferredoxin (see FIG. 13). Enzyme enzymes and the corresponding genes required for these activities are described herein.

Carbon from syngas or other gaseous carbon sources can be fixed via the reverse TCA cycle and components thereof. Specifically, the combination of certain carbon gas-utilization pathway components with the pathways for formation of methacrylic acid, methacrylate ester, 3-hydroxyisobutyrate and/or 2-hydroxyisobutyrate from acetyl-CoA results in high yields of these products by providing an efficient mechanism for fixing the carbon present in carbon dioxide, fed exogenously or produced endogenously from CO, into acetyl-CoA.

In some embodiments, a methacrylic acid, methacrylate ester, 3-hydroxyisobutyrate and/or 2-hydroxyisobutyrate pathway in a non-naturally occurring microbial organism of the invention can utilize any combination of (1) CO, (2) $CO_2$, (3) $H_2$, or mixtures thereof to enhance the yields of biosynthetic steps involving reduction, including addition to driving the reductive TCA cycle.

In some embodiments a non-naturally occurring microbial organism having an methacrylic acid, methacrylate ester, 3-hydroxyisobutyrate and/or 2-hydroxyisobutyrate pathway includes at least one exogenous nucleic acid encoding a reductive TCA pathway enzyme. The at least one exogenous nucleic acid is selected from an ATP-citrate lyase, citrate lyase, a fumarate reductase, isocitrate dehydrogenase, aconitase, and an alpha-ketoglutarate:ferredoxin oxidoreductase; and at least one exogenous enzyme selected from a carbon monoxide dehydrogenase, a hydrogenase, a NAD(P)H:ferredoxin oxidoreductase, and a ferredoxin, expressed in a sufficient amount to allow the utilization of (1) CO, (2) $CO_2$, (3) $H_2$, (4) $CO_2$ and $H_2$, (5) CO and $CO_2$, (6) CO and $H_2$, or (7) CO, $CO_2$, and $H_2$.

In some embodiments a method includes culturing a non-naturally occurring microbial organism having a methacrylic acid, methacrylate ester, 3-hydroxyisobutyrate and/or 2-hydroxyisobutyrate pathway also comprising at least one exogenous nucleic acid encoding a reductive TCA pathway enzyme. The at least one exogenous nucleic acid is selected from an ATP-citrate lyase, citrate lyase, a fumarate reductase, isocitrate dehydrogenase, aconitase, and an alpha-ketoglutarate:ferredoxin oxidoreductase. Additionally, such an organism can also include at least one exogenous enzyme selected from a carbon monoxide dehydrogenase, a hydrogenase, a NAD(P)H:ferredoxin oxidoreductase, and a ferredoxin, expressed in a sufficient amount to allow the utilization of (1) CO, (2) $CO_2$, (3) $H_2$, (4) $CO_2$ and $H_2$, (5) CO and $CO_2$, (6) CO and $H_2$, or (7) CO, $CO_2$, and $H_2$ to produce a product.

In some embodiments a non-naturally occurring microbial organism having an methacrylic acid, methacrylate ester, 3-hydroxyisobutyrate and/or 2-hydroxyisobutyrate pathway further includes at least one exogenous nucleic acid encoding a reductive TCA pathway enzyme expressed in a sufficient amount to enhance carbon flux through acetyl-CoA. The at least one exogenous nucleic acid is selected from an ATP-citrate lyase, citrate lyase, a fumarate reductase, a pyruvate: ferredoxin oxidoreductase, isocitrate dehydrogenase, aconitase and an alpha-ketoglutarate:ferredoxin oxidoreductase.

In some embodiments a non-naturally occurring microbial organism having an methacrylic acid, methacrylate ester, 3-hydroxyisobutyrate and/or 2-hydroxyisobutyrate pathway includes at least one exogenous nucleic acid encoding an enzyme expressed in a sufficient amount to enhance the availability of reducing equivalents in the presence of carbon monoxide and/or hydrogen, thereby increasing the yield of redox-limited products via carbohydrate-based carbon feedstock. The at least one exogenous nucleic acid is selected from a carbon monoxide dehydrogenase, a hydrogenase, an NAD(P)H:ferredoxin oxidoreductase, and a ferredoxin. In some embodiments, the present invention provides a method for enhancing the availability of reducing equivalents in the presence of carbon monoxide or hydrogen thereby increasing the yield of redox-limited products via carbohydrate-based carbon feedstock, such as sugars or gaseous carbon sources, the method includes culturing this non-naturally occurring microbial organism under conditions and for a sufficient period of time to produce methacrylic acid, methacrylate ester, 3-hydroxyisobutyrate and/or 2-hydroxyisobutyrate.

In some embodiments, the non-naturally occurring microbial organism having an methacrylic acid, methacrylate ester, 3-hydroxyisobutyrate and/or 2-hydroxyisobutyrate pathway includes two exogenous nucleic acids each encoding a reductive TCA pathway enzyme. In some embodiments, the non-naturally occurring microbial organism having an methacrylic acid, methacrylate ester, 3-hydroxyisobutyrate and/or 2-hydroxyisobutyrate pathway includes three exogenous nucleic acids each encoding a reductive TCA pathway enzyme. In some embodiments, the non-naturally occurring microbial organism includes three exogenous nucleic acids encoding an ATP-citrate lyase, a fumarate reductase, and an alpha-ketoglutarate:ferredoxin oxidoreductase. In some embodiments, the non-naturally occurring microbial organism includes three exogenous nucleic acids encoding a citrate lyase, a fumarate reductase, and an alpha-ketoglutarate:ferredoxin oxidoreductase. In some embodiments, the non-naturally occurring microbial organism includes four exogenous nucleic acids encoding a pyruvate:ferredoxin oxidoreductase; a phosphoenolpyruvate carboxylase or a phosphoenolpyruvate carboxykinase, a CO dehydrogenase; and an $H_2$ hydrogenase. In some embodiments, the non-naturally occurring microbial organism includes two exogenous nucleic acids encoding a CO dehydrogenase and an $H_2$ hydrogenase.

In some embodiments, the non-naturally occurring microbial organisms having an methacrylic acid, methacrylate ester, 3-hydroxyisobutyrate and/or 2-hydroxyisobutyrate pathway further include an exogenous nucleic acid encoding an enzyme selected from a pyruvate:ferredoxin oxidoreductase, an aconitase, an isocitrate dehydrogenase, a succinyl-CoA synthetase, a succinyl-CoA transferase, a fumarase, a malate dehydrogenase, an acetate kinase, a phosphotransacetylase, an acetyl-CoA synthetase, an NAD(P)H:ferredoxin oxidoreductase, and combinations thereof.

In some embodiments, the non-naturally occurring microbial organism having an methacrylic acid, methacrylate ester, 3-hydroxyisobutyrate and/or 2-hydroxyisobutyrate pathway further includes an exogenous nucleic acid encoding an enzyme selected from carbon monoxide dehydrogenase, acetyl-CoA synthase, ferredoxin, NAD(P)H:ferredoxin oxidoreductase and combinations thereof.

In some embodiments, the non-naturally occurring microbial organism having an methacrylic acid, methacrylate ester, 3-hydroxyisobutyrate and/or 2-hydroxyisobutyrate pathway utilizes a carbon feedstock selected from (1) CO, (2) $CO_2$, (3) $CO_2$ and $H_2$, (4) CO and $H_2$, or (5) CO, $CO_2$, and $H_2$. In some embodiments, the non-naturally occurring microbial organism having an methacrylic acid, methacrylate ester, 3-hydroxyisobutyrate and/or 2-hydroxyisobutyrate pathway utilizes hydrogen for reducing equivalents. In some embodiments, the non-naturally occurring microbial organism having an methacrylic acid, methacrylate ester, 3-hydroxyisobutyrate and/or 2-hydroxyisobutyrate pathway utilizes CO for reducing equivalents. In some embodiments, the non-naturally occurring microbial organism having an methacrylic acid, methacrylate ester, 3-hydroxyisobutyrate and/or 2-hydroxyisobutyrate pathway utilizes combinations of CO and hydrogen for reducing equivalents.

In some embodiments, the non-naturally occurring microbial organism having an methacrylic acid, methacrylate ester, 3-hydroxyisobutyrate and/or 2-hydroxyisobutyrate pathway further includes one or more nucleic acids encoding an enzyme selected from a phosphoenolpyruvate carboxylase, a phosphoenolpyruvate carboxykinase, a pyruvate carboxylase, and a malic enzyme.

In some embodiments, the non-naturally occurring microbial organism having an methacrylic acid, methacrylate ester, 3-hydroxyisobutyrate and/or 2-hydroxyisobutyrate pathway further includes one or more nucleic acids encoding an enzyme selected from a malate dehydrogenase, a fumarase, a fumarate reductase, a succinyl-CoA synthetase, and a succinyl-CoA transferase.

In some embodiments, the non-naturally occurring microbial organism having an methacrylic acid, methacrylate ester, 3-hydroxyisobutyrate and/or 2-hydroxyisobutyrate pathway can have or optionally further includes at least one exogenous nucleic acid encoding a citrate lyase, an ATP-citrate lyase, a citryl-CoA synthetase, a citryl-CoA lyase an aconitase, an isocitrate dehydrogenase, a succinyl-CoA synthetase, a succinyl-CoA transferase, a fumarase, a malate dehydrogenase, an acetate kinase, a phosphotransacetylase, an acetyl-CoA synthetase, and a ferredoxin.

It is understood by those skilled in the art that the pathways described herein for increasing product yield can be combined with any of the pathways disclosed herein, including those pathways depicted in the figures. One skilled in the art will understand that, depending on the pathway to a desired product and the precursors and intermediates of that pathway, a particular pathway for improving product yield, as discussed herein and in the examples, or combination of such pathways, can be used in combination with a pathway to a desired product to increase the yield of that product or a pathway intermediate.

The invention also provides a non-naturally occurring microbial organism, comprising a microbial organism having a methacrylic acid pathway comprising at least one exogenous nucleic acid encoding a methacrylic acid pathway enzyme expressed in a sufficient amount to produce methacrylic acid; said non-naturally occurring microbial organism further comprising: (i) a reductive TCA pathway comprising at least one exogenous nucleic acid encoding a reductive TCA pathway enzyme, wherein said at least one exogenous nucleic acid is selected from an ATP-citrate lyase, citrate lyase, a fumarate reductase, and an alpha-ketoglutarate:ferredoxin oxidoreductase, or optionally isocitrate dehydrogenase, aconitase, citryl-CoA synthetase or citryl-CoA lyase; (ii) a reductive TCA pathway comprising at least one exogenous nucleic acid encoding a reductive TCA pathway enzyme, wherein said at least one exogenous nucleic acid is selected from a pyruvate:ferredoxin oxidoreductase, a phosphoenolpyruvate carboxylase, a phosphoenolpyruvate carboxykinase, a CO dehydrogenase, and an $H_2$ hydrogenase; or (iii) at least one exogenous nucleic acid encodes an enzyme selected from a CO dehydrogenase, an $H_2$ hydrogenase, and combinations thereof; wherein said methacrylic acid pathway comprises a pathway selected from: (a) citramalate synthase, citramalate dehydratase (citraconate forming), and citraconate decarboxylase; (b) citramalate synthase, citramalate dehydratase (citraconate forming), citraconate isomerase, and mesaconate decarboxylase; (c) citramalate synthase, citramalate dehydratase (mesaconate forming), citraconate isomerase, and citraconate decarboxylase; (d) citramalate synthase, citramalate dehydratase (mesaconate forming), and mesaconate decarboxylase; (e) citramalyl-CoA lyase, citramalyl-CoA transferase, synthetase or hydrolase, citramalate dehydratase (citraconate forming), and citraconate decarboxylase; (f) citramalyl-CoA lyase, citramalyl-CoA transferase, synthetase or hydrolase, citramalate dehydratase (citraconate forming), citraconate isomerase, and mesaconate decarboxylase; (g) citramalyl-CoA lyase, citramalyl-CoA transferase, synthetase or hydrolase, citramalate dehydratase (mesaconate forming), and mesaconate decarboxylase; (h) citramalyl-CoA lyase, citramalyl-CoA transferase, synthetase or hydrolase, citramalate dehydratase (mesaconate forming), citraconate isomerase, and citraconate decarboxylase; (i) aconitate decarboxylase, itaconate isomerase, and citraconate decarboxylase; (j) aconitate decarboxylase, itaconate isomerase, citraconate isomerase, and mesaconate decarboxylase; (k) aconitate decarboxylase, itaconyl-CoA transferase, synthetase or hydrolase, citramalyl-CoA dehydratase, citramalyl-CoA transferase, synthetase or hydrolase, citramalate dehydratase (citraconate forming), and citraconate decarboxylase; (l) aconitate decarboxylase, itaconyl-CoA transferase, synthetase or hydrolase, citramalyl-CoA dehydratase, citramalyl-CoA transferase, synthetase or hydrolase, citramalate dehydratase (citraconate forming), citraconate isomerase, and mesaconate decarboxylase; (m) aconitate decarboxylase, itaconyl-CoA transferase, synthetase or hydrolase, citramalyl-CoA dehydratase, citramalyl-CoA transferase, synthetase or hydrolase, citramalate dehydratase (mesaconate forming), and mesaconate decarboxylase; (n) aconitate decarboxylase, itaconyl-CoA transferase, synthetase or hydrolase, citramalyl-CoA dehydratase, citramalyl-CoA transferase, synthetase or hydrolase, citramalate dehydratase (mesaconate forming), citraconate isomerase, and citraconate decarboxylase; (o) 3-hydroxyisobutyrate dehydratase; (p) methylmalonyl-CoA mutase, methylmalonyl-CoA reductase, 3-hydroxyisobutyrate dehydrogenase, and 3-hydroxyisobutyrate dehydratase; (q) methylmalonyl-CoA mutase, methylmalonyl-CoA epimerase, methylmalonyl-CoA reductase, 3-hydroxyisobutyrate dehydrogenase, and 3-hydroxyisobutyrate dehydratase; (r) methylmalonyl-CoA mutase, alcohol/aldehyde dehydrogenase, and 3-hydroxyisobutyrate dehydratase; (s) methylmalonyl-CoA mutase, methylmalonyl-CoA epimerase, alcohol/aldehyde dehydrogenase, and 3-hydroxyisobutyrate dehydratase; (t) methylmalonyl-CoA mutase, methylmalonyl-CoA reductase, 3-amino-2-methylpropionate transaminase, and 3-amino-2-methylpropionate ammonia lyase; (u) methylmalonyl-CoA mutase, methylmalonyl-CoA epimerase, methylmalonyl-CoA reductase, 3-amino-2-methylpropionate transaminase, and 3-amino-2-methylpropionate ammonia lyase; (v) 4-hydroxybutyryl-CoA mutase, 3-hydroxyisobutyryl-CoA synthetase or 3-hydroxyisobutyryl-CoA hydrolase or 3-hydroxyisobutyryl-CoA transferase, and 3-hydroxyisobutyrate dehydratase; (w) aspartate aminotransferase, glutamate mutase, 3-methylaspartase, and mesaconate decarboxylase; (x) alpha-ketoglutarate reductase, 2-hydroxyglutamate mutase, 3-methylmalate dehydratase, and mesaconate decarboxylase; (y) acetoacetyl-CoA thiolase, acetoacetyl-CoA reductase, 3-hydroxybutyryl-CoA mutase, 2-hydroxyisobutyryl-CoA dehydratase, and methacrylyl-CoA transferase or methacrylyl-CoA hydrolase or methacrylyl-CoA synthetase; (z) acetoacetyl-CoA thiolase, acetoacetyl-CoA reductase, 3-hydroxybutyryl-CoA mutase, 2-hydroxyisobutyryl-CoA dehydratase, enoyl-CoA hydratase, and 3-hydroxyisobutyryl-CoA hydrolase or 3-hydroxyisobutyryl-CoA synthetase or 3-hydroxyisobutyryl-CoA transferase, and 3-hydroxyisobutyrate dehydratase; (aa) 4-hydroxybutyryl-CoA dehydratase, vinylacetyl-CoA Δ-isomerase, crotonase, 3-hydroxybutyryl-CoA mutase, 2-hydroxyisobutyryl-CoA dehydratase, and any of methacrylyl-CoA hydrolase or methacrylyl-CoA synthetase or methacrylyl-CoA transferase; (bb) 4-hydroxybutyryl-CoA mutase, 3-hydroxyisobutyryl-CoA dehydratase, and methacrylyl-CoA synthetase or methacrylyl-CoA hydrolase or methacrylyl-CoA transferase; (cc) acetoacetyl-CoA thiolase, acetoacetyl-CoA reductase, crotonase, butyryl-CoA dehydrogenase, isobutyryl-CoA mutase, isobutyryl-CoA dehydrogenase, and methacrylyl-CoA synthetase or methacrylyl-CoA hydrolase or methacrylyl-CoA transferase; (dd) lactate dehydrogenase, lactate-CoA transferase, lactoyl-CoA dehydratase, acyl-CoA dehydrogenase, propionyl-CoA carboxylase, methylmalonyl-CoA reductase, 3-hydroxyisobutyrate dehydrogenase, and 3-hydroxyisobutyrate dehydratase; (ee) valine aminotransferase, 2-ketoisovalerate dehydrogenase, isobutyryl-CoA dehydrogenase, and methacrylyl-CoA synthetase or methacrylyl-CoA hydrolase or methacrylyl-CoA transferase; (ff) valine aminotransferase, 2-ketoisovalerate dehydrogenase, isobutyryl-CoA dehydrogenase, methacrylyl-CoA synthetase or methacrylyl-CoA hydrolase or methacrylyl-CoA transferase, acetolactate synthase, acetohydroxy acid isomeroreductase and dihydroxy-acid dehydratase; (gg) acetoacetyl-CoA thiolase, acetoacetyl-CoA reductase, crotonase, 4-hydroxybutyryl-CoA dehydratase, 4-hydroxybutyryl-CoA mutase, 3-hydroxyisobutyryl-CoA synthetase or 3-hydroxyisobutyryl-CoA hydrolase or 3-hydroxyisobutyryl-CoA transferase, and 3-hydroxyisobutyrate dehydratase; and (hh) acetoacetyl-CoA thiolase, acetoacetyl-CoA reductase, crotonase, 4-hydroxybutyryl-CoA dehydratase, 4-hydroxybutyryl-CoA mutase, 3-hydroxyisobutyryl-CoA dehydratase, and methacrylyl-CoA synthetase or methacrylyl-CoA hydrolase or methacrylyl-CoA transferase.

The invention additionally provides a non-naturally occurring microbial organism having a 2-hydroxyisobutyric acid pathway comprising at least one exogenous nucleic acid encoding a 2-hydroxyisobutyric acid pathway enzyme expressed in a sufficient amount to produce 2-hydroxyisobutyric acid. Such a non-naturally occurring microbial organism can further comprise (i) a reductive TCA pathway comprising at least one exogenous nucleic acid encoding a reductive TCA pathway enzyme, wherein the at least one exogenous nucleic acid is selected from an ATP-citrate lyase, citrate lyase, a fumarate reductase, and an alpha-ketoglutarate:ferredoxin oxidoreductase, or optionally isocitrate dehydrogenase, aconitase, citryl-CoA synthetase or citryl-CoA lyase; (ii) a reductive TCA pathway comprising at least one exogenous nucleic acid encoding a reductive TCA pathway enzyme, wherein the at least one exogenous nucleic acid is selected from a pyruvate:ferredoxin oxidoreductase, a phosphoenolpyruvate carboxylase, a phosphoenolpyruvate carboxykinase, a CO dehydrogenase, and an $H_2$ hydrogenase; or (iii) at least one exogenous nucleic acid encodes an enzyme selected from a CO dehydrogenase, an $H_2$ hydrogenase, and combinations thereof; wherein the 2-hydroxyisobutyric acid pathway comprises a pathway selected from (a) acetoacetyl-CoA thiolase, acetoacetyl-CoA reductase, 3-hydroxybutyryl-CoA mutase, and 2-hydroxyisobutyryl-CoA transferase or 2-hydroxyisobutyryl-CoA hydrolase or 2-hydroxyisobutyryl-CoA synthetase; and (b) 4-hydroxybutyryl-CoA dehydratase, vinylacetyl-CoA Δ-isomerase, crotonase, 3-hydroxybutyryl-CoA mutase, and any of 2-hydroxyisobutyryl-CoA hydrolase or 2-hydroxyisobutyryl-CoA synthetase or 2-hydroxyisobutyryl-CoA transferase (see FIG. 16C). The non-naturally occurring microbial organism can comprise two, three, four or five exogenous nucleic acids each encoding a methacrylic acid pathway enzyme, up to all enzymes of the pathway.

The invention further provides a non-naturally occurring microbial organism comprising a microbial organism having a 3-hydroxyisobutyric acid pathway comprising at least one exogenous nucleic acid encoding a 3-hydroxyisobutyric acid pathway enzyme expressed in a sufficient amount to produce 3-hydroxyisobutyric acid. The non-naturally occurring microbial organism can further comprise (i) a reductive TCA pathway comprising at least one exogenous nucleic acid encoding a reductive TCA pathway enzyme, wherein said at least one exogenous nucleic acid is selected from an ATP-citrate lyase, citrate lyase, a fumarate reductase, and an alpha-ketoglutarate:ferredoxin oxidoreductase, or optionally isocitrate dehydrogenase, aconitase, citryl-CoA synthetase or citryl-CoA lyase; (ii) a reductive TCA pathway comprising at least one exogenous nucleic acid encoding a reductive TCA pathway enzyme, wherein the at least one exogenous nucleic acid is selected from a pyruvate:ferredoxin oxidoreductase, a phosphoenolpyruvate carboxylase, a phosphoenolpyruvate carboxykinase, a CO dehydrogenase, and an H$_2$ hydrogenase; or (iii) at least one exogenous nucleic acid encodes an enzyme selected from a CO dehydrogenase, an H$_2$ hydrogenase, and combinations thereof; wherein the 3-hydroxyisobutyric acid pathway comprises a pathway selected from (a) 4-hydroxybutyryl-CoA mutase; and (b) 4-hydroxybutyryl-CoA mutase and 3-hydroxyisobutyryl-CoA synthetase or 3-hydroxyisobutyryl-CoA hydrolase or 3-hydroxyisobutyryl-CoA transferase (see FIG. 16B). The non-naturally occurring microbial organism can comprise two exogenous nucleic acids each encoding a methacrylic acid pathway enzyme.

The invention also provides a non-naturally occurring microbial organism comprising a microbial organism having a 3-hydroxyisobutyryl-CoA pathway comprising at least one exogenous nucleic acid encoding a 3-hydroxyisobutyric acid pathway enzyme expressed in a sufficient amount to produce 3-hydroxyisobutyric acid. The non-naturally occurring microbial organism can further comprise (i) a reductive TCA pathway comprising at least one exogenous nucleic acid encoding a reductive TCA pathway enzyme, wherein the at least one exogenous nucleic acid is selected from an ATP-citrate lyase, citrate lyase, a fumarate reductase, and an alpha-ketoglutarate:ferredoxin oxidoreductase, or optionally isocitrate dehydrogenase, aconitase, citryl-CoA synthetase or citryl-CoA lyase; (ii) a reductive TCA pathway comprising at least one exogenous nucleic acid encoding a reductive TCA pathway enzyme, wherein the at least one exogenous nucleic acid is selected from a pyruvate:ferredoxin oxidoreductase, a phosphoenolpyruvate carboxylase, a phosphoenolpyruvate carboxykinase, a CO dehydrogenase, and an H$_2$ hydrogenase; or (iii) at least one exogenous nucleic acid encodes an enzyme selected from a CO dehydrogenase, an H$_2$ hydrogenase, and combinations thereof; wherein the 3-hydroxyisobutyryl-CoA pathway comprises 4-hydroxybutyryl-CoA mutase (see FIG. 16B).

In a further embodiment, the microbial organism comprising (i) further comprises an exogenous nucleic acid encoding an enzyme selected from a pyruvate:ferredoxin oxidoreductase, an aconitase, an isocitrate dehydrogenase, a succinyl-CoA synthetase, a succinyl-CoA transferase, a fumarase, a malate dehydrogenase, an acetate kinase, a phosphotransacetylase, an acetyl-CoA synthetase, an NAD(P)H:ferredoxin oxidoreductase, ferredoxin, and combinations thereof; a microbial organism comprising (ii) further comprises an exogenous nucleic acid encoding an enzyme selected from an aconitase, an isocitrate dehydrogenase, a succinyl-CoA synthetase, a succinyl-CoA transferase, a fumarase, a malate dehydrogenase, and combinations thereof.

Such a microbial organism can comprise two, three, four, five, six or seven exogenous nucleic acids each encoding a methacrylic acid pathway enzyme, up to all of the enzymes of a pathway. For example, the microbial organism can comprises (a) three exogenous nucleic acids encoding citramalate synthase, citramalate dehydratase (citraconate forming), and citraconate decarboxylase; (b) four exogenous nucleic acids encoding citramalate synthase, citramalate dehydratase (citraconate forming), citraconate isomerase, and mesaconate decarboxylase; (c) four exogenous nucleic acids encoding citramalate synthase, citramalate dehydratase (mesaconate forming), citraconate isomerase, and citraconate decarboxylase; (d) three exogenous nucleic acids encoding citramalate synthase, citramalate dehydratase (mesaconate forming), and mesaconate decarboxylase; (e) four exogenous nucleic acids encoding citramalyl-CoA lyase, citramalyl-CoA transferase, synthetase or hydrolase, citramalate dehydratase (citraconate forming), and citraconate decarboxylase; (f) five exogenous nucleic acids encoding citramalyl-CoA lyase, citramalyl-CoA transferase, synthetase or hydrolase, citramalate dehydratase (citraconate forming), citraconate isomerase, and mesaconate decarboxylase; (g) four exogenous nucleic acids encoding citramalyl-CoA lyase, citramalyl-CoA transferase, synthetase or hydrolase, citramalate dehydratase (mesaconate forming), and mesaconate decarboxylase; (h) five exogenous nucleic acids encoding citramalyl-CoA lyase, citramalyl-CoA transferase, synthetase or hydrolase, citramalate dehydratase (mesaconate forming), citraconate isomerase, and citraconate decarboxylase; (i) three exogenous nucleic acids encoding aconitate decarboxylase, itaconate isomerase, and citraconate decarboxylase; (j) four exogenous nucleic acids encoding aconitate decarboxylase, itaconate isomerase, citraconate isomerase, and mesaconate decarboxylase; (k) six exogenous nucleic acids encoding aconitate decarboxylase, itaconyl-CoA transferase, synthetase or hydrolase, citramalyl-CoA dehydratase, citramalyl-CoA transferase, synthetase or hydrolase, citramalate dehydratase (citraconate forming), and citraconate decarboxylase; (l) seven exogenous nucleic acids encoding aconitate decarboxylase, itaconyl-CoA transferase, synthetase or hydrolase, citramalyl-CoA dehydratase, citramalyl-CoA transferase, synthetase or hydrolase, citramalate dehydratase (citraconate forming), citraconate isomerase, and mesaconate decarboxylase; (m) six exogenous nucleic acids encoding aconitate decarboxylase, itaconyl-CoA transferase, synthetase or hydrolase, citramalyl-CoA dehydratase, citramalyl-CoA transferase, synthetase or hydrolase, citramalate dehydratase (mesaconate forming), and mesaconate decarboxylase; or (n) seven exogenous nucleic acids encoding aconitate decarboxylase, itaconyl-CoA transferase, synthetase or hydrolase, citramalyl-CoA dehydratase, citramalyl-CoA transferase, synthetase or hydrolase, citramalate dehydratase (mesaconate forming), citraconate isomerase, and citraconate decarboxylase; (o) one exogenous nucleic acid encoding 3-hydroxyisobutyrate dehydratase; (p) four exogenous nucleic acids encoding methylmalonyl-CoA mutase, methylmalonyl-CoA reductase, 3-hydroxyisobutyrate dehydrogenase, and 3-hydroxyisobutyrate dehydratase; (q) five exogenous nucleic acids encoding methylmalonyl-CoA mutase, methylmalonyl-CoA epimerase, methylmalonyl-CoA reductase, 3-hydroxyisobutyrate dehydrogenase, and 3-hydroxyisobutyrate dehydratase; (r) three exogenous nucleic acids encoding methylmalonyl-CoA mutase, alcohol/aldehyde dehydrogenase, and 3-hydroxyisobutyrate dehydratase; (s) four exogenous nucleic acids encoding methylmalonyl-CoA mutase, methylmalonyl-CoA epimerase, alcohol/aldehyde dehydrogenase, and 3-hydroxyisobutyrate dehydratase; (t) four exogenous nucleic acids encoding methylmalonyl-CoA mutase, methylmalonyl-CoA reductase, 3-amino-2-methylpropionate transaminase, and 3-amino-2-methylpropionate ammonia lyase; (u) five exogenous nucleic acids encoding methylmalonyl- CoA mutase, methylmalonyl-CoA epimerase, methylmalonyl-CoA reductase, 3-amino-2-methylpropionate transaminase, and 3-amino-2-methylpropionate ammonia lyase; (v) three exogenous nucleic acids encoding 4-hydroxybutyryl-CoA mutase, 3-hydroxyisobutyryl-CoA synthetase or 3-hydroxyisobutyryl-CoA hydrolase or 3-hydroxyisobutyryl-CoA transferase, and 3-hydroxyisobutyrate dehydratase; (w) four exogenous nucleic acids encoding aspartate aminotransferase, glutamate mutase, 3-methylaspartase, and mesaconate decarboxylase; (x) four exogenous nucleic acids encoding alpha-ketoglutarate reductase, 2-hydroxyglutamate mutase, 3-methylmalate dehydratase, and mesaconate decarboxylase; (y) five exogenous nucleic acids encoding acetoacetyl-CoA thiolase, acetoacetyl-CoA reductase, 3-hydroxybutyryl-CoA mutase, 2-hydroxyisobutyryl-CoA dehydratase, and methacrylyl-CoA transferase or methacrylyl-CoA hydrolase or methacrylyl-CoA synthetase; (z) seven exogenous nucleic acids encoding acetoacetyl-CoA thiolase, acetoacetyl-CoA reductase, 3-hydroxybutyryl-CoA mutase, 2-hydroxyisobutyryl-CoA dehydratase, enoyl-CoA hydratase, and 3-hydroxyisobutyryl-CoA hydrolase or 3-hydroxyisobutyryl-CoA synthetase or 3-hydroxyisobutyryl-CoA transferase, and 3-hydroxyisobutyrate dehydratase; (aa) six exogenous nucleic acids encoding 4-hydroxybutyryl-CoA dehydratase, vinylacetyl-CoA Δ-isomerase, crotonase, 3-hydroxybutyryl-CoA mutase, 2-hydroxyisobutyryl-CoA dehydratase, and any of methacrylyl-CoA hydrolase or methacrylyl-CoA synthetase or methacrylyl-CoA transferase; (bb) three exogenous nucleic acids encoding 4-hydroxybutyryl-CoA mutase, 3-hydroxyisobutyryl-CoA dehydratase, and methacrylyl-CoA synthetase or methacrylyl-CoA hydrolase or methacrylyl-CoA transferase; (cc) acetoacetyl-CoA thiolase, acetoacetyl-CoA reductase, crotonase, butyryl-CoA dehydrogenase, isobutyryl-CoA mutase, isobutyryl-CoA dehydrogenase, and methacrylyl-CoA synthetase or methacrylyl-CoA hydrolase or methacrylyl-CoA transferase; (dd) lactate dehydrogenase, lactate-CoA transferase, lactoyl-CoA dehydratase, acyl-CoA dehydrogenase, propionyl-CoA carboxylase, methylmalonyl-CoA reductase, 3-hydroxyisobutyrate dehydrogenase, and 3-hydroxyisobutyrate dehydratase; (ee) valine aminotransferase, 2-ketoisovalerate dehydrogenase, isobutyryl-CoA dehydrogenase, and methacrylyl-CoA synthetase or methacrylyl-CoA hydrolase or methacrylyl-CoA transferase; (ff) valine aminotransferase, 2-ketoisovalerate dehydrogenase, isobutyryl-CoA dehydrogenase, methacrylyl-CoA synthetase or methacrylyl-CoA hydrolase or methacrylyl-CoA transferase, acetolactate synthase, acetohydroxy acid isomeroreductase and dihydroxy-acid dehydratase; (gg) acetoacetyl-CoA thiolase, acetoacetyl-CoA reductase, crotonase, 4-hydroxybutyryl-CoA dehydratase, 4-hydroxybutyryl-CoA mutase, 3-hydroxyisobutyryl-CoA synthetase or 3-hydroxyisobutyryl-CoA hydrolase or 3-hydroxyisobutyryl-CoA transferase, and 3-hydroxyisobutyrate dehydratase; and (hh) acetoacetyl-CoA thiolase, acetoacetyl-CoA reductase, crotonase, 4-hydroxybutyryl-CoA dehydratase, 4-hydroxybutyryl-CoA mutase, 3-hydroxyisobutyryl-CoA dehydratase, and methacrylyl-CoA synthetase or methacrylyl-CoA hydrolase or methacrylyl-CoA transferase.

In another embodiment, a microbial organism can comprise two, three, four or five exogenous nucleic acids each encoding enzymes of (i), (ii) or (iii). For example, a microbial organism comprising (i) can comprise four exogenous nucleic acids encoding ATP-citrate lyase, citrate lyase, a fumarate reductase, and an alpha-ketoglutarate:ferredoxin oxidoreductase; a microbial organism comprising (ii) can comprise five exogenous nucleic acids encoding pyruvate: ferredoxin oxidoreductase, a phosphoenolpyruvate carboxylase, a phosphoenolpyruvate carboxykinase, a CO dehydrogenase, and an $H_2$ hydrogenase; or a microbial organism comprising (iii) can comprise two exogenous nucleic acids encoding CO dehydrogenase and $H_2$ hydrogenase.

Figure 16A:
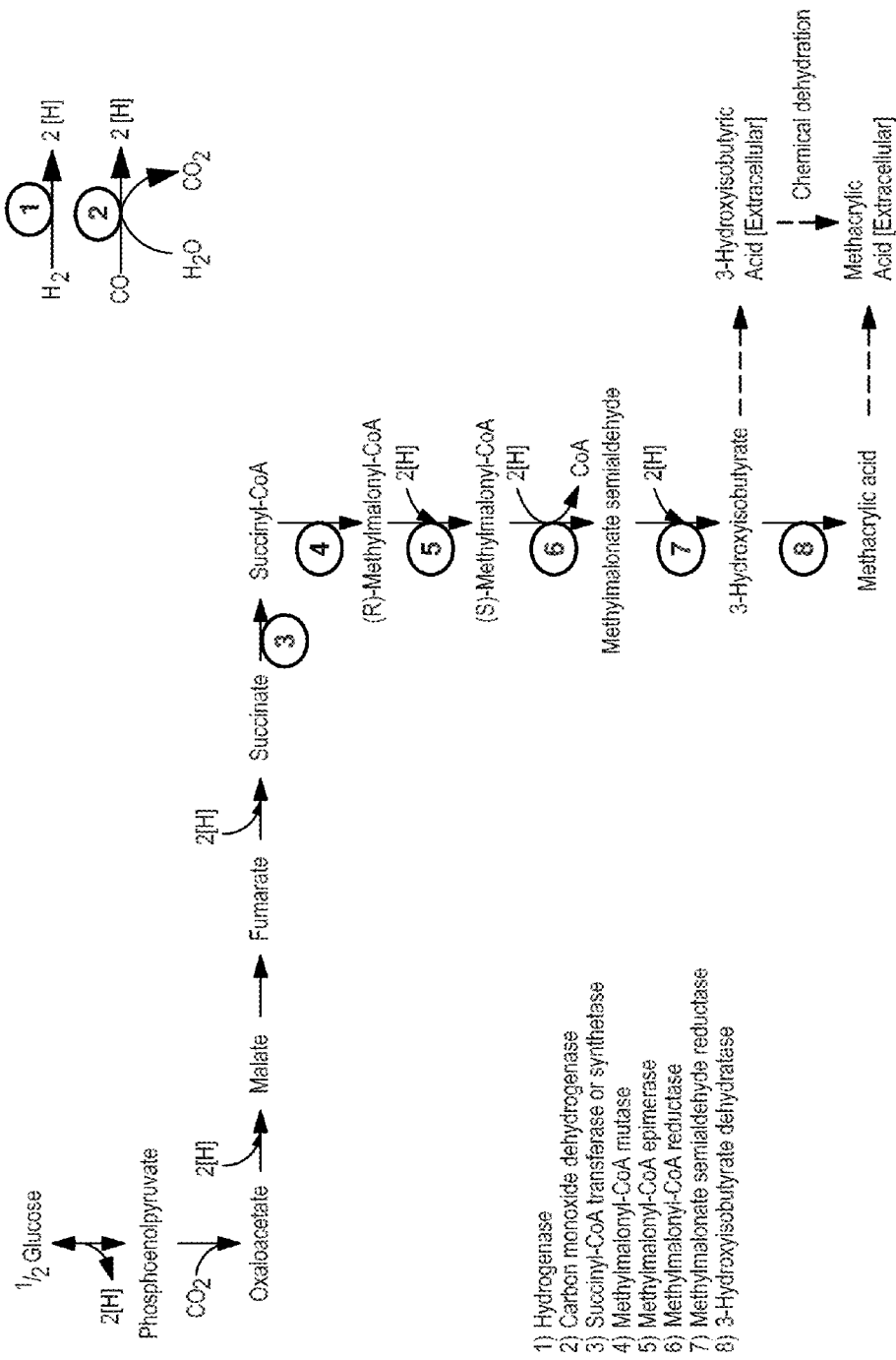
FIG. 16A shows the pathways for the biosynthesis of methacrylic acid and 3-hydroxyisobutyric acid. The enzymatic transformations shown are carried out by the following enzymes: (1) hydrogenase, (2) carbon monoxide dehydrogenase, (3) succinyl-CoA transferase, succinyl-CoA synthetase, (4) methylmalonyl-CoA mutase, (5) methylmalonyl-CoA epimerase, (6) methylmalonyl-CoA reductase, (7) methylmalonate semialdehyde reductase and (8) 3-hydroxyisobutyrate dehydratase.
Figure 16B:
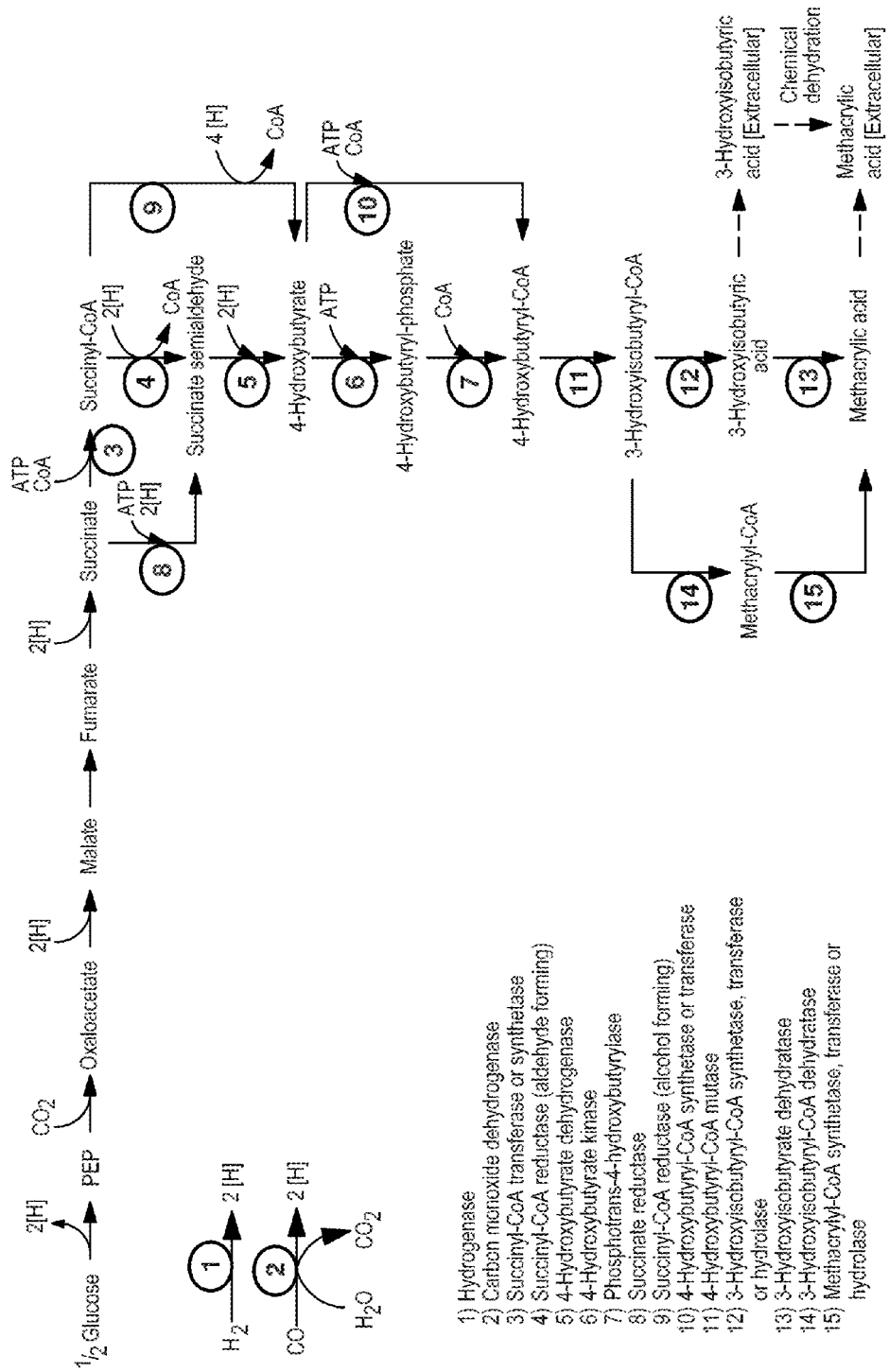
FIG. 16B shows the pathway for biosynthesis of methacrylic acid from glucose via a 4-hydroxybutyryl-CoA intermediate. The enzymatic transformations are carried out by the enzymes: (1) hydrogenase, (2) carbon monoxide dehydrogenase, (3) succinyl-CoA transferase, succinyl-CoA synthetase, (4) succinyl-CoA reductase (aldehyde forming), (5) 4-hydroxybutyrate dehydrogenase, (6) 4-hydroxybutyrate kinase, (7) phosphotrans-4-hydroxybutyrylase, (8) succinate reductase, (9) succinyl-CoA reductase (alcohol forming), (10) 4-hydroxybutyryl-CoA synthetase, 4-hydroxybutyryl-CoA transferase, (11) 4-hydroxybutyryl-CoA mutase, (12) 3-hydroxyisobutyryl-CoA synthetase, transferase or hydrolase, (13) 3-hydroxyisobutyrate dehydratase, (14) 3-hydroxyisobutyryl-CoA dehydratase, (15) methacrylyl-CoA synthetase, transferase or hydrolase.
Figure 16C:
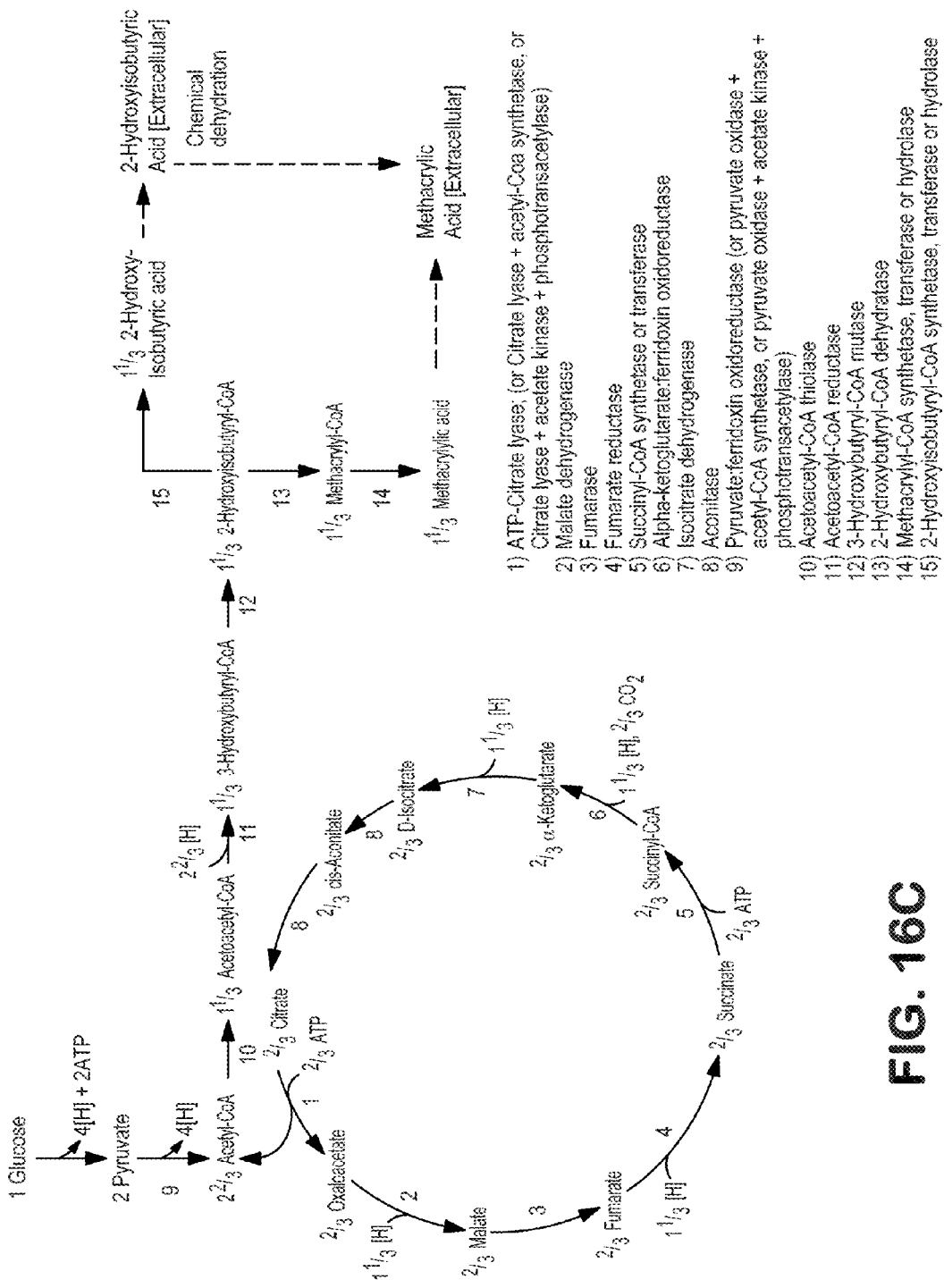
FIG. 16C shows the flux distribution showing an enhanced maximum theoretical yield of methacrylic acid on glucose when carbon is routed via the reductive TCA cycle. The enzymatic transformations are carried out by: (1) ATP-citrate lyase; citrate lyase, acetyl-CoA synthetase; or citrate lyase, acetate kinse, phosphotransacetylase, (2) malate dehydrogenase, (3) fumarase, (4) fumarate reductase, (5) succinyl-CoA synthetase or transferase, (6) alpha-ketoglutarate:ferridoxin oxidoreductase, (7) isocitrate dehydrogenase, (8) aconitase, (9) pyruvate:ferridoxin oxidoreductase; pyruvate oxidase, acetyl-CoA synthetase; or pyruvate oxidase, acetate kinase, phosphotransacetylase, (10) acetoacetyl-CoA thiolase, (11) acetoacetyl-CoA reductase, (12) 3-hydroxybutyryl-CoA mutase, (13) 2-hydroxybutyryl-CoA dehydratase, (14) methacrylyl-CoA synthetase, transferase or hydrolase, (15) 2-hydroxybutyryl-CoA synthetase, transferase or hydrolase.

The invention additionally provides a non-naturally occurring microbial organism comprising a microbial organism having a 2-hydroxyisobutyric acid pathway comprising at least one exogenous nucleic acid encoding a 2-hydroxyisobutyric acid pathway enzyme expressed in a sufficient amount to produce 2-hydroxyisobutyric acid; wherein said 2-hydroxyisobutyric acid pathway enzymes are selected from those shown in FIG. 16C; said non-naturally occurring microbial organism further comprising: (i) a reductive TCA pathway comprising at least one exogenous nucleic acid encoding a reductive TCA pathway enzyme, wherein said at least one exogenous nucleic acid is selected from an ATP-citrate lyase, citrate lyase, a fumarate reductase, and an alpha-ketoglutarate:ferredoxin oxidoreductase, or optionally isocitrate dehydrogenase, aconitase, citryl-CoA synthetase or citryl-CoA lyase; (ii) a reductive TCA pathway comprising at least one exogenous nucleic acid encoding a reductive TCA pathway enzyme, wherein said at least one exogenous nucleic acid is selected from a pyruvate:ferredoxin oxidoreductase, a phosphoenolpyruvate carboxylase, a phosphoenolpyruvate carboxykinase, a CO dehydrogenase, and an $H_2$ hydrogenase; or (iii) at least one exogenous nucleic acid encodes an enzyme selected from a CO dehydrogenase, an $H_2$ hydrogenase, and combinations thereof.

In a further embodiment, the invention provides a non-naturally occurring microbial organism comprising a microbial organism having a 3-hydroxyisobutyric acid pathway comprising at least one exogenous nucleic acid encoding a 3-hydroxyisobutyric acid pathway enzyme expressed in a sufficient amount to produce 3-hydroxyisobutyric acid; wherein said 2-hydroxyisobutyric acid pathway enzymes are selected from those shown in FIG. 16B; said non-naturally occurring microbial organism further comprising (i) a reductive TCA pathway comprising at least one exogenous nucleic acid encoding a reductive TCA pathway enzyme, wherein said at least one exogenous nucleic acid is selected from an ATP-citrate lyase, citrate lyase, a fumarate reductase, and an alpha-ketoglutarate:ferredoxin oxidoreductase, or optionally isocitrate dehydrogenase, aconitase, citryl-CoA synthetase or citryl-CoA lyase; (ii) a reductive TCA pathway comprising at least one exogenous nucleic acid encoding a reductive TCA pathway enzyme, wherein said at least one exogenous nucleic acid is selected from a pyruvate:ferredoxin oxidoreductase, a phosphoenolpyruvate carboxylase, a phosphoenolpyruvate carboxykinase, a CO dehydrogenase, and an $H_2$ hydrogenase; or (iii) at least one exogenous nucleic acid encodes an enzyme selected from a CO dehydrogenase, an $H_2$ hydrogenase, and combinations thereof.

This invention is directed, in part, to improving the theoretical yields of products using syngas or its components, hydrogen, carbon dioxide and carbon monoxide, as a source of reducing equivalents. In numerous engineered pathways, realization of maximum product yields based on carbohydrate feedstock is hampered by insufficient reducing equivalents or by loss of reducing equivalents and/or carbon to byproducts. The theoretical yields of several products on carbohydrate feedstocks increase substantially if hydrogen and/or carbon monoxide can supply sufficient reducing equivalents. For example, the theoretical yields of MAA, 2-hydroxyisobutyrate and 3-hydroxyisobutyrate increase to 2 mol/mol glucose in the presence of $H_2$.

Reducing equivalents, or electrons, can be extracted from synthesis gas components such as CO and $H_2$ using carbon monoxide dehydrogenase (CODH) and hydrogenase enzymes, respectively. The reducing equivalents are then passed to acceptors such as oxidized ferredoxins, oxidized quinones, oxidized cytochromes, NADP+, water, or hydrogen peroxide to form reduced ferredoxin, reduced quinones, reduced cytochromes, NAD(P)H, $H_2$, or water, respectively. Reduced ferredoxin and NAD(P)H are particularly useful as they can serve as redox carriers for various Wood-Ljungdahl pathway and reductive TCA cycle enzymes.

Here, we show specific examples of how additional redox availability from CO and/or $H_2$ can improve the yields of reduced products such as methacrylic acid, 2-hydroxyisobutyrate and 3-hydroxyisobutyrate.

Methacrylic acid (MAA), 3-hydroxybutyric acid and 2-hydroxyisobutyric acid are exemplary reduced products. The production of MAA through fermentation has a theoretical yield of 1.33 moles MAA per mole of glucose. It is most commonly produced from the acetone cyanohydrin (ACH) route using the raw materials acetone and hydrogen cyanide as raw materials. The intermediate cyanohydrin is converted with sulfuric acid to a sulfate ester of the methacrylamide, hydrolysis of which gives ammonium bisulfate and MAA. Other producers start with an isobutylene or, equivalently, tert-butanol, which is oxidized to methacrolein, and again oxidized to methacrylic acid. MAA is then esterified with methanol to MMA. Methacrylic acid is used industrially in the preparation of its esters, known collectively as methacrylates, such as methyl methacrylate. The methacrylates have numerous uses, most notably in the manufacture of polymers.

$$C_6H_{12}O_6 \rightarrow 1.33C_4H_6O_2 + 0.67CO_2 + 2H_2O$$

When the combined feedstocks strategy is applied to MAA production, the reducing equivalents generated from syngas can increase the MAA theoretical yield from glucose to 2 mol MAA per mol of glucose with the pathways detailed in FIGS. 16A and 16B.

$$1C_6H_{12}O_6 + 2CO_2 + 6H_2 \rightarrow 2C_4H_6O_2 + 6H_2O$$

Or $$1C_6H_{12}O_6 + 2CO + 4H_2 \rightarrow 2C_4H_6O_2 + 4H_2O$$

Similarly, the production of 3-hydroxyisobutyric acid through fermentation can be improved by the combined feedstock strategy. The production of 3-hydroxyisobutyric acid through fermentation has a theoretical yield of 1.33 mol 3-hydroxyisobutyric acid per mol of glucose.

$$3C_6H_{12}O_6 \rightarrow 4C_4H_8O_3 + 2CO_2 + 2H_2O$$

When the combined feedstocks strategy is applied to 3-hydroxyisobutyric acid production, the reducing equivalents generated from syngas can increase the 3-hydroxyisobutyric acid theoretical yield from glucose to 2 mol 3-hydroxyisobutyric acid per mol of glucose with the pathways detailed in FIGS. 16A and 16B.

$$1C_6H_{12}O_6 + 2CO_2 + 6H_2 \rightarrow 2C_4H_8O_3 + 4H_2O$$

Similarly, the production of 2-hydroxyisobutyric acid through fermentation can be improved by the combined feedstock strategy. The production of 2-hydroxyisobutyric acid through fermentation has a theoretical yield of 1.33 mol 2-hydroxyisobutyric acid per mol of glucose.

$$3C_6H_{12}O_6 \rightarrow 4C_4H_8O_3 + 2CO_2 + 2H_2O$$

When the combined feedstocks strategy is applied to 3-hydroxyisobutyric acid production, the reducing equivalents generated from syngas can increase the 3-hydroxyisobutyric acid theoretical yield from glucose to 2 mol 2-hydroxyisobutyric acid per mol of glucose with the pathways detailed in FIG. 16B.

$$1C_6H_{12}O_6 + 2CO_2 + 6H_2 \rightarrow 2C_4H_8O_3 + 4H_2O$$

The invention is also directed in part to increasing carbon flux through the central metabolism intermediate, acetyl-CoA, en route to product molecules by enhancing carbon fixation via the reductive TCA cycle. Exemplary product molecules include methacrylic acid and 2-hydroxyisobutyrate, although given the teachings and guidance provided herein, it will be recognized by one skilled in the art that any product molecule that has acetyl-CoA as a building block can exhibit enhanced production through increased carbon flux through acetyl-CoA. The present invention provides non-naturally occurring microbial organisms having one or more exogenous genes encoding enzymes that can catalyze various enzymatic transformations en route to acetyl-CoA. In some embodiments, these enzymatic transformations are part of the reductive tricarboxylic acid (RTCA) cycle and are used to improve product yields from carbohydrate-based carbon feedstock. In other embodiments, these enzymatic transformations are part of the Wood-Ljungdahl pathway.

The $CO_2$-fixing reductive tricarboxylic acid (RTCA) cycle is an endergenic anabolic pathway of $CO_2$ assimilation which uses NAD(P)H and ATP. One turn of the RTCA cycle assimilates two moles of $CO_2$ into one mole of acetyl-CoA, or four moles of $CO_2$ into one mole of oxaloacetate. This additional availability of acetyl-CoA improves the maximum theoretical yield of product molecules derived from carbohydrate-based carbon feedstock. Exemplary carbohydrates include but are not limited to glucose, sucrose, xylose, arabinose and glycerol. Note that the pathways for the exemplary product molecules described herein all proceed through acetyl-CoA.

Figure 16D:
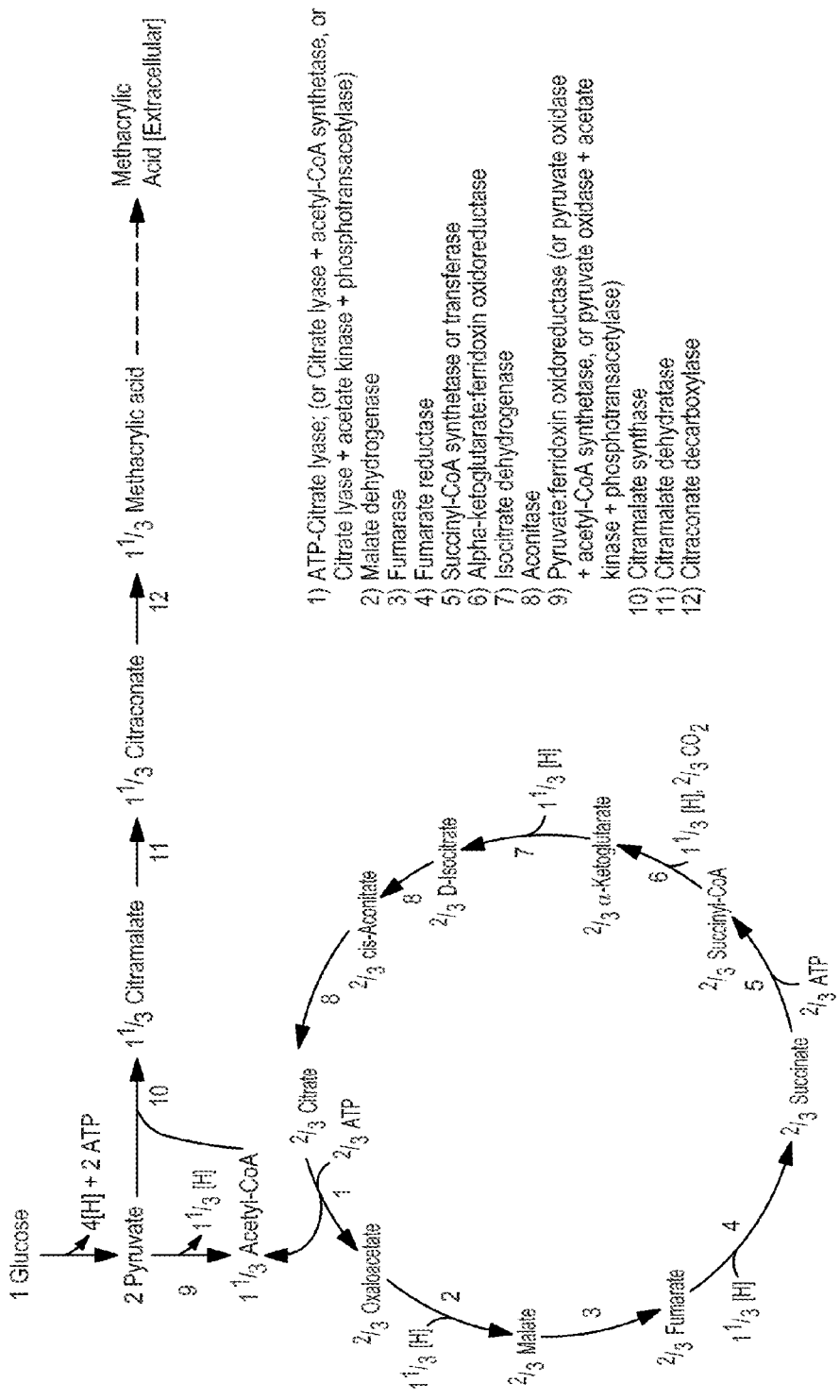
FIG. 16D shows the flux distribution showing an enhanced maximum theoretical yield of methacrylic acid on glucose via citramalate when carbon is routed via the reductive TCA cycle. The enzymatic transformations are carried out by (1) ATP-citrate lyase; citrate lyase, acetyl-CoA synthetase; or citrate lyase, acetate kinse, phosphotransacetylase, (2) malate dehydrogenase, (3) fumarase, (4) fumarate reductase, (5) succinyl-CoA synthetase or transferase, (6) alpha-ketoglutarate:ferridoxin oxidoreductase, (7) isocitrate dehydrogenase, (8) aconitase, (9) pyruvate:ferridoxin oxidoreductase; pyruvate oxidase, acetate kinase, phosphotransacetylase, (10) citramalate synthase, (11) citramalate dehydratase and (12) citraconate decarboxylase.
Figure 16E:
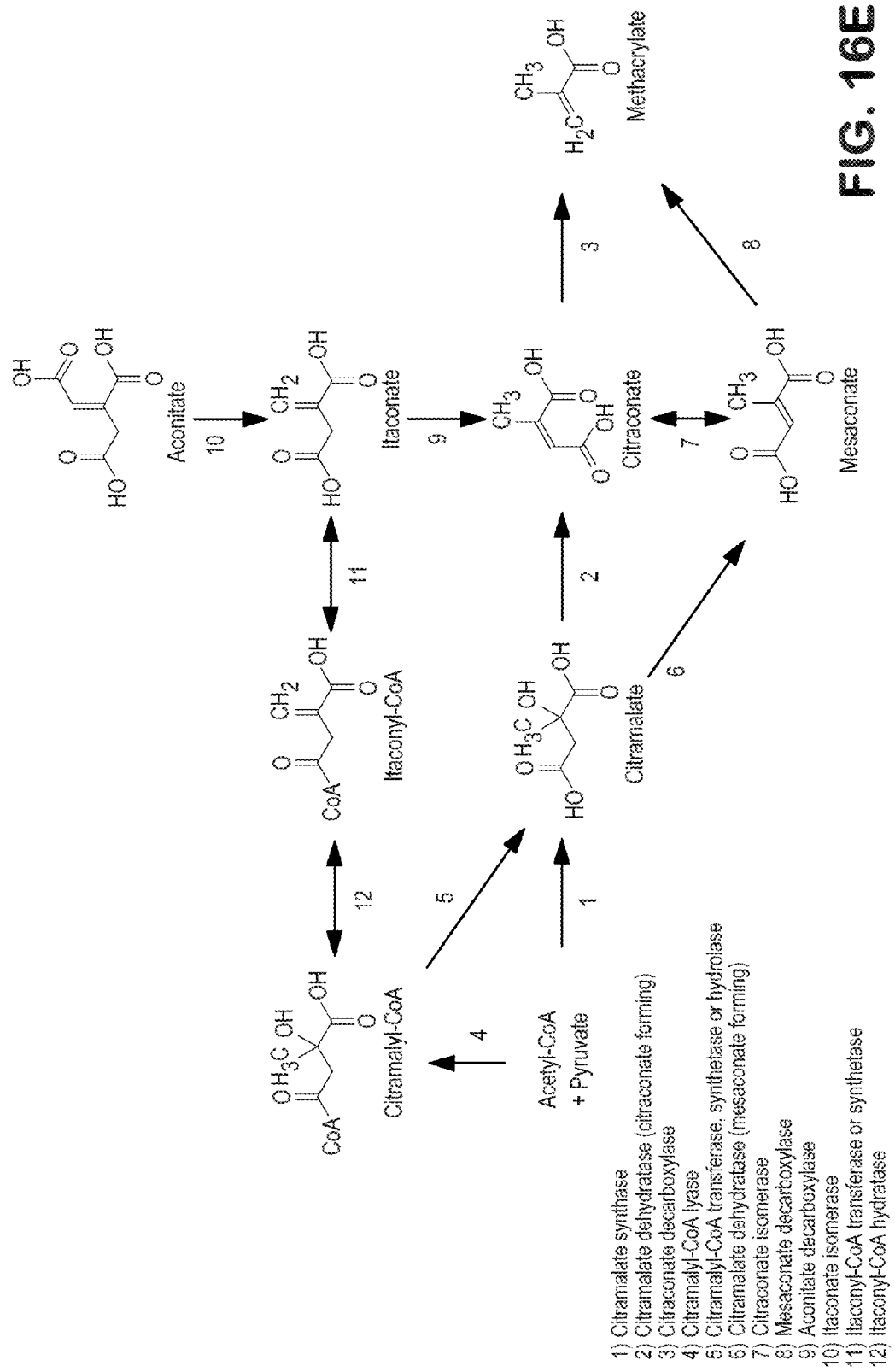
FIG. 16E shows pathways for biosynthesis of methacrylic acid from acetyl-CoA and pyruvate. The enzymatic transformations are carried out by the enzymes as shown. Enzymes are (1) citramalate synthase, (2) citramalate dehydratase (citraconate forming), (3) citraconate decarboxylase, (4) citramalyl-CoA lyase, (5) citramalyl-CoA transferase, synthetase or hydrolase, (6) citramalate dehydratase (mesaconate forming), (7) citraconate isomerase, (8) mesaconate decarboxylase, (9) aconitate decarboxylase, (10) itaconate isomerase, (11) itaconyl-CoA transferase or synthetase and (12) itaconyl-CoA hydratase.

The production of MAA from sugars via the pathways shown in FIGS. 16C, 16D and 16E has a maximum yield of 1 mole MAA per mole glucose consumed, in the absence of reductive TCA cycle activity. The fixation of carbon by the reductive TCA cycle increases the yield of these pathways to the maximum theoretical yield of MAA from sugars. FIGS. 16C and 16D are exemplary flux distributions showing how additional carbon generated by the reductive TCA cycle increases the yield of methacrylic acid produced by these pathways from 1 mole/mole glucose to 1.33 moles per mole glucose.

$$C_6H_{12}O_6 \rightarrow 1.33C_4H_6O_2 + 0.67CO_2 + 2H_2O$$

In one embodiment, the invention provides a non-naturally occurring microbial organism, comprising a microbial organism having a methacrylate ester pathway comprising at least one exogenous nucleic acid encoding a methacrylate ester pathway enzyme expressed in a sufficient amount to produce a methacrylate ester; said non-naturally occurring microbial organism further comprising: (i) a reductive TCA pathway comprising at least one exogenous nucleic acid encoding a reductive TCA pathway enzyme, wherein said at least one exogenous nucleic acid is selected from an ATP-citrate lyase, a citrate lyase, a fumarate reductase, and an alpha-ketoglutarate:ferredoxin oxidoreductase, or optionally isocitrate dehydrogenase, aconitase, citryl-CoA synthetase or citryl-CoA lyase; (ii) a reductive TCA pathway comprising at least one exogenous nucleic acid encoding a reductive TCA pathway enzyme, wherein said at least one exogenous nucleic acid is selected from a pyruvate:ferredoxin oxidoreductase, a phosphoenolpyruvate carboxylase, a phosphoenolpyruvate carboxykinase, a CO dehydrogenase, and an H2 hydrogenase; or (iii) at least one exogenous nucleic acid encodes an enzyme selected from a CO dehydrogenase, an H2 hydrogenase, and combinations thereof; wherein said methacrylate ester pathway comprises an alcohol transferase or an ester-forming enzyme, and a dehydratase. In one aspect, the dehydratase converts a 3-hydroxyisobutyrate ester or a 2-hydroxyisobutyrate ester to said methacrylate ester. In one aspect, the alcohol transferase coverts 3-hydroxyisobutyryl-CoA to a 3-hydroxyisobutyrate ester or 2-hydroxyisobutyryl-CoA to 2-hydroxyisobutyrate ester.

In one embodiment, the invention provides a microbial organism, wherein the microbial organism further comprises a methacyrlate ester pathway comprising at least one exogenous nucleic acid encoding a methacrylate ester pathway enzyme expressed in a sufficient amount to produce a methacrylate ester, said methacrylate ester pathway comprising a pathway selected from: (a) a 3-hydroxyisobutyrate-CoA transferase or a 3-hydroxyisobutyrate-CoA synthetase; an alcohol transferase; and a dehydratase; (b) a 3-hydroxyisobutyrate ester-forming enzyme and a dehydratase; (c) a 2-hydroxyisobutyrate-CoA transferase or a 2-hydroxyisobutyrate-CoA synthetase; an alcohol transferase; and a dehydratase; or (d) a 2-hydroxyisobutyrate ester-forming enzyme and a dehydratase. In another aspect, the microbial organism comprising (i) further comprises an exogenous nucleic acid encoding an enzyme selected from a pyruvate:ferredoxin oxidoreductase, an aconitase, an isocitrate dehydrogenase, a succinyl-CoA synthetase, a succinyl-CoA transferase, a fumarase, a malate dehydrogenase, an acetate kinase, a phosphotransacetylase, an acetyl-CoA synthetase, an NAD(P)H:ferredoxin oxidoreductase, ferredoxin, and combinations thereof. In another aspect, the microbial organism comprising (ii) further comprises an exogenous nucleic acid encoding an enzyme selected from an aconitase, an isocitrate dehydrogenase, a succinyl-CoA synthetase, a succinyl-CoA transferase, a fumarase, a malate dehydrogenase, and combinations thereof.

In one aspect, the microbial organism comprises two exogenous nucleic acids each encoding a methacrylic acid pathway enzyme. In another aspect, the two exogenous nucleic acids encode an alcohol transferase and a dehydratase or alternatively an ester-forming enzyme and a dehydratase.

In one embodiment the invention provides a non-naturally occurring microbial, wherein said microbial organism comprising (i) comprises four exogenous nucleic acids encoding an ATP-citrate lyase, citrate lyase, a fumarate reductase, and an alpha-ketoglutarate:ferredoxin oxidoreductase; wherein said microbial organism comprising (ii) comprises five exogenous nucleic acids encoding a pyruvate:ferredoxin oxidoreductase, a phosphoenolpyruvate carboxylase, a phosphoenolpyruvate carboxykinase, a CO dehydrogenase, and an H2 hydrogenase; or wherein said microbial organism comprising (iii) comprises two exogenous nucleic acids encoding a CO dehydrogenase and an H2 hydrogenase.

In one embodiment, the invention provide a method for producing a methacrylate ester comprising, culturing the non-naturally occurring microbial organism as described herein under conditions and for a sufficient period of time to produce methacrylate ester.

The invention is described herein with general reference to the metabolic reaction, reactant or product thereof, or with specific reference to one or more nucleic acids or genes encoding an enzyme associated with or catalyzing, or a protein associated with, the referenced metabolic reaction, reactant or product. Unless otherwise expressly stated herein, those skilled in the art will understand that reference to a reaction also constitutes reference to the reactants and products of the reaction. Similarly, unless otherwise expressly stated herein, reference to a reactant or product also references the reaction, and reference to any of these metabolic constituents also references the gene or genes encoding the enzymes that catalyze or proteins involved in the referenced reaction, reactant or product. Likewise, given the well known fields of metabolic biochemistry, enzymology and genomics, reference herein to a gene or encoding nucleic acid also constitutes a reference to the corresponding encoded enzyme and the reaction it catalyzes or a protein associated with the reaction as well as the reactants and products of the reaction.

As disclosed herein, the product methacrylic acid, as well as other intermediates, are carboxylic acids, which can occur in various ionized forms, including fully protonated, partially protonated, and fully deprotonated forms. Accordingly, the suffix "-ate," or the acid form, can be used interchangeably to describe both the free acid form as well as any deprotonated form, in particular since the ionized form is known to depend on the pH in which the compound is found. It is understood that carboxylate products or intermediates includes ester forms of carboxylate products or pathway intermediates, such as O-carboxylate and S-carboxylate esters. O- and S-carboxylates can include lower alkyl, that is C1 to C6, branched or straight chain carboxylates. Some such O- or S-carboxylates include, without limitation, methyl, ethyl, n-propyl, n-butyl, i-propyl, sec-butyl, and tert-butyl, pentyl, hexyl O- or S-carboxylates, any of which can further possess an unsaturation, providing for example, propenyl, butenyl, pentyl, and hexenyl O- or S-carboxylates. O-carboxylates can be the product of a biosynthetic pathway. Exemplary O-carboxylates accessed via biosynthetic pathways can include, without limitation, methyl methacrylate, ethyl methacrylate, and n-propyl methacrylate. Other biosynthetically accessible O-carboxylates can include medium to long chain groups, that is C7-C22, O-carboxylate esters derived from fatty alcohols, such heptyl, octyl, nonyl, decyl, undecyl, lauryl, tridecyl, myristyl, pentadecyl, cetyl, palmitolyl, heptadecyl, stearyl, nonadecyl, arachidyl, heneicosyl, and behenyl alcohols, any one of which can be optionally branched and/or contain unsaturations. O-carboxylate esters can also be accessed via a chemical process, such as esterification of a free carboxylic acid product or transesterification of an O- or S-carboxylate. S-carboxylates are exemplified by CoA S-esters, cysteinyl S-esters, alkylthioesters, and various aryl and heteroaryl thioesters. Additionally, the formation of methacrylic acid esters via a methacryl-CoA intermediate has been proposed (WO/2007/039415 and U.S. Pat. No. 7,901,915). Methacryl-CoA can be formed from methacrylate using a methacryl-CoA synthetase as described in WO/2007/039415 and U.S. Pat. No. 7,901,915 or by applying a methacryl-CoA transferase (see FIG. 2 and Example III). A methacrylyl-CoA transferase can transfer a CoA moiety to methacrylate from several CoA donors including, but not limited to, acetyl-CoA, succinyl-CoA, butyryl-CoA, and propionyl-CoA. Methacrylate can be formed from the pathways depicted in FIG. 1 or the pathways described in WO/2009/135074 or U.S. publication 2009/0275096. Methacrylyl-CoA can alternatively be produced from 2-hydroxyisobutyryl-CoA, 3-hydroxyisobutyryl-CoA, 3-hydroxyisobutyrate, or isobutyryl-CoA via 2-hydroxyisobutyryl-CoA dehydratase, 3-hydroxyisobutyryl-CoA dehydratase, 3-hydroxyisobutyrate dehydratase, or isobutyryl-CoA dehydrogenase as described in WO/2009/135074.

Thus, the invention additionally provides microbial organisms for producing methacrylate esters. Such organisms can comprise a methacrylate ester pathway comprising methacrylyl-CoA transferase. Such a microbial organism can further comprise a methacrylate ester pathway comprising methacrylyl-CoA synthetase and/or alcohol transferase (see FIG. 2 and Example III). It is understood that such an organism that produces a methacrylate ester can be engineered to contain a microbial organism containing a methacrylic acid or methacrylyl-CoA pathway, including but not limited to the methacrylic acid pathways disclosed herein (see Examples I and V-XIV and FIGS. 1-11) or described in WO2009/135074 or U.S. publication 2009/0275096. Thus, any of the disclosed microbial organisms that produce methacrylic acid can further comprise at least one exogenous nucleic acid encoding a methacrylate ester pathway enzyme expressed in a sufficient amount to produce methacrylate ester, the methacrylate ester pathway comprising methacrylyl-CoA synthetase, methacrylyl-CoA transferase and alcohol transferase. Exemplary enzymatic and chemical conversion of methacrylic acid to methacrylate esters is described in Example IV.

Thus, the invention additionally provides a microbial organism comprising a methacrylate ester pathway and further comprising a methacrylic acid pathway disclosed herein, including the methacrylic acid pathways described in FIGS. 1 and 3-11 and in Examples I and V-XIV. In a particular embodiment, the microbial organism comprising a methacrylate ester pathway further comprises a methacrylic acid pathway selected from 3-hydroxyisobutyrate dehydratase; methylmalonyl-CoA mutase, methylmalonyl-CoA reductase, 3-hydroxyisobutyrate dehydrogenase, and 3-hydroxyisobutyrate dehydratase; methylmalonyl-CoA mutase, methylmalonyl-CoA epimerase, methylmalonyl-CoA reductase, 3-hydroxyisobutyrate dehydrogenase, and 3-hydroxyisobutyrate dehydratase; methylmalonyl-CoA mutase, alcohol/aldehyde dehydrogenase, and 3-hydroxyisobutyrate dehydratase; methylmalonyl-CoA mutase, methylmalonyl-CoA epimerase, alcohol/aldehyde dehydrogenase, and 3-hydroxyisobutyrate dehydratase; methylmalonyl-CoA mutase, methylmalonyl-CoA reductase, 3-amino-2-methylpropionate transaminase, and 3-amino-2-methylpropionate ammonia lyase; methylmalonyl-CoA mutase, methylmalonyl-CoA epimerase, methylmalonyl-CoA reductase, 3-amino-2-methylpropionate transaminase, and 3-amino-2-methylpropionate ammonia lyase; 4-hydroxybutyryl-CoA mutase, 3-hydroxyisobutyryl-CoA synthetase or 3-hydroxyisobutyryl-CoA hydrolase or 3-hydroxyisobutyryl-CoA transferase, and 3-hydroxyisobutyrate dehydratase; aspartate aminotransferase, glutamate mutase, 3-methylaspartase, and mesaconate decarboxylase; alpha-ketoglutarate reductase, 2-hydroxyglutamate mutase, 3-methylmalate dehydratase, and mesaconate decarboxylase; acetoacetyl-CoA thiolase, acetoacetyl-CoA reductase, 3-hydroxybutyryl-CoA mutase, 2-hydroxyisobutyryl-CoA dehydratase, and methacrylyl-CoA transferase or methacrylyl-CoA hydrolase or methacrylyl-CoA synthetase; acetoacetyl-CoA thiolase, acetoacetyl-CoA reductase, 3-hydroxybutyryl-CoA mutase, 2-hydroxyisobutyryl-CoA dehydratase, enoyl-CoA hydratase, and 3-hydroxyisobutyryl-CoA hydrolase or 3-hydroxyisobutyryl-CoA synthetase or 3-hydroxyisobutyryl-CoA transferase, and 3-hydroxyisobutyrate dehydratase; 4-hydroxybutyryl-CoA dehydratase, vinylacetyl-CoA Δ-isomerase, crotonase, 3-hydroxybutyryl-CoA mutase, 2-hydroxyisobutyryl-CoA dehydratase, and any of methacrylyl-CoA hydrolase or methacrylyl-CoA synthetase or methacrylyl-CoA transferase; and 4-hydroxybutyryl-CoA mutase, 3-hydroxyisobutyryl-CoA dehydratase, and methacrylyl-CoA synthetase or methacrylyl-CoA hydrolase or methacrylyl-CoA transferase (see Examples V-XIV).

Exemplary non-naturally occurring microbial organisms capable of producing methacrylic acid are disclosed herein. For example, a methacrylic acid pathway is provided in which succinyl-CoA is a precursor (see Examples V-VI, FIGS. 3 and 4). In one embodiment, a non-naturally occurring microbial organism has a methacrylic acid pathway comprising at least one exogenous nucleic acid encoding a methacrylic acid pathway enzyme expressed in a sufficient amount to produce methacrylic acid, the methacrylic acid pathway comprising methylmalonyl-CoA mutase, methylmalonyl-CoA epimerase, methylmalonyl-CoA reductase, 3-hydroxyisobutyrate dehydrogenase and 3-hydroxyisobutyrate dehydratase (see Examples V and VI and FIG. 3). In another embodiment, a non-naturally occurring microbial organism has a methacrylic acid pathway comprising at least one exogenous nucleic acid encoding a methacrylic acid pathway enzyme expressed in a sufficient amount to produce methacrylic acid, the methacrylic acid pathway comprising methylmalonyl-CoA mutase, methylmalonyl-CoA epimerase, alcohol/aldehyde dehydrogenase, and 3-hydroxyisobutyrate dehydratase (see Example V). Additionally, a non-naturally occurring microbial organism can have a methacrylic acid pathway comprising at least one exogenous nucleic acid encoding a methacrylic acid pathway enzyme expressed in a sufficient amount to produce methacrylic acid, the methacrylic acid pathway comprising methylmalonyl-CoA mutase, methylmalonyl-CoA epimerase, methylmalonyl-CoA reductase, 3-amino-2-methylpropionate transaminase, and 3-amino-2-methylpropionate ammonia lyase (see Examples VI and FIG. 4).

Additionally provided is a non-naturally occurring microbial organism containing a methacrylic acid pathway having 4-hydroxybutyryl-CoA as a precursor. One such embodiment is a non-naturally occurring microbial organism having a methacrylic acid pathway comprising at least one exogenous nucleic acid encoding a methacrylic acid pathway enzyme expressed in a sufficient amount to produce methacrylic acid, the methacrylic acid pathway comprising 4-hydroxybutyryl-CoA mutase, 3-hydroxyisobutyryl-CoA synthetase or 3-hydroxyisobutyryl-CoA hydrolase or 3-hydroxyisobutyryl-CoA transferase, and 3-hydroxyisobutyrate dehydratase (see Examples VII and FIG. 5). Alternatively, the pathway could include 4-hydroxybutyryl-CoA mutase, 3-hydroxyisobutyryl-CoA dehydratase; and methacrylyl-CoA synthetase or methacrylyl-CoA hydrolase or methacrylyl-CoA transferase.

Further provided is a non-naturally occurring microbial organism containing a methacrylic acid pathway having alpha-ketoglutarate as a precursor. One such embodiment is a non-naturally occurring microbial organism having a methacrylic acid pathway comprising at least one exogenous nucleic acid encoding a methacrylic acid pathway enzyme expressed in a sufficient amount to produce methacrylic acid, the methacrylic acid pathway comprising aspartate aminotransferase, glutamate mutase, 3-methylaspartase, and mesaconate decarboxylase (see Examples VIII and FIG. 6). In yet another embodiment, a non-naturally occurring microbial organism has a methacrylic acid pathway comprising at least one exogenous nucleic acid encoding a methacrylic acid pathway enzyme expressed in a sufficient amount to produce methacrylic acid, the methacrylic acid pathway comprising alpha-ketoglutarate reductase, 2-hydroxyglutamate mutase, 3-methylmalate dehydratase, and mesaconate decarboxylase (see Examples IX and FIG. 7).

In still another embodiment, a non-naturally occurring microbial organism containing a methacrylic acid pathway has acetyl-CoA as a precursor. For example, a non-naturally occurring microbial organism can have a methacrylic acid pathway comprising at least one exogenous nucleic acid encoding a methacrylic acid pathway enzyme expressed in a sufficient amount to produce methacrylic acid, the methacrylic acid pathway comprising acetoacetyl-CoA thiolase, acetoacetyl-CoA reductase, 3-hydroxybutyryl-CoA mutase, 2-hydroxyisobutyryl-CoA dehydratase, and methacrylyl-CoA transferase or methacrylyl-CoA hydrolase or methacrylyl-CoA synthetase (see Examples X and FIG. 8). In another embodiment, a non-naturally occurring microbial organism hays a methacrylic acid pathway comprising at least one exogenous nucleic acid encoding a methacrylic acid pathway enzyme expressed in a sufficient amount to produce methacrylic acid, the methacrylic acid pathway comprising acetoacetyl-CoA thiolase, acetoacetyl-CoA reductase, 3-hydroxybutyryl-CoA mutase, 2-hydroxyisobutyryl-CoA dehydratase, enoyl-CoA hydratase, and 3-hydroxyisobutyryl-CoA hydrolase or 3-hydroxyisobutyryl-CoA synthetase or 3-hydroxyisobutyryl-CoA transferase, and 3-hydroxyisobutyrate dehydratase (see Example X).

In further embodiments, non-naturally occurring microbial organisms can contain a methacrylic acid having 4-hydroxybutyryl-CoA as a precursor. For example, a non-naturally occurring microbial organism has a methacrylic acid pathway comprising at least one exogenous nucleic acid encoding a methacrylic acid pathway enzyme expressed in a sufficient amount to produce methacrylic acid, the methacrylic acid pathway comprising 4-hydroxybutyryl-CoA dehydratase; vinylacetyl-CoA Δ-isomerase; crotonase; 3-hydroxybutyryl-CoA mutase; 2-hydroxyisobutyryl-CoA dehydratase; and methacrylyl-CoA hydrolase or methacrylyl-CoA synthetase or methacrylyl-CoA transferase (see Example XIV and FIG. 8).

Figure 9:
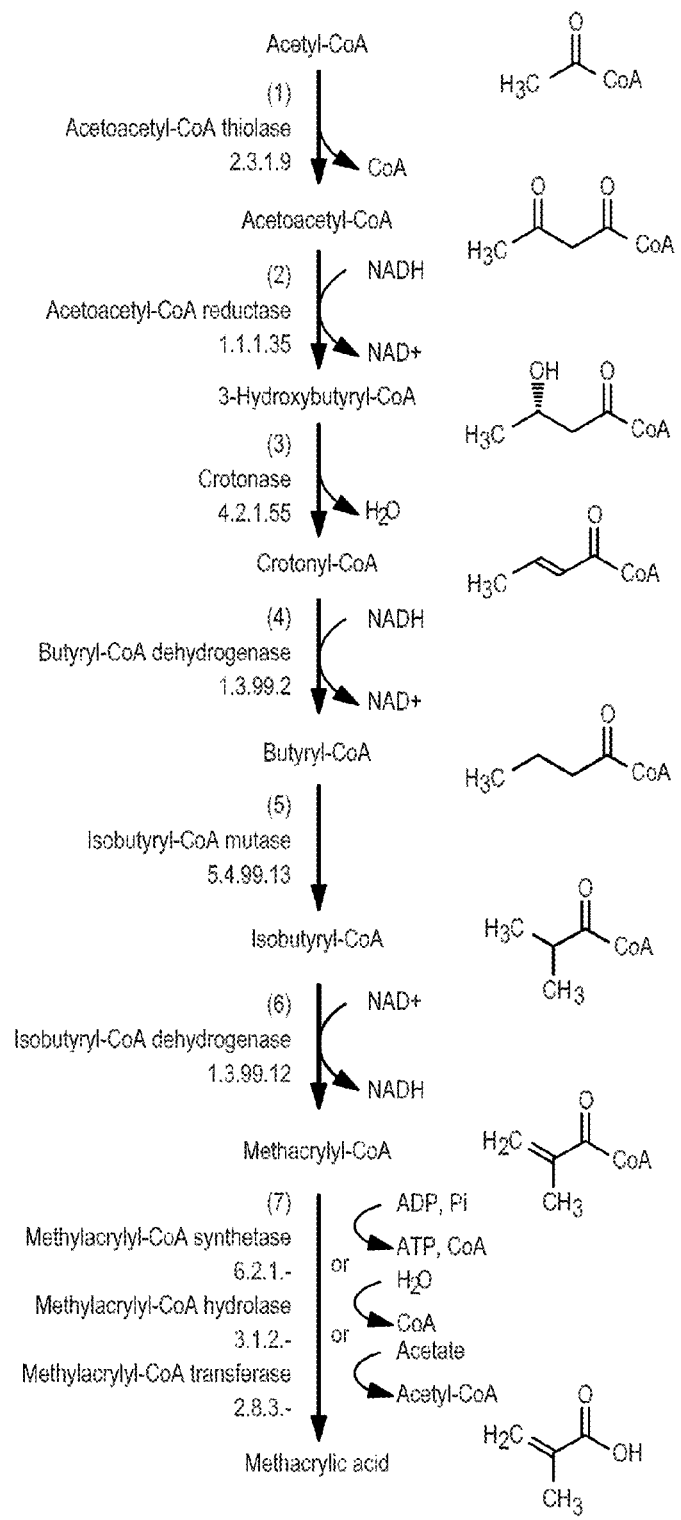
FIG. 9 shows an exemplary pathway from acetyl-CoA to MAA.

In yet another embodiment, a non-naturally occurring microbial organism has a methacrylic acid pathway comprising at least one exogenous nucleic acid encoding a methacrylic acid pathway enzyme expressed in a sufficient amount to produce methacrylic acid, the methacrylic acid pathway comprising acetoacetyl-CoA thiolase, acetoacetyl-CoA reductase, crotonase, butyryl-CoA dehydrogenase, isobutyryl-CoA mutase, isobutyryl-CoA dehydrogenase, and methacrylyl-CoA synthetase or methacrylyl-CoA hydrolase or methacrylyl-CoA transferase (see Example XI and FIG. 9).

Further provided is a non-naturally occurring organism containing a methacrylic acid pathway having pyruvate as a precursor. For example, a non-naturally occurring microbial organism can have a methacrylic acid pathway comprising at least one exogenous nucleic acid encoding a methacrylic acid pathway enzyme expressed in a sufficient amount to produce methacrylic acid, the methacrylic acid pathway comprising lactate dehydrogenase, lactate-CoA transferase, lactoyl-CoA dehydratase, acyl-CoA dehydrogenase, propionyl-CoA carboxylase, methylmalonyl-CoA reductase, 3-hydroxyisobutyrate dehydrogenase, and 3-hydroxyisobutyrate dehydratase (see Example XII and FIG. 10).

Figure 11:
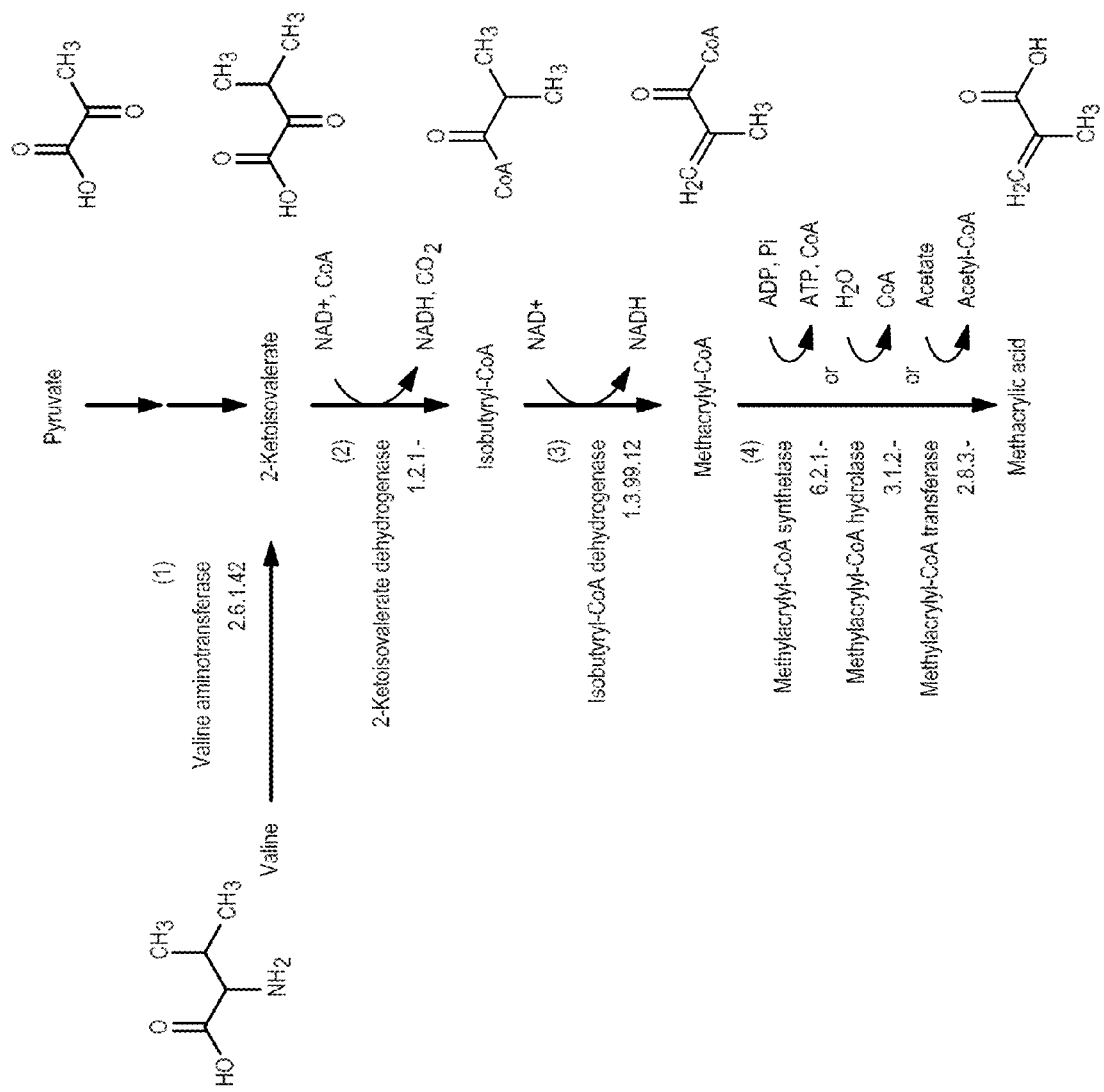
FIG. 11 shows an exemplary 2-ketovalerate to MAA pathway. 2-Ketoisovalerate can be produced either from valine or pyruvate. An exemplary set of enzymes for pyruvate conversion to 2-ketoisovalerate is comprised of acetolactate synthase, acetohydroxy acid isomeroreductase, and dihydroxyacid dehydratase.

Also provided is a non-naturally occurring microbial organism containing a methacrylic acid pathway having 2-ketoisovalerate as a precursor. For example, a non-naturally occurring microbial organism can have a methacrylic acid pathway comprising at least one exogenous nucleic acid encoding a methacrylic acid pathway enzyme expressed in a sufficient amount to produce methacrylic acid, the methacrylic acid pathway comprising valine aminotransferase, 2-ketoisovalerate dehydrogenase, isobutyryl-CoA dehydrogenase, and methacrylyl-CoA synthetase or methacrylyl-CoA hydrolase or methacrylyl-CoA transferase (see Example XIII and FIG. 11). Such a methacrylic acid pathway can further contain valine aminotransferase, which convert valine to 2-ketoisovalerate (FIG. 11). In addition, such a methacrylic acid pathway can further contain enzymes that convert pyruvate to 2-ketoisovalerate (FIG. 11), such as acetolactate synthase, acetohydroxy acid isomeroreductase and dihydroxy-acid dehydratase (see Example XIII).

The invention also provides a non-naturally occurring microbial organism having a methacrylate ester pathway comprising at least one exogenous nucleic acid encoding a methacrylate ester pathway enzyme expressed in a sufficient amount to produce a methacrylate ester, the methacrylate ester pathway comprising a methacrylyl-CoA transferase and an alcohol transferase. In a further embodiment, such a methacrylate ester pathway can further comprise methacrylyl-CoA synthetase. In a particular embodiment, the microbial organism having a methacrylate ester pathway can comprise two exogenous nucleic acids encoding methacrylyl-CoA and alcohol transferase. In a still further embodiment, the invention provides a microbial organism having a methacrylate ester pathway can comprise three exogenous nucleic acids encoding methacrylyl-CoA synthetase, methacrylyl-CoA transferase, and alcohol transferase.

The non-naturally occurring microbial organisms of the invention can be produced by introducing expressible nucleic acids encoding one or more of the enzymes or proteins participating in one or more methacrylic acid biosynthetic pathways. Depending on the host microbial organism chosen for biosynthesis, nucleic acids for some or all of a particular methacrylic acid biosynthetic pathway can be expressed. For example, if a chosen host is deficient in one or more enzymes or proteins for a desired biosynthetic pathway, then expressible nucleic acids for the deficient enzyme(s) or protein(s) are introduced into the host for subsequent exogenous expression. Alternatively, if the chosen host exhibits endogenous expression of some pathway genes, but is deficient in others, then an encoding nucleic acid is needed for the deficient enzyme(s) or protein(s) to achieve methacrylic acid biosynthesis. Thus, a non-naturally occurring microbial organism of the invention can be produced by introducing exogenous enzyme or protein activities to obtain a desired biosynthetic pathway or a desired biosynthetic pathway can be obtained by introducing one or more exogenous enzyme or protein activities that, together with one or more endogenous enzymes or proteins, produces a desired product such as methacrylic acid.

Host microbial organisms can be selected from, and the non-naturally occurring microbial organisms generated in, for example, bacteria, yeast, fungus or any of a variety of other microorganisms applicable to fermentation processes. Exemplary bacteria include species selected from *Escherichia coli, Klebsiella oxytoca, Anaerobiospirillum succiniciproducens, Actinobacillus succinogenes, Mannheimia succiniciproducens, Rhizobium etli, Bacillus subtilis, Corynebacterium glutamicum, Gluconobacter oxydans, Zymomonas mobilis, Lactococcus lactis, Lactobacillus plantarum, Streptomyces coelicolor, Clostridium acetobutylicum, Pseudomonas fluorescens,* and *Pseudomonas putida*. Exemplary yeasts or fungi include species selected from *Saccharomyces cerevisiae, Schizosaccharomyces pombe, Kluyveromyces lactis, Kluyveromyces marxianus, Aspergillus terreus, Aspergillus niger, Pichia pastoris, Rhizopus arrhizus, Rhizobus oryzae, Yarrowia lipolytica*, and the like. *E. coli* is a particularly useful host organisms since it is a well characterized microbial organism suitable for genetic engineering. Other particularly useful host organisms include yeast such as *Saccharomyces cerevisiae*. It is understood that any suitable microbial host organism can be used to introduce metabolic and/or genetic modifications to produce a desired product.

Depending on the methacrylic acid, methacrylate ester, 3-hydroxyisobutyrate and/or 2-hydroxyisobutyrate biosynthetic pathway constituents of a selected host microbial organism, the non-naturally occurring microbial organisms of the invention will include at least one exogenously expressed methacrylic acid, methacrylate ester, 3-hydroxyisobutyrate and/or 2-hydroxyisobutyrate pathway-encoding nucleic acid and up to all encoding nucleic acids for one or more methacrylic acid, methacrylate ester, 3-hydroxyisobutyrate and/or 2-hydroxyisobutyrate biosynthetic pathways. For example, methacrylic acid, methacrylate ester, 3-hydroxyisobutyrate and/or 2-hydroxyisobutyrate biosynthesis can be established in a host deficient in a pathway enzyme or protein through exogenous expression of the corresponding encoding nucleic acid. In a host deficient in all enzymes or proteins of a methacrylic acid, methacrylate ester, 3-hydroxyisobutyrate and/or 2-hydroxyisobutyrate pathway, exogenous expression of all enzyme or proteins in the pathway can be included, although it is understood that all enzymes or proteins of a pathway can be expressed even if the host contains at least one of the pathway enzymes or proteins. For example, exogenous expression of all enzymes or proteins in a pathway for production of methacrylic acid can be included, such as citramalate synthase (A), citramalate dehydratase (citraconate forming) (B), and citraconate decarboxylase (C) (FIG. 1, pathway (1) A/B/C); citramalate synthase (A), citramalate dehydratase (citraconate forming) (B), citraconate isomerase (G), and mesaconate decarboxylase (H) (FIG. 1, pathway (2) A/B/G/H); citramalate synthase (A), citramalate dehydratase (mesaconate forming) (F) citraconate isomerase (G), and citraconate decarboxylase (C) (FIG. 1, pathway (3) A/F/G/C); citramalate synthase (A), citramalate dehydratase (mesaconate forming) (F), and mesaconate decarboxylase (H) (FIG. 1, pathway (4) A/F/H); citramalyl-CoA lyase (D), citramalyl-CoA transferase, synthetase or hydrolase (E), citramalate dehydratase (citraconate forming) (B), and citraconate decarboxylase (C) (FIG. 1, pathway (5) D/E/B/C); citramalyl-CoA lyase (D), citramalyl-CoA transferase, synthetase or hydrolase (E), citramalate dehydratase (citraconate forming) (B), citraconate isomerase (G), and mesaconate decarboxylase (H) (FIG. 1, pathway (6) D/E/B/G/H); citramalyl-CoA lyase (D), citramalyl-CoA transferase, synthetase or hydrolase (E), citramalate dehydratase (mesaconate forming) (F), and mesaconate decarboxylase (H) (FIG. 1, pathway (7) D/E/F/H); citramalyl-CoA lyase (D), citramalyl-CoA transferase, synthetase or hydrolase (E), citramalate dehydratase (mesaconate forming) (F), citraconate isomerase (G), and citraconate decarboxylase (C) (FIG. 1, pathway (8) D/E/F/G/C); aconitate decarboxylase (I), itaconate isomerase (J), and citraconate decarboxylase (C) (FIG. 1, pathway (9) I/J/C); aconitate decarboxylase (I), itaconate isomerase (J), citraconate isomerase (G), and mesaconate decarboxylase (H) (FIG. 1, pathway (10) I/J/G/H); aconitate decarboxylase (I), itaconyl-CoA transferase, synthetase or hydrolase (L), citramalyl-CoA dehydratase (K), citramalyl-CoA transferase, synthetase or hydrolase (E), citramalate dehydratase (citraconate forming) (B), and citraconate decarboxylase (C) (FIG. 1, pathway (11) I/L/K/E/B/C); aconitate decarboxylase (I), itaconyl-CoA transferase, synthetase or hydrolase (L), citramalyl-CoA dehydratase (K), citramalyl-CoA transferase, synthetase or hydrolase (E), citramalate dehydratase (citraconate forming) (B), citraconate isomerase (G), and mesaconate decarboxylase (H) (FIG. 1, pathway (12) I/L/K/E/B/G/H); aconitate decarboxylase (I), itaconyl-CoA transferase, synthetase or hydrolase (L), citramalyl-CoA dehydratase (K), citramalyl-CoA transferase, synthetase or hydrolase (E), citramalate dehydratase (mesaconate forming) (F), and mesaconate decarboxylase (H) (FIG. 1, pathway (13) I/L/K/E/F/H); and aconitate decarboxylase (I), itaconyl-CoA transferase, synthetase or hydrolase (L), citramalyl-CoA dehydratase (K), citramalyl-CoA transferase, synthetase or hydrolase (E), citramalate dehydratase (mesaconate forming) (F), citraconate isomerase (G), and citraconate decarboxylase (C) (FIG. 1, pathway (14) I/L/K/E/F/G/C).

Given the teachings and guidance provided herein, those skilled in the art will understand that the number of encoding nucleic acids to introduce in an expressible form will, at least, parallel the methacrylic acid, methacrylate ester, 3-hydroxyisobutyrate and/or 2-hydroxyisobutyrate pathway deficiencies of the selected host microbial organism. Therefore, a non-naturally occurring microbial organism of the invention can have one, two, three, four, five, six, or seven, depending on the pathway, including up to all nucleic acids encoding the enzymes or proteins constituting a methacrylic acid, methacrylate ester, 3-hydroxyisobutyrate and/or 2-hydroxyisobutyrate biosynthetic pathway disclosed herein. In some embodiments, the non-naturally occurring microbial organisms also can include other genetic modifications that facilitate or optimize methacrylic acid, methacrylate ester, 3-hydroxyisobutyrate and/or 2-hydroxyisobutyrate biosynthesis or that confer other useful functions onto the host microbial organism. One such other functionality can include, for example, augmentation of the synthesis of one or more of the methacrylic acid, methacrylate ester, 3-hydroxyisobutyrate and/or 2-hydroxyisobutyrate pathway precursors such as acetyl-CoA, pyruvate or aconitate.

Generally, a host microbial organism is selected such that it produces the precursor of a methacrylic acid, methacrylate ester, 3-hydroxyisobutyrate and/or 2-hydroxyisobutyrate pathway, either as a naturally produced molecule or as an engineered product that either provides de novo production of a desired precursor or increased production of a precursor naturally produced by the host microbial organism. For example, aconitate, acetyl-CoA, and pyruvate are produced naturally in a host organism such as *E. coli*. A host organism can be engineered to increase production of a precursor, as disclosed herein. In addition, a microbial organism that has been engineered to produce a desired precursor can be used as a host organism and further engineered to express enzymes or proteins of a methacrylic acid, methacrylate ester, 3-hydroxyisobutyrate and/or 2-hydroxyisobutyrate pathway.

In some embodiments, a non-naturally occurring microbial organism of the invention is generated from a host that contains the enzymatic capability to synthesize methacrylic acid, methacrylate ester, 3-hydroxyisobutyrate and/or 2-hydroxyisobutyrate. In this specific embodiment it can be useful to increase the synthesis or accumulation of a methacrylic acid, methacrylate ester, 3-hydroxyisobutyrate and/or 2-hydroxyisobutyrate pathway product to, for example, drive methacrylic acid, methacrylate ester, 3-hydroxyisobutyrate and/or 2-hydroxyisobutyrate pathway reactions toward methacrylic acid, methacrylate ester, 3-hydroxyisobutyrate and/or 2-hydroxyisobutyrate production. Increased synthesis or accumulation can be accomplished by, for example, overexpression of nucleic acids encoding one or more of the methacrylic acid, methacrylate ester, 3-hydroxyisobutyrate and/or 2-hydroxyisobutyrate pathway enzymes or proteins described herein. Over expression of the enzyme or enzymes and/or protein or proteins of the methacrylic acid, methacrylate ester, 3-hydroxyisobutyrate and/or 2-hydroxyisobutyrate pathway can occur, for example, through exogenous expression of the endogenous gene or genes, or through exogenous expression of the heterologous gene or genes. Therefore, naturally occurring organisms can be readily generated to be non-naturally occurring microbial organisms of the invention, for example, producing methacrylic acid, methacrylate ester, 3-hydroxyisobutyrate and/or 2-hydroxyisobutyrate, through overexpression of one, two, three, four, five, six or seven, depending on the number of enzymes in the pathway, that is, up to all nucleic acids encoding methacrylic acid, methacrylate ester, 3-hydroxyisobutyrate and/or 2-hydroxyisobutyrate biosynthetic pathway enzymes or proteins. In addition, a non-naturally occurring organism can be generated by mutagenesis of an endogenous gene that results in an increase in activity of an enzyme in the methacrylic acid, methacrylate ester, 3-hydroxyisobutyrate and/or 2-hydroxyisobutyrate biosynthetic pathway.

In particularly useful embodiments, exogenous expression of the encoding nucleic acids is employed. Exogenous expression confers the ability to custom tailor the expression and/or regulatory elements to the host and application to achieve a desired expression level that is controlled by the user. However, endogenous expression also can be utilized in other embodiments such as by removing a negative regulatory effector or induction of the gene's promoter when linked to an inducible promoter or other regulatory element. Thus, an endogenous gene having a naturally occurring inducible promoter can be up-regulated by providing the appropriate inducing agent, or the regulatory region of an endogenous gene can be engineered to incorporate an inducible regulatory element, thereby allowing the regulation of increased expression of an endogenous gene at a desired time. Similarly, an inducible promoter can be included as a regulatory element for an exogenous gene introduced into a non-naturally occurring microbial organism.

It is understood that, in methods of the invention, any of the one or more exogenous nucleic acids can be introduced into a microbial organism to produce a non-naturally occurring microbial organism of the invention. The nucleic acids can be introduced so as to confer, for example, a methacrylic acid, methacrylate ester, 3-hydroxyisobutyrate and/or 2-hydroxyisobutyrate biosynthetic pathway onto the microbial organism. Alternatively, encoding nucleic acids can be introduced to produce an intermediate microbial organism having the biosynthetic capability to catalyze some of the required reactions to confer methacrylic acid, methacrylate ester, 3-hydroxyisobutyrate and/or 2-hydroxyisobutyrate biosynthetic capability. For example, a non-naturally occurring microbial organism having a methacrylic acid, methacrylate ester, 3-hydroxyisobutyrate and/or 2-hydroxyisobutyrate biosynthetic pathway can comprise at least two exogenous nucleic acids encoding desired enzymes or proteins, such as the combination of citramalate synthase and citraconate decarboxylase; citraconate isomerase and mesaconate decarboxylase; or itaconyl-CoA transferase, synthetase or hydrolase and itaconate isomerase, and the like. Thus, it is understood that any combination of two or more enzymes of a biosynthetic pathway can be included in a non-naturally occurring microbial organism of the invention. Similarly, it is understood that any combination of three or more enzymes of a biosynthetic pathway can be included in a non-naturally occurring microbial organism of the invention, for example, citramalate dehydratase (citraconate forming), citraconate isomerase and mesaconate decarboxylase; citramalyl-CoA lyase, citramalyl-CoA transferase, synthetase or hydrolase and citramalate dehydratase; or aconitate decarboxylase, itaconate isomerase and mesaconate decarboxylase, and so forth, as desired, so long as the combination of enzymes and/or proteins of the desired biosynthetic pathway results in production of the corresponding desired product. Similarly, any combination of four, for example, citramalyl-CoA lyase, citramalyl-CoA transferase, synthetase or hydrolase, citramalate dehydratase (citraconate forming) and mesaconate decarboxylase; aconitate decarboxylase, itaconate isomerase, citraconate isomerase and mesaconate decarboxylase, and the like, or more enzymes of a biosynthetic pathway as disclosed herein can be included in a non-naturally occurring microbial organism of the invention, as desired, including up to all enzymes in a pathway, so long as the combination of enzymes of the desired biosynthetic pathway results in production of the corresponding desired product.

In addition to the biosynthesis of methacrylic acid, methacrylate ester, 3-hydroxyisobutyrate and/or 2-hydroxyisobutyrate as described herein, the non-naturally occurring microbial organisms and methods of the invention also can be utilized in various combinations with each other and with other microbial organisms and methods well known in the art to achieve product biosynthesis by other routes. For example, one alternative to produce methacrylic acid, methacrylate ester, 3-hydroxyisobutyrate and/or 2-hydroxyisobutyrate other than use of the methacrylic acid, methacrylate ester, 3-hydroxyisobutyrate and/or 2-hydroxyisobutyrate producers is through addition of another microbial organism capable of converting a methacrylic acid, methacrylate ester, 3-hydroxyisobutyrate and/or 2-hydroxyisobutyrate pathway intermediate to methacrylic acid, methacrylate ester, 3-hydroxyisobutyrate and/or 2-hydroxyisobutyrate. One such procedure includes, for example, the fermentation of a microbial organism that produces a methacrylic acid, methacrylate ester, 3-hydroxyisobutyrate and/or 2-hydroxyisobutyrate pathway intermediate. The methacrylic acid, methacrylate ester, 3-hydroxyisobutyrate and/or 2-hydroxyisobutyrate pathway intermediate can then be used as a substrate for a second microbial organism that converts the methacrylic acid, methacrylate ester, 3-hydroxyisobutyrate and/or 2-hydroxyisobutyrate pathway intermediate to methacrylic acid, methacrylate ester, 3-hydroxyisobutyrate and/or 2-hydroxyisobutyrate. The methacrylic acid, methacrylate ester, 3-hydroxyisobutyrate and/or 2-hydroxyisobutyrate pathway intermediate can be added directly to another culture of the second organism or the original culture of the methacrylic acid, methacrylate ester, 3-hydroxyisobutyrate and/or 2-hydroxyisobutyrate pathway intermediate producers can be depleted of these microbial organisms by, for example, cell separation, and then subsequent addition of the second organism to the fermentation broth can be utilized to produce the final product without intermediate purification steps.

In other embodiments, the non-naturally occurring microbial organisms and methods of the invention can be assembled in a wide variety of subpathways to achieve biosynthesis of, for example, methacrylic acid, methacrylate ester, 3-hydroxyisobutyrate and/or 2-hydroxyisobutyrate. In these embodiments, biosynthetic pathways for a desired product of the invention can be segregated into different microbial organisms, and the different microbial organisms can be co-cultured to produce the final product. In such a biosynthetic scheme, the product of one microbial organism is the substrate for a second microbial organism until the final product is synthesized. For example, the biosynthesis of methacrylic acid, methacrylate ester, 3-hydroxyisobutyrate and/or 2-hydroxyisobutyrate can be accomplished by constructing a microbial organism that contains biosynthetic pathways for conversion of one pathway intermediate to another pathway intermediate or the product. Alternatively, methacrylic acid, methacrylate ester, 3-hydroxyisobutyrate and/or 2-hydroxyisobutyrate also can be biosynthetically produced from microbial organisms through co-culture or co-fermentation using two organisms in the same vessel, where the first microbial organism produces a methacrylic acid, methacrylate ester, 3-hydroxyisobutyrate and/or 2-hydroxyisobutyrate intermediate and the second microbial organism converts the intermediate to methacrylic acid, methacrylate ester, 3-hydroxyisobutyrate and/or 2-hydroxyisobutyrate.

Given the teachings and guidance provided herein, those skilled in the art will understand that a wide variety of combinations and permutations exist for the non-naturally occurring microbial organisms and methods of the invention together with other microbial organisms, with the co-culture of other non-naturally occurring microbial organisms having subpathways and with combinations of other chemical and/or biochemical procedures well known in the art to produce methacrylic acid, methacrylate ester, 3-hydroxyisobutyrate and/or 2-hydroxyisobutyrate.

Sources of encoding nucleic acids for a methacrylic acid, methacrylate ester, 3-hydroxyisobutyrate and/or 2-hydroxyisobutyrate pathway enzyme or protein can include, for example, any species where the encoded gene product is capable of catalyzing the referenced reaction. Such species include both prokaryotic and eukaryotic organisms including, but not limited to, bacteria, including archaea and eubacteria, and eukaryotes, including yeast, plant, insect, animal, and mammal, including human. Exemplary species for such sources include, for example, *Escherichia* species, including *Escherichia coli, Escherichia fergusonii, Methanocaldococcus jannaschii, Leptospira interrrogans, Geobacter sulfurreducens, Chloroflexus aurantiacus, Roseiflexus* sp. RS-1, *Chloroflexus aggregans, Achromobacter xylosoxydans, Clostrdia* species, including *Clostridium kluyveri, Clostridium symbiosum, Clostridium acetobutylicum, Clostridium saccharoperbutylacetonicum, Clostridium ljungdahlii, Trichomonas vaginalis* G3, *Trypanosoma brucei, Acidaminococcus fermentans, Fusobacterium* species, including *Fusobacterium nucleatum, Fusobacterium mortiferum, Corynebacterium glutamicum, Rattus norvegicus, Homo sapiens, Saccharomyces* species, including *Saccharomyces cerevisiae, Apsergillus* species, including *Aspergillus terreus, Aspergillus oryzae, Aspergillus niger, Gibberella zeae, Pichia stipitis, Mycobacterium* species, including *Mycobacterium smegmatis, Mycobacterium avium*, including subsp. *pratuberculosis, Salinispora arenicola Pseudomonas* species, including *Pseudomonas* sp. CF600, *Pseudomonas putida, Pseudomonas fluorescens, Pseudomonas aeruginosa, Ralstonia* species, including *Ralstonia eutropha, Ralstonia eutropha* JMP134, *Ralstonia eutropha* H16, *Ralstonia pickettii, Lactobacillus plantarum, Klebsiella oxytoca, Bacillus* species, including *Bacillus subtilis, Bacillus pumilus, Bacillus megaterium, Pediococcus pentosaceus, Chlorofexus* species, including *Chloroflexus aurantiacus, Chloroflexus aggregans, Rhodobacter sphaeroides, Methanocaldococcus jannaschii, Leptospira interrrogans, Candida maltosa, Salmonella* species, including *Salmonella enterica serovar Typhimurium, Shewanella* species, including *Shewanella oneidensis, Shewanella* sp. MR-4, *Alcaligenes faecalis, Geobacillus stearothermophilus, Serratia marcescens, Vibrio cholerae, Eubacterium barkeri, Bacteroides capillosus, Archaeoglobus fulgidus, Archaeoglobus fulgidus, Haloarcula marismortui, Pyrobaculum aerophilum* str. IM2, *Rhizobium* species, including *Rhizobium leguminosarum*, as well as other exemplary species disclosed herein or available as source organisms for corresponding genes. However, with the complete genome sequence available for now more than 550 species (with more than half of these available on public databases such as the NCBI), including 395 microorganism genomes and a variety of yeast, fungi, plant, and mammalian genomes, the identification of genes encoding the requisite methacrylic acid, methacrylate ester, 3-hydroxyisobutyrate and/or 2-hydroxyisobutyrate biosynthetic activity for one or more genes in related or distant species, including for example, homologues, orthologs, paralogs and nonorthologous gene displacements of known genes, and the interchange of genetic alterations between organisms is routine and well known in the art. Accordingly, the metabolic alterations allowing biosynthesis of methacrylic acid, methacrylate ester, 3-hydroxyisobutyrate and/or 2-hydroxyisobutyrate described herein with reference to a particular organism such as *E. coli* can be readily applied to other microorganisms, including prokaryotic and eukaryotic organisms alike. Given the teachings and guidance provided herein, those skilled in the art will know that a metabolic alteration exemplified in one organism can be applied equally to other organisms.

In some instances, such as when an alternative methacrylic acid, methacrylate ester, 3-hydroxyisobutyrate and/or 2-hydroxyisobutyrate biosynthetic pathway exists in an unrelated species, methacrylic acid, methacrylate ester, 3-hydroxyisobutyrate and/or 2-hydroxyisobutyrate biosynthesis can be conferred onto the host species by, for example, exogenous expression of a paralog or paralogs from the unrelated species that catalyzes a similar, yet non-identical metabolic reaction to replace the referenced reaction. Because certain differences among metabolic networks exist between different organisms, those skilled in the art will understand that the actual gene usage between different organisms may differ. However, given the teachings and guidance provided herein, those skilled in the art also will understand that the teachings and methods of the invention can be applied to all microbial organisms using the cognate metabolic alterations to those exemplified herein to construct a microbial organism in a species of interest that will synthesize methacrylic acid, methacrylate ester, 3-hydroxyisobutyrate and/or 2-hydroxyisobutyrate.

Methods for constructing and testing the expression levels of a non-naturally occurring methacrylic acid-, methacrylate ester-, 3-hydroxyisobutyrate- and/or 2-hydroxyisobutyrate-producing host can be performed, for example, by recombinant and detection methods well known in the art. Such methods can be found described in, for example, Sambrook et al., *Molecular Cloning: A Laboratory Manual*, Third Ed., Cold Spring Harbor Laboratory, New York (2001); and Ausubel et al., *Current Protocols in Molecular Biology*, John Wiley and Sons, Baltimore, Md. (1999).

Exogenous nucleic acid sequences involved in a pathway for production of methacrylic acid, methacrylate ester, 3-hydroxyisobutyrate and/or 2-hydroxyisobutyrate can be introduced stably or transiently into a host cell using techniques well known in the art including, but not limited to, conjugation, electroporation, chemical transformation, transduction, transfection, and ultrasound transformation. For exogenous expression in *E. coli* or other prokaryotic cells, some nucleic acid sequences in the genes or cDNAs of eukaryotic nucleic acids can encode targeting signals such as an N-terminal mitochondrial or other targeting signal, which can be removed before transformation into prokaryotic host cells, if desired. For example, removal of a mitochondrial leader sequence led to increased expression in *E. coli* (Hoffmeister et al., *J. Biol. Chem.* 280:4329-4338 (2005)). For exogenous expression in yeast or other eukaryotic cells, genes can be expressed in the cytosol without the addition of leader sequence, or can be targeted to mitochondrion or other organelles, or targeted for secretion, by the addition of a suitable targeting sequence such as a mitochondrial targeting or secretion signal suitable for the host cells. Thus, it is understood that appropriate modifications to a nucleic acid sequence to remove or include a targeting sequence can be incorporated into an exogenous nucleic acid sequence to impart desirable properties. Furthermore, genes can be subjected to codon optimization with techniques well known in the art to achieve optimized expression of the proteins.

An expression vector or vectors can be constructed to include one or more methacrylic acid, methacrylate ester, 3-hydroxyisobutyrate and/or 2-hydroxyisobutyrate biosynthetic pathway encoding nucleic acids as exemplified herein operably linked to expression control sequences functional in the host organism. Expression vectors applicable for use in the microbial host organisms of the invention include, for example, plasmids, phage vectors, viral vectors, episomes and artificial chromosomes, including vectors and selection sequences or markers operable for stable integration into a host chromosome. Additionally, the expression vectors can include one or more selectable marker genes and appropriate expression control sequences. Selectable marker genes also can be included that, for example, provide resistance to antibiotics or toxins, complement auxotrophic deficiencies, or supply critical nutrients not in the culture media. Expression control sequences can include constitutive and inducible promoters, transcription enhancers, transcription terminators, and the like which are well known in the art. When two or more exogenous encoding nucleic acids are to be co-expressed, both nucleic acids can be inserted, for example, into a single expression vector or in separate expression vectors. For single vector expression, the encoding nucleic acids can be operationally linked to one common expression control sequence or linked to different expression control sequences, such as one inducible promoter and one constitutive promoter. The transformation of exogenous nucleic acid sequences involved in a metabolic or synthetic pathway can be confirmed using methods well known in the art. Such methods include, for example, nucleic acid analysis such as Northern blots or polymerase chain reaction (PCR) amplification of mRNA, or immunoblotting for expression of gene products, or other suitable analytical methods to test the expression of an introduced nucleic acid sequence or its corresponding gene product. It is understood by those skilled in the art that the exogenous nucleic acid is expressed in a sufficient amount to produce the desired product, and it is further understood that expression levels can be optimized to obtain sufficient expression using methods well known in the art and as disclosed herein.

The invention additionally provides methods of producing methacrylic acid, methacrylate ester, 3-hydroxyisobutyrate and/or 2-hydroxyisobutyrate using the microbial organisms of the invention comprising a methacrylic acid pathway. In a particular embodiment, the invention provides a method for producing methacrylic acid by culturing a non-naturally occurring microbial organism, comprising a microbial organism having a methacrylic acid pathway comprising at least one exogenous nucleic acid encoding a methacrylic acid pathway enzyme expressed in a sufficient amount to produce methacrylic acid, the methacrylic acid pathway comprising citramalate synthase (A), citramalate dehydratase (citraconate forming) (B), and citraconate decarboxylase (C) (FIG. 1, pathway (1) A/B/C), under conditions and for a sufficient period of time to produce methacrylic acid. As disclosed herein, the microbial organism can comprise more than one exogenous nucleic acid encoding a methacrylic acid pathway enzyme, including up to all enzymes in a pathway, for example, three exogenous nucleic acids encode citramalate synthase, citramalate dehydratase (citraconate forming), and citraconate decarboxylase.

In a particular embodiment, MAA producing non-naturally occurring microbial organism of the invention can have at least one exogenous nucleic acid that is a heterologous nucleic acid. In another embodiment the non-naturally occurring microbial organism producing MAA can be in a substantially anaerobic culture medium.

In another embodiment, the invention provides a method for producing methacrylic acid by culturing a non-naturally occurring microbial organism comprising a methacrylic acid pathway comprising at least one exogenous nucleic acid encoding a methacrylic acid pathway enzyme expressed in a sufficient amount to produce methacrylic acid, the methacrylic acid pathway comprising citramalate synthase (A), citramalate dehydratase (citraconate forming) (B), citraconate isomerase (G), and mesaconate decarboxylase (H) (FIG. 1, pathway (2) A/B/G/H), under conditions and for a sufficient period of time to produce methacrylic acid. In still another embodiment, the invention provides a method for producing methacrylic acid by culturing a non-naturally occurring microbial organism, comprising a methacrylic acid pathway comprising at least one exogenous nucleic acid encoding a methacrylic acid pathway enzyme expressed in a sufficient amount to produce methacrylic acid, the methacrylic acid pathway comprising citramalate synthase (A), citramalate dehydratase (mesaconate forming) (F) citraconate isomerase (G), and citraconate decarboxylase (C) (FIG. 1, pathway (3) A/F/G/C), under conditions and for a sufficient period of time to produce methacrylic acid.

In a further embodiment, the invention provides a method for producing methacrylic acid by culturing a non-naturally occurring microbial organism, comprising a methacrylic acid pathway comprising at least one exogenous nucleic acid encoding a methacrylic acid pathway enzyme expressed in a sufficient amount to produce methacrylic acid, the methacrylic acid pathway comprising citramalate synthase (A), citramalate dehydratase (mesaconate forming) (F), and mesaconate decarboxylase (H) (FIG. 1, pathway (4) A/F/H), under conditions and for a sufficient period of time to produce methacrylic acid. In yet a further embodiment, the invention provides a method for producing methacylic acid by culturing a non-naturally occurring microbial organism, comprising a methacrylic acid pathway comprising at least one exogenous nucleic acid encoding a methacrylic acid pathway enzyme expressed in a sufficient amount to produce methacrylic acid, the methacrylic acid pathway comprising citramalyl-CoA lyase (D), citramalyl-CoA transferase, synthetase or hydrolase (E), citramalate dehydratase (citraconate forming) (B), and citraconate decarboxylase (C) (FIG. 1, pathway (5) D/E/B/C), under conditions and for a sufficient period of time to produce methacrylic acid.

In an additional embodiment, the invention provides a method for producing methacrylic acid by culturing a non-naturally occurring microbial organism, comprising a methacrylic acid pathway comprising at least one exogenous nucleic acid encoding a methacrylic acid pathway enzyme expressed in a sufficient amount to produce methacrylic acid, the methacrylic acid pathway comprising citramalyl-CoA lyase (D), citramalyl-CoA transferase, synthetase or hydrolase (E), citramalate dehydratase (citraconate forming) (B), citraconate isomerase (G), and mesaconate decarboxylase (H) (FIG. 1, pathway (6) D/E/B/G/H), under conditions and for a sufficient period of time to produce methacrylic acid. In still another embodiment, the invention provides a method for producing methacrylic acid by culturing a non-naturally occurring microbial organism, comprising a methacrylic acid pathway comprising at least one exogenous nucleic acid encoding a methacrylic acid pathway enzyme expressed in a sufficient amount to produce methacrylic acid, the methacrylic acid pathway comprising citramalyl-CoA lyase (D), citramalyl-CoA transferase, synthetase or hydrolase (E), citramalate dehydratase (mesaconate forming) (F), and mesaconate decarboxylase (H) (FIG. 1, pathway (7) D/E/F/H), under conditions and for a sufficient period of time to produce methacrylic acid.

In another embodiment, the invention provides a method for producing methacrylic acid by culturing a non-naturally occurring microbial organism, comprising a methacrylic acid pathway comprising at least one exogenous nucleic acid encoding a methacrylic acid pathway enzyme expressed in a sufficient amount to produce methacrylic acid, the methacrylic acid pathway comprising citramalyl-CoA lyase (D), citramalyl-CoA transferase, synthetase or hydrolase (E), citramalate dehydratase (mesaconate forming) (F), citraconate isomerase (G), and citraconate decarboxylase (C) (FIG. 1, pathway (8) D/E/F/G/C), under conditions and for a sufficient period of time to produce methacrylic acid. Additionally, the invention provides a method for producing methacrylic acid by culturing a non-naturally occurring microbial organism, comprising a methacrylic acid pathway comprising at least one exogenous nucleic acid encoding a methacrylic acid pathway enzyme expressed in a sufficient amount to produce methacrylic acid, the methacrylic acid pathway comprising aconitate decarboxylase (I), itaconate isomerase (J), and citraconate decarboxylase (C) (FIG. 1, pathway (9) I/J/C), under conditions and for a sufficient period of time to produce methacrylic acid.

In yet a further embodiment, the invention provides a method for producing methacrylic acid by culturing a non-naturally occurring microbial organism, comprising a methacrylic acid pathway comprising at least one exogenous nucleic acid encoding a methacrylic acid pathway enzyme expressed in a sufficient amount to produce methacrylic acid, the methacrylic acid pathway comprising aconitate decarboxylase (I), itaconate isomerase (J), citraconate isomerase (G), and mesaconate decarboxylase (H) (FIG. 1, pathway (10) I/J/G/H), under conditions and for a sufficient period of time to produce methacrylic acid. In an additional embodiment, the invention provides a method for producing methacrylic acid by culturing a non-naturally occurring microbial organism, comprising a methacrylic acid pathway comprising at least one exogenous nucleic acid encoding a methacrylic acid pathway enzyme expressed in a sufficient amount to produce methacrylic acid, the methacrylic acid pathway comprising aconitate decarboxylase (I), itaconyl-CoA transferase, synthetase or hydrolase (L), citramalyl-CoA dehydratase (K), citramalyl-CoA transferase, synthetase or hydrolase (E), citramalate dehydratase (citraconate forming) (B), and citraconate decarboxylase (C) (FIG. 1, pathway (11) I/L/K/E/B/C), under conditions and for a sufficient period of time to produce methacrylic acid.

The invention also provides a method for producing methacrylic acid by culturing a non-naturally occurring microbial organism, comprising a methacrylic acid pathway comprising at least one exogenous nucleic acid encoding a methacrylic acid pathway enzyme expressed in a sufficient amount to produce methacrylic acid, the methacrylic acid pathway comprising aconitate decarboxylase (I), itaconyl-CoA transferase, synthetase or hydrolase (L), citramalyl-CoA dehydratase (K), citramalyl-CoA transferase, synthetase or hydrolase (E), citramalate dehydratase (citraconate forming) (B), citraconate isomerase (G), and mesaconate decarboxylase (H) (FIG. 1, pathway (12) I/L/K/E/B/G/H), under conditions and for a sufficient period of time to produce methacrylic acid. In still a further embodiment, the invention provides a method for producing methacrylic acid by culturing a non-naturally occurring microbial organism, comprising a microbial organism having a methacrylic acid pathway comprising at least one exogenous nucleic acid encoding a methacrylic acid pathway enzyme expressed in a sufficient amount to produce methacrylic acid, the methacrylic acid pathway comprising aconitate decarboxylase (I), itaconyl-CoA transferase, synthetase or hydrolase (L), citramalyl-CoA dehydratase (K), citramalyl-CoA transferase, synthetase or hydrolase (E), citramalate dehydratase (mesaconate forming) (F), and mesaconate decarboxylase (H) (FIG. 1, pathway (13) I/L/K/E/F/H), under conditions and for a sufficient period of time to produce methacrylic acid. In an additional embodiment, the invention provides a method for producing methacrylic acid by culturing a non-naturally occurring microbial organism, comprising a methacrylic acid pathway comprising at least one exogenous nucleic acid encoding a methacrylic acid pathway enzyme expressed in a sufficient amount to produce methacrylic acid, the methacrylic acid pathway comprising aconitate decarboxylase (I), itaconyl-CoA transferase, synthetase or hydrolase (L), citramalyl-CoA dehydratase (K), citramalyl-CoA transferase, synthetase or hydrolase (E), citramalate dehydratase (mesaconate forming) (F), citraconate isomerase (G), and citraconate decarboxylase (C) (FIG. 1, pathway (14) I/L/K/E/F/G/C), under conditions and for a sufficient period of time to produce methacrylic acid.

Figure 28:
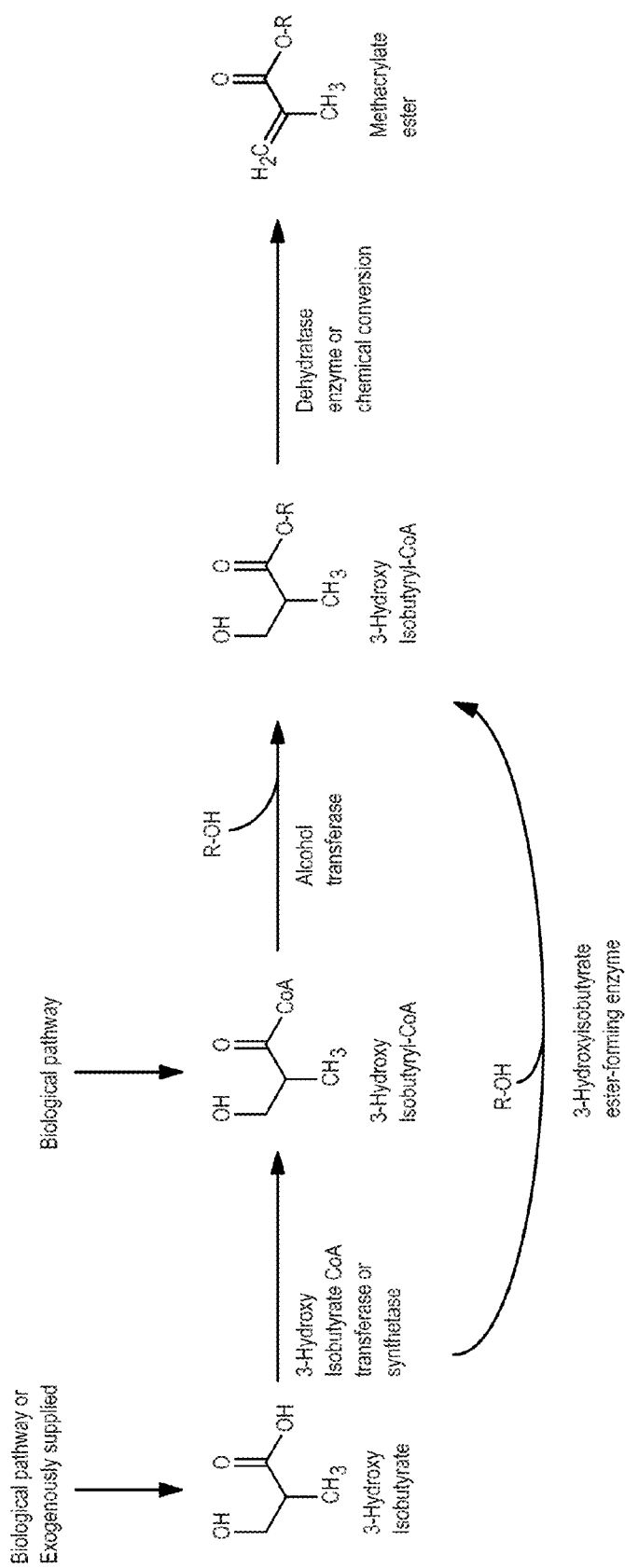
FIG. 28 shows an exemplary pathway to a methacrylate ester via 3-hydroxyisobutyrate and/or 3-hydroxyisobutyryl-CoA. R—OH refers to any organic alcohol.
Figure 29:
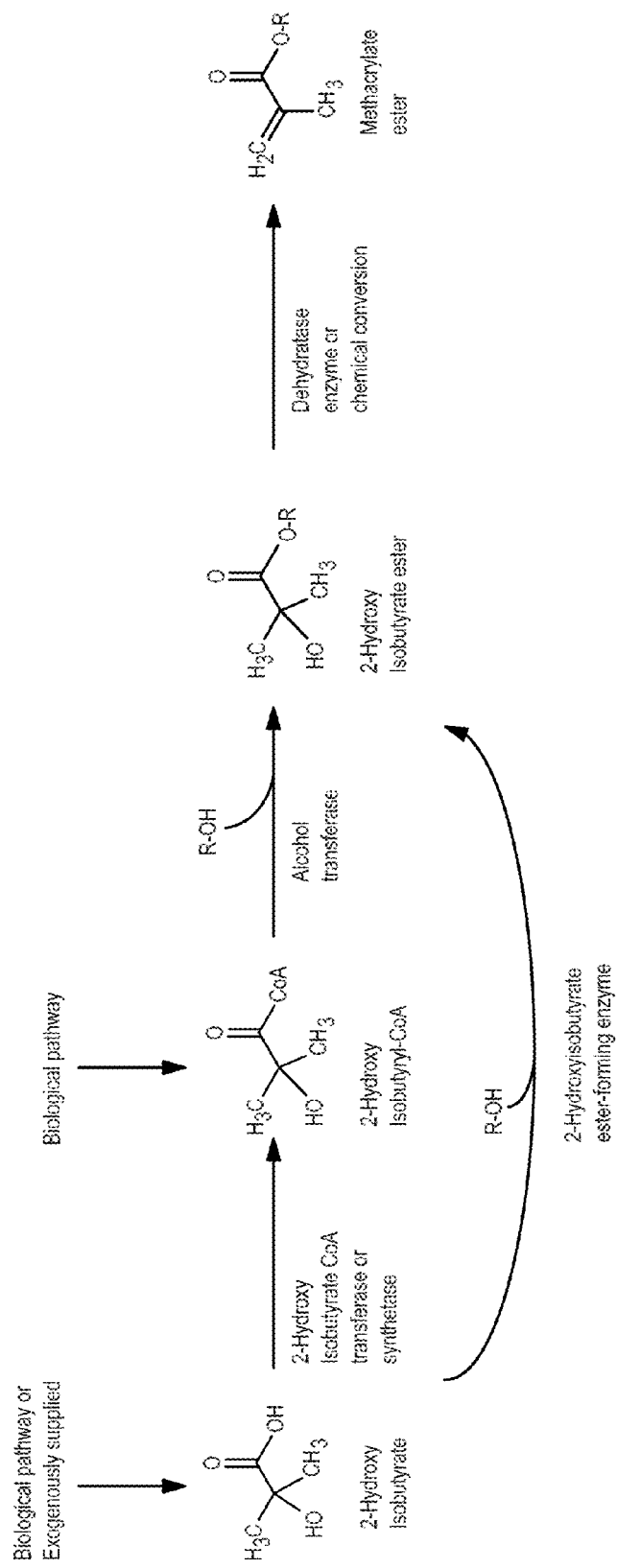
FIG. 29 shows an exemplary pathway to a methacrylate ester via 2-hydroxyisobutyrate and/or 2-hydroxyisobutyryl-CoA. R—OH refers to any organic alcohol.
Figure 30:
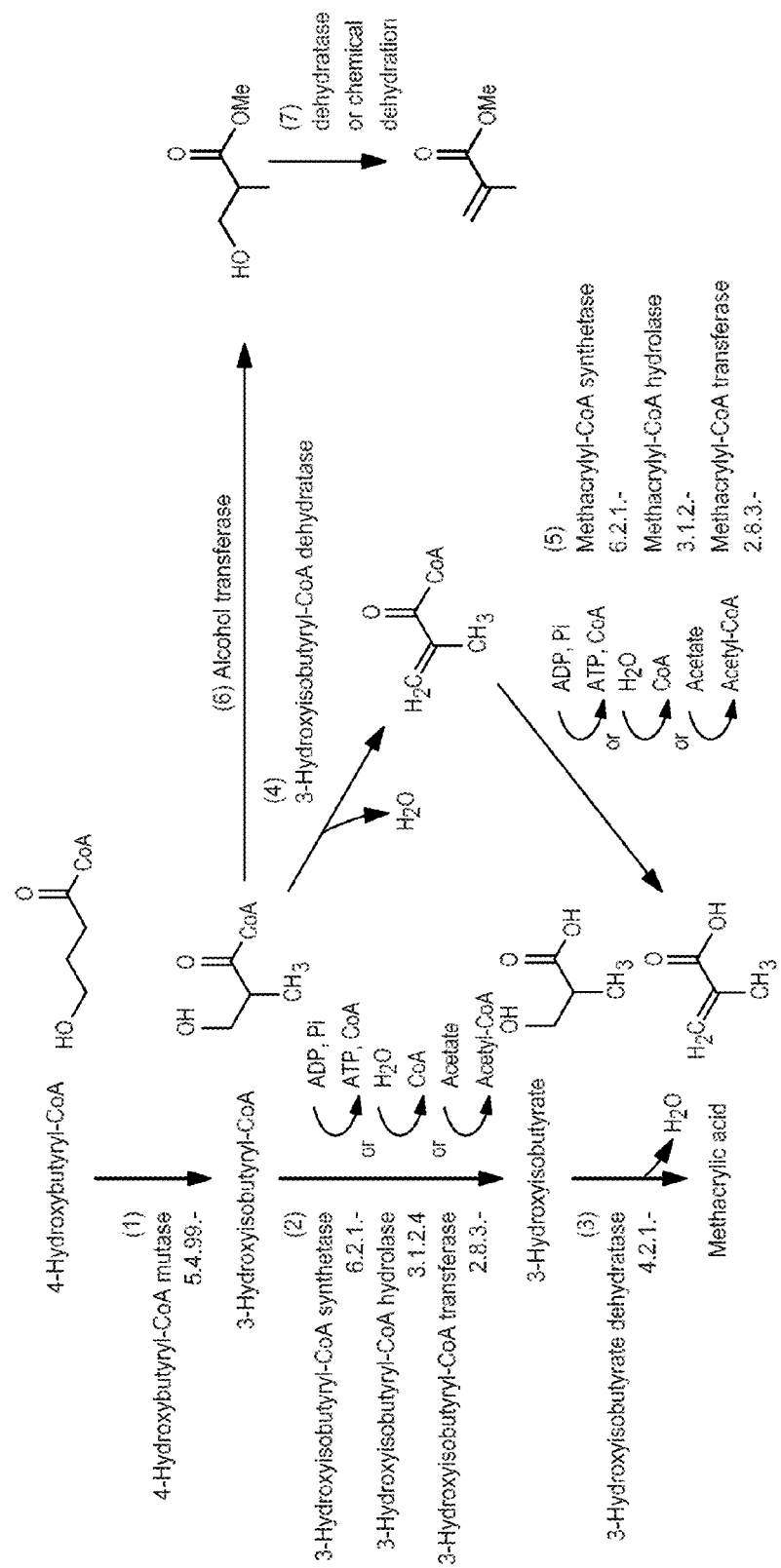
FIG. 30 shows an exemplary pathway to an exemplary methacrylate ester, methyl methacrylate.

The invention also provides a method for producing a methacrylate ester by culturing a non-naturally occurring microbial organism under conditions and for a sufficient period of time to produce a 3-hydroxyisobutyrate ester, wherein the non-naturally occurring microbial organism includes an exogenous nucleic acid encoding an alcohol transferase or a 3-hydroxyisobutyrate ester-forming enzyme expressed in a sufficient amount to produce a 3-hydroxyisobutyrate ester, and chemically dehydrating the 3-hydroxyisobutyrate ester to produce a methacrylate ester as exemplified in FIG. 28 and FIG. 30, steps 6 and 7. In another embodiment, the invention provides a method for producing methyl methacrylate by culturing a non-naturally occurring microbial organism under conditions and for a sufficient period of time to produce methyl-3-hydroxyisobutyrate, wherein the non-naturally occurring microbial organism includes an exogenous nucleic acid encoding an alcohol transferase or an ester-forming enzyme expressed in a sufficient amount to produce methyl-3-hydroxyisobutyrate, and chemically dehydrating said methyl-3-hydroxyisobutyrate to produce methyl methacrylate as exemplified in FIG. 30, steps 6 and 7. In some aspects of the invention, the methods for producing a methacrylate ester or methyl methacrylate as disclosed herein further include that the non-naturally occurring microbial organism includes at least one exogenous nucleic acid encoding 3-hydroxyisobutyryl-CoA pathway enzymes as described in FIGS. 1-11 and 28-30 or any combination thereof. In some aspects, the invention provides that the exogenous nucleic acid is a heterologous nucleic acid. In some aspects, the invention provides that the non-naturally occurring microbial organism is in a substantially anaerobic culture medium.

In one embodiment, the invention provides a non-naturally occurring microbial organism, comprising a microbial organism having a methyl methacrylate pathway comprising at least one exogenous nucleic acid encoding a methyl methacrylate pathway enzyme expressed in a sufficient amount to produce methyl methacrylate; said non-naturally occurring microbial organism further comprising: (i) a reductive TCA pathway comprising at least one exogenous nucleic acid encoding a reductive TCA pathway enzyme, wherein said at least one exogenous nucleic acid is selected from an ATP-citrate lyase, a citrate lyase, a fumarate reductase, and an alpha-ketoglutarate:ferredoxin oxidoreductase, or optionally isocitrate dehydrogenase, aconitase, citryl-CoA synthetase or citryl-CoA lyase; (ii) a reductive TCA pathway comprising at least one exogenous nucleic acid encoding a reductive TCA pathway enzyme, wherein said at least one exogenous nucleic acid is selected from a pyruvate:ferredoxin oxidoreductase, a phosphoenolpyruvate carboxylase, a phosphoenolpyruvate carboxykinase, a CO dehydrogenase, and an $H_2$ hydrogenase; or (iii) at least one exogenous nucleic acid encodes an enzyme selected from a CO dehydrogenase, an $H_2$ hydrogenase, and combinations thereof; wherein said methyl methacrylate pathway comprises an alcohol transferase or an ester-forming enzyme, and a dehydratase. In another aspect, the invention provides a method wherein the microbial organism comprising (i) further comprises an exogenous nucleic acid encoding an enzyme selected from a pyruvate:ferredoxin oxidoreductase, an aconitase, an isocitrate dehydrogenase, a succinyl-CoA synthetase, a succinyl-CoA transferase, a fumarase, a malate dehydrogenase, an acetate kinase, a phosphotransacetylase, an acetyl-CoA synthetase, an NAD(P)H:ferredoxin oxidoreductase, ferredoxin, and combinations thereof. In another aspect, the invention provides a method wherein the microbial organism comprising (ii) further comprises an exogenous nucleic acid encoding an enzyme selected from an aconitase, an isocitrate dehydrogenase, a succinyl-CoA synthetase, a succinyl-CoA transferase, a fumarase, a malate dehydrogenase, and combinations thereof. In one aspect, the microbial organism comprises two exogenous nucleic acids each encoding a methyl methacrylate enzyme. In a further aspect, the two exogenous nucleic acids encode an alcohol transferase and a dehydratase or alternatively a ester-forming enzyme and a dehydratase.

In one embodiment, the invention provides a method, wherein the microbial organism comprising (i) comprises four exogenous nucleic acids encoding an ATP-citrate lyase, citrate lyase, a fumarate reductase, and an alpha-ketoglutarate:ferredoxin oxidoreductase; wherein said microbial organism comprising (ii) comprises five exogenous nucleic acids encoding a pyruvate:ferredoxin oxidoreductase, a phosphoenolpyruvate carboxylase, a phosphoenolpyruvate carboxykinase, a CO dehydrogenase, and an $H_2$ hydrogenase; or wherein said microbial organism comprising (iii) comprises two exogenous nucleic acids encoding a CO dehydrogenase and an $H_2$ hydrogenase.

In one embodiment, the invention provides a method for producing methyl methacrylate comprising, culturing the non-naturally occurring microbial organism as disclosed herein under conditions and for a sufficient period of time to produce methyl methacrylate.

In another embodiment, the invention provides a method for producing a methacrylate ester comprising, culturing a non-naturally occurring microbial organism under conditions and for a sufficient period of time to produce a 3-hydroxyisobutyrate ester, wherein said non-naturally occurring microbial organism comprises an exogenous nucleic acid encoding an alcohol transferase or a 3-hydroxyisobutyrate ester-forming enzyme expressed in a sufficient amount to produce a 3-hydroxyisobutyrate ester and said non-naturally occurring microbial organism further comprising: (i) a reductive TCA pathway comprising at least one exogenous nucleic acid encoding a reductive TCA pathway enzyme, wherein said at least one exogenous nucleic acid is selected from an ATP-citrate lyase, a citrate lyase, a fumarate reductase, and an alpha-ketoglutarate:ferredoxin oxidoreductase, or optionally isocitrate dehydrogenase, aconitase, citryl-CoA synthetase or citryl-CoA lyase; (ii) a reductive TCA pathway comprising at least one exogenous nucleic acid encoding a reductive TCA pathway enzyme, wherein said at least one exogenous nucleic acid is selected from a pyruvate:ferredoxin oxidoreductase, a phosphoenolpyruvate carboxylase, a phosphoenolpyruvate carboxykinase, a CO dehydrogenase, and an $H_2$ hydrogenase; or (iii) at least one exogenous nucleic acid encoding an enzyme selected from a CO dehydrogenase, an $H_2$ hydrogenase, and combinations thereof, and chemically dehydrating said 3-hydroxyisobutyrate ester to produce a methacrylate ester. In another embodiment, the invention provides a method for producing a methacrylate ester comprising, culturing a non-naturally occurring microbial organism under conditions and for a sufficient period of time to produce a 2-hydroxyisobutyrate ester, wherein said non-naturally occurring microbial organism comprises an exogenous nucleic acid encoding an alcohol transferase or a 2-hydroxyisobutyrate ester-forming enzyme expressed in a sufficient amount to produce a 2-hydroxy isobutyrate ester and said non-naturally occurring microbial organism further comprising: (i) a reductive TCA pathway comprising at least one exogenous nucleic acid encoding a reductive TCA pathway enzyme, wherein said at least one exogenous nucleic acid is selected from an ATP-citrate lyase, a citrate lyase, a fumarate reductase, and an alpha-ketoglutarate:ferredoxin oxidoreductase, or optionally isocitrate dehydrogenase, aconitase, citryl-CoA synthetase or citryl-CoA lyase; (ii) a reductive TCA pathway comprising at least one exogenous nucleic acid encoding a reductive TCA pathway enzyme, wherein said at least one exogenous nucleic acid is selected from a pyruvate:ferredoxin oxidoreductase, a phosphoenolpyruvate carboxylase, a phosphoenolpyruvate carboxykinase, a CO dehydrogenase, and an $H_2$ hydrogenase; or (iii) at least one exogenous nucleic acid encoding an enzyme selected from a CO dehydrogenase, an $H_2$ hydrogenase, and combinations thereof, and chemically dehydrating said 2-hydroxy isobutyrate ester to produce a methacrylate ester. In yet another embodiment, the invention provides a method for producing methyl methacrylate comprising, culturing a non-naturally occurring microbial organism under conditions and for a sufficient period of time to produce methyl-3-hydroxyisobutyrate, wherein said non-naturally occurring microbial organism comprises an exogenous nucleic acid encoding an alcohol transferase or an ester-forming enzyme expressed in a sufficient amount to produce methyl-3-hydroxyisobutyrate and said non-naturally occurring microbial organism further comprising: (i) a reductive TCA pathway comprising at least one exogenous nucleic acid encoding a reductive TCA pathway enzyme, wherein said at least one exogenous nucleic acid is selected from an ATP-citrate lyase, a citrate lyase, a fumarate reductase, and an alpha-ketoglutarate:ferredoxin oxidoreductase, or optionally isocitrate dehydrogenase, aconitase, citryl-CoA synthetase or citryl-CoA lyase; (ii) a reductive TCA pathway comprising at least one exogenous nucleic acid encoding a reductive TCA pathway enzyme, wherein said at least one exogenous nucleic acid is selected from a pyruvate:ferredoxin oxidoreductase, a phosphoenolpyruvate carboxylase, a phosphoenolpyruvate carboxykinase, a CO dehydrogenase, and an $H_2$ hydrogenase; or (iii) at least one exogenous nucleic acid encoding an enzyme selected from a CO dehydrogenase, an $H_2$ hydrogenase, and combinations thereof, and chemically dehydrating said methyl-3-hydroxyisobutyrate to produce methyl methacrylate. In one aspect of the above methods, at least one of said exogenous nucleic acids is a heterologous nucleic acid. In another aspect of the above methods, the non-naturally occurring microbial organism is in a substantially anaerobic culture medium.

In one embodiment, the invention provides a method as disclosed above and herein, wherein said microbial organism comprising (i) further comprises an exogenous nucleic acid encoding an enzyme selected from a pyruvate:ferredoxin oxidoreductase, an aconitase, an isocitrate dehydrogenase, a succinyl-CoA synthetase, a succinyl-CoA transferase, a fumarase, a malate dehydrogenase, an acetate kinase, a phosphotransacetylase, an acetyl-CoA synthetase, an NAD(P)H:ferredoxin oxidoreductase, ferredoxin, and combinations thereof. In another embodiment, the invention provides a method as disclosed above and herein, wherein said microbial organism comprising (ii) further comprises an exogenous nucleic acid encoding an enzyme selected from an aconitase, an isocitrate dehydrogenase, a succinyl-CoA synthetase, a succinyl-CoA transferase, a fumarase, a malate dehydrogenase, and combinations thereof. In yet another embodiment, the invention provides a method as disclosed above and herein, wherein said microbial organism comprising (i) comprises four exogenous nucleic acids encoding an ATP-citrate lyase, citrate lyase, a fumarate reductase, and an alpha-ketoglutarate:ferredoxin oxidoreductase; wherein said microbial organism comprising (ii) comprises five exogenous nucleic acids encoding a pyruvate:ferredoxin oxidoreductase, a phosphoenolpyruvate carboxylase, a phosphoenolpyruvate carboxykinase, a CO dehydrogenase, and an $H_2$ hydrogenase; or wherein said microbial organism comprising (iii) comprises two exogenous nucleic acids encoding a CO dehydrogenase and an $H_2$ hydrogenase.

In one aspect, the methods disclosed herein can further a microbial organism comprising a 3-hydroxyisobutyrate ester pathway comprising at least one exogenous nucleic acid encoding a 3-hydroxyisobutyrate ester pathway enzyme expressed in a sufficient amount to produce a 3-hydroxyisobutyrate ester, said 3-hydroxyisobutyrate ester pathway comprising a pathway selected from: (a) a 3-hydroxyisobutyrate-CoA transferase or a 3-hydroxyisobutyrate-CoA synthetase; and an alcohol transferase; or (b) 3-hydroxyisobutyrate ester-forming enzyme. In one aspect, the methods disclosed herein can further a microbial organism comprising a 2-hydroxyisobutyrate ester pathway comprising at least one exogenous nucleic acid encoding a 2-hydroxyisobutyrate ester pathway enzyme expressed in a sufficient amount to produce a 2-hydroxyisobutyrate ester, said 2-hydroxyisobutyrate ester pathway comprising a pathway selected from: (a) a 2-hydroxyisobutyrate-CoA transferase or a 2-hydroxyisobutyrate-CoA synthetase; and an alcohol transferase; or (b) a 2-hydroxyisobutyrate ester-forming enzyme.

Suitable purification and/or assays to test for the production of methacrylic acid, methacrylate ester, 3-hydroxyisobutyrate and/or 2-hydroxyisobutyrate can be performed using well known methods. Suitable replicates such as triplicate cultures can be grown for each engineered strain to be tested. For example, product and byproduct formation in the engineered production host can be monitored. The final product and intermediates, and other organic compounds, can be analyzed by methods such as HPLC (High Performance Liquid Chromatography), GC-MS (Gas Chromatography-Mass Spectroscopy) and LC-MS (Liquid Chromatography-Mass Spectroscopy) or other suitable analytical methods using routine procedures well known in the art. The release of product in the fermentation broth can also be tested with the culture supernatant. Byproducts and residual glucose can be quantified by HPLC using, for example, a refractive index detector for glucose and alcohols, and a UV detector for organic acids (Lin et al., *Biotechnol. Bioeng.* 90:775-779 (2005)), or other suitable assay and detection methods well known in the art. The individual enzyme or protein activities from the exogenous DNA sequences can also be assayed using methods well known in the art. For example, citramalate synthase activity can be assayed by monitoring the production of CoA over time in a solution of purified protein, acetyl-CoA, pyruvate and buffer (Atsumi et al., AEM74:7802-7808 (2008)).

The methacrylic acid, methacrylate ester, 3-hydroxyisobutyrate and/or 2-hydroxyisobutyrate can be separated from other components in the culture using a variety of methods well known in the art. Such separation methods include, for example, extraction procedures as well as methods that include continuous liquid-liquid extraction, pervaporation, membrane filtration, membrane separation, reverse osmosis, electrodialysis, distillation, crystallization, centrifugation, extractive filtration, ion exchange chromatography, size exclusion chromatography, adsorption chromatography, and ultrafiltration. All of the above methods are well known in the art.

Any of the non-naturally occurring microbial organisms described herein can be cultured to produce and/or secrete the biosynthetic products of the invention. For example, the methacrylic acid, methacrylate ester, 3-hydroxyisobutyrate and/or 2-hydroxyisobutyrate producers can be cultured for the biosynthetic production of methacrylic acid, methacrylate ester, 3-hydroxyisobutyrate and/or 2-hydroxyisobutyrate.

For the production of methacrylic acid, methacrylate ester, 3-hydroxyisobutyrate and/or 2-hydroxyisobutyrate, the recombinant strains are cultured in a medium with carbon source and other essential nutrients. It is sometimes desirable and can be highly desirable to maintain anaerobic conditions in the fermenter to reduce the cost of the overall process. Such conditions can be obtained, for example, by first sparging the medium with nitrogen and then sealing the flasks with a septum and crimp-cap. For strains where growth is not observed anaerobically, microaerobic or substantially anaerobic conditions can be applied by perforating the septum with a small hole for limited aeration. Exemplary anaerobic conditions have been described previously and are well-known in the art. Exemplary aerobic and anaerobic conditions are described, for example, in United State publication 2009/0047719, filed Aug. 10, 2007. Fermentations can be performed in a batch, fed-batch or continuous manner, as disclosed herein.

If desired, the pH of the medium can be maintained at a desired pH, in particular neutral pH, such as a pH of around 7 by addition of a base, such as NaOH or other bases, or acid, as needed to maintain the culture medium at a desirable pH. The growth rate can be determined by measuring optical density using a spectrophotometer (600 nm), and the glucose uptake rate by monitoring carbon source depletion over time.

The growth medium can include, for example, any carbohydrate source which can supply a source of carbon to the non-naturally occurring microorganism. Such sources include, for example, sugars such as glucose, xylose, arabinose, galactose, mannose, fructose, sucrose and starch. Other sources of carbohydrate include, for example, renewable feedstocks and biomass. Exemplary types of biomasses that can be used as feedstocks in the methods of the invention include cellulosic biomass, hemicellulosic biomass and lignin feedstocks or portions of feedstocks. Such biomass feedstocks contain, for example, carbohydrate substrates useful as carbon sources such as glucose, xylose, arabinose, galactose, mannose, fructose and starch. Given the teachings and guidance provided herein, those skilled in the art will understand that renewable feedstocks and biomass other than those exemplified above also can be used for culturing the microbial organisms of the invention for the production of methacrylic acid, methacrylate ester, 3-hydroxyisobutyrate and/or 2-hydroxyisobutyrate.

In some embodiments, the present invention provides methacrylic acid, methacrylate ester, 3-hydroxyisobutyrate and/or 2-hydroxyisobutyrate or a methacrylic acid, methacrylate ester, 3-hydroxyisobutyrate and/or 2-hydroxyisobutyrate intermediate that has a carbon-12, carbon-13, and carbon-14 ratio that reflects an atmospheric carbon uptake source. In some such embodiments, the uptake source is $CO_2$. In some embodiments, In some embodiments, the present invention provides methacrylic acid, methacrylate ester, 3-hydroxyisobutyrate and/or 2-hydroxyisobutyrate or a methacrylic acid, methacrylate ester, 3-hydroxyisobutyrate and/or 2-hydroxyisobutyrate intermediate that has a carbon-12, carbon-13, and carbon-14 ratio that reflects petroleum-based carbon uptake source. In some embodiments, the present invention provides methacrylic acid, methacrylate ester, 3-hydroxyisobutyrate and/or 2-hydroxyisobutyrate or a methacrylic acid, methacrylate ester, 3-hydroxyisobutyrate and/or 2-hydroxyisobutyrate intermediate that has a carbon-12, carbon-13, and carbon-14 ratio that is obtained by a combination of an atmospheric carbon uptake source with a petroleum-based uptake source. Such combination of uptake sources is one means by which the carbon-12, carbon-13, and carbon-14 ratio can be varied.

In addition to renewable feedstocks such as those exemplified above and herein, the methacrylic acid methacrylic acid, methacrylate ester, 3-hydroxyisobutyrate and/or 2-hydroxyisobutyrate microbial organisms of the invention also can be modified for growth on syngas as its source of carbon. In this specific embodiment, one or more proteins or enzymes are expressed in the methacrylic acid, methacrylate ester, 3-hydroxyisobutyrate and/or 2-hydroxyisobutyrate producing organisms to provide a metabolic pathway for utilization of syngas or other gaseous carbon source.

Synthesis gas, also known as syngas or producer gas, is the major product of gasification of coal and of carbonaceous materials such as biomass materials, including agricultural crops and residues. Syngas is a mixture primarily of $H_2$ and CO and can be obtained from the gasification of any organic feedstock, including but not limited to coal, coal oil, natural gas, biomass, and waste organic matter. Gasification is generally carried out under a high fuel to oxygen ratio. Although largely $H_2$ and CO, syngas can also include $CO_2$ and other gases in smaller quantities. Thus, synthesis gas provides a cost effective source of gaseous carbon such as CO and, additionally, $CO_2$.

The Wood-Ljungdahl pathway catalyzes the conversion of CO and $H_2$ to acetyl-CoA and other products such as acetate. Organisms capable of utilizing CO and syngas also generally have the capability of utilizing $CO_2$ and $CO_2/H_2$ mixtures through the same basic set of enzymes and transformations encompassed by the Wood-Ljungdahl pathway. $H_2$-dependent conversion of $CO_2$ to acetate by microorganisms was recognized long before it was revealed that CO also could be used by the same organisms and that the same pathways were involved. Many acetogens have been shown to grow in the presence of $CO_2$ and produce compounds such as acetate as long as hydrogen is present to supply the necessary reducing equivalents (see for example, Drake, *Acetogenesis*, pp. 3-60 Chapman and Hall, New York, (1994)). This can be summarized by the following equation:

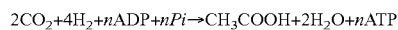

$$2CO_2 + 4H_2 + nADP + nPi \rightarrow CH_3COOH + 2H_2O + nATP$$

Hence, non-naturally occurring microorganisms possessing the Wood-Ljungdahl pathway can utilize $CO_2$ and $H_2$ mixtures as well for the production of acetyl-CoA and other desired products.

The Wood-Ljungdahl pathway is well known in the art and consists of 12 reactions which can be separated into two branches: (1) methyl branch and (2) carbonyl branch. The methyl branch converts syngas to methyl-tetrahydrofolate (methyl-THF) whereas the carbonyl branch converts methyl-THF to acetyl-CoA. The reactions in the methyl branch are catalyzed in order by the following enzymes or proteins: ferredoxin oxidoreductase, formate dehydrogenase, formyltetrahydrofolate synthetase, methenyltetrahydrofolate cyclodehydratase, methylenetetrahydrofolate dehydrogenase and methylenetetrahydrofolate reductase. The reactions in the carbonyl branch are catalyzed in order by the following enzymes or proteins: methyltetrahydrofolate:corrinoid protein methyltransferase (for example, AcsE), corrinoid iron-sulfur protein, nickel-protein assembly protein (for example, AcsF), ferredoxin, acetyl-CoA synthase, carbon monoxide dehydrogenase and nickel-protein assembly protein (for example, CooC). Following the teachings and guidance provided herein for introducing a sufficient number of encoding nucleic acids to generate a methacrylic acid, methacrylate ester, 3-hydroxyisobutyrate and/or 2-hydroxyisobutyrate pathway, those skilled in the art will understand that the same engineering design also can be performed with respect to introducing at least the nucleic acids encoding the Wood-Ljungdahl enzymes or proteins absent in the host organism. Therefore, introduction of one or more encoding nucleic acids into the microbial organisms of the invention such that the modified organism contains the complete Wood-Ljungdahl pathway will confer syngas utilization ability.

Additionally, the reductive (reverse) tricarboxylic acid cycle is and/or hydrogenase activities can also be used for the conversion of CO, $CO_2$ and/or $H_2$ to acetyl-CoA and other products such as acetate. Organisms capable of fixing carbon via the reductive TCA pathway can utilize one or more of the following enzymes: ATP citrate-lyase, citrate lyase, aconitase, isocitrate dehydrogenase, alpha-ketoglutarate:ferredoxin oxidoreductase, succinyl-CoA synthetase, succinyl-CoA transferase, fumarate reductase, fumarase, malate dehydrogenase, NAD(P)H:ferredoxin oxidoreductase, carbon monoxide dehydrogenase, and hydrogenase. Specifically, the reducing equivalents extracted from CO and/or $H_2$ by carbon monoxide dehydrogenase and hydrogenase are utilized to fix $CO_2$ via the reductive TCA cycle into acetyl-CoA or acetate. Acetate can be converted to acetyl-CoA by enzymes such as acetyl-CoA transferase, acetate kinase/phosphotransacetylase, and acetyl-CoA synthetase. Acetyl-CoA can be converted to methacrylic acid precursors, methacrylate ester, 3-hydroxyisobutyrate and/or 2-hydroxyisobutyrate. for example, glyceraldehyde-3-phosphate, phosphoenolpyruvate, and pyruvate, by pyruvate:ferredoxin oxidoreductase and the enzymes of gluconeogenesis. Following the teachings and guidance provided herein for introducing a sufficient number of encoding nucleic acids to generate a methacrylic acid, methacrylate ester, 3-hydroxyisobutyrate and/or 2-hydroxyisobutyrate pathway, those skilled in the art will understand that the same engineering design also can be performed with respect to introducing at least the nucleic acids encoding the reductive TCA pathway enzymes or proteins absent in the host organism. Therefore, introduction of one or more encoding nucleic acids into the microbial organisms of the invention such that the modified organism contains the complete reductive TCA pathway will confer syngas utilization ability.

Accordingly, given the teachings and guidance provided herein, those skilled in the art will understand that a non-naturally occurring microbial organism can be produced that secretes the biosynthesized compounds of the invention when grown on a carbon source such as a carbohydrate. Such compounds include, for example, methacrylic acid, methacrylate ester, 3-hydroxyisobutyrate and/or 2-hydroxyisobutyrate and any of the intermediate metabolites in the methacrylic acid, methacrylate ester, 3-hydroxyisobutyrate and/or 2-hydroxyisobutyrate pathway. All that is required is to engineer in one or more of the required enzyme or protein activities to achieve biosynthesis of the desired compound or intermediate including, for example, inclusion of some or all of the methacrylic acid, methacrylate ester, 3-hydroxyisobutyrate and/or 2-hydroxyisobutyrate biosynthetic pathways. Accordingly, the invention provides a non-naturally occurring microbial organism that produces and/or secretes methacrylic acid, methacrylate ester, 3-hydroxyisobutyrate and/or 2-hydroxyisobutyrate when grown on a carbohydrate or other carbon source and produces and/or secretes any of the intermediate metabolites shown in the methacrylic acid, methacrylate ester, 3-hydroxyisobutyrate and/or 2-hydroxyisobutyrate pathway when grown on a carbohydrate or other carbon source. The methacrylic acid, methacrylate ester, 3-hydroxyisobutyrate and/or 2-hydroxyisobutyrate producing microbial organisms of the invention can initiate synthesis from an intermediate, for example, citramalyl-CoA, itaconyl-CoA, itaconate, citramalate, mesaconate or citraconate.

The non-naturally occurring microbial organisms of the invention are constructed using methods well known in the art as exemplified herein to exogenously express at least one nucleic acid encoding a methacrylic acid, methacrylate ester, 3-hydroxyisobutyrate and/or 2-hydroxyisobutyrate pathway enzyme or protein in sufficient amounts to produce methacrylic acid, methacrylate ester, 3-hydroxyisobutyrate and/or 2-hydroxyisobutyrate. It is understood that the microbial organisms of the invention are cultured under conditions sufficient to produce methacrylic acid, methacrylate ester, 3-hydroxyisobutyrate and/or 2-hydroxyisobutyrate. Following the teachings and guidance provided herein, the non-naturally occurring microbial organisms of the invention can achieve biosynthesis of methacrylic acid, methacrylate ester, 3-hydroxyisobutyrate and/or 2-hydroxyisobutyrate resulting in intracellular concentrations between about 0.1-200 mM or more. Generally, the intracellular concentration of methacrylic acid, methacrylate ester, 3-hydroxyisobutyrate and/or 2-hydroxyisobutyrate is between about 3-150 mM, particularly between about 5-125 mM and more particularly between about 8-100 mM, including about 10 mM, 20 mM, 50 mM, 80 mM, or more. Intracellular concentrations between and above each of these exemplary ranges also can be achieved from the non-naturally occurring microbial organisms of the invention.

In some embodiments, culture conditions include anaerobic or substantially anaerobic growth or maintenance conditions. Exemplary anaerobic conditions have been described previously and are well known in the art. Exemplary anaerobic conditions for fermentation processes are described herein and are described, for example, in U.S. publication 2009/0047719, filed Aug. 10, 2007. Any of these conditions can be employed with the non-naturally occurring microbial organisms as well as other anaerobic conditions well known in the art. Under such anaerobic or substantially anaerobic conditions, the methacrylic acid, methacrylate ester, 3-hydroxyisobutyrate and/or 2-hydroxyisobutyrate producers can synthesize methacrylic acid, methacrylate ester, 3-hydroxyisobutyrate and/or 2-hydroxyisobutyrate at intracellular concentrations of 5-10 mM or more as well as all other concentrations exemplified herein. It is understood that, even though the above description refers to intracellular concentrations, methacrylic acid, methacrylate ester, 3-hydroxyisobutyrate and/or 2-hydroxyisobutyrate producing microbial organisms can produce methacrylic acid, methacrylate ester, 3-hydroxyisobutyrate and/or 2-hydroxyisobutyrate intracellularly and/or secrete the product into the culture medium.

In addition to the culturing and fermentation conditions disclosed herein, growth condition for achieving biosynthesis of methacrylic acid, methacrylate ester, 3-hydroxyisobutyrate and/or 2-hydroxyisobutyrate can include the addition of an osmoprotectant to the culturing conditions. In certain embodiments, the non-naturally occurring microbial organisms of the invention can be sustained, cultured or fermented as described herein in the presence of an osmoprotectant. Briefly, an osmoprotectant refers to a compound that acts as an osmolyte and helps a microbial organism as described herein survive osmotic stress. Osmoprotectants include, but are not limited to, betaines, amino acids, and the sugar trehalose. Non-limiting examples of such are glycine betaine, praline betaine, dimethylthetin, dimethylslfoniopoprionate, 3-dimethylsulfonio-2-methylproprionate, pipecolic acid, dimethylsulfonioacetate, choline, L-carnitine and ectoine. In one aspect, the osmoprotectant is glycine betaine. It is understood to one of ordinary skill in the art that the amount and type of osmoprotectant suitable for protecting a microbial organism described herein from osmotic stress will depend on the microbial organism used. The amount of osmoprotectant in the culturing conditions can be, for example, no more than about 0.1 mM, no more than about 0.5 mM, no more than about 1.0 mM, no more than about 1.5 mM, no more than about 2.0 mM, no more than about 2.5 mM, no more than about 3.0 mM, no more than about 5.0 mM, no more than about 7.0 mM, no more than about 10 mM, no more than about 50 mM, no more than about 100 mM or no more than about 500 mM.

In some embodiments, the carbon feedstock and other cellular uptake sources such as phosphate, ammonia, sulfate, chloride and other halogens can be chosen to alter the isotopic distribution of the atoms present in methacrylic acid, methacrylate este, methyl methacrylate, 3-hydroxyisobutyrate and/or 2-hydroxyisobutyrate or any methacrylic acid, methacrylate este, methyl methacrylate, 3-hydroxyisobutyrate and/or 2-hydroxyisobutyrate pathway intermediate. The various carbon feedstock and other uptake sources enumerated above will be referred to herein, collectively, as "uptake sources." Uptake sources can provide isotopic enrichment for any atom present in the product methacrylic acid, methacrylate este, methyl methacrylate, 3-hydroxyisobutyrate and/or 2-hydroxyisobutyrate pathway intermediate, or for side products generated in reactions diverging away from a methacrylic acid, methacrylate este, methyl methacrylate, 3-hydroxyisobutyrate and/or 2-hydroxyisobutyrate pathway. Isotopic enrichment can be achieved for any target atom including, for example, carbon, hydrogen, oxygen, nitrogen, sulfur, phosphorus, chloride or other halogens.

In some embodiments, the uptake sources can be selected to alter the carbon-12, carbon-13, and carbon-14 ratios. In some embodiments, the uptake sources can be selected to alter the oxygen-16, oxygen-17, and oxygen-18 ratios. In some embodiments, the uptake sources can be selected to alter the hydrogen, deuterium, and tritium ratios. In some embodiments, the uptake sources can be selected to alter the nitrogen-14 and nitrogen-15 ratios. In some embodiments, the uptake sources can be selected to alter the sulfur-32, sulfur-33, sulfur-34, and sulfur-35 ratios. In some embodiments, the uptake sources can be selected to alter the phosphorus-31, phosphorus-32, and phosphorus-33 ratios. In some embodiments, the uptake sources can be selected to alter the chlorine-35, chlorine-36, and chlorine-37 ratios.

In some embodiments, the isotopic ratio of a target atom can be varied to a desired ratio by selecting one or more uptake sources. An uptake source can be derived from a natural source, as found in nature, or from a man-made source, and one skilled in the art can select a natural source, a man-made source, or a combination thereof, to achieve a desired isotopic ratio of a target atom. An example of a man-made uptake source includes, for example, an uptake source that is at least partially derived from a chemical synthetic reaction. Such isotopically enriched uptake sources can be purchased commercially or prepared in the laboratory and/or optionally mixed with a natural source of the uptake source to achieve a desired isotopic ratio. In some embodiments, a target atom isotopic ratio of an uptake source can be achieved by selecting a desired origin of the uptake source as found in nature. For example, as discussed herein, a natural source can be a biobased derived from or synthesized by a biological organism or a source such as petroleum-based products or the atmosphere. In some such embodiments, a source of carbon, for example, can be selected from a fossil fuel-derived carbon source, which can be depleted of carbon-14, or an environmental or atmospheric carbon source, such as $CO_2$, which can possess a larger amount of carbon-14 than its petroleum-derived counterpart.

The unstable carbon isotope carbon-14 or radiocarbon makes up for roughly 1 in $10^{12}$ carbon atoms in the earth's atmosphere and has a half-life of about 5700 years. The stock of carbon is replenished in the upper atmosphere by a nuclear reaction involving cosmic rays and ordinary nitrogen ($^{14}N$). Fossil fuels contain no carbon-14, as it decayed long ago. Burning of fossil fuels lowers the atmospheric carbon-14 fraction, the so-called "Suess effect".

Methods of determining the isotopic ratios of atoms in a compound are well known to those skilled in the art. Isotopic enrichment is readily assessed by mass spectrometry using techniques known in the art such as accelerated mass spectrometry (AMS), Stable Isotope Ratio Mass Spectrometry (SIRMS) and Site-Specific Natural Isotopic Fractionation by Nuclear Magnetic Resonance (SNIF-NMR). Such mass spectral techniques can be integrated with separation techniques such as liquid chromatography (LC), high performance liquid chromatography (HPLC) and/or gas chromatography, and the like.

In the case of carbon, ASTM D6866 was developed in the United States as a standardized analytical method for determining the biobased content of solid, liquid, and gaseous samples using radiocarbon dating by the American Society for Testing and Materials (ASTM) International. The standard is based on the use of radiocarbon dating for the determination of a product's biobased content. ASTM D6866 was first published in 2004, and the current active version of the standard is ASTM D6866-11 (effective Apr. 1, 2011). Radiocarbon dating techniques are well known to those skilled in the art, including those described herein.

The biobased content of a compound is estimated by the ratio of carbon-14 ($^{14}C$) to carbon-12 ($^{12}C$). Specifically, the Fraction Modern (Fm) is computed from the expression: Fm= (S−B)/(M−B), where B, S and M represent the $^{14}C/^{12}C$ ratios of the blank, the sample and the modern reference, respectively. Fraction Modern is a measurement of the deviation of the $^{14}C/^{12}C$ ratio of a sample from "Modern." Modern is defined as 95% of the radiocarbon concentration (in AD 1950) of National Bureau of Standards (NBS) Oxalic Acid I (i.e., standard reference materials (SRM) 4990b) normalized to $\delta^{13}C_{VPDB}$=−19 per mil (Olsson, *The use of Oxalic acid as a Standard*. In, *Radiocarbon Variations and Absolute Chronology*, Nobel Symposium, 12th Proc., John Wiley & Sons, New York (1970)). Mass spectrometry results, for example, measured by ASM, are calculated using the internationally agreed upon definition of 0.95 times the specific activity of NBS Oxalic Acid I (SRM 4990b) normalized to $\delta^{13}C_{VPDB}$=−19 per mil. This is equivalent to an absolute (AD 1950) $^{14}C/^{12}C$ ratio of 1.176±0.010×10$^{-12}$ (Karlen et al., *Arkiv Geoftsik*, 4:465-471 (1968)). The standard calculations take into account the differential uptake of one isotope with respect to another, for example, the preferential uptake in biological systems of $C^{12}$ over $C^{13}$ over $C^{14}$, and these corrections are reflected as a Fm corrected for $\delta^{13}$.

An oxalic acid standard (SRM 4990b or HOx 1) was made from a crop of 1955 sugar beet. Although there were 1000 lbs made, this oxalic acid standard is no longer commercially available. The Oxalic Acid II standard (HOx 2; N.I.S.T designation SRM 4990 C) was made from a crop of 1977 French beet molasses. In the early 1980's, a group of 12 laboratories measured the ratios of the two standards. The ratio of the activity of Oxalic acid II to 1 is 1.2933±0.001 (the weighted mean). The isotopic ratio of HOx II is −17.8 per mille. ASTM D6866-11 suggests use of the available Oxalic Acid II standard SRM 4990 C (Hox2) for the modern standard (see discussion of original vs. currently available oxalic acid standards in Mann, *Radiocarbon*, 25(2):519-527 (1983)). A Fm=0% represents the entire lack of carbon-14 atoms in a material, thus indicating a fossil (for example, petroleum based) carbon source. A Fm=100%, after correction for the post-1950 injection of carbon-14 into the atmosphere from nuclear bomb testing, indicates an entirely modern carbon source. As described herein, such a "modern" source includes biobased sources.

As described in ASTM D6866, the percent modern carbon (pMC) can be greater than 100% because of the continuing but diminishing effects of the 1950s nuclear testing programs, which resulted in a considerable enrichment of carbon-14 in the atmosphere as described in ASTM D6866-11. Because all sample carbon-14 activities are referenced to a "pre-bomb" standard, and because nearly all new biobased products are produced in a post-bomb environment, all pMC values (after correction for isotopic fraction) must be multiplied by 0.95 (as of 2010) to better reflect the true biobased content of the sample. A biobased content that is greater than 103% suggests that either an analytical error has occurred, or that the source of biobased carbon is more than several years old.

ASTM D6866 quantifies the biobased content relative to the material's total organic content and does not consider the inorganic carbon and other non-carbon containing substances present. For example, a product that is 50% starch-based material and 50% water would be considered to have a Biobased Content=100% (50% organic content that is 100% biobased) based on ASTM D6866. In another example, a product that is 50% starch-based material, 25% petroleum-based, and 25% water would have a Biobased Content=66.7% (75% organic content but only 50% of the product is biobased). In another example, a product that is 50% organic carbon and is a petroleum-based product would be considered to have a Biobased Content=0% (50% organic carbon but from fossil sources). Thus, based on the well known methods and known standards for determining the biobased content of a compound or material, one skilled in the art can readily determine the biobased content and/or prepared downstream products that utilize of the invention having a desired biobased content.

Applications of carbon-14 dating techniques to quantify bio-based content of materials are known in the art (Currie et al., *Nuclear Instruments and Methods in Physics Research B*, 172:281-287 (2000)). For example, carbon-14 dating has been used to quantify bio-based content in terephthalate-containing materials (Colonna et al., *Green Chemistry*, 13:2543-2548 (2011)). Notably, polypropylene terephthalate (PPT) polymers derived from renewable 1,3-propanediol and petroleum-derived terephthalic acid resulted in Fm values near 30% (i.e., since 3/11 of the polymeric carbon derives from renewable 1,3-propanediol and 8/11 from the fossil end member terephthalic acid) (Currie et al., supra, 2000). In contrast, polybutylene terephthalate polymer derived from both renewable 1,4-butanediol and renewable terephthalic acid resulted in bio-based content exceeding 90% (Colonna et al., supra, 2011).

Accordingly, in some embodiments, the present invention provides methacrylic acid, methacrylate ester, methyl methacrylate, 3-hydroxyisobutyrate and/or 2-hydroxyisobutyrate or a methacrylic acid, methacrylate ester, methyl methacrylate, 3-hydroxyisobutyrate and/or 2-hydroxyisobutyrate pathway intermediate that has a carbon-12, carbon-13, and carbon-14 ratio that reflects an atmospheric carbon, also referred to as environmental carbon, uptake source. For example, in some aspects the methacrylic acid, methacrylate ester, methyl methacrylate, 3-hydroxyisobutyrate and/or 2-hydroxyisobutyrate or a methacrylic acid, methacrylate ester, methyl methacrylate, 3-hydroxyisobutyrate and/or 2-hydroxyisobutyrate intermediate can have an Fm value of at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 98% or as much as 100%. In some such embodiments, the uptake source is $CO_2$. In some embodiments, the present invention provides methacrylic acid, methacrylate ester, methyl methacrylate, 3-hydroxyisobutyrate and/or 2-hydroxyisobutyrate or a methacrylic acid, methacrylate ester, methyl methacrylate, 3-hydroxyisobutyrate and/or 2-hydroxyisobutyrate intermediate that has a carbon-12, carbon-13, and carbon-14 ratio that reflects petroleum-based carbon uptake source. In this aspect, the methacrylic acid, methacrylate ester, methyl methacrylate, 3-hydroxyisobutyrate and/or 2-hydroxyisobutyrate or a methacrylic acid, methacrylate ester, methyl methacrylate, 3-hydroxyisobutyrate and/or 2-hydroxyisobutyrate intermediate can have an Fm value of less than 95%, less than 90%, less than 85%, less than 80%, less than 75%, less than 70%, less than 65%, less than 60%, less than 55%, less than 50%, less than 45%, less than 40%, less than 35%, less than 30%, less than 25%, less than 20%, less than 15%, less than 10%, less than 5%, less than 2% or less than 1%. In some embodiments, the present invention provides methacrylic acid, methacrylate ester, methyl methacrylate, 3-hydroxyisobutyrate and/or 2-hydroxyisobutyrate or a methacrylic acid, methacrylate ester, methyl methacrylate, 3-hydroxyisobutyrate and/or 2-hydroxyisobutyrate intermediate that has a carbon-12, carbon-13, and carbon-14 ratio that is obtained by a combination of an atmospheric carbon uptake source with a petroleum-based uptake source. Using such a combination of uptake sources is one way by which the carbon-12, carbon-13, and carbon-14 ratio can be varied, and the respective ratios would reflect the proportions of the uptake sources.

Further, the present invention relates to the biologically produced methacrylic acid, methacrylate ester, methyl methacrylate, 3-hydroxyisobutyrate and/or 2-hydroxyisobutyrate or methacrylic acid, methacrylate ester, methyl methacrylate, 3-hydroxyisobutyrate and/or 2-hydroxyisobutyrate intermediate as disclosed herein, and to the products derived therefrom, wherein the methacrylic acid, methacrylate ester, methyl methacrylate, 3-hydroxyisobutyrate and/or 2-hydroxyisobutyrate or a methacrylic acid, methacrylate ester, methyl methacrylate, 3-hydroxyisobutyrate and/or 2-hydroxyisobutyrate intermediate has a carbon-12, carbon-13, and carbon-14 isotope ratio of about the same value as the $CO_2$ that occurs in the environment. For example, in some aspects the invention provides bioderived methacrylic acid, methacrylate ester, methyl methacrylate, 3-hydroxyisobutyrate and/or 2-hydroxyisobutyrate or a bioderived methacrylic acid, methacrylate ester, methyl methacrylate, 3-hydroxyisobutyrate and/or 2-hydroxyisobutyrate intermediate having a carbon-12 versus carbon-13 versus carbon-14 isotope ratio of about the same value as the $CO_2$ that occurs in the environment, or any of the other ratios disclosed herein. It is understood, as disclosed herein, that a product can have a carbon-12 versus carbon-13 versus carbon-14 isotope ratio of about the same value as the $CO_2$ that occurs in the environment, or any of the ratios disclosed herein, wherein the product is generated from bioderived methacrylic acid, methacrylate ester, methyl methacrylate, 3-hydroxyisobutyrate and/or 2-hydroxyisobutyrate or a bioderived methacrylic acid, methacrylate ester, methyl methacrylate, 3-hydroxyisobutyrate and/or 2-hydroxyisobutyrate intermediate as disclosed herein, wherein the bioderived product is chemically modified to generate a final product. Methods of chemically modifying a bioderived product of methacrylic acid, methacrylate ester, methyl methacrylate, 3-hydroxyisobutyrate and/or 2-hydroxyisobutyrate, or an intermediate thereof, to generate a desired product are well known to those skilled in the art, as described herein. The invention further provides polymers, including polymethyl methacrylate (PMMA), acrylic plastics, and co-polymers, such as the co-polymer methyl methacrylate-butadiene-styrene (MBS), and the like, having a carbon-12 versus carbon-13 versus carbon-14 isotope ratio of about the same value as the $CO_2$ that occurs in the environment, wherein the polymers, including polymethyl methacrylate, acrylic plastics and the co-polymer methyl methacrylate-butadiene-styrene (MBS), are generated directly from or in combination with bioderived methacrylic acid, methacrylate ester, methyl methacrylate, 3-hydroxyisobutyrate and/or 2-hydroxyisobutyrate or a bioderived methacrylic acid, methacrylate ester, methyl methacrylate, 3-hydroxyisobutyrate and/or 2-hydroxyisobutyrate intermediate as disclosed herein.

Methacrylic acid, methacrylate ester, methyl methacrylate, 3-hydroxyisobutyrate and/or 2-hydroxyisobutyrate are chemicals used in commercial and industrial applications. Non-limiting examples of such applications include production of polymers, including polymethyl methacrylate (PMMA), also referred to as acrylic glass, Lucite™ or Plexiglas™, acrylic plastics and co-polymers, such as the co-polymer methyl methacrylate-butadiene-styrene (MBS). Moreover, methacrylic acid, methacrylate ester, methyl methacrylate, 3-hydroxyisobutyrate and/or 2-hydroxyisobutyrate are also used as raw materials in the production of a wide range of products including polymers, including polymethyl methacrylate acrylic plastics and the co-polymer methyl methacrylate-butadiene-styrene (MBS). Accordingly, in some embodiments, the invention provides biobased polymers, including polymethyl methacrylate, acrylic plastics, and co-polymers, including methyl methacrylate-butadiene-styrene (MBS), comprising one or more bioderived methacrylic acid, methacrylate ester, methyl methacrylate, 3-hydroxyisobutyrate and/or 2-hydroxyisobutyrate or bioderived methacrylic acid, methacrylate ester, methyl methacrylate, 3-hydroxyisobutyrate and/or 2-hydroxyisobutyrate intermediate produced by a non-naturally occurring microorganism of the invention or produced using a method disclosed herein. Such polymers, including polymethyl methacrylate, acrylic plastics, and co-polymers, including methyl methacrylate-butadiene-styrene, can have a mixture of bioderived and petroleum based precursors, in desired ratios as described above.

As used herein, the term "bioderived" means derived from or synthesized by a biological organism and can be considered a renewable resource since it can be generated by a biological organism. Such a biological organism, in particular the microbial organisms of the invention disclosed herein, can utilize feedstock or biomass, such as, sugars or carbohydrates obtained from an agricultural, plant, bacterial, or animal source. Alternatively, the biological organism can utilize atmospheric carbon As used herein, the term "biobased" means a product as described above that is composed, in whole or in part, of a bioderived compound of the invention. A biobased or bioderived product is in contrast to a petroleum derived product, wherein such a product is derived from or synthesized from petroleum or a petrochemical feedstock.

In some embodiments, the invention provides polymers, including polymethyl methacrylate acrylic plastics and the co-polymer methyl methacrylate-butadiene-styrene (MBS), comprising bioderived methacrylic acid, methacrylate ester, methyl methacrylate, 3-hydroxyisobutyrate and/or 2-hydroxyisobutyrate or bioderived methacrylic acid, methacrylate ester, methyl methacrylate, 3-hydroxyisobutyrate and/or 2-hydroxyisobutyrate intermediate, wherein the bioderived methacrylic acid, methacrylate ester, methyl methacrylate, 3-hydroxyisobutyrate and/or 2-hydroxyisobutyrate or bioderived methacrylic acid, methacrylate ester, methyl methacrylate, 3-hydroxyisobutyrate and/or 2-hydroxyisobutyrate intermediate includes all or part of the methacrylic acid, methacrylate ester, methyl methacrylate, 3-hydroxyisobutyrate and/or 2-hydroxyisobutyrate or methacrylic acid, methacrylate ester, methyl methacrylate, 3-hydroxyisobutyrate and/or 2-hydroxyisobutyrate intermediate used in the production of polymers, including polymethyl methacrylate acrylic plastics and the co-polymer methyl methacrylate-butadiene-styrene (MBS). Thus, in some aspects, the invention provides a biobased polymers, including polymethyl methacrylate acrylic plastics and the co-polymer methyl methacrylate-butadiene-styrene (MBS), comprising at least 2%, at least 3%, at least 5%, at least 10%, at least 15%, at least 20%, at least 25%, at least 30%, at least 35%, at least 40%, at least 50%, at least 60%, at least 70%, at least 80%, at least 90%, at least 95%, at least 98% or 100% bioderived methacrylic acid, methacrylate ester, methyl methacrylate, 3-hydroxyisobutyrate and/or 2-hydroxyisobutyrate or bioderived methacrylic acid, methacrylate ester, methyl methacrylate, 3-hydroxyisobutyrate and/or 2-hydroxyisobutyrate intermediate as disclosed herein. Additionally, in some aspects, the invention provides a biobased polymers, including polymethyl methacrylate acrylic plastics and the co-polymer methyl methacrylate-butadiene-styrene (MBS), wherein the methacrylic acid, methacrylate ester, methyl methacrylate, 3-hydroxyisobutyrate and/or 2-hydroxyisobutyrate or methacrylic acid, methacrylate ester, methyl methacrylate, 3-hydroxyisobutyrate and/or 2-hydroxyisobutyrate intermediate used in its production is a combination of bioderived and petroleum derived methacrylic acid, methacrylate ester, methyl methacrylate, 3-hydroxyisobutyrate and/or 2-hydroxyisobutyrate or methacrylic acid, methacrylate ester, methyl methacrylate, 3-hydroxyisobutyrate and/or 2-hydroxyisobutyrate intermediate. For example, a biobased polymers, including polymethyl methacrylate acrylic plastics and the co-polymer methyl methacrylate-butadiene-styrene (MBS), can be produced using 50% bioderived methacrylic acid, methacrylate ester, methyl methacrylate, 3-hydroxyisobutyrate and/or 2-hydroxyisobutyrate and 50% petroleum derived methacrylic acid, methacrylate ester such as methyl methacrylate, 3-hydroxyisobutyrate and/or 2-hydroxyisobutyrate, or other desired ratios such as 60%/40%, 70%/30%, 80%/20%, 90%/10%, 95%/5%, 100%/0%, 40%/60%, 30%/70%, 20%/80%, 10%/90% of bioderived/petroleum derived precursors, so long as at least a portion of the product comprises a bioderived product produced by the microbial organisms disclosed herein. It is understood that methods for producing polymers, including polymethyl methacrylate acrylic plastics and the co-polymer methyl methacrylate-butadiene-styrene (MBS), using the bioderived methacrylic acid, methacrylate ester, methyl methacrylate, 3-hydroxyisobutyrate and/or 2-hydroxyisobutyrate or bioderived methacrylic acid, methacrylate ester, methyl methacrylate, 3-hydroxyisobutyrate and/or 2-hydroxyisobutyrate intermediate of the invention are well known in the art.

The culture conditions can include, for example, liquid culture procedures as well as fermentation and other large scale culture procedures. As described herein, particularly useful yields of the biosynthetic products of the invention can be obtained under anaerobic or substantially anaerobic culture conditions.

As described herein, one exemplary growth condition for achieving biosynthesis of methacrylic acid, methacrylate ester, 3-hydroxyisobutyrate and/or 2-hydroxyisobutyrate includes anaerobic culture or fermentation conditions. In certain embodiments, the non-naturally occurring microbial organisms of the invention can be sustained, cultured or fermented under anaerobic or substantially anaerobic conditions. Briefly, anaerobic conditions refers to an environment devoid of oxygen. Substantially anaerobic conditions include, for example, a culture, batch fermentation or continuous fermentation such that the dissolved oxygen concentration in the medium remains between 0 and 10% of saturation. Substantially anaerobic conditions also includes growing or resting cells in liquid medium or on solid agar inside a sealed chamber maintained with an atmosphere of less than 1% oxygen. The percent of oxygen can be maintained by, for example, sparging the culture with an $N_2/CO_2$ mixture or other suitable non-oxygen gas or gases.

The culture conditions described herein can be scaled up and grown continuously for manufacturing of methacrylic acid, methacrylate ester, 3-hydroxyisobutyrate and/or 2-hydroxyisobutyrate. Exemplary growth procedures include, for example, fed-batch fermentation and batch separation; fed-batch fermentation and continuous separation, or continuous fermentation and continuous separation. All of these processes are well known in the art. Fermentation procedures are particularly useful for the biosynthetic production of commercial quantities of methacrylic acid, methacrylate ester, 3-hydroxyisobutyrate and/or 2-hydroxyisobutyrate. Generally, and as with non-continuous culture procedures, the continuous and/or near-continuous production of methacrylic acid, methacrylate ester, 3-hydroxyisobutyrate and/or 2-hydroxyisobutyrate will include culturing a non-naturally occurring methacrylic acid, methacrylate ester, 3-hydroxyisobutyrate and/or 2-hydroxyisobutyrate producing organism of the invention in sufficient nutrients and medium to sustain and/or nearly sustain growth in an exponential phase. Continuous culture under such conditions can include, for example, growth for 1 day, 2, 3, 4, 5, 6 or 7 days or more.

Additionally, continuous culture can include longer time periods of 1 week, 2, 3, 4 or 5 or more weeks and up to several months. Alternatively, organisms of the invention can be cultured for hours, if suitable for a particular application. It is to be understood that the continuous and/or near-continuous culture conditions also can include all time intervals in between these exemplary periods. It is further understood that the time of culturing the microbial organism of the invention is for a sufficient period of time to produce a sufficient amount of product for a desired purpose.

Fermentation procedures are well known in the art. Briefly, fermentation for the biosynthetic production of methacrylic acid, methacrylate ester, 3-hydroxyisobutyrate and/or 2-hydroxyisobutyrate can be utilized in, for example, fed-batch fermentation and batch separation; fed-batch fermentation and continuous separation, or continuous fermentation and continuous separation. Examples of batch and continuous fermentation procedures are well known in the art.

In addition to the above fermentation procedures using the methacrylic acid, methacrylate ester, methyl methacrylate, 3-hydroxyisobutyrate, 3-hydroxyisobutyrate ester, 2-hydroxyisobutyrate and/or 2-hydroxyisobutyrate ester producers of the invention for continuous production of substantial quantities of methacrylic acid, methacrylate ester, methyl methacrylate, 3-hydroxyisobutyrate, 3-hydroxyisobutyrate ester, 2-hydroxyisobutyrate and/or 2-hydroxyisobutyrate ester producers also can be, for example, simultaneously subjected to chemical synthesis procedures to convert the product to other compounds or the product can be separated from the fermentation culture and sequentially subjected to chemical or enzymatic conversion to convert the product to other compounds, if desired. For example, in some embodiments, the invention provides chemical dehydration of a 3-hydroxyisobutyrate ester such as methyl-3-hydroxyisobutyrate or a 2-hydroxyisobutyrate ester such as methyl-2-hydroxyisobutyrate to a methacrylate ester such as methyl methacrylate. It is understood that methods and chemical compounds for catalyzing the dehydration of such compounds are well known in the art.

3-hydroxyisobutyrate esters and 2-hydroxyisobutyrate esters can be chemically dehydrated with formation of methacrylate esters, starting with pure 3-hydroxyisobutyrate or 2-hydroxyisobutyrate isolated from the fermentation solution or starting with aqueous or organic solutions of 3-hydroxyisobutyrate ester or 2-hydroxyisobutyrate ester, isolated in work up of the fermentation solution. Such solutions of 3-hydroxyisobutyrate ester or 2-hydroxyisobutyrate ester can also be concentrated before the dehydration step, for example by means of distillation, optionally in the presence of a suitable entrainer.

The dehydration reaction can be carried out in liquid phase or in the gas phase. The dehydration reaction can be carried out in the presence of a catalyst, the nature of the catalyst employed depending on whether a gas-phase or a liquid-phase reaction is carried out.

Suitable dehydration catalysts include both acidic catalysts and alkaline catalysts. Acidic catalysts, in particular can exhibit a decreased tendency to form oligomers. The dehydration catalyst can be employed as a homogeneous catalyst, a heterogeneous catalyst, or combinations thereof. Heterogeneous catalysts can be used in conjunction with a suitable support material. Such a support can itself be acidic or alkaline and provide the acidic or alkaline dehydration catalyst or a catalyst can be applied to an inert support.

Suitable supports which serve as dehydration catalysts include natural or synthetic silicates such as mordenite, montmorillonite, acidic zeolites; supports which are coated with monobasic, dibasic or polybasic inorganic acids, such as phosphoric acid, or with acidic salts of inorganic acids, such as oxides or silicates, for example $Al_2O_3$, $TiO_2$; oxides and mixed oxides such as $\gamma$-$Al_2O_3$ and ZnO—$Al_2O_3$ mixed oxides of heteropolyacids. Alkaline substances which act both as dehydration catalyst and as a support a support material include alkali, alkaline earth, lanthanum, lanthoids or a combinations thereof as their oxides. A further class of materials that can effect dehydration are ion exchangers which can be used in either alkaline or acidic form.

Suitable homogeneous dehydration catalysts include inorganic acids, such as phosphorus-containing acids such as phosphoric acid. Inorganic acids can be immobilized on the support material by immersion or impregnation.

In some embodiments, dehydration reaction is carried out in the gas phase using conventional apparatuses known in the art, for example tubular reactors, shell-and-tube heat exchangers and reactors which comprise thermoplates as heat exchangers. In some embodiments, gas-phase dehydration can utilize isolated 3-hydroxyisobutyrate esters or solutions of the ester, the ester being introduced into a reactor with fixed-bed catalysts. Thermal dehydration in the liquid phase can be carried out in a temperature range of between 200° C. and 350° C., and in some embodiments between 250 and 300° C.

To generate better producers, metabolic modeling can be utilized to optimize growth conditions. Modeling can also be used to design gene knockouts that additionally optimize utilization of the pathway (see, for example, U.S. patent publications US 2002/0012939, US 2003/0224363, US 2004/0029149, US 2004/0072723, US 2003/0059792, US 2002/0168654 and US 2004/0009466, and U.S. Pat. No. 7,127,379). Modeling analysis allows reliable predictions of the effects on cell growth of shifting the metabolism towards more efficient production of methacrylic acid, methacrylate ester, 3-hydroxyisobutyrate and/or 2-hydroxyisobutyrate.

One computational method for identifying and designing metabolic alterations favoring biosynthesis of a desired product is the OptKnock computational framework (Burgard et al., *Biotechnol. Bioeng.* 84:647-657 (2003)). OptKnock is a metabolic modeling and simulation program that suggests gene deletion or disruption strategies that result in genetically stable microorganisms which overproduce the target product. Specifically, the framework examines the complete metabolic and/or biochemical network of a microorganism in order to suggest genetic manipulations that force the desired biochemical to become an obligatory byproduct of cell growth. By coupling biochemical production with cell growth through strategically placed gene deletions or other functional gene disruption, the growth selection pressures imposed on the engineered strains after long periods of time in a bioreactor lead to improvements in performance as a result of the compulsory growth-coupled biochemical production. Lastly, when gene deletions are constructed there is a negligible possibility of the designed strains reverting to their wild-type states because the genes selected by OptKnock are to be completely removed from the genome. Therefore, this computational methodology can be used to either identify alternative pathways that lead to biosynthesis of a desired product or used in connection with the non-naturally occurring microbial organisms for further optimization of biosynthesis of a desired product.

Briefly, OptKnock is a term used herein to refer to a computational method and system for modeling cellular metabolism. The OptKnock program relates to a framework of models and methods that incorporate particular constraints into flux balance analysis (FBA) models. These constraints include, for example, qualitative kinetic information, qualitative regulatory information, and/or DNA microarray experimental data. OptKnock also computes solutions to various metabolic problems by, for example, tightening the flux boundaries derived through flux balance models and subsequently probing the performance limits of metabolic networks in the presence of gene additions or deletions. OptKnock computational framework allows the construction of model formulations that allow an effective query of the performance limits of metabolic networks and provides methods for solving the resulting mixed-integer linear programming problems. The metabolic modeling and simulation methods referred to herein as OptKnock are described in, for example, U.S. publication 2002/0168654, filed Jan. 10, 2002, in International Patent No. PCT/US02/00660, filed Jan. 10, 2002, and U.S. publication 2009/0047719, filed Aug. 10, 2007.

Another computational method for identifying and designing metabolic alterations favoring biosynthetic production of a product is a metabolic modeling and simulation system termed SimPheny®. This computational method and system is described in, for example, U.S. publication 2003/0233218, filed Jun. 14, 2002, and in International Patent Application No. PCT/US03/18838, filed Jun. 13, 2003. SimPheny® is a computational system that can be used to produce a network model in silico and to simulate the flux of mass, energy or charge through the chemical reactions of a biological system to define a solution space that contains any and all possible functionalities of the chemical reactions in the system, thereby determining a range of allowed activities for the biological system. This approach is referred to as constraints-based modeling because the solution space is defined by constraints such as the known stoichiometry of the included reactions as well as reaction thermodynamic and capacity constraints associated with maximum fluxes through reactions. The space defined by these constraints can be interrogated to determine the phenotypic capabilities and behavior of the biological system or of its biochemical components.

These computational approaches are consistent with biological realities because biological systems are flexible and can reach the same result in many different ways. Biological systems are designed through evolutionary mechanisms that have been restricted by fundamental constraints that all living systems must face. Therefore, constraints-based modeling strategy embraces these general realities. Further, the ability to continuously impose further restrictions on a network model via the tightening of constraints results in a reduction in the size of the solution space, thereby enhancing the precision with which physiological performance or phenotype can be predicted.

Given the teachings and guidance provided herein, those skilled in the art will be able to apply various computational frameworks for metabolic modeling and simulation to design and implement biosynthesis of a desired compound in host microbial organisms. Such metabolic modeling and simulation methods include, for example, the computational systems exemplified above as SimPheny® and OptKnock. For illustration of the invention, some methods are described herein with reference to the OptKnock computation framework for modeling and simulation. Those skilled in the art will know how to apply the identification, design and implementation of the metabolic alterations using OptKnock to any of such other metabolic modeling and simulation computational frameworks and methods well known in the art.

The methods described above will provide one set of metabolic reactions to disrupt. Elimination of each reaction within the set or metabolic modification can result in a desired product as an obligatory product during the growth phase of the organism. Because the reactions are known, a solution to the bilevel OptKnock problem also will provide the associated gene or genes encoding one or more enzymes that catalyze each reaction within the set of reactions. Identification of a set of reactions and their corresponding genes encoding the enzymes participating in each reaction is generally an automated process, accomplished through correlation of the reactions with a reaction database having a relationship between enzymes and encoding genes.

Once identified, the set of reactions that are to be disrupted in order to achieve production of a desired product are implemented in the target cell or organism by functional disruption of at least one gene encoding each metabolic reaction within the set. One particularly useful means to achieve functional disruption of the reaction set is by deletion of each encoding gene. However, in some instances, it can be beneficial to disrupt the reaction by other genetic aberrations including, for example, mutation, deletion of regulatory regions such as promoters or cis binding sites for regulatory factors, or by truncation of the coding sequence at any of a number of locations. These latter aberrations, resulting in less than total deletion of the gene set can be useful, for example, when rapid assessments of the coupling of a product are desired or when genetic reversion is less likely to occur.

To identify additional productive solutions to the above described bilevel OptKnock problem which lead to further sets of reactions to disrupt or metabolic modifications that can result in the biosynthesis, including growth-coupled biosynthesis of a desired product, an optimization method, termed integer cuts, can be implemented. This method proceeds by iteratively solving the OptKnock problem exemplified above with the incorporation of an additional constraint referred to as an integer cut at each iteration. Integer cut constraints effectively prevent the solution procedure from choosing the exact same set of reactions identified in any previous iteration that obligatorily couples product biosynthesis to growth. For example, if a previously identified growth-coupled metabolic modification specifies reactions 1, 2, and 3 for disruption, then the following constraint prevents the same reactions from being simultaneously considered in subsequent solutions. The integer cut method is well known in the art and can be found described in, for example, Burgard et al., *Biotechnol. Prog.* 17:791-797 (2001). As with all methods described herein with reference to their use in combination with the OptKnock computational framework for metabolic modeling and simulation, the integer cut method of reducing redundancy in iterative computational analysis also can be applied with other computational frameworks well known in the art including, for example, SimPheny®.

The methods exemplified herein allow the construction of cells and organisms that biosynthetically produce a desired product, including the obligatory coupling of production of a target biochemical product to growth of the cell or organism engineered to harbor the identified genetic alterations. Therefore, the computational methods described herein allow the identification and implementation of metabolic modifications that are identified by an in silico method selected from OptKnock or SimPheny®. The set of metabolic modifications can include, for example, addition of one or more biosynthetic pathway enzymes and/or functional disruption of one or more metabolic reactions including, for example, disruption by gene deletion.

As discussed above, the OptKnock methodology was developed on the premise that mutant microbial networks can be evolved towards their computationally predicted maximum-growth phenotypes when subjected to long periods of growth selection. In other words, the approach leverages an organism's ability to self-optimize under selective pressures. The OptKnock framework allows for the exhaustive enumeration of gene deletion combinations that force a coupling between biochemical production and cell growth based on network stoichiometry. The identification of optimal gene/reaction knockouts requires the solution of a bilevel optimization problem that chooses the set of active reactions such that an optimal growth solution for the resulting network overproduces the biochemical of interest (Burgard et al., *Biotechnol. Bioeng.* 84:647-657 (2003)).

An in silico stoichiometric model of *E. coli* metabolism can be employed to identify essential genes for metabolic pathways as exemplified previously and described in, for example, U.S. patent publications US 2002/0012939, US 2003/0224363, US 2004/0029149, US 2004/0072723, US 2003/0059792, US 2002/0168654 and US 2004/0009466, and in U.S. Pat. No. 7,127,379. As disclosed herein, the OptKnock mathematical framework can be applied to pinpoint gene deletions leading to the growth-coupled production of a desired product. Further, the solution of the bilevel OptKnock problem provides only one set of deletions. To enumerate all meaningful solutions, that is, all sets of knockouts leading to growth-coupled production formation, an optimization technique, termed integer cuts, can be implemented. This entails iteratively solving the OptKnock problem with the incorporation of an additional constraint referred to as an integer cut at each iteration, as discussed above.

As disclosed herein, a nucleic acid encoding a desired activity of a methacrylic acid, methacrylate ester, 3-hydroxyisobutyrate and/or 2-hydroxyisobutyrate pathway can be introduced into a host organism. In some cases, it can be desirable to modify an activity of a methacrylic acid, methacrylate ester, 3-hydroxyisobutyrate and/or 2-hydroxyisobutyrate pathway enzyme or protein to increase production of methacrylic acid, methacrylate ester, 3-hydroxyisobutyrate and/or 2-hydroxyisobutyrate. For example, known mutations that increase the activity of a protein or enzyme can be introduced into an encoding nucleic acid molecule. Additionally, optimization methods can be applied to increase the activity of an enzyme or protein and/or decrease an inhibitory activity, for example, decrease the activity of a negative regulator.

One such optimization method is directed evolution. Directed evolution is a powerful approach that involves the introduction of mutations targeted to a specific gene in order to improve and/or alter the properties of an enzyme. Improved and/or altered enzymes can be identified through the development and implementation of sensitive high-throughput screening assays that allow the automated screening of many enzyme variants (for example, $>10^4$). Iterative rounds of mutagenesis and screening typically are performed to afford an enzyme with optimized properties. Computational algorithms that can help to identify areas of the gene for mutagenesis also have been developed and can significantly reduce the number of enzyme variants that need to be generated and screened. Numerous directed evolution technologies have been developed (for reviews, see Hibbert et al., *Biomol. Eng* 22:11-19 (2005); Huisman and Lalonde, In Biocatalysis in the pharmaceutical and biotechnology industries pgs. 717-742 (2007), Patel (ed.), CRC Press; Otten and Quax. *Biomol. Eng* 22:1-9 (2005); and Sen et al., *Appl Biochem. Biotechnol* 143:212-223 (2007)) to be effective at creating diverse variant libraries, and these methods have been successfully applied to the improvement of a wide range of properties across many enzyme classes. Enzyme characteristics that have been improved and/or altered by directed evolution technologies include, for example: selectivity/specificity, for conversion of non-natural substrates; temperature stability, for robust high temperature processing; pH stability, for bioprocessing under lower or higher pH conditions; substrate or product tolerance, so that high product titers can be achieved; binding ($K_m$), including broadening substrate binding to include non-natural substrates; inhibition ($K_i$), to remove inhibition by products, substrates, or key intermediates; activity (kcat), to increases enzymatic reaction rates to achieve desired flux; expression levels, to increase protein yields and overall pathway flux; oxygen stability, for operation of air sensitive enzymes under aerobic conditions; and anaerobic activity, for operation of an aerobic enzyme in the absence of oxygen.

Described below in more detail are exemplary methods that have been developed for the mutagenesis and diversification of genes to target desired properties of specific enzymes. Such methods are well known to those skilled in the art. Any of these can be used to alter and/or optimize the activity of a methacrylic acid, methacrylate ester, 3-hydroxyisobutyrate and/or 2-hydroxyisobutyrate pathway enzyme or protein.

EpPCR (Pritchard et al., *J Theor. Biol.* 234:497-509 (2005)) introduces random point mutations by reducing the fidelity of DNA polymerase in PCR reactions by the addition of $Mn^{2+}$ ions, by biasing dNTP concentrations, or by other conditional variations. The five step cloning process to confine the mutagenesis to the target gene of interest involves: 1) error-prone PCR amplification of the gene of interest; 2) restriction enzyme digestion; 3) gel purification of the desired DNA fragment; 4) ligation into a vector; 5) transformation of the gene variants into a suitable host and screening of the library for improved performance. This method can generate multiple mutations in a single gene simultaneously, which can be useful to screen a larger number of potential variants having a desired activity. A high number of mutants can be generated by EpPCR, so a high-throughput screening assay or a selection method, for example, using robotics, is useful to identify those with desirable characteristics.

Error-prone Rolling Circle Amplification (epRCA) (Fujii et al., *Nucleic Acids Res.* 32:e145 (2004); and Fujii et al., *Nat. Protoc.* 1:2493-2497 (2006)) has many of the same elements as epPCR except a whole circular plasmid is used as the template and random 6-mers with exonuclease resistant thiophosphate linkages on the last 2 nucleotides are used to amplify the plasmid followed by transformation into cells in which the plasmid is re-circularized at tandem repeats. Adjusting the $Mn^{2+}$ concentration can vary the mutation rate somewhat. This technique uses a simple error-prone, single-step method to create a full copy of the plasmid with 3-4 mutations/kbp. No restriction enzyme digestion or specific primers are required. Additionally, this method is typically available as a commercially available kit.

DNA or Family Shuffling (Stemmer, *Proc Natl Acad Sci USA* 91:10747-10751 (1994)); and Stemmer, *Nature* 370:389-391 (1994)) typically involves digestion of two or more variant genes with nucleases such as Dnase I or EndoV to generate a pool of random fragments that are reassembled by cycles of annealing and extension in the presence of DNA polymerase to create a library of chimeric genes. Fragments prime each other and recombination occurs when one copy primes another copy (template switch). This method can be used with >1 kbp DNA sequences. In addition to mutational recombinants created by fragment reassembly, this method introduces point mutations in the extension steps at a rate similar to error-prone PCR. The method can be used to remove deleterious, random and neutral mutations.

Staggered Extension (StEP) (Zhao et al., *Nat. Biotechnol.* 16:258-261 (1998)) entails template priming followed by repeated cycles of 2 step PCR with denaturation and very short duration of annealing/extension (as short as 5 sec). Growing fragments anneal to different templates and extend further, which is repeated until full-length sequences are made. Template switching means most resulting fragments have multiple parents. Combinations of low-fidelity polymerases (Taq and Mutazyme) reduce error-prone biases because of opposite mutational spectra.

In Random Priming Recombination (RPR) random sequence primers are used to generate many short DNA fragments complementary to different segments of the template (Shao et al., *Nucleic Acids Res* 26:681-683 (1998)). Base misincorporation and mispriming via epPCR give point mutations. Short DNA fragments prime one another based on homology and are recombined and reassembled into full-length by repeated thermocycling. Removal of templates prior to this step assures low parental recombinants. This method, like most others, can be performed over multiple iterations to evolve distinct properties. This technology avoids sequence bias, is independent of gene length, and requires very little parent DNA for the application.

In Heteroduplex Recombination linearized plasmid DNA is used to form heteroduplexes that are repaired by mismatch repair (Volkov et al, *Nucleic Acids Res.* 27:e18 (1999); and Volkov et al., *Methods Enzymol.* 328:456-463 (2000)). The mismatch repair step is at least somewhat mutagenic. Heteroduplexes transform more efficiently than linear homoduplexes. This method is suitable for large genes and whole operons.

Random Chimeragenesis on Transient Templates (RACHITT) (Coco et al., *Nat. Biotechnol.* 19:354-359 (2001)) employs Dnase I fragmentation and size fractionation of single stranded DNA (ssDNA). Homologous fragments are hybridized in the absence of polymerase to a complementary ssDNA scaffold. Any overlapping unhybridized fragment ends are trimmed down by an exonuclease. Gaps between fragments are filled in and then ligated to give a pool of full-length diverse strands hybridized to the scaffold, which contains U to preclude amplification. The scaffold then is destroyed and is replaced by a new strand complementary to the diverse strand by PCR amplification. The method involves one strand (scaffold) that is from only one parent while the priming fragments derive from other genes, and the parent scaffold is selected against. Thus, no reannealing with parental fragments occurs. Overlapping fragments are trimmed with an exonuclease. Otherwise, this is conceptually similar to DNA shuffling and StEP. Therefore, there should be no siblings, few inactives, and no unshuffled parentals. This technique has advantages in that few or no parental genes are created and many more crossovers can result relative to standard DNA shuffling.

Recombined Extension on Truncated templates (RETT) entails template switching of unidirectionally growing strands from primers in the presence of unidirectional ssDNA fragments used as a pool of templates (Lee et al., *J. Molec. Catalysis* 26:119-129 (2003)). No DNA endonucleases are used. Unidirectional ssDNA is made by DNA polymerase with random primers or serial deletion with exonuclease. Unidirectional ssDNA are only templates and not primers. Random priming and exonucleases do not introduce sequence bias as true of enzymatic cleavage of DNA shuffling/RACHITT. RETT can be easier to optimize than StEP because it uses normal PCR conditions instead of very short extensions. Recombination occurs as a component of the PCR steps, that is, no direct shuffling. This method can also be more random than StEP due to the absence of pauses.

In Degenerate Oligonucleotide Gene Shuffling (DOGS) degenerate primers are used to control recombination between molecules; (Bergquist and Gibbs, *Methods Mol. Biol.* 352:191-204 (2007); Bergquist et al., *Biomol. Eng* 22:63-72 (2005); Gibbs et al., *Gene* 271:13-20 (2001)) this can be used to control the tendency of other methods such as DNA shuffling to regenerate parental genes. This method can be combined with random mutagenesis (epPCR) of selected gene segments. This can be a good method to block the reformation of parental sequences. No endonucleases are needed. By adjusting input concentrations of segments made, one can bias towards a desired backbone. This method allows DNA shuffling from unrelated parents without restriction enzyme digests and allows a choice of random mutagenesis methods.

Incremental Truncation for the Creation of Hybrid Enzymes (ITCHY) creates a combinatorial library with 1 base pair deletions of a gene or gene fragment of interest (Ostermeier et al., *Proc. Natl. Acad. Sci. USA* 96:3562-3567 (1999); and Ostermeier et al., *Nat. Biotechnol.* 17:1205-1209 (1999)). Truncations are introduced in opposite direction on pieces of 2 different genes. These are ligated together and the fusions are cloned. This technique does not require homology between the 2 parental genes. When ITCHY is combined with DNA shuffling, the system is called SCRATCHY (see below). A major advantage of both is no need for homology between parental genes; for example, functional fusions between an *E. coli* and a human gene were created via ITCHY. When ITCHY libraries are made, all possible crossovers are captured.

Thio-Incremental Truncation for the Creation of Hybrid Enzymes (THIO-ITCHY) is similar to ITCHY except that phosphothioate dNTPs are used to generate truncations (Lutz et al., *Nucleic Acids Res* 29:E16 (2001)). Relative to ITCHY, THIO-ITCHY can be easier to optimize, provide more reproducibility, and adjustability.

SCRATCHY combines two methods for recombining genes, ITCHY and DNA shuffling (Lutz et al., *Proc. Natl. Acad. Sci. USA* 98:11248-11253 (2001)). SCRATCHY combines the best features of ITCHY and DNA shuffling. First, ITCHY is used to create a comprehensive set of fusions between fragments of genes in a DNA homology-independent fashion. This artificial family is then subjected to a DNA-shuffling step to augment the number of crossovers. Computational predictions can be used in optimization. SCRATCHY is more effective than DNA shuffling when sequence identity is below 80%.

In Random Drift Mutagenesis (RNDM) mutations are made via epPCR followed by screening/selection for those retaining usable activity (Bergquist et al., *Biomol. Eng.* 22:63-72 (2005)). Then, these are used in DOGS to generate recombinants with fusions between multiple active mutants or between active mutants and some other desirable parent. Designed to promote isolation of neutral mutations; its purpose is to screen for retained catalytic activity whether or not this activity is higher or lower than in the original gene. RNDM is usable in high throughput assays when screening is capable of detecting activity above background. RNDM has been used as a front end to DOGS in generating diversity. The technique imposes a requirement for activity prior to shuffling or other subsequent steps; neutral drift libraries are indicated to result in higher/quicker improvements in activity from smaller libraries. Though published using epPCR, this could be applied to other large-scale mutagenesis methods.

Sequence Saturation Mutagenesis (SeSaM) is a random mutagenesis method that: 1) generates a pool of random length fragments using random incorporation of a phosphothioate nucleotide and cleavage; this pool is used as a template to 2) extend in the presence of "universal" bases such as inosine; 3) replication of an inosine-containing complement gives random base incorporation and, consequently, mutagenesis (Wong et al., *Biotechnol. J.* 3:74-82 (2008); Wong et al., *Nucleic Acids Res.* 32:e26 (2004); and Wong et al., *Anal. Biochem.* 341:187-189 (2005)). Using this technique it can be possible to generate a large library of mutants within 2 to 3 days using simple methods. This technique is non-directed in comparison to the mutational bias of DNA polymerases. Differences in this approach makes this technique complementary (or an alternative) to epPCR.

In Synthetic Shuffling, overlapping oligonucleotides are designed to encode "all genetic diversity in targets" and allow a very high diversity for the shuffled progeny (Ness et al., *Nat. Biotechnol.* 20:1251-1255 (2002)). In this technique, one can design the fragments to be shuffled. This aids in increasing the resulting diversity of the progeny. One can design sequence/codon biases to make more distantly related sequences recombine at rates approaching those observed with more closely related sequences. Additionally, the technique does not require physically possessing the template genes.

Nucleotide Exchange and Excision Technology NexT exploits a combination of dUTP incorporation followed by treatment with uracil DNA glycosylase and then piperidine to perform endpoint DNA fragmentation (Muller et al., *Nucleic Acids Res.* 33:e117 (2005)). The gene is reassembled using internal PCR primer extension with proofreading polymerase. The sizes for shuffling are directly controllable using varying dUPT::dTTP ratios. This is an end point reaction using simple methods for uracil incorporation and cleavage. Other nucleotide analogs, such as 8-oxo-guanine, can be used with this method. Additionally, the technique works well with very short fragments (86 bp) and has a low error rate. The chemical cleavage of DNA used in this technique results in very few unshuffled clones.

In Sequence Homology-Independent Protein Recombination (SHIPREC), a linker is used to facilitate fusion between two distantly related or unrelated genes. Nuclease treatment is used to generate a range of chimeras between the two genes. These fusions result in libraries of single-crossover hybrids (Sieber et al., *Nat. Biotechnol.* 19:456-460 (2001)). This produces a limited type of shuffling and a separate process is required for mutagenesis. In addition, since no homology is needed, this technique can create a library of chimeras with varying fractions of each of the two unrelated parent genes. SHIPREC was tested with a heme-binding domain of a bacterial CP450 fused to N-terminal regions of a mammalian CP450; this produced mammalian activity in a more soluble enzyme.

In Gene Site Saturation Mutagenesis™ (GSSM™) the starting materials are a supercoiled dsDNA plasmid containing an insert and two primers which are degenerate at the desired site of mutations (Kretz et al., *Methods Enzymol.* 388:3-11 (2004)). Primers carrying the mutation of interest, anneal to the same sequence on opposite strands of DNA. The mutation is typically in the middle of the primer and flanked on each side by approximately 20 nucleotides of correct sequence. The sequence in the primer is NNN or NNK (coding) and MNN (noncoding) (N=all 4, K=G, T, M=A, C). After extension, DpnI is used to digest dam-methylated DNA to eliminate the wild-type template. This technique explores all possible amino acid substitutions at a given locus (that is, one codon). The technique facilitates the generation of all possible replacements at a single-site with no nonsense codons and results in equal to near-equal representation of most possible alleles. This technique does not require prior knowledge of the structure, mechanism, or domains of the target enzyme. If followed by shuffling or Gene Reassembly, this technology creates a diverse library of recombinants containing all possible combinations of single-site up-mutations. The usefulness of this technology combination has been demonstrated for the successful evolution of over 50 different enzymes, and also for more than one property in a given enzyme.

Combinatorial Cassette Mutagenesis (CCM) involves the use of short oligonucleotide cassettes to replace limited regions with a large number of possible amino acid sequence alterations (Reidhaar-Olson et al. *Methods Enzymol.* 208:564-586 (1991); and Reidhaar-Olson et al. *Science* 241:53-57 (1988)). Simultaneous substitutions at two or three sites are possible using this technique. Additionally, the method tests a large multiplicity of possible sequence changes at a limited range of sites. This technique has been used to explore the information content of the lambda repressor DNA-binding domain.

Combinatorial Multiple Cassette Mutagenesis (CMCM) is essentially similar to CCM except it is employed as part of a larger program: 1) use of epPCR at high mutation rate to 2) identify hot spots and hot regions and then 3) extension by CMCM to cover a defined region of protein sequence space (Reetz et al., *Angew. Chem. Int. Ed Engl.* 40:3589-3591 (2001)). As with CCM, this method can test virtually all possible alterations over a target region. If used along with methods to create random mutations and shuffled genes, it provides an excellent means of generating diverse, shuffled proteins. This approach was successful in increasing, by 51-fold, the enantioselectivity of an enzyme.

In the Mutator Strains technique, conditional is mutator plasmids allow increases of 20 to 4000-X in random and natural mutation frequency during selection and block accumulation of deleterious mutations when selection is not required (Selifonova et al., *Appl. Environ. Microbiol.* 67:3645-3649 (2001)). This technology is based on a plasmid-derived mutD5 gene, which encodes a mutant subunit of DNA polymerase III. This subunit binds to endogenous DNA polymerase III and compromises the proofreading ability of polymerase III in any strain that harbors the plasmid. A broad-spectrum of base substitutions and frameshift mutations occur. In order for effective use, the mutator plasmid should be removed once the desired phenotype is achieved; this is accomplished through a temperature sensitive (ts) origin of replication, which allows for plasmid curing at 41° C. It should be noted that mutator strains have been explored for quite some time (see Low et al., *J. Mol. Biol.* 260:359-3680 (1996)). In this technique, very high spontaneous mutation rates are observed. The conditional property minimizes non-desired background mutations. This technology could be combined with adaptive evolution to enhance mutagenesis rates and more rapidly achieve desired phenotypes.

Look-Through Mutagenesis (LTM) is a multidimensional mutagenesis method that assesses and optimizes combinatorial mutations of selected amino acids (Rajpal et al., *Proc. Natl. Acad. Sci. USA* 102:8466-8471 (2005)). Rather than saturating each site with all possible amino acid changes, a set of nine is chosen to cover the range of amino acid R-group chemistry. Fewer changes per site allows multiple sites to be subjected to this type of mutagenesis. A >800-fold increase in binding affinity for an antibody from low nanomolar to picomolar has been achieved through this method. This is a rational approach to minimize the number of random combinations and can increase the ability to find improved traits by greatly decreasing the numbers of clones to be screened. This has been applied to antibody engineering, specifically to increase the binding affinity and/or reduce dissociation. The technique can be combined with either screens or selections.

Gene Reassembly is a DNA shuffling method that can be applied to multiple genes at one time or to create a large library of chimeras (multiple mutations) of a single gene (Tunable GeneReassembly™ (TGR™) Technology supplied by Verenium Corporation). Typically this technology is used in combination with ultra-high-throughput screening to query the represented sequence space for desired improvements. This technique allows multiple gene recombination independent of homology. The exact number and position of cross-over events can be pre-determined using fragments designed via bioinformatic analysis. This technology leads to a very high level of diversity with virtually no parental gene reformation and a low level of inactive genes. Combined with GSSM™, a large range of mutations can be tested for improved activity. The method allows "blending" and "fine tuning" of DNA shuffling, for example, codon usage can be optimized.

In Silico Protein Design Automation (PDA) is an optimization algorithm that anchors the structurally defined protein backbone possessing a particular fold, and searches sequence space for amino acid substitutions that can stabilize the fold and overall protein energetics (Hayes et al., *Proc. Natl. Acad. Sci. USA* 99:15926-15931 (2002)). This technology uses in silico structure-based entropy predictions in order to search for structural tolerance toward protein amino acid variations. Statistical mechanics is applied to calculate coupling interactions at each position. Structural tolerance toward amino acid substitution is a measure of coupling. Ultimately, this technology is designed to yield desired modifications of protein properties while maintaining the integrity of structural characteristics. The method computationally assesses and allows filtering of a very large number of possible sequence variants ($10^{50}$). The choice of sequence variants to test is related to predictions based on the most favorable thermodynamics. Ostensibly only stability or properties that are linked to stability can be effectively addressed with this technology. The method has been successfully used in some therapeutic proteins, especially in engineering immunoglobulins. In silico predictions avoid testing extraordinarily large numbers of potential variants. Predictions based on existing three-dimensional structures are more likely to succeed than predictions based on hypothetical structures. This technology can readily predict and allow targeted screening of multiple simultaneous mutations, something not possible with purely experimental technologies due to exponential increases in numbers.

Iterative Saturation Mutagenesis (ISM) involves: 1) using knowledge of structure/function to choose a likely site for enzyme improvement; 2) performing saturation mutagenesis at chosen site using a mutagenesis method such as Stratagene QuikChange (Stratagene; San Diego Calif.); 3) screening/selecting for desired properties; and 4) using improved clone(s), start over at another site and continue repeating until a desired activity is achieved (Reetz et al., *Nat. Protoc.* 2:891-903 (2007); and Reetz et al., *Angew. Chem. Int. Ed Engl.* 45:7745-7751 (2006)). This is a proven methodology, which assures all possible replacements at a given position are made for screening/selection.

Any of the aforementioned methods for mutagenesis can be used alone or in any combination. Additionally, any one or combination of the directed evolution methods can be used in conjunction with adaptive evolution techniques, as described herein.

EXAMPLE I

Exemplary Methacrylic Acid Pathway Enzymes

This example describes exemplary pathways for production of methacrylic acid.

FIG. 1 depicts exemplary pathways to MAA from acetyl-CoA and pyruvate via intermediate citramalate. Also shown are pathways to MAA from aconitate. In one pathway acetyl-CoA and pyruvate are first converted to citramalate by citramalate synthase. Dehydration of citramalate can yield either citraconate (Step B) or mesaconate (Step C). Mesaconate and citraconate are interconverted by a cis/trans isomerase in Step G. Decarboxylation of mesaconate (Step H) or citraconate (Step C) yields MAA. In an alternate pathway, citramalate is formed from acetyl-CoA and pyruvate via a citramalyl-CoA intermediate in Steps D and E, catalyzed by citramalyl-CoA lyase and citramalyl-coA hydrolase, transferase or synthetase.

Also exemplified are pathways from aconitate to MAA. In one pathway, aconitate is first decarboxylated to itaconate by aconitate decarboxylase (Step I). Itaconate is then isomerized to citraconate by itaconate delta-isomerase (Step J). Conversion of citraconate to MAA proceeds either directly by decarboxylation or indirectly via mesaconate. In an alternate pathway, the itaconate intermediate is first converted to itaconyl-CoA by a CoA transferase or synthetase (Step L). Hydration of itaconyl-CoA yields citramalyl-CoA, which can then be converted to MAA as described above and shown in FIG. 1.

Table 1 shows enzyme classes that can perform the steps depicted in FIG. 1. Exemplary enzymes are described in further detail below.

TABLE 1

Enzyme classes for the enzymes shown in FIG. 1.

| Label | Function | Step |
|---|---|---|
| 2.3.1.a | Synthase | A |
| 2.8.3.a | Coenzyme-A transferase | E, L |
| 3.1.2.a | Thiolester hydrolase (CoA specific) | E |
| 4.1.1.a | Decarboxylase | C, H, J |
| 4.1.3.a | Lyase | D |
| 4.2.1.a | Dehydratase | B, F, K |
| 5.2.1.a | Cis/trans isomerase | G |
| 5.3.3.a | Delta-Isomerase | I |
| 6.2.1.a | Acid-thiol ligase | E, L |

EC 2.3.1.a Synthase (Step A).

Citramalate synthase (EC 2.3.1.182) catalyzes the conversion of acetyl-CoA and pyruvate to citramalate and coenzyme A. The enzyme participates in the threonine-independent pathway of isoleucine biosynthesis found in archaea such as *Methanocaldococcus jannaschii* (Howell et al., *J. Bacteriol.* 181:331-333 (1999)), *Leptospira interrrogans* (Xu et al., *J. Bacteriol.* 186:5400-5409 (2004)) and *Geobacter sulfurreducens* (Risso et al., *J. Bacteriol.* 190:2266-2274 (2008)). This enzyme operates in the synthetic direction in vivo, is highly specific for pyruvate as a substrate, and is typically inhibited by isoleucine. A recombinant citramalate synthase from *M. jannaschii* developed by directed evolution is highly active and lacks inhibition by isoleucine (Atsumi et al., *Appl Environ Microbiol* 74:7802-7808 (2008)). Citramalate synthase activity was also demonstrated in the citramalate cycle acetate assimilation pathway of *Rhodospirillum rubrum*, although the gene associated with this activity was not been identified (Berg et al., *Mikrobiologiia* 78:22-31 (2009)).

| Gene | GenBank | GI Number | Organism |
| --- | --- | --- | --- |
| CimA | Q58787.1 | 2492795 | Methanocaldococcus jannaschii |
| CimA | ABK13749.1 | 116664671 | Leptospira interrrogans |
| CimA | ADI84633.1 | 298505910 | Geobacter sulfurreducens |

EC 2.8.3.a CoA Transferase (Step E).

CoA transferases catalyze the reversible transfer of a CoA moiety from one molecule to another. Two transformations in FIG. 1 utilize a CoA transferase: conversion of citramalyl-CoA to citramalate (Step E) and activation of itaconate to itaconyl-CoA (Step L). Citramalyl-CoA transferase (EC 2.8.3.7 and 2.8.3.11) in Step E of FIG. 1 transfers a CoA moiety from citramalyl-CoA to a donor. A citramalate:succinyl-CoA transferase enzyme is active in the 3-hydroxypropionate cycle of glyoxylate assimilation. The enzyme is encoded by sst in *Chloroflexus aurantiacus*, where it is located upstream of the gene encoding citramalyl-CoA lyase (Friedmann et al., *J. Bacteriol.* 188:6460-6468 (2006)). This enzyme was cloned, heterologously expressed and characterized in *E. coli*. The enzyme is also active as an itaconate: succinyl-CoA transferase. Similar enzymes are found in *Roseiflexus* sp. RS-1 and *Chloroflexus aggregans* by sequence identity and proximity to the citramalyl-CoA lyase gene. A CoA transferase characterized in *Pseudomonas* sp. B2aba exhibits both citramlayl-CoA transferase and itaconyl-CoA transferase activities, allowing the organism to grow on both itaconate and citramalate (Cooper et al., *Biochem. J* 91:82-91 (1964)). The gene associated with this enzyme has not been identified. Citramalyl-CoA transferase activity was also detected in cell extracts of *Achromobacter xylosoxydans*, which efficiently converts itaconate to citramalate (He et al., *J Biosci Bioeng.* 89:388-391 (2000)). The associated gene is not known, but the gene bears the highest protein sequence similarity Sst.

| Gene | GenBank | GI Number | Organism |
| --- | --- | --- | --- |
| Sst | YP_001635864.1 | 163847820 | Chloroflexus aurantiacus |
| RoseRS_0050 | YP_001274443.1 | 148654238 | Roseiflexus sp. RS-1 |
| Cagg_3093 | YP_002464387.1 | 219849954 | Chloroflexus aggregans |
| AXYL_05983 | YP_003981992.1 | 311109139 | Achromobacter xylosoxydans |

Additional candidate enzymes for catalyzing these transformations include the gene products of cat1, cat2, and cat3 of *Clostridium kluyveri*, which have been shown to exhibit succinyl-CoA, 4-hydroxybutyryl-CoA, and butyryl-CoA transferase activity, respectively (See dorf et al., *Proc. Natl. Acad. Sci USA* 105:2128-2133 (2008); Sohling et al., *J Bacteriol.* 178:871-880 (1996)). Similar CoA transferase activities are also present in *Trichomonas vaginalis* (van Grinsven et al., *J. Biol. Chem.* 283:1411-1418 (2008)) and *Trypanosoma brucei* (Riviere et al., *J. Biol. Chem.* 279:45337-45346 (2004)).

| Protein | GenBank ID | GI Number | Organism |
| --- | --- | --- | --- |
| cat1 | P38946.1 | 729048 | Clostridium kluyveri |
| cat2 | P38942.2 | 172046066 | Clostridium kluyveri |
| cat3 | EDK35586.1 | 146349050 | Clostridium kluyveri |
| TVAG_395550 | XP_001330176 | 123975034 | Trichomonas vaginalis G3 |
| Tb11.02.0290 | XP_828352 | 71754875 | Trypanosoma brucei |

The glutaconyl-CoA-transferase (EC 2.8.3.12) enzyme from anaerobic bacterium *Acidaminococcus fermentans* reacts with glutaconyl-CoA and 3-butenoyl-CoA (Mack et al., *Eur. J. Biochem.* 226:41-51 (1994)), substrates similar in structure to 2,3-dehydroadipyl-CoA. The genes encoding this enzyme are gctA and gctB. This enzyme has reduced but detectable activity with other CoA derivatives including glutaryl-CoA, 2-hydroxyglutaryl-CoA, adipyl-CoA, crotonyl-CoA and acrylyl-CoA (Buckel et al., *Eur. J. Biochem.* 118: 315-321 (1981)). The enzyme has been cloned and expressed in *E. coli* (Mack et al., *Eur. J. Biochem.* 226:41-51 (1994)). Glutaconate CoA-transferase activity has also been detected in *Clostridium sporosphaeroides* and *Clostridium symbiosum*. Additional glutaconate CoA-transferase enzymes can be inferred by homology to the *Acidaminococcus fermentans* protein sequence.

| Protein | GenBank ID | GI Number | Organism |
| --- | --- | --- | --- |
| gctA | CAA57199.1 | 559392 | Acidaminococcus fermentans |
| gctB | CAA57200.1 | 559393 | Acidaminococcus fermentans |
| gctA | ACJ24333.1 | 212292816 | Clostridium symbiosum |
| gctB | ACJ24326.1 | 212292808 | Clostridium symbiosum |
| gctA | NP_603109.1 | 19703547 | Fusobacterium nucleatum |
| gctB | NP_603110.1 | 19703548 | Fusobacterium nucleatum |

A CoA transferase that can utilize acetyl-CoA as the CoA donor is acetoacetyl-CoA transferase, encoded by the *E. coli* atoA (alpha subunit) and atoD (beta subunit) genes (Korolev et al., *Acta Crystallogr. D. Biol. Crystallogr.* 58:2116-2121 (2002); Vanderwinkel et al., *Biochem. Biophys. Res. Commun.* 33:902-908 (1968)). This enzyme has a broad substrate range (Sramek et al., *Arch. Biochem. Biophys.* 171:14-26 (1975)) and has been shown to transfer the CoA moiety to acetate from a variety of branched and linear acyl-CoA substrates, including isobutyrate (Matthies et al., *Appl Environ. Microbiol* 58:1435-1439 (1992)), valerate (Vanderwinkel et al., *Biochem. Biophys. Res. Commun.* 33:902-908 (1968)) and butanoate (Vanderwinkel et al., *Biochem. Biophys. Res. Commun.* 33:902-908 (1968)). This enzyme is induced at the transcriptional level by acetoacetate, so modification of regulatory control can be useful for engineering this enzyme into a pathway (Pauli et al., *Eur. J Biochem.* 29:553-562 (1972)). Similar enzymes exist in *Corynebacterium glutamicum* ATCC 13032 (Duncan et al., *Appl. Environ. Microbiol* 68:5186-5190 (2002)), *Clostridium acetobutylicum* (Cary et al., *Appl. Environ. Microbiol* 56:1576-1583 (1990); Wiesenborn et al., *Appl. Environ. Microbiol* 55:323-329 (1989)), and *Clostridium saccharoperbutylacetonicum* (Kosaka et al., *Biosci. Biotechnol Biochem.* 71:58-68 (2007)).

| Gene | Accession No. | GI Number | Organism |
| --- | --- | --- | --- |
| atoA | P76459.1 | 2492994 | Escherichia coli |
| atoD | P76458.1 | 2492990 | Escherichia coli |
| actA | YP_226809.1 | 62391407 | Corynebacterium glutamicum |
| cg0592 | YP_224801.1 | 62389399 | Corynebacterium glutamicum |
| ctfA | NP_149326.1 | 15004866 | Clostridium acetobutylicum |
| ctfB | NP_149327.1 | 15004867 | Clostridium acetobutylicum |
| ctfA | AAP42564.1 | 31075384 | Clostridium saccharoperbutylacetonicum |
| ctfB | AAP42565.1 | 31075385 | Clostridium saccharoperbutylacetonicum |

EC 3.2.1.a CoA Hydrolase (Step E).

Enzymes in the 3.1.2 family hydrolyze acyl-CoA molecules to their corresponding acids. Several CoA hydrolases with broad substrate ranges are suitable candidates for exhibiting citramalyl-CoA hydrolase activity. For example, the enzyme encoded by acot12 from *Rattus norvegicus* brain (Robinson et al., *Biochem. Biophys. Res. Commun.* 71:959-965 (1976)) can react with butyryl-CoA, hexanoyl-CoA and malonyl-CoA. The human dicarboxylic acid thioesterase, encoded by acot8, exhibits activity on glutaryl-CoA, adipyl-CoA, suberyl-CoA, sebacyl-CoA, and dodecanedioyl-CoA (Westin et al., *J. Biol. Chem.* 280:38125-38132 (2005)). The closest *E. coli* homolog to this enzyme, tesB, can also hydrolyze a range of CoA thiolesters (Naggert et al., *J Biol Chem* 266:11044-11050 (1991)). A similar enzyme has also been characterized in the rat liver (Deana R., *Biochem Int* 26:767-773 (1992)). Additional enzymes with hydrolase activity in *E. coli* include ybgC, paaI, and ybdB (Kuznetsova, et al., FEMS Microbiol Rev, 2005, 29(2):263-279; Song et al., J Biol Chem, 2006, 281(16):11028-38). Though its sequence has not been reported, the enzyme from the mitochondrion of the pea leaf has a broad substrate specificity, with demonstrated activity on acetyl-CoA, propionyl-CoA, butyryl-CoA, palmitoyl-CoA, oleoyl-CoA, succinyl-CoA, and crotonyl-CoA (Zeiher et al., *Plant. Physiol.* 94:20-27 (1990)). The acetyl-CoA hydrolase, ACH1, from *S. cerevisiae* represents another candidate hydrolase (Buu et al., *J. Biol. Chem.* 278:17203-17209 (2003)).

| Gene name | GenBank ID | GI Number | Organism |
| --- | --- | --- | --- |
| acot12 | NP_570103.1 | 18543355 | *Rattus norvegicus* |
| tesB | NP_414986 | 16128437 | *Escherichia coli* |
| acot8 | CAA15502 | 3191970 | *Homo sapiens* |
| acot8 | NP_570112 | 51036669 | *Rattus norvegicus* |
| tesA | NP_415027 | 16128478 | *Escherichia coli* |
| ybgC | NP_415264 | 16128711 | *Escherichia coli* |
| paaI | NP_415914 | 16129357 | *Escherichia coli* |
| ybdB | NP_415129 | 16128580 | *Escherichia coli* |
| ACH1 | NP_009538 | 6319456 | *Saccharomyces cerevisiae* |

Yet another candidate hydrolase is the glutaconate CoA-transferase from *Acidaminococcus fermentans*. This enzyme was transformed by site-directed mutagenesis into an acyl-CoA hydrolase with activity on glutaryl-CoA, acetyl-CoA and 3-butenoyl-CoA (Mack et al., *FEBS. Lett.* 405:209-212 (1997)). This indicates that the enzymes encoding succinyl-CoA:3-ketoacid-CoA transferases and acetoacetyl-CoA:acetyl-CoA transferases can also serve as candidates for this reaction step, with appropriate mutations introduced to change their function as described above.

| Gene | GenBank | GI Number | Organism |
| --- | --- | --- | --- |
| gctA | CAA57199 | 559392 | *Acidaminococcus fermentans* |
| gctB | CAA57200 | 559393 | *Acidaminococcus fermentans* |

EC 4.1.1.a Decarboxylase (Steps C, H, J).

The final step of MAA in FIG. 1 is the decarboxylation of either mesaconate or citraconate. Although enzymes with citraconate or mesaconate decarboxylase activity have not been identified to date, suitable enzyme candidates include aconitate decarboxylase (EC 4.1.1.6), which catalyzes the conversion of aconitate to itaconate, 4-oxalocrotonate decarboxylase (EC 4.1.1.77), which catalyzes the conversion of 4-oxalocrotonate to 2-oxopentenoate, and enzymes in the cinnamate decarboxylase family (EC 4.1.1.-). Aconitate decarboxylase (EC 4.1.1.6) catalyzes the final step in itaconate biosynthesis in a strain of *Candida* and also in the filamentous fungus *Aspergillus terreus* (Bonnarme et al. *J. Bacteriol.* 177:3573-3578 (1995); Willke and Vorlop, *Appl Microbiol. Biotechnol* 56:289-295 (2001)). A cis-aconitate decarboxylase (CAD) (EC 4.1.16) has been purified and characterized from *Aspergillus terreus* (Dwiarti et al., *J. Biosci. Bioeng.* 94(1): 29-33 (2002)). Recently, the gene has been cloned and functionally characterized (Kanamasa et al., *Appl. Microbiol Biotechnol* 80:223-229 (2008)) and (WO/2009/014437). Several close homologs of CAD are listed below (EP 2017344A1; WO 2009/014437 A1). The gene and protein sequence of CAD were reported previously (EP 2017344 A1; WO 2009/014437 A1), along with several close homologs listed below.

| Gene | GenBank | GI Number | Organism |
| --- | --- | --- | --- |
| CAD | XP_001209273 | 115385453 | *Aspergillus terreus* |
| | XP_001217495 | 115402837 | *Aspergillus terreus* |
| | XP_001209946 | 115386810 | *Aspergillus terreus* |
| | BAE66063 | 83775944 | *Aspergillus oryzae* |
| | XP_001393934 | 145242722 | *Aspergillus niger* |
| | XP_391316 | 46139251 | *Gibberella zeae* |
| | XP_001389415 | 145230213 | *Aspergillus niger* |
| | XP_001383451 | 126133853 | *Pichia stipitis* |
| | YP_891060 | 118473159 | *Mycobacterium smegmatis* |
| | NP_961187 | 41408351 | *Mycobacterium avium* subsp. *pratuberculosis* |
| | YP_880968 | 118466464 | *Mycobacterium avium* |
| | ZP_01648681 | 119882410 | *Salinispora arenicola* |

4-Oxalocronate decarboxylase catalyzes the decarboxylation of 4-oxalocrotonate to 2-oxopentanoate. This enzyme has been isolated from numerous organisms and characterized. Genes encoding this enzyme include dmpH and dmpE in *Pseudomonas* sp. (strain 600) (Shingler et al., 174:711-724 (1992)), xylII and xylIII from *Pseudomonas putida* (Kato et al., *Arch. Microbiol* 168:457-463 (1997); Stanley et al., *Biochemistry* 39:3514 (2000); Lian et al., *J. Am. Chem. Soc.* 116:10403-10411 (1994)) and Reut_B5691 and Reut_B5692 from *Ralstonia eutropha* JMP134 (Hughes et al., 158:79-83 (1984)). The genes encoding the enzyme from *Pseudomonas* sp. (strain 600) have been cloned and expressed in *E. coli* (Shingler et al., *J. Bacteriol.* 174:711-724 (1992)). The 4-oxalocrotonate decarboxylase encoded by xylI in *Pseudomonas putida* functions in a complex with vinylpyruvate hydratase. A recombinant form of this enzyme devoid of the hydratase activity and retaining wild type decarboxylase activity has been characterized (Stanley et al., *Biochem.* 39:718-26 (2000)). A similar enzyme is found in *Ralstonia pickettii* (formerly *Pseudomonas pickettii*) (Kukor et al., *J Bacteriol.* 173:4587-94 (1991)).

| Gene | GenBank | GI Number | Organism |
| --- | --- | --- | --- |
| dmpH | CAA43228.1 | 45685 | *Pseudomonas* sp. CF600 |
| dmpE | CAA43225.1 | 45682 | *Pseudomonas* sp. CF600 |
| xylII | YP_709328.1 | 111116444 | *Pseudomonas putida* |
| xylIII | YP_709353.1 | 111116469 | *Pseudomonas putida* |
| Reut_B5691 | YP_299880.1 | 73539513 | *Ralstonia eutropha* JMP134 |
| Reut_B5692 | YP_299881.1 | 73539514 | *Ralstonia eutropha* JMP134 |
| xylI | P49155.1 | 1351446 | *Pseudomonas putida* |
| tbuI | YP_002983475.1 | 241665116 | *Ralstonia pickettii* |

Finally, a class of decarboxylases has been characterized that catalyze the conversion of cinnamate (phenylacrylate) and substituted cinnamate derivatives to their corresponding styrene derivatives. These enzymes are common in a variety of organisms and specific genes encoding these enzymes that have been cloned and expressed in *E. coli* include: pad1 from *Saccharomyces cerevisae* (Clausen et al., *Gene* 142:107-112 (1994)), pdc from *Lactobacillus plantarum* (Barthelmebs et al., 67:1063-1069 (2001); Qi et al., *Metab Eng* 9:268-276 (2007); Rodriguez et al., *J. Agric. Food Chem.* 56:3068-3072 (2008)), pofK (pad) from *Klebsiella oxytoca* (Uchiyama et al., *Biosci. Biotechnol. Biochem.* 72:116-123 (2008); Hashidoko et al., *Biosci. Biotech. Biochem.* 58:217-218 (1994)), *Pedicoccus pentosaceus* (Barthelmebs et al., 67:1063-1069 (2001)), and padC from *Bacillus subtilis* and *Bacillus pumilus* (Shingler et al., 174:711-724 (1992)). A ferulic acid decarboxylase from *Pseudomonas fluorescens* also has been purified and characterized (Huang et al., *J. Bacteriol.* 176:5912-5918 (1994)). Enzymes in this class are stable and do not require either exogenous or internally bound co-factors, thus making these enzymes ideally suitable for biotransformations (Sariaslani, *Annu. Rev. Microbiol.* 61:51-69 (2007)).

| Gene name | GenBankID | GI Number | Organism |
|---|---|---|---|
| pad1 | BAG32372.1 | 188496949 | *Saccharomyces cerevisae* |
| pdc | AAC45282.1 | 1762616 | *Lactobacillus plantarum* |
| pofK (pad) | BAF65031.1 | 149941607 | *Klebsiella oxytoca* |
| padC | AAC46254.1 | 2394282 | *Bacillus subtilis* |
| pad | CAC16793.1 | 11322457 | *Pedicoccus pentosaceus* |
| pad | CAC18719.1 | 11691810 | *Bacillus pumilus* |

Another suitable enzyme is sorbic acid decarboxylase which converts sorbic acid to 1,3-pentadiene. Sorbic acid decarboxylation by *Aspergillus niger* requires three genes: padA1, ohbA1, and sdrA (Plumridge et al. *Fung. Genet. Bio,* 47:683-692 (2010). PadA1 is annotated as a phenylacrylic acid decarboxylase, ohbA1 is a putative 4-hydroxybenzoic acid decarboxylase, and sdrA is a sorbic acid decarboxylase regulator. Additional species have also been shown to decarboxylate sorbic acid including several fungal and yeast species (Kinderlerler and Hatton, *Food Addit Contam.,* 7(5):657-69 (1990); Casas et al., *Int J Food Micro.,* 94(1):93-96 (2004); Pinches and Apps, *Int. J. Food Microbiol.* 116: 182-185 (2007)). For example, *Aspergillus oryzae* and *Neosartorya fischeri* have been shown to decarboxylate sorbic acid and have close homologs to padA1, ohbA1, and sdrA.

| Gene name | GenBankID | GI Number | Organism |
|---|---|---|---|
| padA1 | XP_001390532.1 | 145235767 | *Aspergillus niger* |
| ohbA1 | XP_001390534.1 | 145235771 | *Aspergillus niger* |
| sdrA | XP_001390533.1 | 145235769 | *Aspergillus niger* |
| padA1 | XP_001818651.1 | 169768362 | *Aspergillus oryzae* |
| ohbA1 | XP_001818650.1 | 169768360 | *Aspergillus oryzae* |
| sdrA | XP_001818649.1 | 169768358 | *Aspergillus oryzae* |
| padA1 | XP_001261423.1 | 119482790 | *Neosartorya fischeri* |
| ohbA1 | XP_001261424.1 | 119482792 | *Neosartorya fischeri* |
| sdrA | XP_001261422.1 | 119482788 I | *Neosartorya fischeri* |

Each of the decarboxylases listed above represents a possible suitable enzyme for decarboxylating mesaconate or citraconate. If the desired activity or productivity of the enzyme is not observed in the desired conversions, the decarboxylase enzymes can be evolved using known protein engineering methods to achieve the required performance. Importantly, it was shown through the use of chimeric enzymes that the C-terminal region of decarboxylases appears to be responsible for substrate specificity (Barthelmebs et al., AEM 67, 1063-1069 (2001)). Accordingly, directed evolution experiments to broaden the specificity of decarboxylases in order to gain activity with mesaconate or citraconate can be focused on the C-terminal region of these enzymes.

EC 4.1.3.a Lyase (Step D).

Citramalyl-CoA lyase (EC 4.1.3.25) converts acetyl-CoA and pyruvate to citramalyl-CoA, shown in Step D of FIG. 1. This enzyme participates in the 3-hydroxypropionate (3-HP) cycle of glyoxylate assimilation, where it acts in the citramalyl-CoA degrading direction. The enzyme is encoded by the ccl gene in the green nonsulfur phototrophic bacterium *Chloroflexus aurantiacus* (Friedmann et al., *J. Bacteriol.* 189: 2906-2914 (2007)), where it is located downstream of a gene encoding citramalyl-CoA transferase. The ccl gene was cloned and heterologously expressed in *E. coli*. Similar gene clusters are found in *Roseiflexus* sp. RS-1 and *Chloroflexus aggregans*, although the enzymes have not been characterized to date. The 3-HP cycle is also active in *Rhodobacter sphaeroides*, whose genome encodes a protein with high sequence similarity to the ccl gene product (Filatova et al., *Mikrobiologiia* 74:319-328 (2005)). The citramalyl-CoA lyase from a *Bacillus* sp. was shown to be reversible, although the associated gene has not been identified to date (Sasaki et al., *J. Biochem.* 73:599-608 (1973)).

| Gene | GenBank | GI Number | Organism |
|---|---|---|---|
| Caur_2265 | YP_001635863.1 | 163847819 | *Chloroflexus aurantiacus* |
| RoseRS_0049 | YP_001274442.1 | 148654237 | *Roseiflexus* sp. RS-1 |
| Cagg_3093 | YP_002464386.1 | 219849953 | *Chloroflexus aggregans* |
| Rsph17029_1172 | YP_001043054.1 | 126461940 | *Rhodobacter sphaeroides* |

EC 4.2.1.a Dehydratase (Steps B, F).

The dehydration of citramalate to citraconate in Step B of FIG. 1 is catalyzed by an enzyme with citramalate dehydratase (citraconate forming) activity (EC 4.2.1.35). This enzyme, along with citramalate synthase, participates in the threonine-independent isoleucine biosynthesis pathway characterized in *Methanocaldococcus jannaschii* and *Leptospira interrrogans*. The dehydration of citramalate in these organisms catalyzed by isopropylmalate isomerase (IPMI), which catalyzes both the dehydration of citramalate to citraconate and the subsequent trans-addition of water to citraconate to form methylmalate (Xu et al., *J. Bacteriol.* 186:5400-5409 (2004); Drevland et al., *J. Bacteriol.* 189:4391-4400 (2007)). The *M. jannaschii* homoaconitase (EC 4.2.1.114) encoded by hacAB is also a suitable candidate, and mutants of this enzyme with altered substrate specificity and isopropylmalate isomerase activity have been characterized (Jeyakanthan et al., *Biochemistry* 49:2687-2696 (2010)). The *L. interrogans* IPMI genes were cloned into *E. coli*, where they were able to complement strains deficient in native aconitase activity when expressed together (Xu et al., *J. Bacteriol.* 186: 5400-5409 (2004)). Citramalate dehydratase has also been characterized in *Pseudomonas putida*, where it participates in 3,5-xylenol degradation. The genes encoding the enzymes of this pathway, including citramalate dehydratase, are located on the transmissible plasmid pRA500, and they have been cloned into *E. coli* (Jain, Appl. Microbiol. Biotechnol., 45:502-508 (1996)). Citraconate is also a substrate of the *Saccharomyces cerevisiae* 3-isopropylmalate dehydratase (EC 4.2.1.33) enzyme encoded by LEU1 (Kohlhaw, *Methods Enzymol.* 166:423-429 (1988)). The 3-isopropylmalate dehydratase LEU1 of *Candida maltosa* exhibits higher activity on citraconate than the native substrate (Bode, R. and Birnbaum, D., J. Basic Microbiol. 31:21-26 (1991)). Attenuation or selective inhibition of the citraconate to methylmalate hydration activity may be required to increase accumulation of the citraconate intermediate.

| Gene | GenBank | GI Number | Organism |
|---|---|---|---|
| LeuC | P81291.1 | 3219823 | Methanocaldococcus jannaschii |
| LeuD | Q58673.1 | 3122345 | Methanocaldococcus jannaschii |
| hacA | Q58409.1 | 3122347 | Methanocaldococcus jannaschii |
| hacB | Q58667.1 | 3122344 | Methanocaldococcus jannaschii |
| LeuC | NP_712276.1 | 24214795 | Leptospira interrrogans |
| LeuD | NP_712277.1 | 24214796 | Leptospira interrrogans |
| LEU1 | AAB19612.1 | 234318 | Saccharomyces cerevisiae |
| cmLEU1 | AAB03335.1 | 1399939 | Candida maltosa |

Another suitable citramalate dehydratase candidate is the 2-methylcitrate dehydratase enzymes that form cis-2-methylaconitate (EC 4.2.1.79) and trans-2-methylaconitate (EC 4.2.1.117). The 2-methylcitrate cis-dehydratase of *E. coli* encoded by prpD is active on citramalate as a substrate (Blank et al., *Microbiology* 148:133-146 (2002)). Neither citraconate nor mesaconate were active as substrates, indicating that PrpD is strictly a dehydratase enzyme rather than an isomerase. The PrpD enzyme of *Salmonella enterica serovar Typhimurium* has also been characterized, but activity on citramalate has not been demonstrated (Horswill et al., *Biochemistry* 40:4703-4713 (2001)). The 2-methylcitrate dehydratase enzymes of *Shewanella oneidensis* encoded by acnB and acnD are also candidates (Grimek et al., *J. Bacteriol.* 186:454-462 (2004)). The AcnD enzyme requires a cofactor encoded by prpF to function in vivo. Crystal structure studies of PrpF in complex with aconitate show that the enzyme functions as a cis/trans isomerase, interconverting the cis/trans isomers of aconitate and 2-methylaconitate (Garvey et al., *Protein Sci* 16:1274-1284 (2007)). An additional candidate from *S. oneidensis* is a predicted isopropylmalate isomerase encoded by leuCD.

| Gene | GenBank | GI Number | Organism |
|---|---|---|---|
| prpD | AAC73437.1 | 1786528 | Escherichia coli |
| prpD | AAC44816.1 | 1648968 | Salmonella enterica serovar Typhimurium |
| acnB | NP_716069.1 | 24372027 | Shewanella oneidensis |
| acnD | AAN53428.1 | 24345782 | Shewanella oneidensis |
| prpF | AAN53427.1 | 24345781 | Shewanella oneidensis |
| leuC | NP_719761.1 | 24375718 | Shewanella oneidensis |
| leuD | NP_719760.1 | 24375717 | Shewanella oneidensis |

The dehydration of citramalate to mesaconate in Step F is catalyzed by citramalate dehydratase (mesaconate forming, EC 4.2.1.34), also called 2-methylmalate dehydratase or mesaconase. This enzyme has been only partially characterized in *Clostridium tetanomorphum*, and gene candidates are not available to date. The activity has also been demonstrated in cell extracts of *Rhodospirillum rubrum*, where it participates in the citramalate cycle of acetate utilization (Berg and Ivanovskii, *Mikrobiologiia* 78:22-31 (2009)), although the associated gene has not been identified.

Itaconyl-CoA is converted to citramalyl-CoA (Step K of FIG. 1) by itaconyl-CoA hydratase (EC 4.2.1.56), an enzyme that participates in itaconate assimilation pathways in organisms such as *Pseudomonas* sp. B2aba (Cooper and Kornberg, *Biochem. J* 91:82-91 (1964)), *Achromobacter xylosoxydans* (He et al., *J Biosci Bioeng.* 89:388-391 (2000)) and *Pseudomonas fluorescens* (Nagai, J., *J. Biochem*, 53:181-7 (1963)). This enzyme activity has not been associated with a gene to date.

EC 5.2.1.a Cis/Trans Isomerase (Step G).

The cis/trans isomerization of mesaconate and citraconate is catalyzed by an enzyme with citraconate isomerase activity. Suitable candidates include aconitate isomerase (EC 5.3.3.7), maleate cis, trans-isomerase (EC 5.2.1.1), maleylacetone cis, trans-isomerase and cis, trans-isomerase of unsaturated fatty acids (Cti).

Aconitate isomerase interconverts cis- and trans-aconitate. The aconitate isomerase of *Shewanella oneidensis*, encoded by prpF, interconverts the cis/trans isomers of aconitate and 2-methylaconitate (Garvey et al., *Protein Sci* 16:1274-1284 (2007)). This enzyme operates in complex with the methylcitrate dehydratase, AcnD. Aconitate isomerase activity was detected in many gram-negative bacteria including *Pseudomonas fluorescens* and *Pseudomonas putida*, but not in gram-positive bacteria (Watanabe et al., *Curr Microbiol* 35:97-102 (1997)). Purified enzyme from *Pseudomonas putida* has been characterized (Klinman et al., *Biochemistry* 10:2253-2259 (1971)). Aconitate isomerase enzymes have also been studied in plants, but the genes have not been identified to date (Thompson et al., *Anal. Biochem.* 184:39-47 (1990)). Some predicted proteins with high sequence homology to the prpF protein are listed below.

| Gene | GenBank | GI Number | Organism |
|---|---|---|---|
| prpF | AAN53427.1 | 24345781 | Shewanella oneidensis |
| prpF | PP_2337 | 26989061 | Pseudomonas putida |
| Pfl01_1767 | YP_347499.1 | 77457994 | Pseudomonas fluorescens |
| Reut_A1811 | YP_296020.1 | 73541500 | Ralstonia eutropha |

Therefore, the addition of a cis, trans isomerase may help to improve the yield of terepthalic acid. Enzymes for similar isomeric conversions include maleate cis, trans-isomerase (EC 5.2.1.1), maleylacetone cis-trans-isomerase (EC 5.2.1.2), and cis, trans-isomerase of unsaturated fatty acids (Cti).

Maleate cis, trans-isomerase (EC 5.2.1.1) catalyzes the conversion of maleic acid in cis formation to fumarate in trans formation (Scher et al., *J Biol. Chem.* 244:1878-1882 (1969)). The *Alcalidgenes faecalis* maiA gene product has been cloned and characterized (Hatakeyama et al., *Biochem. Biophys. Res. Commun.* 239:74-79 (1997)). Other maleate cis, trans-isomerases are available in *Serratia marcescens* (Hatakeyama et al., *Biosci. Biotechnol Biochem.* 64:1477-1485 (2000)), *Ralstonia eutropha* and *Geobacillus stearothermophilus*.

| Gene | GenBank | GI Number | Organism |
|---|---|---|---|
| maiA | BAA23002 | 2575787 | Alcaligenes faecalis |
| maiA | YP_725437 | 113866948 | Ralstonia eutropha H16 |
| maiA | BAA77296 | 4760466 | Geobacillus stearothermophilus |
| maiA | BAA96747.1 | 8570038 | Serratia marcescens |

Maleylacetone cis, trans-isomerase (EC 5.2.1.2) catalyzes the conversion of 4-maleyl-acetoacetate to 4-fumaryl-acetyacetate, a cis to trans conversion. This enzyme is encoded by maiA in *Pseudomonas aeruginosa* (Fernandez-Canon et al., *J. Biol. Chem.* 273:329-337 (1998)) and *Vibrio cholera* (Seltzer, J. Biol. Chem. 248:215-222 (1973)). A similar enzyme was identified by sequence homology in *E. coli* O157.

| Gene | GenBank | GI Number | Organism |
|---|---|---|---|
| maiA | NP_250697 | 15597203 | *Pseudomonas aeruginosa* |
| maiA | NP_230991 | 15641359 | *Vibrio cholerae* |
| maiA | EDU73766 | 189355347 | *Escherichia coli* O157 |

The cti gene product catalyzes the conversion of cis-unsaturated fatty acids (UFA) to trans-UFA. The enzyme has been characterized in *P. putida* (Junker et al., *J Bacteriol*. 181: 5693-5700 (1999)). Similar enzymes are found in *Shewanella* sp. MR-4 and *Vibrio cholerae*.

| Gene | GenBank | GI Number | Organism |
|---|---|---|---|
| cti | AAD41252 | 5257178 | *Pseudomonas putida* |
| cti | YP_732637 | 113968844 | *Shewanella* sp. MR-4 |
| cti | ZP_04395785 | 229506276 | *Vibrio cholerae* |

EC 5.3.3.a Delta-Isomerase (Steps I).

The conversion of itaconate to citraconate is catalyzed by itaconate delta-isomerase. An enzyme with this activity is the methylitaconate delta-isomerase (EC 5.3.3.6) of *Eubacterium barkeri* (Velarde et al., *J Mol Biol* 391:609-620 (2009)). This enzyme was heterologously expressed and characterized in *E. coli*. Homologs with high protein sequence similarity are listed below.

| Gene | GenBank | GI Number | Organism |
|---|---|---|---|
| mii | Q0QLE6.1 | 122953534 | *Eubacterium barkeri* |
| FMAG_01516 | ZP_04567526.1 | 237737045 | *Fusobacterium mortiferum* |
| BACCAP_02290 | ZP_02036679.1 | 154498301 | *Bacteroides capillosus* |
| CLJU_c30450 | YP_003781195.1 | 300856211 | *Clostridium ljungdahlii* |
| BMD_3790 | YP_003598973.1 | 295705898 | *Bacillus megaterium* |
| EFER_3666 | YP_002384731.1 | 218550940 | *Escherichia fergusonii* |

EC 6.2.1 CoA Synthetase (Step E).

The conversion of citramalyl-CoA to citramalate (FIG. 1, Step E) and itaconate to itaconyl-CoA (FIG. 1, Step L) can be catalyzed by a CoA acid-thiol ligase or CoA synthetase in the 6.2.1 family of enzymes. A succinyl-CoA synthetase enzyme with itaconyl-CoA synthetase (EC 6.2.1.4) activity was characterized in *Pseudomonas* sp. B2aba, but the gene has not been identified (Cooper and Kornberg, *Biochem. J* 91:82-91 (1964)). Additional CoA ligase enzyme candidates include succinyl-CoA synthetase (EC 6.3.1.4), acetyl-CoA synthetase (EC 6.2.1.13), acyl-CoA ligase and malonyl-CoA synthetase (EC 6.3.4.9). Several enzymes with broad substrate ranges have been described in the literature. ADP-forming acetyl-CoA synthetase (ACD, EC 6.2.1.13) is an enzyme that couples the conversion of acyl-CoA esters to their corresponding acids with the concomitant synthesis of ATP. ACD I from *Archaeoglobus fulgidus*, encoded by AF 1211, was shown to operate on a variety of linear and branched-chain substrates including isobutyrate, isopentanoate, and fumarate (Musfeldt et al., *J. Bacteriol*. 184:636-644 (2002)). A second reversible ACD in *Archaeoglobus fulgidus*, encoded by AF 1983, was also shown to have a broad substrate range with high activity on cyclic compounds phenylacetate and indoleacetate (Musfeldt and Schonheit, *J. Bacteriol*. 184:636-644 (2002)). The enzyme from *Haloarcula marismortui* (annotated as a succinyl-CoA synthetase) accepts propionate, butyrate, and branched-chain acids (isovalerate and isobutyrate) as substrates, and was shown to operate in the forward and reverse directions (Brasen et al., *Arch. Microbiol* 182:277-287 (2004)). The ACD encoded by PAE3250 from hyperthermophilic crenarchaeon *Pyrobaculum aerophilum* showed the broadest substrate range of all characterized ACDs, reacting with acetyl-CoA, isobutyryl-CoA (preferred substrate) and phenylacetyl-CoA (Brasen and Schonheit, *Arch. Microbiol* 182:277-287 (2004)). Directed evolution or engineering can be used to modify this enzyme to operate at the physiological temperature of the host organism. The enzymes from *A. fulgidus, H. marismortui* and *P. aerophilum* have all been cloned, functionally expressed, and characterized in *E. coli* (Brasen and Schonheit, *Arch. Microbiol* 182:277-287 (2004); Musfeldt and Schonheit, *J. Bacteriol*. 184:636-644 (2002)). The acyl-CoA ligase from *Pseudomonas putida* encoded by paaF has been demonstrated to work on several aliphatic substrates including acetic, propionic, butyric, valeric, hexanoic, heptanoic, and octanoic acids and on aromatic compounds such as phenylacetic and phenoxyacetic acids (Fernandez-Valverde et al., *Appl. Environ. Microbiol*. 59:1149-1154 (1993)). A related enzyme, malonyl CoA synthetase (6.3.4.9) from *Rhizobium leguminosarum* can convert several diacids, namely, ethyl-, propyl-, allyl-, isopropyl-, dimethyl-, cyclopropyl-, cyclopropylmethylene-, cyclobutyl-, and benzyl-malonate into their corresponding monothioesters (Pohl et al., *J. Am. Chem. Soc*. 123:5822-5823 (2001)). Additional candidates are the succinyl-CoA synthetase enzymes encoded by sucCD in *E. coli* and LSC12 in *S. cerevisiae*, which naturally catalyze the formation of succinyl-CoA from succinate with the concomitant consumption of one ATP, a reaction which is reversible in vivo (Buck et al., *Biochemistry* 24:6245-6252 (1985)).

| Protein | GenBank ID | GI Number | Organism |
|---|---|---|---|
| AF1211 | NP_070039.1 | 11498810 | *Archaeoglobus fulgidus* |
| AF1983 | NP_070807.1 | 11499565 | *Archaeoglobus fulgidus* |
| scs | YP_135572.1 | 55377722 | *Haloarcula marismortui* |
| PAE3250 | NP_560604.1 | 18313937 | *Pyrobaculum aerophilum* str. IM2 |
| paaF | AAC24333.2 | 22711873 | *Pseudomonas putida* |
| matB | AAC83455.1 | 3982573 | *Rhizobium leguminosarum* |
| sucC | NP_415256.1 | 16128703 | *Escherichia coli* |
| sucD | AAC73823.1 | 1786949 | *Escherichia coli* |
| LSC1 | NP_014785 | 6324716 | *Saccharomyces cerevisiae* |
| LSC2 | NP_011760 | 6321683 | *Saccharomyces cerevisiae* |

EXAMPLE II

Preparation of a MAA Producing Microbial Organism Having an Actyl-CoA to MAA Pathway This example describes the generation of a microbial organism capable of producing MAA from acetyl-CoA and pyruvate. This exemplary pathway is shown in Steps A/B/C of FIG. 1.

*Escherichia coli* is used as a target organism to engineer a MAA-producing pathway from acetyl-CoA and pyruvate as shown in FIG. 1 in steps A, B and C. *E. coli* provides a good host for generating a non-naturally occurring microorganism capable of producing MAA. *E. coli* is amenable to genetic manipulation and is known to be capable of producing various products, like ethanol, acetic acid, formic acid, lactic acid, succinic acid and 1,4-butanediol, effectively under anaerobic or microaerobic conditions.

To generate an *E. coli* strain engineered to produce MAA from acetyl-CoA, nucleic acids encoding the enzymes utilized in the pathway of FIG. 1, described previously, are expressed in *E. coli* using well known molecular biology techniques (see, for example, Sambrook et al, *Molecular Cloning: A Laboratory Manual*, Third Ed. (2001); Ausubel et al, Current Protocols in Molecular Biology (1999)). In particular, an *E. coli* strain is engineered to produce MAA from acetyl-CoA via the route outlined in FIG. 1 (Steps A/B/C). Genes encoding enzymes to transform acetyl-CoA to MAA are assembled onto vectors. In particular, the genes cimA (Q58787.1), leuCD (P81291.1 and Q58673.1) and cad (XP_001209273), encoding citramalate synthase, citramalate dehydratase and citraconate decarboxylase, respectively, are cloned into the pZE13 vector (Expressys, Ruelzheim, Germany), under the control of the PA1/lacO promoter. The plasmid is then transformed into the host strain *E. coli* MG1655 containing lacI$^Q$, which allows inducible expression by addition of isopropyl-beta-D-1-thiogalactopyranoside (IPTG). The resulting strain expresses the proteins and enzymes required for synthesis of MAA from acetyl-CoA.

The resulting genetically engineered organism is cultured in glucose containing medium following procedures well known in the art (see, for example, Sambrook et al., supra, 2001). The expression of MAA pathway genes is corroborated using methods well known in the art for determining polypeptide expression or enzymatic activity, including for example, Northern blots, PCR amplification of mRNA and immunoblotting. Enzymatic activities of the expressed enzymes are confirmed using assays specific for the individually activities. The ability of the engineered *E. coli* strain to produce MAA is confirmed using HPLC, gas chromatography-mass spectrometry (GCMS) or liquid chromatography-mass spectrometry (LCMS).

Microbial strains engineered to have a functional MAA synthesis pathway are further augmented by optimization for efficient utilization of the pathway. Briefly, the engineered strain is assessed to determine whether any of the exogenous genes are expressed at a rate limiting level. Expression is increased for any enzymes expressed at low levels that can limit the flux through the pathway by, for example, introduction of additional gene copy numbers or codon optimization. Strategies are also applied to alter activity, regulation and/or expression of MAA pathway enzymes, such as mutagenesis and/or directed evolution.

To generate better producers, metabolic modeling is utilized to optimize growth conditions. Modeling is also used to design optional gene knockouts that additionally optimize utilization of the pathway (see, for example, U.S. patent publications US 2002/0012939, US 2003/0224363, US 2004/0029149, US 2004/0072723, US 2003/0059792, US 2002/0168654 and US 2004/0009466, and in U.S. Pat. No. 7,127,379). Modeling analysis allows reliable predictions of the effects on cell growth of shifting the metabolism towards more efficient production of MAA. One modeling method is the bilevel optimization approach, OptKnock (Burgard et al., *Biotechnol. Bioengineer.* 84:647-657 (2003)), which is applied to select gene knockouts that collectively result in better production of MAA. Adaptive evolution also can be used to generate better producers of, for example, the citraconate intermediate or the MAA product. Adaptive evolution is performed to improve tolerance, growth and production characteristics (Fong and Palsson, *Nat. Genet.* 36:1056-1058 (2004); Alper et al., *Science* 314:1565-1568 (2006)). Based on the results, subsequent rounds of modeling, genetic engineering and adaptive evolution can be applied to the MAA producer to further increase production.

For large-scale production of MAA, the above MAA pathway-containing organism is cultured in a fermenter using a medium known in the art to support growth of the organism under anaerobic conditions. Fermentations are performed in either a batch, fed-batch or continuous manner. Anaerobic conditions are maintained by first sparging the medium with nitrogen and then sealing culture vessel (e.g., flasks can be sealed with a septum and crimp-cap). Microaerobic conditions also can be utilized by providing a small hole for limited aeration. The pH of the medium is maintained at a pH of 7 by addition of an acid, such as $H_2SO_4$. The growth rate is determined by measuring optical density using a spectrophotometer (600 nm), and the glucose uptake rate by monitoring carbon source depletion over time. Byproducts such as undesirable alcohols, organic acids, and residual glucose can be quantified by HPLC (Shimadzu) with an HPX-087 column (BioRad), using a refractive index detector for glucose and alcohols, and a UV detector for organic acids, Lin et al., *Biotechnol. Bioeng.*, 775-779 (2005).

EXAMPLE III

Exemplary Enzymes for the Formation of Methacrylate Esters from Methacrylate and Alcohols This example describes enzymes for an exemplary pathway for production of methacrylate esters.

Figure 2:
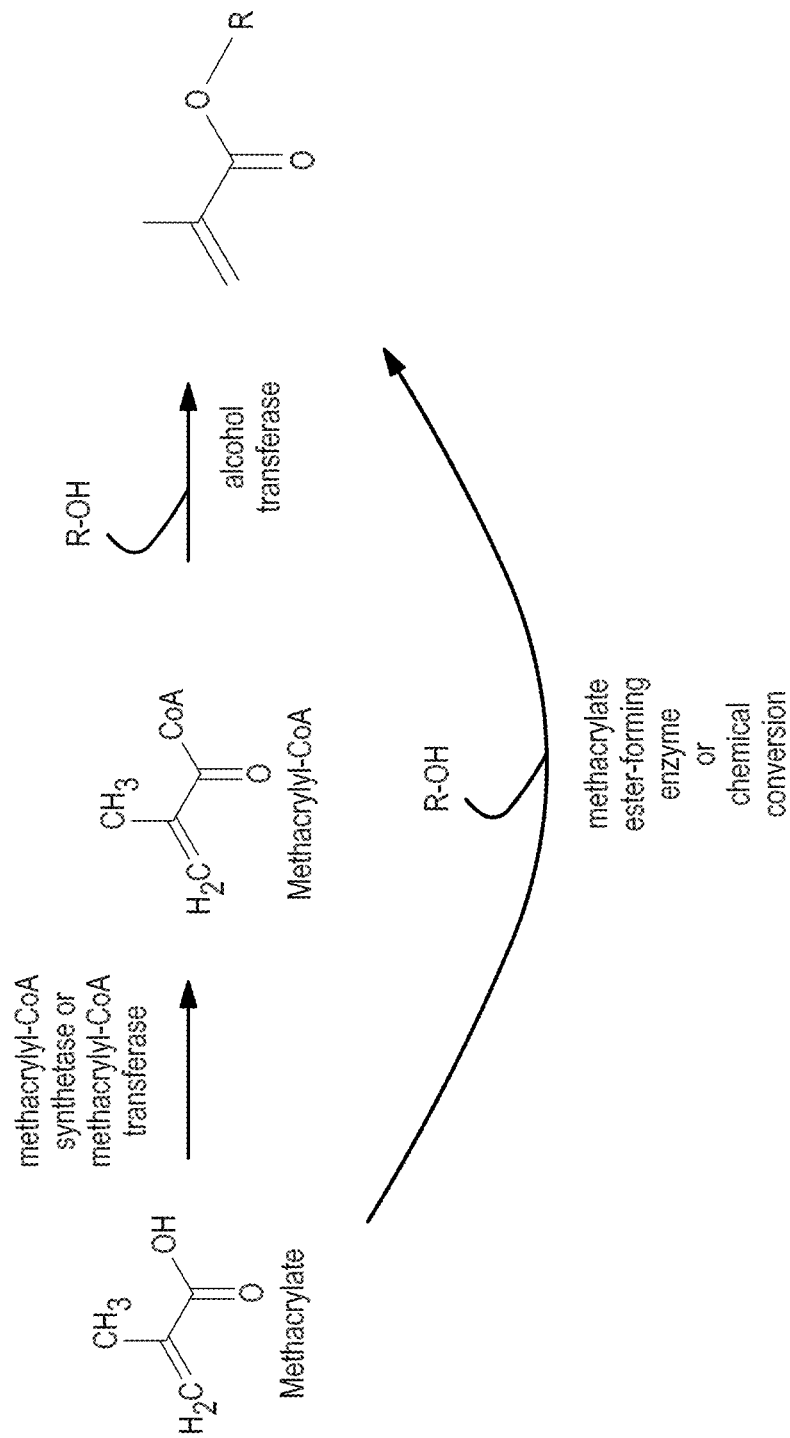
FIG. 2 shows exemplary pathways from methacrylate to methacrylate esters. Methacrylate can be formed from the pathways depicted in FIG. 1 or other methacrylate pathways such as those described in WO 2009/135074 and U.S. publication 2009/0275096. Methacrylyl-CoA can be formed from methacrylate via a methacrylyl-CoA transferase or a methacrylyl-CoA synthetase. Methacrylate esters can be formed from methacrylyl-CoA and an alcohol in the presence of an alcohol transferase enzyme. Methacrylate esters can also be formed directly from methacrylate and an alcohol by a methacrylate ester-forming enzyme or by chemical conversion (for example, heating in the presence of a dehydrating agent such as an acid). R denotes any organic functional group including, but not limited to, a methyl, ethyl, n-propyl, n-butyl, i-propyl, sec-butyl, and tert-butyl, pentyl, or hexyl functional group. For example, if R denotes a methyl-group, R—OH denotes methanol and the product of the pathway is methylmethacrylate.

FIG. 2 depicts an exemplary pathway from MAA and alcohols to methacrylate esters. A methacrylyl-CoA synthetase or methacrylyl-CoA transferase can be applied to form methacrylyl-CoA from methacrylate. Enzymes with alcohol transferase activity can be applied to form methacrylate esters from methacrylyl-CoA and alcohols.

The conversion of methacrylate to methacrylyl-CoA can be catalyzed by a CoA acid-thiol ligase or CoA synthetase in the 6.2.1 family of enzymes. Exemplary enzymes with this activity are provided in Example I. Alternatively, conversion of methacrylate to methacrylyl-CoA can be catalyzed by a transferase enzyme in the 2.8.3 family of enzymes. CoA transferases catalyze the transfer of a CoA moiety from one molecule to another. Exemplary enzymes with this activity are provided in Example I.

Formation of methacrylate esters from methacrylyl-CoA and alcohols is catalyzed by enzymes having alcohol transferase activity. Several enzymes with alcohol transferase activity were demonstrated in Examples 1-10 of U.S. Pat. No. 7,901,915. These include Novozyme 435 (immobilized lipase B from *Candida antarctica*, Sigma), Lipase C2 from *Candida cylindracea* (Alphamerix Ltd), lipase from *Pseudomonas fluorescens* (Alphamerix Ltd), L-aminoacylase ex *Aspergillus* spp., and protease ex *Aspergillus oryzae*. Such enzymes were shown to form methyl acrylate and ethyl acrylate from acrylyl-CoA and methanol or ethanol, respectively. Such transferase enzymes can therefore be used to form methacrylate esters.

Other suitable enzymes include the lipase encoded by calB from *Candida antarctica* (Efe et al., *Biotechnol. Bioeng.* 99:1392-1406 (2008)) and the EstF1 esterase from *Pseudomonas fluorescens* (Khalameyzer et al., *Appl. Environ. Microbiol.* 65:477-482 (1999)). Lipase enzymes encoded by lipB from *Pseudomonas fluorescens* and estA from *Bacillus subtilis* may also catalyze this transformation. The *B. subtilis* and *P. fluorescens* genes encode triacylglycerol lipase enzymes which have been cloned and characterized in *E. coli* (Dartois et al., *Biochim. Biophys. Acta* 1131: 253-260 (1992); Tan et al., *Appl. Environ. Microbiol.* 58:1402-1407 (1992)).

| Gene | Accession No. | GI No. | Organism |
|---|---|---|---|
| calB | P41365.1 | 1170790 | Candida antarctica |
| EstF1 | AAC36352.1 | 3641341 | Pseudomonas fluorescens |
| lipB | P41773.1 | 1170792 | Pseudomonas fluorescens |
| estA | P37957.1 | 7676155 | Bacillus subtilis |

Additional candidate genes that encode enzymes for forming methacrylate esters from methacrylyl-CoA and alcohols include the *Acinetobacter* sp. ADP1 atfA encoding a bifunctional enzyme with both wax ester synthase (WS) and acyl-CoA:diacylglycerol acyltransferase (DGAT) activities (Kalscheuer et al. AJ Biol Chem 2003, 278: 8075-8082); the *Simmondsia chinensis* gene AAD38041 encoding a enzyme required for the accumulation of waxes in jojoba seeds (Lardizabal et al. Plant Physiology 2000, 122: 645-655); the *Alcanivorax borkumensis* atfA1 and atfA2 encoding bifunctional WS/DGAT enzymes (Kalscheuer et al. J Bacteriol 2007, 189: 918-928); ths *Fragaria×ananassa* AAT encoding an alcohol acetyltransferasae (Noichinda et al. Food Sci Technol Res 1999, 5: 239-242); the *Rosa* hybrid cultivar AAT1 encoding an alcohol acetyltransferase (Guterman et al. *Plant Mol Biol* 2006, 60: 555-563); the *Saccharomyces cerevisiae* ATF1 and ATF2 encoding alcohol acetyltransferases (Mason et al. Yeast 2000, 16: 1287-1298); and Ws1 and Ws2 from *Marinobacter hydrocarbonoclasticus* (Holtzapple, E. and Schmidt-Dannert, C., J. Bacteriol. 189 (10), 3804-3812, 2007). The carboxylesterase from *Lactococcus lactis*, encoded by estA, catalyzes the formation of esters from acetyl-CoA and alcohols such as ethanol and methanethiol (Nardi et al. J. Appl. Microbiol. 93:994-1002 (2002)). The alcohol O-acetyltransferase from *Saccharomyces uvarum* converts a wide range of alcohol substrates including branched-chain alcohols to their corresponding acetate esters (Yoshioka and Hashimoto, Agricul and Biol Chem, 45:2183-2191 (1981). The protein sequences of the enzymes encoded by these genes are provided below.

| Gene | GenBank ID | GI Number | Organism |
|---|---|---|---|
| atfA | Q8GGG1 | 81478805 | Acinetobacter sp. ADP1 |
| AF149919.1:13...1071 | AAD38041 | 5020219 | Simmondsia chinensis |
| atfAl | YP694462 | 110835603 | Alcanivorax borkumensis SK2 |
| atfA2 | YP693524 | 110834665 | Alcanivorax borkumensis SK2 |
| AAT | AAG13130.1 | 10121328 | Fragaria x ananassa |
| AATl | Q5I6B5 | 75105208 | Rosa hybrid cultivar |
| ATFl | P40353 | 2506980 | Saccharomyces cerevisiae |
| ATF2 | P53296 | 1723729 | Saccharomyces cerevisiae |
| Ws2 | ABO21021.1 | 126567232 | Marinobacter hydrocarbonoclasticus |
| Ws1 | ABO21020.1 | 126567230 | Marinobacter hydrocarbonoclasticus |
| EstA | AAF62859.1 | 7453516 | Lactococcus lactis |

EXAMPLE IV

Exemplary Enzymes for the Formation of Methacrylate Esters from Methacrylate and Alcohols This example describes enzymes for an exemplary pathway for production of methacrylate esters.

FIG. 2 depicts an exemplary pathway from MAA and alcohols to methacrylate esters. Methacrylate esters can be produced chemically, for example, by heating methacrylate in the presence of an alcohol or multiple alcohols in the presence of a dehydrating agent such as an acid catalyst. Enzymes with methacrylate ester-forming activity can also be applied to form methacrylate esters directly from methacrylate and alcohols. Genes encoding such enzymes can be expressed in an organism containing a methacrylate synthesis pathway. Several such organisms containing methacrylate synthesis pathways are disclosed herein and in WO/2009/135074. The methacrylate ester-forming enzymes can be targeted to the cytosol to enable intracellular conversion of alcohols and methacrylate to methacrylate esters. Alternatively, the methacrylate ester-forming enzymes can be secreted into the fermentation medium to enable extracellular conversion of alcohols and methacrylate to methacrylate esters. Another option is to add methacrylate ester-forming enzymes to a mixture containing methacrylate and alcohols, such as a fermentation broth. Several enzymes with methacrylate-ester forming activity are described below.

The amidase from *Brevibacterium* sp. R312 (EC 3.5.1.4) is a likely enzyme with methacrylate ester-forming activity. This enzyme was shown to hydrolyze ethylacrylate (Thiery et al., J. Gen. Microbiol., 132:2205-8, 1986; Soubrier et al., Gene, 116:99-104, 1992). The microsomal epoxide hydrolase from *Rattus norvegicus* (EC 3.3.2.9) has activity on hydrolyzing glycidyl methacrylate and is another suitable enzyme (Guengerich et al., Rev. Biochem. Toxicol. 4:5-30, 1982). The protein sequences of these genes are provided below.

| Gene | GenBank ID | GI Number | Organism |
|---|---|---|---|
| amiE | JC1174 | 98711 | Brevibacterium sp. |
| Eph-1 | P07687.1 | 123928 | Rattus norvegicus |

Additional genes encoding potential methacrylate ester-forming enzymes include the *Acinetobacter* sp. ADP1 atfA encoding a bifunctional enzyme with both wax ester synthase (WS) and acyl-CoA:diacylglycerol acyltransferase (DGAT) activities (Kalscheuer et al. AJ Biol Chem 2003, 278: 8075-8082); the *Simmondsia chinensis* gene AAD38041 encoding a enzyme required for the accumulation of waxes in jojoba seeds (Lardizabal et al. Plant Physiology 2000, 122: 645-655); the *Alcanivorax borkumensis* atfA1 and atfA2 encoding bifunctional WS/DGAT enzymes (Kalscheuer et al. J Bacteriol 2007, 189: 918-928); the *Fragaria×ananassa* AAT encoding an alcohol acetyltransferasae (Noichinda et al. Food Sci Technol Res 1999, 5: 239-242); the *Rosa* hybrid cultivar AAT1 encoding an alcohol acetyltransferase (Guterman et al. Plant Mol Biol 2006, 60: 555-563); and the *Saccharomyces cerevisiae* ATF1 and ATF2 encoding alcohol acetyltransferases (Mason et al. Yeast 2000, 16: 1287-1298); and Ws1 and Ws2 from *Marinobacter hydrocarbonoclasticus* (Holtzapple, E. and Schmidt-Dannert, C., J. Bacteriol. 189 (10), 3804-3812, 2007). The carboxylesterase from *Lactococcus lactis*, encoded by estA, catalyzes the formation of esters from acetyl-CoA and alcohols such as ethanol and methanethiol (Nardi et al. *J. Appl. Microbiol.* 93:994-1002 (2002)). The alcohol O-acetyltransferase from *Saccharomyces uvarum* converts a wide range of alcohol substrates including branched-chain alcohols to their corresponding acetate esters (Yoshioka and Hashimoto, *Agricul and Biol Chem*, 45:2183-2191 (1981). The gene associated with this activity has not been identified to date. The protein sequences of the enzymes encoded by these genes are provided below.

| Gene | GenBank ID | GI Number | Organism |
|---|---|---|---|
| atfA | Q8GGG1 | 81478805 | Acinetobacter sp. ADP1 |
| AF149919.1:13...1071 | AAD38041 | 5020219 | Simmondsia chinensis |
| atfA1 | YP694462 | 110835603 | Alcanivorax borkumensis SK2 |
| atfA2 | YP693524 | 110834665 | Alcanivorax borkumensis SK2 |
| AAT | AAG13130.1 | 10121328 | Fragaria x ananassa |
| AATl | Q5I6B5 | 75105208 | Rosa hybrid cultivar |
| ATF1 | P40353 | 2506980 | Saccharomyces cerevisiae |
| ATF2 | P53296 | 1723729 | Saccharomyces cerevisiae |
| Ws2 | ABO21021.1 | 126567232 | Marinobacter hydrocarbonoclasticus |
| Ws1 | ABO21020.1 | 126567230 | Marinobacter hydrocarbonoclasticus |
| EstA | AAF62859.1 | 7453516 | Lactococcus lactis |

The *Homo sapiens* paraoxonase enzymes PON1, PON1 (G3C9), and PON3 (EC 3.1.8.1) possess both arylesterase and organophosphatase activities and also may possess methacrylate ester-forming activity. PON1 has a common polymorphic site at residue 192, glutamine (R) or arginine (Q), that results in qualitative differences. For example, the R isozyme has a higher esterase activity on GBL than the S isozyme (Billecke et al., *Drug Metab Dispos.* 28:1335-1342 (2000)). In *H. sapiens* cells, PON1 resides on high-density lipoprotein (HDL) particles, and its activity and stability require this environment. Wild type and recombinant PON1 enzymes have been functionally expressed in other organisms (Rochu et al., *Biochem. Soc. Trans.* 35:1616-1620 (2007); Martin et al., *Appl. Environ. Microbiol.* (2009)). A directed evolution study of PON1 yielded several mutant enzymes with improved solubility and catalytic properties in *E. coli* (nucleotide accession numbers AY499188-AY499199) (Aharoni et al., *Proc. Natl. Acad. Sci. U.S.A* 101:482-487 (2004)). One recombinant variant from this study, G3C9 (Aharoni et al., *Proc. Natl. Acad. Sci. U.S.A* 101:482-487 (2004)), was recently used in an integrated bioprocess for the pH-dependent production of 4-valerolactone from levulinate (Martin et al., *Appl. Environ. Microbiol.* (2009)). Human PON3 is yet another suitable enzyme that may possess methacrylate ester-forming activity (Draganov et al., *J. Lipid Res.* 46:1239-1247 (2005)).

| Gene | Accession No. | GI No. | Organism |
|---|---|---|---|
| PON1 | NP_000437.3 | 19923106 | Homo sapiens |
| PON1 (G3C9) | AAR95986.1 | 40850544 | Synthetic variant |
| PON3 | NP_000931.1 | 29788996 | Homo sapiens |

Additionally, the *Candida antarctica* lipase B is another suitable candidate enzyme with methacrylate ester-forming activity (Efe et al., *Biotechnol. Bioeng.* 99:1392-1406 (2008)). The esterase from *Pseudomonas fluorescens*, encoded by EstF1, is yet another suitable enzyme (Khalameyzer et al., *Appl. Environ. Microbiol.* 65:477-482 (1999)). Other lipase enzymes from organisms such as *Pseudomonas fluorescens* and *Bacillus subtilis* may also catalyze this transformation. The *B. subtilis* and *P. fluorescens* genes encode triacylglycerol lipase enzymes which have been cloned and characterized in *E. coli* (Dartois et al., *Biochim. Biophys. Acta* 1131:253-260 (1992); Tan et al., *Appl. Environ. Microbiol.* 58:1402-1407 (1992)).

| Gene | Accession No. | GI No. | Organism |
|---|---|---|---|
| calB | P41365.1 | 1170790 | Candida antarctica |
| EstF1 | AAC36352.1 | 3641341 | Pseudomonas fluorescens |
| lipB | P41773.1 | 1170792 | Pseudomonas fluorescens |
| estA | P37957.1 | 7676155 | Bacillus subtilis |

Formation of methacrylate esters may also be catalyzed by enzymes in the 3.1.1 family that act on carboxylic ester bonds molecules for the interconversion between cyclic lactones and the open chain hydroxycarboxylic acids. The L-lactonase from *Fusarium proliferatum* ECU2002 exhibits lactonase and esterase activities on a variety of lactone substrates (Zhang et al., *Appl. Microbiol. Biotechnol.* 75:1087-1094 (2007)). The 1,4-lactone hydroxyacylhydrolase (EC 3.1.1.25), also known as 1,4-lactonase or gamma-lactonase, is specific for 1,4-lactones with 4-8 carbon atoms. The gamma lactonase in human blood and rat liver microsomes was purified (Fishbein et al., *J Biol Chem* 241:4835-4841 (1966)) and the lactonase activity was activated and stabilized by calcium ions (Fishbein et al., *J Biol Chem* 241:4842-4847 (1966)). The optimal lactonase activities were observed at pH 6.0, whereas high pH resulted in hydrolytic activities (Fishbein and Bessman, *J Biol Chem* 241:4842-4847 (1966)). Genes from *Xanthomonas campestris, Aspergillus niger* and *Fusarium oxysporum* have been annotated as 1,4-lactonase and can be utilized to catalyze the transformation of 4-hydroxybutyrate to GBL (Zhang et al., *Appl Microbiol Biotechnol* 75:1087-1094 (2007)).

| Gene | Accession No. | GI No. | Organism |
|---|---|---|---|
| EU596535.1:1...1206 | ACC61057.1 | 183238971 | Fusarium proliferatum |
| xccb100_2516 | YP_001903921.1 | 188991911 | Xanthomonas campestris |
| An16g06620 | CAK46996.1 | 134083519 | Aspergillus niger |
| BAA34062 | BAA34062.1 | 3810873 | Fusarium oxysporum |

EXAMPLE V

Pathway for Conversion of Succinyl-CoA to MAA Via 3-Hydroxyisobutyrate

This example describes an exemplary MAA synthesis pathway from succinyl-CoA to methacrylic acid via 3-hydroxyisobutyrate.

Figure 3:
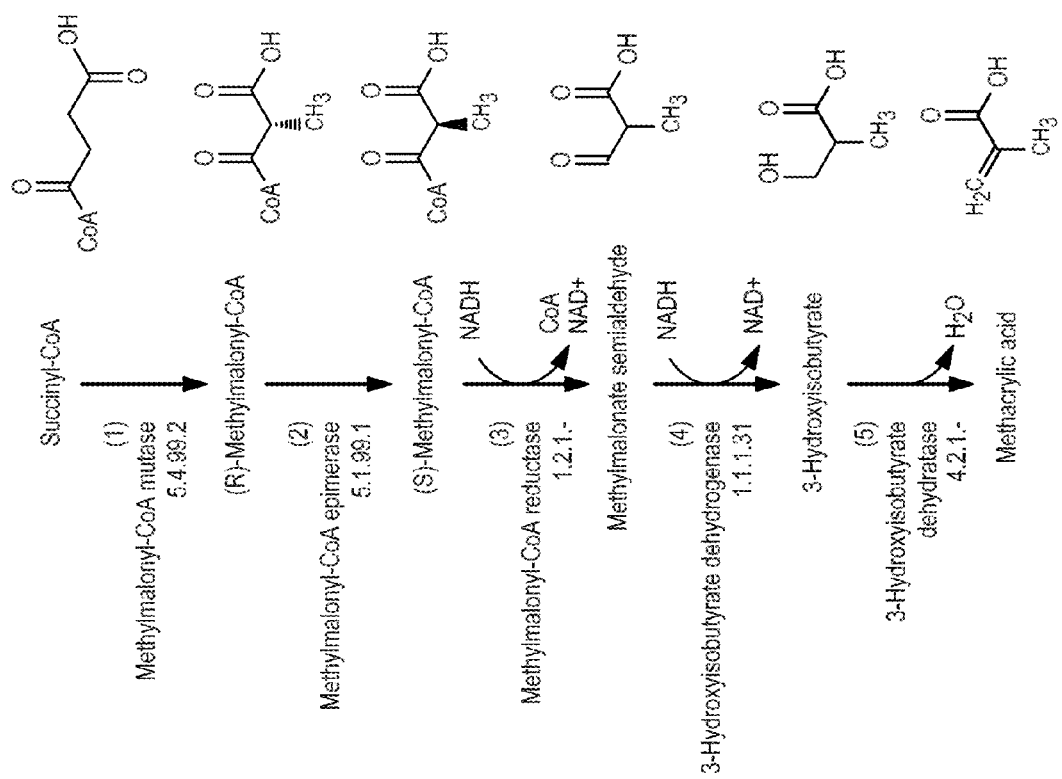
FIG. 3 shows an exemplary metabolic pathway from succinyl-CoA to MMA via 3-hydroxyisobutyrate.

One exemplary pathway for MAA synthesis proceeds from succinyl-CoA (see FIG. 3). This pathway uses at least three and at most five enzymatic steps to form MAA from succinyl-CoA. In this pathway (see FIG. 3), succinyl-CoA is first converted to (R)-methylmalonyl-CoA, which is potentially converted to (S)-methylmalonyl-CoA by an epimerase. Either the (R)- or (S)-stereoisomer of methylmalonyl-CoA is then reduced to (R)- or (S)-3-hydroxyisobutyrate, respectively, by either a pair of enzymes (as shown in FIG. 3) or a single enzyme that exhibits acyl-CoA reductase and alcohol dehydrogenase activities. The pathway from succinyl-CoA to 3-hydroxyisobutyrate has also been described in WO 2007/141208. In the final step, 3-hydroxyisobutyrate is dehydrated to form MAA.

Successfully engineering this pathway involves identifying an appropriate set of enzymes with sufficient activity and specificity. This entails identifying an appropriate set of enzymes, cloning their corresponding genes into a production host, optimizing fermentation conditions, and assaying for product formation following fermentation. To engineer a production host for the production of methacrylic acid, one or more exogenous DNA sequence(s) are expressed in microorganisms. In addition, the microorganisms can have endogenous gene(s) functionally deleted. These modifications allow the production of methacrylic acid using renewable feedstock.

Below and herein are described a number of biochemically characterized candidate genes capable of encoding enzymes that catalyze each step of the desired pathway. Although described using *E. coli* as a host organism to engineer the pathway, essentially any suitable host organism can be used. Specifically listed are genes that are native to *E. coli* as well as genes in other organisms that can be applied to catalyze the appropriate transformations when properly cloned and expressed.

Referring to FIG. 3, step 1 involves methylmalonyl-CoA mutase (EC 5.4.99.2). In the first step, succinyl-CoA is converted into methylmalonyl-CoA by methylmalonyl-CoA mutase (MCM). Methylmalonyl-CoA mutase is a cobalamin-dependent enzyme that converts succinyl-CoA to methylmalonyl-CoA. In *E. coli*, the reversible adenosylcobalamin-dependant mutase participates in a three-step pathway leading to the conversion of succinate to propionate (Haller et al., *Biochemistry* 39:4622-4629 (2000)). Overexpression of the MCM gene candidate along with the deletion of YgfG can be used to prevent the decarboxylation of methylmalonyl-CoA to propionyl-CoA and to maximize the methylmalonyl-CoA available for MAA synthesis. MCM is encoded by genes scpA in *Escherichia coli* (Bobik and Rasche, *Anal. Bioanal. Chem.* 375:344-349 (2003); Haller et al., *Biochemistry* 39:4622-4629 (2000)) and mutA in *Homo sapiens* (Padovani and Banerjee, *Biochemistry* 45:9300-9306 (2006)). In several other organisms MCM contains alpha and beta subunits and is encoded by two genes. Exemplary gene candidates encoding the two-subunit protein are *Propionibacterium fredenreichii* sp. *shermani* mutA and mutB (Korotkova and Lidstrom, *J. Biol. Chem.* 279:13652-13658 (2004)), *Methylobacterium extorquens* mcmA and mcmB (Korotkova and Lidstrom, supra, 2004), and *Ralstonia eutropha* sbm1 and sbm2 (Peplinski et al., *Appl. Microbiol. Biotech.* 88:1145-59 (2010)). Additional enzyme candidates identified based on high homology to the *E. coli* spcA gene product are also listed below.

| Protein | GenBank ID | GI Number | Organism |
|---|---|---|---|
| scpA | NP_417392.1 | 16130818 | *Escherichia coli* K12 |
| mutA | P22033.3 | 67469281 | *Homo sapiens* |
| mutA | P11652.3 | 127549 | *Propionibacterium fredenreichii* sp. *shermanii* |
| mutB | P11653.3 | 127550 | *Propionibacterium fredenreichii* sp. *shermanii* |
| mcmA | Q84FZ1 | 75486201 | *Methylobacterium extorquens* |
| mcmB | Q6TMA2 | 75493131 | *Methylobacterium extorquens* |
| Sbm1 | YP_724799.1 | 113866310 | *Ralstonia eutropha* H16 |
| Sbm2 | YP_726418.1 | 113867929 | *Ralstonia eutropha* H16 |
| sbm | NP_838397.1 | 30064226 | *Shigella flexneri* |

| Protein | GenBank ID | GI Number | Organism |
|---|---|---|---|
| SARI_04585 | ABX24358.1 | 160867735 | *Salmonella enterica* |
| YfreA_01000861 | ZP_00830776.1 | 77975240 | *Yersinia frederiksenii* |

These sequences can be used to identify homologue proteins in GenBank or other databases through sequence similarity searches (for example, BLASTp). The resulting homologue proteins and their corresponding gene sequences provide additional exogenous DNA sequences for transformation into *E. coli* or other suitable host microorganisms to generate production hosts. Additional gene candidates include the following, which were identified based on high homology to the *E. coli* spcA gene product.

There further exists evidence that genes adjacent to the methylmalonyl-CoA mutase catalytic genes contribute to maximum activity. For example, it has been demonstrated that the meaB gene from *M. extorquens* forms a complex with methylmalonyl-CoA mutase, stimulates in vitro mutase activity, and possibly protects it from irreversible inactivation (Korotkova and Lidstrom, *J. Biol. Chem.* 279:13652-13658 (2004)). The *M. extorquens* meaB gene product is highly similar to the product of the *E. coli* argK gene (BLASTp: 45% identity, e-value: 4e-67), which is adjacent to scpA on the chromosome. No sequence for a meaB homolog in *P. freudenreichii* is catalogued in GenBank. However, the *Propionibacterium acnes* KPA171202 gene product, YP_055310.1, is 51% identical to the *M. extorquens* meaB protein and its gene is also adjacent to the methylmalonyl-CoA mutase gene on the chromosome. A similar gene is encoded by H16_B1839 of *Ralstonia eutropha* H16.

| Gene | GenBank ID | GI Number | Organism |
|---|---|---|---|
| argK | AAC75955.1 | 1789285 | *Escherichia coli* K12 |
| PPA0597 | YP_055310.1 | 50842083 | *Propionibacterium acnes* |
| KPA171202 | 2QM8_B | 158430328 | *Methylobacterium extorquens* |
| H16_B1839 | YP_841351.1 | 116695775 | *Ralstonia eutropha* H16 |

*E. coli* can synthesize adenosylcobalamin, a necessary cofactor for this reaction, only when supplied with the intermediates cobinamide or cobalamin (Lawrence and Roth. *J. Bacteriol.* 177:6371-6380 (1995); Lawrence and Roth, *Genetics* 142:11-24 (1996)). Alternatively, the ability to synthesize cobalamins de novo has been conferred upon *E. coli* following the expression of heterologous genes (Raux et al., *J. Bacteriol.* 178:753-767 (1996)).

Referring to FIG. 3, step 2 involves methylmalonyl-CoA epimerase (EC 5.1.99.1). The second enzyme in the pathway, methylmalonyl-CoA epimerase (MMCE), interconverts (R)-methylmalonyl-CoA and (S)-methylmalonyl-CoA. MMCE is an essential enzyme in the breakdown of odd-numbered fatty acids and of the amino acids valine, isoleucine, and methionine. Methylmalonyl-CoA epimerase activity is not believed to be encoded in the *E. coli* genome (Boynton et al., *J. Bacteriol.* 178:3015-3024 (1996)), but is present in other organisms such as *Homo sapiens* (YqjC) (Fuller and Leadlay, *Biochem. J.* 213:643-650 (1983)), *Rattus norvegicus* (Mcee) (Bobik and Rasche, *J. Biol. Chem.* 276:37194-37198 (2001)), *Propionibacterium shermanii* (AF454511) (Fuller. and Leadlay, *Biochem. J.* 213:643-650 (1983); Haller et al., *Biochemistry* 39:4622-4629 (2000); McCarthy et al., *Structure* 9:637-646.2001)) and *Caenorhabditis elegans* (mmce) (Kuhnl et al., *FEBS J.* 272:1465-1477 (2005)). An additional gene candidate, AE016877 in *Bacillus cereus*, has high sequence homology to other characterized enzymes. This enzymatic step may or may not be necessary depending upon the stereospecificity of the enzyme or enzymes used for the conversion of methylmalonyl-CoA to 3-hydroxyisobutyrate (steps 3-4 in FIG. 3). These genes/proteins are described below.

| Gene | GenBank ID | GI Number | Organism |
|---|---|---|---|
| YqjC | NP_390273 | 255767522 | *Bacillus subtilis* |
| MCEE | Q96PE7.1 | 50401130 | *Homo sapiens* |
| Mcee_predicted | NP_001099811.1 | 157821869 | *Rattus norvegicus* |
| AF454511 | AAL57846.1 | 18042135 | *Propionibacterium fredenreichii* sp. *shermanii* |
| mmce | AAT92095.1 | 51011368 | *Caenorhabditis elegans* |
| AE016877 | AAP08811.1 | 29895524 | *Bacillus cereus* ATCC 14579 |

Referring to FIG. 3, step 3 involves methylmalonyl-CoA reductase (EC 1.2.1.-). As shown in FIG. 3, the reduction of methylmalonyl-CoA to its corresponding alcohol, 3-hydroxyisobutyrate, can proceed by two enzymatic steps. The first step, conversion of methylmalonyl-CoA to methylmalonic semialdehyde, is accomplished by a CoA-dependent aldehyde dehydrogenase. An enzyme encoded by a malonyl-CoA reductase gene from *Sulfolobus tokodaii* (Alber et. al., *J. Bacteriol.* 188(24):8551-8559 (2006)), has been shown to catalyze the conversion of methylmalonyl-CoA to its corresponding aldehyde (WO2007141208). A similar enzyme exists in *Metallosphaera sedula* (Alber et. al., *J. Bacteriol.* 188(24):8551-8559 (2006)). Several additional CoA dehydrogenases are capable also of reducing an acyl-CoA to its corresponding aldehyde. The reduction of methylmalonyl-CoA to its corresponding aldehyde, methylmalonate semialdehyde, is catalyzed by a CoA-dependent aldehyde dehydrogenase. Exemplary enzymes include fatty acyl-CoA reductase, succinyl-CoA reductase (EC 1.2.1.76), acetyl-CoA reductase and butyryl-CoA reductase. Exemplary fatty acyl-CoA reductase enzymes are encoded by acyl of *Acinetobacter calcoaceticus* (Reiser and Somerville. *J. Bacteriol.* 179:2969-2975 (1997)), and *Acinetobacter* sp. M-1 fatty acyl-CoA reductase (Ishige et al., *Appl. Environ. Microbiol.* 68:1192-1195 (2002)). Also known is a CoA- and NADP-dependent succinate semialdehyde dehydrogenase (also referred to as succinyl-CoA reductase) encoded by the sucD gene in *Clostridium kluyveri* (Sohling and Gottschalk, *J. Bacteriol.* 178:871-880 (1996); Sohling and Gottschalk, *J. Bacteriol.* 178:871-880 (1996)) and sucD of *P. gingivalis* (Takahashi, *J. Bacteriol* 182:4704-4710 (2000)). Additional succinyl-CoA reductase enzymes participate in the 3-hydroxypropionate/4-hydroxybutyrate cycle of thermophilic archaea including *Metallosphaera sedula* (Berg et al., *Science* 318:1782-1786 (2007)) and *Thermoproteus neutrophilus* (Ramos-Vera et al., *J Bacteriol*, 191:4286-4297 (2009)). The *M. sedula* enzyme, encoded by Msed_0709, is strictly NADPH-dependent and also has malonyl-CoA reductase activity. The *T. neutrophilus* enzyme is active with both NADPH and NADH. The enzyme acylating acetaldehyde dehydrogenase in *Pseudomonas* sp, encoded by bphG, is also a good candidate as it has been demonstrated to oxidize and acylate acetaldehyde, propionaldehyde, butyraldehyde, formaldehyde and the branched-chain compound isobutyraldehyde (Powlowski et al., *J. Bacteriol.* 175:377-385 (1993)). In addition to reducing acetyl-CoA to ethanol, the enzyme encoded by adhE in *Leuconostoc mesenteroides* has been shown to oxidize the branched chain compound isobutyraldehyde to isobutyryl-CoA (Kazahaya, *J. Gen. Appl. Microbiol.* 18:43-55 (1972); and Koo et al., *Biotechnol Lett.* 27:505-510 (2005)). Butyraldehyde dehydrogenase catalyzes a similar reaction, conversion of butyryl-CoA to butyraldehyde, in solventogenic organisms such as *Clostridium saccharoperbutylacetonicum* (Kosaka et al., *Biosci Biotechnol Biochem.*, 71:58-68 (2007)).

| Protein | GenBank ID | GI Number | Organism |
|---|---|---|---|
| acr1 | YP_047869.1 | 50086359 | *Acinetobacter calcoaceticus* |
| acr1 | AAC45217 | 1684886 | *Acinetobacter baylyi* |
| acr1 | BAB85476.1 | 18857901 | *Acinetobacter* sp. Strain M-1 |
| MSED_0709 | YP_001190808.1 | 146303492 | *Metallosphaera sedula* |
| Tneu_0421 | | | *Thermoproteus neutrophilus* |
| sucD | P38947.1 | 172046062 | *Clostridium kluyveri* |
| sucD | NP_904963.1 | 34540484 | *Porphyromonas gingivalis* |
| bphG | BAA03892.1 | 425213 | *Pseudomonas* sp |
| adhE | AAV66076.1 | 55818563 | *Leuconostoc mesenteroides* |
| bld | AAP42563.1 | 31075383 | *Clostridium saccharoperbutylacetonicum* |

An additional enzyme type that converts an acyl-CoA to its corresponding aldehyde is malonyl-CoA reductase which transforms malonyl-CoA to malonic semialdehyde. Malonyl-CoA reductase is a key enzyme in autotrophic carbon fixation via the 3-hydroxypropionate cycle in thermoacidophilic archaeal bacteria (Berg, *Science* 318:1782-1786 (2007); and Thauer, *Science* 318:1732-1733 (2007)). The enzyme utilizes NADPH as a cofactor and has been characterized in *Metallosphaera* and *Sulfolobus* sp. (Alber et al., *J. Bacteriol.* 188: 8551-8559 (2006); and Hugler, *J. Bacteriol.* 184:2404-2410 (2002)). The enzyme is encoded by Msed_0709 in *Metallosphaera sedula* (Alber et al., *J. Bacteriol.* 188:8551-8559 (2006); and Berg, *Science* 318:1782-1786 (2007)). A gene encoding a malonyl-CoA reductase from *Sulfolobus tokodaii* was cloned and heterologously expressed in *E. coli* (Alber et al., *J. Bacteriol* 188:8551-8559 (2006). This enzyme has also been shown to catalyze the conversion of methylmalonyl-CoA to its corresponding aldehyde (WO2007141208 (2007)). Although the aldehyde dehydrogenase functionality of these enzymes is similar to the bifunctional dehydrogenase from *Chloroflexus aurantiacus*, there is little sequence similarity. Both malonyl-CoA reductase enzyme candidates have high sequence similarity to aspartate-semialdehyde dehydrogenase, an enzyme catalyzing the reduction and concurrent dephosphorylation of aspartyl-4-phosphate to aspartate semialdehyde. Additional gene candidates can be found by sequence homology to proteins in other organisms including *Sulfolobus solfataricus* and *Sulfolobus acidocaldarius* and have been listed below. Yet another candidate for CoA-acylating aldehyde dehydrogenase is the ald gene from *Clostridium beijerinckii* (Toth, *Appl. Environ. Microbiol.* 65:4973-4980 (1999). This enzyme has been reported to reduce acetyl-CoA and butyryl-CoA to their corresponding aldehydes. This gene is very similar to eutE that encodes acetaldehyde dehydrogenase of *Salmonella typhimurium* and *E. coli* (Toth, *Appl. Environ. Microbiol.* 65:4973-4980 (1999).

| Gene | GenBank ID | GI Number | Organism |
|---|---|---|---|
| Msed_0709 | YP_001190808.1 | 146303492 | *Metallosphaera sedula* |
| mcr | NP_378167.1 | 15922498 | *Sulfolobus tokodaii* |
| asd-2 | NP_343563.1 | 15898958 | *Sulfolobus solfataricus* |
| Saci_2370 | YP_256941.1 | 70608071 | *Sulfolobus acidocaldarius* |
| Ald | AAT66436 | 49473535 | *Clostridium beijerinckii* |
| eutE | AAA80209 | 687645 | *Salmonella typhimurium* |
| eutE | P77445 | 2498347 | *Escherichia coli* |

A bifunctional enzyme with acyl-CoA reductase and alcohol dehydrogenase activity can directly convert methylmalonyl-CoA to 3-hydroxyisobutyrate. Exemplary bifunctional oxidoreductases that convert an acyl-CoA to alcohol include those that transform substrates such as acetyl-CoA to ethanol (for example, adhE from *E. coli* (Kessler et al., *FEBS. Lett.* 281:59-63 (1991))) and butyryl-CoA to butanol (for example, adhE2 from *C. acetobutylicum* (Fontaine et al., *J. Bacteriol.* 184:821-830 (2002)). The *C. acetobutylicum* enzymes encoded by bdh I and bdh II (Walter, et al., *J. Bacteriol.* 174:7149-7158 (1992)), reduce acetyl-CoA and butyryl-CoA to ethanol and butanol, respectively. In addition to reducing acetyl-CoA to ethanol, the enzyme encoded by adhE in *Leuconostoc mesenteroides* has been shown to oxide the branched chain compound isobutyraldehyde to isobutyryl-CoA (Kazahaya et al., *J. Gen. Appl. Microbiol.* 18:43-55 (1972); Koo et al., *Biotechnol Lett,* 27:505-510 (2005)). Another exemplary enzyme can convert malonyl-CoA to 3-HP. An NADPH-dependent enzyme with this activity has characterized in *Chloroflexus aurantiacus* where it participates in the 3-hydroxypropionate cycle (Hugler et al., *J Bacteriol,* 184:2404-2410 (2002); Strauss et al., *Eur J Biochem,* 215:633-643 (1993)). This enzyme, with a mass of 300 kDa, is highly substrate-specific and shows little sequence similarity to other known oxidoreductases (Hugler et al., supra). No enzymes in other organisms have been shown to catalyze this specific reaction; however there is bioinformatic evidence that other organisms may have similar pathways (Klatt et al., *Env Microbiol,* 9:2067-2078 (2007)). Enzyme candidates in other organisms including *Roseiflexus castenholzii, Erythrobacter* sp. NAP1 and marine gamma proteobacterium HTCC2080 can be inferred by sequence similarity.

| Protein | GenBank ID | GI Number | Organism |
| --- | --- | --- | --- |
| adhE | NP_415757.1 | 16129202 | *Escherichia coli* |
| adhE2 | AAK09379.1 | 12958626 | *Clostridium acetobutylicum* |
| adhE | AAV66076.1 | 55818563 | *Leuconostoc mesenteroides* |
| bdh I | NP_349892.1 | 15896543 | *Clostridium acetobutylicum* |
| bdh II | NP_349891.1 | 15896542 | *Clostridium acetobutylicum* |
| mcr | AAS20429.1 | 42561982 | *Chloroflexus aurantiacus* |
| Rcas_2929 | YP_001433009.1 | 156742880 | *Roseiflexus castenholzii* |
| NAP1_02720 | ZP_01039179.1 | 85708113 | *Erythrobacter* sp. NAP1 |
| MGP2080_00535 | ZP_01626393.1 | 119504313 | marine gamma proteobacterium HTCC2080 |

Referring to FIG. 3, step 4 involves 3-hydroxyisobutyrate dehydrogenase (EC 1.1.1.31). 3-hydroxyisobutyrate dehydrogenase catalyzes the reversible oxidation of 3-hydroxyisobutyrate to methylmalonate semialdehyde. The reduction of methylmalonate semialdehyde to 3-hydroxyisobutyrate is catalyzed by methylmalonate semialdehyde reductase or 3-hydroxyisobutyrate dehydrogenase. This enzyme participates in valine, leucine and isoleucine degradation and has been identified in bacteria, eukaryotes, and mammals. The enzyme encoded by P84067 from *Thermus thermophilus* HB8 has been structurally characterized (Lokanath et al., *J. Mol. Biol.* 352:905-917 (2005)). The reversibility of the human 3-hydroxyisobutyrate dehydrogenase was demonstrated using isotopically-labeled substrate (Manning and Pollitt, *Biochem. J.* 231:481-484 (1985)). Additional genes encoding this enzyme include 3hidh in *Homo sapiens* (Hawes et al., *Methods Enzymol.* 324:218-228 (2000)) and *Oryctolagus cuniculus* (Chowdhury et al., *Biosci. Biotechnol. Biochem.* 60:2043-2047 (1996); Hawes et al., *Methods Enzymol.* 324:218-228 (2000)), mmsb in *Pseudomonas aeruginosa,* and dhat in *Pseudomonas putida* (Aberhart and Hsu. *J. Chem. Soc. [Perkin* 1] 6:1404-1406 (1979); Chowdhury et al., *Biosci. Biotechnol. Biochem.* 67:438-441 (2003); Chowdhury et al., *Biosci. Biotechnol. Biochem.* 60:2043-2047 (1996)). Several 3-hydroxyisobutyrate dehydrogenase enzymes have been characterized in the reductive direction, including mmsB from *Pseudomonas aeruginosa* (Gokarn et al., U.S. Pat. No. 7,393,676 (2008)) and mmsB from *Pseudomonas putida.*

| PROTEIN | GENBANK ID | GI NUMBER | ORGANISM |
| --- | --- | --- | --- |
| P84067 | P84067 | 75345323 | *Thermus thermophilus* |
| 3hidh | P31937.2 | 12643395 | *Homo sapiens* |
| 3hidh | P32185.1 | 416872 | *Oryctolagus cuniculus* |
| mmsB | NP_746775.1 | 26991350 | *Pseudomonas putida* |
| mmsB | P28811.1 | 127211 | *Pseudomonas aeruginosa* |
| dhat | Q59477.1 | 2842618 | *Pseudomonas putida* |

Referring to FIG. 3, as an alternative, steps 3 and 4 can involve a combined Alcohol/Aldehyde dehydrogenase (EC 1.2.1.-). Methylmalonyl-CoA can be reduced to 3-hydroxyisobutyrate in one step by a multifunctional enzyme with dual acyl-CoA reductase and alcohol dehydrogenase activity. Although the direct conversion of methylmalonyl-CoA to 3-hydroxyisobutyrate has not been reported, this reaction is similar to the common conversions such as acetyl-CoA to ethanol and butyryl-CoA to butanol, which are catalyzed by CoA-dependant enzymes with both alcohol and aldehyde dehydrogenase activities. Gene candidates include the *E. coli* adhE (Kessler et al., *FEBS Lett.* 281:59-63 (1991)) and *C. acetobutylicum* bdh I and bdh II (Walter, et al., *J. Bacteriol.* 174:7149-7158 (1992)), which can reduce acetyl-CoA and butyryl-CoA to ethanol and butanol, respectively. In addition to reducing acetyl-CoA to ethanol, the enzyme encoded by adhE in *Leuconostoc mesenteroides* has been shown to oxide the branched chain compound isobutyraldehyde to isobutyryl-CoA (Kazahaya et al., *J. Gen. Appl. Microbiol.* 18:43-55 (1972); Koo et al., *Biotechnol. Lett.* 27:505-510 (2005)). An additional candidate enzyme for converting methylmalonyl-CoA directly to 3-hydroxyisobutyrate is encoded by a malonyl-CoA reductase from *Chloroflexus aurantiacus* (Hagler, et al., *J. Bacteriol.* 184(9):2404-2410 (2002).

| Protein | GenBank ID | GI Number | Organism |
| --- | --- | --- | --- |
| mcr | YP_001636209.1 | 163848165 | *Chloroflexus aurantiacus* |
| adhE | NP_415757.1 | 16129202 | *Escherichia coli* |
| bdh I | NP_349892.1 | 15896543 | *Clostridium acetobutylicum* |
| bdh II | NP_349891.1 | 15896542 | *Clostridium acetobutylicum* |
| adhE | AAV66076.1 | 55818563 | *Leuconostoc mesenteroides* |

Referring to FIG. 3, step 5 involves 3-hydroxyisobutyrate dehydratase (EC 4.2.1.-). The final step involves the dehydration of 3-hydroxyisobutyrate to methacrylic acid. The dehydration of 3-hydroxyisobutyrate to methylacrylic acid is catalyzed by an enzyme with 3-hydroxyisobutyrate dehydratase activity. Although no direct evidence for this specific enzymatic transformation has been identified, most dehydratases catalyze the α,β-elimination of water, which involves activation of the α-hydrogen by an electron-withdrawing carbonyl, carboxylate, or CoA-thiol ester group and removal of the hydroxyl group from the β-position (Buckel and Barker, *J Bacteriol.* 117:1248-1260 (1974); Martins et al, *Proc. Natl. Acad. Sci. USA* 101:15645-15649 (2004)). This is the exact type of transformation proposed for the final step in the methacrylate pathway. In addition, the proposed transformation is highly similar to the 2-(hydroxymethyl)glutarate dehydratase of *Eubacterium barkeri*, which can catalyze the conversion of 2-hydroxymethyl glutarate to 2-methylene glutarate. This enzyme has been studied in the context of nicotinate catabolism and is encoded by hmd (Alhapel et al., *Proc. Natl. Acad. Sci. USA* 103:12341-12346 (2006)). Similar enzymes with high sequence homology are found in *Bacteroides capillosus*, *Anaerotruncus colihominis*, and *Natranaerobius thermophilius*. Several enzymes are known to catalyze the alpha, beta elimination of hydroxyl groups. Exemplary enzymes include 2-(hydroxymethyl)glutarate dehydratase (EC 4.2.1.-), fumarase (EC 4.2.1.2), 2-keto-4-pentenoate dehydratase (EC 4.2.1.80), citramalate hydrolyase and dimethylmaleate hydratase.

2-(Hydroxymethyl)glutarate dehydratase is a [4Fe-4S]-containing enzyme that dehydrates 2-(hydroxymethyl)glutarate to 2-methylene-glutarate, studied for its role in nicontinate catabolism in *Eubacterium barkeri* (formerly *Clostridium barkeri*) (Alhapel et al., *Proc Natl Acad Sci USA* 103:12341-12346 (2006)). Similar enzymes with high sequence homology are found in *Bacteroides capillosus*, *Anaerotruncus colihominis*, and *Natranaerobius thermophilius*. These enzymes are also homologous to the α- and β-subunits of [4Fe-4S]-containing bacterial serine dehydratases, for example, *E. coli* enzymes encoded by tdcG, sdhB, and sdaA). An enzyme with similar functionality in *E. barkeri* is dimethylmaleate hydratase, a reversible Fe2+-dependent and oxygen-sensitive enzyme in the aconitase family that hydrates dimethylmaeate to form (2R,3S)-2,3-dimethylmalate. This enzyme is encoded by dmdAB (Alhapel et al., *Proc Natl Acad Sci USA* 103:12341-6 (2006); Kollmann-Koch et al., *Hoppe Seylers. Z. Physiol Chem.* 365:847-857 (1984)).

| Protein | GenBank ID | GI Number | Organism |
|---|---|---|---|
| hmd | ABC88407.1 | 86278275 | Eubacterium barkeri |
| BACCAP_02294 | ZP_02036683.1 | 154498305 | Bacteroides capillosus |
| ANACOL_02527 | ZP_02443222.1 | 167771169 | Anaerotruncus colihominis |
| NtherDRAFT_2368 | ZP_02852366.1 | 169192667 | Natranaerobius thermophilus |
| dmdA | ABC88408 | 86278276 | Eubacterium barkeri |
| dmdB | ABC88409 | 86278277 | Eubacterium barkeri |

Fumarate hydratase enzymes, which naturally catalyze the reversible hydration of fumarate to malate. Although the ability of fumarate hydratase to react on branched substrates with 3-oxobutanol as a substrate has not been described, a wealth of structural information is available for this enzyme and other researchers have successfully engineered the enzyme to alter activity, inhibition and localization (Weaver, *Acta Crystallogr. D Biol. Crystallogr.* 61:1395-1401 (2005)). *E. coli* has three fumarases: FumA, FumB, and FumC that are regulated by growth conditions. FumB is oxygen sensitive and only active under anaerobic conditions. FumA is active under microanaerobic conditions, and FumC is the only active enzyme in aerobic growth (Tseng et al., *J. Bacteriol.* 183:461-467 (2001); Woods et al., *Biochm. Biophys. Acta* 954:14-26 (1988); Guest et al., *J Gen Microbiol* 131:2971-2984 (1985)). Exemplary enzyme candidates include those encoded by fumC from *Escherichia coli* (Estevez et al., *Protein Sci.* 11:1552-1557 (2002); Hong and Lee, *Biotechnol. Bioprocess Eng.* 9:252-255 (2004); Rose and Weaver, *Proc. Natl. Acad. Sci. USA* 101:3393-3397 (2004)), and enzymes found in *Campylobacter jejuni* (Smith et al., *Int. J. Biochem. Cell Biol.* 31:961-975 (1999)), *Thermus thermophilus* (Mizobata et al., *Arch. Biochem. Biophys.* 355:49-55 (1998)), and *Rattus norvegicus* (Kobayashi et al., *J. Biochem.* 89:1923-1931 (1981)). Similar enzymes with high sequence homology include fum1 from *Arabidopsis thaliana* and fumC from *Corynebacterium glutamicum*. The MmcBC fumarase from *Pelotomaculum thermopropionicum* is another class of fumarase with two subunits (Shimoyama et al., *FEMS Microbiol Lett.* 270:207-213 (2007)).

| Protein | GenBank ID | GI Number | Organism |
|---|---|---|---|
| fumA | NP_416129.1 | 16129570 | Escherichia coli |
| fumB | NP_418546.1 | 16131948 | Escherichia coli |
| fumC | NP_416128.1 | 16129569 | Escherichia coli |
| fumC | O69294 | 9789756 | Campylobacter jejuni |

| Protein | GenBank ID | GI Number | Organism |
|---|---|---|---|
| fumC | P84127 | 75427690 | Thermus thermophilus |
| fumH | P14408 | 120605 | Rattus norvegicus |
| fum1 | P93033 | 39931311 | Arabidopsis thaliana |
| fumC | Q8NRN8 | 39931596 | Corynebacterium glutamicum |
| MmcB | YP_001211906 | 147677691 | Pelotomaculum thermopropionicum |
| MmcC | YP_001211907 | 147677692 | Pelotomaculum thermopropionicum |

Dehydration of 4-hydroxy-2-oxovalerate to 2-oxopentenoate is catalyzed by 4-hydroxy-2-oxovalerate hydratase (EC 4.2.1.80). This enzyme participates in aromatic degradation pathways and is typically co-transcribed with a gene encoding an enzyme with 4-hydroxy-2-oxovalerate aldolase activity. Exemplary gene products are encoded by mhpD of *E. coli* (Ferrandez et al., *J Bacteriol.* 179:2573-2581 (1997); Pollard et al., *Eur J Biochem.* 251:98-106 (1998)), todG and cmtF of *Pseudomonas putida* (Lau et al., *Gene* 146:7-13 (1994); Eaton, *J. Bacteriol.* 178:1351-1362 (1996)), cnbE of *Comamonas* sp. CNB-1 (Ma et al., *Appl Environ Microbiol* 73:4477-4483 (2007)) and mhpD of *Burkholderia xenovorans* (Wang et al., *FEBS J* 272:966-974 (2005)). A closely related enzyme, 2-oxohepta-4-ene-1,7-dioate hydratase, participates in 4-hydroxyphenylacetic acid degradation, where it converts 2-oxo-hept-4-ene-1,7-dioate (OHED) to 2-oxo-4-hydroxy-hepta-1,7-dioate using magnesium as a cofactor (Burks et al., *J. Am. Chem. Soc.* 120: (1998)). OHED hydratase enzyme candidates have been identified and characterized in *E. coli* C (Roper et al., *Gene* 156:47-51 (1995); Izumi et al., *J Mol. Biol.* 370:899-911 (2007)) and *E. coli* W (Prieto et al., *J Bacteriol.* 178:111-120 (1996)). Sequence comparison reveals homologs in a wide range of bacteria, plants and animals. Enzymes with highly similar sequences are contained in *Klebsiella pneumonia* (91% identity, eval=2e-138) and *Salmonella enterica* (91% identity, eval=4e-138), among others.

| Gene | GenBank Accession No. | GI No. | Organism |
| --- | --- | --- | --- |
| mhpD | AAC73453.2 | 87081722 | Escherichia coli |
| cmtF | AAB62293.1 | 1263188 | Pseudomonas putida |
| todG | AAA61942.1 | 485738 | Pseudomonas putida |
| cnbE | YP_001967714.1 | 190572008 | Comamonas sp. CNB-1 |
| mhpD | Q13VU0 | 123358582 | Burkholderia xenovorans |
| hpcG | CAA57202.1 | 556840 | Escherichia coli C |
| hpaH | CAA86044.1 | 757830 | Escherichia coli W |
| hpaH | ABR80130.1 | 150958100 | Klebsiella pneumoniae |
| Sari_01896 | ABX21779.1 | 160865156 | Salmonella enterica |

Another enzyme candidate is citramalate hydrolyase (EC 4.2.1.34), an enzyme that naturally dehydrates 2-methylmalate to mesaconate. This enzyme has been studied in *Methanocaldococcus jannaschii* in the context of the pyruvate pathway to 2-oxobutanoate, where it has been shown to have a broad substrate specificity (Drevland et al., *J Bacteriol.* 189:4391-4400 (2007)). This enzyme activity was also detected in *Clostridium tetanomorphum, Morganella morganii, Citrobacter amalonaticus* where it is thought to participate in glutamate degradation (Kato et al., *Arch. Microbiol* 168:457-463 (1997)). The *M. jannaschii* protein sequence does not bear significant homology to genes in these organisms.

| Protein | GenBank ID | GI Number | Organism |
| --- | --- | --- | --- |
| leuD | Q58673.1 | 3122345 | Methanocaldococcus jannaschii |

Dimethylmaleate hydratase (EC 4.2.1.85) is a reversible $Fe^{2+}$-dependent and oxygen-sensitive enzyme in the aconitase family that hydrates dimethylmaeate to form (2R,3S)-2,3-dimethylmalate. This enzyme is encoded by dmdAB in *Eubacterium barkeri* (Alhapel et al., supra; Kollmann-Koch et al., *Hoppe Seylers. Z. Physiol Chem.* 365:847-857 (1984)).

| Protein | GenBank ID | GI Number | Organism |
| --- | --- | --- | --- |
| dmdA | ABC88408 | 86278276 | Eubacterium barkeri |
| dmdB | ABC88409.1 | 86278277 | Eubacterium barkeri |

This example describes a biosynthetic pathway for production of MMA from succinyl-CoA.

EXAMPLE VI

Pathway for Conversion of Succinyl-CoA to MAA via 3-Amino-2-Methylpropanoate

This example describes an exemplary MAA synthesis pathway from succinyl-CoA to MAA via 3-amino-methylpropanoate.

Figure 4:
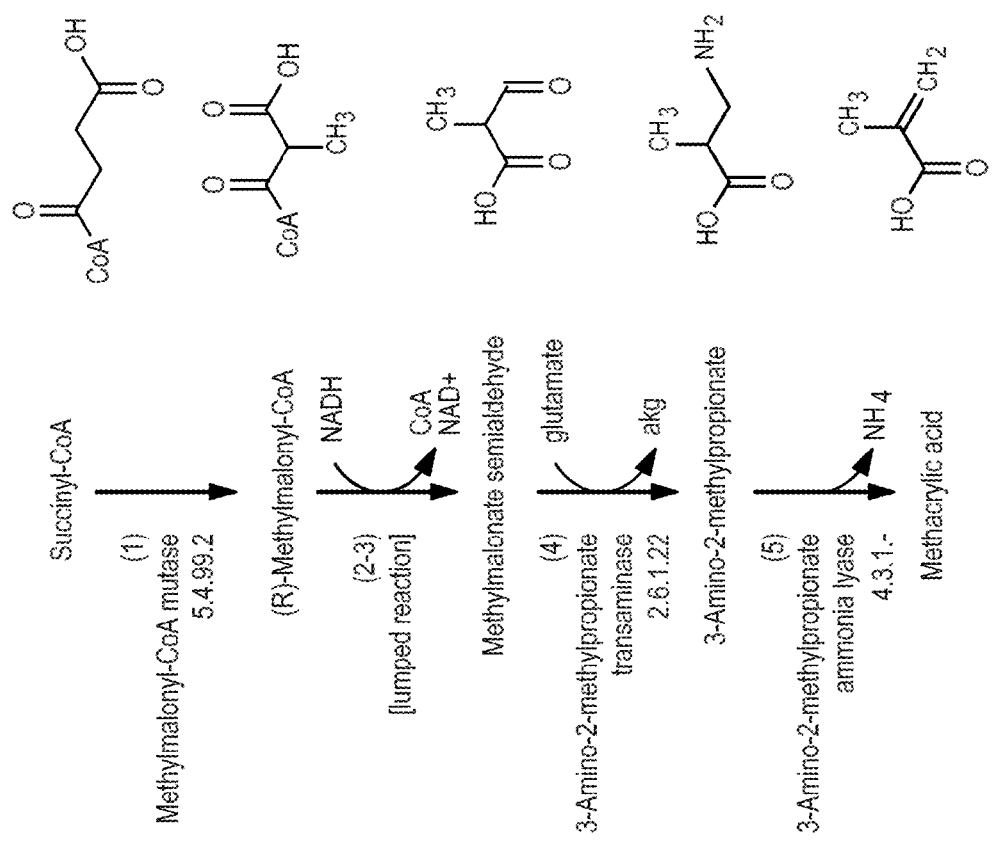
FIG. 4 shows an exemplary succinyl-CoA to MAA pathway via 3-amino-2-methylpropionate. The "lumped reaction" (steps 2-3) is catalyzed by 1) methylmalonyl-CoA epimerase and 2) methylmalonyl-CoA reductase.

Another exemplary pathway for MAA biosynthesis proceeds from succinyl-CoA through 3-amino-2-methylpropanoate (see FIG. 4). The first three steps of this pathway, involving the conversion of succinyl-CoA to methylmalonate semialdehyde, are identical to the succinyl-CoA to MAA pathway described in Example V (see FIG. 3). The pathway diverges at step 4, where methylmalonate semialdehyde is converted to 3-amino-2-methylpropionate by a transaminase. The final pathway step entails deamination of 3-amino-2-methylpropionate to methacrylic acid.

Enzyme and gene candidates for catalyzing the first three pathway steps are described in Example V. Gene candidates for steps 4 and 5 are discussed below.

Referring to FIG. 4, step 4 involves 3-amino-2-methylpropionate transaminase (EC 2.6.1.22). 3-amino-2-methylpropionate transaminase catalyzes the transformation from methylmalonate semialdehyde to 3-amino-2-methylpropionate. The enzyme, characterized in *Rattus norvegicus* and *Sus scrofa* and encoded by Abat, has been shown to catalyze this transformation in the direction of interest in the pathway (Kakimoto et al., *Biochim. Biophys. Acta* 156:374-380 (1968); Tamaki et al., *Methods Enzymol.* 324:376-389 (2000)). Enzyme candidates in other organisms with high sequence homology to 3-amino-2-methylpropionate transaminase include Gta-1 in *C. elegans* and gabT in *Bacillus subtilus*. Additionally, one of the native GABA aminotransferases in *E. coli*, encoded by gene gabT, has been shown to have broad substrate specificity and may utilize 3-amino-2-methylpropionate as a substrate (Liu et al., *Biochemistry* 43:10896-10905 (2004); Schulz et al., *Appl. Environ. Microbiol.* 56:1-6 (1990)).

| Protein | GenBank ID | GI Number | Organism |
| --- | --- | --- | --- |
| Abat | P50554.3 | 122065191 | Rattus norvegicus |
| Abat | P80147.2 | 120968 | Sus scrofa |
| Gta-1 | Q21217.1 | 6016091 | Caenorhabditis elegans |
| gabT | P94427.1 | 6016090 | Bacillus subtilus |
| gabT | P22256.1 | 16130576 | Escherichia coli K12 |

Referring to FIG. 4, step 5 involves 3-amino-2-methylpropionate ammonia lyase (EC 4.3.1.-). In the final step of this pathway, 3-amino-2-methylpropionate is deaminated to methacrylic acid. An enzyme catalyzing this exact transformation has not been demonstrated experimentally; however the native *E. coli* enzyme, aspartate ammonia lyase (EC 4.3.1.1), may be able to catalyze this reaction. Encoded by aspA in *E. coli*, aspartate ammonia lyase deaminates aspartate to form fumarate but can also react with alternate substrates aspartatephenylmethylester, asparagine, benzyl-aspartate and malate (Ma et al., *Ann. N.Y. Acad. Sci.* 672:60-65 (1992)). In a separate study, directed evolution was been employed on this enzyme to alter substrate specificity (Asano et al., *Biomol. Eng.* 22:95-101 (2005)). Genes encoding aspartase in other organisms include ansB in *Bacillus subtilus* (Sjostrom et al., *Biochim. Biophys. Acta* 1324:182-190 (1997)) and aspA in *Pseudomonas fluorescens* (Takagi et al., *J. Biochem.* 96:545-552 (1984); Takagi et al., *J. Biochem.* 100:697-705 (1986)) and *Serratia marcescens* (Takagi et al., *J. Bacteriol.* 161:1-6 (1985)).

| Protein | GenBank ID | GI Number | Organism |
| --- | --- | --- | --- |
| aspA | P0AC38.1 | 90111690 | Escherichia coli K12 |
| ansB | P26899.1 | 251757243 | Bacillus subtilus |
| aspA | P07346.1 | 114273 | Pseudomonas fluorescens |
| aspA | P33109.1 | 416661 | Serratia marcescens |

This example describes an MAA biosynthetic pathway from succinyl-CoA.

EXAMPLE VII

Pathway for Conversion of 4-Hydroxybutyryl-CoA to 3-Hydroxyisobutyric Acid or MAA This example describes an exemplary 3-hydroxyisobutyric acid or MAA synthesis pathway from 4-hydroxybutyryl-CoA.

Figure 5:
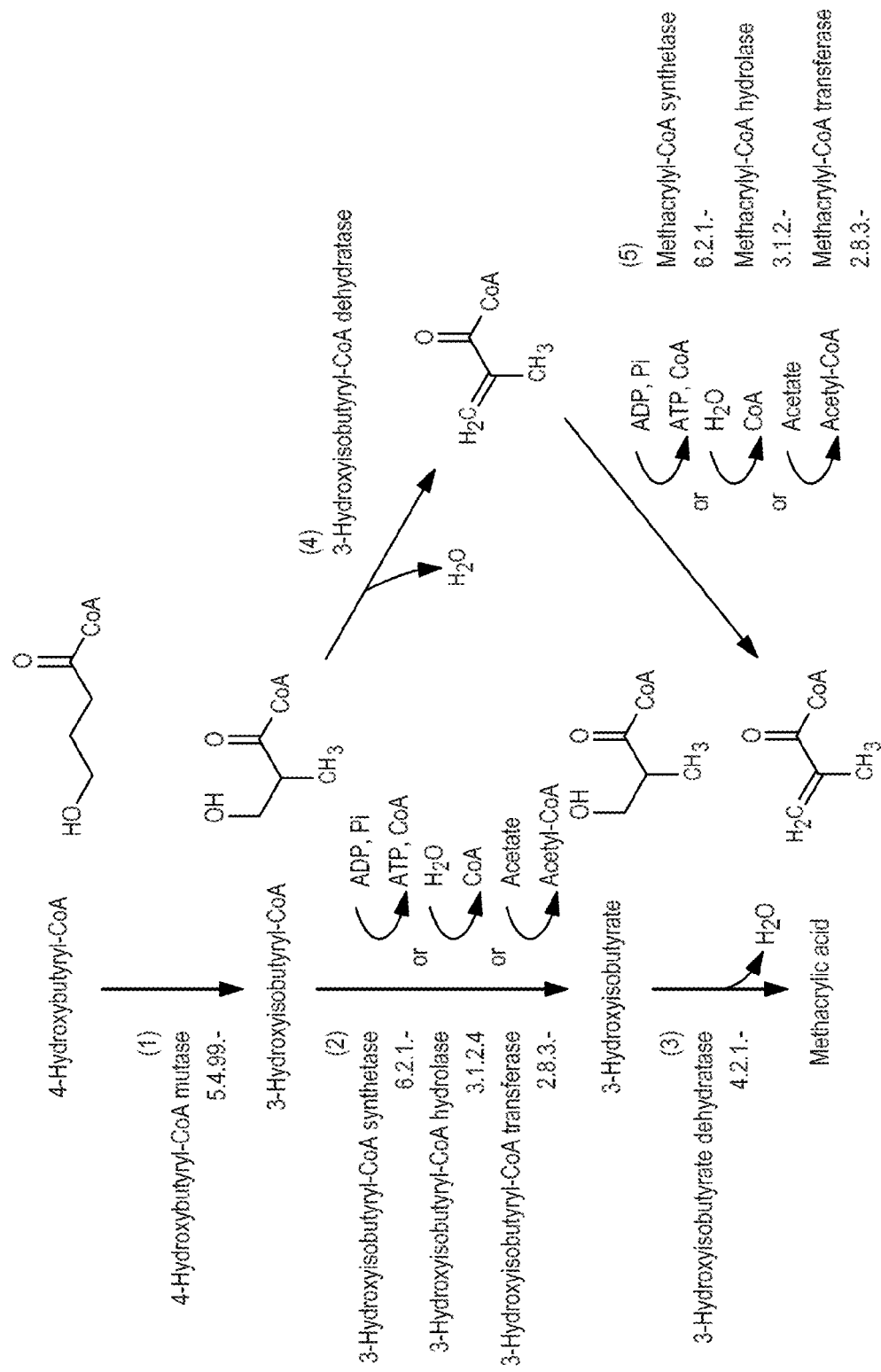
FIG. 5 shows an exemplary 4-hydroxybutyryl-CoA to MAA pathway that proceeds via 3-hydroxyisobutyrate or methacrylyl-CoA. Step 2 can be catalyzed by three alternative enzymes: 3-hydroxyisobutyryl-CoA synthetase, 3-hydroxyisobutyryl-CoA hydrolase or 3-hydroxyisobutyryl-CoA transferase. Similarly, step 5 can be catalyzed by three alternative enzymes:methacrylyl-CoA synthetase, methacrylyl-CoA hydrolase or methacrylyl-CoA transferase.

An additional exemplary pathway entails the conversion of 4HB-CoA to MAA (see FIG. 5). In the first step, 4HB-CoA is converted to 3-hydroxyisobutyryl-CoA (3-Hib-CoA) by a methylmutase. 3-Hib-CoA can then be converted to 3-hydroxyisobutyrate by a CoA hydrolase, synthase or transferase. 3-hydroxyisobutyrate can be secreted and recovered as a product or as a final step in the production of methacrylic acid. 3-Hydroxybutyrate can be dehydrated to form methacrylic acid. Alternatively, 3-Hib-CoA can be dehydrated to methacrylyl-CoA which is then converted to MAA by a hydrolase, synthase, or transferase. The enzymes required for converting the tricarboxylic acid cycle intermediates, alpha-ketoglutarate, succinate, or succinyl-CoA, into 4HB-CoA, are well-documented (Burk et al., U.S. application Ser. No. 12/049,256, filed Mar. 14, 2008; Lutke-Eversloh and Steinbuchel. *FEMS Microbiol. Lett.* 181:63-71 (1999); Sohling and Gottschalk, *Eur. J. Biochem.* 212:121-127 (1993); Sohling and Gottschalk, *J. Bacteriol.* 178:871-880 (1996); Valentin et al., *Eur. J. Biochem.* 227:43-60 (1995); Wolff and Kenealy, *Protein Expr. Pur* 6:206-212. (1995)).

Referring to FIG. 5, step 1 involves 4-hydroxybutyryl-CoA mutase (EC 5.4.99.-). The conversion of 4HB-CoA to 3-hydroxyisobutyryl-CoA has yet to be demonstrated experimentally. However, two methylmutases, that is, isobutyryl-CoA mutase (ICM) and methylmalonyl-CoA mutase (MCM), which catalyze similar reactions, are good candidates given the structural similarity of their corresponding substrates. Methylmalonyl-CoA mutase is a cobalamin-dependent enzyme that converts succinyl-CoA to methylmalonyl-CoA. This enzyme and suitable gene candidates were discussed in the succinyl-CoA to MAA pathway (see Example V).

Alternatively, isobutyryl-CoA (ICM, EC 5.4.99.13) could catalyze the proposed transformation. ICM is a cobalamin-dependent methylmutase in the MCM family that reversibly rearranges the carbon backbone of butyryl-CoA into isobutyryl-CoA (Ratnatilleke et al., *J. Biol. Chem.* 274:31679-31685 (1999)). A recent study of a novel ICM in *Methylibium petroleiphilum*, along with previous work, provides evidence that changing a single amino acid near the active site alters the substrate specificity of the enzyme (Ratnatilleke et al., *J. Biol. Chem.* 274:31679-31685 (1999); Rohwerder et al., *Appl. Environ. Microbiol.* 72:4128-4135. (2006)). This indicates that, if a native enzyme is unable to catalyze or exhibits low activity for the conversion of 4HB-CoA to 3HIB-CoA, the enzyme can be rationally engineered to increase this activity. Exemplary ICM genes encoding homodimeric enzymes include icmA in *Streptomyces coelicolor* A3 (Alhapel et al., *Proc. Natl. Acad. Sci. USA* 103:12341-12346 (2006)) and Mpe_B0541 in *Methylibium petroleiphilum* PM1 (Ratnatilleke et al., *J. Biol. Chem.* 274:31679-31685 (1999); Rohwerder et al., *Appl. Environ. Microbiol.* 72:4128-4135 (2006)). Genes encoding heterodimeric enzymes include icm and icmB in *Streptomyces cinnamonensis* (Ratnatilleke et al., *J. Biol. Chem.* 274:31679-31685 (1999); Vrijbloed et al., *J. Bacteriol.* 181:5600-5605. (1999); Zerbe-Burkhardt et al., *J. Biol. Chem.* 273:6508-6517 (1998)). Enzymes encoded by icmA and icmB genes in *Streptomyces avermitilis* MA-4680 show high sequence similarity to known ICMs. These genes/proteins are identified below.

| Gene | GenBank ID | GI Number | Organism |
|---|---|---|---|
| icmA | CAB40912.1 | 4585853 | *Streptomyces coelicolor* A3(2) |
| Mpe_B0541 | YP_001023546.1 | 124263076 | *Methylibium petroleiphilum* PM1 |
| icm | AAC08713.1 | 3002492 | *Streptomyces cinnamonensis* |
| icmB | CAB59633.1 | 6137077 | *Streptomyces cinnamonensis* |
| icmA | NP_824008.1 | 29829374 | *Streptomyces avermitilis* |
| icmB | NP_824637.1 | 29830003 | *Streptomyces avermitilis* |

Referring to FIG. 5, step 2 involves 3-hydroxyisobutyryl-CoA hydrolase (EC 3.1.2.4), synthetase (EC 6.2.1.-) or 3-hydroxyisobutyryl-CoA transferase (EC 2.8.3.-). Step 5 involves methacrylyl-CoA hydrolase, synthetase, or transferase. These transformations can be performed by different classes of enzymes including CoA hydrolases (EC 3.1.2.-), CoA transferases (EC 2.8.3.-), and CoA synthetases (EC 6.1.2.-). As discussed earlier, pathway energetics are most favorable if a CoA transferase or a CoA synthetase is employed to accomplish this transformation (Table 1).

In the CoA-transferase family, *E. coli* enzyme acyl-CoA: acetate-CoA transferase, also known as acetate-CoA transferase (EC 2.8.3.8), has been shown to transfer the CoA moiety to acetate from a variety of branched and linear acyl-CoA substrates, including isobutyrate (Matthies and Schink, *Appl. Environ. Microbiol.* 58:1435-1439 (1992)), valerate (Vanderwinkel et al., *Biochem. Biophys. Res. Commun.* 33:902-908 (1968)) and butanoate (Vanderwinkel et al. supra, 1968). This enzyme is encoded by atoA (alpha subunit) and atoD (beta subunit) in *E. coli* sp. K12 (Korolev et al., *Acta Crystallogr. D Biol. Crystallogr.* 58:2116-2121 (2002); Vanderwinkel et al., supra, 1968) and actA and cg0592 in *Corynebacterium glutamicum* ATCC 13032 (Duncan et al., *Appl. Environ. Microbiol.* 68:5186-5190 (2002)) and represents an ideal candidate to catalyze the desired 3-hydroxyisobutyryl-CoA transferase or methacrylyl-CoA transferase biotransformations shown in FIG. 5, steps 2 and 5. Candidate genes by sequence homology include atoD and atoA in *Escherichia coli* UT189. Similar enzymes also exist in *Clostridium acetobutylicum* and *Clostridium saccharoperbutylacetonicum*.

| Gene | GenBank ID | GI Number | Organism |
|---|---|---|---|
| atoA | P76459.1 | 2492994 | *Escherichia coli* K12 |
| atoD | P76458.1 | 2492990 | *Escherichia coli* K12 |

| Gene | GenBank ID | GI Number | Organism |
|---|---|---|---|
| actA | YP_226809.1 | 62391407 | *Corynebacterium glutamicum* ATCC 13032 |
| cg0592 | YP_224801.1 | 62389399 | *Corynebacterium glutamicum* ATCC 13032 |
| atoA | ABE07971.1 | 91073090 | *Escherichia coli* UT189 |
| atoD | ABE07970.1 | 91073089 | *Escherichia coli* UT189 |
| ctfA | NP_149326.1 | 15004866 | *Clostridium acetobutylicum* |
| ctfB | NP_149327.1 | 15004867 | *Clostridium acetobutylicum* |
| ctfA | AAP42564.1 | 31075384 | *Clostridium saccharoperbutylacetonicum* |
| ctfB | AAP42565.1 | 31075385 | *Clostridium saccharoperbutylacetonicum* |

Additional exemplary transferase transformations are catalyzed by the gene products of cat1, cat2, and cat3 of *Clostridium kluyveri* which have been shown to exhibit succinyl-CoA, 4-hydroxybutyryl-CoA, and butyryl-CoA acetyltransferase activity, respectively (Sohling and Gottschalk, *J. Bacteriol.* 178(3): 871-880 (1996); Seedorf et al., *Proc. Natl. Acad. Sci. USA,* 105(6):2128-2133 (2008)).

| Gene | GenBank ID | GI Number | Organism |
|------|------------|-----------|----------|
| cat1 | P38946.1   | 729048    | *Clostridium kluyveri* |
| cat2 | P38942.2   | 172046066 | *Clostridium kluyveri* |
| cat3 | EDK35586.1 | 146349050 | *Clostridium kluyveri* |

The glutaconate-CoA-transferase (EC 2.8.3.12) enzyme from anaerobic bacterium *Acidaminococcus fermentans* reacts with diacid glutaconyl-CoA and 3-butenoyl-CoA (Mack and Buckel, *FEBS Lett.* 405:209-212 (1997)). The genes encoding this enzyme are gctA and gctB. This enzyme has reduced but detectable activity with other CoA derivatives including glutaryl-CoA, 2-hydroxyglutaryl-CoA, adipyl-CoA and acrylyl-CoA (Buckel et al., *Eur. J. Biochem.* 118: 315-321 (1981)). The enzyme has been cloned and expressed in *E. coli* (Mack et al., *Eur. J. Biochem.* 226:41-51 (1994)).

| Gene | GenBank ID | GI Number | Organism |
|------|------------|-----------|----------|
| gctA | CAA57199.1 | 559392 | *Acidaminococcus fermentans* |
| gctB | CAA57200.1 | 559393 | *Acidaminococcus fermentans* |

Additional enzyme candidates include succinyl-CoA:3-ketoacid CoA transferases which utilize succinate as the CoA acceptor. Exemplary succinyl-CoA:3:ketoacid-CoA transferases are present in *Helicobacter pylori* (Corthesy-Theulaz et al., *J. Biol. Chem.* 272:25659-25667 (1997)) and *Bacillus subtilis* (Stols et al., *Protein Expr. Purif.* 53:396-403 (2007)).

| Gene | GenBank ID | GI Number | Organism |
|------|------------|-----------|----------|
| HPAG1_0676 | YP_627417 | 108563101 | *Helicobacter pylori* |
| HPAG1_0677 | YP_627418 | 108563102 | *Helicobacter pylori* |
| ScoA | NP_391778 | 16080950 | *Bacillus subtilis* |
| ScoB | NP_391777 | 16080949 | *Bacillus subtilis* |

A candidate ATP synthase is ADP-forming acetyl-CoA synthetase (ACD, EC 6.2.1.13), an enzyme that couples the conversion of acyl-CoA esters to their corresponding acids with the concurrent synthesis of ATP. Although this enzyme has not been shown to react with 3-hydroxyisobutyryl-CoA or methacrylyl-CoA as a substrate, several enzymes with broad substrate specificities have been described in the literature. ACD I from *Archaeoglobus fulgidus*, encoded by AF1211, was shown to operate on a variety of linear and branched-chain substrates including isobutyrate, isopentanoate, and fumarate (Musfeldt and Schonheit, *J. Bacteriol.* 184:636-644 (2002)). The enzyme from *Haloarcula marismortui* (annotated as a succinyl-CoA synthetase) accepts priopionate, butyrate, and branched-chain acids (isovalerate and isobutyrate) as substrates, and was shown to operate in the forward and reverse directions (Brasen and Schonheit, *Arch. Microbiol.* 182:277-287 (2004)). The ACD encoded by PAE3250 from hyperthermophilic crenarchaeon *Pyrobaculum aerophilum* showed the broadest substrate range of all characterized ACDs, reacting with acetyl-CoA, isobutyryl-CoA (preferred substrate) and phenylacetyl-CoA (Brasen and Schonheit, supra, 2004). However, directed evolution or engineering can be used to modify this enzyme to operate at the physiological temperature of the host organism. The enzymes from *A. fulgidus*, *H. marismortui* and *P. aerophilum* have all been cloned, functionally expressed, and characterized in *E. coli* (Brasen and Schonheit, supra, 2004; Musfeldt and Schonheit, *J. Bacteriol.* 184:636-644 (2002)).

| Gene | GenBank ID | GI Number | Organism |
|------|------------|-----------|----------|
| AF1211 | NP_070039.1 | 11498810 | *Archaeoglobus fulgidus* DSM 4304 |
| scs | YP_135572.1 | 55377722 | *Haloarcula marismortui* ATCC 43049 |
| PAE3250 | NP_560604.1 | 18313937 | *Pyrobaculum aerophilum* str. IM2 |

In the CoA hydrolase family, the enzyme 3-hydroxyisobutyryl-CoA hydrolase is specific for 3-HIBCoA and has been described to efficiently catalyze the desired transformation during valine degradation (Shimomura et al., *J. Biol. Chem.* 269:14248-14253 (1994)). Genes encoding this enzyme include hibch of *Rattus norvegicus* (Shimomura et al., *J. Biol. Chem.* 269:14248-14253 (1994); Shimomura et al., *Methods Enzymol.* 324:229-240 (2000)) and *Homo sapiens* (Shimomura et al., supra, 2000). Candidate genes by sequence homology include hibch of *Saccharomyces cerevisiae* and BC_2292 of *Bacillus cereus*.

| Gene | GenBank ID | GI Number | Organism |
|------|------------|-----------|----------|
| hibch | Q5XIE6.2 | 146324906 | *Rattus norvegicus* |
| hibch | Q6NVY1.2 | 146324905 | *Homo sapiens* |
| hibch | P28817.2 | 2506374 | *Saccharomyces cerevisiae* |
| BC_2292 | Q81DR3 | 29895975 | *Bacillus cereus* |

Referring to FIG. 5, step 3 involves 3-hydroxyisobutyrate dehydratase (EC 4.2.1.-). The entails dehydration of 3-hydroxyisobutyrate to MAA by 3-hydroxyisobutyrate dehydratase. Gene candidates for this enzyme are described in the succinyl-CoA to MAA pathway (see Example V). Also referring to FIG. 5, step 4 involves 3-hydroxyisobutyryl-CoA dehydratase (EC 4.2.1.-). Dehydration of 3-hydroxyisobutyryl-CoA to methacrylyl-CoA can be accomplished by a reversible 3-hydroxyacyl-CoA dehydratase such as crotonase (also called 3-hydroxybutyryl-CoA dehydratase, EC 4.2.1.55) or enoyl-CoA hydratase (also called 3-hydroxyacyl-CoA dehydratase, EC 4.2.1.17). These enzymes are generally reversible (Moskowitz and Merrick, *Biochemistry* 8:2748-2755 (1969); Durre et al., *FEMS Microbiol. Rev.* 17:251-262 (1995)). Exemplary genes encoding crotonase enzymes can be found in *C. acetobutylicum* (Boynton, et al., *J. Bacteriol.* 178(11):3015-3024 (1996)), *C. kluyveri* (Hillmer and Gottschalk, *FEBS Lett.* 21(3):351-354 (1972)), and *Metallosphaera sedula* (Berg et al., *Science* 318(5857) 1782-1786 (2007)) though the sequence of the latter gene is not known. Enoyl-CoA hydratases, which are involved in fatty acid beta-oxidation and/or the metabolism of various amino acids, can also catalyze the hydration of crotonyl-CoA to form 3-hydroxybutyryl-CoA (Agnihotri and Liu, *Bioorg. Med. Chem.* 11(1):9-20 (2003); Roberts et al., *Arch. Microbiol.* 117(1):99-108 (1978); Conrad et al., *J. Bacteriol.* 118 (1):103-111 (1974)). The enoyl-CoA hydratases, phaA and phaB, of *P. putida* are believed to carry out the hydroxylation of double bonds during phenylacetate catabolism (Olivera et al., *Proc. Natl. Acad. Sci. USA* 95:6419-6424 (1998)). The paaA and paaB from *P. fluorescens* catalyze analogous transformations (Olivera et al., supra, 1998). Lastly, a number of *Escherichia coli* genes have been shown to demonstrate enoyl-CoA hydratase functionality including maoC (Park and Lee, *J. Bacteriol.* 185:5391-5397 (2003)), paaF (Ismail et al., *Eur. J. Biochem.* 270:3047-3054 (2003); Park and Lee, *Appl. Biochem. Biotechnol.* 113-116:335-346 (2004); Park and Yup, *Biotechnol. Bioeng.* 86:681-686. (2004)), and paaG (Ismail et al., *Eur. J. Biochem.* 270:3047-3054 (2003); Park and Lee, *Appl. Biochem. Biotechnol.* 113-116:335-346 (2004); Park and Yup, *Biotechnol. Bioeng.* 86:681-686 (2004)).

| Gene | GenBank ID | GI Number | Organism |
|---|---|---|---|
| crt | NP_349318.1 | 15895969 | *Clostridium acetobutylicum* |
| crt1 | YP_001393856 | 153953091 | *Clostridium kluyveri* DSM 555 |
| paaA | NP_745427.1 | 26990002 | *Pseudomonas fluorescens* |
| paaB | NP_745426.1 | 26990001 | *Pseudomonas fluorescens* |
| phaA | ABF82233.1 | 106636093 | *Pseudomonas putida* |
| phaB | ABF82234.1 | 106636094 | *Pseudomonas putida* |
| maoC | NP_415905.1 | 16129348 | *Escherichia coli* |
| paaF | NP_415911.1 | 16129354 | *Escherichia coli* |
| paaG | NP_415912.1 | 16129355 | *Escherichia coli* |

This example describes a biosynthetic pathway for production of 3-hydroxyisobutyric acid or methacrylic acid from 4-hydroxybutyryl-CoA.

EXAMPLE VIII

Pathway for Conversion of Alpha-Ketoglutarate to MAA Via Threo-3-Methylaspartate This example describes an exemplary MAA synthesis pathway from alpha-ketoglutarate to threo-3-methylaspartate.

Figure 6:
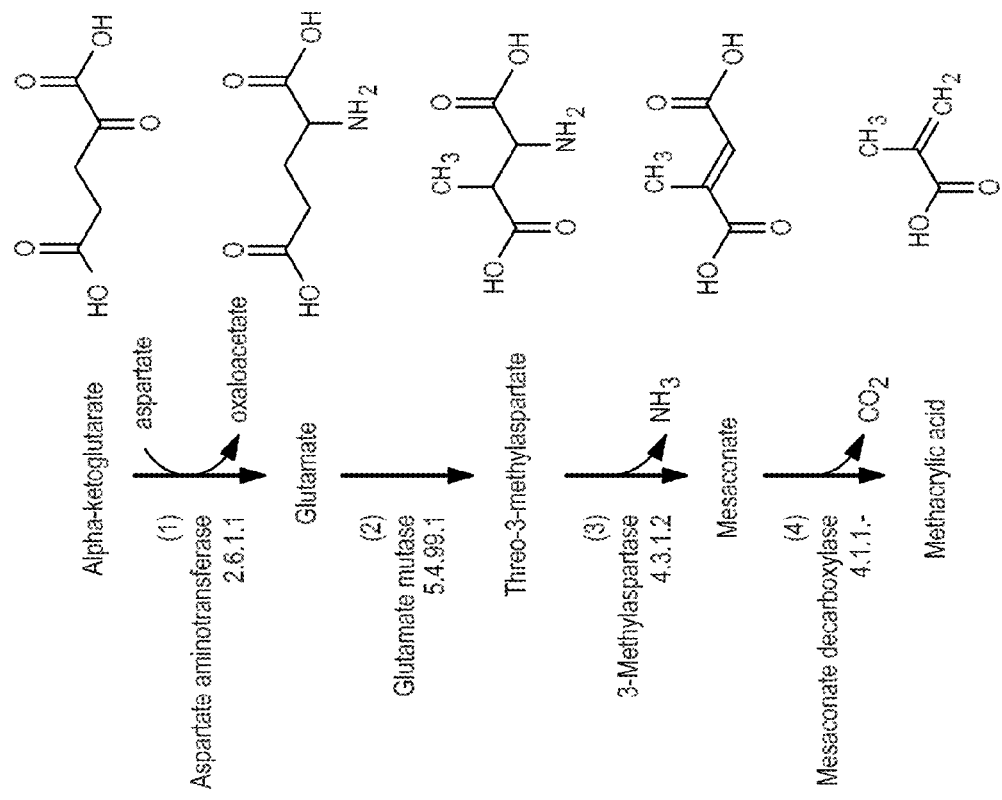
FIG. 6 shows an exemplary alpha-ketoglutarate to MAA pathway via threo-3-methylaspartate.

Another exemplary pathway for MAA biosynthesis proceeds through alpha-ketoglutarate, a metabolite in *E. coli* produced in the TCA cycle (see FIG. 6).

The first step of the pathway, catalyzed by the enzyme aspartate aminotransferase, transfers an amino group from aspartate to alpha-ketoglutarate, forming glutamate and oxaloacetate. The subsequent two steps include rearrangement of the carbon backbone and subsequent deamination to form mesaconate. Enzymes catalyzing these conversions are found in the energy-yielding fermentation of glutamate in soil *Clostridia* and other organisms capable of fermenting amino acids (Buckel and Barker, *J. Bacteriol.* 117:1248-1260 (1974)). The directionality of the pathway in these organisms is in agreement with the direction required for MAA synthesis in the biopathway. The final pathway step entails decarboxylation of mesaconate to yield methacrylic acid.

Referring to FIG. 6, step 1 involves aspartate aminotransferase (EC 2.6.1.1). The first step of the pathway transfers an amino group from aspartate to alpha-ketoglutarate, forming glutamate and oxaloacetate. The genes aspC from *Escherichia coli* (Yagi et al., *FEBS Lett.* 100:81-84 (1979); Yagi et al., *Methods Enzymol.* 113:83-89 (1985)), AAT2 from *Saccharomyces cerevisiae* (Yagi et al., *J. Biochem.* 92:35-43 (1982)) and ASPS from *Arabidopsis thaliana* (de la Torre et al., *Plant J.* 46:414-425 (2006); Kwok and Hanson, *J. Exp. Bot.* 55:595-604 (2004); Wilkie and Warren, *Protein Expr. Purif.* 12:381-389 (1998)), encode the enzyme that catalyzes this conversion, aspartate aminotransferase.

| Gene | GenBank ID | GI Number | Organism |
|---|---|---|---|
| aspC | NP_415448.1 | 16128895 | *Escherichia coli* |
| AAT2 | P23542.3 | 1703040 | *Saccharomyces cerevisiae* |
| ASP5 | P46248.2 | 20532373 | *Arabidopsis thaliana* |

Referring to FIG. 6, step 2 involves glutamate mutase (EC 5.4.99.1). In step 2, the linear carbon chain of glutamate is rearranged to the branched structure of threo-3-methylaspartate. This transformation is catalyzed by glutamate mutase, a cobalamin-dependent enzyme composed of two subunits. Two glutamate mutases, from *Clostridium cochlearium* and *Clostridium tetanomorphum*, have been cloned and functionally expressed in *E. coli* (Holloway and Marsh, *J. Biol. Chem.* 269:20425-20430 (1994); Reitzer et al., *Acta Crystallogr. D Biol. Crystallogr.* 54:1039-1042 (1998)). The genes encoding this two-subunit protein are glmE and glmS from *Clostridium cochlearium*, mamA and glmE from *Clostridium tetanomorphum*, and mutE and mutS from *Clostridium tetani* (Switzer, Glutamate mutase, pp. 289-305 Wiley, New York (1982)).

| Gene | GenBank ID | GI Number | Organism |
|---|---|---|---|
| glmE | P80077.2 | 2507035 | *Clostridium cochlearium* |
| glmS | P80078.2 | 17865765 | *Clostridium cochlearium* |
| mamA | Q05488.1 | 729588 | *Clostridium tetanomorphum* |
| glmE | Q05509.1 | 729586 | *Clostridium tetanomorphum* |
| mutE | NP_783086.1 | 28212142 | *Clostridium tetani* E88 |
| mutS | NP_783088.1 | 28212144 | *Clostridium tetani* E88 |

Referring to FIG. 6, step 3 involves 3-methylaspartase (EC 4.3.1.2). 3-methylaspartase, also referred to as beta-methylaspartase or 3-methylaspartate ammonia-lyase, catalyzes the deamination of threo-3-methylasparatate to mesaconate. The 3-methylaspartase from *Clostridium tetanomorphum* has been cloned, functionally expressed in *E. coli*, and crystallized (Asuncion et al., *Acta Crystallogr. D Biol. Crystallogr.* 57:731-733 (2001); Asuncion et al., *J. Biol. Chem.* 277:8306-8311 (2002); Botting et al., *Biochemistry* 27:2953-2955 (1988); Goda et al., *Biochemistry* 31:10747-10756 (1992)). In *Citrobacter amalonaticus*, this enzyme is encoded by BAA28709 (Kato and Asano, *Arch. Microbiol.* 168:457-463 (1997)). 3-methylaspartase has also been crystallized from *E. coli* YG1002 (Asano and Kato, *FEMS Microbiol. Lett.* 118:255-258 (1994)), although the protein sequence is not listed in public databases such as GenBank. Sequence homology can be used to identify additional candidate genes, including CTC_02563 in *C. tetani* and ECs0761 in *Escherichia coli* O157:H7.

| Gene | GenBank ID | GI Number | Organism |
|---|---|---|---|
| MAL | AAB24070.1 | 259429 | *Clostridium tetanomorphum* |
| BAA28709 | BAA28709.1 | 3184397 | *Citrobacter amalonaticus* |
| CTC_02563 | NP_783085.1 | 28212141 | *Clostridium tetani* |
| ECs0761 | BAB34184.1 | 13360220 | *Escherichia coli* O157:H7 str. Sakai |

Referring to FIG. 6, step 4 involves mesaconate decarboxylase (EC 4.1.1.-). The final step of the pathway entails the decarboxylation of mesaconate to methacrylic acid. An enzyme catalyzing this exact reaction has not been demonstrated experimentally. However, several enzymes catalyzing highly similar reactions exist. One enzyme with closely related function is aconitate decarboxylase. This enzyme catalyzes the final step in itaconate biosynthesis in a strain of *Candida* and the filamentous fungi *Aspergillus terreus* (Bonnarme et al., *J. Bacteriol.* 177:3573-3578 (1995); Willke and Vorlop, *Appl. Microbiol. Biotechnol.* 56:289-295 (2001)). Although itaconate is a compound of biotechnological interest, no efforts have been made thus far to identify or clone the aconitate decarboxylase gene.

A second enzyme with similar function is 4-oxalocronate decarboxylase. This enzyme is common in a variety of organisms and the genes encoding the enzyme from *Pseudomonas* sp. (strain 600) have been cloned and expressed in *E. coli* (Shingler et al., *J. Bacteriol.* 174:711-724 (1992)). The methyl group in mesaconate may cause steric hindrance, but this problem could likely be overcome with directed evolution or protein engineering. 4-oxalocronate decarboxylase is composed of two subunits. Genes encoding this enzyme include dmpH and dmpE in *Pseudomonas* sp. (strain 600) (Shingler et al., *J. Bacteriol.* 174:711-724 (1992)), xylII and xylIII from *Pseudomonas putida* (Kato and Asano, *Arch. Microbiol.* 168:457-463 (1997); Stanley et al., *Biochemistry* 39:718-726 (2000)), and Reut_B5691 and Reut_B5692 from *Ralstonia eutropha* JMP134 (Hughes et al., *J. Bacteriol.* 158: 79-83 (1984)).

| Gene | GenBank ID | GI Number | Organism |
| --- | --- | --- | --- |
| dmpH | CAA43228.1 | 45685 | *Pseudomonas* sp. CF600 |
| dmpE | CAA43225.1 | 45682 | *Pseudomonas* sp. CF600 |
| xylII | YP_709328.1 | 111116444 | *Pseudomonas putida* |
| xylIII | YP_709353.1 | 111116469 | *Pseudomonas putida* |
| Reut_B5691 | YP_299880.1 | 73539513 | *Ralstonia eutropha* JMP134 |
| Reut_B5692 | YP_299881.1 | 73539514 | *Ralstonia eutropha* JMP134 |

This example describes a biosynthetic pathway for production of MMA from alpha-ketoglutarate.

EXAMPLE IX

Pathway for Conversion of Alpha-Ketoglutarate to MAA Via 2-Hydroxyglutarate

This example describes an exemplary MAA synthesis pathway from alph-ketoglutarate to MAA via 2-hydroxyglutarate.

Another exemplary pathway for MAA biosynthesis has a scheme similar to the pathway described in Example VIII, but it passes through the hydroxylated intermediates 2-hydroxyglutarate and 3-methylmalate (see FIG. 7), rather than amine-substituted intermediates (see FIG. 6).

Figure 7:
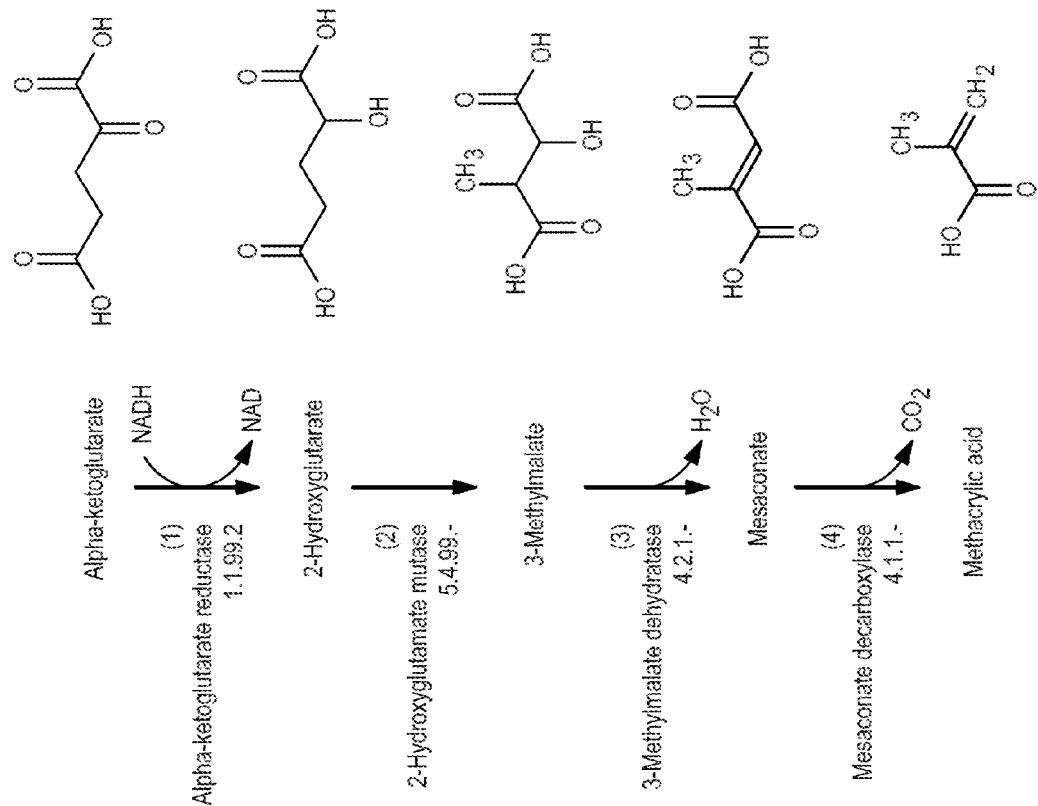
FIG. 7 shows an exemplary alpha-ketoglutarate to MAA pathway via 2-hydroxyglutarate.

Referring to FIG. 7, step 1 involves alpha-ketoglutarate reductase (EC 1.1.99.2). The first step of this pathway entails the reduction of alpha-ketoglutarate to 2-hydroxyglutarate by native enzyme alpha-ketoglutarate reductase. This enzyme is encoded by serA, a multifunctional enzyme which also catalyzes the reduction of 3-phosphoglycerate in central metabolism (Zhao and Winkler, *J. Bacteriol.* 178:232-239 (1996)). Genes L2HGDH in *Homo sapiens* (Jansen and Wanders, *Biochim. Biophys. Acta* 1225:53-56 (1993)), FN0487 in L2hgdh in *Fusobacterium nucleatum* (Hayashi et al., *J. Nihon Univ. Sch. Dent.* 28:12-21 (1986)), and L2hgdh_predicted in *Rattus norvegicus* (Jansen and Wanders, *Biochim. Biophys. Acta* 1225:53-56 (1993)) encode this enzyme. Gene candidates with high sequence homology include L2hgdh in *Mus musculus* and L2HGDH in *Bos taurus*. At high concentrations, 2-hydroxyglutarate has been shown to feed back on alpha-ketoglutarate reductase activity by competitive inhibition (Zhao and Winkler, *J. Bacteriol.* 178:232-239. (1996)).

| Gene | GenBank ID | GI Number | Organism |
| --- | --- | --- | --- |
| serA | CAA01762.1 | 1247677 | *Escherichia coli* |
| L2HGDH | Q9H9P8.3 | 317373422 | *Homo sapiens* |
| L2hgdh | NP_663418.1 | 21703884 | *Mus musculus* |
| L2hgdh_predicted | NP_001101498.1 | 157820173 | *Rattus norvegicus* |
| L2HGDH | NP_001094560.1 | 155371911 | *Bos taurus* |
| FN0487 | Q8RG31 | 81763568 | *Fusobacterium nucleatum* subsp. *Nucleatum* |

Referring to FIG. 7, step 2 involves 2-hydroxyglutamate mutase (EC 5.4.99.-). In the second step of the pathway, the carbon backbone undergoes rearrangement by a glutamate mutase enzyme. The most common reaction catalyzed by such an enzyme is the conversion of glutamate to threo-3-methylasparate, shown in step 2 of FIG. 6. The adenosylcobalamin-dependent glutamate mutase from *Clostridium cochlearium* has also been shown to react with 2-hydroxyglutarate as an alternate substrate (Roymoulik et al., *Biochemistry* 39:10340-10346 (2000)), although the rate of this reaction is two orders of magnitude lower with 2-hydroxyglutarate compared to the rate with native substrate glutamate. Directed evolution of the enzyme can be used to increase glutamate mutase affinity for 2-hydroxyglutarate. GenBank accession numbers of protein sequences encoding glutamate mutases are found in Example VIII, step 2 of the pathway.

Referring to FIG. 7, step 3 involves 3-methylmalate dehydratase (EC 4.2.1.-). In the third step, 3-methylmalate is dehydrated to form mesaconate. Although an enzyme catalyzing this exact transformation has not been described in the literature, several enzymes are able to catalyze a similar reaction. One such enzyme is 2-methylmalate dehydratase, also called citramalate hydrolyase, which converts 2-methylmalate to mesaconate. 2-Methylmalate and 3-methylmalate are closely related, with the only difference in structure being the location of the hydroxyl group. 2-Methylmalate dehydratase activity was detected in *Clostridium tetanomorphum, Morganella morganii, Citrobacter amalonaticus* in the context of the glutamate degradation VI pathway (Kato and Asano, *Arch. Microbiol.* 168:457-463 (1997)); however the genes encoding this enzyme have not been sequenced to date.

A second candidate enzyme is fumarate hydratase, which catalyzes the dehydration of malate to fumarate. As described in Example V (step 5), a wealth of structural information is available for this enzyme and other studies have successfully engineered the enzyme to alter activity, inhibition and localization (Weaver, *Acta Crystallogr. D Biol. Crystallogr.* 61:1395-1401 (2005)). Gene candidates are discussed in Example V, step 5 of the pathway.

Referring to FIG. 7, step 4 involves mesaconate decarboxylase (EC 4.1.1.-). The final pathway step involves the decarboxylation of mesaconate to methacrylic acid. This reaction is identical to the final step of the pathway described in Example VIII.

This example describes a biosynthetic pathway for production of MMA from alpha-ketoglutarate.

EXAMPLE X

Pathway for Conversion of Acetyl-CoA to 2-Hydroxyisobutyric Acid or MAA

This example describes an exemplary 2-hydroxyisobutyric acid or MAA synthesis pathway from acetyl-CoA.

Figure 8:
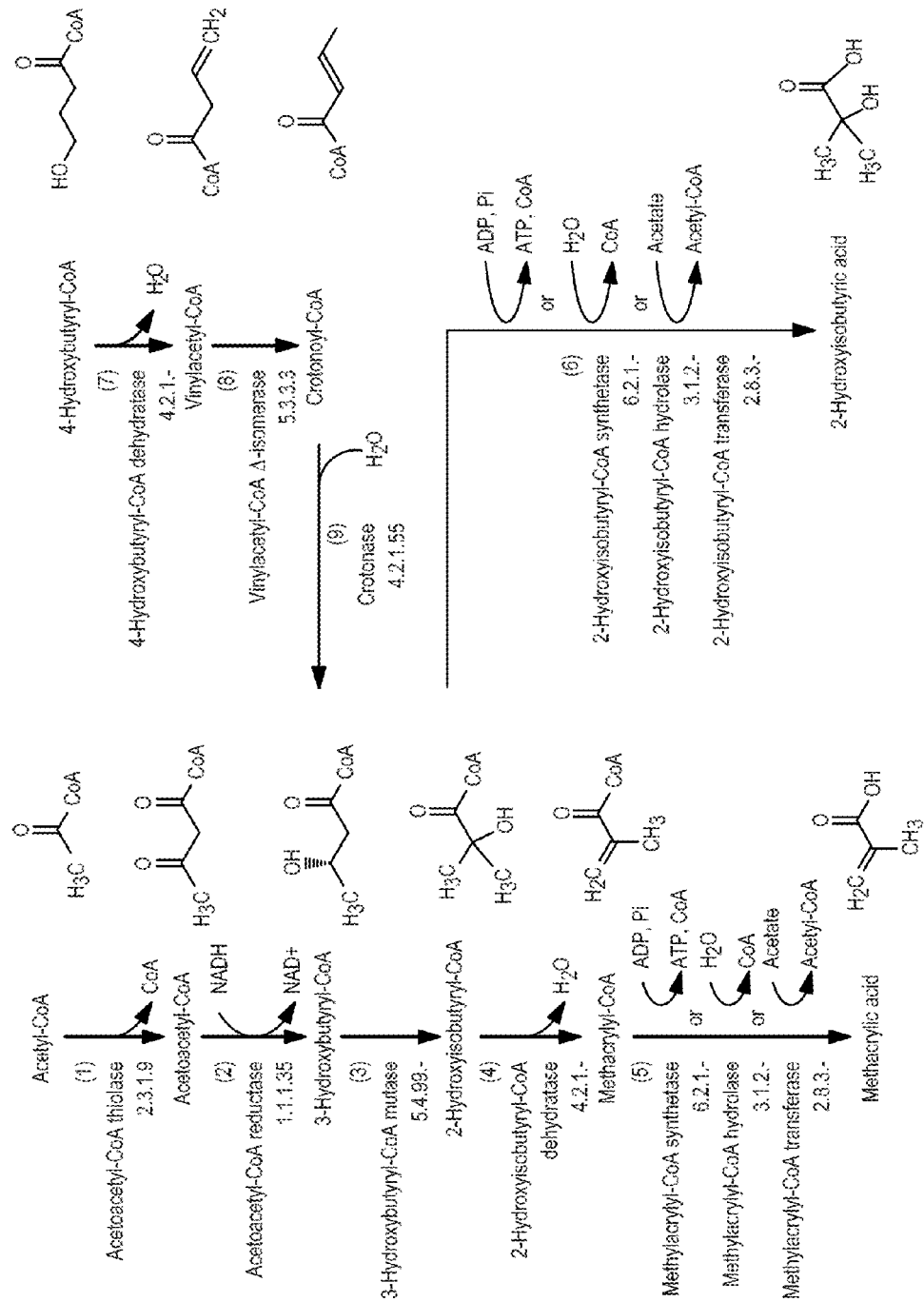
FIG. 8 shows exemplary metabolic pathways for the conversion of acetyl-CoA or 4-hydroxybutyryl-CoA into MAA or 2-hydroxyisobutyrate.

MAA biosynthesis can proceed from acetyl-CoA in a minimum of five enzymatic steps (see FIG. 8). In this pathway, two molecules of acetyl-CoA are combined to form acetoacetyl-coA, which is then reduced to 3-hydroxybutyryl-CoA. Alternatively, 4-hydroxybutyryl-CoA can be converted to 3-hydroxybutyryl-CoA by way of 4-hydroxybutyryl-CoA dehydratase and crotonase (Martins et al., *Proc. Nat. Acad. Sci. USA* 101(44) 15645-15649 (2004); Jones and Woods, *Microbiol. Rev.* 50:484-524 (1986); Berg et al., *Science* 318 (5857) 1782-1786 (2007)). A methylmutase then rearranges the carbon backbone of 3-hydroxybutyryl-CoA to 2-hydroxyisobutyryl-CoA, which is then dehydrated to form methacrylyl-CoA. Alternatively, 2-hydroxyisobutyryl-CoA can be converted to 2-hydroxyisobutyrate, secreted, and recovered as product. The final step converting methacrylyl-CoA to MAA can be performed by a single enzyme (shown in FIG. 8) or a series of enzymes.

Referring to FIG. 8, step 1 involves acetoacetyl-CoA thiolase (EC 2.3.1.9). The formation of acetoacetyl-CoA from two acetyl-CoA units is catalyzed by acetyl-CoA thiolase. This enzyme is native to *E. coli*, encoded by gene atoB, and typically operates in the acetoacetate-degrading direction during fatty acid oxidation (Duncombe and Frerman, *Arch. Biochem. Biophys.* 176:159-170 (1976); Frerman and Duncombe, *Biochim. Biophys. Acta* 580:289-297 (1979)). The gene thlA from *Clostridium acetobutylicum* was engineered into an isopropanol-producing strain of *E. coli* (Hanai et al., *Appl. Environ. Microbiol.* 73:7814-7818 (2007); Stim-Herndon et al., *Gene* 154:81-85 (1995)). Additional gene candidates include thl from *Clostridium pasteurianum* (Meng and Li. Cloning, *Biotechnol. Lett.* 28:1227-1232 (2006)) and ERG10 from *S. cerevisiae* (Hiser et al, *J Biol Chem* 269: 31383-89 (1994)).

| Protein | GenBank ID | GI Number | Organism |
| --- | --- | --- | --- |
| atoB | NP_416728 | 16130161 | *Escherichia coli* |
| thlA | NP_349476.1 | 15896127 | *Clostridium acetobutylicum* |
| thlB | NP_149242.1 | 15004782 | *Clostridium acetobutylicum* |
| thl | ABA18857.1 | 75315385 | *Clostridium pasteurianum* |
| ERG10 | NP_015297 | 6325229 | *Saccharomyces cerevisiae* |

Referring to FIG. 8, step 2 involves acetoacetyl-CoA reductase (EC#: 1.1.1.35). The second step entails the reduction of acetoacetyl-CoA to 3-hydroxybutyryl-CoA by acetoacetyl-CoA reductase. This enzyme participates in the acetyl-CoA fermentation pathway to butyrate in several species of *Clostridia* and has been studied in detail (Jones and Woods, *Microbiol. Rev.* 50:484-524 (1986)). The enzyme from *Clostridium acetobutylicum*, encoded by hbd, has been cloned and functionally expressed in *E. coli* (Youngleson et al., *J. Bacteriol.* 171:6800-6807 (1989)). Additionally, subunits of two fatty acid oxidation complexes in *E. coli*, encoded by fadB and fadJ, function as 3-hydroxyacyl-CoA dehydrogenases (Binstock and Schulz, *Methods Enzymol.* 71 Pt C:403-411 (1981)). Yet other genes demonstrated to reduce acetoacetyl-CoA to 3-hydroxybutyryl-CoA are phbB from *Zoogloea ramigera* (Ploux et al., *Eur. J Biochem.* 174:177-182 (1988)) and phaB from *Rhodobacter sphaeroides* (Alber et al., *Mol. Microbiol* 61:297-309 (2006)). The former gene is NADPH-dependent, its nucleotide sequence has been determined (Peoples et al., *Mol. Microbiol* 3:349-357 (1989)) and the gene has been expressed in *E. coli*. Substrate specificity studies on the gene led to the conclusion that it could accept 3-oxopropionyl-CoA as a substrate besides acetoacetyl-CoA (Ploux et al., *Eur. J. Biochem.* 174:177-182 (1988)). Additional gene candidates include Hbd1 (C-terminal domain) and Hbd2 (N-terminal domain) in *Clostridium kluyveri* (Hillmer and Gottschalk, *Biochim. Biophys. Acta* 3334:12-23 (1974)) and HSD17B10 in *Bos taurus* (Wakil et al., *J. Biol.*

*Chem.* 207:631-638 (1954)). The enzyme from *Paracoccus denitrificans* has been functionally expressed and characterized in *E. coli* (Yabutani et al., *FEMS Microbiol Lett.* 133:85-90 (1995)). A number of similar enzymes have been found in other species of *Clostridia* and in *Metallosphaera sedula* (Berg et al., *Science.* 318:1782-1786 (2007)). The enzyme from *Candida tropicalis* is a component of the peroxisomal fatty acid beta-oxidation multifunctional enzyme type 2 (MFE-2). The dehydrogenase B domain of this protein is catalytically active on acetoacetyl-CoA. The domain has been functionally expressed in *E. coli*, a crystal structure is available, and the catalytic mechanism is well-understood (Ylianttila et al., *Biochem Biophys Res Commun* 324:25-30 (2004); Ylianttila et al., *J Mol Biol* 358:1286-1295 (2006)).

| Protein | GENBANK ID | GI NUMBER | ORGANISM |
| --- | --- | --- | --- |
| fadB | P21177.2 | 119811 | *Escherichia coli* |
| fadJ | P77399.1 | 3334437 | *Escherichia coli* |
| Hbd2 | EDK34807.1 | 146348271 | *Clostridium kluyveri* |
| Hbd1 | EDK32512.1 | 146345976 | *Clostridium kluyveri* |
| HSD17B10 | O02691.3 | 3183024 | *Bos taurus* |
| phbB | P23238.1 | 130017 | *Zoogloea ramigera* |
| phaB | YP_353825.1 | 77464321 | *Rhodobacter sphaeroides* |
| phaB | BAA08358 | 675524 | *Paracoccus denitrificans* |
| Hbd | NP_349314.1 | 15895965 | *Clostridium acetobutylicum* |
| Hbd | AAM14586.1 | 20162442 | *Clostridium beijerinckii* |
| Msed_1423 | YP_001191505 | 146304189 | *Metallosphaera sedula* |
| Msed_0399 | YP_001190500 | 146303184 | *Metallosphaera sedula* |
| Msed_0389 | YP_001190490 | 146303174 | *Metallosphaera sedula* |
| Msed_1993 | YP_001192057 | 146304741 | *Metallosphaera sedula* |
| Fox2 | Q02207 | 399508 | *Candida tropicalis* |

Referring to FIG. 8, step 3 involves 3-hydroxybutyryl-CoA mutase (EC 5.4.99.-). In the next step, 3-hydroxybutyryl-CoA is rearranged to form 2-hydroxyisobutyryl-CoA (2-HIBCoA) by 3-hydroxybutyryl-CoA mutase. This enzyme is a novel ICM-like methylmutase recently discovered and characterized in *Methylibium petroleiphilum* (Ratnatilleke et al., *J. Biol. Chem.* 274:31679-31685 (1999); Rohwerder et al., *Appl. Environ. Microbiol.* 72:4128-4135 (2006)). This enzyme, encoded by Mpe_B0541 in *Methylibium petroleiphilum* PM1, has high sequence homology to the large subunit of methylmalonyl-CoA mutase in other organisms including Rsph17029_3657 in *Rhodobacter sphaeroides* and Xaut_5021 in *Xanthobacter autotrophicus*. As discussed in Example VII (step 1), changes to a single amino acid near the active site alters the substrate specificity of the enzyme (Ratnatilleke et al., supra, 1999; Rohwerder et al., supra, 2006), so directed engineering of similar enzymes at this site, such as methylmalonyl-CoA mutase or isobutyryl-CoA mutase described previously, can be used to achieve the desired reactivity.

| Gene | GenBank ID | GI Number | Organism |
| --- | --- | --- | --- |
| Mpe_B0541 | YP_001023546.1 | 124263076 | *Methylibium petroleiphilum* PM1 |
| Rsph17029_3657 | YP_001045519.1 | 126464406 | *Rhodobacter sphaeroides* |
| Xaut_5021 | YP_001409455.1 | 154243882 | *Xanthobacter autotrophicus* Py2 |

Referring to FIG. 8, step 4 involves 2-hydroxyisobutyryl-CoA dehydratase. The dehydration of 2-hydroxyacyl-CoA such as 2-hydroxyisobutyryl-CoA can be catalyzed by a special class of oxygen-sensitive enzymes that dehydrate 2-hydroxyacyl-CoA derivatives via a radical-mechanism (Buckel and Golding, *Annu. Rev. Microbiol.* 60:27-49 (2006); Buckel et al., *Curr. Opin. Chem. Biol.* 8:462-467 (2004); Buckel et al., *Biol. Chem.* 386:951-959 (2005); Kim et al., *FEBS J.* 272:550-561 (2005); Kim et al., *FEMS Microbiol. Rev.* 28:455-468 (2004); Zhang et al., *Microbiology* 145 (Pt 9):2323-2334 (1999)). One example of such an enzyme is the lactyl-CoA dehydratase from *Clostridium propionicum*, which catalyzes the dehydration of lactoyl-CoA to form acryl-CoA (Kuchta and Abeles, *J. Biol. Chem.* 260:13181-13189 (1985); Hofineister and Buckel, *Eur. J. Biochem.* 206:547-552 (1992)). An additional example is 2-hydroxyglutaryl-CoA dehydratase encoded by hgdABC from *Acidaminococcus fermentans* (Mueller and Buckel, *Eur. J. Biochem.* 230:698-704 (1995); Schweiger et al., *Eur. J. Biochem.* 169:441-448 (1987)). Yet another example is the 2-hydroxyisocaproyl-CoA dehydratase from *Clostridium difficile* catalyzed by hadBC and activated by hadI (Darley et al., *FEBS J.* 272:550-61 (2005)). The corresponding sequences for *A. fermentans* and *C. difficile* can be found as listed below. The sequence of the complete *C. propionicum* lactoyl-CoA dehydratase is not yet listed in publicly available databases. However, the sequence of the beta-subunit corresponds to the GenBank accession number AJ276553 (Selmer et al, *Eur J Biochem*, 269:372-80 (2002)).

| Gene | GenBank Accession No. | GI No. | Organism |
|---|---|---|---|
| hgdA | P11569 | 296439332 | *Acidaminococcus fermentans* |
| hgdB | P11570 | 296439333 | *Acidaminococcus fermentans* |
| hgdC | P11568 | 2506909 | *Acidaminococcus fermentans* |
| hadB | YP_001086863 | 126697966 | *Clostridium difficile* |
| hadC | YP_001086864 | 126697967 | *Clostridium difficile* |
| hadI | YP_001086862 | 126697965 | *Clostridium difficile* |
| lcdB | AJ276553 | 7242547 | *Clostridium propionicum* |

Referring to FIG. 8, steps 5 or 6 involve a transferase (EC 2.8.3.-), hydrolase (EC 3.1.2.-), or synthetase (EC 6.2.1.-) with activity on a methacrylic acid or 2-hydroxyisobutyric acid, respectively. Direct conversion of methacrylyl-CoA to MAA or 2-hydroxyisobutyryl-CoA to 2-hydrioxyisobutyrate can be accomplished by a CoA transferase, synthetase or hydrolase. As discussed in Example VII, pathway energetics are most favorable if a CoA transferase or a CoA synthetase is employed to accomplish this transformation. In the transferase family, the enzyme acyl-CoA:acetate-CoA transferase, also known as acetate-CoA transferase, is a suitable candidate to catalyze the desired 2-hydroxyisobutyryl-CoA or methacryl-CoA transferase activity due to its broad substrate specificity that includes branched acyl-CoA substrates (Matthies and Schink, *Appl. Environ. Microbiol.* 58:1435-1439 (1992); Vanderwinkel et al., *Biochem. Biophys. Res. Commun.* 33:902-908 (1968)). ADP-forming acetyl-CoA synthetase (ACD) is a promising enzyme in the CoA synthetase family operating on structurally similar branched chain compounds (Brasen and Schonheit, *Arch. Microbiol.* 182:277-287 (2004); Musfeldt and Schonheit, *J. Bacteriol.* 184:636-644 (2002)). In the CoA-hydrolase family, the enzyme 3-hydroxyisobutyryl-CoA hydrolase has been shown to operate on a variety of branched chain acyl-CoA substrates including 3-hydroxyisobutyryl-CoA, methylmalonyl-CoA, and 3-hydroxy-2-methylbutanoyl-CoA (Hawes et al., *Methods Enzymol.* 324:218-228 (2000); Hawes et al., *J. Biol. Chem.* 271:26430-26434 (1996); Shimomura et al., *J. Biol. Chem.* 269:14248-14253 (1994)). Additional exemplary gene candidates for CoA transferases, synthetases, and hydrolases are discussed in Example VII (step 2 and 5).

Referring to FIG. 8, an alternative step 5 involves indirect conversion to MAA. As an alternative to direct conversion of MAA-CoA to MAA, an alternate strategy for converting methacrylyl-CoA into MAA entails a multi-step process in which MAA-CoA is converted to MAA via 3-hydroxyisobutyrate. By this process, MAA-CoA is first converted to 3-hydroxyisobutyryl-CoA, which can subsequently be converted to MAA as described in Example VII.

The first step of this indirect route entails the conversion of MAA-CoA to 3-hydroxyisobutyryl-CoA (3HIB-CoA) by enoyl-CoA hydratase (EC 4.2.1.17 and 4.2.1.74). In *E. coli*, the gene products offadA and fadB encode a multienzyme complex involved in fatty acid oxidation that exhibits enoyl-CoA hydratase activity (Nakahigashi and Inokuchi, *Nucleic Acids Research* 18:4937 (1990); Yang, *J. Bacteriol.* 173:7405-7406 (1991); Yang et al., *J. Biol. Chem.* 265:10424-10429 (1990); Yang et al., *Biochemistry* 30:6788-6795 (1991)). Knocking out a negative regulator encoded by fadR can be utilized to activate the fadB gene product (Sato et al., *J. Biosci. Bioengineer.* 103:38-44 (2007)). The fadI and fadJ genes encode similar functions and are naturally expressed under anaerobic conditions (Campbell et al., *Mol. Microbiol.* 47:793-805 (2003)).

| Gene | GenBank Accession No. | GI No. | Organism |
|---|---|---|---|
| fadA | YP_026272.1 | 49176430 | *Escherichia coli* |
| fadB | NP_418288.1 | 16131692 | *Escherichia coli* |
| fadI | NP_416844.1 | 16130275 | *Escherichia coli* |
| fadJ | NP_416843.1 | 16130274 | *Escherichia coli* |
| fadR | NP_415705.1 | 16129150 | *Escherichia coli* |

Additional native gene candidates encoding an enoyl-CoA hydratase include maoC (Park and Lee, *J. Bacteriol.* 185:5391-5397 (2003)), paaF (Ismail et al., *Eur. J. Biochem.* 270:3047-3054 (2003); Park and Lee, *Appl. Biochem. Biotechnol.* 113-116:335-346 (2004); Park and Yup, *Biotechnol. Bioeng.* 86:681-686. (2004)), and paaG (Ismail et al., *Eur. J. Biochem.* 270:3047-3054 (2003); Park and Lee, *Appl. Biochem. Biotechnol.* 113-116:335-346 (2004); Park and Yup, *Biotechnol. Bioeng.* 86:681-686 (2004)). Other candidates include paaA, paaB, and paaN from *P. putida* (Olivera et al., *Proc. Natl. Acad. Sci. USA* 95:6419-6424 (1998)) and *P. fluorescens* (Di Gennaro et al., *Arch. Microbiol.* 188:117-125 (2007)). The gene product of crt from *C. acetobutylicum* is another candidate (Atsumi et al., *Metab. Eng. epub Sep.* 14, 2007; Boynton et al., *J. Bacteriol.* 178:3015-3024 (1996)). The enoyl-CoA hydratase of *Pseudomonas putida*, encoded by ech, catalyzes the conversion of 3-hydroxybutyryl-CoA to crotonyl-CoA (Roberts et al., *Arch. Microbiol* 117:99-108 (1978)). This transformation is also catalyzed by the crt gene product of *Clostridium acetobutylicum*, the crt1 gene product of *C. kluyveri*, and other clostridial organisms Atsumi et al., *Metab Eng* 10:305-311 (2008); Boynton et al., *J Bacteriol.* 178:3015-3024 (1996); Hillmer et al., *FEBS Lett.* 21:351-354 (1972)). Additional enoyl-CoA hydratase candidates are phaA and phaB, of *P. putida*, and paaA and paaB from *P. fluorescens* (Olivera et al., *Proc. Natl. Acad. Sci U.S.A* 95:6419-6424 (1998)).

| Gene | GenBank Accession No. | GI No. | Organism |
|---|---|---|---|
| maoC | NP_415905.1 | 16129348 | Escherichia coli |
| paaF | NP_415911.1 | 16129354 | Escherichia coli |
| paaG | NP_415912.1 | 16129355 | Escherichia coli |
| paaN (phaL) | NP_745413.1 | 26989988 | Pseudomonas putida |
| paaN | ABF82246.1 | 106636106 | Pseudomonas fluorescens |
| ech | NP_745498.1 | 26990073 | Pseudomonas putida |
| crt | NP_349318.1 | 15895969 | Clostridium acetobutylicum |
| crt1 | YP_001393856 | 153953091 | Clostridium kluyveri |
| phaA | NP_745427.1 | 26990002 | Pseudomonas putida |
| phaB | NP_745426.1 | 26990001 | Pseudomonas putida |
| paaA | ABF82233.1 | 106636093 | Pseudomonas fluorescens |
| paaB | ABF82234.1 | 106636094 | Pseudomonas fluorescens |

This example describes a biosynthetic pathway for production of 2-hydroxyisobutyrate or MAA from acetyl-CoA.

EXAMPLE XI

Pathway for Conversion of Acetyl-CoA to MAA Via Crotonoyl-CoA

This example describes an exemplary MAA synthetic pathway from acetyl-CoA via crotonoyl-CoA.

Another route for converting acetyl-CoA to MAA in a minimum of seven enzymatic steps is described (see FIG. 9). The yields of this pathway under aerobic and anaerobic conditions are similar to the pathway described in Example X.

The first two steps of the pathway are identical to steps 1 and 2 in the pathway described in Example X. In the third step, 3-HBCoA is dehydrated to form crotonyl-CoA by a crotonase (EC#: 4.2.1.55). The double bond in crotonyl-CoA is reduced by butyryl-CoA dehydrogenase (EC#: 1.3.99.2). Both of these enzymes, just like the acetoacetyl-CoA reductase, are a part of the acetyl-CoA fermentation pathway to butyrate in Clostridia species (Jones and Woods, Microbiol. Rev. 50:484-524 (1986)). In the subsequent step, butyryl-CoA is converted into isobutyryl-CoA by isobutyryl-CoA mutase (5.4.99.12), an enzyme that can reversibly convert butyryl-CoA into isobutyryl-CoA. This enzyme has been cloned and sequenced from Streptomyces cinnamonensis, and the recombinant enzyme has been characterized in E. coli (Ratnatilleke et al., J. Biol. Chem. 274:31679-31685 (1999)). The next step in the pathway entails the conversion of isobutyryl-CoA into methacrylyl-CoA via 2-methyl-acylCoA dehydrogenase (EC #: 1.3.99.12). This transformation towards methacrylyl-CoA has been observed in Streptomyces species, and the associated enzyme has been isolated and expressed in E. coli (Youngleson et al., J. Bacteriol. 171: 6800-6807 (1989)). In the final step, methacrylyl-CoA is converted to MAA by either a single enzyme or a series of enzymes, as described in Example X (step 5).

This example describes a biosynthetic pathway for production of MAA from acetyl-CoA.

EXAMPLE XII

Pathway for Conversion of Acrylyl-CoA to MAA

This example describes an exemplary MAA synthesis pathway from acrylyl-CoA.

Figure 10:
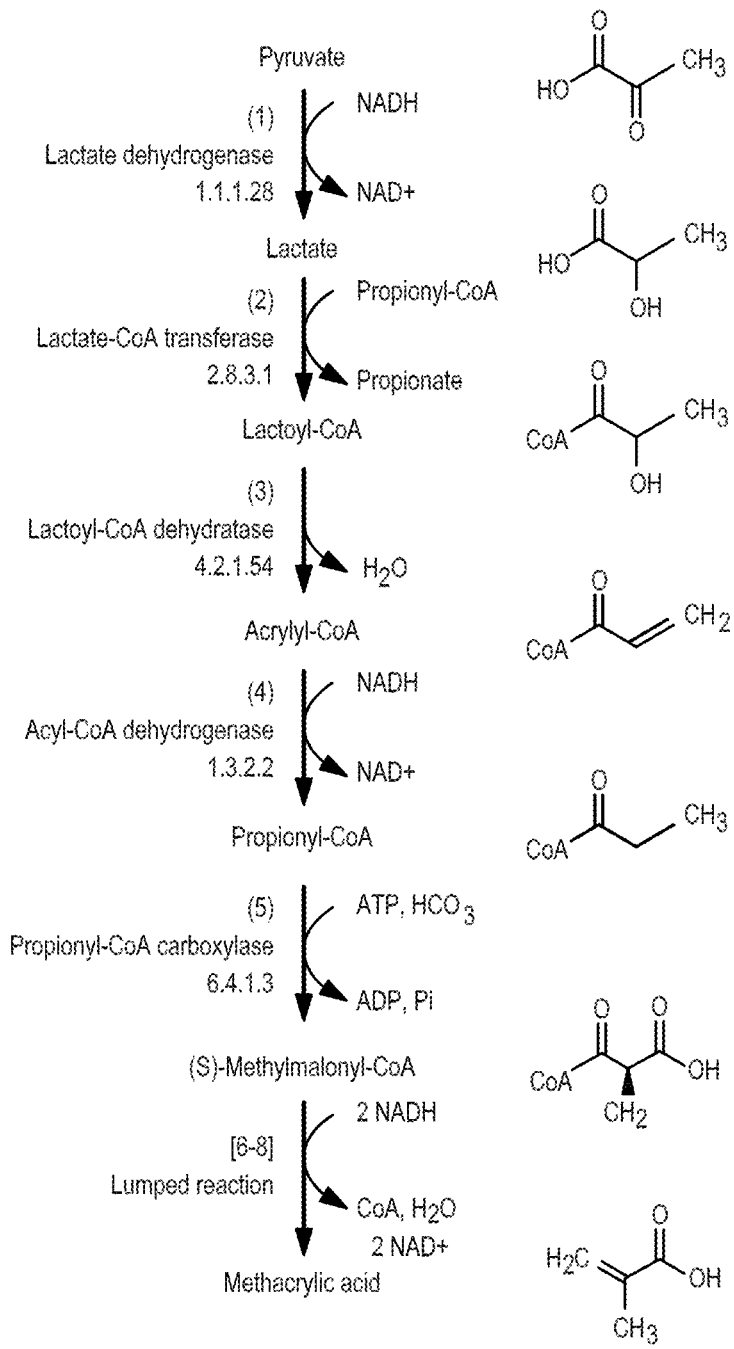
FIG. 10 shows an exemplary pyruvate to acrylyl-CoA to MAA pathway.

High yields of MAA can be obtained through the acrylyl-CoA pathway (see FIG. 10). This pathway requires the activation of lactate to lactoyl-CoA followed by five, or optionally six, more steps for the conversion of this activated CoA molecule into MAA. The MAA yield from glucose using this pathway is 1.28 mol/mol of glucose and oxygen uptake is required for attaining these yields. In the absence of oxygen, the expected yield decreases from 1.28 mol to 1.09 mol/mol glucose consumed. Both the aerobic and anaerobic pathways are energy limited at maximum MAA yield and do not generate any ATP.

MAA biosynthesis through the acrylyl-CoA pathway first requires the conversion of pyruvate into lactate via lactate dehydrogenase (EC 1.1.1.28), an enzyme native to E. coli and many other organisms. The three subsequent steps, converting lactate into propionyl-CoA, are catalyzed by enzymes in pyruvate fermentation pathways in several unrelated bacteria such as Clostridium propionicum and Megasphaera elsdenii (MetaCyc). Lactate-CoA transferase (EC 2.8.3.1), also known as propionate-CoA transferase, converts lactate into lactoyl-CoA and can use both propionate and lactate as substrates. This enzyme has been purified and characterized (Schweiger et al., Eur. J. Biochem. 169:441-448 (1987)). Lactoyl-CoA is dehydrated into acrylyl-CoA using lactoyl-CoA dehydratase (EC 4.2.1.54), an enzyme that has been a subject of numerous studies (Hofineister and Buckel, Eur. J. Biochem. 206:547-552. (1992); Kuchta and Abeles, J. Biol. Chem. 260:13181-13189 (1985)). Subsequently, acrylyl-CoA is reduced to propionyl-CoA using the acryloyl-CoA reductase (EC 1.3.2.2, formerly 1.3.99.3) (Hetzel et al., Eur. J Biochem. 270:902-910 (2003); Kuchta and Abeles, supra, 1985).

Referring to FIG. 10, in step 5, propionyl-CoA is converted into S-methylmalonyl-CoA by propionyl-CoA carboxylase (6.4.1.3). Propionyl-CoA carboxylase has been purified from rat liver (Browner et al., J. Biol. Chem. 264:12680-12685 (1989); Kraus et al., J. Biol. Chem. 258:7245-7248 (1983)) and has been isolated and characterized from human liver as well (Kalousek et al., J. Biol. Chem. 255:60-65 (1980)). Carboxylation of propionyl-CoA into succinyl-CoA via this enzyme has been identified as one of the mechanisms of propionate metabolism in E. coli (Evans et al., Biochem. J. 291 (Pt 3):927-932 (1993)), but very little is known about the genetics of the pathway.

The final steps of the pathway entail conversion of methylmalonyl-CoA into MAA (lumped reaction in FIG. 10). Enzymes catalyzing these reactions are described in Example V.

This example describes a biosynthetic pathway for production of MAA from pyruvate.

EXAMPLE XIII

Pathway for Conversion of 2-Ketoisovalerate to MAA

This example describes an exemplary MAA synthetic pathway from 2-ketoisovalerate.

The pathway (see FIG. 11) exploits multiple steps of the valine degradation route described in several organisms, including Bacillus subtilis, Arabidopsis thaliana, and several species of Pseuodomonas but not known to be present in E. coli or in S. cerevisiae. In the first step of the valine degradation pathway, valine is converted into 2-ketoisovalerate by branched-chain amino acid aminotransferase (EC 2.6.1.24), an enzyme also native to E. coli (Matthies and Schink, Appl. Environ. Microbiol. 58:1435-1439 (1992); Rudman and Meister, J. Biol. Chem. 200:591-604 (1953)). The subsequent conversion of 2-ketoisovalerate into isobutyryl-CoA, catalyzed by a branched-chain keto-acid dehydrogenase complex (EC 1.2.1.25), is the committing step for MAA biosynthesis via this route. Next, isobutyryl-CoA is converted to methacrylyl-CoA via isobutyryl-CoA dehydrogenase (EC 1.3.99.12). Details for this step are described in Example XI. The final step, conversion of MAA-CoA to MAA, is described in Example V.

This example describes a biosynthetic pathway for production of MMA from 2-ketoisovalerate.

EXAMPLE XIV

Pathway for Conversion of 4-Hydroxybutyryl-CoA to 2-Hydroxyisobutyrate or MAA Via 2-Hydroxyisobutyryl-CoA This example describes an exemplary 2-hydroxyisobutyrate or MAA synthesis pathway proceeding from 4-hydroxybutyryl-CoA that passes through 2-hydroxyisobutyryl-CoA.

The pathway first entails the dehydration of 4-hydroxybutyryl-CoA to vinylacetyl-CoA which is subsequently isomerized to crotonoyl-CoA. Crotonyl-CoA is hydrated to form 3-hydroxybutyryl-CoA, which is rearranged into 2-hydroxyisobutyryl-CoA. The final step of the 2-hydroxyisobutyrate pathway involves eliminating the CoA functional group from 2-hydroxyisobutyryl-CoA. The final steps in MAA synthesis involve the dehydration of 2-hydroxyisobutyryl-CoA followed by the removal of the CoA functional group from methacrylyl-CoA. Gene candidates for the first three pathway steps, steps 7, 8, and 9 of FIG. 8, are described below. Gene candidates for steps 3, 4, 5, and 6 of FIG. 8 are discussed in Example X.

Referring to FIG. 8, steps 7 and 8 are carried out by 4-hydroxybutyryl-CoA dehydratase enzymes. The enzymes from both *Clostridium aminobutyrium* and *C. kluyveri* catalyze the reversible conversion of 4-hydroxybutyryl-CoA to crotonyl-CoA and also possess an intrinsic vinylacetyl-CoA Δ-isomerase activity (Scherf and Buckel, *Eur. J. Biochem.* 215:421-429 (1993); Scherf et al., *Arch. Microbiol.* 161:239-245 (1994)). Both native enzymes have been purified and characterized, including the N-terminal amino acid sequences (Scherf and Buckel, supra, 1993; Scherf et al., supra, 1994). The abfD genes from *C. aminobutyrium* and *C. kluyveri* match exactly with these N-terminal amino acid sequences, thus are encoding the 4-hydroxybutyryl-CoA dehydratases/vinylacetyl-CoA Δ-isomerase. In addition, abfD from *Porphyromonas gingivalis* ATCC 33277 is another exemplary 4-hydroxybutyryl-CoA dehydratase that can be identified through homology. The abfD gene product from *Porphyromonas gingivalis* and the Msed_1220 gene product from *Metallosphaera sedula* are closely related by sequence homology to the *Clostridial* gene products.

| Gene | GenBank Accession No. | GI No. | Organism |
| --- | --- | --- | --- |
| abfD | YP_001396399.1 | 153955634 | Clostridium kluyveri DSM 555 |
| abfD | P55792 | 84028213 | Clostridium aminobutyricum |
| abfD | YP_001928843 | 188994591 | Porphyromonas gingivalis (ATCC 33277) |
| Msed_1220 | YP_001191305.1 | 146303989 | Metallosphaera sedula |

Step 9 of FIG. 8 is carried out by a crotonase enzyme. Such enzymes are required for n-butanol formation in some organisms, particularly *Clostridial* species, and also comprise one step of the 3-hydroxypropionate/4-hydroxybutyrate cycle in thermoacidophilic Archaea of the genera *Sulfolobus, Acidianus*, and *Metallosphaera*. Exemplary genes encoding crotonase enzymes can be found in *C. acetobutylicum* (Boynton, et al., *J. Bacteriol.* 178(11):3015-3024 (1996)), *C. kluyveri* (Hillmer and Gottschalk, *FEBS Lett.* 21(3):351-354 (1972)), and *Metallosphaera sedula* (Berg et al., *Science* 318(5857): 1782-1786 (2007)) though the sequence of the latter gene is not known. Enoyl-CoA hydratases, which are involved in fatty acid beta-oxidation and/or the metabolism of various amino acids, can also catalyze the hydration of crotonyl-CoA to form 3-hydroxybutyryl-CoA (Agnihotri and Liu, *Bioorg. Med. Chem.* 11(1):9-20 (2003); Roberts et al., *Arch. Microbiol.* 117(1):99-108 (1978); Conrad et al., *J. Bacteriol.* 118 (1); 103-11 (1974)). The enoyl-CoA hydratases, phaA and phaB, of *P. putida* are believed to carry out the hydroxylation of double bonds during phenylacetate catabolism (Olivera et al., *Proc Natl Acad Sci USA* 95(11):6419-6424 (1998)). The paaA and paaB from *P. fluorescens* catalyze analogous transformations (Olivera et al., supra, 1998). Lastly, a number of *Escherichia coli* genes have been shown to demonstrate enoyl-CoA hydratase functionality including maoC (Park and Lee, *J. Bacteriol.* 185(18):5391-5397 (2003)), paaF (Park and Lee, *Biotechnol. Bioeng.* 86(6):681-686 (2004a)); Park and Lee, *Appl. Biochem. Biotechnol.* 113-116: 335-346 (2004b)); Ismail et al. *Eur. J. Biochem.* 270(14):3047-3054 (2003), and paaG (Park and Lee, supra, 2004; Park and Lee, supra, 2004b; Ismail et al., supra, 2003).

| Gene | GenBank Accession No. | GI No. | Organism |
| --- | --- | --- | --- |
| crt | NP_349318.1 | 15895969 | Clostridium acetobutylicum |
| crt1 | YP_001393856 | 153953091 | Clostridium kluyveri DSM 555 |
| phaA | NP_745427.1 | 26990002 | Pseudomonas putida |
| phaB | NP_745426.1 | 26990001 | Pseudomonas putida |
| paaA | ABF82233.1 | 106636093 | Pseudomonas fluorescens |
| paaB | ABF82234.1 | 106636094 | Pseudomonas fluorescens |
| maoC | NP_415905.1 | 16129348 | Escherichia coli |
| paaF | NP_415911.1 | 16129354 | Escherichia coli |
| paaG | NP_415912.1 | 16129355 | Escherichia coli |

This example describes a biosynthesis pathway for 2-hydroxyisobutyrate or methacylic acid from 4-hydroxybutyryl-CoA.

EXAMPLE XV

Exemplary Hydrogenase and CO Dehydrogenase Enzymes for Extracting Reducing Equivalents from Syngas and Exemplary Reductive TCA Cycle Enzymes Enzymes of the reductive TCA cycle useful in the non-naturally occurring microbial organisms of the present invention include one or more of ATP-citrate lyase and three $CO_2$-fixing enzymes: isocitrate dehydrogenase, alpha-ketoglutarate:ferredoxin oxidoreductase, pyruvate:ferredoxin oxidoreductase. The presence of ATP-citrate lyase or citrate lyase and alpha-ketoglutarate:ferredoxin oxidoreductase indicates the presence of an active reductive TCA cycle in an organism. Enzymes for each step of the reductive TCA cycle are shown below and described herein.

ATP-citrate lyase (ACL, EC 2.3.3.8), also called ATP citrate synthase, catalyzes the ATP-dependent cleavage of citrate to oxaloacetate and acetyl-CoA. ACL is an enzyme of the RTCA cycle that has been studied in green sulfur bacteria

*Chlorobium limicola* and *Chlorobium tepidum*. The alpha(4) beta(4) heteromeric enzyme from *Chlorobium limicola* was cloned and characterized in *E. coli* (Kanao et al., *Eur. J. Biochem.* 269:3409-3416 (2002). The *C. limicola* enzyme, encoded by aclAB, is irreversible and activity of the enzyme is regulated by the ratio of ADP/ATP. A recombinant ACL from *Chlorobium tepidum* was also expressed in *E. coli* and the holoenzyme was reconstituted in vitro, in a study elucidating the role of the alpha and beta subunits in the catalytic mechanism (Kim and Tabita, *J. Bacteriol.* 188:6544-6552 (2006). ACL enzymes have also been identified in *Balnearium lithotrophicum*, *Sulfurihydrogenibium subterraneum* and other members of the bacterial phylum *Aquificae* (Hugler et al., *Environ. Microbiol.* 9:81-92 (2007)). This activity has been reported in some fungi as well. Exemplary organisms include *Sordaria macrospora* (Nowrousian et al., *Curr. Genet.* 37:189-93 (2000), *Aspergillus nidulans*, *Yarrowia lipolytica* (Hynes and Murray, *Eukaryotic Cell*, July: 1039-1048, (2010) and *Aspergillus niger* (Meijer et al. *J. Ind. Microbiol. Biotechnol.* 36:1275-1280 (2009). Other candidates can be found based on sequence homology. Information related to these enzymes is tabulated below:

| Protein | GenBank ID | GI Number | Organism |
|---|---|---|---|
| aclA | BAB21376.1 | 12407237 | *Chlorobium limicola* |
| aclB | BAB21375.1 | 12407235 | *Chlorobium limicola* |
| aclA | AAM72321.1 | 21647054 | *Chlorobium tepidum* |
| aclB | AAM72322.1 | 21647055 | *Chlorobium tepidum* |
| aclA | ABI50076.1 | 114054981 | *Balnearium lithotrophicum* |
| aclB | ABI50075.1 | 114054980 | *Balnearium lithotrophicum* |
| aclA | ABI50085.1 | 114055040 | *Sulfurihydrogenibium subterraneum* |
| aclB | ABI50084.1 | 114055039 | *Sulfurihydrogenibium subterraneum* |
| aclA | AAX76834.1 | 62199504 | *Sulfurimonas denitrificans* |
| aclB | AAX76835.1 | 62199506 | *Sulfurimonas denitrificans* |
| acl1 | XP_504787.1 | 50554757 | *Yarrowia lipolytica* |
| acl2 | XP_503231.1 | 50551515 | *Yarrowia lipolytica* |
| SPBC1703.07 | NP_596202.1 | 19112994 | *Schizosaccharomyces pombe* |
| SPAC22A12.16 | NP_593246.1 | 19114158 | *Schizosaccharomyces pombe* |
| acl1 | CAB76165.1 | 7160185 | *Sordaria macrospora* |
| acl2 | CAB76164.1 | 7160184 | *Sordaria macrospora* |
| aclA | CBF86850.1 | 259487849 | *Aspergillus nidulans* |
| aclB | CBF86848 | 259487848 | *Aspergillus nidulans* |

In some organisms the conversion of citrate to oxaloacetate and acetyl-CoA proceeds through a citryl-CoA intermediate and is catalyzed by two separate enzymes, citryl-CoA synthetase (EC 6.2.1.18) and citryl-CoA lyase (EC 4.1.3.34) (Aoshima, M., *Appl. Microbiol. Biotechnol.* 75:249-255 (2007). Citryl-CoA synthetase catalyzes the activation of citrate to citryl-CoA. The *Hydrogenobacter thermophilus* enzyme is composed of large and small subunits encoded by ccsA and ccsB, respectively (Aoshima et al., *Mol. Micrbiol.* 52:751-761 (2004)). The citryl-CoA synthetase of *Aquifex aeolicus* is composed of alpha and beta subunits encoded by sucC1 and sucD1 (Hugler et al., *Environ. Microbiol.* 9:81-92 (2007)). Citryl-CoA lyase splits citryl-CoA into oxaloacetate and acetyl-CoA. This enzyme is a homotrimer encoded by ccl in *Hydrogenobacter thermophilus* (Aoshima et al., *Mol. Microbiol.* 52:763-770 (2004)) and aq_150 in *Aquifex aeolicus* (Hugler et al., supra (2007)). The genes for this mechanism of converting citrate to oxaloacetate and citryl-CoA have also been reported recently in *Chlorobium tepidum* (Eisen et al., PNAS 99(14): 9509-14 (2002).

| Protein | GenBank ID | GI Number | Organism |
|---|---|---|---|
| ccsA | BAD17844.1 | 46849514 | *Hydrogenobacter thermophilus* |
| ccsB | BAD17846.1 | 46849517 | *Hydrogenobacter thermophilus* |
| sucC1 | AAC07285 | 2983723 | *Aquifex aeolicus* |
| sucD1 | AAC07686 | 2984152 | *Aquifex aeolicus* |
| ccl | BAD17841.1 | 46849510 | *Hydrogenobacter thermophilus* |
| aq_150 | AAC06486 | 2982866 | *Aquifex aeolicus* |
| CT0380 | NP_661284 | 21673219 | *Chlorobium tepidum* |
| CT0269 | NP_661173.1 | 21673108 | *Chlorobium tepidum* |
| CT1834 | AAM73055.1 | 21647851 | *Chlorobium tepidum* |

Oxaloacetate is converted into malate by malate dehydrogenase (EC 1.1.1.37), an enzyme which functions in both the forward and reverse direction. *S. cerevisiae* possesses three copies of malate dehydrogenase, MDH1 (McAlister-Henn and Thompson, *J. Bacteriol.* 169:5157-5166 (1987), MDH2 (Minard and McAlister-Henn, *Mol. Cell. Biol.* 11:370-380 (1991); Gibson and McAlister-Henn, *J. Biol. Chem.* 278: 25628-25636 (2003)), and MDH3 (Steffan and McAlister-Henn, *J. Biol. Chem.* 267:24708-24715 (1992)), which localize to the mitochondrion, cytosol, and peroxisome, respectively. *E. coli* is known to have an active malate dehydrogenase encoded by mdh.

| Protein | GenBank ID | GI Number | Organism |
|---|---|---|---|
| MDH1 | NP_012838 | 6322765 | *Saccharomyces cerevisiae* |
| MDH2 | NP_014515 | 116006499 | *Saccharomyces cerevisiae* |
| MDH3 | NP_010205 | 6320125 | *Saccharomyces cerevisiae* |
| Mdh | NP_417703.1 | 16131126 | *Escherichia coli* |

Fumarate hydratase (EC 4.2.1.2) catalyzes the reversible hydration of fumarate to malate. The three fumarases of *E. coli*, encoded by fumA, fumB and fumC, are regulated under different conditions of oxygen availability. FumB is oxygen sensitive and is active under anaerobic conditions. FumA is active under microanaerobic conditions, and FumC is active under aerobic growth conditions (Tseng et al., *J. Bacteriol.* 183:461-467 (2001); Woods et al., *Biochim. Biophys. Acta* 954:14-26 (1988); Guest et al., *J. Gen. Microbiol.* 131:2971-2984 (1985)). *S. cerevisiae* contains one copy of a fumarase-encoding gene, FUM1, whose product localizes to both the cytosol and mitochondrion (Sass et al., *J. Biol. Chem.* 278: 45109-45116 (2003)). Additional fumarase enzymes are found in *Campylobacter jejuni* (Smith et al., *Int. J. Biochem. Cell. Biol.* 31:961-975 (1999)), *Thermus thermophilus* (Mizobata et al., *Arch. Biochem. Biophys.* 355:49-55 (1998)) and *Rattus norvegicus* (Kobayashi et al., *J. Biochem.* 89:1923-1931 (1981)). Similar enzymes with high sequence homology include fum1 from *Arabidopsis thaliana* and fumC from *Corynebacterium glutamicum*. The MmcBC fumarase from *Pelotomaculum thermopropionicum* is another class of fumarase with two subunits (Shimoyama et al., *FEMS Microbiol. Lett.* 270:207-213 (2007)).

| Protein | GenBank ID | GI Number | Organism |
|---|---|---|---|
| fumA | NP_416129.1 | 16129570 | *Escherichia coli* |
| fumB | NP_418546.1 | 16131948 | *Escherichia coli* |
| fumC | NP_416128.1 | 16129569 | *Escherichia coli* |
| FUM1 | NP_015061 | 6324993 | *Saccharomyces cerevisiae* |
| fumC | Q8NRN8.1 | 39931596 | *Corynebacterium glutamicum* |
| fumC | O69294.1 | 9789756 | *Campylobacter jejuni* |
| fumC | P84127 | 75427690 | *Thermus thermophilus* |

| Protein | GenBank ID | GI Number | Organism |
|---------|------------|-----------|----------|
| fumH | P14408.1 | 120605 | Rattus norvegicus |
| MmcB | YP_001211906 | 147677691 | Pelotomaculum thermopropionicum |
| MmcC | YP_001211907 | 147677692 | Pelotomaculum thermopropionicum |

Fumarate reductase catalyzes the reduction of fumarate to succinate. The fumarate reductase of E. coli, composed of four subunits encoded by frdABCD, is membrane-bound and active under anaerobic conditions. The electron donor for this reaction is menaquinone and the two protons produced in this reaction do not contribute to the proton gradient (Iverson et al., Science 284:1961-1966 (1999)). The yeast genome encodes two soluble fumarate reductase isozymes encoded by FRDS1 (Enomoto et al., DNA Res. 3:263-267 (1996)) and FRDS2 (Muratsubaki et al., Arch. Biochem. Biophys. 352: 175-181 (1998)), which localize to the cytosol and promitochondrion, respectively, and are used during anaerobic growth on glucose (Arikawa et al., FEMS Microbiol. Lett. 165:111-116 (1998)).

| Protein | GenBank ID | GI Number | Organism |
|---------|------------|-----------|----------|
| FRDS1 | P32614 | 418423 | Saccharomyces cerevisiae |
| FRDS2 | NP_012585 | 6322511 | Saccharomyces cerevisiae |
| frdA | NP_418578.1 | 16131979 | Escherichia coli |
| frdB | NP_418577.1 | 16131978 | Escherichia coli |
| frdC | NP_418576.1 | 16131977 | Escherichia coli |
| frdD | NP_418475.1 | 16131877 | Escherichia coli |

The ATP-dependent acylation of succinate to succinyl-CoA is catalyzed by succinyl-CoA synthetase (EC 6.2.1.5). The product of the LS' and LSC2 genes of S. cerevisiae and the sucC and sucD genes of E. coli naturally form a succinyl-CoA synthetase complex that catalyzes the formation of succinyl-CoA from succinate with the concomitant consumption of one ATP, a reaction which is reversible in vivo (Buck et al., Biochemistry 24:6245-6252 (1985)). These proteins are identified below:

| Protein | GenBank ID | GI Number | Organism |
|---------|------------|-----------|----------|
| LSC1 | NP_014785 | 6324716 | Saccharomyces cerevisiae |
| LSC2 | NP_011760 | 6321683 | Saccharomyces cerevisiae |
| sucC | NP_415256.1 | 16128703 | Escherichia coli |
| sucD | AAC73823.1 | 1786949 | Escherichia coli |

Alpha-ketoglutarate:ferredoxin oxidoreductase (EC 1.2.7.3), also known as 2-oxoglutarate synthase or 2-oxoglutarate:ferredoxin oxidoreductase (OFOR), forms alpha-ketoglutarate from $CO_2$ and succinyl-CoA with concurrent consumption of two reduced ferredoxin equivalents. OFOR and pyruvate:ferredoxin oxidoreductase (PFOR) are members of a diverse family of 2-oxoacid:ferredoxin (flavodoxin) oxidoreductases which utilize thiamine pyrophosphate, CoA and iron-sulfur clusters as cofactors and ferredoxin, flavodoxin and FAD as electron carriers (Adams et al., Archaea. Adv. Protein Chem. 48:101-180 (1996)). Enzymes in this class are reversible and function in the carboxylation direction in organisms that fix carbon by the RTCA cycle such as Hydrogenobacter thermophilus, Desulfobacter hydrogenophilus and Chlorobium species (Shiba et al. 1985; Evans et al., Proc. Natl. Acad. Scl. U.S.A. 55:92934 (1966); Buchanan, 1971). The two-subunit enzyme from H. thermophilus, encoded by korAB, has been cloned and expressed in E. coli (Yun et al., Biochem. Biophys. Res. Commun. 282:589-594 (2001)). A five subunit OFOR from the same organism with strict substrate specificity for succinyl-CoA, encoded by forDABGE, was recently identified and expressed in E. coli (Yun et al. 2002). The kinetics of $CO_2$ fixation of both H. thermophilus OFOR enzymes have been characterized (Yamamoto et al., Extremophiles 14:79-85 (2010)). A $CO_2$-fixing OFOR from Chlorobium thiosulfatophilum has been purified and characterized but the genes encoding this enzyme have not been identified to date. Enzyme candidates in Chlorobium species can be inferred by sequence similarity to the H. thermophilus genes. For example, the Chlorobium limicola genome encodes two similar proteins. Acetogenic bacteria such as Moorella thermoacetica are predicted to encode two OFOR enzymes. The enzyme encoded by Moth_0034 is predicted to function in the $CO_2$-assimilating direction. The genes associated with this enzyme, Moth_0034 have not been experimentally validated to date but can be inferred by sequence similarity to known OFOR enzymes.

OFOR enzymes that function in the decarboxylation direction under physiological conditions can also catalyze the reverse reaction. The OFOR from the thermoacidophilic archaeon Sulfolobus sp. strain 7, encoded by ST2300, has been extensively studied (Zhang et al. 1996. A plasmid-based expression system has been developed for efficiently expressing this protein in E. coli (Fukuda et al., Eur. J. Biochem. 268:5639-5646 (2001)) and residues involved in substrate specificity were determined (Fukuda and Wakagi, Biochim. Biophys. Acta 1597:74-80 (2002)). The OFOR encoded by Ape1472/Ape1473 from Aeropyrum pernix str. K1 was recently cloned into E. coli, characterized, and found to react with 2-oxoglutarate and a broad range of 2-oxoacids (Nishizawa et al., FEBS Lett. 579:2319-2322 (2005)). Another exemplary OFOR is encoded by oorDABC in Helicobacter pylori (Hughes et al. 1998). An enzyme specific to alpha-ketoglutarate has been reported in Thauera aromatics (Dorner and Boll, J, Bacteriol. 184 (14), 3975-83 (2002). A similar enzyme can be found in Rhodospirillum rubrum by sequence homology. A two subunit enzyme has also been identified in Chlorobium tepidum (Eisen et al., PNAS 99(14): 9509-14 (2002)).

| Protein | GenBank ID | GI Number | Organism |
|---------|------------|-----------|----------|
| korA | BAB21494 | 12583691 | Hydrogenobacter thermophilus |
| korB | BAB21495 | 12583692 | Hydrogenobacter thermophilus |
| forD | BAB62132.1 | 14970994 | Hydrogenobacter thermophilus |
| forA | BAB62133.1 | 14970995 | Hydrogenobacter thermophilus |
| forB | BAB62134.1 | 14970996 | Hydrogenobacter thermophilus |
| forG | BAB62135.1 | 14970997 | Hydrogenobacter thermophilus |
| forE | BAB62136.1 | 14970998 | Hydrogenobacter thermophilus |
| Clim_0204 | ACD89303.1 | 189339900 | Chlorobium limicola |
| Clim_0205 | ACD89302.1 | 189339899 | Chlorobium limicola |
| Clim_1123 | ACD90192.1 | 189340789 | Chlorobium limicola |
| Clim_1124 | ACD90193.1 | 189340790 | Chlorobium limicola |
| Moth_1984 | YP_430825.1 | 83590816 | Moorella thermoacetica |
| Moth_1985 | YP_430826.1 | 83590817 | Moorella thermoacetica |
| Moth_0034 | YP_428917.1 | 83588908 | Moorella thermoacetica |
| ST2300 | NP_378302.1 | 15922633 | Sulfolobus sp. strain 7 |
| Ape1472 | BAA80470.1 | 5105156 | Aeropyrum pernix |
| Ape1473 | BAA80471.2 | 116062794 | Aeropyrum pernix |
| oorD | NP_207383.1 | 15645213 | Helicobacter pylori |

| Protein | GenBank ID | GI Number | Organism |
| --- | --- | --- | --- |
| oorA | NP_207384.1 | 15645214 | Helicobacter pylori |
| oorB | NP_207385.1 | 15645215 | Helicobacter pylori |
| oorC | NP_207386.1 | 15645216 | Helicobacter pylori |
| CT0163 | NP_661069.1 | 21673004 | Chlorobium tepidum |
| CT0162 | NP_661068.1 | 21673003 | Chlorobium tepidum |
| korA | CAA12243.2 | 19571179 | Thauera aromatica |
| korB | CAD27440.1 | 19571178 | Thauera aromatica |
| Rru_A2721 | YP_427805.1 | 83594053 | Rhodospirillum rubrum |
| Rru_A2722 | YP_427806.1 | 83594054 | Rhodospirillum rubrum |

Isocitrate dehydrogenase catalyzes the reversible decarboxylation of isocitrate to 2-oxoglutarate coupled to the reduction of NAD(P)$^+$. IDH enzymes in *Saccharomyces cerevisiae* and *Escherichia coli* are encoded by IDP1 and icd, respectively (Haselbeck and McAlister-Henn, *J. Biol. Chem.* 266:2339-2345 (1991); Nimmo, H. G., *Biochem. J.* 234:317-2332 (1986)). The reverse reaction in the reductive TCA cycle, the reductive carboxylation of 2-oxoglutarate to isocitrate, is favored by the NADPH-dependent $CO_2$-fixing IDH from *Chlorobium limicola* and was functionally expressed in *E. coli* (Kanao et al., *Eur. J. Biochem.* 269:1926-1931 (2002)). A similar enzyme with 95% sequence identity is found in the *C. tepidum* genome in addition to some other candidates listed below.

| Protein | GenBank ID | GI Number | Organism |
| --- | --- | --- | --- |
| Icd | ACI84720.1 | 209772816 | Escherichia coli |
| IDP1 | AAA34703.1 | 171749 | Saccharomyces cerevisiae |
| Idh | BAC00856.1 | 21396513 | Chlorobium limicola |
| Icd | AAM71597.1 | 21646271 | Chlorobium tepidum |
| icd | NP_952516.1 | 39996565 | Geobacter sulfurreducens |
| icd | YP_393560. | 78777245 | Sulfurimonas denitrificans |

In *H. thermophilus* the reductive carboxylation of 2-oxoglutarate to isocitrate is catalyzed by two enzymes: 2-oxoglutarate carboxylase and oxalosuccinate reductase. 2-Oxoglutarate carboxylase (EC 6.4.1.7) catalyzes the ATP-dependent carboxylation of alpha-ketoglutarate to oxalosuccinate (Aoshima and Igarashi, *Mol. Microbiol.* 62:748-759 (2006)). This enzyme is a large complex composed of two subunits. Biotinylation of the large (A) subunit is required for enzyme function (Aoshima et al., *Mol. Microbiol.* 51:791-798 (2004)). Oxalosuccinate reductase (EC 1.1.1.-) catalyzes the NAD-dependent conversion of oxalosuccinate to D-threo-isocitrate. The enzyme is a homodimer encoded by icd in *H. thermophilus*. The kinetic parameters of this enzyme indicate that the enzyme only operates in the reductive carboxylation direction in vivo, in contrast to isocitrate dehydrogenase enzymes in other organisms (Aoshima and Igarashi, *J. Bacteriol.* 190:2050-2055 (2008)). Based on sequence homology, gene candidates have also been found in *Thiobacillus denitrificans* and *Thermocrinis albus*.

| Protein | GenBank ID | GI Number | Organism |
| --- | --- | --- | --- |
| cfiA | BAF34932.1 | 116234991 | Hydrogenobacter thermophilus |
| cifB | BAF34931.1 | 116234990 | Hydrogenobacter thermophilus |
| Icd | BAD02487.1 | 38602676 | Hydrogenobacter thermophilus |
| Tbd_1556 | YP_315314 | 74317574 | Thiobacillus denitrificans |
| Tbd_1555 | YP_315313 | 74317573 | Thiobacillus denitrificans |
| Tbd_0854 | YP_314612 | 74316872 | Thiobacillus denitrificans |
| Thal_0268 | YP_003473030 | 289548042 | Thermocrinis albus |
| Thal_0267 | YP_003473029 | 289548041 | Thermocrinis albus |
| Thal_0646 | YP_003473406 | 289548418 | Thermocrinis albus |

Aconitase (EC 4.2.1.3) is an iron-sulfur-containing protein catalyzing the reversible isomerization of citrate and isocitrate via the intermediate cis-aconitate. Two aconitase enzymes are encoded in the *E. coli* genome by acnA and acnB. AcnB is the main catabolic enzyme, while AcnA is more stable and appears to be active under conditions of oxidative or acid stress (Cunningham et al., *Microbiology* 143 (Pt 12):3795-3805 (1997)). Two isozymes of aconitase in *Salmonella typhimurium* are encoded by acnA and acnB (Horswill and Escalante-Semerena, *Biochemistry* 40:4703-4713 (2001)). The *S. cerevisiae* aconitase, encoded by ACO1, is localized to the mitochondria where it participates in the TCA cycle (Gangloff et al., *Mol. Cell. Biol.* 10:3551-3561 (1990)) and the cytosol where it participates in the glyoxylate shunt (Regev-Rudzki et al., *Mol. Biol. Cell.* 16:4163-4171 (2005)).

| Protein | GenBank ID | GI Number | Organism |
| --- | --- | --- | --- |
| acnA | AAC7438.1 | 1787531 | Escherichia coli |
| acnB | AAC73229.1 | 2367097 | Escherichia coli |
| acnA | NP_460671.1 | 16765056 | Salmonella typhimurium |
| acnB | NP_459163.1 | 16763548 | Salmonella typhimurium |
| ACO1 | AAA34389.1 | 170982 | Saccharomyces cerevisiae |
| HP0779 | NP_207572.1 | 15645398 | Helicobacter pylori 26695 |
| H16_B0568 | CAJ95365.1 | 113529018 | Ralstonia eutropha |
| DesfrDRAFT_3783 | ZP_07335307.1 | 303249064 | Desulfovibrio fructosovorans JJ |
| Suden_1040 (acnB) | ABB44318.1 | 78497778 | Sulfurimonas denitrificans |
| Hydth_0755 | ADO45152.1 | 308751669 | Hydrogenobacter thermophilus |
| CT0543 (acn) | AAM71785.1 | 21646475 | Chlorobium tepidum |
| Clim_2436 | YP_001944436.1 | 189347907 | Chlorobium limicola |
| Clim_0515 | ACD89607.1 | 189340204 | Chlorobium limicola |

Pyruvate:ferredoxin oxidoreductase (PFOR) catalyzes the reversible oxidation of pyruvate to form acetyl-CoA. The PFOR from *Desulfovibrio africanus* has been cloned and expressed in *E. coli* resulting in an active recombinant enzyme that was stable for several days in the presence of oxygen (Pieulle et al., *J. Bacteriol.* 179:5684-5692 (1997)). Oxygen stability is relatively uncommon in PFORs and is believed to be conferred by a 60 residue extension in the polypeptide chain of the *D. africanus* enzyme. Two cysteine residues in this enzyme form a disulfide bond that protects it against inactivation in the form of oxygen. This disulfide bond and the stability in the presence of oxygen has been found in other *Desulfovibrio* species also (Vita et al., Biochemistry, 47: 957-64 (2008)). The *M. thermoacetica* PFOR is also well characterized (Menon and Ragsdale, *Biochemistry* 36:8484-8494 (1997)) and was shown to have high activity in the direction of pyruvate synthesis during autotrophic growth (Furdui and Ragsdale, *J. Biol. Chem.* 275:28494-28499 (2000)). Further, *E. coli* possesses an uncharacterized open reading frame, ydbK, encoding a protein that is 51% identical to the *M. thermoacetica* PFOR. Evidence for pyruvate oxidoreductase activity in *E. coli* has been described (Blaschkowski et al., *Eur. J. Biochem.* 123:563-569 (1982)). PFORs have also been described in other organisms, including *Rhodobacter capsulatas* (Yakunin and Hallenbeck, Biochimica et Biophysica Acta 1409 (1998) 39-49 (1998)) and *Choloboum tepidum* (Eisen et al., PNAS 99(14): 9509-14 (2002)). The five subunit PFOR from *H. thermophilus*, encoded by porEDABG, was cloned into *E. coli* and shown to function in both the decarboxylating and $CO_2$-assimilating directions (Ikeda et al. 2006; Yamamoto et al., *Extremophiles* 14:79-85 (2010)). Homologs also exist in *C. carboxidivorans* P7. Several additional PFOR enzymes are described in the following review (Ragsdale, S. W., *Chem. Rev.* 103:2333-2346 (2003)). Finally, flavodoxin reductases (e.g., fqrB from *Helicobacter pylori* or *Campylobacter jejuni*) (St Maurice et al., *J. Bacteriol.* 189:4764-4773 (2007)) or Rnf-type proteins (Seedorf et al., *Proc. Natl. Acad. Sci. U.S.A.* 105:2128-2133 (2008); and Herrmann, *J. Bacteriol* 190:784-791 (2008)) provide a means to generate NADH or NADPH from the reduced ferredoxin generated by PFOR. These proteins are identified below.

ide dehydrogenase (E3). This enzyme is naturally present in several organisms, including *E. coli* and *S. cerevisiae*. In the *E. coli* enzyme, specific residues in the E1 component are responsible for substrate specificity (Bisswanger, H., J. Biol. Chem. 256:815-82 (1981); Bremer, J., Eur. J. Biochem. 8:535-540 (1969); Gong et al., J. Biol. Chem. 275:13645-13653 (2000)). Enzyme engineering efforts have improved the *E. coli* PDH enzyme activity under anaerobic conditions (Kim et al., J. Bacteriol. 190:3851-3858 (2008); Kim et al., Appl. Environ. Microbiol. 73:1766-1771 (2007); Zhou et al., Biotechnol. Lett. 30:335-342 (2008)). In contrast to the *E. coli* PDH, the *B. subtilis* complex is active and required for growth under anaerobic conditions (Nakano et al., J. Bacteriol. 179:6749-6755 (1997)). The *Klebsiella pneumoniae* PDH, characterized during growth on glycerol, is also active under anaerobic conditions (5). Crystal structures of the enzyme complex from bovine kidney (18) and the E2 catalytic domain from *Azotobacter vinelandii* are available (4). Yet another enzyme that can catalyze this conversion is pyruvate formate lyase. This enzyme catalyzes the conversion of pyruvate and CoA into acetyl-CoA and formate. Pyruvate formate lyase is a common enzyme in prokaryotic organisms that is used to help modulate anaerobic redox balance. Exemplary enzymes can be found in *Escherichia coli* encoded by pflB (Knappe and Sawers, FEMS. Microbiol Rev. 6:383-398 (1990)), *Lactococcus lactis* (Melchiorsen et al., Appl Microbiol Biotechnol 58:338-344 (2002)), and *Streptococcus mutans* (Takahashi-Abbe et al., Oral. Microbiol Immunol. 18:293-297 (2003)). *E. coli* possesses an additional pyruvate formate lyase, encoded by tdcE, that catalyzes the conversion of pyruvate or 2-oxobutanoate to acetyl-CoA or propionyl-CoA, respectively (Hesslinger et al., Mol. Microbiol. 27:477-

| Protein | GenBank ID | GI Number | Organism |
|---|---|---|---|
| DesfrDRAFT_0121 | ZP_07331646.1 | 303245362 | *Desulfovibrio fructosovorans* JJ |
| Por | CAA70873.1 | 1770208 | *Desulfovibrio africanus* |
| por | YP_012236.1 | 46581428 | *Desulfovibrio vulgaris* str. Hildenborough |
| Dde_3237 | ABB40031.1 | 78220682 | *DesulfoVibrio desulfuricans* G20 |
| Ddes_0298 | YP_002478891.1 | 220903579 | *Desulfovibrio desulfuricans* subsp. *desulfuricans* str. ATCC27774 |
| Por | YP_428946.1 | 83588937 | *Moorella thermoacetica* |
| YdbK | NP_415896.1 | 16129339 | *Escherichia coli* |
| nifJ (CT1628) | NP_662511.1 | 21674446 | *Chlorobium tepidum* |
| CJE1649 | YP_179630.1 | 57238499 | *Campylobacter jejuni* |
| nifJ | ADE85473.1 | 294476085 | *Rhodobacter capsulatus* |
| porE | BAA95603.1 | 7768912 | *Hydrogenobacter thermophilus* |
| porD | BAA95604.1 | 7768913 | *Hydrogenobacter thermophilus* |
| porA | BAA95605.1 | 7768914 | *Hydrogenobacter thermophilus* |
| porB | BAA95606.1 | 776891 | *Hydrogenobacter thermophilus* |
| porG | BAA95607.1 | 7768916 | *Hydrogenobacter thermophilus* |
| FqrB | YP_001482096.1 | 157414840 | *Campylobacter jejuni* |
| HP1164 | NP_207955.1 | 15645778 | *Helicobacter pylori* |
| RnfC | EDK33306.1 | 146346770 | *Clostridium kluyveri* |
| RnfD | EDK33307.1 | 146346771 | *Clostridium kluyveri* |
| RnfG | EDK33308.1 | 146346772 | *Clostridium kluyveri* |
| RnfE | EDK33309.1 | 146346773 | *Clostridium kluyveri* |
| RnfA | EDK33310.1 | 146346774 | *Clostridium kluyveri* |
| RnfB | EDK33311.1 | 146346775 | *Clostridium kluyveri* |

The conversion of pyruvate into acetyl-CoA can be catalyzed by several other enzymes or their combinations thereof. For example, pyruvate dehydrogenase can transform pyruvate into acetyl-CoA with the concomitant reduction of a molecule of NAD into NADH. It is a multi-enzyme complex that catalyzes a series of partial reactions which results in acylating oxidative decarboxylation of pyruvate. The enzyme comprises of three subunits: the pyruvate decarboxylase (E1), dihydrolipoamide acyltransferase (E2) and dihydrolipoam- 492 (1998)). Both pflB and tdcE from *E. coli* require the presence of pyruvate formate lyase activating enzyme, encoded by pflA. Further, a short protein encoded by yfiD in *E. coli* can associate with and restore activity to oxygen-cleaved pyruvate formate lyase (Vey et al., Proc. Natl. Acad. Sci. U.S.A. 105:16137-16141 (2008). Note that pflA and pflB from *E. coli* were expressed in *S. cerevisiae* as a means to increase cytosolic acetyl-CoA for butanol production as described in WO/2008/080124]. Additional pyruvate formate lyase and activating enzyme candidates, encoded by pfl and act, respectively, are found in *Clostridium pasteurianum* (Weidner et al., J. Bacteriol. 178:2440-2444 (1996)).

Further, different enzymes can be used in combination to convert pyruvate into acetyl-CoA. For example, in *S. cerevisiae*, acetyl-CoA is obtained in the cytosol by first decarboxylating pyruvate to form acetaldehyde; the latter is oxidized to acetate by acetaldehyde dehydrogenase and subsequently activated to form acetyl-CoA by acetyl-CoA synthetase. Acetyl-CoA synthetase is a native enzyme in several other organisms including *E. coli* (Kumari et al., J. Bacteriol. 177: 2878-2886 (1995)), *Salmonella enterica* (Starai et al., Microbiology 151:3793-3801 (2005); Starai et al., J. Biol. Chem. 280:26200-26205 (2005)), and *Moorella thermoacetica* (described already). Alternatively, acetate can be activated to form acetyl-CoA by acetate kinase and phosphotransacetylase. Acetate kinase first converts acetate into acetyl-phosphate with the accompanying use of an ATP molecule. Acetyl-phosphate and CoA are next converted into acetyl-CoA with the release of one phosphate by phosphotransacetylase. Both acetate kinase and phosphotransacetylase are well-studied enzymes in several *Clostridia* and *Methanosarcina thermophile*.

Yet another way of converting pyruvate to acetyl-CoA is via pyruvate oxidase. Pyruvate oxidase converts pyruvate into acetate, using ubiquione as the electron acceptor. In *E. coli*, this activity is encoded by poxB. PoxB has similarity to pyruvate decarboxylase of *S. cerevisiae* and *Zymomonas mobilis*. The enzyme has a thiamin pyrophosphate cofactor (Koland and Gennis, Biochemistry 21:4438-4442 (1982)); O'Brien et al., Biochemistry 16:3105-3109 (1977); O'Brien and Gennis, J. Biol. Chem. 255:3302-3307 (1980)) and a flavin adenine dinucleotide (FAD) cofactor. Acetate can then be converted into acetyl-CoA by either acetyl-CoA synthetase or by acetate kinase and phosphotransacetylase, as described earlier. Some of these enzymes can also catalyze the reverse reaction from acetyl-CoA to pyruvate.

For enzymes that use reducing equivalents in the form of NADH or NADPH, these reduced carriers can be generated by transferring electrons from reduced ferredoxin. Two enzymes catalyze the reversible transfer of electrons from reduced ferredoxins to $NAD(P)^+$, ferredoxin:$NAD^+$ oxidoreductase (EC 1.18.1.3) and ferredoxin:$NADP^+$ oxidoreductase (FNR, EC 1.18.1.2). Ferredoxin:$NADP^+$ oxidoreductase (FNR, EC 1.18.1.2) has a noncovalently bound FAD cofactor that facilitates the reversible transfer of electrons from NADPH to low-potential acceptors such as ferredoxins or flavodoxins (Blaschkowski et al., Eur. J. Biochem. 123:563-569 (1982); Fujii et al., 1977). The *Helicobacter pylori* FNR, encoded by HP1164 (fqrB), is coupled to the activity of pyruvate:ferredoxin oxidoreductase (PFOR) resulting in the pyruvate-dependent production of NADPH (St et al. 2007). An analogous enzyme is found in *Campylobacter jejuni* (St et al. 2007). A ferredoxin:$NADP^+$ oxidoreductase enzyme is encoded in the *E. coli* genome by fpr (Bianchi et al. 1993). Ferredoxin:$NAD^+$ oxidoreductase utilizes reduced ferredoxin to generate NADH from $NAD^+$. In several organisms, including *E. coli*, this enzyme is a component of multifunctional dioxygenase enzyme complexes. The ferredoxin:$NAD^+$ oxidoreductase of *E. coli*, encoded by hcaD, is a component of the 3-phenylproppionate dioxygenase system involved in involved in aromatic acid utilization (Diaz et al. 1998). NADH:ferredoxin reductase activity was detected in cell extracts of *Hydrogenobacter thermophilus* strain TK-6, although a gene with this activity has not yet been indicated (Yoon et al. 2006). Finally, the energy-conserving membrane-associated Rnf-type proteins (Seedorf et al., Proc. Natl. Acad. Sci. U.S.A. 105:2128-2133 (2008); Herrmann et al., J. Bacteriol. 190:784-791 (2008)) provide a means to generate NADH or NADPH from reduced ferredoxin. Additional ferredoxin:NAD(P)+ oxidoreductases have been annotated in *Clostridium carboxydivorans* P7.

| Protein | GenBank ID | GI Number | Organism |
|---|---|---|---|
| HP1164 | NP_207955.1 | 15645778 | *Helicobacter pylori* |
| RPA3954 | CAE29395.1 | 39650872 | *Rhodopseudomonas palustris* |
| fpr | BAH29712.1 | 225320633 | *Hydrogenobacter thermophilus* |
| yumC | NP_391091.2 | 255767736 | *Bacillus subtilis* |
| CJE0663 | AAW35824.1 | 57167045 | *Campylobacter jejuni* |
| fpr | P28861.4 | 399486 | *Escherichia coli* |
| hcaD | AAC75595.1 | 1788892 | *Escherichia coli* |
| LOC100282643 | NP_001149023.1 | 226497434 | *Zea mays* |
| RnfC | EDK33306.1 | 146346770 | *Clostridium kluyveri* |
| RnfD | EDK33307.1 | 146346771 | *Clostridium kluyveri* |
| RnfG | EDK33308.1 | 146346772 | *Clostridium kluyveri* |
| RnfE | EDK33309.1 | 146346773 | *Clostridium kluyveri* |
| RnfA | EDK33310.1 | 146346774 | *Clostridium kluyveri* |
| RnfB | EDK33311.1 | 146346775 | *Clostridium kluyveri* |
| CcarbDRAFT_2639 | ZP_05392639.1 | 255525707 | *Clostridium carboxidivorans* P7 |
| CcarbDRAFT_2638 | ZP_05392638.1 | 255525706 | *Clostridium carboxidivorans* P7 |
| CcarbDRAFT_2636 | ZP_05392636.1 | 255525704 | *Clostridium carboxidivorans* P7 |
| CcarbDRAFT_5060 | ZP_05395060.1 | 255528241 | *Clostridium carboxidivorans* P7 |
| CcarbDRAFT_2450 | ZP_05392450.1 | 255525514 | *Clostridium carboxidivorans* P7 |
| CcarbDRAFT_1084 | ZP_05391084.1 | 255524124 | *Clostridium carboxidivorans* P7 |

Ferredoxins are small acidic proteins containing one or more iron-sulfur clusters that function as intracellular electron carriers with a low reduction potential. Reduced ferredoxins donate electrons to Fe-dependent enzymes such as ferredoxin-$NADP^+$ oxidoreductase, pyruvate:ferredoxin oxidoreductase (PFOR) and 2-oxoglutarate:ferredoxin oxidoreductase (OFOR). The *H. thermophilus* gene fdx1 encodes a [4Fe-4S]-type ferredoxin that is required for the reversible carboxylation of 2-oxoglutarate and pyruvate by OFOR and PFOR, respectively (Yamamoto et al., Extremophiles 14:79-85 (2010)). The ferredoxin associated with the *Sulfolobus solfataricus* 2-oxoacid:ferredoxin reductase is a monomeric dicluster [3Fe-4S][4Fe-4S] type ferredoxin (Park et al. 2006). While the gene associated with this protein has not been fully sequenced, the N-terminal domain shares 93% homology with the zfx ferredoxin from *S. acidocaldarius*. The *E. coli* genome encodes a soluble ferredoxin of unknown physiological function, fdx. Some evidence indicates that this protein can function in iron-sulfur cluster assembly (Takahashi and Nakamura, 1999). Additional ferredoxin proteins have been characterized in *Helicobacter pylori* (Mukhopadhyay et al. 2003) and *Campylobacter jejuni* (van Vliet et al. 2001). A 2Fe-2S ferredoxin from *Clostridium pasteurianum* has been cloned and expressed in *E. coli* (Fujinaga and Meyer, Biochemical and Biophysical Research Communications, 192(3): (1993)). Acetogenic bacteria such as *Moorella thermoacetica, Clostridium carboxidivorans* P7 and *Rhodospirillum rubrum* are predicted to encode several ferredoxins, listed below.

nosoma brucei (Riviere et al. 2004). The succinyl-CoA:acetate CoA-transferase from *Acetobacter aceti*, encoded by aarC, replaces succinyl-CoA synthetase in a variant TCA cycle (Mullins et al. 2008). Similar succinyl-CoA transferase activities are also present in *Trichomonas vaginalis* (van Grinsven et al. 2008), *Trypanosoma brucei* (Riviere et al. 2004) and *Clostridium kluyveri* (Sohling and Gottschalk, 1996c). The beta-ketoadipate:succinyl-CoA transferase encoded by pcaI and pcaJ in *Pseudomonas putida* is yet another candidate (Kaschabek et al. 2002). The aforementioned proteins are identified below.

| Protein | GenBank ID | GI Number | Organism |
| --- | --- | --- | --- |
| fdx1 | BAE02673.1 | 68163284 | *Hydrogenobacter thermophilus* |
| M11214.1 | AAA83524.1 | 144806 | *Clostridium pasteurianum* |
| Zfx | AAY79867.1 | 68566938 | *Sulfolobus acidocalarius* |
| Fdx | AAC75578.1 | 1788874 | *Escherichia coli* |
| hp_0277 | AAD07340.1 | 2313367 | *Helicobacter pylori* |
| fdxA | CAL34484.1 | 112359698 | *Campylobacter jejuni* |
| Moth_0061 | ABC18400.1 | 83571848 | *Moorella thermoacetica* |
| Moth_1200 | ABC19514.1 | 83572962 | *Moorella thermoacetica* |
| Moth_1888 | ABC20188.1 | 83573636 | *Moorella thermoacetica* |
| Moth_2112 | ABC20404.1 | 83573852 | *Moorella thermoacetica* |
| Moth_1037 | ABC19351.1 | 83572799 | *Moorella thermoacetica* |
| CcarbDRAFT_4383 | ZP_05394383.1 | 255527515 | *Clostridium carboxidivorans* P7 |
| CcarbDRAFT_2958 | ZP_05392958.1 | 255526034 | *Clostridium carboxidivorans* P7 |
| CcarbDRAFT_2281 | ZP_05392281.1 | 255525342 | *Clostridium carboxidivorans* P7 |
| CcarbDRAFT_5296 | ZP_05395295.1 | 255528511 | *Clostridium carboxidivorans* P7 |
| CcarbDRAFT_1615 | ZP_05391615.1 | 255524662 | *Clostridium carboxidivorans* P7 |
| CcarbDRAFT_1304 | ZP_05391304.1 | 255524347 | *Clostridium carboxidivorans* P7 |
| cooF | AAG29808.1 | 11095245 | *Carboxydothermus hydrogenoformans* |
| fdxN | CAA35699.1 | 46143 | *Rhodobacter capsulatus* |
| Rru_A2264 | ABC23064.1 | 83576513 | *Rhodospirillum rubrum* |
| Rru_A1916 | ABC22716.1 | 83576165 | *Rhodospirillum rubrum* |
| Rru_A2026 | ABC22826.1 | 83576275 | *Rhodospirillum rubrum* |
| cooF | AAC45122.1 | 1498747 | *Rhodospirillum rubrum* |
| fdxN | AAA26460.1 | 152605 | *Rhodospirillum rubrum* |
| Alvin_2884 | ADC63789.1 | 288897953 | *Allochromatium vinosum* DSM 180 |
| fdx | YP_002801146.1 | 226946073 | *Azotobacter vinelandii* DJ |
| CKL_3790 | YP_001397146.1 | 153956381 | *Clostridium kluyveri* DSM 555 |
| fer1 | NP_949965.1 | 39937689 | *Rhodopseudomonas palustris* CGA009 |
| fdx | CAA12251.1 | 3724172 | *Thauera aromatica* |
| CHY_2405 | YP_361202.1 | 78044690 | *Carboxydothermus hydrogenoformans* |
| fer | YP_359966.1 | 78045103 | *Carboxydothermus hydrogenoformans* |
| fer | AAC83945.1 | 1146198 | *Bacillus subtilis* |
| fdx1 | NP_249053.1 | 15595559 | *Pseudomonas aeruginosa* PA01 |
| yfhL | AP_003148.1 | 89109368 | *Escherichia coli* K-12 |

Succinyl-CoA transferase catalyzes the conversion of succinyl-CoA to succinate while transferring the CoA moiety to a CoA acceptor molecule. Many transferases have broad specificity and can utilize CoA acceptors as diverse as acetate, succinate, propionate, butyrate, 2-methylacetoacetate, 3-ketohexanoate, 3-ketopentanoate, valerate, crotonate, 3-mercaptopropionate, propionate, vinylacetate, and butyrate, among others.

The conversion of succinate to succinyl-CoA can be carried by a transferase which does not require the direct consumption of an ATP or GTP. This type of reaction is common in a number of organisms. The conversion of succinate to succinyl-CoA can also be catalyzed by succinyl-CoA:Acetyl-CoA transferase. The gene product of cat1 of *Clostridium kluyveri* has been shown to exhibit succinyl-CoA:acetyl-CoA transferase activity (Sohling and Gottschalk, J. Bacteriol. 178:871-880 (1996)). In addition, the activity is present in *Trichomonas vaginalis* (van Grinsven et al. 2008) and *Trypa-*

| Protein | GenBank ID | GI Number | Organism |
| --- | --- | --- | --- |
| cat1 | P38946.1 | 729048 | *Clostridium kluyveri* |
| TVAG_395550 | XP_001330176 | 123975034 | *Trichomonas vaginalis* G3 |
| Tb11.02.0290 | XP_828352 | 71754875 | *Trypanosoma brucei* |
| pcaI | AAN69545.1 | 24985644 | *Pseudomonas putida* |
| pcaJ | NP_746082.1 | 26990657 | *Pseudomonas putida* |
| aarC | ACD85596.1 | 189233555 | *Acetobacter aceti* |

An additional exemplary transferase that converts succinate to succinyl-CoA while converting a 3-ketoacyl-CoA to a 3-ketoacid is succinyl-CoA:3:ketoacid-CoA transferase (EC 2.8.3.5). Exemplary succinyl-CoA:3:ketoacid-CoA transferases are present in *Helicobacter pylori* (Corthesy-Theulaz et al. 1997), *Bacillus subtilis*, and *Homo sapiens* (Fukao et al. 2000; Tanaka et al. 2002). The aforementioned proteins are identified below.

| Protein | GenBank ID | GI Number | Organism |
|---|---|---|---|
| HPAG1_0676 | YP_627417 | 108563101 | Helicobacter pylori |
| HPAG1_0677 | YP_627418 | 108563102 | Helicobacter pylori |
| ScoA | NP_391778 | 16080950 | Bacillus subtilis |
| ScoB | NP_391777 | 16080949 | Bacillus subtilis |
| OXCT1 | NP_000427 | 4557817 | Homo sapiens |
| OXCT2 | NP_071403 | 11545841 | Homo sapiens |

Converting succinate to succinyl-CoA by succinyl-CoA:3-ketoacid-CoA transferase requires the simultaneous conversion of a 3-ketoacyl-CoA such as acetoacetyl-CoA to a 3-ketoacid such as acetoacetate. Conversion of a 3-ketoacid back to a 3-ketoacyl-CoA can be catalyzed by an acetoacetyl-CoA:acetate:CoA transferase. Acetoacetyl-CoA:acetate:CoA transferase converts acetoacetyl-CoA and acetate to acetoacetate and acetyl-CoA, or vice versa. Exemplary enzymes include the gene products of atoAD from E. coli (Hanai et al., Appl Environ Microbiol 73:7814-7818 (2007), ctfAB from C. acetobutylicum (Jojima et al., Appl Microbiol Biotechnol 77:1219-1224 (2008), and ctfAB from Clostridium saccharoperbutylacetonicum (Kosaka et al., Biosci. Biotechnol Biochem. 71:58-68 (2007)) are shown below.

| Protein | GenBank ID | GI Number | Organism |
|---|---|---|---|
| AtoA | NP_416726.1 | 2492994 | Escherichia coli |
| AtoD | NP_416725.1 | 2492990 | Escherichia coli |
| CtfA | NP_149326.1 | 15004866 | Clostridium acetobutylicum |
| CtfB | NP_149327.1 | 15004867 | Clostridium acetobutylicum |
| CtfA | AAP42564.1 | 31075384 | Clostridium saccharoperbutylacetonicum |
| CtfB | AAP42565.1 | 31075385 | Clostridium saccharoperbutylacetonicum |

Yet another possible CoA acceptor is benzylsuccinate. Succinyl-CoA:(R)-Benzylsuccinate CoA-Transferase functions as part of an anaerobic degradation pathway for toluene in organisms such as Thauera aromatics (Leutwein and Heider, J. Bact. 183(14) 4288-4295 (2001)). Homologs can be found in Azoarcus sp. T, Aromatoleum aromaticum EbN1, and Geobacter metallireducens GS-15. The aforementioned proteins are identified below.

| Protein | GenBank ID | GI Number | Organism |
|---|---|---|---|
| bbsE | AAF89840 | 9622535 | Thauera aromatic |
| Bbsf | AAF89841 | 9622536 | Thauera aromatic |
| bbsE | AAU45405.1 | 52421824 | Azoarcus sp. T |
| bbsF | AAU45406.1 | 52421825 | Azoarcus sp. T |
| bbsE | YP_158075.1 | 56476486 | Aromatoleum aromaticum EbN1 |
| bbsF | YP_158074.1 | 56476485 | Aromatoleum aromaticum EbN1 |
| Gmet_1521 | YP_384480.1 | 78222733 | Geobacter metallireducens GS-15 |
| Gmet_1522 | YP_384481.1 | 78222734 | Geobacter metallireducens GS-15 |

Additionally, yell encodes a propionyl CoA:succinate CoA transferase in E. coli (Haller et al., Biochemistry, 39(16) 4622-4629). Close homologs can be found in, for example, Citrobacter youngae ATCC 29220, Salmonella enterica subsp. arizonae serovar, and Yersinia intermedia ATCC 29909. The aforementioned proteins are identified below.

| Protein | GenBank ID | GI Number | Organism |
|---|---|---|---|
| ygfH | NP_417395.1 | 16130821 | Escherichia coli str. K-12 substr. MG1655 |
| CIT292_04485 | ZP_03838384.1 | 227334728 | Citrobacter youngae ATCC 29220 |
| SARI_04582 | YP_001573497.1 | 161506385 | Salmonella enterica subsp. arizonae serovar |
| yinte0001_14430 | ZP_04635364.1 | 238791727 | Yersinia intermedia ATCC 29909 |

Citrate lyase (EC 4.1.3.6) catalyzes a series of reactions resulting in the cleavage of citrate to acetate and oxaloacetate. The enzyme is active under anaerobic conditions and is composed of three subunits: an acyl-carrier protein (ACP, gamma), an ACP transferase (alpha), and a acyl lyase (beta). Enzyme activation uses covalent binding and acetylation of an unusual prosthetic group, 2'-(5"-phosphoribosyl)-3-'-dephospho-CoA, which is similar in structure to acetyl-CoA. Acylation is catalyzed by CitC, a citrate lyase synthetase. Two additional proteins, CitG and CitX, are used to convert the apo enzyme into the active holo enzyme (Schneider et al., Biochemistry 39:9438-9450 (2000)). Wild type E. coli does not have citrate lyase activity; however, mutants deficient in molybdenum cofactor synthesis have an active citrate lyase (Clark, FEMS Microbiol. Lett. 55:245-249 (1990)). The E. coli enzyme is encoded by citEFD and the citrate lyase synthetase is encoded by citC (Nilekani and SivaRaman, Biochemistry 22:4657-4663 (1983)). The Leuconostoc mesenteroides citrate lyase has been cloned, characterized and expressed in E. coli (Bekal et al., J. Bacteriol. 180:647-654 (1998)). Citrate lyase enzymes have also been identified in enterobacteria that utilize citrate as a carbon and energy source, including Salmonella typhimurium and Klebsiella pneumoniae (Bott, Arch. Microbiol. 167: 78-88 (1997); Bott and Dimroth, Mol. Microbiol. 14:347-356 (1994)). The aforementioned proteins are tabulated below.

| Protein | GenBank ID | GI Number | Organism |
|---|---|---|---|
| citF | AAC73716.1 | 1786832 | Escherichia coli |
| Cite | AAC73717.2 | 87081764 | Escherichia coli |
| citD | AAC73718.1 | 1786834 | Escherichia coli |
| citC | AAC73719.2 | 87081765 | Escherichia coli |
| citG | AAC73714.1 | 1786830 | Escherichia coli |
| citX | AAC73715.1 | 1786831 | Escherichia coli |
| citF | CAA71633.1 | 2842397 | Leuconostoc mesenteroides |
| Cite | CAA71632.1 | 2842396 | Leuconostoc mesenteroides |
| citD | CAA71635.1 | 2842395 | Leuconostoc mesenteroides |
| citC | CAA71636.1 | 3413797 | Leuconostoc mesenteroides |
| citG | CAA71634.1 | 2842398 | Leuconostoc mesenteroides |
| citX | CAA71634.1 | 2842398 | Leuconostoc mesenteroides |
| citF | NP_459613.1 | 16763998 | Salmonella typhimurium |
| cite | AAL19573.1 | 16419133 | Salmonella typhimurium |
| citD | NP_459064.1 | 16763449 | Salmonella typhimurium |
| citC | NP_459616.1 | 16764001 | Salmonella typhimurium |
| citG | NP_459611.1 | 16763996 | Salmonella typhimurium |
| citX | NP_459612.1 | 16763997 | Salmonella typhimurium |
| citF | CAA56217.1 | 565619 | Klebsiella pneumoniae |
| cite | CAA56216.1 | 565618 | Klebsiella pneumoniae |
| citD | CAA56215.1 | 565617 | Klebsiella pneumoniae |
| citC | BAH66541.1 | 238774045 | Klebsiella pneumoniae |
| citG | CAA56218.1 | 565620 | Klebsiella pneumoniae |
| citX | AAL60463.1 | 18140907 | Klebsiella pneumoniae |

Acetate kinase (EC 2.7.2.1) catalyzes the reversible ATP-dependent phosphorylation of acetate to acetylphosphate. Exemplary acetate kinase enzymes have been characterized in many organisms including E. coli, Clostridium acetobutylicum and Methanosarcina thermophile (Ingram-Smith et al., J. Bacteriol. 187:2386-2394 (2005); Fox and Roseman, J. Biol. Chem. 261:13487-13497 (1986); Winzer et al., Microbioloy 143 (Pt 10):3279-3286 (1997)). Acetate kinase activity has also been demonstrated in the gene product of E. coli purT (Marolewski et al., Biochemistry 33:2531-2537 (1994). Some butyrate kinase enzymes (EC 2.7.2.7), for example buk1 and buk2 from Clostridium acetobutylicum, also accept acetate as a substrate (Hartmanis, M. G., J. Biol. Chem. 262:617-621 (1987)).

| Protein | GenBank ID | GI Number | Organism |
| --- | --- | --- | --- |
| ackA | NP_416799.1 | 16130231 | Escherichia coli |
| Ack | AAB18301.1 | 1491790 | Clostridium acetobutylicum |
| Ack | AAA72042.1 | 349834 | Methanosarcina thermophila |
| purT | AAC74919.1 | 1788155 | Escherichia coli |
| buk1 | NP_349675 | 15896326 | Clostridium acetobutylicum |
| buk2 | Q97II1 | 20137415 | Clostridium acetobutylicum |

The formation of acetyl-CoA from acetylphosphate is catalyzed by phosphotransacetylase (EC 2.3.1.8). The pta gene from E. coli encodes an enzyme that reversibly converts acetyl-CoA into acetyl-phosphate (Suzuki, T., Biochim. Biophys. Acta 191:559-569 (969)). Additional acetyltransferase enzymes have been characterized in Bacillus subtilis (Rado and Hoch, Biochim. Biophys. Acta 321:114-125 (1973), Clostridium kluyveri (Stadtman, E., Methods Enzymol. 1:5896-599 (1955), and Thermotoga maritima (Bock et al., J. Bacteriol. 181:1861-1867 (1999)). This reaction is also catalyzed by some phosphotranbutyrylase enzymes (EC 2.3.1.19) including the ptb gene products from Clostridium acetobutylicum (Wiesenborn et al., App. Environ. Microbiol. 55:317-322 (1989); Walter et al., Gene 134:107-111 (1993)). Additional ptb genes are found in butyrate-producing bacterium L2-50 (Louis et al., J. Bacteriol. 186:2099-2106 (2004) and Bacillus megaterium (Vazquez et al., Curr. Microbiol. 42:345-349 (2001).

| Protein | GenBank ID | GI Number | Organism |
| --- | --- | --- | --- |
| Pta | NP_1416800.1 | 71152910 | Escherichia coli |
| Pta | P39646 | 730415 | Bacillus subtilis |
| Pta | A5N801 | 146346896 | Clostridium kluyveri |
| Pta | Q9X0L4 | 6685776 | Thermotoga maritima |
| Ptb | NP_349676 | 34540484 | Clostridium acetobutylicum |
| Ptb | AAR19757.1 | 38425288 | butyrate-producing bacterium L2-50 |
| Ptb | CAC07932.1 | 10046659 | Bacillus megaterium |

The acylation of acetate to acetyl-CoA is catalyzed by enzymes with acetyl-CoA synthetase activity. Two enzymes that catalyze this reaction are AMP-forming acetyl-CoA synthetase (EC 6.2.1.1) and ADP-forming acetyl-CoA synthetase (EC 6.2.1.13). AMP-forming acetyl-CoA synthetase (ACS) is the predominant enzyme for activation of acetate to acetyl-CoA. Exemplary ACS enzymes are found in E. coli (Brown et al., J. Gen. Microbiol. 102:327-336 (1977)), Ralstonia eutropha (Priefert and Steinbuchel, J. Bacteriol. 174: 6590-6599 (1992)), Methanothermobacter thermautotrophicus (Ingram-Smith and Smith, Archaea 2:95-107 (2007)), Salmonella enterica (Gulick et al., Biochemistry 42:2866-2873 (2003)) and Saccharomyces cerevisiae (Jogl and Tong, Biochemistry 43:1425-1431 (2004)). ADP-forming acetyl-CoA synthetases are reversible enzymes with a generally broad substrate range (Musfeldt and Schonheit, J. Bacteriol. 184:636-644 (2002)). Two isozymes of ADP-forming acetyl-CoA synthetases are encoded in the Archaeoglobus fulgidus genome by are encoded by AF1211 and AF1983 (Musfeldt and Schonheit, supra (2002)). The enzyme from Haloarcula marismortui (annotated as a succinyl-CoA synthetase) also accepts acetate as a substrate and reversibility of the enzyme was demonstrated (Brasen and Schonheit, Arch. Microbiol. 182:277-287 (2004)). The ACD encoded by PAE3250 from hyperthermophilic crenarchaeon Pyrobaculum aerophilum showed the broadest substrate range of all characterized ACDs, reacting with acetate, isobutyryl-CoA (preferred substrate) and phenylacetyl-CoA (Brasen and Schonheit, supra (2004)). Directed evolution or engineering can be used to modify this enzyme to operate at the physiological temperature of the host organism. The enzymes from A. fulgidus, H. marismortui and P. aerophilum have all been cloned, functionally expressed, and characterized in E. coli (Brasen and Schonheit, supra (2004); Musfeldt and Schonheit, supra (2002)). Additional candidates include the succinyl-CoA synthetase encoded by sucCD in E. coli (Buck et al., Biochemistry 24:6245-6252 (1985)) and the acyl-CoA ligase from Pseudomonas putida (Fernandez-Valverde et al., Appl. Environ. Microbiol. 59:1149-1154 (1993)). The aforementioned proteins are tabulated below.

| Protein | GenBank ID | GI Number | Organism |
| --- | --- | --- | --- |
| acs | AAC77039.1 | 1790505 | Escherichia coli |
| acoE | AAA21945.1 | 141890 | Ralstonia eutropha |
| acs1 | ABC87079.1 | 86169671 | Methanothermobacter thermautotrophicus |
| acs1 | AAL23099.1 | 16422835 | Salmonella enterica |
| ACS1 | Q01574.2 | 257050994 | Saccharomyces cerevisiae |
| AF1211 | NP_070039.1 | 11498810 | Archaeoglobus fulgidus |
| AF1983 | NP_070807.1 | 11499565 | Archaeoglobus fulgidus |
| scs | YP_135572.1 | 55377722 | Haloarcula marismortui |
| PAE3250 | NP_560604.1 | 18313937 | Pyrobaculum aerophilum str. IM2 |
| sucC | NP_415256.1 | 16128703 | Escherichia coli |
| sucD | AAC73823.1 | 1786949 | Escherichia coli |
| paaF | AAC24333.2 | 22711873 | Pseudomonas putida |

The product yields per C-mol of substrate of microbial cells synthesizing reduced fermentation products such as methacrylic acid, methacrylate ester, 3-hydroxyisobutyrate and/or 2-hydroxyisobutyrate, are limited by insufficient reducing equivalents in the carbohydrate feedstock. Reducing equivalents, or electrons, can be extracted from synthesis gas components such as CO and $H_2$ using carbon monoxide dehydrogenase (CODH) and hydrogenase enzymes, respectively. The reducing equivalents are then passed to acceptors such as oxidized ferredoxins, oxidized quinones, oxidized cytochromes, NAD(P)+, water, or hydrogen peroxide to form reduced ferredoxin, reduced quinones, reduced cytochromes, NAD(P)H, $H_2$, or water, respectively. Reduced ferredoxin and NAD(P)H are particularly useful as they can serve as redox carriers for various Wood-Ljungdahl pathway and reductive TCA cycle enzymes.

Additional redox availability from CO and/or $H_2$ can improve the yields of reduced products such as methacrylic acid, methacrylate ester, 3-hydroxyisobutyrate and/or 2-hydroxyisobutyrate. The maximum theoretical yield to produce methacrylic acid, methacrylate ester, 3-hydroxyisobutyrate and/or 2-hydroxyisobutyrate from glucose is 1.33 mole MAA per mole of glucose under aerobic conditions via the pathways disclosed herein:

$$C_6H_{12}O_6 \rightarrow 1.33 C_4H_6O_2 + 0.67 CO_2 + 2H_2O$$

When both feedstocks of sugar and syngas are available, the syngas components CO and $H_2$ can be utilized to generate reducing equivalents by employing the hydrogenase and CO dehydrogenase. The reducing equivalents generated from syngas components will be utilized to power the glucose to methacrylic acid, methacrylate ester, 3-hydroxyisobutyrate and/or 2-hydroxyisobutyrate production pathways. Theoretically, all carbons in glucose will be conserved, thus resulting in a maximal theoretical yield to produce methacrylic acid, methacrylate ester, 3-hydroxyisobutyrate and/or 2-hydroxyisobutyrate from glucose at 2 mol methacrylic acid, methacrylate ester, 3-hydroxyisobutyrate and/or 2-hydroxyisobutyrate per mol of glucose under either aerobic or anaerobic conditions as described herein.

$$1C_6H_{12}O_6 + 2CO_2 + 6H_2 \rightarrow 2C_4H_6O_2 + 6H_2O$$

Or $$1C_6H_{12}O_6 + 2CO + 4H_2 \rightarrow 2C_4H_6O_2 + 4H_2O$$

As shown in above example, a combined feedstock strategy where syngas is combined with a sugar-based feedstock or other carbon substrate can greatly improve the theoretical yields. In this co-feeding approach, syngas components $H_2$ and CO can be utilized by the hydrogenase and CO dehydrogenase to generate reducing equivalents, that can be used to power chemical production pathways in which the carbons from sugar or other carbon substrates will be maximally conserved and the theoretical yields improved. In case of methacrylic acid, methacrylate ester, 3-hydroxyisobutyrate and/or 2-hydroxyisobutyrate production from glucose or sugar, the theoretical yields improve from 1.33 mol methacrylic acid, methacrylate ester, 3-hydroxyisobutyrate and/or 2-hydroxyisobutyrate per mol of glucose to 2 mol methacrylic acid, methacrylate ester, 3-hydroxyisobutyrate and/or 2-hydroxyisobutyrate per mol of glucose. Such improvements provide environmental and economic benefits and greatly enhance sustainable chemical production.

Herein the enzymes and the corresponding genes used for extracting redox from syngas components are described. CODH is a reversible enzyme that interconverts CO and $CO_2$ at the expense or gain of electrons. The natural physiological role of the CODH in ACS/CODH complexes is to convert $CO_2$ to CO for incorporation into acetyl-CoA by acetyl-CoA synthase. Nevertheless, such CODH enzymes are suitable for the extraction of reducing equivalents from CO due to the reversible nature of such enzymes. Expressing such CODH enzymes in the absence of ACS allows them to operate in the direction opposite to their natural physiological role (i.e., CO oxidation).

In *M. thermoacetica, C. hydrogenoformans, C. carboxidivorans* P7, and several other organisms, additional CODH encoding genes are located outside of the ACS/CODH operons. These enzymes provide a means for extracting electrons (or reducing equivalents) from the conversion of carbon monoxide to carbon dioxide. The *M. thermoacetica* gene (Genbank Accession Number: YP_430813) is expressed by itself in an operon and is believed to transfer electrons from CO to an external mediator like ferredoxin in a "Ping-pong" reaction. The reduced mediator then couples to other reduced nicotinamide adenine dinucleotide phosphate (NAD(P)H) carriers or ferredoxin-dependent cellular processes (Ragsdale, *Annals of the New York Academy of Sciences* 1125: 129-136 (2008)). The genes encoding the *C. hydrogenoformans* CODH-II and CooF, a neighboring protein, were cloned and sequenced (Gonzalez and Robb, *FEMS Microbiol Lett.* 191:243-247 (2000)). The resulting complex was membrane-bound, although cytoplasmic fractions of CODH-II were shown to catalyze the formation of NADPH suggesting an anabolic role (Svetlitchnyi et al., *J Bacteriol.* 183:5134-5144 (2001)). The crystal structure of the CODH-II is also available (Dobbek et al., *Science* 293:1281-1285 (2001)). Similar ACS-free CODH enzymes can be found in a diverse array of organisms including *Geobacter metallireducens* GS-15, *Chlorobium phaeobacteroides* DSM 266, *Clostridium cellulolyticum* H10, *Desulfovibrio desulfuricans* subsp. *desulfuricans* str. ATCC 27774, *Pelobacter carbinolicus* DSM 2380, and *Campylobacter curvus* 525.92.

| Protein | GenBank ID | GI Number | Organism |
|---|---|---|---|
| CODH (putative) | YP_430813 | 83590804 | Moorella thermoacetica |
| CODH-II (CooS-II) | YP_358957 | 78044574 | Carboxydothermus hydrogenoformans |
| CooF | YP_358958 | 78045112 | Carboxydothermus hydrogenoformans |
| CODH (putative) | ZP_05390164.1 | 255523193 | Clostridium carboxidivorans P7 |
| CcarbDRAFT_0341 | ZP_05390341.1 | 255523371 | Clostridium carboxidivorans P7 |
| CcarbDRAFT_1756 | ZP_05391756.1 | 255524806 | Clostridium carboxidivorans P7 |
| CcarbDRAFT_2944 | ZP_05392944.1 | 255526020 | Clostridium carboxidivorans P7 |
| CODH | YP_384856.1 | 78223109 | Geobacter metallireducens GS-15 |
| Cpha266_0148 (cytochrome c) | YP_910642.1 | 119355998 | Chlorobium phaeobacteroides DSM 266 |
| Cpha266_0149 (CODH) | YP_910643.1 | 119355999 | Chlorobium phaeobacteroides DSM 266 |
| Ccel_0438 | YP_002504800.1 | 220927891 | Clostridium cellulolyticum H10 |
| Ddes_0382 (CODH) | YP_002478973.1 | 220903661 | Desulfovibrio desulfuricans subsp. desulfuricans str. ATCC 27774 |
| Ddes_0381 (CooC) | YP_002478972.1 | 220903660 | Desulfovibrio desulfuricans subsp. desulfuricans str. ATCC 27774 |
| Pcar_0057 (CODH) | YP_355490.1 | 7791767 | Pelobacter carbinolicus DSM 2380 |
| Pcar_0058 (CooC) | YP_355491.1 | 7791766 | Pelobacter carbinolicus DSM 2380 |
| Pcar_0058 (HypA) | YP_355492.1 | 7791765 | Pelobacter carbinolicus DSM 2380 |
| CooS (CODH) | YP_001407343.1 | 154175407 | Campylobacter curvus 525.92 |

In some cases, hydrogenase encoding genes are located adjacent to a CODH. In *Rhodospirillum rubrum*, the encoded CODH/hydrogenase proteins form a membrane-bound enzyme complex that has been indicated to be a site where energy, in the form of a proton gradient, is generated from the conversion of CO and $H_2O$ to $CO_2$ and $H_2$ (Fox et al., *J. Bacteriol.* 178:6200-6208 (1996)). The CODH-I of *C. hydrogenoformans* and its adjacent genes have been proposed to catalyze a similar functional role based on their similarity to the *R. rubrum* CODH/hydrogenase gene cluster (Wu et al., *PLoS Genet.* 1:e65 (2005)). The *C. hydrogenoformans* CODH-I was also shown to exhibit intense CO oxidation and $CO_2$ reduction activities when linked to an electrode (Parkin et al., *J Am. Chem. Soc.* 129:10328-10329 (2007)). The protein sequences of exemplary CODH and hydrogenase genes can be identified by the following GenBank accession numbers.

| Protein | GenBank ID | GI Number | Organism |
|---|---|---|---|
| CODH-I (CooS-I) | YP_360644 | 78043418 | Carboxydothermus hydrogenoformans |
| CooF | YP_360645 | 78044791 | Carboxydothermus hydrogenoformans |
| HypA | YP_360646 | 78044340 | Carboxydothermus hydrogenoformans |
| CooH | YP_360647 | 78043871 | Carboxydothermus hydrogenoformans |
| CooU | YP_360648 | 78044023 | Carboxydothermus hydrogenoformans |
| CooX | YP_360649 | 78043124 | Carboxydothermus hydrogenoformans |
| CooL | YP_360650 | 78043938 | Carboxydothermus hydrogenoformans |
| CooK | YP_360651 | 78044700 | Carboxydothermus hydrogenoformans |
| CooM | YP_360652 | 78043942 | Carboxydothermus hydrogenoformans |
| CooC | YP_360654.1 | 78043296 | Carboxydothermus hydrogenoformans |
| CooA-1 | YP_360655.1 | 78044021 | Carboxydothermus hydrogenoformans |
| CooL | AAC45118 | 1515468 | Rhodospirillum rubrum |
| CooX | AAC45119 | 1515469 | Rhodospirillum rubrum |
| CooU | AAC45120 | 1515470 | Rhodospirillum rubrum |
| CooH | AAC45121 | 1498746 | Rhodospirillum rubrum |
| CooF | AAC45122 | 1498747 | Rhodospirillum rubrum |
| CODH (CooS) | AAC45123 | 1498748 | Rhodospirillum rubrum |
| CooC | AAC45124 | 1498749 | Rhodospirillum rubrum |
| CooT | AAC45125 | 1498750 | Rhodospirillum rubrum |
| CooJ | AAC45126 | 1498751 | Rhodospirillum rubrum |

Native to *E. coli* and other enteric bacteria are multiple genes encoding up to four hydrogenases (Sawers, G., *Antonie Van Leeuwenhoek* 66:57-88 (1994); Sawers et al., *J. Bacteriol.* 164:1324-1331 (1985); Sawers and Boxer, *Eur. J Biochem.* 156:265-275 (1986); Sawers et al., *J Bacteriol.* 168: 398-404 (1986)). Given the multiplicity of enzyme activities, *E. coli* or another host organism can provide sufficient hydrogenase activity to split incoming molecular hydrogen and reduce the corresponding acceptor. *E. coli* possesses two uptake hydrogenases, Hyd-1 and Hyd-2, encoded by the hyaABCDEF and hybOABCDEFG gene clusters, respectively (Lukey et al., How *E. coli* is equipped to oxidize hydrogen under different redox conditions, *J Biol Chem* published online Nov. 16, 2009). Hyd-1 is oxygen-tolerant, irreversible, and is coupled to quinone reduction via the hyaC cytochrome. Hyd-2 is sensitive to $O_2$, reversible, and transfers electrons to the periplasmic ferredoxin hybA which, in turn, reduces a quinone via the hybB integral membrane protein. Reduced quinones can serve as the source of electrons for fumarate reductase in the reductive branch of the TCA cycle. Reduced ferredoxins can be used by enzymes such as NAD(P)H:ferredoxin oxidoreductases to generate NADPH or NADH. They can alternatively be used as the electron donor for reactions such as pyruvate ferredoxin oxidoreductase, AKG ferredoxin oxidoreductase, and 5,10-methylene-H4folate reductase.

| Protein | GenBank ID | GI Number | Organism |
|---|---|---|---|
| HyaA | AAC74057.1 | 1787206 | Escherichia coli |
| HyaB | AAC74058.1 | 1787207 | Escherichia coli |
| HyaC | AAC74059.1 | 1787208 | Escherichia coli |
| HyaD | AAC74060.1 | 1787209 | Escherichia coli |
| HyaE | AAC74061.1 | 1787210 | Escherichia coli |
| HyaF | AAC74062.1 | 1787211 | Escherichia coli |

| Protein | GenBank ID | GI Number | Organism |
|---|---|---|---|
| HybO | AAC76033.1 | 1789371 | Escherichia coli |
| HybA | AAC76032.1 | 1789370 | Escherichia coli |
| HybB | AAC76031.1 | 2367183 | Escherichia coli |
| HybC | AAC76030.1 | 1789368 | Escherichia coli |
| HybD | AAC76029.1 | 1789367 | Escherichia coli |
| HybE | AAC76028.1 | 1789366 | Escherichia coli |
| HybF | AAC76027.1 | 1789365 | Escherichia coli |
| HybG | AAC76026.1 | 1789364 | Escherichia coli |

The hydrogen-lyase systems of *E. coli* include hydrogenase 3, a membrane-bound enzyme complex using ferredoxin as an acceptor, and hydrogenase 4 that also uses a ferredoxin acceptor. Hydrogenase 3 and 4 are encoded by the hyc and hyf gene clusters, respectively. Hydrogenase 3 has been shown to be a reversible enzyme (Maeda et al., *Appl Microbiol Biotechnol* 76(5):1035-42 (2007)). Hydrogenase activity in *E. coli* is also dependent upon the expression of the hyp genes whose corresponding proteins are involved in the assembly of the hydrogenase complexes (Jacobi et al., *Arch. Microbiol* 158:444-451 (1992); Rangarajan et al., *J. Bacteriol*, 190: 1447-1458 (2008)).

| Protein | GenBank ID | GI Number | Organism |
|---|---|---|---|
| HycA | NP_417205 | 16130632 | Escherichia coli |
| HycB | NP_417204 | 16130631 | Escherichia coli |
| HycC | NP_417203 | 16130630 | Escherichia coli |
| HycD | NP_417202 | 16130629 | Escherichia coli |
| HycE | NP_417201 | 16130628 | Escherichia coli |
| HycF | NP_417200 | 16130627 | Escherichia coli |
| HycG | NP_417199 | 16130626 | Escherichia coli |
| HycH | NP_417198 | 16130625 | Escherichia coli |
| HycI | NP_417197 | 16130624 | Escherichia coli |

| Protein | GenBank ID | GI Number | Organism |
|---|---|---|---|
| HyfA | NP_416976 | 90111444 | Escherichia coli |
| HyfB | NP_416977 | 16130407 | Escherichia coli |
| HyfC | NP_416978 | 90111445 | Escherichia coli |
| HyfD | NP_416979 | 16130409 | Escherichia coli |
| HyfE | NP_416980 | 16130410 | Escherichia coli |
| HyfF | NP_416981 | 16130411 | Escherichia coli |
| HyfG | NP_416982 | 16130412 | Escherichia coli |
| HyfH | NP_416983 | 16130413 | Escherichia coli |
| HyfI | NP_416984 | 16130414 | Escherichia coli |
| HyfJ | NP_416985 | 90111446 | Escherichia coli |
| HyfR | NP_416986 | 90111447 | Escherichia coli |

| Protein | GenBank ID | GI Number | Organism |
|---|---|---|---|
| HypA | NP_417206 | 16130633 | Escherichia coli |
| HypB | NP_417207 | 16130634 | Escherichia coli |
| HypC | NP_417208 | 16130635 | Escherichia coli |
| HypD | NP_417209 | 16130636 | Escherichia coli |
| HypE | NP_417210 | 226524740 | Escherichia coli |
| HypF | NP_417192 | 16130619 | Escherichia coli |

The *M. thermoacetica* hydrogenases are suitable for a host that lacks sufficient endogenous hydrogenase activity. *M. thermoacetica* can grow with $CO_2$ as the exclusive carbon source indicating that reducing equivalents are extracted from $H_2$ to enable acetyl-CoA synthesis via the Wood-Ljungdahl pathway (Drake, H. L., *J. Bacteriol.* 150:702-709 (1982); Drake and Daniel, *Res. Microbiol.* 155:869-883 (2004); Kellum and Drake, *J. Bacteriol.* 160:466-469 (1984)) (see FIGS. 12 and 13). *M. thermoacetica* has homologs to several hyp, hyc, and hyf genes from *E. coli*. The protein sequences encoded for by these genes are identified by the following GenBank accession numbers.

Proteins in *M. thermoacetica* whose genes are homologous to the *E. coli* hyp genes are shown below.

| Protein | GenBank ID | GI Number | Organism |
| --- | --- | --- | --- |
| Moth_2175 | YP_431007 | 83590998 | *Moorella thermoacetica* |
| Moth_2176 | YP_431008 | 83590999 | *Moorella thermoacetica* |
| Moth_2177 | YP_431009 | 83591000 | *Moorella thermoacetica* |
| Moth_2178 | YP_431010 | 83591001 | *Moorella thermoacetica* |
| Moth_2179 | YP_431011 | 83591002 | *Moorella thermoacetica* |
| Moth_2180 | YP_431012 | 83591003 | *Moorella thermoacetica* |
| Moth_2181 | YP_431013 | 83591004 | *Moorella thermoacetica* |

Proteins in *M. thermoacetica* that are homologous to the *E. coli* Hydrogenase 3 and/or 4 proteins are listed below.

| Protein | GenBank ID | GI Number | Organism |
| --- | --- | --- | --- |
| Moth_2182 | YP_431014 | 83591005 | *Moorella thermoacetica* |
| Moth_2183 | YP_431015 | 83591006 | *Moorella thermoacetica* |
| Moth_2184 | YP_431016 | 83591007 | *Moorella thermoacetica* |
| Moth_2185 | YP_431017 | 83591008 | *Moorella thermoacetica* |
| Moth_2186 | YP_431018 | 83591009 | *Moorella thermoacetica* |
| Moth_2187 | YP_431019 | 83591010 | *Moorella thermoacetica* |
| Moth_2188 | YP_431020 | 83591011 | *Moorella thermoacetica* |
| Moth_2189 | YP_431021 | 83591012 | *Moorella thermoacetica* |
| Moth_2190 | YP_431022 | 83591013 | *Moorella thermoacetica* |
| Moth_2191 | YP_431023 | 83591014 | *Moorella thermoacetica* |
| Moth_2192 | YP_431024 | 83591015 | *Moorella thermoacetica* |

In addition, several gene clusters encoding hydrogenase functionality are present in *M. thermoacetica* and their corresponding protein sequences are provided below.

| Protein | GenBank ID | GI Number | Organism |
| --- | --- | --- | --- |
| Moth_0439 | YP_429313 | 83589304 | *Moorella thermoacetica* |
| Moth_0440 | YP_429314 | 83589305 | *Moorella thermoacetica* |
| Moth_0441 | YP_429315 | 83589306 | *Moorella thermoacetica* |
| Moth_0442 | YP_429316 | 83589307 | *Moorella thermoacetica* |
| Moth_0809 | YP_429670 | 83589661 | *Moorella thermoacetica* |
| Moth_0810 | YP_429671 | 83589662 | *Moorella thermoacetica* |
| Moth_0811 | YP_429672 | 83589663 | *Moorella thermoacetica* |
| Moth_0812 | YP_429673 | 83589664 | *Moorella thermoacetica* |
| Moth_0814 | YP_429674 | 83589665 | *Moorella thermoacetica* |
| Moth_0815 | YP_429675 | 83589666 | *Moorella thermoacetica* |
| Moth_0816 | YP_429676 | 83589667 | *Moorella thermoacetica* |
| Moth_1193 | YP_430050 | 83590041 | *Moorella thermoacetica* |
| Moth_1194 | YP_430051 | 83590042 | *Moorella thermoacetica* |
| Moth_1195 | YP_430052 | 83590043 | *Moorella thermoacetica* |
| Moth_1196 | YP_430053 | 83590044 | *Moorella thermoacetica* |
| Moth_1717 | YP_430562 | 83590553 | *Moorella thermoacetica* |
| Moth_1718 | YP_430563 | 83590554 | *Moorella thermoacetica* |
| Moth_1719 | YP_430564 | 83590555 | *Moorella thermoacetica* |
| Moth_1883 | YP_430726 | 83590717 | *Moorella thermoacetica* |
| Moth_1884 | YP_430727 | 83590718 | *Moorella thermoacetica* |
| Moth_1885 | YP_430728 | 83590719 | *Moorella thermoacetica* |
| Moth_1886 | YP_430729 | 83590720 | *Moorella thermoacetica* |
| Moth_1887 | YP_430730 | 83590721 | *Moorella thermoacetica* |
| Moth_1888 | YP_430731 | 83590722 | *Moorella thermoacetica* |
| Moth_1452 | YP_430305 | 83590296 | *Moorella thermoacetica* |
| Moth_1453 | YP_430306 | 83590297 | *Moorella thermoacetica* |
| Moth_1454 | YP_430307 | 83590298 | *Moorella thermoacetica* |

*Ralstonia eutropha* H16 uses hydrogen as an energy source with oxygen as a terminal electron acceptor. Its membrane-bound uptake [NiFe]-hydrogenase is an "O2-tolerant" hydrogenase (Cracknell, et al. Proc Nat Acad Sci, 106(49) 20681-20686 (2009)) that is periplasmically-oriented and connected to the respiratory chain via a b-type cytochrome (Schink and Schlegel, *Biochim. Biophys. Acta,* 567, 315-324 (1979); Bernhard et al., *Eur. J. Biochem.* 248, 179-186 (1997)). *R. eutropha* also contains an $O_2$-tolerant soluble hydrogenase encoded by the Hox operon which is cytoplasmic and directly reduces NAD+ at the expense of hydrogen (Schneider and Schlegel, *Biochim. Biophys. Acta* 452, 66-80 (1976); Burgdorf, *J. Bact.* 187(9) 3122-3132 (2005)). Soluble hydrogenase enzymes are additionally present in several other organisms including *Geobacter sulfurreducens* (Coppi, *Microbiology* 151, 1239-1254 (2005)), *Synechocystis* str. PCC 6803 (Germer, *J. Biol. Chem.,* 284(52), 36462-36472 (2009)), and *Thiocapsa roseopersicina* (Rakhely, *Appl. Environ. Microbiol.* 70(2) 722-728 (2004)). The *Synechocystis* enzyme is capable of generating NADPH from hydrogen. Overexpression of both the Hox operon from *Synechocystis* str. PCC 6803 and the accessory genes encoded by the Hyp operon from *Nostoc* sp. PCC 7120 led to increased hydrogenase activity compared to expression of the Hox genes alone (Germer, *J. Biol. Chem.* 284(52), 36462-36472 (2009)).

| Protein | GenBank ID | GI Number | Organism |
| --- | --- | --- | --- |
| HoxF | NP_942727.1 | 38637753 | *Ralstonia eutropha* H16 |
| HoxU | NP_942728.1 | 38637754 | *Ralstonia eutropha* H16 |
| HoxY | NP_942729.1 | 38637755 | *Ralstonia eutropha* H16 |
| HoxH | NP_942730.1 | 38637756 | *Ralstonia eutropha* H16 |
| HoxW | NP_942731.1 | 38637757 | *Ralstonia eutropha* H16 |
| HoxI | NP_942732.1 | 38637758 | *Ralstonia eutropha* H16 |
| HoxE | NP_953767.1 | 39997816 | *Geobacter sulfurreducens* |
| HoxF | NP_953766.1 | 39997815 | *Geobacter sulfurreducens* |
| HoxU | NP_953765.1 | 39997814 | *Geobacter sulfurreducens* |
| HoxY | NP_953764.1 | 39997813 | *Geobacter sulfurreducens* |
| HoxH | NP_953763.1 | 39997812 | *Geobacter sulfurreducens* |
| GSU2717 | NP_953762.1 | 39997811 | *Geobacter sulfurreducens* |
| HoxE | NP_441418.1 | 16330690 | *Synechocystis* str. PCC 6803 |
| HoxF | NP_441417.1 | 16330689 | *Synechocystis* str. PCC 6803 |
| Unknown function | NP_441416.1 | 16330688 | *Synechocystis* str. PCC 6803 |
| HoxU | NP_441415.1 | 16330687 | *Synechocystis* str. PCC 6803 |
| HoxY | NP_441414.1 | 16330686 | *Synechocystis* str. PCC 6803 |
| Unknown function | NP_441413.1 | 16330685 | *Synechocystis* str. PCC 6803 |
| Unknown function | NP_441412.1 | 16330684 | *Synechocystis* str. PCC 6803 |
| HoxH | NP_441411.1 | 16330683 | *Synechocystis* str. PCC 6803 |
| HypF | NP_484737.1 | 17228189 | *Nostoc* sp. PCC 7120 |
| HypC | NP_484738.1 | 17228190 | *Nostoc* sp. PCC 7120 |
| HypD | NP_484739.1 | 17228191 | *Nostoc* sp. PCC 7120 |
| Unknown function | NP_484740.1 | 17228192 | *Nostoc* sp. PCC 7120 |
| HypE | NP_484741.1 | 17228193 | *Nostoc* sp. PCC 7120 |
| HypA | NP_484742.1 | 17228194 | *Nostoc* sp. PCC 7120 |
| HypB | NP_484743.1 | 17228195 | *Nostoc* sp. PCC 7120 |

| Protein | GenBank ID | GI Number | Organism |
|---|---|---|---|
| Hox1E | AAP50519.1 | 37787351 | Thiocapsa roseopersicina |
| Hox1F | AAP50520.1 | 37787352 | Thiocapsa roseopersicina |
| Hox1U | AAP50521.1 | 37787353 | Thiocapsa roseopersicina |
| Hox1Y | AAP50522.1 | 37787354 | Thiocapsa roseopersicina |
| Hox1H | AAP50523.1 | 37787355 | Thiocapsa roseopersicina |

Several enzymes and the corresponding genes used for fixing carbon dioxide to either pyruvate or phosphoenolpyruvate to form the TCA cycle intermediates, oxaloacetate or malate are described below.

Carboxylation of phosphoenolpyruvate to oxaloacetate is catalyzed by phosphoenolpyruvate carboxylase. Exemplary PEP carboxylase enzymes are encoded by ppc in *E. coli* (Kai et al., *Arch. Biochem. Biophys.* 414:170-179 (2003), ppcA in *Methylobacterium extorquens* AM1 (Arps et al., *J. Bacteriol.* 175:3776-3783 (1993), and ppc in *Corynebacterium glutamicum* (Eikmanns et al., *Mol. Gen. Genet.* 218:330-339 (1989).

| Protein | GenBank ID | GI Number | Organism |
|---|---|---|---|
| Ppc | NP_418391 | 16131794 | Escherichia coli |
| ppcA | AAB58883 | 28572162 | Methylobacterium extorquens |
| Ppc | ABB53270 | 80973080 | Corynebacterium glutamicum |

An alternative enzyme for converting phosphoenolpyruvate to oxaloacetate is PEP carboxykinase, which simultaneously forms an ATP while carboxylating PEP. In most organisms PEP carboxykinase serves a gluconeogenic function and converts oxaloacetate to PEP at the expense of one ATP. *S. cerevisiae* is one such organism whose native PEP carboxykinase, PCKJ, serves a gluconeogenic role (Valdes-Hevia et al., *FEBS Lett.* 258:313-316 (1989). *E. coli* is another such organism, as the role of PEP carboxykinase in producing oxaloacetate is believed to be minor when compared to PEP carboxylase, which does not form ATP, possibly due to the higher $K_m$ for bicarbonate of PEP carboxykinase (Kim et al., *Appl. Environ. Microbiol.* 70:1238-1241 (2004)). Nevertheless, activity of the native *E. coli* PEP carboxykinase from PEP towards oxaloacetate has been recently demonstrated in ppc mutants of *E. coli* K-12 (Kwon et al., *J. Microbiol. Biotechnol.* 16:1448-1452 (2006)). These strains exhibited no growth defects and had increased succinate production at high NaHCO$_3$ concentrations. Mutant strains of *E. coli* can adopt Pck as the dominant CO2-fixing enzyme following adaptive evolution (Zhang et al. 2009). In some organisms, particularly rumen bacteria, PEP carboxykinase is quite efficient in producing oxaloacetate from PEP and generating ATP. Examples of PEP carboxykinase genes that have been cloned into *E. coli* include those from *Mannheimia succiniciproducens* (Lee et al., *Biotechnol. Bioprocess Eng.* 7:95-99 (2002)), *Anaerobiospirillum succiniciproducens* (Laivenieks et al., *Appl. Environ. Microbiol.* 63:2273-2280 (1997), and *Actinobacillus succinogenes* (Kim et al. supra). The PEP carboxykinase enzyme encoded by *Haemophilus influenza* is effective at forming oxaloacetate from PEP.

| Protein | GenBank ID | GI Number | Organism |
|---|---|---|---|
| PCK1 | NP_013023 | 6322950 | Saccharomyces cerevisiae |
| pck | NP_417862.1 | 16131280 | Escherichia coli |
| pckA | YP_089485.1 | 52426348 | Mannheimia succiniciproducens |
| pckA | O09460.1 | 3122621 | Anaerobiospirillum succiniciproducens |
| pckA | Q6W6X5 | 75440571 | Actinobacillus succinogenes |
| pckA | P43923.1 | 1172573 | Haemophilus influenza |

Pyruvate carboxylase (EC 6.4.1.1) directly converts pyruvate to oxaloacetate at the cost of one ATP. Pyruvate carboxylase enzymes are encoded by PYC1 (Walker et al., *Biochem. Biophys. Res. Commun.* 176:1210-1217 (1991) and PYC2 (Walker et al., supra) in *Saccharomyces cerevisiae*, and pyc in *Mycobacterium smegmatis* (Mukhopadhyay and Purwantini, *Biochim. Biophys. Acta* 1475:191-206 (2000)).

| Protein | GenBank ID | GI Number | Organism |
|---|---|---|---|
| PYC1 | NP_011453 | 6321376 | Saccharomyces cerevisiae |
| PYC2 | NP_009777 | 6319695 | Saccharomyces cerevisiae |
| Pyc | YP_890857.1 | 118470447 | Mycobacterium smegmatis |

Malic enzyme can be applied to convert $CO_2$ and pyruvate to malate at the expense of one reducing equivalent. Malic enzymes for this purpose can include, without limitation, malic enzyme (NAD-dependent) and malic enzyme (NADP-dependent). For example, one of the *E. coli* malic enzymes (Takeo, *J. Biochem.* 66:379-387 (1969)) or a similar enzyme with higher activity can be expressed to enable the conversion of pyruvate and $CO_2$ to malate. By fixing carbon to pyruvate as opposed to PEP, malic enzyme allows the high-energy phosphate bond from PEP to be conserved by pyruvate kinase whereby ATP is generated in the formation of pyruvate or by the phosphotransferase system for glucose transport. Although malic enzyme is typically assumed to operate in the direction of pyruvate formation from malate, overexpression of the NAD-dependent enzyme, encoded by maeA, has been demonstrated to increase succinate production in *E. coli* while restoring the lethal Δpfl-ΔldhA phenotype under anaerobic conditions by operating in the carbon-fixing direction (Stols and Donnelly, *Appl. Environ. Microbiol.* 63(7) 2695-2701 (1997)). A similar observation was made upon overexpressing the malic enzyme from *Ascaris suum* in *E. coli* (Stols et al., *Appl. Biochem. Biotechnol.* 63-65(1), 153-158 (1997)). The second *E. coli* malic enzyme, encoded by maeB, is NADP-dependent and also decarboxylates oxaloacetate and other alpha-keto acids (Iwakura et al., *J. Biochem.* 85(5):1355-65 (1979)).

| Protein | GenBank ID | GI Number | Organism |
|---|---|---|---|
| maeA | NP_415996 | 90111281 | Escherichia coli |
| maeB | NP_416958 | 16130388 | Escherichia coli |
| NAD-ME | P27443 | 126732 | Ascaris suum |

The enzymes used for converting oxaloacetate (formed from, for example, PEP carboxylase, PEP carboxykinase, or pyruvate carboxylase) or malate (formed from, for example, malic enzyme or malate dehydrogenase) to succinyl-CoA via the reductive branch of the TCA cycle are malate dehydrogenase, fumarate dehydratase (fumarase), fumarate reductase, and succinyl-CoA transferase. The genes for each of the enzymes are described herein above.

Enzymes, genes and methods for engineering pathways from succinyl-CoA to various products into a microorganism are now known in the art. The additional reducing equivalents obtained from CO and/or $H_2$, as disclosed herein, improve the yields of methacrylic acid, methacrylate ester, 3-hydroxyisobutyrate and/or 2-hydroxyisobutyrate when utilizing carbohydrate-based feedstock. For example, methacrylic acid, methacrylate ester, 3-hydroxyisobutyrate and/or 2-hydroxyisobutyrate can be produced from succinyl-CoA (see Figures). Exemplary enzymes for the conversion succinyl-CoA to methacrylic acid, methacrylate ester, 3-hydroxyisobutyrate and/or 2-hydroxyisobutyrate include enzymes disclosed herein.

Enzymes, genes and methods for engineering pathways from glycolysis intermediates to various products into a microorganism are known in the art. The additional reducing equivalents obtained from CO and $H_2$, as described herein, improve the yields of all these products on carbohydrates. For example, methacrylic acid, methacrylate ester, 3-hydroxyisobutyrate and/or 2-hydroxyisobutyrate can be produced from the glycolysis intermediate, succinate. Exemplary enzymes for the conversion of succinate to MAA include succinyl-CoA transferase, succinyl-CoA synthetase, succinyl-CoA reductase (aldehyde forming), 4-hydroxybutyrate dehydrogenase, 4-hydroxybutyrate kinase, phosphotrans-4-hydroxybutyrylase, succinate reductase, succinyl-CoA reductase (alcohol forming), 4-hydroxybutyryl-CoA synthetase, 4-hydroxybutyryl-CoA transferase, 4-hydroxybutyryl-CoA mutase, 3-hydroxyisobutyryl-CoA synthetase, 3-hydroxyisobutyryl-CoA transferase, 3-hydroxyisobutyryl-CoA hydrolase, 3-hydroxyisobutyrate dehydratase, 3-hydroxyisobutyryl-CoA dehydratase, methacrylyl-CoA synthetase, methacrylyl-CoA transferase and methacrylyl-CoA hydrolase.

EXAMPLE XVI

Methods for Handling CO and Anaerobic Cultures

This example describes methods used in handling CO and anaerobic cultures.

A. Handling of CO in Small Quantities for Assays and Small Cultures.

CO is an odorless, colorless and tasteless gas that is a poison. Therefore, cultures and assays that utilized CO required special handling. Several assays, including CO oxidation, acetyl-CoA synthesis, CO concentration using myoglobin, and CO tolerance/utilization in small batch cultures, called for small quantities of the CO gas that were dispensed and handled within a fume hood. Biochemical assays called for saturating very small quantities (<2 mL) of the biochemical assay medium or buffer with CO and then performing the assay. All of the CO handling steps were performed in a fume hood with the sash set at the proper height and blower turned on; CO was dispensed from a compressed gas cylinder and the regulator connected to a Schlenk line. The latter ensures that equal concentrations of CO were dispensed to each of several possible cuvettes or vials. The Schlenk line was set up containing an oxygen scrubber on the input side and an oil pressure release bubbler and vent on the other side. Assay cuvettes were both anaerobic and CO-containing, Therefore, the assay cuvettes were tightly sealed with a rubber stopper and reagents were added or removed using gas-tight needles and syringes. Secondly, small (~50 mL) cultures were grown with saturating CO in tightly stoppered serum bottles. As with the biochemical assays, the CO-saturated microbial cultures were equilibrated in the fume hood using the Schlenk line setup. Both the biochemical assays and microbial cultures were in portable, sealed containers and in small volumes making for safe handling outside of the fume hood. The compressed CO tank was adjacent to the fume hood.

Typically, a Schlenk line was used to dispense CO to cuvettes, each vented. Rubber stoppers on the cuvettes were pierced with 19 or 20 gage disposable syringe needles and were vented with the same. An oil bubbler was used with a CO tank and oxygen scrubber. The glass or quartz spectrophotometer cuvettes have a circular hole on top into which a Kontes stopper sleeve, Sz7 774250-0007 was fitted. The CO detector unit was positioned proximal to the fume hood.

B. Handling of CO in Larger Quantities Fed to Large-Scale Cultures.

Fermentation cultures are fed either CO or a mixture of CO and $H_2$ to simulate syngas as a feedstock in fermentative production. Therefore, quantities of cells ranging from 1 liter to several liters can include the addition of CO gas to increase the dissolved concentration of CO in the medium. In these circumstances, fairly large and continuously administered quantities of CO gas are added to the cultures. At different points, the cultures are harvested or samples removed. Alternatively, cells are harvested with an integrated continuous flow centrifuge that is part of the fermenter.

The fermentative processes are carried out under anaerobic conditions. In some cases, it is uneconomical to pump oxygen or air into fermenters to ensure adequate oxygen saturation to provide a respiratory environment. In addition, the reducing power generated during anaerobic fermentation may be needed in product formation rather than respiration. Furthermore, many of the enzymes for various pathways are oxygen-sensitive to varying degrees. Classic acetogens such as *M. thermoacetica* are obligate anaerobes and the enzymes in the Wood-Ljungdahl pathway are highly sensitive to irreversible inactivation by molecular oxygen. While there are oxygen-tolerant acetogens, the repertoire of enzymes in the Wood-Ljungdahl pathway might be incompatible in the presence of oxygen because most are metallo-enzymes, key components are ferredoxins, and regulation can divert metabolism away from the Wood-Ljungdahl pathway to maximize energy acquisition. At the same time, cells in culture act as oxygen scavengers that moderate the need for extreme measures in the presence of large cell growth.

C. Anaerobic Chamber and Conditions.

Exemplary anaerobic chambers are available commercially (see, for example, Vacuum Atmospheres Company, Hawthorne Calif.; MBraun, Newburyport Mass.). Conditions included an $O_2$ concentration of 1 ppm or less and 1 atm pure $N_2$. In one example, 3 oxygen scrubbers/catalyst regenerators were used, and the chamber included an $O_2$ electrode (such as Teledyne; City of Industry Calif.). Nearly all items and reagents were cycled four times in the airlock of the chamber prior to opening the inner chamber door. Reagents with a volume >5 mL were sparged with pure $N_2$ prior to introduction into the chamber. Gloves are changed twice/yr and the catalyst containers were regenerated periodically when the chamber displays increasingly sluggish response to changes in oxygen levels. The chamber's pressure was controlled through one-way valves activated by solenoids. This feature allowed setting the chamber pressure at a level higher than the surroundings to allow transfer of very small tubes through the purge valve.

The anaerobic chambers achieved levels of $O_2$ that were consistently very low and were needed for highly oxygen sensitive anaerobic conditions. However, growth and handling of cells does not usually require such precautions. In an alternative anaerobic chamber configuration, platinum or palladium can be used as a catalyst that requires some hydrogen gas in the mix. Instead of using solenoid valves, pressure release can be controlled by a bubbler. Instead of using instrument-based $O_2$ monitoring, test strips can be used instead.

D. Anaerobic Microbiology.

Small cultures were handled as described above for CO handling. In particular, serum or media bottles are fitted with thick rubber stoppers and aluminum crimps are employed to seal the bottle. Medium, such as Terrific Broth, is made in a conventional manner and dispensed to an appropriately sized serum bottle. The bottles are sparged with nitrogen for ~30 min of moderate bubbling. This removes most of the oxygen from the medium and, after this step, each bottle is capped with a rubber stopper (such as Bellco 20 mm septum stoppers; Bellco, Vineland, N.J.) and crimp-sealed (Bellco 20 mm). Then the bottles of medium are autoclaved using a slow (liquid) exhaust cycle. At least sometimes a needle can be poked through the stopper to provide exhaust during autoclaving; the needle needs to be removed immediately upon removal from the autoclave. The sterile medium has the remaining medium components, for example buffer or antibiotics, added via syringe and needle. Prior to addition of reducing agents, the bottles are equilibrated for 30-60 minutes with nitrogen (or CO depending upon use). A reducing agent such as a 100×150 mM sodium sulfide, 200 mM cysteine-HCl is added. This is made by weighing the sodium sulfide into a dry beaker and the cysteine into a serum bottle, bringing both into the anaerobic chamber, dissolving the sodium sulfide into anaerobic water, then adding this to the cysteine in the serum bottle. The bottle is stoppered immediately as the sodium sulfide solution generates hydrogen sulfide gas upon contact with the cysteine. When injecting into the culture, a syringe filter is used to sterilize the solution. Other components are added through syringe needles, such as B12 (10 μM cyanocobalamin), nickel chloride ($NiCl_2$, 20 microM final concentration from a 40 mM stock made in anaerobic water in the chamber and sterilized by autoclaving or by using a syringe filter upon injection into the culture), and ferrous ammonium sulfate (final concentration needed is 100 μM—made as 100-1000× stock solution in anaerobic water in the chamber and sterilized by autoclaving or by using a syringe filter upon injection into the culture). To facilitate faster growth under anaerobic conditions, the 1 liter bottles were inoculated with 50 mL of a preculture grown anaerobically. Induction of the pA1-lacO1 promoter in the vectors was performed by addition of isopropyl β-D-1-thiogalactopyranoside (IPTG) to a final concentration of 0.2 mM and was carried out for about 3 hrs.

Large cultures can be grown in larger bottles using continuous gas addition while bubbling. A rubber stopper with a metal bubbler is placed in the bottle after medium addition and sparged with nitrogen for 30 minutes or more prior to setting up the rest of the bottle. Each bottle is put together such that a sterile filter will sterilize the gas bubbled in and the hoses on the bottles are compressible with small C clamps. Medium and cells are stirred with magnetic stir bars. Once all medium components and cells are added, the bottles are incubated in an incubator in room air but with continuous nitrogen sparging into the bottles.

EXAMPLE XVIII

CO Oxidation (CODH) Assay

This example describes assay methods for measuring CO oxidation (CO dehydrogenase; CODH).

The 7 gene CODH/ACS operon of *Moorella thermoacetica* was cloned into *E. coli* expression vectors. The intact ~10 kbp DNA fragment was cloned, and it is likely that some of the genes in this region are expressed from their own endogenous promoters and all contain endogenous ribosomal binding sites. These clones were assayed for CO oxidation, using an assay that quantitatively measures CODH activity. Antisera to the *M. thermoacetica* gene products was used for Western blots to estimate specific activity. *M. thermoacetica* is Gram positive, and ribosome binding site elements are expected to work well in *E. coli*. This activity, described below in more detail, was estimated to be ~1/50th of the *M. thermoacetica* specific activity. It is possible that CODH activity of recombinant *E. coli* cells could be limited by the fact that *M. thermoacetica* enzymes have temperature optima around 55° C. Therefore, a mesophilic CODH/ACS pathway could be advantageous such as the close relative of *Moorella* that is mesophilic and does have an apparently intact CODH/ACS operon and a Wood-Ljungdahl pathway, *Desulfitobacterium hafniense*. Acetogens as potential host organisms include, but are not limited to, *Rhodospirillum rubrum*, *Moorella thermoacetica* and *Desulfitobacterium hafniense*.

CO oxidation is both the most sensitive and most robust of the CODH/ACS assays. It is likely that an *E. coli*-based syngas using system will ultimately need to be about as anaerobic as *Clostridial* (i.e., *Moorella*) systems, especially for maximal activity. Improvement in CODH should be possible but will ultimately be limited by the solubility of CO gas in water.

Initially, each of the genes was cloned individually into expression vectors. Combined expression units for multiple subunits/1 complex were generated. Expression in *E. coli* at the protein level was determined. Both combined *M. thermoacetica* CODH/ACS operons and individual expression clones were made.

CO oxidation assay. This assay is one of the simpler, reliable, and more versatile assays of enzymatic activities within the Wood-Ljungdahl pathway and tests CODH (Seravalli et al., *Biochemistry* 43:3944-3955 (2004)). A typical activity of *M. thermoacetica* CODH specific activity is 500 U at 55° C. or ~60 U at 25° C. This assay employs reduction of methyl viologen in the presence of CO. This is measured at 578 nm in stoppered, anaerobic, glass cuvettes.

In more detail, glass rubber stoppered cuvettes were prepared after first washing the cuvette four times in deionized water and one time with acetone. A small amount of vacuum grease was smeared on the top of the rubber gasket. The cuvette was gassed with CO, dried 10 min with a 22 Ga. needle plus an exhaust needle. A volume of 0.98 mL of reaction buffer (50 mM Hepes, pH 8.5, 2 mM dithiothreitol (DTT) was added using a 22 Ga. needle, with exhaust needled, and 100% CO. Methyl viologen ($CH_3$ viologen) stock was 1 M in water. Each assay used 20 microliters for 20 mM final concentration. When methyl viologen was added, an 18 Ga needle (partial) was used as a jacket to facilitate use of a Hamilton syringe to withdraw the $CH_3$ viologen. 4-5 aliquots were drawn up and discarded to wash and gas equilibrate the syringe. A small amount of sodium dithionite (0.1 M stock) was added when making up the $CH_3$ viologen stock to slightly reduce the $CH_3$ viologen. The temperature was equilibrated to 55° C. in a heated Olis spectrophotometer (Bogart GA). A blank reaction ($CH_3$ viologen+buffer) was run first to measure the base rate of $CH_3$ viologen reduction. Crude *E. coli* cell extracts of ACS90 and ACS91 (CODH-ACS operon of *M. thermoacetica* with and without, respectively, the first cooC). 10 microliters of extract were added at a time, mixed and assayed. Reduced $CH_3$ viologen turns purple. The results of an assay are shown in Table 2.

TABLE 2

Crude extract CO Oxidation Activities.

| ACS90 | 7.7 mg/ml | ACS91 | 11.8 mg/ml |
| Mta98 | 9.8 mg/ml | Mta99 | 11.2 mg/ml |

| Extract | Vol | OD/ | U/ml | U/mg |
|---|---|---|---|---|
| ACS90 | 10 microliters | 0.073 | 0.376 | 0.049 |
| ACS91 | 10 microliters | 0.096 | 0.494 | 0.042 |
| Mta99 | 10 microliters | 0.0031 | 0.016 | 0.0014 |
| ACS90 | 10 microliters | 0.099 | 0.51 | 0.066 |
| Mta99 | 25 microliters | 0.012 | 0.025 | 0.0022 |
| ACS91 | 25 microliters | 0.215 | 0.443 | 0.037 |
| Mta98 | 25 microliters | 0.019 | 0.039 | 0.004 |
| ACS91 | 10 microliters | 0.129 | 0.66 | 0.056 |

Averages
ACS90 0.057 U/mg
ACS91 0.045 U/mg
Mta99 0.0018 U/mg

Mta98/Mta99 are *E. coli* MG1655 strains that express methanol methyltransferase genes from *M. thermoacetia* and, therefore, are negative controls for the ACS90 ACS91 *E. coli* strains that contain *M. thermoacetica* CODH operons.

If ~1% of the cellular protein is CODH, then these figures would be approximately 100× less than the 500 U/mg activity of pure *M. thermoacetica* CODH. Actual estimates based on Western blots are 0.5% of the cellular protein, so the activity is about 50× less than for *M. thermoacetica* CODH. Nevertheless, this experiment demonstrates CO oxidation activity in recombinant *E. coli* with a much smaller amount in the negative controls. The small amount of CO oxidation (CH$_3$ viologen reduction) seen in the negative controls indicates that *E. coli* may have a limited ability to reduce CH$_3$ viologen.

Figure 14:
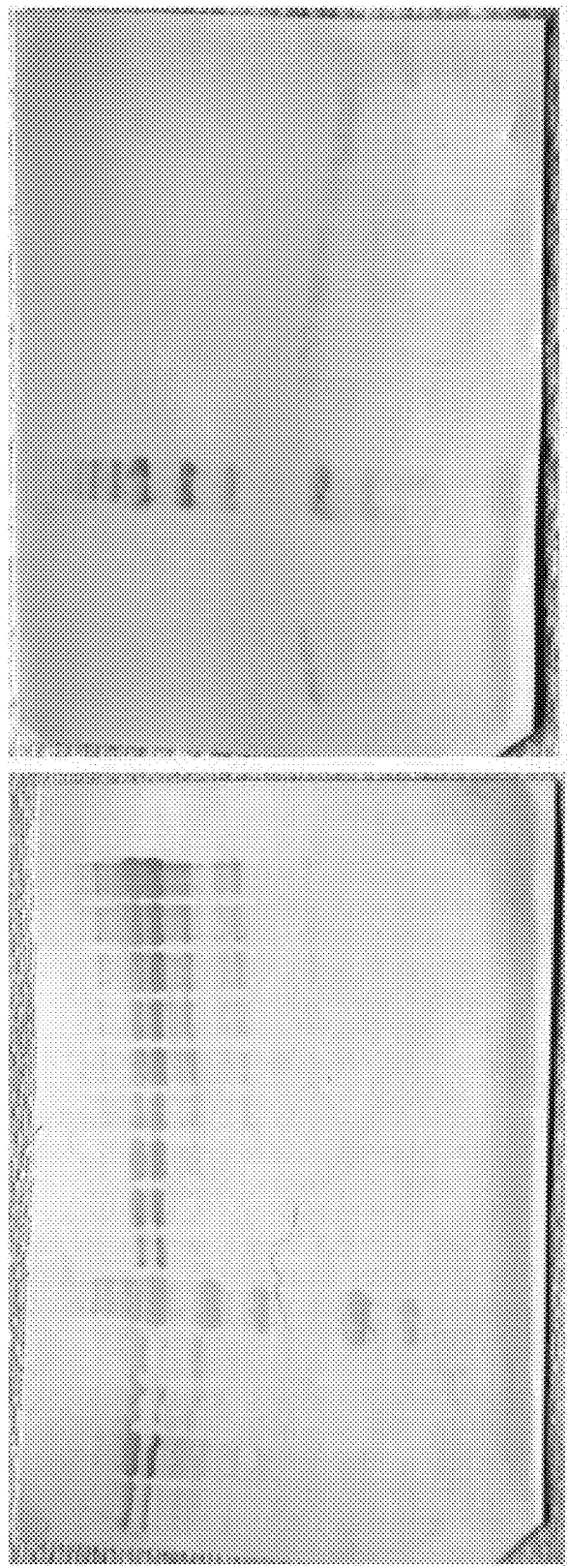
FIG. 14 shows Western blots of 10 micrograms ACS90 (lane 1), ACS91 (lane2), Mta98/99 (lanes 3 and 4) cell extracts with size standards (lane 5) and controls of *M. thermoacetica* CODH (Moth_1202/1203) or Mtr (Moth_1197) proteins (50, 150, 250, 350, 450, 500, 750, 900, and 1000 ng).

To estimate the final concentrations of CODH and Mtr proteins, SDS-PAGE followed by Western blot analyses were performed on the same cell extracts used in the CO oxidation, ACS, methyltransferase, and corrinoid Fe—S assays. The antisera used were polyclonal to purified *M. thermoacetica* CODH-ACS and Mtr proteins and were visualized using an alkaline phosphatase-linked goat-anti-rabbit secondary antibody. The Westerns were performed and results are shown in FIG. 14. The amounts of CODH in ACS90 and ACS91 were estimated at 50 ng by comparison to the control lanes. Expression of CODH-ACS operon genes including 2 CODH subunits and the methyltransferase were confirmed via Western blot analysis. Therefore, the recombinant *E. coli* cells express multiple components of a 7 gene operon. In addition, both the methyltransferase and corrinoid iron sulfur protein were active in the same recombinant *E. coli* cells. These proteins are part of the same operon cloned into the same cells.

Figure 15:
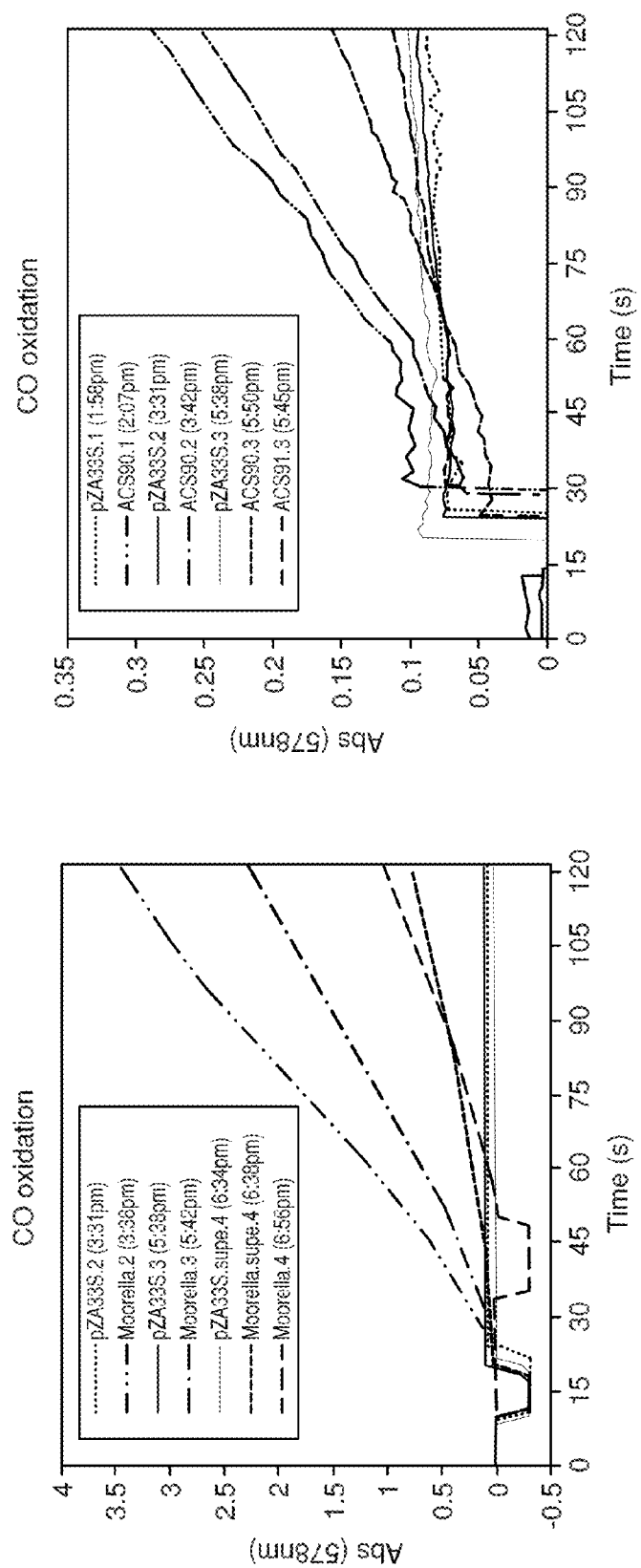
FIG. 15 shows CO oxidation assay results. Cells (*M. thermoacetica* or *E. coli* with the CODH/ACS operon; ACS90 or ACS91 or empty vector: pZA33S) were grown and extracts prepared. Assays were performed at 55° C. at various times on the day the extracts were prepared. Reduction of methylviologen was followed at 578 nm over a 120 sec time course.

The CO oxidation assays were repeated using extracts of *Moorella thermoacetica* cells for the positive controls. Though CODH activity in *E. coli* ACS90 and ACS91 was measurable, it was at about 130-150× lower than the *M. thermoacetica* control. The results of the assay are shown in FIG. 15. Briefly, cells (*M. thermoacetica* or *E. coli* with the CODH/ACS operon; ACS90 or ACS91 or empty vector: pZA33S) were grown and extracts prepared as described above. Assays were performed as described above at 55° C. at various times on the day the extracts were prepared. Reduction of methylviologen was followed at 578 nm over a 120 sec time course.

These results describe the CO oxidation (CODH) assay and results. Recombinant *E. coli* cells expressed CO oxidation activity as measured by the methyl viologen reduction assay.

EXAMPLE XVIII

*E. coli* CO Tolerance Experiment and CO Concentration Assay (Myoglobin Assay)

This example describes the tolerance of *E. coli* for high concentrations of CO.

To test whether or not *E. coli* can grow anaerobically in the presence of saturating amounts of CO, cultures were set up in 120 ml serum bottles with 50 ml of Terrific Broth medium (plus reducing solution, NiCl$_2$, Fe(II)NH$_4$SO$_4$, cyanocobalamin, IPTG, and chloramphenicol) as described above for anaerobic microbiology in small volumes. One half of these bottles were equilibrated with nitrogen gas for 30 min. and one half was equilibrated with CO gas for 30 min. An empty vector (pZA33) was used as a control, and cultures containing the pZA33 empty vector as well as both ACS90 and ACS91 were tested with both N$_2$ and CO. All were inoculated and grown for 36 hrs with shaking (250 rpm) at 37° C. At the end of the 36 hour period, examination of the flasks showed high amounts of growth in all. The bulk of the observed growth occurred overnight with a long lag.

Given that all cultures appeared to grow well in the presence of CO, the final CO concentrations were confirmed. This was performed using an assay of the spectral shift of myoglobin upon exposure to CO. Myoglobin reduced with sodium dithionite has an absorbance peak at 435 nm; this peak is shifted to 423 nm with CO. Due to the low wavelength and need to record a whole spectrum from 300 nm on upwards, quartz cuvettes must be used. CO concentration is measured against a standard curve and depends upon the Henry's Law constant for CO of maximum water solubility=970 micromolar at 20° C. and 1 atm.

For the myoglobin test of CO concentration, cuvettes were washed 10× with water, 1× with acetone, and then stoppered as with the CODH assay. N$_2$ was blown into the cuvettes for ~10 min. A volume of 1 ml of anaerobic buffer (HEPES, pH 8.0, 2 mM DTT) was added to the blank (not equilibrated with CO) with a Hamilton syringe. A volume of 10 microliter myoglobin (~1 mM—can be varied, just need a fairly large amount) and 1 microliter dithionite (20 mM stock) were added. A CO standard curve was made using CO saturated buffer added at 1 microliter increments. Peak height and shift was recorded for each increment. The cultures tested were pZA33/CO, ACS90/CO, and ACS91/CO. Each of these was added in 1 microliter increments to the same cuvette. Midway through the experiment a second cuvette was set up and used. The results are shown in Table 3.

TABLE 3

Carbon Monoxide Concentrations, 36 hrs.

| Strain and Growth Conditions | Final CO concentration (micromolar) |
|---|---|
| pZA33-CO | 930 |
| ACS90-CO | 638 |
|  | 494 |
|  | 734 |
|  | 883 |
| ave | 687 |
| SD | 164 |
| ACS91-CO | 728 |
|  | 812 |
|  | 760 |
|  | 611 |
| ave. | 728 |
| SD | 85 |

The results shown in Table 3 indicate that the cultures grew whether or not a strain was cultured in the presence of CO or not. These results indicate that E. coli can tolerate exposure to CO under anaerobic conditions and that E. coli cells expressing the CODH-ACS operon can metabolize some of the CO.

These results demonstrate that E. coli cells, whether expressing CODH/ACS or not, were able to grow in the presence of saturating amounts of CO. Furthermore, these grew equally well as the controls in nitrogen in place of CO. This experiment demonstrated that laboratory strains of E. coli are insensitive to CO at the levels achievable in a syngas project performed at normal atmospheric pressure. In addition, preliminary experiments indicated that the recombinant E. coli cells expressing CODH/ACS actually consumed some CO, probably by oxidation to carbon dioxide.

EXAMPLE XVIX

Pathways for the Production of MAA and 3-Hydroxyisobutyric Acid from Succinate Via Methylmalonyl-CoA The reductive TCA cycle improves the yield of methacrylic acid (MAA) when utilizing a carbohydrate-based feedstock. MAA production can be achieved in a recombinant organism by the pathway shown in FIG. 16A.

For example, MAA and/or 3-hydroxyisobutyric acid can be produced from succinate via a methylmalonyl-CoA intermediate as shown in FIG. 16A. Exemplary enzymes for the conversion of succinate to MAA or 3-hydroxyisobutyric acid by this route include succinyl-CoA transferase, succinyl-CoA synthetase, methylmalonyl-CoA mutase, methylmalonyl-CoA epimerase, methylmalonyl-CoA reductase, methylmalonate semialdehyde reductase and 3-hydroxyisobutyrate dehydratase.

In this pathway, central metabolic intermediates are first channeled into succinate. For formation of succinate, phosphoenolpyruvate (PEP) is converted into oxaloacetate either via PEP carboxykinase or PEP carboxylase. Alternatively, PEP is converted first to pyruvate by pyruvate kinase and then to oxaloacetate by methylmalonyl-CoA carboxytransferase or pyruvate carboxylase. Oxaloacetate is then converted to succinate by means of the reductive TCA cycle.

Succinate is then activated to succinyl-CoA by a succinyl-CoA transferase or synthetase. Methylmalonyl-CoA mutase then forms methylmalonyl-CoA from succinyl-CoA. Methylmalonyl-CoA is then reduced to methylmalonate semialdehyde. Further reduction of methylmalonate semialdehyde yields 3-hydroxyisobutyric acid, which can be secreted as a product or further transformed to MAA via dehydration.

Exemplary enzyme candidates for the transformations shown in FIG. 16A are described below. Succinyl-CoA transferase and synthetase enzymes were described previously in Example XV (RTCA cycle).

Methylmalonyl-CoA Mutase.

Methylmalonyl-CoA mutase is a cobalamin-dependent enzyme that converts succinyl-CoA to methylmalonyl-CoA. In E. coli, the reversible adenosylcobalamin-dependant mutase participates in a three-step pathway leading to the conversion of succinate to propionate. Exemplary MCM enzymes are described in Example V.

Alternatively, isobutyryl-CoA mutase (ICM) could catalyze the proposed transformation. ICM is a cobalamin-dependent methylmutase in the MCM family that reversibly rearranges the carbon backbone of butyryl-CoA into isobutyryl-CoA (Ratnatilleke, *J Biol. Chem.* 274:31679-31685 (1999)). Exemplary ICM enzymes are described in Example VII.

Methylmalonyl-CoA Epimerase.

Methylmalonyl-CoA epimerase (MMCE) is the enzyme that interconverts (R)-methylmalonyl-CoA and (S)-methylmalonyl-CoA. MMCE is an essential enzyme in the breakdown of odd-numbered fatty acids and of the amino acids valine, isoleucine, and methionine. Exemplary MMCE enzymes are described in Example V.

Methylmalonyl-CoA Reductase.

The reduction of methylmalonyl-CoA to its corresponding aldehyde, methylmalonate semialdehyde, is catalyzed by a CoA-dependent aldehyde dehydrogenase. Exemplary enzymes are described in Example V.

Methylmalonate Semialdehyde Reductase.

The reduction of methylmalonate semialdehyde to 3-hydroxyisobutyrate is catalyzed by methylmalonate semialdehyde reductase or 3-hydroxyisobutyrate dehydrogenase. This enzyme participates in valine, leucine and isoleucine degradation and has been identified in bacteria, eukaryotes, and mammals. Exemplary methylmalonate semialdehyde reductase enzymes are described in Example V.

3-Hydroxyisobutyrate Dehydratase.

The dehydration of 3-hydroxyisobutyrate to methylacrylic acid is catalyzed by an enzyme with 3-hydroxyisobutyrate dehydratase activity. Exemplary 3-hydroxyisobutyrate dehydratase enzymes are described in Example V.

Figures 17A, 17B:
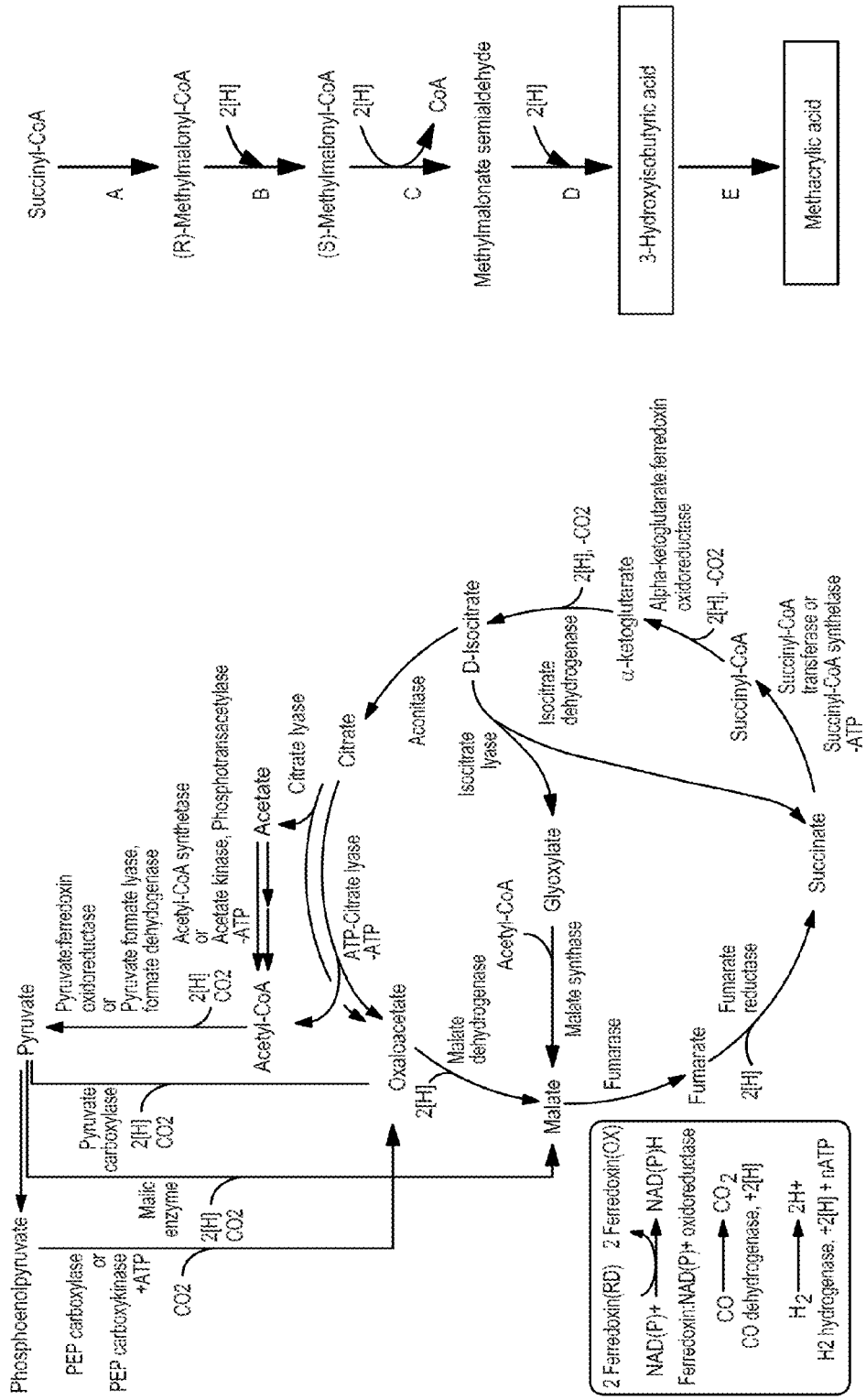
FIGS. 17A and 17B show exemplary pathways. The enzymatic transformations are carried out by the enzymes as shown.

An active reductive TCA cycle improves the yield of the acetyl-CoA derived product methacrylic acid (MAA), as shown in the exemplary pathways of FIG. 17. Pathways of the reductive TCA cycle are described herein as well as the conversion of succinyl-CoA to methacrylic acid (see also FIGS. 3 and 16A and Example V). FIGS. 17A and 17B show exemplary pathways. The enzymatic transformations are carried out by the enzymes as shown. FIG. 17A shows the pathways for fixation of $CO_2$ to succinyl-CoA using the reductive TCA cycle. FIG. 17B shows exemplary pathways for the biosynthesis of 3-hydroxyisobutric acid and methacrylic acid from succinyl-CoA; the enzymatic transformations shown are carried out by the following enzymes: A. Methylmalonyl-CoA mutase, B. Methylmalonyl-CoA epimerase, C. Methylmalonyl-CoA reductase, D. Methylmalonate semialdehyde reductase, E. 3-Hydroxyisobutyrate dehydratase.

EXAMPLE XX

Pathways for the Production of MAA and 3-Hydroxyisobutyric Acid from Succinate Via 4-Hydroxybutyryl-CoA The reductive TCA cycle improves the yield of methacrylic acid (MAA) when utilizing a carbohydrate-based feedstock. MAA production can be achieved in a recombinant organism by as shown in FIG. 16B.

For example, MAA and/or 3-hydroxyisobutyric acid can be produced from succinate via a 4-hydroxybutyryl-CoA intermediate by a number of alternate routes depicted in FIG. 16B. Exemplary enzymes for these routes include: succinyl-CoA transferase, succinyl-CoA synthetase, succinyl-CoA reductase (aldehyde forming), 4-hydroxybutyrate dehydrogenase, 4-hydroxybutyrate kinase, phosphotrans-4-hydroxybutyrylase, succinate reductase, succinyl-CoA reductase (alcohol forming), 4-hydroxybutyryl-CoA synthetase, 4-hydroxybutyryl-CoA transferase, 4-hydroxybutyryl-CoA mutase, 3-hydroxyisobutyryl-CoA synthetase, 3-hydroxyisobutyryl-CoA transferase, 3-hydroxyisobutyryl-CoA hydrolase, 3-hydroxyisobutyrate dehydratase, 3-hydroxyisobutyryl-CoA dehydratase, methacrylyl-CoA synthetase, methacrylyl-CoA transferase and methacrylyl-CoA hydrolase.

Formation of the 4-hydroxybutyryl-CoA intermediate from succinate proceeds through several routes depicted in FIG. 16B. Succinate is first converted to succinyl-CoA by a CoA transferase or synthetase. Succinyl-CoA is then converted to succinic semialdehyde by a CoA-dependent aldehyde dehydrogenase. Alternately, succinate is directly converted to succinic semialdehyde by an acid reductase. The succinic semialdehyde intermediate is reduced to 4-hydroxybutyrate (4-HB) by 4-hydroxybutyrate dehydrogenase. A bifunctional aldehyde dehydrogenase/alcohol dehydrogenase directly converts succinyl-CoA to 4-HB. Activation of 4-HB to its acyl-CoA is catalyzed by a CoA transferase or synthetase. Alternatively, 4-HB can be converted into a 4-hydroxybutyryl-phosphate intermediate and subsequently transformed into 4-HB-CoA by a phosphotrans-4-hydroxybutyrylase.

Isomerization of 4-hydroxybutyryl-CoA to 3-hydroxyisobutyryl-CoA is catalyzed by a 4-HB-CoA methylmutase. Removal of the CoA moiety of 3-hydroxyisobutyryl-CoA yields 3-hydroxyisobutyrate, which can be secreted as a product or further transformed to MAA by dehydration. Dehydration of 3-hydroxyisobutyryl-CoA to methacrylyl-CoA, followed by removal of the CoA moiety by a CoA hydrolase, transferase or synthetase, is another route for MAA formation.

Exemplary enzyme candidates for the transformations shown in FIGS. 16A and 16B are described below. Succinyl-CoA transferase and synthetase enzymes were described previously in Example I (RTCA cycle). Methylmalonyl-CoA mutase and methylmalonyl-CoA epimerase were described in Example III. 3-Hydroxyisobutyrate dehydratase enzyme candidates were described in Example III.

Table 4 shows enzyme classes that can perform the steps depicted in FIG. 16B. Exemplary enzymes are described in further detail below.

TABLE 4

Exemplary enzymes that carry out the steps in FIG. 16B.

| Label | Function | Step |
|---|---|---|
| 1.1.1.a | Oxidoreductase (oxo to alcohol) | 5 |
| 1.1.1.c | CoA reducatse (alcohol forming) | 9 |
| 1.2.1.b | CoA reductase (aldehyde forming) | 4 |
| 1.2.1.e | Oxidoreductase (acid to aldehyde) | 8 |
| 2.3.1.a | Phosphotransacylase | 7 |
| 2.7.2.a | Kinase | 6 |
| 2.8.3.a | Coenzyme-A transferase | 3, 10, 12, 15 |
| 3.1.2.a | Thiolester hydrolase (CoA specific) | 12, 15 |
| 4.2.1.a | Dehydratase | 13, 14 |
| 5.4.99.a | Methyl mutase | 11 |
| 6.2.1.a | Acid-thiol ligase/CoA synthetase | 3, 10, 12, 15 |

1.1.1.a.

Enzymes exhibiting 4-hydroxybutyrate dehydrogenase activity (EC 1.1.1.61) reduce succinate semialdehyde to 4-hydroxybutyrate (Step 5 of FIG. 16B). Such enzymes have been characterized in *Ralstonia eutropha* (Bravo et al., *J Forens Sci*, 49:379-387 (2004)), *Clostridium kluyveri* (Wolff et al., *Protein Expr. Purif.* 6:206-212 (1995)) and *Arabidopsis thaliana* (Breitkreuz et al., *J Biol Chem*, 278:41552-41556 (2003)). The *A. thaliana* enzyme was cloned and characterized in yeast (Breitkreuz et al., *J. Biol. Chem.* 278:41552-41556 (2003)). Yet another gene is the alcohol dehydrogenase adhI from *Geobacillus thermoglucosidasius* (Jeon et al., *J Biotechnol* 135:127-133 (2008)).

| PROTEIN | GENBANK ID | GI NUMBER | ORGANISM |
|---|---|---|---|
| 4hbd | YP_726053.1 | 113867564 | *Ralstonia eutropha* H16 |
| 4hbd | L21902.1 | 146348486 | *Clostridium kluyveri* DSM 555 |
| 4hbd | Q94B07 | 75249805 | *Arabidopsis thaliana* |
| adhI | AAR91477.1 | 40795502 | *Geobacillus thermoglucosidasius* |

1.1.1.c.

A bifunctional enzyme with acyl-CoA reductase and alcohol dehydrogenase activity can directly convert succinyl-CoA to 4-hydroxybutyrate. Exemplary bifunctional oxidoreductases that convert an acyl-CoA to alcohol include those that transform substrates such as acetyl-CoA to ethanol (for example, adhE from *E. coli* (Kessler et al., *FEBS. Lett.* 281:59-63 (1991))) and butyryl-CoA to butanol (for example, adhE2 from *C. acetobutylicum* (Fontaine et al., *J. Bacteriol.* 184:821-830 (2002))). The *C. acetobutylicum* enzymes encoded by bdh I and bdh II (Walter, et al., *J. Bacteriol.* 174:7149-7158 (1992)), reduce acetyl-CoA and butyryl-CoA to ethanol and butanol, respectively. In addition to reducing acetyl-CoA to ethanol, the enzyme encoded by adhE in *Leuconostoc mesenteroides* has been shown to oxide the branched chain compound isobutyraldehyde to isobutyryl-CoA (Kazahaya et al., *J. Gen. Appl. Microbiol.* 18:43-55 (1972); Koo et al., *Biotechnol Lett*, 27:505-510 (2005)). Another exemplary enzyme can convert malonyl-CoA to 3-HP. An NADPH-dependent enzyme with this activity has characterized in *Chloroflexus aurantiacus* where it participates in the 3-hydroxypropionate cycle (Hugler et al., *J Bacteriol*, 184:2404-2410 (2002); Strauss et al., *Eur J Biochem*, 215:633-643 (1993)). This enzyme, with a mass of 300 kDa, is highly substrate-specific and shows little sequence similarity to other known oxidoreductases (Hugler et al., supra). No enzymes in other organisms have been shown to catalyze this specific reaction; however there is bioinformatic evidence that other organisms may have similar pathways (Klatt et al., *Env Microbiol*, 9:2067-2078 (2007)). Enzyme candidates in other organisms including *Roseiflexus castenholzii, Erythrobacter* sp. NAP1 and marine gamma proteobacterium HTCC2080 can be inferred by sequence similarity.

| Protein | GenBank ID | GI Number | Organism |
|---|---|---|---|
| adhE | NP_415757.1 | 16129202 | *Escherichia coli* |
| adhE2 | AAK09379.1 | 12958626 | *Clostridium acetobutylicum* |
| adhE | AAV66076.1 | 55818563 | *Leuconostoc mesenteroides* |
| bdh I | NP_349892.1 | 15896543 | *Clostridium acetobutylicum* |
| bdh II | NP_349891.1 | 15896542 | *Clostridium acetobutylicum* |
| mcr | AAS20429.1 | 42561982 | *Chloroflexus aurantiacus* |
| Rcas_2929 | YP_001433009.1 | 156742880 | *Roseiflexus castenholzii* |
| NAP1_02720 | ZP_01039179.1 | 85708113 | *Erythrobacter* sp. NAP1 |
| MGP2080_00535 | ZP_01626393.1 | 119504313 | marine gamma proteobacterium HTCC2080 |

Longer chain acyl-CoA molecules can be reduced to their corresponding alcohols by enzymes such as the jojoba (*Simmondsia chinensis*) FAR which encodes an alcohol-forming fatty acyl-CoA reductase. Its overexpression in *E. coli* resulted in FAR activity and the accumulation of fatty alcohol (Metz et al., *Plant Physiol*, 122:635-644 (2000)).

| Protein | GenBank ID | GI Number | Organism |
|---------|------------|-----------|----------|
| FAR | AAD38039.1 | 5020215 | *Simmondsia chinensis* |

1.2.1.b.

The reduction of succinyl-CoA to its corresponding aldehyde, succinate semialdehyde, is catalyzed by succinyl-CoA reductase (aldehyde forming). Exemplary enzymes include succinyl-CoA reductase (EC 1.2.1.76), acetyl-CoA reductase, butyryl-CoA reductase and fatty acyl-CoA reductase. Enzymes with succinyl-CoA reductase activity are encoded by sucD of *Clostridium kluyveri* (Sohling, *J. Bacteriol.* 178: 871-880 (1996)) and sucD of *P. gingivalis* (Takahashi, *J. Bacteriol* 182:4704-4710 (2000)). Additional succinyl-CoA reductase enzymes participate in the 3-hydroxypropionate/4-hydroxybutyrate cycle of thermophilic archaea including *Metallosphaera sedula* (Berg et al., *Science* 318:1782-1786 (2007)) and *Thermoproteus neutrophilus* (Ramos-Vera et al., *J Bacteriol*, 191:4286-4297 (2009)). The *M. sedula* enzyme, encoded by Msed_0709, is strictly NADPH-dependent and also has malonyl-CoA reductase activity. The *T. neutrophilus* enzyme is active with both NADPH and NADH. The enzyme acylating acetaldehyde dehydrogenase in *Pseudomonas* sp, encoded by bphG, is yet another as it has been demonstrated to oxidize and acylate acetaldehyde, propionaldehyde, butyraldehyde, isobutyraldehyde and formaldehyde (Powlowski, *J. Bacteriol.* 175:377-385 (1993)). In addition to reducing acetyl-CoA to ethanol, the enzyme encoded by adhE in *Leuconostoc mesenteroides* has been shown to oxidize the branched chain compound isobutyraldehyde to isobutyryl-CoA (Kazahaya, *J. Gen. Appl. Microbiol.* 18:43-55 (1972); and Koo et al., *Biotechnol Lett.* 27:505-510 (2005)). Butyraldehyde dehydrogenase catalyzes a similar reaction, conversion of butyryl-CoA to butyraldehyde, in solventogenic organisms such as *Clostridium saccharoperbutylacetonicum* (Kosaka et al., *Biosci Biotechnol Biochem.*, 71:58-68 (2007)). Exemplary fatty acyl-CoA reductases enzymes are encoded by acyl of *Acinetobacter calcoaceticus* (Reiser, *Journal of Bacteriology* 179:2969-2975 (1997)) and *Acinetobacter* sp. M-1 (Ishige et al., *Appl. Environ. Microbiol.* 68:1192-1195 (2002)).

| Protein | GenBank ID | GI Number | Organism |
|---------|------------|-----------|----------|
| MSED_0709 | YP_001190808.1 | 146303492 | *Metallosphaera sedula* |
| Tneu_0421 | | | *Thermoproteus neutrophilus* |
| sucD | P38947.1 | 172046062 | *Clostridium kluyveri* |
| sucD | NP_904963.1 | 34540484 | *Porphyromonas gingivalis* |
| bphG | BAA03892.1 | 425213 | *Pseudomonas* sp |
| adhE | AAV66076.1 | 55818563 | *Leuconostoc mesenteroides* |
| bld | AAP42563.1 | 31075383 | *Clostridium saccharoperbutylacetonicum* |

| Protein | GenBank ID | GI Number | Organism |
|---------|------------|-----------|----------|
| acr1 | YP_047869.1 | 50086359 | *Acinetobacter calcoaceticus* |
| acr1 | AAC45217 | 1684886 | *Acinetobacter baylyi* |
| acr1 | BAB85476.1 | 18857901 | *Acinetobacter* sp. Strain M-1 |

1.2.1.e.

Direct conversion of succinate to succinate semialdehyde is catalyzed by a carboxylic acid reductase. Exemplary enzymes include carboxylic acid reductase, alpha-aminoadipate reductase and retinoic acid reductase. Carboxylic acid reductase (CAR), found in *Nocardia iowensis*, catalyzes the magnesium, ATP and NADPH-dependent reduction of carboxylic acids to their corresponding aldehydes (Venkitasubramanian et al., *J Biol. Chem.* 282:478-485 (2007)). The natural substrate of this enzyme is benzoate and the enzyme exhibits broad acceptance of aromatic substrates including p-toluate (Venkitasubramanian et al., *Biocatalysis in Pharmaceutical and Biotechnology Industries.* CRC press (2006)). The enzyme from *Nocardia iowensis*, encoded by car, was cloned and functionally expressed in *E. coli* (Venkitasubramanian et al., *J Biol. Chem.* 282:478-485 (2007)). CAR requires post-translational activation by a phosphopantetheine transferase (PPTase) that converts the inactive apo-enzyme to the active holo-enzyme (Hansen et al., *Appl. Environ. Microbiol* 75:2765-2774 (2009)). Expression of the npt gene, encoding a specific PPTase, product improved activity of the enzyme. An additional enzyme candidate found in *Streptomyces griseus* is encoded by the griC and griD genes. This enzyme is believed to convert 3-amino-4-hydroxybenzoic acid to 3-amino-4-hydroxybenzaldehyde as deletion of either griC or griD led to accumulation of extracellular 3-acetylamino-4-hydroxybenzoic acid, a shunt product of 3-amino-4-hydroxybenzoic acid metabolism (Suzuki, et al., *J. Antibiot.* 60(6):380-387 (2007)). Co-expression of griC and griD with SGR_665, an enzyme similar in sequence to the *Nocardia iowensis* npt, can be beneficial.

| Gene | GenBank Accession No. | GI No. | Organism |
|------|----------------------|--------|----------|
| car | AAR91681.1 | 40796035 | *Nocardia iowensis* |
| npt | ABI83656.1 | 114848891 | *Nocardia iowensis* |
| griC | YP_001825755.1 | 182438036 | *Streptomyces griseus* |
| griD | YP_001825756.1 | 182438037 | *Streptomyces griseus* |

Additional car and npt genes can be identified based on sequence homology.

| Gene name | GI No. | GenBank Accession No. | Organism |
|---|---|---|---|
| fadD9 | 121638475 | YP_978699.1 | *Mycobacterium bovis* BCG |
| BCG_2812c | 121638674 | YP_978898.1 | *Mycobacterium bovis* BCG |
| nfa20150 | 54023983 | YP_118225.1 | *Nocardia farcinica* IFM 10152 |
| nfa40540 | 54026024 | YP_120266.1 | *Nocardia farcinica* IFM 10152 |
| SGR_6790 | 182440583 | YP_001828302.1 | *Streptomyces griseus* subsp. *griseus* NBRC 13350 |
| SGR_665 | 182434458 | YP_001822177.1 | *Streptomyces griseus* subsp. *griseus* NBRC 13350 |
| MSMEG_2956 | YP_887275.1 | YP_887275.1 | *Mycobacterium smegmatis* MC2 155 |
| MSMEG_5739 | YP_889972.1 | 118469671 | *Mycobacterium smegmatis* MC2 155 |
| MSMEG_2648 | YP_886985.1 | 118471293 | *Mycobacterium smegmatis* MC2 155 |
| MAP1040c | NP_959974.1 | 41407138 | *Mycobacterium avium* subsp. *paratuberculosis* K-10 |
| MAP2899c | NP_961833.1 | 41408997 | *Mycobacterium avium* subsp. *paratuberculosis* K-10 |
| MMAR_2117 | YP_001850422.1 | 183982131 | *Mycobacterium marinum* M |
| MMAR_2936 | YP_001851230.1 | 183982939 | *Mycobacterium marinum* M |
| MMAR_1916 | YP_001850220.1 | 183981929 | *Mycobacterium marinum* M |
| TpauDRAFT_33060 | ZP_04027864.1 | 227980601 | *Tsukamurella paurometabola* DSM 20162 |
| TpauDRAFT_20920 | ZP_04026660.1 | ZP_04026660.1 | *Tsukamurella paurometabola* DSM 20162 |
| CPCC7001_1320 | ZP_05045132.1 | 254431429 | *Cyanobium* PCC7001 |
| DDBDRAFT_0187729 | XP_636931.1 | 66806417 | *Dictyostelium discoideum* AX4 |

An enzyme with similar characteristics, alpha-aminoadipate reductase (AAR, EC 1.2.1.31), participates in lysine biosynthesis pathways in some fungal species. This enzyme naturally reduces alpha-aminoadipate to alpha-aminoadipate semialdehyde. The carboxyl group is first activated through the ATP-dependent formation of an adenylate that is then reduced by NAD(P)H to yield the aldehyde and AMP. Like CAR, this enzyme utilizes magnesium and requires activation by a PPTase. Enzyme candidates for AAR and its corresponding PPTase are found in *Saccharomyces cerevisiae* (Morris et al., *Gene* 98:141-145 (1991)), *Candida albicans* (Guo et al., *Mol. Genet. Genomics* 269:271-279 (2003)), and *Schizosaccharomyces pombe* (Ford et al., *Curr. Genet.* 28:131-137 (1995)). The AAR from *S. pombe* exhibited significant activity when expressed in *E. coli* (Guo et al., *Yeast* 21:1279-1288 (2004)). The AAR from *Penicillium chrysogenum* accepts S-carboxymethyl-L-cysteine as an alternate substrate, but did not react with adipate, L-glutamate or diaminopimelate (Hijarrubia et al., *J Biol. Chem.* 278:8250-8256 (2003)). The gene encoding the *P. chrysogenum* PPTase has not been identified to date and no high-confidence hits were identified by sequence comparison homology searching.

| Gene | GenBank Accession No. | GI No. | Organism |
|---|---|---|---|
| LYS2 | AAA34747.1 | 171867 | *Saccharomyces cerevisiae* |
| LYS5 | P50113.1 | 1708896 | *Saccharomyces cerevisiae* |
| LYS2 | AAC02241.1 | 2853226 | *Candida albicans* |
| LYS5 | AAO26020.1 | 28136195 | *Candida albicans* |
| Lys1p | P40976.3 | 13124791 | *Schizosaccharomyces pombe* |
| Lys7p | Q10474.1 | 1723561 | *Schizosaccharomyces pombe* |
| Lys2 | CAA74300.1 | 3282044 | *Penicillium chrysogenum* |

2.3.1.a.

An enzyme with phosphotrans-4-hydroxybutyrylase activity is required to convert 4-hydroxybutyryl-phosphate to 4-hydroxybutyryl-CoA. Exemplary phosphate-transferring acyltransferases include phosphotransacetylase (EC 2.3.1.8) and phosphotransbutyrylase (EC 2.3.1.19). The pta gene from *E. coli* encodes a phosphotransacetylase that reversibly converts acetyl-CoA into acetyl-phosphate (Suzuki, *Biochim. Biophys. Acta* 191:559-569 (1969)). This enzyme can also utilize propionyl-CoA as a substrate, forming propionate in the process (Hesslinger et al., *Mol. Microbiol* 27:477-492 (1998)). Other phosphate acetyltransferases that exhibit activity on propionyl-CoA are found in *Bacillus subtilis* (Rado et al., *Biochim. Biophys. Acta* 321:114-125 (1973)), *Clostridium kluyveri* (Stadtman, *Methods Enzymol* 1:596-599 (1955)), and *Thermotoga maritima* (Bock et al., *J. Bacteriol.* 181:1861-1867 (1999)). Similarly, the ptb gene from *C. acetobutylicum* encodes phosphotransbutyrylase, an enzyme that reversibly converts butyryl-CoA into butyryl-phosphate (Wiesenborn et al., *Appl Environ. Microbiol* 55:317-322 (1989); Walter et al., *Gene* 134:107-111 (1993)). Additional ptb genes are found in butyrate-producing bacterium L2-50 (Louis et al., *J. Bacteriol.* 186:2099-2106 (2004)) and *Bacillus megaterium* (Vazquez et al., *Curr. Microbiol* 42:345-349 (2001)).

| Protein | GenBank ID | GI Number | Organism |
|---|---|---|---|
| pta | NP_416800.1 | 71152910 | *Escherichia coli* |
| pta | P39646 | 730415 | *Bacillus subtilis* |
| pta | A5N801 | 146346896 | *Clostridium kluyveri* |
| pta | Q9X0L4 | 6685776 | *Thermotoga maritima* |
| ptb | NP_349676 | 34540484 | *Clostridium acetobutylicum* |
| ptb | AAR19757.1 | 38425288 | butyrate-producing bacterium L2-50 |
| ptb | CAC07932.1 | 10046659 | *Bacillus megaterium* |

2.7.2.a.

Kinase or phosphotransferase enzymes in the EC class 2.7.2 transform carboxylic acids to phosphonic acids with concurrent hydrolysis of one ATP. Exemplary 4-Hydroxybutyrate kinase enzyme candidates include butyrate kinase (EC 2.7.2.7), isobutyrate kinase (EC 2.7.2.14), aspartokinase (EC 2.7.2.4), acetate kinase (EC 2.7.2.1) and gamma-glutamyl kinase (EC 2.7.2.11). Butyrate kinase catalyzes the reversible conversion of butyryl-phosphate to butyrate during acidogenesis in *Clostridial* species (Cary et al., *Appl Environ Microbiol* 56:1576-1583 (1990)). The *Clostridium acetobutylicum* enzyme is encoded by either of the two buk gene products (Huang et al., *J Mol. Microbiol Biotechnol* 2:33-38 (2000)). Other butyrate kinase enzymes are found in *C. butyricum* and *C. tetanomorphum* (Twarog et al., *J. Bacteriol.* 86:112-117 (1963)). A related enzyme, isobutyrate kinase from *Thermotoga maritima*, was expressed in *E. coli* and crystallized (Diao et al., *J Bacteriol.* 191:2521-2529 (2009); Diao et al., *Acta Crystallogr. D. Biol. Crystallogr.* 59:1100-1102 (2003)). Aspartokinase catalyzes the ATP-dependent phosphorylation of aspartate and participates in the synthesis of several amino acids. The aspartokinase III enzyme in *E. coli*, encoded by lysC, has a broad substrate range and the catalytic residues involved in substrate specificity have been elucidated (Keng et al., *Arch Biochem Biophys* 335:73-81 (1996)). Two additional kinases in *E. coli* are also acetate kinase and gamma-glutamyl kinase. The *E. coli* acetate kinase, encoded by ackA (Skarstedt et al., *J. Biol. Chem.* 251:6775-6783 (1976)), phosphorylates propionate in addition to acetate (Hesslinger et al., *Mol. Microbiol* 27:477-492 (1998)). The *E. coli* gamma-glutamyl kinase, encoded by proB (Smith et al., *J. Bacteriol.* 157:545-551 (1984)), phosphorylates the gamma carbonic acid group of glutamate.

| Protein | GenBank ID | GI Number | Organism |
| --- | --- | --- | --- |
| buk1 | NP_349675 | 15896326 | *Clostridium acetobutylicum* |
| buk2 | Q97II1 | 20137415 | *Clostridium acetobutylicum* |
| buk2 | Q9X278.1 | 6685256 | *Thermotoga maritima* |
| lysC | NP_418448.1 | 16131850 | *Escherichia coli* |
| ackA | NP_416799.1 | 16130231 | *Escherichia coli* |
| proB | NP_414777.1 | 16128228 | *Escherichia coli* |

2.8.3.a.

CoA transferases catalyze the reversible transfer of a CoA moiety from one molecule to another. Several transformations in FIG. 16B require a CoA transferase activity: succinyl-CoA transferase, 4-hydroxybutyryl-CoA transferase, 3-hydroxyisobutyryl-CoA transferase and methacrylyl-CoA transferase. Enzyme candidates for succinyl-CoA transferase have been described previously herein and are also applicable to this pathway. Additional exemplary CoA transferase enzymes include the gene products of cat1, cat2, and cat3 of *Clostridium kluyveri* which have been shown to exhibit succinyl-CoA, 4-hydroxybutyryl-CoA, and butyryl-CoA transferase activity, respectively (Seedorf et al., *Proc. Natl. Acad. Sci U.S.A* 105:2128-2133 (2008); Sohling et al., *J Bacteriol.* 178:871-880 (1996)). Similar CoA transferase activities are also present in *Trichomonas vaginalis* (van Grinsven et al., *J. Biol. Chem.* 283:1411-1418 (2008)) and *Trypanosoma brucei* (Riviere et al., *J. Biol. Chem.* 279:45337-45346 (2004)).

| Protein | GenBank ID | GI Number | Organism |
| --- | --- | --- | --- |
| cat1 | P38946.1 | 729048 | *Clostridium kluyveri* |
| cat2 | P38942.2 | 172046066 | *Clostridium kluyveri* |
| cat3 | EDK35586.1 | 146349050 | *Clostridium kluyveri* |
| TVAG_395550 | XP_001330176 | 123975034 | *Trichomonas vaginalis* G3 |
| Tb11.02.0290 | XP_828352 | 71754875 | *Trypanosoma brucei* |

The glutaconyl-CoA-transferase (EC 2.8.3.12) enzyme from anaerobic bacterium *Acidaminococcus fermentans* reacts with glutaconyl-CoA and 3-butenoyl-CoA (Mack et al., 226:41-51 (1994)), substrates similar in structure to 2,3-dehydroadipyl-CoA. The genes encoding this enzyme are gctA and gctB. This enzyme has reduced but detectable activity with other CoA derivatives including glutaryl-CoA, 2-hydroxyglutaryl-CoA, adipyl-CoA, crotonyl-CoA and acrylyl-CoA (Buckel et al., *Eur. J. Biochem.* 118:315-321 (1981)). The enzyme has been cloned and expressed in *E. coli* (Mack et al., *Eur. J. Biochem.* 226:41-51 (1994)). Glutaconate CoA-transferase activity has also been detected in *Clostridium sporosphaeroides* and *Clostridium symbiosum*. Additional glutaconate CoA-transferase enzymes can be inferred by homology to the *Acidaminococcus fermentans* protein sequence.

| Protein | GenBank ID | GI Number | Organism |
| --- | --- | --- | --- |
| gctA | CAA57199.1 | 559392 | *Acidaminococcus fermentans* |
| gctB | CAA57200.1 | 559393 | *Acidaminococcus fermentans* |
| gctA | ACJ24333.1 | 212292816 | *Clostridium symbiosum* |
| gctB | ACJ24326.1 | 212292808 | *Clostridium symbiosum* |
| gctA | NP_603109.1 | 19703547 | *Fusobacterium nucleatum* |
| gctB | NP_603110.1 | 19703548 | *Fusobacterium nucleatum* |

A CoA transferase that can utilize acetyl-CoA as the CoA donor is acetoacetyl-CoA transferase, encoded by the *E. coli* atoA (alpha subunit) and atoD (beta subunit) genes (Korolev et al., *Acta Crystallogr. D. Biol. Crystallogr.* 58:2116-2121 (2002); Vanderwinkel et al., 33:902-908 (1968)). This enzyme has a broad substrate range (Sramek et al., *Arch Biochem Biophys* 171:14-26 (1975)) and has been shown to transfer the CoA moiety to acetate from a variety of branched and linear acyl-CoA substrates, including isobutyrate (Matthies et al., *Appl Environ. Microbiol* 58:1435-1439 (1992)), valerate (Vanderwinkel et al., *Biochem. Biophys. Res. Commun.* 33:902-908 (1968)) and butanoate (Vanderwinkel et al., *Biochem. Biophys. Res. Commun.* 33:902-908 (1968)). This enzyme is induced at the transcriptional level by acetoacetate, so modification of regulatory control may be necessary for engineering this enzyme into a pathway (Pauli et al., *Eur. J. Biochem.* 29:553-562 (1972)). Similar enzymes exist in *Corynebacterium glutamicum* ATCC 13032 (Duncan et al., 68:5186-5190 (2002)), *Clostridium acetobutylicum* (Cary et al., *Appl Environ Microbiol* 56:1576-1583 (1990); Wiesenborn et al., *Appl Environ Microbiol* 55:323-329 (1989)), and *Clostridium* saccharoperbutylacetonicum (Kosaka et al., *Biosci. Biotechnol Biochem.* 71:58-68 (2007)).

| Gene | GI # | Accession No. | Organism |
| --- | --- | --- | --- |
| atoA | 2492994 | P76459.1 | *Escherichia coli* |
| atoD | 2492990 | P76458.1 | *Escherichia coli* |
| actA | 62391407 | YP_226809.1 | *Corynebacterium glutamicum* |
| cg0592 | 62389399 | YP_224801.1 | *Corynebacterium glutamicum* |
| ctfA | 15004866 | NP_149326.1 | *Clostridium acetobutylicum* |
| ctfB | 15004867 | NP_149327.1 | *Clostridium acetobutylicum* |
| ctfA | 31075384 | AAP42564.1 | *Clostridium saccharoperbutylacetonicum* |
| ctfB | 31075385 | AAP42565.1 | *Clostridium saccharoperbutylacetonicum* |

3.1.2.a.

3-Hydroxyisobutyryl-CoA hydrolase catalyzes the conversion of 3-hydroxyisobutyryl-CoA to 3-hydroxyisobutyrate. This enzyme participates in valine degradation pathways (Shimomura et al., *J Biol. Chem.* 269:14248-14253 (1994)).

Genes encoding this enzyme include hibch of *Rattus norvegicus* (Shimomura et al., *Methods Enzymol.* 324:229-240 (2000)) and *Homo sapiens* (Shimomura et al., supra). Similar gene candidates can also be identified by sequence homology, including hibch of *Saccharomyces cerevisiae* and BC_2292 of *Bacillus cereus*.

| Gene name | GenBank Accession # | GI# | Organism |
|---|---|---|---|
| hibch | Q5XIE6.2 | 146324906 | Rattus norvegicus |
| hibch | Q6NVY1.2 | 146324905 | Homo sapiens |
| hibch | P28817.2 | 2506374 | Saccharomyces cerevisiae |
| BC_2292 | AP09256 | 29895975 | Bacillus cereus |

Methylmalonyl-CoA is converted to methylmalonate by methylmalonyl-CoA hydrolase (EC 3.1.2.7). This enzyme, isolated from *Rattus norvegicus* liver, is also active on malonyl-CoA and propionyl-CoA as alternative substrates (Kovachy et al., *J. Biol. Chem.*, 258: 11415-11421 (1983)). The gene associated with this enzyme has not been identified to date. Exemplary CoA hydrolases with broad substrate ranges are suitable candidates, as are the 3-HIB-CoA hydrolase enzymes described above. The enzyme encoded by acot12 from *Rattus norvegicus* brain (Robinson et al., *Biochem. Biophys. Res. Commun.* 71:959-965 (1976)) can react with butyryl-CoA, hexanoyl-CoA and malonyl-CoA. The human dicarboxylic acid thioesterase, encoded by acot8, exhibits activity on glutaryl-CoA, adipyl-CoA, suberyl-CoA, sebacyl-CoA, and dodecanedioyl-CoA (Westin et al., *J. Biol. Chem.* 280:38125-38132 (2005)). The closest *E. coli* homolog to this enzyme, tesB, can also hydrolyze a range of CoA thioesters (Naggert et al., *J Biol Chem* 266:11044-11050 (1991)). A similar enzyme has also been characterized in the rat liver (Deana R., *Biochem Int* 26:767-773 (1992)). Additional enzymes with hydrolase activity in *E. coli* include ybgC, paaI, and ybdB (Kuznetsova, et al., *FEMS Microbiol Rev,* 2005, 29(2):263-279; Song et al., *J Biol Chem,* 2006, 281(16): 11028-38). Though its sequence has not been reported, the enzyme from the mitochondrion of the pea leaf has a broad substrate range, with demonstrated activity on acetyl-CoA, propionyl-CoA, butyryl-CoA, palmitoyl-CoA, oleoyl-CoA, succinyl-CoA, and crotonyl-CoA (Zeiher et al., *Plant. Physiol.* 94:20-27 (1990)). The acetyl-CoA hydrolase, ACH1, from *S. cerevisiae* represents another candidate hydrolase (Buu et al., *J. Biol. Chem.* 278:17203-17209 (2003)).

| Gene name | GenBank Accession # | GI# | Organism |
|---|---|---|---|
| acot12 | NP_570103.1 | 18543355 | Rattus norvegicus |
| tesB | NP_414986 | 16128437 | Escherichia coli |
| acot8 | CAA15502 | 3191970 | Homo sapiens |
| acot8 | NP_570112 | 51036669 | Rattus norvegicus |
| tesA | NP_415027 | 16128478 | Escherichia coli |
| ybgC | NP_415264 | 16128711 | Escherichia coli |
| paaI | NP_415914 | 16129357 | Escherichia coli |
| ybdB | NP_415129 | 16128580 | Escherichia coli |
| ACH1 | NP_009538 | 6319456 | Saccharomyces cerevisiae |

Yet another candidate hydrolase is the glutaconate CoA-transferase from *Acidaminococcus fermentans*. This enzyme was transformed by site-directed mutagenesis into an acyl-CoA hydrolase with activity on glutaryl-CoA, acetyl-CoA and 3-butenoyl-CoA (Mack et al., *FEBS. Lett.* 405:209-212 (1997)). This suggests that the enzymes encoding succinyl-CoA:3-ketoacid-CoA transferases and acetoacetyl-CoA: acetyl-CoA transferases may also serve as candidates for this reaction step but would require certain mutations to change their function.

| Gene name | GenBank Accession # | GI# | Organism |
|---|---|---|---|
| gctA | CAA57199 | 559392 | Acidaminococcus fermentans |
| gctB | CAA57200 | 559393 | Acidaminococcus fermentans |

4.2.1.a.

Two transformations in FIG. 16B require dehydratase enzymes. The dehydration of 3-hydroxyisobutyrate to MAA is catalyzed by 3-hydroxyisobutyrate. Enzyme candidates for this transformation are described in Example VII. The dehydration of 3-hydroxyisobutyryl-CoA to methacrylyl-CoA is catalyzed by an enzyme with 3-hydroxyisobutyryl-CoA dehydratase activity. Exemplary enzymes include enoyl-CoA hydratases and crotonases.

Enoyl-CoA hydratases (EC 4.2.1.17) catalyze the dehydration of a range of 3-hydroxyacyl-CoA substrates (Roberts et al., *Arch. Microbiol* 117:99-108 (1978); Agnihotri et al., *Bioorg. Med. Chem.* 11:9-20 (2003); Conrad et al., *J. Bacteriol.* 118:103-111 (1974)). The enoyl-CoA hydratase of *Pseudomonas putida*, encoded by ech, catalyzes the conversion of 3-hydroxybutyryl-CoA to crotonyl-CoA (Roberts et al., *Arch. Microbiol* 117:99-108 (1978)). This transformation is also catalyzed by the crt gene product of *Clostridium acetobutylicum*, the crt1 gene product of *C. kluyveri*, and other clostridial organisms Atsumi et al., *Metab Eng* 10:305-311 (2008); Boynton et al., *J. Bacteriol.* 178:3015-3024 (1996); Hillmer et al., *FEBS Lett.* 21:351-354 (1972)). Additional enoyl-CoA hydratase candidates are phaA and phaB, of *P. putida*, and paaA and paaB from *P. fluorescens* (Olivera et al., *Proc. Natl. Acad. Sci U.S.A* 95:6419-6424 (1998)). The gene product of pimF in *Rhodopseudomonas palustris* is predicted to encode an enoyl-CoA hydratase that participates in pimeloyl-CoA degradation (Harrison et al., *Microbiology* 151:727-736 (2005)). Lastly, a number of *Escherichia coli* genes have been shown to demonstrate enoyl-CoA hydratase functionality including maoC (Park et al., *J. Bacteriol.* 185: 5391-5397 (2003)), paaF (Ismail et al., *Eur. J. Biochem.* 270: 3047-3054 (2003); Park et al., *Appl. Biochem. Biotechnol* 113-116:335-346 (2004); Park et al., *Biotechnol Bioeng* 86:681-686 (2004)) and paaG (Ismail et al., *Eur. J. Biochem.* 270:3047-3054 (2003); Park and Lee, *Appl. Biochem. Biotechnol* 113-116:335-346 (2004); Park and Yup, *Biotechnol Bioeng* 86:681-686 (2004)).

| Gene | GenBank Accession No. | GI No. | Organism |
|---|---|---|---|
| ech | NP_745498.1 | 26990073 | Pseudomonas putida |
| crt | NP_349318.1 | 15895969 | Clostridium acetobutylicum |
| crt1 | YP_001393856 | 153953091 | Clostridium kluyveri |
| phaA | NP_745427.1 | 26990002 | Pseudomonas putida |
| phaB | NP_745426.1 | 26990001 | Pseudomonas putida |
| paaA | ABF82233.1 | 106636093 | Pseudomonas fluorescens |
| paaB | ABF82234.1 | 106636094 | Pseudomonas fluorescens |
| maoC | NP_415905.1 | 16129348 | Escherichia coli |
| paaF | NP_415911.1 | 16129354 | Escherichia coli |

| Gene | GenBank Accession No. | GI No. | Organism |
|---|---|---|---|
| paaG | NP_415912.1 | 16129355 | *Escherichia coli* |

Alternatively, the *E. coli* gene products of fadA and fadB encode a multienzyme complex involved in fatty acid oxidation that exhibits enoyl-CoA hydratase activity (Yang et al., *Biochemistry* 30:6788-6795 (1991); Yang, *J Bacteriol.* 173: 7405-7406 (1991); Nakahigashi et al., *Nucleic Acids Res.* 18:4937 (1990)). Knocking out a negative regulator encoded by fadR can be utilized to activate the fadB gene product (Sato et al., *J Biosci. Bioeng* 103:38-44 (2007)). The fadI and fadJ genes encode similar functions and are naturally expressed under anaerobic conditions (Campbell et al., *Mol. Microbiol* 47:793-805 (2003)).

| Protein | GenBank ID | GI Number | Organism |
|---|---|---|---|
| fadA | YP_026272.1 | 49176430 | *Escherichia coli* |
| fadB | NP_418288.1 | 16131692 | *Escherichia coli* |
| fadI | NP_416844.1 | 16130275 | *Escherichia coli* |
| fadJ | NP_416843.1 | 16130274 | *Escherichia coli* |
| fadR | NP_415705.1 | 16129150 | *Escherichia coli* |

5.4.99.a.

4-Hydroxybutyryl-CoA is rearranged to form 3-hydroxyisobutyryl-CoA by an enzyme with 4-hydroxybutyryl-CoA mutase activity. This activity has not been demonstrated to date. Methylmalonyl-CoA mutase and isobutyryl-CoA mutase catalyze similar transformations. Exemplary methylmalonyl-CoA mutase and isobutyryl-CoA mutase enzyme candidates are described in Examples V and VII.

6.2.1.a.

The conversion of acyl-CoA substrates to their acid products can be catalyzed by a CoA acid-thiol ligase or CoA synthetase in the 6.2.1 family of enzymes. Enzymes of FIG. 16B in this class include succinyl-CoA synthetase, 4-hydroxybutyryl-CoA synthetase, 3-hydroxyisobutyryl-CoA synthetase and methacrylyl-CoA synthetase. Succinyl-CoA synthetase enzyme candidates were described previously. Exemplary enzymes for catalyzing 4-hydroxybutyryl-CoA synthetase, 3-hydroxyisobutyryl-CoA synthetase and methacrylyl-CoA synthetase activities are described herein and below. ADP-forming acetyl-CoA synthetase (ACD, EC 6.2.1.13) is an enzyme that couples the conversion of acyl-CoA esters to their corresponding acids with the concomitant synthesis of ATP. ACD I from *Archaeoglobus fulgidus*, encoded by AF1211, was shown to operate on a variety of linear and branched-chain substrates including isobutyrate, isopentanoate, and fumarate (Musfeldt et al., *J. Bacteriol.* 184:636-644 (2002)). A second reversible ACD in *Archaeoglobus fulgidus*, encoded by AF1983, was also shown to have a broad substrate range with high activity on cyclic compounds phenylacetate and indoleacetate (Musfeldt and Schonheit, *J. Bacteriol.* 184:636-644 (2002)). The enzyme from *Haloarcula marismortui* (annotated as a succinyl-CoA synthetase) accepts propionate, butyrate, and branched-chain acids (isovalerate and isobutyrate) as substrates, and was shown to operate in the forward and reverse directions (Brasen et al., *Arch Microbiol* 182:277-287 (2004)). The ACD encoded by PAE3250 from hyperthermophilic crenarchaeon *Pyrobaculum aerophilum* showed the broadest substrate range of all characterized ACDs, reacting with acetyl-CoA, isobutyryl-CoA (preferred substrate) and phenylacetyl-CoA (Brasen et al, supra). Directed evolution or engineering can be used to modify this enzyme to operate at the physiological temperature of the host organism. The enzymes from *A. fulgidus*, *H. marismortui* and *P. aerophilum* have all been cloned, functionally expressed, and characterized in *E. coli* (Brasen and Schonheit, supra; Musfeldt and Schonheit, *J. Bacteriol.* 184:636-644 (2002)). An additional candidate is succinyl-CoA synthetase, encoded by sucCD of *E. coli* and LSO and LSC2 genes of *Saccharomyces cerevisiae*. These enzymes catalyze the formation of succinyl-CoA from succinate with the concomitant consumption of one ATP in a reaction which is reversible in vivo (Buck et al., *Biochemistry* 24:6245-6252 (1985)). The acyl CoA ligase from *Pseudomonas putida* has been demonstrated to work on several aliphatic substrates including acetic, propionic, butyric, valeric, hexanoic, heptanoic, and octanoic acids and on aromatic compounds such as phenylacetic and phenoxyacetic acids (Fernandez-Valverde et al., *Appl. Environ. Microbiol.* 59:1149-1154 (1993)). A related enzyme, malonyl CoA synthetase (6.3.4.9) from *Rhizobium leguminosarum* could convert several diacids, namely, ethyl-, propyl-, allyl-, isopropyl-, dimethyl-, cyclopropyl-, cyclopropylmethylene-, cyclobutyl-, and benzylmalonate into their corresponding monothioesters (Pohl et al., *J. Am. Chem. Soc.* 123:5822-5823 (2001)).

| Protein | GenBank ID | GI Number | Organism |
|---|---|---|---|
| AF1211 | NP_070039.1 | 11498810 | *Archaeoglobus fulgidus* |
| AF1983 | NP_070807.1 | 11499565 | *Archaeoglobus fulgidus* |
| scs | YP_135572.1 | 55377722 | *Haloarcula marismortui* |
| PAE3250 | NP_560604.1 | 18313937 | *Pyrobaculum aerophilum* str. IM2 |
| sucC | NP_415256.1 | 16128703 | *Escherichia coli* |
| sucD | AAC73823.1 | 1786949 | *Escherichia coli* |
| LSC1 | NP_014785 | 6324716 | *Saccharomyces cerevisiae* |
| LSC2 | NP_011760 | 6321683 | *Saccharomyces cerevisiae* |
| paaF | AAC24333.2 | 22711873 | *Pseudomonas putida* |
| matB | AAC83455.1 | 3982573 | *Rhizobium leguminosarum* |

Figures 18A, 18B:
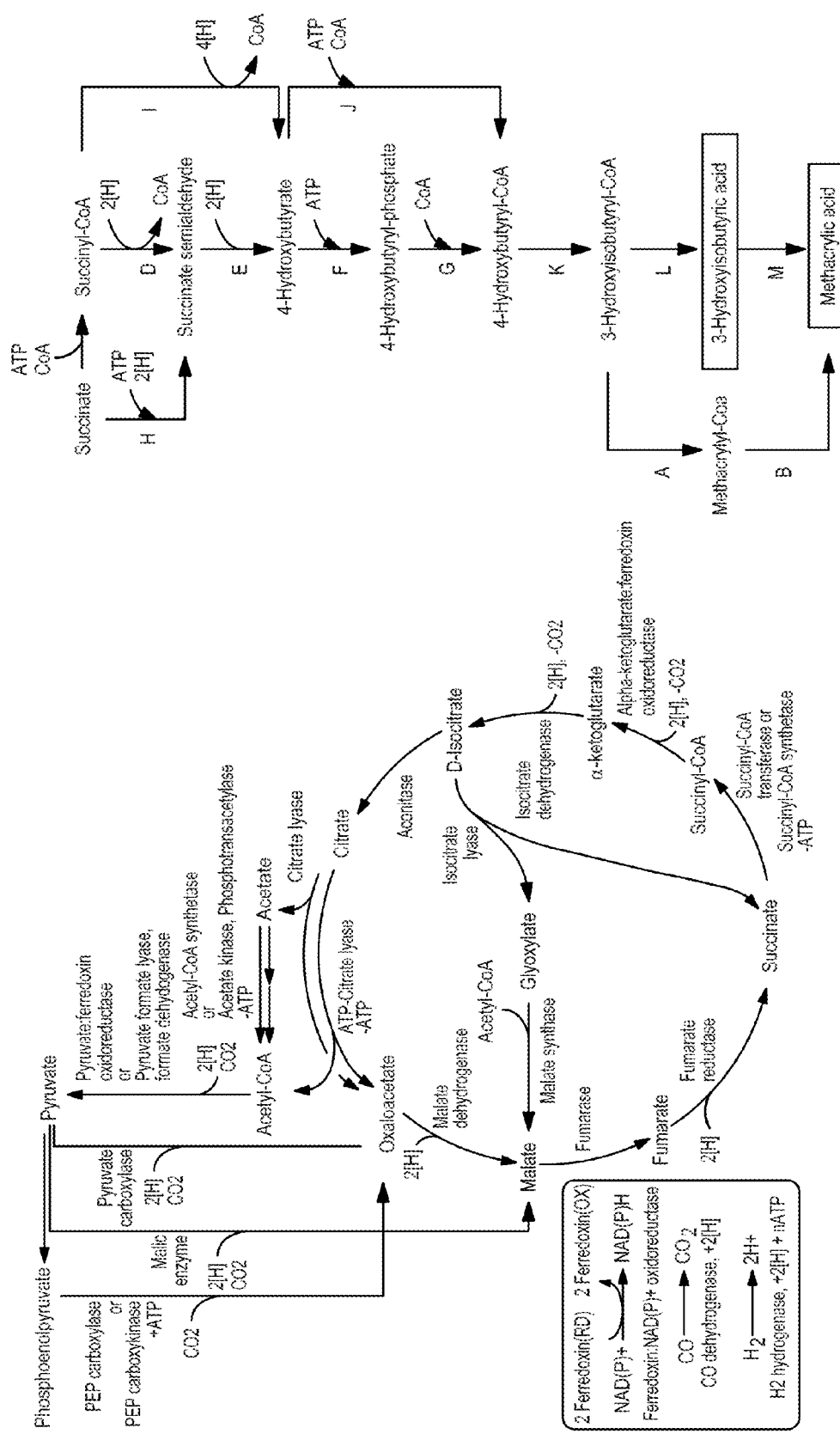
FIGS. 18A and 18B show exemplary pathways. The enzymatic transformations are carried out by the enzymes as shown.

An active reductive TCA cycle improves the yield of the acetyl-CoA derived product methacrylic acid (MAA), as shown in the exemplary pathways of FIG. 18. Pathways of the reductive TCA cycle are described herein as well as the conversion of succinate to 4-hydroxybutyryl-CoA and methacrylic acid (see also FIGS. 5 and 16B and Example VII). FIGS. 18A and 18B show exemplary pathways. The enzymatic transformations are carried out by the enzymes as shown. FIG. 18A shows the pathways for fixation of $CO_2$ to succinate using the reductive TCA cycle. FIG. 18B shows exemplary pathways for the biosynthesis of 3-hydroxyisobutyric acid and methacrylic acid from succinate; the enzymatic transformations shown are carried out by the following enzymes: A. 3-Hydroxyisobutyryl-CoA dehydratase, B. Methacrylyl-CoA synthetase, transferase or hydrolase, C. Succinyl-CoA transferase or synthetase, D. Succinyl-CoA reductase (aldehyde forming), E. 4-Hydroxybutyrate dehydrogenase, F. 4-Hydroxybutyrate kinase, G. Phosphotrans-4-hydroxybutyrylase, H. Succinate reductase, I. Succinyl-CoA reductase (alcohol forming), J. 4-Hydroxybutyryl-CoA synthetase or transferase, K. 4-Hydroxybutyryl-CoA mutase, L. 3-Hydroxyisobutyryl-CoA synthetase, transferase or hydrolase, M. 3-Hydroxyisobutyrate dehydratase.

EXAMPLE XXI

Pathways for the Production of MAA and 2-Hydroxyisobutyric Acid from Acetyl-CoA

An active reductive TCA cycle improves the yield of the acetyl-CoA derived product methacrylic acid (MAA), as shown in the flux distribution of FIG. 16C. In this pathway, MAA is produced from acetyl-CoA in five enzymatic steps. In the first step, two molecules of acetyl-CoA are combined to form acetoacetyl-CoA. Acetoacetyl-CoA is subsequently reduced to 3-hydroxybutyryl-CoA. A methylmutase then rearranges the carbon backbone of 3-hydroxybutyryl-CoA to 2-hydroxyisobutyryl-CoA, which is then dehydrated to form methacrylyl-CoA. Alternatively, 2-hydroxyisobutyryl-CoA can be converted to 2-hydroxyisobutyrate, secreted, and recovered as product. The final step converting methacrylyl-CoA to MAA can be performed by a single enzyme or a series of enzymes. An alternate strategy for converting methacrylyl-CoA into MAA entails a multi-step process in which MAA-CoA is converted to MAA via 3-hydroxyisobutyrate. By this process, MAA-CoA is first converted to 3-hydroxyisobutyryl-CoA, which can subsequently be converted to 3-hydroxyisobutyrate by 3-hydroxyisobutyryl-CoA transferase, synthetase or hydrolase. 3-Hydroxyisobutyrate can then be converted to MAA biocatalytically via a 3-hydroxyisobutyrate dehydratase, or secreted and converted to MAA by chemical dehydration.

Enzyme candidates for each pathway step are described herein. CoA transferase, synthetase and hydrolase enzymes catalyzing the conversion of methacrylyl-CoA to MAA were described above in Example VII. Enzymes describing the indirect conversion of methacrylyl-CoA to 3-hydroxyisobutyrate and methacrylic acid are also described above.

Acetoacetyl-CoA Thiolase.

The formation of acetoacetyl-CoA from two acetyl-CoA units is catalyzed by acetyl-CoA thiolase. Exemplary enzymes are described in Example X.

EXAMPLE XXII

Pathways for the Production of MAA from Pyruvate and Acetyl-CoA

An active reductive TCA cycle improves the yield of the acetyl-CoA derived product methacrylic acid (MAA). A flux distribution showing this improved yield is shown in FIG. 16D.

FIG. 16E (see also FIG. 1 and Example I) depicts exemplary pathways to MAA from acetyl-CoA and pyruvate via the intermediate citramalate. Also shown are pathways to MAA from aconitate. In one pathway acetyl-CoA and pyruvate are converted to citramalate by citramalate synthase. Dehydration of citramalate can yield either citraconate or mesaconate. Mesaconate and citraconate are interconverted by a cis/trans isomerase. Decarboxylation of mesaconate or citraconate yields MAA. In an alternate pathway, citramalate is formed from acetyl-CoA and pyruvate via a citramalyl-CoA intermediate, catalyzed by citramalyl-CoA lyase and citramalyl-coA hydrolase, transferase or synthetase. Also shown are pathways from aconitate to MAA. In one pathway, aconitate is first decarboxylated to itaconate by aconitate decarboxylase. Itaconate is then isomerized to citraconate by itaconate delta-isomerase. Conversion of citraconate to MAA proceeds either directly by decarboxylation or indirectly via mesaconate. In an alternate pathway, the itaconate intermediate is first converted to itaconyl-CoA by a CoA transferase or synthetase. Hydration of itaconyl-CoA yields citramalyl-CoA, which can then be converted to MAA as described previously.

Table 1 as provided in Example I shows enzyme classes that can perform the steps depicted in FIG. 16E. Exemplary enzymes are described below and in further detail in Example I.

EC 2.3.1.a Synthase.

Citramalate synthase (EC 2.3.1.182) catalyzes the conversion of acetyl-CoA and pyruvate to citramalate and coenzyme A. Exemplary enzymes are described in Example I.

EC 2.8.3.a Transferase (Step E).

CoA transferases catalyze the reversible transfer of a CoA moiety from one molecule to another. Two transformations in FIG. 16E utilize a CoA transferase: conversion of citramalyl-CoA to citramalate and activation of itaconate to itaconyl-CoA. Citramalyl-CoA transferase (EC 2.8.3.7 and 2.8.3.11) transfers a CoA moiety from citramalyl-CoA to a donor. A citramalate:succinyl-CoA transferase enzyme is active in the 3-hydroxypropionate cycle of glyoxylate assimilation. Exemplary enzymes are described in Example I.

EC 3.2.1.a CoA Hydrolase.

Enzymes in the 3.1.2 family hydrolyze acyl-CoA molecules to their corresponding acids. Several CoA hydrolases with broad substrate ranges are suitable candidates for exhibiting citramalyl-CoA hydrolase activity. Exemplary enzymes are described in Example I.

EC 4.1.1.a Decarboxylase.

The final step of MAA synthesis in FIG. 16E is the decarboxylation of either mesaconate or citraconate. Exemplary enzymes are described in Example I.

EC 4.1.3.a Lyase.

Citramalyl-CoA lyase (EC 4.1.3.25) converts acetyl-CoA and pyruvate to citramalyl-CoA. This enzyme participates in the 3-hydroxypropionate (3-HP) cycle of glyoxylate assimilation, where it acts in the citramalyl-CoA degrading direction. Exemplary enzymes are described in Example I.

EC 4.2.1.a Dehydratase.

The dehydration of citramalate to citraconate is catalyzed by an enzyme with citramalate dehydratase (citraconate forming) activity (EC 4.2.1.35). This enzyme, along with citramalate synthase, participates in the threonine-independent isoleucine biosynthesis pathway characterized in *Methanocaldococcus jannaschii* and *Leptospira interrrogans*. The dehydration of citramalate in these organisms catalyzed by isopropylmalate isomerase (IPMI), which catalyzes both the dehydration of citramalate to citraconate and the subsequent trans-addition of water to citraconate to form methylmalate (Xu et al., *J. Bacteriol.* 186:5400-5409 (2004); Drevland et al., *J Bacteriol.* 189:4391-4400 (2007)). Exemplary enzymes are described in Example I.

EC 5.2.1.a Cis/Trans Isomerase.

The cis/trans isomerization of mesaconate and citraconate is catalyzed by an enzyme with citraconate isomerase activity. Suitable candidates include aconitate isomerase (EC 5.3.3.7), maleate cis, trans-isomerase (EC 5.2.1.1), maleylacetone cis, trans-isomerase and cis, trans-isomerase of unsaturated fatty acids (Cti). Aconitate isomerase interconverts cis- and trans-aconitate. Exemplary enzymes are described in Example I.

EC 5.3.3.a Delta-Isomerase.

The conversion of itaconate to citraconate is catalyzed by itaconate delta-isomerase. Exemplary enzymes are described in Example I.

EC 6.2.1 CoA Synthetase.

The conversion of citramalyl-CoA to citramalate and itaconate to itaconyl-CoA can be catalyzed by a CoA acid-thiol ligase or CoA synthetase in the 6.2.1 family of enzymes. Exemplary enzymes are described in Example I.

An active reductive TCA cycle improves the yield of the acetyl-CoA derived product methacrylic acid (MAA), as shown in the exemplary pathways of FIG. 19. Pathways of the reductive TCA cycle are described herein as well as the conversion of acetyl-CoA and/or pyruvate via the intermediate citramalate to methacrylic acid (see also FIGS. 1 and 16E and Example I). FIGS. 19A and 19B show exemplary pathways. FIG. 19A shows the pathways for fixation of $CO_2$ to acetyl-CoA and pyruvate using the reductive TCA cycle. FIG. 19B shows exemplary pathways for the biosynthesis of methacrylate from acetyl-CoA and pyruvate; the enzymatic transformations shown are carried out by the following enzymes: 1. Citramalate synthase, 2. Citramalate dehydratase (citraconate forming), 3. Citraconate decarboxylase, 4. Citramalyl-CoA lyase, 5. Citramalyl-CoA transferase, synthetase or hydrolase, 6. Citramalate dehydratase (mesaconate forming), 7. Citraconate isomerase, 8. Mesaconate decarboxylase, 9. Aconitate decarboxylase, 10. Itaconate isomerase, 11. Itaconyl-CoA transferase or synthetase, 12. Itaconyl-CoA hydratase.

An active reductive TCA cycle improves the yield of the acetyl-CoA derived product methacrylic acid (MAA), as shown in the exemplary pathways of FIG. 20. Pathways of the reductive TCA cycle are described herein as well as the conversion of acetyl-CoA to methacrylic acid or 2-hydroxyisobutyric acid (see also FIG. 8 and Example X). FIGS. 20A and 20B show exemplary pathways. FIG. 20A shows the pathways for fixation of $CO_2$ to acetyl-CoA using the reductive TCA cycle. FIG. 20B shows exemplary pathways for the biosynthesis of methacrylic acid and 2-hydroxyisobutyric acid from acetyl-CoA.

Figures 21A, 21B:
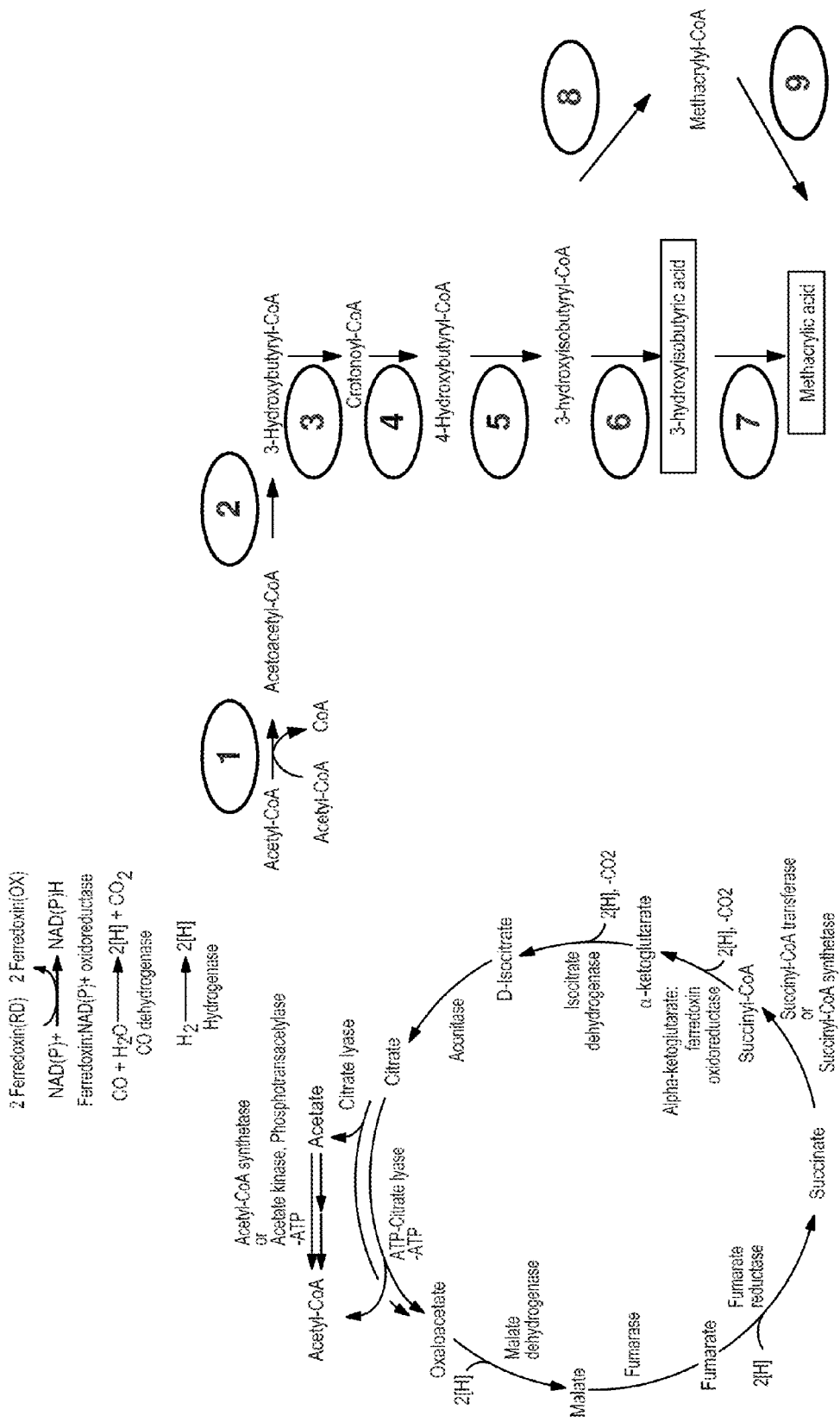
FIGS. 21A and 21B show exemplary pathways.

An active reductive TCA cycle improves the yield of the acetyl-CoA derived product methacrylic acid (MAA), as shown in the exemplary pathways of FIG. 21. Pathways of the reductive TCA cycle are described herein as well as the conversion of acetyl-CoA via the intermediate 3-hydroxyisobutyryl-CoA to methacrylic acid (see also FIGS. 5, 8 and 9 and Examples VII, X, XI and XIV). FIGS. 21A and 21B show exemplary pathways. FIG. 21A shows the pathways for fixation of $CO_2$ to acetyl-CoA using the reductive TCA cycle. FIG. 21B shows exemplary pathways for the biosynthesis of methacrylic acid and 3-hydroxyisobutyric acid from acetyl-CoA; the enzymatic transformations shown are carried out by the following enzymes: 1) Acetoacetyl-CoA thiolase (AtoB), 2) 3-Hydroxybutyryl-CoA dehydrogenase (Hbd), 3) Crotonase (Crt), 4) Crotonyl-CoA hydratase (4-Budh), 5) 4-hydroxybutyryl-CoA mutase, 6) 3-hydroxyisobutyryl-CoA hydrolase, synthetase, or transferase, 7) 3-hydroxyisobutyric acid dehydratase, 8) 3-hydroxyisobutyryl-CoA dehydratase, 9) methacrylyl-CoA hydrolase, synthetase, or transferase. Crotonyl-CoA hydratase, forming 4-hydroxybutyrl-CoA, is the reverse reaction of 4-hydroxybutyrl-CoA dehydratase, which catalyze the reversible conversion of 4-hydroxybutyryl-CoA to crotonyl-CoA (see Example XIV). Thus, in an embodiment of the invention, a methacrylic acid pathway comprises acetoacetyl-CoA thiolase, acetoacetyl-CoA reductase, also referred to herein as 3-hydroxybutyryl-CoA dehydrogenase (see FIGS. 9 and 21), crotonase, 4-hydroxybutyryl-CoA dehydratase, also referred to herein as crotonyl-CoA hydratase, 4-hydroxybutyryl-CoA mutase, 3-hydroxyisobutyryl-CoA synthetase or 3-hydroxyisobutyryl-CoA hydrolase or 3-hydroxyisobutyryl-CoA transferase, and 3-hydroxyisobutyrate dehydratase. Alternatively, a methacrylic acid pathway comprises acetoacetyl-CoA thiolase, acetoacetyl-CoA reductase, crotonase, 4-hydroxybutyryl-CoA dehydratase, 4-hydroxybutyryl-CoA mutase, 3-hydroxyisobutyryl-CoA dehydratase, and methacrylyl-CoA synthetase or methacrylyl-CoA hydrolase or methacrylyl-CoA transferase (see FIG. 21).

EXAMPLE XXIII

Exemplary Carboxylic Acid Reductases

This example describes the use of carboxylic acid reductases to carry out the conversion of a caroboxylic acid to an aldehyde.

1.2.1.e Acid Reductase.

The conversion of unactivated acids to aldehydes can be carried out by an acid reductase. Examples of such conversions include, but are not limited, the conversion of 4-hydroxybutyrate, succinate, alpha-ketoglutarate, and 4-aminobutyrate to 4-hydroxybutanal, succinate semialdehyde, 2,5-dioxopentanoate, and 4-aminobutanal, respectively. One notable carboxylic acid reductase can be found in *Nocardia iowensis* which catalyzes the magnesium, ATP and NADPH-dependent reduction of carboxylic acids to their corresponding aldehydes (Venkitasubramanian et al., *J. Biol. Chem.* 282:478-485 (2007)). This enzyme is encoded by the car gene and was cloned and functionally expressed in *E. coli* (Venkitasubramanian et al., *J. Biol. Chem.* 282:478-485 (2007)). Expression of the npt gene product improved activity of the enzyme via post-transcriptional modification. The npt gene encodes a specific phosphopantetheine transferase (PPTase) that converts the inactive apo-enzyme to the active holo-enzyme. The natural substrate of this enzyme is vanillic acid, and the enzyme exhibits broad acceptance of aromatic and aliphatic substrates (Venkitasubramanian et al., in *Biocatalysis in the Pharmaceutical and Biotechnology Industires*, ed. R. N. Patel, Chapter 15, pp. 425-440, CRC Press LLC, Boca Raton, Fla. (2006)).

| Gene | Accession No. | GI No. | Organism |
|------|--------------|--------|----------|
| car | AAR91681.1 | 40796035 | *Nocardia iowensis* (sp. NRRL 5646) |
| npt | ABI83656.1 | 114848891 | *Nocardia iowensis* (sp. NRRL 5646) |

Additional car and npt genes can be identified based on sequence homology.

| Gene | Accession No. | GI No. | Organism |
|------|--------------|--------|----------|
| fadD9 | YP_978699.1 | 121638475 | *Mycobacterium bovis* BCG |
| BCG_2812c | YP_978898.1 | 121638674 | *Mycobacterium bovis* BCG |
| nfa20150 | YP_118225.1 | 54023983 | *Nocardia farcinica* IFM 10152 |
| nfa40540 | YP_120266.1 | 54026024 | *Nocardia farcinica* IFM 10152 |
| SGR_6790 | YP_001828302.1 | 182440583 | *Streptomyces griseus* subsp. *griseus* NBRC 13350 |
| SGR_665 | YP_001822177.1 | 182434458 | *Streptomyces griseus* subsp. *griseus* NBRC 13350 |

An additional enzyme candidate found in *Streptomyces griseus* is encoded by the griC and griD genes. This enzyme is believed to convert 3-amino-4-hydroxybenzoic acid to 3-amino-4-hydroxybenzaldehyde as deletion of either griC or griD led to accumulation of extracellular 3-acetylamino-4-hydroxybenzoic acid, a shunt product of 3-amino-4-hydroxybenzoic acid metabolism (Suzuki, et al., *J. Antibiot.* 60(6): 380-387 (2007)). Co-expression of griC and griD with SGR_665, an enzyme similar in sequence to the *Nocardia iowensis* npt, can be beneficial.

| Gene | Accession No. | GI No. | Organism |
|---|---|---|---|
| griC | 182438036 | YP_001825755.1 | Streptomyces griseus subsp. griseus NBRC 13350 |
| griD | 182438037 | YP_001825756.1 | Streptomyces griseus subsp. griseus NBRC 13350 |
| MSMEG_2956 | YP_887275.1 | YP_887275.1 | Mycobacterium smegmatis MC2 155 |
| MSMEG_5739 | YP_889972.1 | 118469671 | Mycobacterium smegmatis MC2 155 |
| MSMEG_2648 | YP_886985.1 | 118471293 | Mycobacterium smegmatis MC2 155 |
| MAP1040c | NP_959974.1 | 41407138 | Mycobacterium avium subsp. paratuberculosis K-10 |
| MAP2899c | NP_961833.1 | 41408997 | Mycobacterium avium subsp. paratuberculosis K-10 |
| MMAR_2117 | YP_001850422.1 | 183982131 | Mycobacterium marinum M |
| MMAR_2936 | YP_001851230.1 | 183982939 | Mycobacterium marinum M |
| MMAR_1916 | YP_001850220.1 | 183981929 | Mycobacterium marinum M |
| TpauDRAFT_33060 | ZP_04027864.1 | 227980601 | Tsukamurella paurometabola DSM 20162 |
| TpauDRAFT_20920 | ZP_04026660.1 | 227979396 | Tsukamurella paurometabola DSM 20162 |
| CPCC7001_1320 | ZP_05045132.1 | 254431429 | Cyanobium PCC7001 |
| DDBDRAFT_0187729 | XP_636931.1 | 66806417 | Dictyostelium discoideum AX4 |

An enzyme with similar characteristics, alpha-aminoadipate reductase (AAR, EC 1.2.1.31), participates in lysine biosynthesis pathways in some fungal species. This enzyme naturally reduces alpha-aminoadipate to alpha-aminoadipate semialdehyde. The carboxyl group is first activated through the ATP-dependent formation of an adenylate that is then reduced by NAD(P)H to yield the aldehyde and AMP. Like CAR, this enzyme utilizes magnesium and requires activation by a PPTase. Enzyme candidates for AAR and its corresponding PPTase are found in Saccharomyces cerevisiae (Morris et al., Gene 98:141-145 (1991)), Candida albicans (Guo et al., Mol. Genet. Genomics 269:271-279 (2003)), and Schizosaccharomyces pombe (Ford et al., Curr. Genet. 28:131-137 (1995)). The AAR from S. pombe exhibited significant activity when expressed in E. coli (Guo et al., Yeast 21:1279-1288 (2004)). The AAR from Penicillium chrysogenum accepts S-carboxymethyl-L-cysteine as an alternate substrate, but did not react with adipate, L-glutamate or diaminopimelate (Hijarrubia et al., J. Biol. Chem. 278:8250-8256 (2003)). The gene encoding the P. chrysogenum PPTase has not been identified to date.

| Gene | Accession No. | GI No. | Organism |
|---|---|---|---|
| LYS2 | AAA34747.1 | 171867 | Saccharomyces cerevisiae |
| LYS5 | P50113.1 | 1708896 | Saccharomyces cerevisiae |
| LYS2 | AAC02241.1 | 2853226 | Candida albicans |
| LYS5 | AAO26020.1 | 28136195 | Candida albicans |
| Lys1p | P40976.3 | 13124791 | Schizosaccharomyces pombe |
| Lys7p | Q10474.1 | 1723561 | Schizosaccharomyces pombe |
| Lys2 | CAA74300.1 | 3282044 | Penicillium chrysogenum |

Cloning and Expression of Carboxylic Acid Reductase.

Escherichia coli is used as a target organism to engineer the pathway for methacrylic acid, methacrylate ester, 3-hydroxyisobutyrate and/or 2-hydroxyisobutyrate. E. coli provides a good host for generating a non-naturally occurring microorganism capable of producing methacrylic acid, methacrylate ester, 3-hydroxyisobutyrate and/or 2-hydroxyisobutyrate. E. coli is amenable to genetic manipulation and is known to be capable of producing various intermediates and products effectively under various oxygenation conditions.

To generate a microbial organism strain such as an E. coli strain engineered to produce methacrylic acid, methacrylate ester, 3-hydroxyisobutyrate and/or 2-hydroxyisobutyrate], nucleic acids encoding a carboxylic acid reductase and phosphopantetheine transferase are expressed in E. coli using well known molecular biology techniques (see, for example, Sambrook, supra, 2001; Ausubel supra, 1999). In particular, car genes from Nocardia iowensis (designated 720), Mycobacterium smegmatis mc(2)155 (designated 890), Mycobacterium avium subspecies paratuberculosis K-10 (designated 891) and Mycobacterium marinum M (designated 892) were cloned into pZS*13 vectors (Expressys, Ruelzheim, Germany) under control of PA1/lacO promoters. The npt (ABI83656.1) gene (i.e., 721) was cloned into the pKJL33S vector, a derivative of the original mini-F plasmid vector PML31 under control of promoters and ribosomal binding sites similar to those used in pZS*13.

The car gene (GNM_720) was cloned by PCR from Nocardia genomic DNA. Its nucleic acid and protein sequences are shown in FIGS. 22A and 22B, respectively. A codon-optimized version of the npt gene (GNM_721) was synthesized by GeneArt (Regensburg, Germany). Its nucleic acid and protein sequences are shown in FIGS. 23A and 23B, respectively. The nucleic acid and protein sequences for the Mycobacterium smegmatis mc(2)155 (designated 890), Mycobacterium avium subspecies paratuberculosis K-10 (designated 891) and Mycobacterium marinum M (designated 892) genes and enzymes can be found in FIGS. 24, 25, and 26, respectively. The plasmids are transformed into a host cell to express the proteins and enzymes required for methacrylic acid, methacrylate ester, 3-hydroxyisobutyrate and/or 2-hydroxyisobutyrate production.

Additional CAR variants were generated. A codon optimized version of CAR 891 was generated and designated 891 GA. The nucleic acid and amino acid sequences of CAR 891GA are shown in FIGS. 27A and 27B, respectively. Over 2000 CAR variants were generated. In particular, all 20 amino acid combinations were made at positions V295, M296, G297, G391, G421, D413, G414, Y415, G416, and S417, and additional variants were tested as well. Exemplary CAR variants include: E16K; Q95L; L100M; A1011T; K823E; T941S; H15Q; D198E; G446C; S392N; F699L; V883I; F467S;

T987S; R12H; V295G; V295A; V295S; V295T; V295G; V295V; V295L; V295I; V295M; V295P; V295F; V295Y; V295W; V295D; V295E; V295N; V295Q; V295H; V295K; V295R; M296G; M296A; M296S; M296T; M296C; M296V; M296L; M296I; M296M; M296P; M296F; M296Y; M296W; M296D; M296E; M296N; M296Q; M296H; M296K; M296R; G297G; G297A; G297S; G297T; G297C; G297V; G297L; G297I; G297M; G297P; G297F; G297Y; G297W; G297D; G297E; G297N; G297Q; G297H; G297K; G297R; G391G; G391A; G391S; G391T; G391C; G391V; G391L; G391I; G391M; G391P; G391F; G391Y; G391W; G391D; G391E; G391N; G391Q; G391H; G391K; G391R; G421G; G421A; G421S; G421T; G421C; G421V; G421L; G421I G421M; G421P; G421F; G421Y; G421W; G421D; G421E; G421N; G421Q; G421H; G421K; G421R; D413G; D413A; D413S; D413T; D413C; D413V; D413L; D413I; D413M; D413P; D413F; D413Y; D413W; D413D; D413E; D413N; D413Q; D413H; D413K; D413R; G414G; G414A; G414S; G414T; G414C; G414V; G414L; G414I; G414M; G414P; G414F; G414Y; G414W; G414D; G414E; G414N; G414Q; G414H; G414K; G414R; Y415G; Y415A; Y415S; Y415T; Y415C; Y415V; Y415L; Y415I; Y415M; Y415P; Y415F; Y415Y; Y415W; Y415D; Y415E; Y415N; Y415Q; Y415H; Y415K; Y415R; G416G; G416A; G416S; G416T; G416C; G416V; G416L; G416I; G416M; G416P; G416F; G416Y; G416W; G416D; G416E; G416N; G416Q; G416H; G416K; G416R; S417G; S417A; S417S; S417T; S417C; S417V S417L; S417I; S417M; S417P; S417F; S417Y; S417W; S417D; S417E; S417N; S417Q; S417H; S417K; and S417R.

The CAR variants were screened for activity, and numerous CAR variants were found to exhibit CAR activity.

This example describes the use of CAR for converting carboxylic acids to aldehydes.

EXAMPLE XXIV

Pathway for the Conversion of 4-Hydroxybutyryl-CoA to Methyl Methacrylate

This example describes a pathway for converting 4-hydroxybutyryl-CoA to methyl methacrylate as an exemplary methacrylate ester.

An exemplary pathway to methyl methacrylate is shown in FIG. 30. Briefly, 4-hydroxybutyryl-CoA can be converted to 3-hydroxybutyryl-CoA as described above. 3-Hydroxyisobutyryl-CoA can be converted to 3-hydroxyisobutyrate methyl ester as shown in FIG. 30 using an alcohol tranferase, as described above, in particular a methyl transferase (see Example III; see also WO/2007/039415 and U.S. Pat. No. 7,901,915). 3-Hydroxyisobutyrate methyl ester can be converted to methyl methacrylate by a dehydratase or by chemical conversion, as described above, for example, for the conversion of methacrylate to methacrylate esters (see FIG. 2). Exemplary dehydratases include those described above, for example, in Examples V, VI, X and XII.

Nucleic acids (especially a DNA) coding for an enzyme capable of effecting the transfer of an alcohol moietyl from an alcohol starting material as defined herein to (meth)acrylyl CoA under removal of the CoA moiety, such as a transferase (EC 2) or hydrolase (EC 3) class of enzymes, e.g. lipase, esterase (such as acetyl choline esterase), transferase (such as choline acetyl transferase), protease or acylase (such as aminoacylase) (including coding for one or more such enzymes).

An EC group 2 enzyme, that is a transferase includes, for example, transaminases, transamidases, transketolases, transphosphorylases or choline acetyl transferase that are known to catalyse the movement of a chemical group from one compound to another. An EC class 3; hydrolase, which are also capable of catalysing transesterification reactions, include, for example, lipases from *Candida antartica* (CAL B), porcine pancreatic lipase (PPL), Candid rugosa (CRL) *Pseudomonas cepacia* (PCL) and the like; esterases such as pig liver esterase (PLE) acetyl choline esterase; also proteases such as subtilisin, protease, for instance from *Aspergillus* spp., *Bacillus* spp., *Rhizopus* spp and other hydrolases such as penicillin amidase or, for example, L-amino acylase can be suitable enzymes to catalyse the transfer.

These enzymes can be derived from a prokaryote such as a bacterium, a eukaryote or a higher organism, such as lipase from *Candida* spp., esterase or choline acetyl transferase from mammalian cells, and they can be supplied to the reaction as such. Alternatively, it can also be produced biosynthetically from appropriate starting materials derived from biomass.

While this example describes conversion to methyl methacrylate, it is understood by those skilled in the art that other methacrylate esters can be made using a similar pathway and selecting an appropriate transferase for the desired ester.

EXAMPLE XXV

Conversion of 3-Hydroxyisobutyrate, 2-Hydroxyisobutyrate, 3-Hydroxyisobutyryl-CoA or 2-Hyrdoxyisobutyryl-CoA to a Methacrylate Ester This example describes the conversion of 3-hydroxyisobutyrate, 2-hydroxyisobutyrate, 3-hydroxyisobutyryl-CoA or 2-hydroxyisobutyryl-CoA to a methacrylate ester.

Alternative scenarios included herein are:

(1) A. Sugars to 3-hydroxyisobutyryl-CoA (enzymatic, pathways described previously), B. 3-hydroxyisobutyryl-CoA to 3-hydroxyisobutyrate ester by an alcohol transferase, C. 3-hydroxyisobutyrate ester to methacrylate ester by a dehydratase enzyme or chemical conversion (2) A. Sugars to 2-hydroxyisobutyryl-CoA (enzymatic, pathways described previously), B. 2-hydroxyisobutyryl-CoA to 2-hydroxyisobutyrate ester by an alcohol transferase, C. 2-hydroxyisobutyrate ester to methacrylate ester by a dehydratase enzyme or chemical conversion (3) A. Sugars to 3-hydroxyisobutyrate (enzymatic, pathway described previously), B. 3-hydroxyisobutyrate to 3-hydroxyisobutyrate ester by a 3-hydroxyisobutyrate ester forming enzyme, C. 3-hydroxyisobutyrate ester to methacrylate ester by a dehydratase enzyme or chemical conversion (4) A. Sugars to 2-hydroxyisobutyrate (enzymatic, pathway described previously), B. 2-hydroxyisobutyrate to 2-hydroxyisobutyrate ester by a 2-hydroxyisobutyrate ester forming enzyme, C. 2-hydroxyisobutyrate ester to methacrylate ester by a dehydratase enzyme or chemical conversion (5) A. Exogenous 3-hydroxyisobutyrate supplied to organism (could be a product of another organism (i.e. co-culture or separate fermentation) or could be derived from other sources), B. 3-hydroxyisobutyrate to 2-hydroxyisobutyrate ester by a 3-hydroxyisobutyrate ester forming enzyme, C. 3-hydroxyisobutyrate ester to methacrylate ester by a dehydratase enzyme or chemical conversion (6) A. Exogenous 3-hydroxyisobutyrate supplied to organism (could be a product of another organism (i.e. co-culture or separate fermentation) or could be derived from other sources), B. 3-hydroxyisobutyrate to 3-hydroxyisobutyryl-CoA by a CoA transferase or synthetase, C. formation of 3-hydroxyisobutyrate ester by an alcohol transferase enzyme, C. 3-hydroxyisobutyrate ester to methacrylate ester by a dehydratase enzyme or chemical conversion (7) A. Exogenous 2-hydroxyisobutyrate supplied to organism (could be a product of another organism (i.e. co-culture or separate fermentation) or could be derived from other sources), B. 2-hydroxyisobutyrate to 2-hydroxyisobutyrate ester by a 2-hydroxyisobutyrate ester forming enzyme, C. 2-hydroxyisobutyrate ester to methacrylate ester by a dehydratase enzyme or chemical conversion (8) A. Exogenous 2-hydroxyisobutyrate supplied to organism (could be a product of another organism (i.e. co-culture or separate fermentation) or could be derived from other sources), B. 2-hydroxyisobutyrate to 2-hydroxyisobutyryl-CoA by a CoA transferase or synthetase, C. formation of 2-hydroxyisobutyrate ester by an alcohol transferase enzyme, C. 2-hydroxyisobutyrate ester to methacrylate ester by a dehydratase enzyme or chemical conversion Pathways to methacrylate esters from 3-hydroxybutyrate, 2-hydroxybutyrate, 3-hydroxyisobutyryl-CoA and 2-hydroxyisobutyryl-CoA are shown in FIGS. 28 and 29. Exemplary pathways to these methacrylate ester precursors have been described previously in this application and are shown in FIGS. 3, 5 and 8. 3-Hydroxybutyrate can be formed from succinyl-CoA by the pathway shown in FIG. 3 or from 4-hydroxybutyryl-CoA as shown in FIG. 5. 3-Hydroxybutyryl-CoA can be formed from 4-hydroxybutyryl-CoA by the pathway shown in FIG. 5. 2-Hydroxyisobutyrate and 2-hydroxybutyryl-CoA can be formed by the pathway described in FIG. 8.

2-Hydroxyisobutyrate and its CoA ester, 2-hydroxyisobutyryl-CoA, can be interconverted by a 2-hydroxyisobutyryl-CoA transferase or 2-hydroxyisobutyryl-CoA synthetase. Likewise, 3-hydroxyisobutyrate and its CoA ester, 3-hydroxyisobutyryl-CoA, can be interconverted by a 3-hydroxyisobutyryl-CoA transferase or 3-hydroxyisobutyryl-CoA synthetase. Exemplary CoA transferase and synethetase enzymes are described above in Examples I and VII.

The dehydration of 3-hydroxyisobutyric ester to methacrylic ester can be performed under similar conditions as the dehydration of 3-hyroxyisobutyric acid to methacrylic acid. These reaction conditions are mild (reference: US Patent application 20100068773).

The chemical dehydration of 2-hydroxyisobutyrate ester to methacrylate ester is analogous to the dehydration of 2-hydroxyisobutyric acid to methacrylic acid, which is disclosed, for example, in U.S. Pat. Nos. 3,666,805 and 5,225,594. In these references, 2-hydroxyisobutryic acid is dehydrated using metal oxides and hydroxides, ion exchange resins, alumina, silica, amines, phosphines, alkali metal alkoxides or carboxylates, at reaction temperatures typically between 160-250 degrees C. In one method (U.S. Pat. No. 5,225,594), 2-hydroxyisobutyric acid and sodiumhydroxide were reacted at 185-195 degrees C. under vacuum (300 torr) with stirring, resulting in a 97.1% conversion of 2-hydroxyisobutyric acid, and a 96% yield of methacrylic acid. A similar approach could be applied to dehydrate 2-hydroxyisobutyric ester to methacrylic ester.

Throughout this application various publications have been referenced. The disclosures of these publications in their entireties, including GenBank and GI number publications, are hereby incorporated by reference in this application in order to more fully describe the state of the art to which this invention pertains. Although the invention has been described with reference to the examples provided above, it should be understood that various modifications can be made without departing from the spirit of the invention.

What is claimed is:

1. A non-naturally occurring bacterial organism having a methacrylic acid pathway, said bacterial organism comprising at least one exogenous nucleic acid encoding a methacrylic acid pathway enzyme expressed in a sufficient amount to produce methacrylic acid, said methacrylic acid pathway comprising a pathway selected from:
   (a) citramalate synthase, citraconate-forming citramalate dehydratase, and a decarboxylase of a C1-C6 carboxylate;
   (b) citramalate synthase, citraconate-forming citramalate dehydratase, citraconate isomerase, and a decarboxylase of a C1-C6 carboxylate;
   (c) citramalate synthase, mesaconate-forming citramalate dehydratase, citraconate isomerase, and a decarboxylase of a C1-C6 carboxylate;
   (d) citramalate synthase, mesaconate-forming citramalate dehydratase, and a decarboxylase of a C1-C6 carboxylate;
   (e) citramalyl-CoA lyase, citramalyl-CoA transferase, synthetase or hydrolase, citraconate-forming citramalate dehydratase and a decarboxylase of a C1-C6 carboxylate;
   (f) citramalyl-CoA lyase, citramalyl-CoA transferase, synthetase or hydrolase, citraconate-forming citramalate dehydratase citraconate isomerase, and a decarboxylase of a C1-C6 carboxylate;
   (g) citramalyl-CoA lyase, citramalyl-CoA transferase, synthetase or hydrolase, mesaconate-forming citramalate dehydratase, and a decarboxylase of a C1-C6 carboxylate;
   (h) citramalyl-CoA lyase, citramalyl-CoA transferase, synthetase or hydrolase, mesaconate-forming citramalate dehydratase, citraconate isomerase, and a decarboxylase of a C1-C6 carboxylate;
   (i) aconitate decarboxylase, itaconate isomerase, and a decarboxylase of a C1-C6 carboxylate;
   (j) aconitate decarboxylase, itaconate isomerase, citraconate isomerase, and a decarboxylase of a C1-C6 carboxylate;
   (k) aconitate decarboxylase, itaconyl-CoA transferase, synthetase or hydrolase, citramalyl-CoA dehydratase, citramalyl-CoA transferase, synthetase or hydrolase, citraconate-forming citramalate dehydratase, and a decarboxylase of a C1-C6 carboxylate;
   (l) aconitate decarboxylase, itaconyl-CoA transferase, synthetase or hydrolase, citramalyl-CoA dehydratase, citramalyl-CoA transferase, synthetase or hydrolase, citraconate-forming citramalate dehydratase, citraconate isomerase, and a decarboxylase of a C1-C6 carboxylate;
   (m) aconitate decarboxylase, itaconyl-CoA transferase, synthetase or hydrolase, citramalyl-CoA dehydratase, citramalyl-CoA transferase, synthetase or hydrolase, mesaconate-forming citramalate dehydratase, and a decarboxylase of a C1-C6 carboxylate; and
   (n) aconitate decarboxylase, itaconyl-CoA transferase, synthetase or hydrolase, citramalyl-CoA dehydratase, citramalyl-CoA transferase, synthetase or hydrolase, mesaconate-forming citramalate dehydratase, citraconate isomerase, and a decarboxylase of a C1-C6 carboxylate.

2. The non-naturally occurring bacterial organism of claim 1, wherein said non-naturally occurring bacterial organism further comprises a methacrylate ester pathway comprising at least one exogenous nucleic acid encoding a methacrylate ester pathway enzyme expressed in a sufficient amount to produce a methacrylate ester, said methacrylate ester pathway comprising methacrylyl-CoA synthetase, methacrylyl-CoA transferase, and alcohol transferase.

3. A method for producing methacrylic acid, comprising culturing the non-naturally occurring bacterial organism of claim 1 under conditions and for a sufficient period of time to produce methacrylic acid.

4. The non-naturally occurring bacterial organism of claim 1 wherein the decarboxylase is a decarboxylase of a C1-C6 carboxylate comprising unsaturation.

5. The non-naturally occurring bacterial organism of claim 1 wherein the decarboxylase is a decarboxylase of a C1-C6 carboxylate having two carboxylate groups.

6. The non-naturally occurring bacterial organism of claim 1 wherein the decarboxylase is selected from the group consisting of aconitate decarboxylase, 4-oxalocrotonate decarboxylase, cinnamate decarboxylase, 4-oxalocronate decarboxylase, and sorbic acid decarboxylase.

7. The non-naturally occurring bacterial organism of claim 1 which is *Escherichia coli*.

* * * * *

UNITED STATES PATENT AND TRADEMARK OFFICE
CERTIFICATE OF CORRECTION

| | | |
|---|---|---|
| PATENT NO. | : 9,133,487 B2 | |
| APPLICATION NO. | : 13/436811 | |
| DATED | : September 15, 2015 | |
| INVENTOR(S) | : Mark J. Burk et al. | |

It is certified that error appears in the above-identified patent and that said Letters Patent is hereby corrected as shown below:

<u>On Title Page item 56, under "References Cited", the following should read:</u>
FOREIGN PATENT DOCUMENTS

WO    2008-145737    12/2008

Signed and Sealed this
Sixteenth Day of August, 2016

Michelle K. Lee
*Director of the United States Patent and Trademark Office*

SEQUENCE LISTING

```
<160> NUMBER OF SEQ ID NOS: 12

<210> SEQ ID NO 1
<211> LENGTH: 3525
<212> TYPE: DNA
<213> ORGANISM: Nocardia iowensis

<400> SEQUENCE: 1
atggcagtgg attcaccgga tgagcggcta cagcgccgca ttgcacagtt gtttgcagaa      60
gatgagcagg tcaaggccgc acgtccgctc gaagcggtga gcgcggcggt gagcgcgccc     120
ggtatgcggc tggcgcagat cgccgccact gttatggcgg gttacgccga ccgcccggcc     180
gccgggcagc gtgcgttcga actgaacacc gacgacgcga cgggccgcac ctcgctgcgg     240
ttacttcccc gattcgagac catcacctat cgcgaactgt ggcagcgagt cggcgaggtt     300
gccgcggcct ggcatcatga tcccgagaac cccttgcgcg caggtgattt cgtcgccctg     360
ctcggcttca ccagcatcga ctacgccacc ctcgacctgg ccgatatcca cctcggcgcg     420
gttaccgtgc cgttgcaggc cagcgcggcg gtgtcccagc tgatcgctat cctcaccgag     480
acttcgccgc ggctgctcgc ctcgacccc gagcacctcg atgcggcggt cgagtgccta     540
ctcgcgggca ccacaccgga acgactggtg gtcttcgact accacccga ggacgacgac     600 cagcgtgcgg ccttcgaatc cgcccgccgc cgccttgccg acgcgggcag cttggtgatc     660
```

```
gtcgaaacgc tcgatgccgt gcgtgcccgg ggccgcgact taccggccgc gccactgttc    720
gttcccgaca ccgacgacga cccgctggcc ctgctgatct acacctccgg cagcaccgga    780
acgccgaagg gcgcgatgta caccaatcgg ttggccgcca cgatgtggca ggggaactcg    840
atgctgcagg ggaactcgca acgggtcggg atcaatctca actacatgcc gatgagccac    900
atcgccggtc gcatatcgct gttcggcgtg ctcgctcgcg gtggcaccgc atacttcgcg    960
gccaagagcg acatgtcgac actgttcgaa gacatcggct tggtacgtcc caccgagatc   1020
ttcttcgtcc cgcgcgtgtg cgacatggtc ttccagcgct atcagagcga gctggaccgg   1080
cgctcggtgg cgggcgccga cctggacacg ctcgatcggg aagtgaaagc cgacctccgg   1140
cagaactacc tcggtgggcg cttcctggtg gcggtcgtcg gcagcgcgcc gctggccgcg   1200
gagatgaaga cgttcatgga gtccgtcctc gatctgccac tgcacgacgg gtacgggtcg   1260
accgaggcgg gcgcaagcgt gctgctcgac aaccagatcc agcggccgcc ggtgctcgat   1320
tacaagctcg tcgacgtgcc cgaactgggt tacttccgca ccgaccggcc gcatccgcgc   1380
ggtgagctgt tgttgaaggc ggagaccacg attccgggct actacaagcg gcccgaggtc   1440
accgcggaga tcttcgacga ggacggcttc tacaagaccg gcgatatcgt ggccgagctc   1500
gagcacgatc ggctggtcta tgtcgaccgt cgcaacaatg tgctcaaact gtcgcagggc   1560
gagttcgtga ccgtcgccca tctcgaggcc gtgttcgcca gcagcccgct gatccggcag   1620
atcttcatct acggcagcag cgaacgttcc tatctgctcg cggtgatcgt ccccaccgac   1680
gacgcgctgc gcggccgcga caccgccacc ttgaaatcgg cactggccga atcgattcag   1740
cgcatcgcca aggacgcgaa cctgcagccc tacgagattc cgcgcgattt cctgatcgag   1800
accgagccgt tcaccatcgc caacggactg ctctccggca tcgcgaagct gctgcgcccc   1860
aatctgaagg aacgctacgg cgctcagctg gagcagatgt acaccgatct cgcgacaggc   1920
caggccgatg agctgctcgc cctgcgccgc gaagccgccg acctgccggt gctcgaaacc   1980
gtcagccgga cagcgaaagc gatgctcggc gtcgcctccg ccgatatgcg tcccgacgcg   2040
cacttcaccg acctgggcgg cgattcccctt tccgcgctgt cgttctcgaa cctgctgcac   2100
gagatcttcg gggtcgaggt gccggtgggt gtcgtcgtca gcccggcgaa cgagctgcgc   2160
gatctggcga attacattga ggcggaacgc aactcgggcg cgaagcgtcc caccttcacc   2220
tcggtgcacg gcggcggttc cgagatccgc gccgccgatc tgaccctcga caagttcatc   2280
gatgcccgca ccctggccgc cgccgacagc attccgcacg cgccggtgcc agcgcagacg   2340
gtgctgctga ccgcgcgcaa cggctacctc ggccggttcc tgtgcctgga atggctggag   2400
cggctggaca agacgggtgg cacgctgatc tgcgtcgtgc gcggtagtga cgcggccgcg   2460
gcccgtaaac ggctggactc ggcgttcgac agcggcgatc ccggcctgct cgagcactac   2520
cagcaactgg ccgcacggac cctggaagtc ctcgccggtg atatcggcga cccgaatctc   2580
ggtctggacg acgcgacttg gcagcggttg gccgaaaccg tcgacctgat cgtccatccc   2640
gccgcgttgg tcaaccacgt ccttccctac acccagctgt tcggcccaa tgtcgtcggc    2700 accgccgaaa tcgtccggtt ggcgatcacg gcgcggcgca agccggtcac ctacctgtcg   2760
accgtcggag tggccgacca ggtcgacccg gcggagtatc aggaggacag cgacgtccgc   2820
gagatgagcg cggtgcgcgt cgtgcgcgag agttacgcca acggctacgg caacagcaag   2880
tgggcggggg aggtcctgct gcgcgaagca cacgatctgt gtggcttgcc ggtcgcggtg   2940
ttccgttcgg acatgatcct ggcgcacagc cggtacgcgg gtcagctcaa cgtccaggac   3000
gtgttcaccc ggctgatcct cagcctggtc gccaccggca tcgcgccgta ctcgttctac   3060
```

-continued

```
cgaaccgacg cggacggcaa ccggcagcgg gcccactatg acggcttgcc ggcggacttc    3120
acggcggcgg cgatcaccgc gctcggcatc caagccaccg aaggcttccg gacctacgac    3180
gtgctcaatc cgtacgacga tggcatctcc ctcgatgaat cgtcgactg gctcgtcgaa     3240 tccggccacc cgatccagcg catcaccgac tacagcgact ggttccaccg tttcgagacg    3300
gcgatccgcg cgctgccgga aaagcaacgc caggcctcgg tgctgccgtt gctggacgcc    3360
taccgcaacc cctgcccggc ggtccgcggc gcgatactcc cggccaagga gttccaagcg    3420
gcggtgcaaa cagccaaaat cggtccggaa caggacatcc cgcatttgtc cgcgccactg    3480
atcgataagt acgtcagcga tctggaactg cttcagctgc tctaa                   3525
```

<210> SEQ ID NO 2
<211> LENGTH: 1174
<212> TYPE: PRT
<213> ORGANISM: Nocardia iowensis

<400> SEQUENCE: 2

```
Met Ala Val Asp Ser Pro Asp Glu Arg Leu Gln Arg Arg Ile Ala Gln
1               5                  10                   15

Leu Phe Ala Glu Asp Glu Gln Val Lys Ala Ala Arg Pro Leu Glu Ala
            20                  25                  30

Val Ser Ala Ala Val Ser Ala Pro Gly Met Arg Leu Ala Gln Ile Ala
        35                  40                  45

Ala Thr Val Met Ala Gly Tyr Ala Asp Arg Pro Ala Ala Gly Gln Arg
    50                  55                  60

Ala Phe Glu Leu Asn Thr Asp Asp Ala Thr Gly Arg Thr Ser Leu Arg
65                  70                  75                  80

Leu Leu Pro Arg Phe Glu Thr Ile Thr Tyr Arg Glu Leu Trp Gln Arg
                85                  90                  95

Val Gly Glu Val Ala Ala Ala Trp His His Asp Pro Glu Asn Pro Leu
            100                 105                 110

Arg Ala Gly Asp Phe Val Ala Leu Leu Gly Phe Thr Ser Ile Asp Tyr
        115                 120                 125

Ala Thr Leu Asp Leu Ala Asp Ile His Leu Gly Ala Val Thr Val Pro
    130                 135                 140

Leu Gln Ala Ser Ala Ala Val Ser Gln Leu Ile Ala Ile Leu Thr Glu
145                 150                 155                 160

Thr Ser Pro Arg Leu Leu Ala Ser Thr Pro Glu His Leu Asp Ala Ala
                165                 170                 175

Val Glu Cys Leu Leu Ala Gly Thr Thr Pro Glu Arg Leu Val Val Phe
            180                 185                 190

Asp Tyr His Pro Glu Asp Asp Gln Arg Ala Ala Phe Glu Ser Ala
        195                 200                 205

Arg Arg Arg Leu Ala Asp Ala Gly Ser Leu Val Ile Val Glu Thr Leu
    210                 215                 220

Asp Ala Val Arg Ala Arg Gly Arg Asp Leu Pro Ala Ala Pro Leu Phe
225                 230                 235                 240

Val Pro Asp Thr Asp Asp Asp Pro Leu Ala Leu Leu Ile Tyr Thr Ser
                245                 250                 255

Gly Ser Thr Gly Thr Pro Lys Gly Ala Met Tyr Thr Asn Arg Leu Ala
            260                 265                 270

Ala Thr Met Trp Gln Gly Asn Ser Met Leu Gln Gly Asn Ser Gln Arg
        275                 280                 285
```

```
Val Gly Ile Asn Leu Asn Tyr Met Pro Met Ser His Ile Ala Gly Arg
290                 295                 300

Ile Ser Leu Phe Gly Val Leu Ala Arg Gly Gly Thr Ala Tyr Phe Ala
305                 310                 315                 320

Ala Lys Ser Asp Met Ser Thr Leu Phe Glu Asp Ile Gly Leu Val Arg
                325                 330                 335

Pro Thr Glu Ile Phe Phe Val Pro Arg Val Cys Asp Met Val Phe Gln
            340                 345                 350

Arg Tyr Gln Ser Glu Leu Asp Arg Ser Val Ala Gly Ala Asp Leu
                355                 360                 365

Asp Thr Leu Asp Arg Glu Val Lys Ala Asp Leu Arg Gln Asn Tyr Leu
370                 375                 380

Gly Gly Arg Phe Leu Val Ala Val Gly Ser Ala Pro Leu Ala Ala
385                 390                 395                 400

Glu Met Lys Thr Phe Met Glu Ser Val Leu Asp Leu Pro Leu His Asp
                405                 410                 415

Gly Tyr Gly Ser Thr Glu Ala Gly Ala Ser Val Leu Leu Asp Asn Gln
            420                 425                 430

Ile Gln Arg Pro Pro Val Leu Asp Tyr Lys Leu Val Asp Val Pro Glu
        435                 440                 445

Leu Gly Tyr Phe Arg Thr Asp Arg Pro His Pro Arg Gly Glu Leu Leu
450                 455                 460

Leu Lys Ala Glu Thr Thr Ile Pro Gly Tyr Tyr Lys Arg Pro Glu Val
465                 470                 475                 480

Thr Ala Glu Ile Phe Asp Glu Asp Gly Phe Tyr Lys Thr Gly Asp Ile
                485                 490                 495

Val Ala Glu Leu Glu His Asp Arg Leu Val Tyr Val Asp Arg Arg Asn
            500                 505                 510

Asn Val Leu Lys Leu Ser Gln Gly Glu Phe Val Thr Val Ala His Leu
        515                 520                 525

Glu Ala Val Phe Ala Ser Ser Pro Leu Ile Arg Gln Ile Phe Ile Tyr
    530                 535                 540

Gly Ser Ser Glu Arg Ser Tyr Leu Leu Ala Val Ile Val Pro Thr Asp
545                 550                 555                 560

Asp Ala Leu Arg Gly Arg Asp Thr Ala Thr Leu Lys Ser Ala Leu Ala
                565                 570                 575

Glu Ser Ile Gln Arg Ile Ala Lys Asp Ala Asn Leu Gln Pro Tyr Glu
            580                 585                 590

Ile Pro Arg Asp Phe Leu Ile Glu Thr Glu Pro Phe Thr Ile Ala Asn
        595                 600                 605

Gly Leu Leu Ser Gly Ile Ala Lys Leu Leu Arg Pro Asn Leu Lys Glu
610                 615                 620

Arg Tyr Gly Ala Gln Leu Glu Gln Met Tyr Thr Asp Leu Ala Thr Gly
625                 630                 635                 640

Gln Ala Asp Glu Leu Leu Ala Leu Arg Arg Glu Ala Ala Asp Leu Pro
                645                 650                 655

Val Leu Glu Thr Val Ser Arg Ala Ala Lys Ala Met Leu Gly Val Ala
            660                 665                 670

Ser Ala Asp Met Arg Pro Asp Ala His Phe Thr Asp Leu Gly Gly Asp
        675                 680                 685

Ser Leu Ser Ala Leu Ser Phe Ser Asn Leu Leu His Glu Ile Phe Gly
690                 695                 700

Val Glu Val Pro Val Gly Val Val Val Ser Pro Ala Asn Glu Leu Arg
```

```
            705                 710                 715                 720
Asp Leu Ala Asn Tyr Ile Glu Ala Glu Arg Asn Ser Gly Ala Lys Arg
                725                 730                 735

Pro Thr Phe Thr Ser Val His Gly Gly Gly Ser Glu Ile Arg Ala Ala
                740                 745                 750

Asp Leu Thr Leu Asp Lys Phe Ile Asp Ala Arg Thr Leu Ala Ala Ala
                755                 760                 765

Asp Ser Ile Pro His Ala Pro Val Pro Ala Gln Thr Val Leu Leu Thr
770                 775                 780

Gly Ala Asn Gly Tyr Leu Gly Arg Phe Leu Cys Leu Glu Trp Leu Glu
785                 790                 795                 800

Arg Leu Asp Lys Thr Gly Gly Thr Leu Ile Cys Val Val Arg Gly Ser
                805                 810                 815

Asp Ala Ala Ala Arg Lys Arg Leu Asp Ser Ala Phe Asp Ser Gly
                820                 825                 830

Asp Pro Gly Leu Leu Glu His Tyr Gln Gln Leu Ala Ala Arg Thr Leu
                835                 840                 845

Glu Val Leu Ala Gly Asp Ile Gly Asp Pro Asn Leu Gly Leu Asp Asp
850                 855                 860

Ala Thr Trp Gln Arg Leu Ala Glu Thr Val Asp Leu Ile Val His Pro
865                 870                 875                 880

Ala Ala Leu Val Asn His Val Leu Pro Tyr Thr Gln Leu Phe Gly Pro
                885                 890                 895

Asn Val Val Gly Thr Ala Glu Ile Val Arg Leu Ala Ile Thr Ala Arg
                900                 905                 910

Arg Lys Pro Val Thr Tyr Leu Ser Thr Val Gly Val Ala Asp Gln Val
                915                 920                 925

Asp Pro Ala Glu Tyr Gln Glu Asp Ser Asp Val Arg Glu Met Ser Ala
                930                 935                 940

Val Arg Val Val Arg Glu Ser Tyr Ala Asn Gly Tyr Gly Asn Ser Lys
945                 950                 955                 960

Trp Ala Gly Glu Val Leu Leu Arg Glu Ala His Asp Leu Cys Gly Leu
                965                 970                 975

Pro Val Ala Val Phe Arg Ser Asp Met Ile Leu Ala His Ser Arg Tyr
                980                 985                 990

Ala Gly Gln Leu Asn Val Gln Asp Val Phe Thr Arg Leu Ile Leu Ser
                995                 1000                1005

Leu Val Ala Thr Gly Ile Ala Pro Tyr Ser Phe Tyr Arg Thr Asp
    1010                1015                1020

Ala Asp Gly Asn Arg Gln Arg Ala His Tyr Asp Gly Leu Pro Ala
    1025                1030                1035

Asp Phe Thr Ala Ala Ala Ile Thr Ala Leu Gly Ile Gln Ala Thr
    1040                1045                1050

Glu Gly Phe Arg Thr Tyr Asp Val Leu Asn Pro Tyr Asp Asp Gly
    1055                1060                1065

Ile Ser Leu Asp Glu Phe Val Asp Trp Leu Val Glu Ser Gly His
    1070                1075                1080

Pro Ile Gln Arg Ile Thr Asp Tyr Ser Asp Trp Phe His Arg Phe
    1085                1090                1095

Glu Thr Ala Ile Arg Ala Leu Pro Glu Lys Gln Arg Gln Ala Ser
    1100                1105                1110

Val Leu Pro Leu Leu Asp Ala Tyr Arg Asn Pro Cys Pro Ala Val
    1115                1120                1125
```

```
Arg Gly Ala Ile Leu Pro Ala Lys Glu Phe Gln Ala Ala Val Gln
            1130                1135                1140

Thr Ala Lys Ile Gly Pro Glu Gln Asp Ile Pro His Leu Ser Ala
        1145                1150                1155

Pro Leu Ile Asp Lys Tyr Val Ser Asp Leu Glu Leu Leu Gln Leu
    1160                1165                1170

Leu

<210> SEQ ID NO 3
<211> LENGTH: 669
<212> TYPE: DNA
<213> ORGANISM: Artificial Sequence
<220> FEATURE:
<223> OTHER INFORMATION: Description of Artificial Sequence: Synthetic
      codon optimized phosphpantetheine transferase
      polynucleotide

<400> SEQUENCE: 3
atgattgaaa ccattctgcc tgcaggcgtt gaaagcgcag aactgctgga atatccggaa      60
gatctgaaag cacatccggc agaagaacat ctgattgcca aaagcgttga aaaacgtcgt     120
cgtgatttta ttggtgcacg tcattgtgca cgtctggcac tggcagaact gggtgaacct     180
ccggttgcaa ttggtaaagg tgaacgtggt gcaccgattt ggcctcgtgg tgttgttggt     240
agcctgaccc attgtgatgg ttatcgtgca gcagcagttg cacataaaat gcgctttcgc     300
agcattggta ttgatgcaga accgcatgca accctgccgg aaggtgttct ggatagcgtt     360
agcctgccgc cggaacgtga atggctgaaa accaccgata gcgcactgca tctggatcgt     420
ctgctgtttt gtgcaaaaga agccacctat aaagcctggt ggccgctgac agcacgttgg     480
ctgggttttg aagaagccca tattaccttt gaaattgaag atggtagcgc agatagcggt     540
aatggcacct ttcatagcga actgctggtt ccgggtcaga ccaatgatgg tggtacaccg     600
ctgctgagct tgatggtcg ttggctgatt gcagatggtt ttattctgac cgcaattgcc     660
tatgcctaa                                                             669

<210> SEQ ID NO 4
<211> LENGTH: 222
<212> TYPE: PRT
<213> ORGANISM: Artificial Sequence
<220> FEATURE:
<223> OTHER INFORMATION: Description of Artificial Sequence: Synthetic
      codon optimized phosphpantetheine transferase
      polypeptide

<400> SEQUENCE: 4

Met Ile Glu Thr Ile Leu Pro Ala Gly Val Glu Ser Ala Glu Leu Leu
1               5                   10                  15

Glu Tyr Pro Glu Asp Leu Lys Ala His Pro Ala Glu Glu His Leu Ile
            20                  25                  30

Ala Lys Ser Val Glu Lys Arg Arg Arg Asp Phe Ile Gly Ala Arg His
        35                  40                  45

Cys Ala Arg Leu Ala Leu Ala Glu Leu Gly Glu Pro Pro Val Ala Ile
    50                  55                  60

Gly Lys Gly Glu Arg Gly Ala Pro Ile Trp Pro Arg Gly Val Val Gly
65                  70                  75                  80

Ser Leu Thr His Cys Asp Gly Tyr Arg Ala Ala Ala Val Ala His Lys
                85                  90                  95

Met Arg Phe Arg Ser Ile Gly Ile Asp Ala Glu Pro His Ala Thr Leu
```

```
                100             105              110
Pro Glu Gly Val Leu Asp Ser Val Ser Leu Pro Pro Glu Arg Glu Trp
            115                 120                 125

Leu Lys Thr Thr Asp Ser Ala Leu His Leu Asp Arg Leu Leu Phe Cys
    130                 135                 140

Ala Lys Glu Ala Thr Tyr Lys Ala Trp Trp Pro Leu Thr Ala Arg Trp
145                 150                 155                 160

Leu Gly Phe Glu Glu Ala His Ile Thr Phe Glu Ile Glu Asp Gly Ser
                165                 170                 175

Ala Asp Ser Gly Asn Gly Thr Phe His Ser Glu Leu Leu Val Pro Gly
            180                 185                 190

Gln Thr Asn Asp Gly Gly Thr Pro Leu Leu Ser Phe Asp Gly Arg Trp
        195                 200                 205

Leu Ile Ala Asp Gly Phe Ile Leu Thr Ala Ile Ala Tyr Ala
    210                 215                 220

<210> SEQ ID NO 5
<211> LENGTH: 3522
<212> TYPE: DNA
<213> ORGANISM: Mycobacterium smegmatis

<400> SEQUENCE: 5
atgaccagcg atgttcacga cgccacagac ggcgtcaccg aaaccgcact cgacgacgag     60
cagtcgaccc gccgcatcgc cgagctgtac gccaccgatc ccgagttcgc cgccgccgca    120
ccgttgcccg ccgtggtcga cgcggcgcac aaacccgggc tgcggctggc agagatcctg    180
cagaccctgt tcaccggcta cggtgaccgc ccggcgctgg ataccgcgc cgtgaactg     240 gccaccgacg agggcgggcg caccgtgacg cgtctgctgc cgcggttcga ccccctcacc    300
tacgcccagg tgtggtcgcg cgtgcaagcg gtcgccgcgg ccctgcgcca caacttcgcg    360
cagccgatct ccccggcga cgccgtcgcg acgatcggtt cgcgagtcc cgattacctg     420 acgctggatc tcgtatgcgc ctacctgggc ctcgtgagtg ttccgctgca gcacaacgca    480
ccggtcagcc ggctcgcccc gatcctggcc gaggtcgaac gcggatcct caccgtgagc    540 gccgaatacc tcgacctcgc agtcgaatcc gtgcgggacg tcaactcggt gtcgcagctc    600
gtggtgttcg accatcaccc cgaggtcgac gaccaccgcg acgcactggc ccgcgcgcgt    660
gaacaactcg ccggcaaggg catcgccgtc accaccctgg acgcgatcgc cgacgagggc    720
gccgggctgc cggccgaacc gatctacacc gccgaccatg atcagcgcct cgcgatgatc    780
ctgtacacct cgggttccac cggcgcaccc aagggtgcga tgtacaccga ggcgatggtg    840
gcgcggctgt ggaccatgtc gttcatcacg ggtgacccca cgccggtcat caacgtcaac    900
ttcatgccgc tcaaccacct gggcgggcgc atcccattt ccaccgccgt gcagaacggt     960
ggaaccagtt acttcgtacc ggaatccgac atgtccacgc tgttcgagga tctcgcgctg   1020
gtgcgcccga ccgaactcgg cctggttccg cgcgtcgccg acatgctcta ccagcaccac   1080
ctcgccaccg tcgaccgcct ggtcacgcag ggcgccgacg aactgaccgc cgagaagcag   1140
gccggtgccg aactgcgtga gcaggtgctc ggcggacgcg tgatcaccgg attcgtcagc   1200
accgcaccgc tggccgcgga gatgagggcg ttcctcgaca tcaccctggg cgcacacatc   1260
gtcgacggct acgggctcac cgagaccggc gccgtgacac gcgacggtgt gatcgtgcgg   1320
ccaccggtga tcgactacaa gctgatcgac gttcccgaac tcggctactt cagcaccgac   1380
aagccctacc gcgtggcga actgctggtc aggtcgcaaa cgctgactcc cgggtactac   1440
```

```
aagcgccccg aggtcaccgc gagcgtcttc gaccgggacg gctactacca caccggcgac    1500
gtcatggccg agaccgcacc cgaccacctg gtgtacgtgg accgtcgcaa caacgtcctc    1560
aaactcgcgc agggcgagtt cgtggcggtc gccaacctgg aggcggtgtt ctccggcgcg    1620
gcgctggtgc gccagatctt cgtgtacggc aacagcgagc gcagtttcct tctggccgtg    1680
gtggtcccga cgccggaggc gctcgagcag tacgatccgg ccgcgctcaa ggccgcgctg    1740
gccgactcgc tgcagcgcac cgcacgcgac gccgaactgc aatcctacga ggtgccggcc    1800
gatttcatcg tcgagaccga gccgttcagc gccgccaacg ggctgctgtc gggtgtcgga    1860
aaactgctgc ggcccaacct caaagaccgc tacgggcagc gcctggagca gatgtacgcc    1920
gatatcgcgg ccacgcaggc caaccagttg cgcgaactgc ggcgcgcggc cgccacacaa    1980
ccggtgatcg acaccctcac ccaggccgct gccacgatcc tcggcaccgg gagcgaggtg    2040
gcatccgacg cccacttcac cgacctgggc ggggattccc tgtcggcgct gacactttcg    2100
aacctgctga gcgatttctt cggtttcgaa gttcccgtcg gcaccatcgt gaacccggcc    2160
accaacctcg cccaactcgc ccagcacatc gaggcgcagc gcaccgcggg tgaccgcagg    2220
ccgagtttca ccaccgtgca cggcgcggac gccaccgaga tccgggcgag tgagctgacc    2280
ctggacaagt tcatcgacgc cgaaacgctc cgggccgcac cggtctgcc caaggtcacc    2340 accgagccac ggacggtgtt gctctcgggc gccaacggct ggctgggccg gttcctcacg    2400
ttgcagtggc tggaacgcct ggcacctgtc ggcggcaccc tcatcacgat cgtgcgggc    2460 cgcgacgacg ccgcggcccg cgcacggctg acccaggcct acgacaccga tcccgagttg    2520
tcccgccgct tcgccgagct ggccgaccgc cacctgcggg tggtcgccgg tgacatcggc    2580
gacccgaatc tgggcctcac acccgagatc tggcaccggc tcgccgccga ggtcgacctg    2640
gtggtgcatc cggcagcgct ggtcaaccac gtgctcccct accggcagct gttcggcccc    2700
aacgtcgtgg gcacggccga ggtgatcaag ctggccctca ccgaacggat caagcccgtc    2760
acgtacctgt ccaccgtgtc ggtggccatg gggatcccg acttcgagga ggacggcgac    2820
atccggaccg tgagcccggt gcgccgctc gacggcggat acgccaacgg ctacggcaac    2880
agcaagtggg ccggcgaggt gctgctgcgg gaggcccacg atctgtgcgg gctgcccgtg    2940
gcgacgttcc gctcggacat gatcctggcg catccgcgct accgcggtca ggtcaacgtg    3000
ccagacatgt tcacgcgact cctgttgagc ctcttgatca ccggcgtcgc gccgcggtcg    3060
ttctacatcg agacggtga cgcccgcgg gcgcactacc ccggcctgac ggtcgatttc    3120
gtggccgagg cggtcacgac gctcggcgcg cagcagcgcg agggatacgt gtcctacgac    3180
gtgatgaacc gcacgacga cgggatctcc ctggatgtgt tcgtggactg gctgatccgg    3240
gcgggccatc cgatcgaccg ggtcgacgac tacgacgact gggtgcgtcg gttcgagacc    3300
gcgttgaccg cgcttcccga aagcgccgc gcacagaccg tactgccgct gctgcacgcg    3360
ttccgcgctc cgcaggcacc gttgcgcggc gcacccgaac ccacggaggt gttccacgcc    3420
gcggtgcgca ccgcgaaggt gggcccggga gacatcccgc acctcgacga ggcgctgatc    3480
gacaagtaca tacgcgatct gcgtgagttc ggtctgatct aa                      3522

<210> SEQ ID NO 6
<211> LENGTH: 1173
<212> TYPE: PRT
<213> ORGANISM: Mycobacterium smegmatis

<400> SEQUENCE: 6

Met Thr Ser Asp Val His Asp Ala Thr Asp Gly Val Thr Glu Thr Ala
```

-continued

```
1               5                   10                  15
Leu Asp Asp Glu Gln Ser Thr Arg Arg Ile Ala Glu Leu Tyr Ala Thr
                20                  25                  30
Asp Pro Glu Phe Ala Ala Ala Pro Leu Pro Ala Val Val Asp Ala
                35                  40                  45
Ala His Lys Pro Gly Leu Arg Leu Ala Glu Ile Leu Gln Thr Leu Phe
 50                  55                  60
Thr Gly Tyr Gly Asp Arg Pro Ala Leu Gly Tyr Arg Ala Arg Glu Leu
 65                  70                  75                  80
Ala Thr Asp Glu Gly Gly Arg Thr Val Thr Arg Leu Leu Pro Arg Phe
                85                  90                  95
Asp Thr Leu Thr Tyr Ala Gln Val Trp Ser Arg Val Gln Ala Val Ala
                100                 105                 110
Ala Ala Leu Arg His Asn Phe Ala Gln Pro Ile Tyr Pro Gly Asp Ala
                115                 120                 125
Val Ala Thr Ile Gly Phe Ala Ser Pro Asp Tyr Leu Thr Leu Asp Leu
                130                 135                 140
Val Cys Ala Tyr Leu Gly Leu Val Ser Val Pro Leu Gln His Asn Ala
145                 150                 155                 160
Pro Val Ser Arg Leu Ala Pro Ile Leu Ala Glu Val Glu Pro Arg Ile
                165                 170                 175
Leu Thr Val Ser Ala Glu Tyr Leu Asp Leu Ala Val Glu Ser Val Arg
                180                 185                 190
Asp Val Asn Ser Val Ser Gln Leu Val Val Phe Asp His His Pro Glu
                195                 200                 205
Val Asp Asp His Arg Asp Ala Leu Ala Arg Ala Arg Glu Gln Leu Ala
                210                 215                 220
Gly Lys Gly Ile Ala Val Thr Thr Leu Asp Ala Ile Ala Asp Glu Gly
225                 230                 235                 240
Ala Gly Leu Pro Ala Glu Pro Ile Tyr Thr Ala Asp His Asp Gln Arg
                245                 250                 255
Leu Ala Met Ile Leu Tyr Thr Ser Gly Ser Thr Gly Ala Pro Lys Gly
                260                 265                 270
Ala Met Tyr Thr Glu Ala Met Val Ala Arg Leu Trp Thr Met Ser Phe
                275                 280                 285
Ile Thr Gly Asp Pro Thr Pro Val Ile Asn Val Asn Phe Met Pro Leu
                290                 295                 300
Asn His Leu Gly Gly Arg Ile Pro Ile Ser Thr Ala Val Gln Asn Gly
305                 310                 315                 320
Gly Thr Ser Tyr Phe Val Pro Glu Ser Asp Met Ser Thr Leu Phe Glu
                325                 330                 335
Asp Leu Ala Leu Val Arg Pro Thr Glu Leu Gly Leu Val Pro Arg Val
                340                 345                 350
Ala Asp Met Leu Tyr Gln His His Leu Ala Thr Val Asp Arg Leu Val
                355                 360                 365
Thr Gln Gly Ala Asp Glu Leu Thr Ala Glu Lys Gln Ala Gly Ala Glu
                370                 375                 380
Leu Arg Glu Gln Val Leu Gly Gly Arg Val Ile Thr Gly Phe Val Ser
385                 390                 395                 400
Thr Ala Pro Leu Ala Ala Glu Met Arg Ala Phe Leu Asp Ile Thr Leu
                405                 410                 415
Gly Ala His Ile Val Asp Gly Tyr Gly Leu Thr Glu Thr Gly Ala Val
                420                 425                 430
```

```
Thr Arg Asp Gly Val Ile Val Arg Pro Val Ile Asp Tyr Lys Leu
        435                 440                 445

Ile Asp Val Pro Glu Leu Gly Tyr Phe Ser Thr Asp Lys Pro Tyr Pro
    450                 455                 460

Arg Gly Glu Leu Leu Val Arg Ser Gln Thr Leu Thr Pro Gly Tyr Tyr
465                 470                 475                 480

Lys Arg Pro Glu Val Thr Ala Ser Val Phe Asp Arg Asp Gly Tyr Tyr
                485                 490                 495

His Thr Gly Asp Val Met Ala Glu Thr Ala Pro Asp His Leu Val Tyr
            500                 505                 510

Val Asp Arg Arg Asn Asn Val Leu Lys Leu Ala Gln Gly Glu Phe Val
            515                 520                 525

Ala Val Ala Asn Leu Glu Ala Val Phe Ser Gly Ala Ala Leu Val Arg
            530                 535                 540

Gln Ile Phe Val Tyr Gly Asn Ser Glu Arg Ser Phe Leu Leu Ala Val
545                 550                 555                 560

Val Val Pro Thr Pro Glu Ala Leu Glu Gln Tyr Asp Pro Ala Ala Leu
                565                 570                 575

Lys Ala Ala Leu Ala Asp Ser Leu Gln Arg Thr Ala Arg Asp Ala Glu
            580                 585                 590

Leu Gln Ser Tyr Glu Val Pro Ala Asp Phe Ile Val Glu Thr Glu Pro
            595                 600                 605

Phe Ser Ala Ala Asn Gly Leu Leu Ser Gly Val Gly Lys Leu Leu Arg
610                 615                 620

Pro Asn Leu Lys Asp Arg Tyr Gly Gln Arg Leu Glu Gln Met Tyr Ala
625                 630                 635                 640

Asp Ile Ala Ala Thr Gln Ala Asn Gln Leu Arg Glu Leu Arg Arg Ala
                645                 650                 655

Ala Ala Thr Gln Pro Val Ile Asp Thr Leu Thr Gln Ala Ala Ala Thr
            660                 665                 670

Ile Leu Gly Thr Gly Ser Glu Val Ala Ser Asp Ala His Phe Thr Asp
            675                 680                 685

Leu Gly Gly Asp Ser Leu Ser Ala Leu Thr Leu Ser Asn Leu Leu Ser
            690                 695                 700

Asp Phe Phe Gly Phe Glu Val Pro Val Gly Thr Ile Val Asn Pro Ala
705                 710                 715                 720

Thr Asn Leu Ala Gln Leu Ala Gln His Ile Glu Ala Gln Arg Thr Ala
                725                 730                 735

Gly Asp Arg Arg Pro Ser Phe Thr Thr Val His Gly Ala Asp Ala Thr
                740                 745                 750

Glu Ile Arg Ala Ser Glu Leu Thr Leu Asp Lys Phe Ile Asp Ala Glu
            755                 760                 765

Thr Leu Arg Ala Ala Pro Gly Leu Pro Lys Val Thr Thr Glu Pro Arg
770                 775                 780

Thr Val Leu Leu Ser Gly Ala Asn Gly Trp Leu Gly Arg Phe Leu Thr
785                 790                 795                 800

Leu Gln Trp Leu Glu Arg Leu Ala Pro Val Gly Gly Thr Leu Ile Thr
                805                 810                 815

Ile Val Arg Gly Arg Asp Asp Ala Ala Ala Arg Ala Arg Leu Thr Gln
            820                 825                 830

Ala Tyr Asp Thr Asp Pro Glu Leu Ser Arg Arg Phe Ala Glu Leu Ala
            835                 840                 845
```

Asp Arg His Leu Arg Val Val Ala Gly Asp Ile Gly Asp Pro Asn Leu
    850                 855                 860

Gly Leu Thr Pro Glu Ile Trp His Arg Leu Ala Ala Glu Val Asp Leu
865                 870                 875                 880

Val Val His Pro Ala Ala Leu Val Asn His Val Leu Pro Tyr Arg Gln
                885                 890                 895

Leu Phe Gly Pro Asn Val Val Gly Thr Ala Glu Val Ile Lys Leu Ala
                900                 905                 910

Leu Thr Glu Arg Ile Lys Pro Val Thr Tyr Leu Ser Thr Val Ser Val
            915                 920                 925

Ala Met Gly Ile Pro Asp Phe Glu Glu Asp Gly Asp Ile Arg Thr Val
    930                 935                 940

Ser Pro Val Arg Pro Leu Asp Gly Gly Tyr Ala Asn Gly Tyr Gly Asn
945                 950                 955                 960

Ser Lys Trp Ala Gly Glu Val Leu Leu Arg Glu Ala His Asp Leu Cys
                965                 970                 975

Gly Leu Pro Val Ala Thr Phe Arg Ser Asp Met Ile Leu Ala His Pro
                980                 985                 990

Arg Tyr Arg Gly Gln Val Asn Val Pro Asp Met Phe Thr Arg Leu Leu
            995                 1000                1005

Leu Ser Leu Leu Ile Thr Gly Val Ala Pro Arg Ser Phe Tyr Ile
    1010                1015                1020

Gly Asp Gly Glu Arg Pro Arg Ala His Tyr Pro Gly Leu Thr Val
    1025                1030                1035

Asp Phe Val Ala Glu Ala Val Thr Thr Leu Gly Ala Gln Gln Arg
    1040                1045                1050

Glu Gly Tyr Val Ser Tyr Asp Val Met Asn Pro His Asp Asp Gly
    1055                1060                1065

Ile Ser Leu Asp Val Phe Val Asp Trp Leu Ile Arg Ala Gly His
    1070                1075                1080

Pro Ile Asp Arg Val Asp Asp Tyr Asp Ser Trp Val Arg Arg Phe
    1085                1090                1095

Glu Thr Ala Leu Thr Ala Leu Pro Glu Lys Arg Arg Ala Gln Thr
    1100                1105                1110

Val Leu Pro Leu Leu His Ala Phe Arg Ala Pro Gln Ala Pro Leu
    1115                1120                1125

Arg Gly Ala Pro Glu Pro Thr Glu Val Phe His Ala Ala Val Arg
    1130                1135                1140

Thr Ala Lys Val Gly Pro Gly Asp Ile Pro His Leu Asp Glu Ala
    1145                1150                1155

Leu Ile Asp Lys Tyr Ile Arg Asp Leu Arg Glu Phe Gly Leu Ile
    1160                1165                1170

<210> SEQ ID NO 7
<211> LENGTH: 3522
<212> TYPE: DNA
<213> ORGANISM: Mycobacterium avium

<400> SEQUENCE: 7
atgtcgactg ccacccatga cgaacgactc gaccgtcgcg tccacgaact catcgccacc    60
gacccgcaat tcgccgccgc ccaacccgac ccggcgatca ccgccgccct cgaacagccc   120
gggctgcggc tgccgcagat catccgcacc gtgctcgacg gctacgccga ccggccggcg   180
ctgggacagc gcgtggtgga gttcgtcacg gacgccaaga ccgggcgcac gtcggcgcag   240

-continued

```
ctgctccccc gcttcgagac catcacgtac agcgaagtag cgcagcgtgt tcggcgctg      300 ggccgcgccc tgtccgacga cgcggtgcac cccggcgacc gggtgtgcgt gctgggcttc     360
aacagcgtcg actacgccac catcgacatg gcgctgggcg ccatcggcgc cgtctcggtg     420
ccgctgcaga ccagcgcggc aatcagctcg ctgcagccga tcgtggccga gaccgagccc    480
accctgatcg cgtccagcgt gaaccagctg tccgacgcgg tgcagctgat caccggcgcc    540
gagcaggcgc ccacccggct ggtggtgttc gactaccacc gcaggtcga cgaccagcgc     600 gaggccgtcc aggacgccgc ggcgcggctg tccagcaccg gcgtggccgt ccagacgctg    660
gccgagctgc tggagcgcgg caaggacctg cccgccgtcg cggagccgcc cgccgacgag    720
gactcgctgg ccctgctgat ctacacctcc gggtccaccg gcgcccccaa gggcgcgatg    780
tacccacaga gcaacgtcgg caagatgtgg cgccgcggca gcaagaactg gttcggcgag    840
agcgccgcgt cgatcaccct gaacttcatg ccgatgagcc acgtgatggg ccgaagcatc    900
ctctacggca cgctgggcaa cggcggcacc gcctacttcg ccgcccgcag cgacctgtcc    960
accctgcttg aggacctcga gctggtgcgg cccaccgagc tcaacttcgt cccgcggatc   1020
tgggagacgc tgtacggcga attccagcgt caggtcgagc ggcggctctc cgaggccggg   1080
gacgccggcg aacgtcgcgc cgtcgaggcc gaggtgctgg ccgagcagcg ccagtacctg   1140
ctgggcgggc ggttcacctt cgcgatgacg ggctcggcgc ccatctcgcc ggagctgcgc   1200
aactgggtcg agtcgctgct cgaaatgcac ctgatggacg gctacggctc caccgaggcc   1260
ggaatggtgt tgttcgacgg ggagattcag cgcccgccgg tgatcgacta caagctggtc   1320
gacgtgccgg acctgggcta cttcagcacc gaccggccgc atccgcgcgg cgagctgctg   1380
ctgcgcaccg agaacatgtt cccgggctac tacaagcggg ccgaaaccac cgcgggcgtc   1440
ttcgacgagg acggctacta ccgcaccggc gacgtgttcg ccgagatcgc cccggaccgg   1500
ctggtctacg tcgaccgccg caacaacgtg ctcaagctgg cgcagggcga attcgtcacg   1560
ctggccaagc tggaggcggt gttcggcaac agcccgctga tccgccagat ctacgtctac   1620
ggcaacagcg cccagcccta cctgctggcg gtcgtggtgc ccaccgagga ggcgctggcc   1680
tcgggtgacc ccgagacgct caagcccaag atcgccgact cgctgcagca ggtcgccaag   1740
gaggccggcc tgcagtccta cgaggtgccg cgcgacttca tcatcgagac caccccgttc   1800
agcctggaaa acgtctgctc gaccgggatc cggaagctgg cgtggccgaa actgaagcag   1860
cactacgggg aacggctgga gcagatgtac gccgacctgg ccgccggaca ggccaacgag   1920
ctggccgagc tgcgccgcaa cggtgcccag gcgccggtgt tgcagaccgt gagccgcgcc   1980
gcgggcgcca tgctgggttc ggccgcctcc gacctgtccc ccgacgccca cttcaccgat   2040
ctgggcggag actcgttgtc ggcgttgaca ttcggcaacc tgctgcgcga tcttcgac    2100 gtcgacgtgc cggtaggcgt gatcgtcagc ccggccaacg acctggcggc catcgcgagc   2160
tacatcgagg ccgagcggca gggcagcaag cgcccgacgt tcgcctcggt gcacggccgg   2220
gacgcgaccg tggtgcgcgc cgccgacctg acgctggaca agttcctcga cgccgagacg   2280
ctggccgccg cgccgaacct gcccaagccg gccaccgagg tgcgcaccgt gctgctgacc   2340
ggcgccaccg gcttcctggg ccgctacctg gccctggaat ggctggagcg gatggacatg   2400
gtggacggca aggtcatcgc cctggtccgg gcccgctccg acgaggaggc acgcgcccgg   2460
ctggacaaga ccttcgacag cggcgacccg aaactgctcg cgcactacca gcagctggcc   2520
gccgatcacc tggaggtcat cgccggcgac aagggcgagg ccaatctggg cctgggccaa   2580
gacgtttggc aacgactggc cgacacggtc gacgtgatcg tcgaccccgc cgcgctggtc   2640
```

-continued

```
aaccacgtgt tgccgtacag cgagctgttc gggcccaacg ccctgggcac cgcggagctg    2700
atccggctgg cgctgacgtc caagcagaag ccgtacacct acgtgtccac catcggcgtg    2760
ggcgaccaga tcgagccggg caagttcgtc gagaacgccg acatccggca gatgagcgcc    2820
acccgggcga tcaacgacag ctacgccaac ggctatggca acagcaagtg ggccggcgag    2880
gtgctgctgc gcgaggcgca cgacctgtgc gggctgcccg tcgcggtgtt ccgctgcgac    2940
atgatcctgg ccgacaccac gtatgccggg cagctcaacc tgccggacat gttcacccgg    3000
ctgatgctga gcctggtggc caccgggatc gcgcccggct cgttctacga gctcgacgcc    3060
gacggcaacc ggcagcgggc gcactacgac ggcctgccgg tcgagttcat cgccgcggcg    3120
atctcgacgc tgggttcgca gatcaccgac agcgacaccg gcttccagac ctaccacgtg    3180
atgaacccct acgatgacgg cgtcggtctg gacgagtacg tcgattggct ggtgacgcc     3240
ggctattcga tcgagcggat cgccgactac tccgaatggc tgcggcggtt cgagacctcg    3300
ctgcgggccc tgccggaccg gcagcgccag tactcgctgc tgccgctgct gcacaactac    3360
cgcacgccgg agaagccgat caacgggtcg atagctccca ccgacgtgtt ccgggcagcg    3420
gtgcaggagg cgaaaatcgg ccccgacaaa gacattccgc acgtgtcgcc gccggtcatc    3480
gtcaagtaca tcaccgacct gcagctgctc gggctgctct aa                      3522
```

<210> SEQ ID NO 8
<211> LENGTH: 1173
<212> TYPE: PRT
<213> ORGANISM: Mycobacterium avium

<400> SEQUENCE: 8

```
Met Ser Thr Ala Thr His Asp Glu Arg Leu Asp Arg Arg Val His Glu
1               5                  10                  15

Leu Ile Ala Thr Asp Pro Gln Phe Ala Ala Gln Pro Asp Pro Ala
            20                  25                  30

Ile Thr Ala Ala Leu Glu Gln Pro Gly Leu Arg Leu Pro Gln Ile Ile
        35                  40                  45

Arg Thr Val Leu Asp Gly Tyr Ala Asp Arg Pro Ala Leu Gly Gln Arg
    50                  55                  60

Val Val Glu Phe Val Thr Asp Ala Lys Thr Gly Arg Thr Ser Ala Gln
65                  70                  75                  80

Leu Leu Pro Arg Phe Glu Thr Ile Thr Tyr Ser Glu Val Ala Gln Arg
                85                  90                  95

Val Ser Ala Leu Gly Arg Ala Leu Ser Asp Asp Ala Val His Pro Gly
            100                 105                 110

Asp Arg Val Cys Val Leu Gly Phe Asn Ser Val Asp Tyr Ala Thr Ile
        115                 120                 125

Asp Met Ala Leu Gly Ala Ile Gly Ala Val Ser Val Pro Leu Gln Thr
    130                 135                 140

Ser Ala Ala Ile Ser Ser Leu Gln Pro Ile Val Ala Glu Thr Glu Pro
145                 150                 155                 160

Thr Leu Ile Ala Ser Ser Val Asn Gln Leu Ser Asp Ala Val Gln Leu
                165                 170                 175

Ile Thr Gly Ala Glu Gln Ala Pro Thr Arg Leu Val Val Phe Asp Tyr
            180                 185                 190

His Pro Gln Val Asp Asp Gln Arg Glu Ala Val Gln Asp Ala Ala Ala
        195                 200                 205

Arg Leu Ser Ser Thr Gly Val Ala Val Gln Thr Leu Ala Glu Leu Leu
```

-continued

```
            210                 215                 220
Glu Arg Gly Lys Asp Leu Pro Ala Val Ala Glu Pro Pro Ala Asp Glu
225                 230                 235                 240

Asp Ser Leu Ala Leu Leu Ile Tyr Thr Ser Gly Ser Thr Gly Ala Pro
                    245                 250                 255

Lys Gly Ala Met Tyr Pro Gln Ser Asn Val Gly Lys Met Trp Arg Arg
                260                 265                 270

Gly Ser Lys Asn Trp Phe Gly Glu Ser Ala Ala Ser Ile Thr Leu Asn
            275                 280                 285

Phe Met Pro Met Ser His Val Met Gly Arg Ser Ile Leu Tyr Gly Thr
        290                 295                 300

Leu Gly Asn Gly Gly Thr Ala Tyr Phe Ala Ala Arg Ser Asp Leu Ser
305                 310                 315                 320

Thr Leu Leu Glu Asp Leu Glu Leu Val Arg Pro Thr Glu Leu Asn Phe
                    325                 330                 335

Val Pro Arg Ile Trp Glu Thr Leu Tyr Gly Glu Phe Gln Arg Gln Val
                340                 345                 350

Glu Arg Arg Leu Ser Glu Ala Gly Asp Ala Gly Glu Arg Arg Ala Val
            355                 360                 365

Glu Ala Glu Val Leu Ala Glu Gln Arg Gln Tyr Leu Leu Gly Gly Arg
        370                 375                 380

Phe Thr Phe Ala Met Thr Gly Ser Ala Pro Ile Ser Pro Glu Leu Arg
385                 390                 395                 400

Asn Trp Val Glu Ser Leu Leu Glu Met His Leu Met Asp Gly Tyr Gly
                    405                 410                 415

Ser Thr Glu Ala Gly Met Val Leu Phe Asp Gly Glu Ile Gln Arg Pro
                420                 425                 430

Pro Val Ile Asp Tyr Lys Leu Val Asp Val Pro Asp Leu Gly Tyr Phe
            435                 440                 445

Ser Thr Asp Arg Pro His Pro Arg Gly Glu Leu Leu Leu Arg Thr Glu
        450                 455                 460

Asn Met Phe Pro Gly Tyr Tyr Lys Arg Ala Glu Thr Thr Ala Gly Val
465                 470                 475                 480

Phe Asp Glu Asp Gly Tyr Tyr Arg Thr Gly Asp Val Phe Ala Glu Ile
                    485                 490                 495

Ala Pro Asp Arg Leu Val Tyr Val Asp Arg Arg Asn Asn Val Leu Lys
                500                 505                 510

Leu Ala Gln Gly Glu Phe Val Thr Leu Ala Lys Leu Glu Ala Val Phe
            515                 520                 525

Gly Asn Ser Pro Leu Ile Arg Gln Ile Tyr Val Tyr Gly Asn Ser Ala
        530                 535                 540

Gln Pro Tyr Leu Leu Ala Val Val Val Pro Thr Glu Glu Ala Leu Ala
545                 550                 555                 560

Ser Gly Asp Pro Glu Thr Leu Lys Pro Lys Ile Ala Asp Ser Leu Gln
                    565                 570                 575

Gln Val Ala Lys Glu Ala Gly Leu Gln Ser Tyr Glu Val Pro Arg Asp
                580                 585                 590

Phe Ile Ile Glu Thr Thr Pro Phe Ser Leu Glu Asn Gly Leu Leu Thr
            595                 600                 605

Gly Ile Arg Lys Leu Ala Trp Pro Lys Leu Lys Gln His Tyr Gly Glu
        610                 615                 620

Arg Leu Glu Gln Met Tyr Ala Asp Leu Ala Ala Gly Gln Ala Asn Glu
625                 630                 635                 640
```

```
Leu Ala Glu Leu Arg Arg Asn Gly Ala Gln Ala Pro Val Leu Gln Thr
            645                 650                 655

Val Ser Arg Ala Ala Gly Ala Met Leu Gly Ser Ala Ala Ser Asp Leu
            660                 665                 670

Ser Pro Asp Ala His Phe Thr Asp Leu Gly Gly Asp Ser Leu Ser Ala
            675                 680                 685

Leu Thr Phe Gly Asn Leu Leu Arg Glu Ile Phe Asp Val Asp Val Pro
            690                 695                 700

Val Gly Val Ile Val Ser Pro Ala Asn Asp Leu Ala Ala Ile Ala Ser
705                 710                 715                 720

Tyr Ile Glu Ala Glu Arg Gln Gly Ser Lys Arg Pro Thr Phe Ala Ser
            725                 730                 735

Val His Gly Arg Asp Ala Thr Val Val Arg Ala Ala Asp Leu Thr Leu
            740                 745                 750

Asp Lys Phe Leu Asp Ala Glu Thr Leu Ala Ala Pro Asn Leu Pro
            755                 760                 765

Lys Pro Ala Thr Glu Val Arg Thr Val Leu Leu Thr Gly Ala Thr Gly
770                 775                 780

Phe Leu Gly Arg Tyr Leu Ala Leu Glu Trp Leu Glu Arg Met Asp Met
785                 790                 795                 800

Val Asp Gly Lys Val Ile Ala Leu Val Arg Ala Arg Ser Asp Glu Glu
            805                 810                 815

Ala Arg Ala Arg Leu Asp Lys Thr Phe Asp Ser Gly Asp Pro Lys Leu
            820                 825                 830

Leu Ala His Tyr Gln Gln Leu Ala Ala Asp His Leu Glu Val Ile Ala
            835                 840                 845

Gly Asp Lys Gly Glu Ala Asn Leu Gly Leu Gly Gln Asp Val Trp Gln
            850                 855                 860

Arg Leu Ala Asp Thr Val Asp Val Ile Val Asp Pro Ala Ala Leu Val
865                 870                 875                 880

Asn His Val Leu Pro Tyr Ser Glu Leu Phe Gly Pro Asn Ala Leu Gly
            885                 890                 895

Thr Ala Glu Leu Ile Arg Leu Ala Leu Thr Ser Lys Gln Lys Pro Tyr
            900                 905                 910

Thr Tyr Val Ser Thr Ile Gly Val Gly Asp Gln Ile Glu Pro Gly Lys
            915                 920                 925

Phe Val Glu Asn Ala Asp Ile Arg Gln Met Ser Ala Thr Arg Ala Ile
            930                 935                 940

Asn Asp Ser Tyr Ala Asn Gly Tyr Gly Asn Ser Lys Trp Ala Gly Glu
945                 950                 955                 960

Val Leu Leu Arg Glu Ala His Asp Leu Cys Gly Leu Pro Val Ala Val
            965                 970                 975

Phe Arg Cys Asp Met Ile Leu Ala Asp Thr Thr Tyr Ala Gly Gln Leu
            980                 985                 990

Asn Leu Pro Asp Met Phe Thr Arg Leu Met Leu Ser Leu Val Ala Thr
            995                 1000                1005

Gly Ile Ala Pro Gly Ser Phe Tyr Glu Leu Asp Ala Asp Gly Asn
            1010                1015                1020

Arg Gln Arg Ala His Tyr Asp Gly Leu Pro Val Glu Phe Ile Ala
            1025                1030                1035

Ala Ala Ile Ser Thr Leu Gly Ser Gln Ile Thr Asp Ser Asp Thr
            1040                1045                1050
```

| | | | | | | | | | | | | |
|---|---|---|---|---|---|---|---|---|---|---|---|---|
| Gly | Phe | Gln | Thr | Tyr | His | Val | Met | Asn | Pro | Tyr | Asp | Asp Gly Val |
| | 1055 | | | | 1060 | | | | 1065 | | | |
| Gly | Leu | Asp | Glu | Tyr | Val | Asp | Trp | Leu | Val | Asp | Ala | Gly Tyr Ser |
| | 1070 | | | | 1075 | | | | 1080 | | | |
| Ile | Glu | Arg | Ile | Ala | Asp | Tyr | Ser | Glu | Trp | Leu | Arg | Arg Phe Glu |
| | 1085 | | | | 1090 | | | | 1095 | | | |
| Thr | Ser | Leu | Arg | Ala | Leu | Pro | Asp | Arg | Gln | Arg | Gln | Tyr Ser Leu |
| | 1100 | | | | 1105 | | | | 1110 | | | |
| Leu | Pro | Leu | Leu | His | Asn | Tyr | Arg | Thr | Pro | Glu | Lys | Pro Ile Asn |
| | 1115 | | | | 1120 | | | | 1125 | | | |
| Gly | Ser | Ile | Ala | Pro | Thr | Asp | Val | Phe | Arg | Ala | Ala | Val Gln Glu |
| | 1130 | | | | 1135 | | | | 1140 | | | |
| Ala | Lys | Ile | Gly | Pro | Asp | Lys | Asp | Ile | Pro | His | Val | Ser Pro Pro |
| | 1145 | | | | 1150 | | | | 1155 | | | |
| Val | Ile | Val | Lys | Tyr | Ile | Thr | Asp | Leu | Gln | Leu | Leu | Gly Leu Leu |
| | 1160 | | | | 1165 | | | | 1170 | | | |

<210> SEQ ID NO 9
<211> LENGTH: 3525
<212> TYPE: DNA
<213> ORGANISM: Mycobacterium marinum

<400> SEQUENCE: 9

```
atgtcgccaa tcacgcgtga agagcggctc gagcgccgca tccaggacct ctacgccaac    60
gacccgcagt tcgccgccgc caaacccgcc acggcgatca ccgcagcaat cgagcggccg   120
ggtctaccgc taccccagat catcgagacc gtcatgaccg atacgccga tcggccggct   180
ctcgctcagc gctcggtcga attcgtgacc gacgccggca ccggccacac cacgctgcga   240
ctgctccccc acttcgaaac catcagctac ggcgagcttt ggaccgcat cagcgcactg   300
gccgacgtgc tcagcaccga acagacggtg aaaccgggcg accgggtctg cttgttgggc   360
ttcaacagcg tcgactacgc cacgatcgac atgactttgg cgcggctggg cgcggtggcc   420
gtaccactgc agaccagcgc ggcgataacc cagctgcagc cgatcgtcgc cgagacccag   480
cccaccatga tcgcggccag cgtcgacgca ctcgctgacg ccaccgaatt ggctctgtcc   540
ggtcagaccg ctacccgagt cctggtgttc gaccaccacc ggcaggttga cgcacaccgc   600
gcagcggtcg aatccgcccg ggagcgcctg gccggctcgg cggtcgtcga accctggcc   660
gaggccatcg cgcgcggcga cgtgccccgc ggtgcgtccg ccggctcggc gcccggcacc   720
gatgtgtccg acgactcgct cgcgctactg atctacacct cgggcagcac gggtgcgccc   780
aagggcgcga tgtaccccg acgcaacgtt gcgaccttct ggcgcaagcg cacctggttc   840
gaaggcggct acgagccgtc gatcacgctg aacttcatgc caatgagcca cgtcatgggc   900
cgccaaatcc tgtacggcac gctgtgcaat ggcggcaccg cctacttcgt ggcgaaaagc   960
gatctctcca ccttgttcga agacctggcg ctggtgcggc ccaccgagct gaccttcgtg  1020
ccgcgcgtgt gggacatggt gttcgacgag tttcagagtg aggtcgaccg ccgcctggtc  1080
gacggcgccg accgggtcgc gctcgaagcc caggtcaagg ccgagatacg caacgacgtg  1140
ctcggtggac ggtataccag cgcactgacc ggctccgccc ctatctccga cgagatgaag  1200
gcgtgggtcg aggagctgct cgacatgcat ctggtcgagg gctacggctc caccgaggcc  1260
gggatgatcc tgatcgacgg agccattcgg cgcccggcgg tactcgacta caagctggtc  1320
gatgttcccg acctgggtta cttcctgacc gaccggccac atccgcgggg cgagttgctg  1380
gtcaagaccg atagtttgtt cccgggctac taccagcgag ccgaagtcac cgccgacgtg  1440
```

```
ttcgatgctg acggcttcta ccggaccggc gacatcatgg ccgaggtcgg ccccgaacag    1500
ttcgtgtacc tcgaccgccg caacaacgtg ttgaagctgt cgcagggcga gttcgtcacc    1560
gtctccaaac tcgaagcggt gtttggcgac agcccactgg tacggcagat ctacatctac    1620
ggcaacagcg cccgtgccta cctgttggcg gtgatcgtcc ccacccagga ggcgctggac    1680
gccgtgcctg tcgaggagct caaggcgcgg ctgggcgact cgctgcaaga ggtcgcaaag    1740
gccgccggcc tgcagtccta cgagatcccg cgcgacttca tcatcgaaac aacaccatgg    1800
acgctggaga acggcctgct caccggcatc cgcaagttgg ccaggccgca gctgaaaaag    1860
cattacggcg agcttctcga gcagatctac acggacctgg cacacggcca ggccgacgaa    1920
ctgcgctcgc tgcgccaaag cggtgccgat gcgccggtgc tggtgacggt gtgccgtgcg    1980
gcggccgcgc tgttgggcgg cagcgcctct gacgtccagc ccgatgcgca cttcaccgat    2040
ttgggcggcg actcgctgtc ggcgctgtcg ttcaccaacc tgctgcacga gatcttcgac    2100
atcgaagtgc cggtgggcgt catcgtcagc cccgccaacg acttgcaggc cctggccgac    2160
tacgtcgagg cggctcgcaa acccggctcg tcacggccga ccttcgcctc ggtccacggc    2220
gcctcgaatg ggcaggtcac cgaggtgcat gccggtgacc tgtccctgga caaattcatc    2280
gatgccgcaa ccctggccga agctccccgg ctgcccgccg caaacaccca agtgcgcacc    2340
gtgctgctga ccgcgccac cggcttcctc gggcgctacc tggccctgga atggctggag    2400
cggatggacc tggtcgacgg caaactgatc tgcctggtcc gggccaagtc cgacaccgaa    2460
gcacgggcgc ggctggacaa gacgttcgac agcggcgacc ccgaactgct ggcccactac    2520
cgcgcactgg ccggcgacca cctcgaggtg ctcgccggtg acaagggcga agccgacctc    2580
ggactggacc ggcagacctg gcaacgcctg gccgacacgg tcgacctgat cgtcgacccc    2640
gcggccctgg tcaaccacgt actgccatac agccagctgt tcgggcccaa cgcgctgggc    2700
accgccgagc tgctgcggct ggcgctcacc tccaagatca gccctacag ctacacctcg    2760 acaatcggtg tcgccgacca gatcccgccg tcggcgttca ccgaggacgc cgacatccgg    2820
gtcatcagcg ccaccccgcgc ggtcgacgac agctacgcca atggctactc gaacagcaag    2880
tgggccggcg aggtgctgtt gcgcgaggcg catgacctgt gtggcctgcc ggttgcggtg    2940
ttccgctgcg acatgatcct ggccgacacc acatgggcgg gacagctcaa tgtgccggac    3000
atgttcaccc ggatgatcct gagcctggcg gccaccggta tcgcgccggg ttcgttctat    3060
gagcttgcgg ccgacggcgc ccggcaacgc gcccactatg acggtctgcc cgtcgagttc    3120
atcgccgagg cgatttcgac tttgggtgcg cagagccagg atggtttcca cacgtatcac    3180
gtgatgaacc cctacgacga cggcatcgga ctcgacgagt tcgtcgactg gctcaacgag    3240
tccggttgcc ccatccagcg catcgctgac tatggcgact ggctgcagcg cttcgaaacc    3300
gcactgcgcg cactgcccga tcggcagcgg cacagctcac tgctgccgct gttgcacaac    3360
tatcggcagc cggagcggcc cgtccgcggg tcgatcgccc ctaccgatcg cttccgggca    3420
gcggtgcaag aggccaagat cggccccgac aaagacattc cgcacgtcgg cgcgccgatc    3480
atcgtgaagt acgtcagcga cctgcgccta ctcggcctgc tctaa                   3525
```

<210> SEQ ID NO 10
<211> LENGTH: 1174
<212> TYPE: PRT
<213> ORGANISM: Mycobacterium marinum

<400> SEQUENCE: 10

-continued

```
Met Ser Pro Ile Thr Arg Glu Glu Arg Leu Glu Arg Arg Ile Gln Asp
1               5                   10                  15
Leu Tyr Ala Asn Asp Pro Gln Phe Ala Ala Lys Pro Ala Thr Ala
            20                  25                  30
Ile Thr Ala Ala Ile Glu Arg Pro Gly Leu Pro Leu Pro Gln Ile Ile
        35                  40                  45
Glu Thr Val Met Thr Gly Tyr Ala Asp Arg Pro Ala Leu Ala Gln Arg
    50                  55                  60
Ser Val Glu Phe Val Thr Asp Ala Gly Thr Gly His Thr Thr Leu Arg
65                  70                  75                  80
Leu Leu Pro His Phe Glu Thr Ile Ser Tyr Gly Glu Leu Trp Asp Arg
                85                  90                  95
Ile Ser Ala Leu Ala Asp Val Leu Ser Thr Glu Gln Thr Val Lys Pro
            100                 105                 110
Gly Asp Arg Val Cys Leu Leu Gly Phe Asn Ser Val Asp Tyr Ala Thr
            115                 120                 125
Ile Asp Met Thr Leu Ala Arg Leu Gly Ala Val Ala Val Pro Leu Gln
        130                 135                 140
Thr Ser Ala Ala Ile Thr Gln Leu Gln Pro Ile Val Ala Glu Thr Gln
145                 150                 155                 160
Pro Thr Met Ile Ala Ala Ser Val Asp Ala Leu Ala Asp Ala Thr Glu
                165                 170                 175
Leu Ala Leu Ser Gly Gln Thr Ala Thr Arg Val Leu Val Phe Asp His
            180                 185                 190
His Arg Gln Val Asp Ala His Arg Ala Ala Val Glu Ser Ala Arg Glu
        195                 200                 205
Arg Leu Ala Gly Ser Ala Val Val Glu Thr Leu Ala Glu Ala Ile Ala
    210                 215                 220
Arg Gly Asp Val Pro Arg Gly Ala Ser Ala Gly Ser Ala Pro Gly Thr
225                 230                 235                 240
Asp Val Ser Asp Asp Ser Leu Ala Leu Leu Ile Tyr Thr Ser Gly Ser
                245                 250                 255
Thr Gly Ala Pro Lys Gly Ala Met Tyr Pro Arg Arg Asn Val Ala Thr
            260                 265                 270
Phe Trp Arg Lys Arg Thr Trp Phe Glu Gly Gly Tyr Glu Pro Ser Ile
        275                 280                 285
Thr Leu Asn Phe Met Pro Met Ser His Val Met Gly Arg Gln Ile Leu
    290                 295                 300
Tyr Gly Thr Leu Cys Asn Gly Gly Thr Ala Tyr Phe Val Ala Lys Ser
305                 310                 315                 320
Asp Leu Ser Thr Leu Phe Glu Asp Leu Ala Leu Val Arg Pro Thr Glu
                325                 330                 335
Leu Thr Phe Val Pro Arg Val Trp Asp Met Val Phe Asp Glu Phe Gln
            340                 345                 350
Ser Glu Val Asp Arg Arg Leu Val Asp Gly Ala Asp Arg Val Ala Leu
        355                 360                 365
Glu Ala Gln Val Lys Ala Glu Ile Arg Asn Asp Val Leu Gly Gly Arg
    370                 375                 380
Tyr Thr Ser Ala Leu Thr Gly Ser Ala Pro Ile Ser Asp Glu Met Lys
385                 390                 395                 400
Ala Trp Val Glu Glu Leu Leu Asp Met His Leu Val Glu Gly Tyr Gly
                405                 410                 415
Ser Thr Glu Ala Gly Met Ile Leu Ile Asp Gly Ala Ile Arg Arg Pro
```

```
            420                 425                 430
Ala Val Leu Asp Tyr Lys Leu Val Asp Val Pro Asp Leu Gly Tyr Phe
            435                 440                 445

Leu Thr Asp Arg Pro His Pro Arg Gly Glu Leu Leu Val Lys Thr Asp
            450                 455                 460

Ser Leu Phe Pro Gly Tyr Tyr Gln Arg Ala Glu Val Thr Ala Asp Val
465                 470                 475                 480

Phe Asp Ala Asp Gly Phe Tyr Arg Thr Gly Asp Ile Met Ala Glu Val
                485                 490                 495

Gly Pro Glu Gln Phe Val Tyr Leu Asp Arg Arg Asn Asn Val Leu Lys
            500                 505                 510

Leu Ser Gln Gly Glu Phe Val Thr Val Ser Lys Leu Glu Ala Val Phe
            515                 520                 525

Gly Asp Ser Pro Leu Val Arg Gln Ile Tyr Ile Tyr Gly Asn Ser Ala
            530                 535                 540

Arg Ala Tyr Leu Leu Ala Val Ile Val Pro Thr Gln Glu Ala Leu Asp
545                 550                 555                 560

Ala Val Pro Val Glu Glu Leu Lys Ala Arg Leu Gly Asp Ser Leu Gln
                565                 570                 575

Glu Val Ala Lys Ala Ala Gly Leu Gln Ser Tyr Glu Ile Pro Arg Asp
            580                 585                 590

Phe Ile Ile Glu Thr Thr Pro Trp Thr Leu Glu Asn Gly Leu Leu Thr
            595                 600                 605

Gly Ile Arg Lys Leu Ala Arg Pro Gln Leu Lys Lys His Tyr Gly Glu
            610                 615                 620

Leu Leu Glu Gln Ile Tyr Thr Asp Leu Ala His Gly Gln Ala Asp Glu
625                 630                 635                 640

Leu Arg Ser Leu Arg Gln Ser Gly Ala Asp Ala Pro Val Leu Val Thr
                645                 650                 655

Val Cys Arg Ala Ala Ala Leu Leu Gly Gly Ser Ala Ser Asp Val
            660                 665                 670

Gln Pro Asp Ala His Phe Thr Asp Leu Gly Gly Asp Ser Leu Ser Ala
            675                 680                 685

Leu Ser Phe Thr Asn Leu Leu His Glu Ile Phe Asp Ile Glu Val Pro
            690                 695                 700

Val Gly Val Ile Val Ser Pro Ala Asn Asp Leu Gln Ala Leu Ala Asp
705                 710                 715                 720

Tyr Val Glu Ala Ala Arg Lys Pro Gly Ser Ser Arg Pro Thr Phe Ala
                725                 730                 735

Ser Val His Gly Ala Ser Asn Gly Gln Val Thr Glu Val His Ala Gly
            740                 745                 750

Asp Leu Ser Leu Asp Lys Phe Ile Asp Ala Ala Thr Leu Ala Glu Ala
            755                 760                 765

Pro Arg Leu Pro Ala Ala Asn Thr Gln Val Arg Thr Val Leu Leu Thr
            770                 775                 780

Gly Ala Thr Gly Phe Leu Gly Arg Tyr Leu Ala Leu Glu Trp Leu Glu
785                 790                 795                 800

Arg Met Asp Leu Val Asp Gly Lys Leu Ile Cys Leu Val Arg Ala Lys
                805                 810                 815

Ser Asp Thr Glu Ala Arg Ala Arg Leu Asp Lys Thr Phe Asp Ser Gly
            820                 825                 830

Asp Pro Glu Leu Leu Ala His Tyr Arg Ala Leu Ala Gly Asp His Leu
            835                 840                 845
```

Glu Val Leu Ala Gly Asp Lys Gly Glu Ala Asp Leu Gly Leu Asp Arg
            850                 855                 860

Gln Thr Trp Gln Arg Leu Ala Asp Thr Val Asp Leu Ile Val Asp Pro
865                 870                 875                 880

Ala Ala Leu Val Asn His Val Leu Pro Tyr Ser Gln Leu Phe Gly Pro
                885                 890                 895

Asn Ala Leu Gly Thr Ala Glu Leu Leu Arg Leu Ala Leu Thr Ser Lys
            900                 905                 910

Ile Lys Pro Tyr Ser Tyr Thr Ser Thr Ile Gly Val Ala Asp Gln Ile
            915                 920                 925

Pro Pro Ser Ala Phe Thr Glu Asp Ala Asp Ile Arg Val Ile Ser Ala
            930                 935                 940

Thr Arg Ala Val Asp Asp Ser Tyr Ala Asn Gly Tyr Ser Asn Ser Lys
945                 950                 955                 960

Trp Ala Gly Glu Val Leu Leu Arg Glu Ala His Asp Leu Cys Gly Leu
                965                 970                 975

Pro Val Ala Val Phe Arg Cys Asp Met Ile Leu Ala Asp Thr Thr Trp
            980                 985                 990

Ala Gly Gln Leu Asn Val Pro Asp Met Phe Thr Arg Met Ile Leu Ser
            995                 1000                1005

Leu Ala Ala Thr Gly Ile Ala Pro Gly Ser Phe Tyr Glu Leu Ala
            1010                1015                1020

Ala Asp Gly Ala Arg Gln Arg Ala His Tyr Asp Gly Leu Pro Val
            1025                1030                1035

Glu Phe Ile Ala Glu Ala Ile Ser Thr Leu Gly Ala Gln Ser Gln
            1040                1045                1050

Asp Gly Phe His Thr Tyr His Val Met Asn Pro Tyr Asp Asp Gly
            1055                1060                1065

Ile Gly Leu Asp Glu Phe Val Asp Trp Leu Asn Glu Ser Gly Cys
            1070                1075                1080

Pro Ile Gln Arg Ile Ala Asp Tyr Gly Asp Trp Leu Gln Arg Phe
            1085                1090                1095

Glu Thr Ala Leu Arg Ala Leu Pro Asp Arg Gln Arg His Ser Ser
            1100                1105                1110

Leu Leu Pro Leu Leu His Asn Tyr Arg Gln Pro Glu Arg Pro Val
            1115                1120                1125

Arg Gly Ser Ile Ala Pro Thr Asp Arg Phe Arg Ala Ala Val Gln
            1130                1135                1140

Glu Ala Lys Ile Gly Pro Asp Lys Asp Ile Pro His Val Gly Ala
            1145                1150                1155

Pro Ile Ile Val Lys Tyr Val Ser Asp Leu Arg Leu Leu Gly Leu
            1160                1165                1170

Leu

<210> SEQ ID NO 11
<211> LENGTH: 3522
<212> TYPE: DNA
<213> ORGANISM: Artificial Sequence
<220> FEATURE:
<223> OTHER INFORMATION: Description of Artificial Sequence: Synthetic
      carboxylic acid reductase polynucleotide
      designated 891GA

<400> SEQUENCE: 11
atgagcaccg caacccatga tgaacgtctg gatcgtcgtg ttcatgaact gattgcaacc    60

-continued

```
gatccgcagt tgcagcagc acagccggat cctgcaatta ccgcagcact ggaacagcct     120
ggtctgcgtc tgccgcagat tattcgtacc gttctggatg gttatgcaga tcgtccggca     180
ctgggtcagc gtgttgttga atttgttacc gatgcaaaaa ccggtcgtac cagcgcacag     240
ctgctgcctc gttttgaaac cattacctat agcgaagttg cacagcgtgt tagcgcactg     300
ggtcgtgcac tgagtgatga tgcagttcat ccgggtgatc gtgtttgtgt tctgggtttt     360
aatagcgttg attatgccac cattgatatg gcactgggtg caattggtgc agttagcgtt     420
ccgctgcaga ccagcgcagc aattagcagc ctgcagccga ttgttgcaga accgaaccg      480
accctgattg caagcagcgt taatcagctg tcagatgcag ttcagctgat taccggtgca     540
gaacaggcac cgacccgtct ggttgttttt gattatcatc cgcaggttga tgatcagcgt     600
gaagcagttc aggatgcagc agcacgtctg agcagcaccg tgttgcagt tcagaccctg      660
gcagaactgc tggaacgtgg taaagatctg cctgcagttg cagaaccgcc tgcagatgaa     720
gatagcctgg cactgctgat ttataccagc ggtagcacag gtgcaccgaa aggtgcaatg     780
tatccgcaga gcaatgttgg taaaatgtgg cgtcgtggta gcaaaaattg gttggtgaa     840
agcgcagcaa gcattaccct gaatttcatg ccgatgagcc atgttatggg tcgtagcatt     900
ctgtatggca ccctgggtaa tggtggcacc gcatattttg cagcacgtag cgatctgagc     960
accctgctgg aagatctgga actggttcgt ccgaccgaac tgaattttgt tccgcgtatt    1020
tgggaaaccc tgtatggtga atttcagcgt caggttgaac gtcgtctgag cgaagctggc    1080
gatgccggtg aacgtcgtgc agttgaagca gaagttctgg cagaacagcg tcagtatctg    1140
ctgggtggtc gttttacctt tgcaatgacc ggtagcgcac cgattagtcc ggaactgcgt    1200
aattgggttg aaagcctgct ggaaatgcat ctgatggatg gctatggtag caccgaagca    1260
ggtatggttc tgtttgatgg cgaaattcag cgtccgcctg tgattgatta taaactggtt    1320
gatgttccgg atctgggtta ttttagcacc gatcgtccgc atccgcgtgg tgaactgctg    1380
ctgcgtaccg aaaatatgtt ccgggttat tataaacgtg cagaaccac cgcaggcgtt      1440
tttgatgaag atggttatta tcgtaccggt gatgtgtttg cagaaattgc accggatcgt    1500
ctggtttatg ttgatcgtcg taataatgtt ctgaaactgg cacagggtga atttgtgacc    1560
ctggccaaac tggaagcagt tttttggtaat agtccgctga ttcgtcagat ttatgtgtat    1620
ggtaatagcg cacagccgta tctgctggca gttgttgttc cgaccgaaga ggcactggca    1680
agcggtgatc cggaaaccct gaaaccgaaa attgcagata cctgcagca ggttgcaaaa     1740
gaagcaggtc tgcagagcta tgaagttccg cgtgatttta ttattgaaac caccccgttt    1800
agcctggaaa atggtctgct gaccggtatt cgtaaactgg catggccgaa actgaaacag    1860
cattatggtg aacgcctgga acaaatgtat gcagatctgg cagcaggtca ggcaaatgaa    1920
ctggccgaac tgcgtcgtaa tggtgcacag gcaccggttc tgcagaccgt tagccgtgca    1980
gccggtgcaa tgctgggtag cgcagccagc gatctgagtc cggatgcaca tttaccgat     2040
ctgggtggtg atagcctgag cgcactgacc tttggtaatc tgctgcgtga atttttgat     2100
gttgatgtgc cggttggtgt tattgttagt ccggctaatg atctggcagc cattgcaagc    2160
tatattgaag cagaacgtca gggtagcaaa cgtccgacct tgcaagcgt tcatggtcgt     2220
gatgcaaccg ttgttcgtgc agcagatctg accctggata aatttctgga tgcagaaacc    2280
ctggcagcag caccgaatct gccgaaaccg gcaaccgaag ttcgtaccgt gctgctgaca    2340
ggtgcaaccg gttttctggg tcgttatctg gcactggaat ggctggaacg tatggatatg    2400
```

```
gttgatggta aagttattgc actggttcgt gcccgtagtg atgaagaagc acgcgcacgt    2460
ctggataaaa cctttgatag tggtgatccg aaactgctgg cacattatca gcagctggct    2520
gcagatcatc tggaagttat tgccggtgat aaaggtgaag caaatctggg tctgggtcag    2580
gatgtttggc agcgtctggc agataccgtt gatgttattg tggatccggc agcactggtt    2640
aatcatgttc tgccgtatag cgaactgttt ggtccgaatg cactgggcac cgcagaactg    2700
attcgtctgg cactgaccag caaacagaaa ccgtatacct atgttagcac cattggtgtt    2760
ggcgatcaga ttgaaccggg taaatttgtt gaaaatgccg atattcgtca gatgagcgca    2820
acccgtgcaa ttaatgatag ctatgcaaat ggctacggca atagcaaatg gcaggcgaa    2880 gttctgctgc gcgaagcaca tgatctgtgt ggtctgccgg ttgcagtttt tcgttgtgat    2940
atgattctgg ccgataccac ctatgcaggt cagctgaatc tgccggatat gtttacccgt    3000
ctgatgctga gcctggttgc aaccggtatt gcaccgggta gcttttatga actggatgca    3060
gatggtaatc gtcagcgtgc acattatgat ggcctgccgg ttgaatttat tgcagcagcc    3120
attagcaccc tgggttcaca gattaccgat agcgataccg ttttcagac ctatcatgtt    3180 atgaacccgt atgatgatgg tgttggtctg atgaatatg ttgattggct ggttgatgcc    3240
ggttatagca ttgaacgtat tgcagattat agcgaatggc tgcgtcgctt tgaaacctca    3300
ctgcgtgcac tgccggatcg tcagcgccag tatagcctgc tgccgctgct gcacaattat    3360
cgtacaccgg aaaaaccgat taatggtagc attgcaccga ccgatgtttt tcgtgcagcc    3420
gttcaagaag ccaaaattgg tccggataaa gatattccgc atgttagccc tccggtgatt    3480
gttaaatata ttaccgatct gcagctgctg ggtctgctgt aa                       3522
```

<210> SEQ ID NO 12
<211> LENGTH: 1173
<212> TYPE: PRT
<213> ORGANISM: Artificial Sequence
<220> FEATURE:
<223> OTHER INFORMATION: Description of Artificial Sequence: Synthetic
carboxylic acid reductase polypeptide
designated 891GA

<400> SEQUENCE: 12

```
Met Ser Thr Ala Thr His Asp Glu Arg Leu Asp Arg Arg Val His Glu
1               5                   10                  15

Leu Ile Ala Thr Asp Pro Gln Phe Ala Ala Ala Gln Pro Asp Pro Ala
            20                  25                  30

Ile Thr Ala Ala Leu Glu Gln Pro Gly Leu Arg Leu Pro Gln Ile Ile
        35                  40                  45

Arg Thr Val Leu Asp Gly Tyr Ala Asp Arg Pro Ala Leu Gly Gln Arg
    50                  55                  60

Val Val Glu Phe Val Thr Asp Ala Lys Thr Gly Arg Thr Ser Ala Gln
65                  70                  75                  80

Leu Leu Pro Arg Phe Glu Thr Ile Thr Tyr Ser Glu Val Ala Gln Arg
                85                  90                  95

Val Ser Ala Leu Gly Arg Ala Leu Ser Asp Asp Ala Val His Pro Gly
            100                 105                 110

Asp Arg Val Cys Val Leu Gly Phe Asn Ser Val Asp Tyr Ala Thr Ile
        115                 120                 125

Asp Met Ala Leu Gly Ala Ile Gly Ala Val Ser Val Pro Leu Gln Thr
    130                 135                 140

Ser Ala Ala Ile Ser Ser Leu Gln Pro Ile Val Ala Glu Thr Glu Pro
145                 150                 155                 160
```

```
Thr Leu Ile Ala Ser Ser Val Asn Gln Leu Ser Asp Ala Val Gln Leu
                165                 170                 175

Ile Thr Gly Ala Glu Gln Ala Pro Thr Arg Leu Val Val Phe Asp Tyr
            180                 185                 190

His Pro Gln Val Asp Asp Gln Arg Glu Ala Val Gln Asp Ala Ala Ala
        195                 200                 205

Arg Leu Ser Ser Thr Gly Val Ala Val Gln Thr Leu Ala Glu Leu Leu
    210                 215                 220

Glu Arg Gly Lys Asp Leu Pro Ala Val Ala Glu Pro Pro Ala Asp Glu
225                 230                 235                 240

Asp Ser Leu Ala Leu Leu Ile Tyr Thr Ser Gly Ser Thr Gly Ala Pro
                245                 250                 255

Lys Gly Ala Met Tyr Pro Gln Ser Asn Val Gly Lys Met Trp Arg Arg
            260                 265                 270

Gly Ser Lys Asn Trp Phe Gly Glu Ser Ala Ala Ser Ile Thr Leu Asn
        275                 280                 285

Phe Met Pro Met Ser His Val Met Gly Arg Ser Ile Leu Tyr Gly Thr
    290                 295                 300

Leu Gly Asn Gly Gly Thr Ala Tyr Phe Ala Ala Arg Ser Asp Leu Ser
305                 310                 315                 320

Thr Leu Leu Glu Asp Leu Glu Leu Val Arg Pro Thr Glu Leu Asn Phe
                325                 330                 335

Val Pro Arg Ile Trp Glu Thr Leu Tyr Gly Glu Phe Gln Arg Gln Val
            340                 345                 350

Glu Arg Arg Leu Ser Glu Ala Gly Asp Ala Gly Glu Arg Arg Ala Val
        355                 360                 365

Glu Ala Glu Val Leu Ala Glu Gln Arg Gln Tyr Leu Leu Gly Gly Arg
    370                 375                 380

Phe Thr Phe Ala Met Thr Gly Ser Ala Pro Ile Ser Pro Glu Leu Arg
385                 390                 395                 400

Asn Trp Val Glu Ser Leu Leu Glu Met His Leu Met Asp Gly Tyr Gly
                405                 410                 415

Ser Thr Glu Ala Gly Met Val Leu Phe Asp Gly Glu Ile Gln Arg Pro
            420                 425                 430

Pro Val Ile Asp Tyr Lys Leu Val Asp Val Pro Asp Leu Gly Tyr Phe
        435                 440                 445

Ser Thr Asp Arg Pro His Pro Arg Gly Glu Leu Leu Leu Arg Thr Glu
    450                 455                 460

Asn Met Phe Pro Gly Tyr Tyr Lys Arg Ala Glu Thr Thr Ala Gly Val
465                 470                 475                 480

Phe Asp Glu Asp Gly Tyr Tyr Arg Thr Gly Asp Val Phe Ala Glu Ile
                485                 490                 495

Ala Pro Asp Arg Leu Val Tyr Val Asp Arg Arg Asn Asn Val Leu Lys
            500                 505                 510

Leu Ala Gln Gly Glu Phe Val Thr Leu Ala Lys Leu Glu Ala Val Phe
        515                 520                 525

Gly Asn Ser Pro Leu Ile Arg Gln Ile Tyr Val Tyr Gly Asn Ser Ala
    530                 535                 540

Gln Pro Tyr Leu Leu Ala Val Val Val Pro Thr Glu Glu Ala Leu Ala
545                 550                 555                 560

Ser Gly Asp Pro Glu Thr Leu Lys Pro Lys Ile Ala Asp Ser Leu Gln
                565                 570                 575
```

-continued

```
Gln Val Ala Lys Glu Ala Gly Leu Gln Ser Tyr Glu Val Pro Arg Asp
            580                 585                 590
Phe Ile Ile Glu Thr Thr Pro Phe Ser Leu Glu Asn Gly Leu Leu Thr
        595                 600                 605
Gly Ile Arg Lys Leu Ala Trp Pro Lys Leu Lys Gln His Tyr Gly Glu
    610                 615                 620
Arg Leu Glu Gln Met Tyr Ala Asp Leu Ala Ala Gly Gln Ala Asn Glu
625                 630                 635                 640
Leu Ala Glu Leu Arg Arg Asn Gly Ala Gln Ala Pro Val Leu Gln Thr
                645                 650                 655
Val Ser Arg Ala Ala Gly Ala Met Leu Gly Ser Ala Ala Ser Asp Leu
            660                 665                 670
Ser Pro Asp Ala His Phe Thr Asp Leu Gly Gly Asp Ser Leu Ser Ala
        675                 680                 685
Leu Thr Phe Gly Asn Leu Leu Arg Glu Ile Phe Asp Val Asp Val Pro
    690                 695                 700
Val Gly Val Ile Val Ser Pro Ala Asn Asp Leu Ala Ala Ile Ala Ser
705                 710                 715                 720
Tyr Ile Glu Ala Glu Arg Gln Gly Ser Lys Arg Pro Thr Phe Ala Ser
                725                 730                 735
Val His Gly Arg Asp Ala Thr Val Val Arg Ala Ala Asp Leu Thr Leu
            740                 745                 750
Asp Lys Phe Leu Asp Ala Glu Thr Leu Ala Ala Ala Pro Asn Leu Pro
        755                 760                 765
Lys Pro Ala Thr Glu Val Arg Thr Val Leu Leu Thr Gly Ala Thr Gly
    770                 775                 780
Phe Leu Gly Arg Tyr Leu Ala Leu Glu Trp Leu Glu Arg Met Asp Met
785                 790                 795                 800
Val Asp Gly Lys Val Ile Ala Leu Val Arg Ala Arg Ser Asp Glu Glu
                805                 810                 815
Ala Arg Ala Arg Leu Asp Lys Thr Phe Asp Ser Gly Asp Pro Lys Leu
            820                 825                 830
Leu Ala His Tyr Gln Gln Leu Ala Ala Asp His Leu Glu Val Ile Ala
        835                 840                 845
Gly Asp Lys Gly Glu Ala Asn Leu Gly Leu Gly Gln Asp Val Trp Gln
    850                 855                 860
Arg Leu Ala Asp Thr Val Asp Val Ile Val Asp Pro Ala Ala Leu Val
865                 870                 875                 880
Asn His Val Leu Pro Tyr Ser Glu Leu Phe Gly Pro Asn Ala Leu Gly
                885                 890                 895
Thr Ala Glu Leu Ile Arg Leu Ala Leu Thr Ser Lys Gln Lys Pro Tyr
            900                 905                 910
Thr Tyr Val Ser Thr Ile Gly Val Gly Asp Gln Ile Glu Pro Gly Lys
        915                 920                 925
Phe Val Glu Asn Ala Asp Ile Arg Gln Met Ser Ala Thr Arg Ala Ile
    930                 935                 940
Asn Asp Ser Tyr Ala Asn Gly Tyr Gly Asn Ser Lys Trp Ala Gly Glu
945                 950                 955                 960
Val Leu Leu Arg Glu Ala His Asp Leu Cys Gly Leu Pro Val Ala Val
                965                 970                 975
Phe Arg Cys Asp Met Ile Leu Ala Asp Thr Thr Tyr Ala Gly Gln Leu
            980                 985                 990
Asn Leu Pro Asp Met Phe Thr Arg  Leu Met Leu Ser Leu  Val Ala Thr
```

-continued

```
                995              1000              1005
Gly Ile Ala Pro Gly Ser Phe Tyr Glu Leu Asp Ala Asp Gly Asn
    1010            1015            1020

Arg Gln Arg Ala His Tyr Asp Gly Leu Pro Val Glu Phe Ile Ala
    1025            1030            1035

Ala Ala Ile Ser Thr Leu Gly Ser Gln Ile Thr Asp Ser Asp Thr
    1040            1045            1050

Gly Phe Gln Thr Tyr His Val Met Asn Pro Tyr Asp Asp Gly Val
    1055            1060            1065

Gly Leu Asp Glu Tyr Val Asp Trp Leu Val Asp Ala Gly Tyr Ser
    1070            1075            1080

Ile Glu Arg Ile Ala Asp Tyr Ser Glu Trp Leu Arg Arg Phe Glu
    1085            1090            1095

Thr Ser Leu Arg Ala Leu Pro Asp Arg Gln Arg Gln Tyr Ser Leu
    1100            1105            1110

Leu Pro Leu Leu His Asn Tyr Arg Thr Pro Glu Lys Pro Ile Asn
    1115            1120            1125

Gly Ser Ile Ala Pro Thr Asp Val Phe Arg Ala Ala Val Gln Glu
    1130            1135            1140

Ala Lys Ile Gly Pro Asp Lys Asp Ile Pro His Val Ser Pro Pro
    1145            1150            1155

Val Ile Val Lys Tyr Ile Thr Asp Leu Gln Leu Leu Gly Leu Leu
    1160            1165            1170
```